US011325948B2

(12) United States Patent
Frost et al.

(10) Patent No.: US 11,325,948 B2
(45) Date of Patent: May 10, 2022

(54) METHODS AND COMPOSITIONS FOR GENETICALLY MODIFYING LYMPHOCYTES TO EXPRESS POLYPEPTIDES COMPRISING THE INTRACELLULAR DOMAIN OF MPL

(71) Applicant: Exuma Biotech Corp., West Palm Beach, FL (US)

(72) Inventors: Gregory Ian Frost, West Palm Beach, FL (US); James Joseph Onuffer, Jr., Alameda, CA (US); Ghiabe H. Guibinga, San Diego, CA (US); Farzad Haerizadeh, San Diego, CA (US); Frederic Vigant, Villers-sous-Saint-Leu (FR); Anirban Kundu, West Bay (KY)

(73) Assignee: Exuma Biotech Corp., West Palm Beach, FL (US)

( * ) Notice: Subject to any disclaimer, the term of this patent is extended or adjusted under 35 U.S.C. 154(b) by 0 days.

(21) Appl. No.: 17/110,028

(22) Filed: Dec. 2, 2020

(65) Prior Publication Data

US 2021/0107949 A1 Apr. 15, 2021

Related U.S. Application Data

(63) Continuation-in-part of application No. PCT/US2019/049259, filed on Sep. 2, 2019, and a continuation-in-part of application No. 16/490,201, filed as application No. PCT/US2018/020818 on Mar. 3, 2018, said application No. PCT/US2019/049259 is a continuation-in-part of application No. PCT/US2018/051392, filed on Sep. 17, 2018, which is a continuation-in-part of application No. PCT/US2018/020818, which is a continuation-in-part of application No. 15/644,778, filed on Jul. 8, 2017, now Pat. No. 11,111,505, and a continuation-in-part of application No. PCT/US2017/041277, filed on Jul. 8, 2017, and a continuation-in-part of application No. PCT/US2017/023112, filed on Mar. 19, 2017, said application No. 15/644,778 is a continuation-in-part of application No. PCT/US2017/023112, filed on Mar. 19, 2017, and a continuation-in-part of application No. 15/462,855, filed on Mar. 19, 2017, now Pat. No. 10,596,274, said application No.

(Continued)

(51) Int. Cl.

| | |
|---|---|
| ***C12N 15/867*** | (2006.01) |
| ***C07K 14/005*** | (2006.01) |
| ***C12N 15/86*** | (2006.01) |
| ***C07K 14/705*** | (2006.01) |
| ***C07K 16/28*** | (2006.01) |
| ***C07K 14/725*** | (2006.01) |
| ***C07K 14/54*** | (2006.01) |
| ***A61K 47/69*** | (2017.01) |
| ***A61K 35/17*** | (2015.01) |
| ***C12N 7/00*** | (2006.01) |
| *A61K 38/00* | (2006.01) |
| *A61K 39/00* | (2006.01) |

(52) U.S. Cl.

CPC ............ *C07K 14/005* (2013.01); *A61K 35/17* (2013.01); *A61K 47/6901* (2017.08); *C07K 14/5418* (2013.01); *C07K 14/7051* (2013.01); *C07K 14/70517* (2013.01); *C07K 14/70578* (2013.01); *C07K 14/70596* (2013.01); *C07K 16/2803* (2013.01); *C07K 16/2809* (2013.01); *C12N 7/00* (2013.01); *C12N 15/86* (2013.01); *A61K 38/00* (2013.01); *A61K 2039/505* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2740/10022* (2013.01); *C12N 2740/10043* (2013.01)

(58) Field of Classification Search

None

See application file for complete search history.

(56) References Cited

U.S. PATENT DOCUMENTS

| | | | |
|---|---|---|---|
| 5,677,425 A | 10/1997 | Bodmer et al. |
| 8,709,755 B2 | 4/2014 | Short et al. |

(Continued)

FOREIGN PATENT DOCUMENTS

| | | | |
|---|---|---|---|
| EP | 2019144 A1 | 1/2009 |
| WO | 9303769 A1 | 3/1993 |

(Continued)

OTHER PUBLICATIONS

Patel N et al: "Functional Replacement of Cytokine Receptor Extracellular Domains by Leucine Zippers", Journal of Biological Chemistry 271(48):30386-30391 Nov. 29, 1996.

(Continued)

*Primary Examiner* — Michael D Burkhart

(74) *Attorney, Agent, or Firm* — Double Helix Law; Emanuel Vacchiano; Michael Mand

(57) ABSTRACT

The present disclosure provides methods and compositions for genetically modifying lymphocytes, for example T cells and/or NK cells, in shorter times than previously and/or in whole blood or a component thereof. In some embodiments a lymphodepletion filter assembly is used before or after forming a reaction mixture where lymphocytes are contacted with recombinant retroviral particles in a closed system, to genetically modify the lymphocytes.

27 Claims, 19 Drawing Sheets

Specification includes a Sequence Listing.

Related U.S. Application Data

PCT/US2017/041277 is a continuation-in-part of application No. 15/462,855, filed on Mar. 19, 2017, now Pat. No. 10,596,274, and a continuation-in-part of application No. PCT/US2017/023112, filed on Mar. 19, 2017, said application No. PCT/US2018/020818 is a continuation-in-part of application No. 15/462,855, filed on Mar. 19, 2017, now Pat. No. 10,596,274.

(60) Provisional application No. 62/894,853, filed on Sep. 1, 2019, provisional application No. 62/821,434, filed on Mar. 20, 2019, provisional application No. 62/732,528, filed on Sep. 17, 2018, provisional application No. 62/728,056, filed on Sep. 6, 2018, provisional application No. 62/726,293, filed on Sep. 2, 2018, provisional application No. 62/726,294, filed on Sep. 2, 2018, provisional application No. 62/564,991, filed on Sep. 28, 2017, provisional application No. 62/564,253, filed on Sep. 27, 2017, provisional application No. 62/560,176, filed on Sep. 18, 2017, provisional application No. 62/467,039, filed on Mar. 3, 2017, provisional application No. 62/360,041, filed on Jul. 8, 2016, provisional application No. 62/390,093, filed on Mar. 19, 2016.

(56) References Cited

U.S. PATENT DOCUMENTS

| | | | |
|---|---|---|---|
| 2004/0131637 A1 | 7/2004 | Chatfield | |
| 2008/0269258 A1 | 10/2008 | Breaker et al. | |
| 2012/0258459 A1 | 10/2012 | Huang | |
| 2016/0251660 A1 | 9/2016 | Gu et al. | |
| 2016/0340691 A1 | 11/2016 | Minshull et al. | |
| 2017/0166877 A1 | 6/2017 | Bayle et al. | |
| 2017/0246278 A1 | 8/2017 | Valdes et al. | |
| 2017/0296678 A1 | 10/2017 | Frost et al. | |
| 2017/0335281 A1 | 11/2017 | Loew et al. | |
| 2017/0356010 A1 | 12/2017 | Frost et al. | |
| 2018/0021378 A1 | 1/2018 | Kang et al. | |
| 2018/0057794 A1 | 3/2018 | Rubinstein et al. | |
| 2019/0008985 A1 | 1/2019 | Angel et al. | |
| 2019/0134091 A1 | 5/2019 | Dropulic et al. | |
| 2019/0161542 A1 | 5/2019 | Gill et al. | |
| 2019/0367621 A1 | 12/2019 | Frost et al. | |
| 2020/0255864 A1 | 8/2020 | Frost et al. | |
| 2020/0397821 A1 | 12/2020 | Frost et al. | |
| 2021/0107949 A1* | 4/2021 | Frost | C07K 16/32 |
| 2021/0317408 A1 | 10/2021 | Frost et al. | |
| 2021/0403952 A1 | 12/2021 | Frost et al. | |

FOREIGN PATENT DOCUMENTS

| | | | |
|---|---|---|---|
| WO | 9309239 | A1 | 5/1993 |
| WO | 9319191 | A1 | 9/1993 |
| WO | 9412649 | A2 | 9/1994 |
| WO | 9428938 | A1 | 12/1994 |
| WO | 9500655 | A1 | 1/1995 |
| WO | 9511984 | A2 | 5/1995 |
| WO | 1995016784 | A1 | 6/1995 |
| WO | 9523846 | A1 | 9/1995 |
| WO | 9617951 | A2 | 6/1996 |
| WO | 1999034836 | A1 | 7/1999 |
| WO | 0218609 | A2 | 3/2002 |
| WO | 2004073641 | A2 | 9/2004 |
| WO | 2006007539 | A1 | 1/2006 |
| WO | 2005110491 | A3 | 4/2006 |
| WO | 2006055351 | A2 | 5/2006 |
| WO | 2008156987 | A2 | 12/2008 |
| WO | 2011059836 | A2 | 5/2011 |
| WO | 2012138858 | A1 | 10/2012 |
| WO | 2012153142 | A2 | 11/2012 |
| WO | 2013045639 | A1 | 4/2013 |
| WO | 2013092720 | A1 | 6/2013 |
| WO | 2013123061 | A1 | 8/2013 |
| WO | 2013127964 | A1 | 9/2013 |
| WO | 2013166051 | A1 | 11/2013 |
| WO | 2014011984 | A1 | 1/2014 |
| WO | 2014028509 | A3 | 5/2014 |
| WO | 2014130657 | A1 | 8/2014 |
| WO | 2014138306 | A1 | 9/2014 |
| WO | 2014151960 | A2 | 9/2014 |
| WO | 2014186469 | A2 | 11/2014 |
| WO | 2015056980 | A1 | 4/2015 |
| WO | 2015066042 | A1 | 5/2015 |
| WO | 2015075195 | A1 | 5/2015 |
| WO | 2016016344 | A1 | 2/2016 |
| WO | 2016030691 | A1 | 3/2016 |
| WO | 2016033331 | A1 | 3/2016 |
| WO | 2016118857 | A1 | 7/2016 |
| WO | 2016139463 | A1 | 9/2016 |
| WO | 2017011804 | A8 | 1/2017 |
| WO | 2017034615 | A2 | 3/2017 |
| WO | 2017103596 | A1 | 6/2017 |
| WO | 2017165245 | A2 | 9/2017 |
| WO | 2017165245 | A3 | 9/2017 |
| WO | 2018009923 | A1 | 1/2018 |
| WO | 2018033726 | A1 | 2/2018 |
| WO | 2018038945 | A1 | 3/2018 |
| WO | 2018075978 | A1 | 4/2018 |
| WO | 2018136570 | A9 | 7/2018 |
| WO | 2018161064 | A1 | 9/2018 |
| WO | 2018175476 | A1 | 9/2018 |
| WO | 2019055946 | A1 | 3/2019 |
| WO | 2019157130 | A1 | 8/2019 |
| WO | 2019169290 | A1 | 9/2019 |
| WO | 2020047527 | A2 | 3/2020 |
| WO | 2020047527 | A3 | 3/2020 |
| WO | 2021042072 | A1 | 3/2021 |
| WO | 2021178701 | A1 | 9/2021 |

OTHER PUBLICATIONS

Kawahara M et al"Growth promotion of genetically modified hematopoietic progenitors using an antibody/c-Mpl chimera", Cytokine 55(3):402-408 Sep. 2011.

Saka K et al: "Activation of target signal transducers utilizing chimeric receptors with signaling-molecule binding motifs", Biotechnology and Bioengineering 109(6):1528-1537 Jun. 2012.

Richard RE et al: "Expansion of genetically modified primary human hemopoietic cells using chemical inducers of dimerization", Blood 95(2):430-436 Jan. 15, 2000.

Saka K et al: "Dissection of Signaling Events Downstream of the c-Mpl Receptor in Murine Hematopoietic Stem Cells Via Motif-Engineered Chimeric Receptors", Stem Cell Reviews and Reports 14(1):101-109 Feb. 2018.

Nishimura CD et al: "c-MPL provides tumor-targeted T-cell receptor-transgenic T cells with costimulation and cytokine signals", Blood 130(25):2739-2749 Dec. 21, 2017.

Belay E et al: "A hyperactive Mpl-based cell growth switch drives macrophage-associated erythropoiesis through an erythroid-megakaryocytic precursor", Blood 125(6):1025-1033 Feb. 5, 2015.

Zhao S et al: "In Vivo Selection of Genetically Modified Erythroid Cells Using a Jak2-Based Cell Growth Switch", Molecular Therapy 10(3):1456-468 Sep. 2004.

Dahlen DD et al: "Internalization of the thrombopoietin receptor is regulated by 2 cytoplasmic motifs", Blood 102(1):102-108 Jul. 1, 2003.

Zhao S: "JAK2, complemented by a second signal from c-kit or flt-3, triggers extensive self-renewal of primary multipotential hemopoietic cells", The EMBO Journal 21(9):2159-2167 May 1, 2002.

Otto KG et al: "Membrane localization is not required for Mpl function in normal hematopoietic cells", Blood 98(7):2077-2083 Oct. 1, 2002.

Drachman JG et al: "Dissecting the thrombopoietin receptor: Functional elements of the Mpl cytoplasmic domain", Proceedings of the National Academy of Sciences 94(6):2350-2355 Mar. 18, 1997.

(56) References Cited

OTHER PUBLICATIONS

Morella KK et al: "Signal transduction by the receptors for thrombopoietin (c-mpL) and interleukin-3 in hematopoietic and nonhematopoietic cells", Blood 86(2):557-571 Jul. 15, 1995.
Bénit L et al: "Characterization of mpl cytoplasmic domain sequences required for myeloproliferative leukemia virus pathogenicity ", Journal of Virology 68(8):5270-5274 1994.
He X et al: "Different mutations of the human c-mpl gene indicate distinct haematopoietic diseases", Journal of Hematology & Oncology 6(1):11 2013.
Pecquet C et al: "Induction of myeloproliferative disorder and myelofibrosis by thrombopoietin receptor W515 mutantsis mediated by cytosolic tyrosine 112 of the receptor", Blood 115(5):1037-1048 Feb. 4, 2010.
Hunter MR et al: "Chimeric ?c cytokine receptors confer cytokine independent engraftment of human T lymphocytes", Molecular Immunology, 56(1-2):1-11, Nov. 2013.
Hurton LV et al: "Tethered IL-15 augments antitumor activity and promotes a stem-cell memory subset in tumor-specific T cells", Proceedings of the National Academy of Sciences, 113(48):E7788-E7797, Nov. 14, 2016.
Jensen MC: "Enhancing the IQ of CAR-modified T Cells", International Society & Gene Therapy abstract, Jun. 1, 2012.
Ji Y et al: "Enhancing adoptive T cell immunotherapy with microRNA therapeutics", Seminars in immunology, 28(1):45-53, Dec. 20, 2015.
Jomary C et al: "Rescue of photoreceptor function by AAV-mediated gene transfer in a mouse model of inherited retinal degeneration", Gene Therapy, 4(7):683-690, Jul. 1997.
Jones S et al: "Lentiviral Vector Design for Optimal T Cell Receptor Gene Expression in the Transduction of Peripheral Blood Lymphocytes and Tumor-Infiltrating Lymphocytes", Human Gene Therapy, 20(6):630-640, Jun. 2009.
Kagoya Y et al: "A novel chimeric antigen receptor containing a JAK-STAT signaling domain mediates superior antitumor effects", Nature Medicine, 24(3):352, Feb. 5, 2018.
Kaiser AD et al: "Towards a commercial process for the manufacture of genetically modified T cells for therapy", Cancer Gene Therapy, 22(2):72-78, Jan. 23, 2015.
Kim D-S et al: "An artificial riboswitch for controlling pre-mRNA splicing", RNA, 11(11):1667-1677, Nov. 1, 2005.
Kim DS et al: "Ligand-induced sequestering of branchpoint sequence allows conditional control of splicing", BMC molecular biology, 9(1):23, Feb. 12, 2008.
Kim JN et al: "Design and Antimicrobial Action of Purine Analogues That Bind Guanine Riboswitches", ACS Chemical Biology, 4(11):915-927, Nov. 20, 2009.
Kim JN et al: "Guanine riboswitch variants from Mesoplasma florum selectively recognize 2'-deoxyguanosine", Proceedings of the National Academy of Sciences, 104(41):16092-16097, Oct. 2, 2007.
Kim JN et al: "Purine sensing by riboswitches", Biology of the Cell, 100(1):1-11, Jan. 1, 2008.
Kimura MY et al: "IL-7 signaling must be intermittent, not continuous, during CD8+ T cell homeostasis to promote cell survival instead of cell death", Nature Immunology, 14(2):143-151, Dec. 16, 2012.
Klingemann H: "Are natural killer cells superior CAR drivers?", Oncoimmunology, 3:e28147, Apr. 15, 2014.
Kloss CC et al: "Combinatorial antigen recognition with balanced signaling promotes selective tumor eradication by engineered T cells", Nature Biotechnology, 31(1):71-75, Dec. 16, 2012.
Kong S et al: "Suppression of human glioma xenografts with second-generation IL 13R-specific chimeric antigen receptor-modified T cells", Clinical Cancer Research, vol. 18, No. 21, Nov. 1, 2012, pp. 5949-5960.
Korin YD et al: "Progression to the G1b Phase of the Cell Cycle Is Required for Completion of Human Immunodeficiency Virus Type 1 Reverse Transcription in T Cells", Journal of Virology, 72(4):3161-3168, Apr. 1, 1998.
Krishnamurthy J et al: "Targeting an ancient retrovirus expressed in melanoma using adoptive T-cell therapy", Dissertation, Feb. 24, 2012, pp. 1-107.
Kueng HJ et al: "General Strategy for Decoration of Enveloped Viruses with Functionally Active Lipid-Modified Cytokines", Journal of Virology, 81(16):8666-8676, May 30, 2007.
Lamers CHJ et al: "Treatment of Metastatic Renal Cell Carcinoma With CAIX CAR-engineered T cells: Clinical Evaluation and Management of On-target Toxicity", Molecular Therapy, 21(4):904-912, Feb. 19, 2013.
Leen AM et al: "Reversal of Tumor Immune Inhibition Using a Chimeric Cytokine Receptor", Molecular Therapy: The Journal Of The American Society Of Gene Therapy, vol. 22, No. 6, Jun. 1, 2014, pp. 1211-1220.
Levay A et al: "Identifying high-affinity aptamer ligands with defined cross-reactivity using high-throughput guided systematic evolution of ligands by exponential enrichment", Nucleic Acids Research, 43(12):e82, May 24, 2015.
Li T et al: "In vivo transfer of a reporter gene to the retina mediated by an adenoviral vector", Investigative Ophthalmology & Visual Science, 35(5):2543-2549, Apr. 1994.
Li T et al: "Phenotype correction in retinal pigment epithelium in murine mucopolysaccharidosis VII by adenovirus-mediated gene transfer", Proceedings of the National Academy of Sciences, 92(17):7700-7704, Aug. 15, 1995.
Lienert F et al: "Synthetic biology in mammalian cells: next generation research tools and therapeutics", Nature reviews Molecular cell biology, 15(2):95, Jan. 17, 2014.
Liu H et al: "Fc Engineering for Developing Therapeutic Bispecific Antibodies and Novel Scaffolds", Frontiers in Immunology, 8:38, Jan. 26, 2017.
Lu X et al: "Active Conformation of the Erythropoietin Receptor: Random and Cysteine-Scanning Mutagenesis of the Extracellular Juxtamembrane and Transmembrane Domains", Journal of Biological Chemistry, 281(11):7002-7011, Jan. 12, 2006.
Mandal M et al: "Riboswitches control fundamental biochemical pathways in Bacillus subtilis and other bacteria", Cell, 113(5):577-586, May 29, 2003.
Marin V et al: "Comparison of Different Suicide-Gene Strategies for the Safety Improvement of Genetically Manipulated T Cells", Human Gene Therapy Methods, 23(6):376-386, Nov. 27, 2012.
Marodon G et al: "Specific transgene expression in human and mouse CD4+cells using lentiviral vectors with regulatory sequences from theCD4 gene", Blood, 101(9):3416-3423, Jan. 2, 2003.
Marrack P et al: "Homeostasis of ?? TCR+ T cells", Nature Immunology, 1(2):107-111, Aug. 2000.
Matyjasik MM et al: "Structural basis for 2'-deoxyguanosine recognition by the 2'-dG-11 class of riboswitches", Nucleic Acids Research, 47(20):10931-10941, Oct. 10, 2019.
Matz MV et al: "Fluorescent proteins from nonbioluminescent *anthozoa* species", Nature Biotechnology, 17(10):969-973, Oct. 1999.
Maurice M et al: "Efficient gene transfer into human primary blood lymphocytes by surface-engineered lentiviral vectors that display a T cell-activating polypeptide", Blood, vol. 99, No. 7, Apr. 1, 2002, pp. 2342-2350.
McElroy CA et al: "Structural reorganization of the interleukin-7 signaling complex", Proceedings of the National Academy of Sciences, 109(7):2503-2508, Jan. 30, 2012.
McKelvie ND et al: "Expression of heterologous antigens in *Salmonella typhimurium* vaccine vectors using the in vivo-inducible, SPI-2 promoter, ssaG", Vaccine, 22(25-26):3243-3255, Sep. 3, 2004.
Melton DA et al: "Efficient in vitro synthesis of biologically active RNA and RNA hybridization probes from plasmids containing a bacteriophage SP6 promoter", Nucleic Acids Research, 12(18):7035-7056, Sep. 25, 1984.
Mendelson E et al: "Expression and rescue of a nonselected marker from an integrated AAV vector", Virology, 166(1):154-165, Sep. 1988.
Miller AD: "Human gene therapy comes of age", Nature, 357(6378):455-460, Jun. 11, 1992.

(56) References Cited

OTHER PUBLICATIONS

Miyoshi H et al: "Stable and efficient gene transfer into the retina using an HIV-based lentiviral vector", Proceedings of the National Academy of Sciences, 94(19):10319-10323, Sep. 16, 1997.
Morgan RA et al: "Case Report of a Serious Adverse Event Following the Administration of T Cells Transduced With a Chimeric Antigen Receptor Recognizing ERBB2", Molecular Therapy, 18(4):843-851, Feb. 23, 2010.
Muhlebach MD et al: "Transduction efficiency of MLV but not of HIV-1 vectors is pseudotype dependent on human primary T lymphocytes", Journal of Molecular Medicine, 81(12):801-810, Oct. 24, 2003.
Nam S et al: "Driving the next wave of innovation in CAR T-cell therapies", McKinsey & Company Pharmaceuticals & Medical Products, Dec. 13, 2019.
Ngo MC et al: "Ex vivo gene transfer for improved adoptive immunotherapy of cancer", Human Molecular Genetics, 20(R1):R93-R99, Mar. 17, 2011.
Nguyen V-T et al: "Multiple GO-SELEX for efficient screening of flexible aptamers", Chemical Communications, 50(72):10513-10516, Jul. 23, 2014.
O'Connor CM et al: "Adoptive T-cell therapy improves treatment of canine non-Hodgkin lymphoma post chemotherapy", Scientific Reports, vol. 2, Feb. 1, 2012.
Ogawa A: "Rational design of artificial riboswitches based on ligand-dependent modulation of internal ribosome entry in wheat germ extract and their applications as label-free biosensors", RNA, 17(3):478-488, Jan. 11, 2011.
Ohno M et al: "Expression of miR-17-92 enhances anti-tumor activity of T-cells transduced with the anti-EGFRvIII chimeric antigen receptor in mice bearing human GBM xenografts", Journal for Immunotherapy of Cancer, 1:21, Dec. 16, 2013.
Okamoto S et al: "A promising vector for TCR gene therapy: differential effect of siRNA, 2A peptide, and disulfide bond on the introduced TCR expression", Molecular Therapy—Nucleic Acids, 1(12):e63, Dec. 18, 2012.
Ali RR et al: "Gene transfer into the mouse retina mediated by an adeno-associated viral vector", Human Molecular Genetics, 5(5):591-594, May 1, 1996.
Cavalieri S et al: "Human T lymphocytes transduced by lentiviral vectors in the absence of TCR activation maintain an intact immune competence", Blood, 102(2):497-505, Mar. 20, 2003.
Chatfield SN et al: "Use of the nirB promoter to direct the stable expression of heterologous antigens in *Salmonella* oral vaccine strains: Development of a single-dose oral tetanus vaccine", Biotechnology (N Y), 10(8):888-892, 1992.
Fuhrmann-Benzakein E et al: "Inducible and irreversible control of gene expression using a single transgene", Nucleic Acids Research, 28(23):E99, Dec. 1, 2000.
Verhoeyen E et al: "IL-7 surface-engineered lentiviral vectors promote survival and efficient gene transfer in resting primary T lymphocytes", Blood, vol. 101, No. 6, Mar. 15, 2003, pp. 2167-2174.
O'Neill LS et al: "Entry kinetics and cell-cell transmission of surface-bound retroviral vector particles", Journal of Gene Medicine, 12(5):463-476, May 2010.
Papapeirou EP et al: "Harnessing endogenous miR-181a to segregate transgenic antigen receptor expression in developing versus post-thymic T cells in murine hematopoietic chimeras", Journal of Clinical Investigation, 119(1):157-168, Dec. 1, 2008.
Park JW et al: "Immobilization-free screening of aptamers assisted by graphene oxide", Chem. Commun., 48(15):2071-2073, Dec. 5, 2011.
Pikovskaya O et al: "Structural principles of nucleoside selectivity in a 2'-deoxyguanosine riboswitch", Nature chemical biology, 7(10):748, Aug. 14, 2011.
Poling BC et al: "A lentiviral vector bearing a reverse intron demonstrates superior expression of both proteins and microRNAs", RNA Biology, 14(11):1570-1579, Jul. 21, 2017.
Pulkkinen WS et al: "A *Salmonella typhimurium* virulence protein is similar to a *Yersinia enterocolitica* invasion protein and a bacteriophage lambda outer membrane protein", Journal of Bacteriology, 173(1):86-93, Jan. 1991.
Reid CA et al: "Development of an inducible anti-VEGF rAAV gene therapy strategy for the treatment of wet AMD", Scientific reports, 8(1):11763, Aug. 6, 2018.
Rolling F et al: "Evaluation of Adeno-Associated Virus-Mediated Gene Transfer into the Rat Retina by Clinical Fluorescence Photography", Human Gene Therapy, 10(4):641-648, Mar. 1999.
Salmon P et al: "Characterization of the human CD4 gene promoter: transcription from the CD4 gene core promoter is tissue-specific and is activated by Ets proteins", Proceedings of the National Academy of Sciences, 90(16):7739-7743, Aug. 15, 1993.
Samulski RJ et al: "Helper-free stocks of recombinant adeno-associated viruses: normal integration does not require viral gene expression", Journal of Virology, 63(9):3822-3828, 1989.
Schütze T et al: "Probing the SELEX Process with Next-Generation Sequencing", PLoS ONE, 6(12):e29604, Dec. 29, 2011.
Shaner NC et al: "A guide to choosing fluorescent proteins", Nature Methods, 2(12):905-909, Dec. 2005.
Sharma S et al: "Efficient infection of a human T-cell line and of human primary peripheral blood leukocytes with a pseudotyped retrovirus vector", Proceedings National Academy of Sciences, vol. 93, No. 21, Jan. 1, 1996, pp. 11842-11847.
Shetron-Rama LM et al: "Intracellular Induction of Listeria monocytogenes actA Expression", Infection and Immunity, 70(3):1087-1096, Mar. 2002.
Shochat C et al: "Gain-of-function mutations in interleukin-7 receptor-? (IL7R) in childhood acute lymphoblastic leukemias", Journal of Experimental Medicine, 208(5):901-908, May 2, 2011.
Shochat C et al: "Novel activating mutations lacking cysteine in type I cytokine receptors in acute lymphoblastic leukemia", Blood, 124(1):106-110, May 1, 2014.
Shum T et al: "Constitutive Signaling from an Engineered IL7 Receptor Promotes Durable Tumor Elimination by Tumor-Redirected T Cells", Cancer Discovery, 7(11):1238-1247, Aug. 22, 2017.
Staerk J et al: "Orientation-specific signalling by thrombopoietin receptor dimers: Orientation-specific TpoR signalling", EMBO Journal, 30(21):4398-4413, Sep. 2, 2011.
Strebel K et al: "Human cellular restriction factors that target HIV-1 replication", BMC Medicine, 7:48, Dec. 2009.
Sun J et al: "The quest for spatio-temporal control of CAR T cells", Cell Research, 25(12):1281-1282, Nov. 17, 2015.
Takahashi M et al: "Rescue from Photoreceptor Degeneration in therd Mouse by Human Immunodeficiency Virus Sector-Mediated Gene Transfer", Journal of Virology, 73(9):7812-7816, Sep. 1, 1999.
Till et al: "CD20-specific adoptive immunotherapy for lymphoma using a chimeric antigen receptor with both CD28 and 4-1 BB domains: pilot clinical trial results.", Blood, Apr. 25, 2012, vol. 119, No. 17, pp. 3940-3950.
Tone Y et al: "Cell fate conversion by conditionally switching the signal-transducing domain of signalobodies: Cell Fate Conversion by Signalobodies", Biotechnology and Bioengineering, 110(12):3219-3226, Dec. 2013.
Townshend B et al: "High-throughput cellular RNA device engineering", Nature methods, 12(10):989-994, Mar. 10, 2015.
Unutmaz D et al: "Cytokine Signals Are Sufficient for HIV-1 Infection of Resting Human T Lymphocytes", Journal of Experimental Medicine, 189(11):1735-1746, Jun. 7, 1999.
Valdivia RH et al: "Bacterial genetics by flow cytometry: rapid isolation of *Salmonella typhimurium* acid-inducible promoters by differential fluorescence induction", Molecular Microbiology, 22(2):367-378, Oct. 1996.
Verhoeyen E et al: "Lentiviral vector gene transfer into human T cells", Antibody-Drug Conjugates in: Methods In Molecular Biology , vol. 1045, Jan. 1, 2009, pp. 97-114.
Vigant F et al: "Same day transduction and in vivo expansion of chimeric antigen receptors and synthetic driver constructs for adoptive cellular therapy", Cancer research: Proceedings: AACR Annual Meeting 2019, Mar. 29-Apr. 3, 2019.

(56) References Cited

OTHER PUBLICATIONS

Vu MM et al: "Convergent evolution of adenosine aptamers spanning bacterial, human, and random sequences revealed by structure-based bioinformatics and genomic SELEX", Chemistry & biology, 19(10):1247-1254, Oct. 25, 2012.
Walsh STR: "Structural insights into the common ?-chain family of cytokines and receptors from the interleukin-7 pathway", Immunological Reviews, 250(1):303-316, Nov. 2012.
Wang J et al: "Particle Display: A Quantitative Screening Method for Generating High-Affinity Aptamers*", Angewandte Chemie International Edition, 53(19):4796-4801, Mar. 18, 2014.
Wang X et al: "Phenotypic and Functional Attributes of Lentivirus-modified CD19-specific Human CD8+ Central Memory T Cells Manufactured at Clinical Scale:", Journal of Immunotherapy, 35(9):689-701, Nov. 2012.
Wang Y et al: "An IL-4/21 Inverted Cytokine Receptor Improving CAR-T Cell Potency in Immunosuppressive Solid-Tumor Microenvironment", Frontiers in Immunology, 10:1691, Jul. 19, 2019.
Welz R et al: "Ligand binding and gene control characteristics of tandem riboswitches in Bacillus anthracis", RNA, 13(4):573-582, Feb. 16, 2007.
Wilkie S et al: "Selective Expansion of Chimeric Antigen Receptor-targeted T-cells with Potent Effector Function using Interleukin-4", Journal of Biological Chemistry, vol. 285, No. 33, Jun. 18, 2010, pp. 25538-25544.
Wu C-Y et al: "Remote control of therapeutic T cells through a small molecule-gated chimeric receptor", Science, 350(6258):aab4077, Sep. 24, 2015.
Yan B et al: "Engineering Upper Hinge Improves Stability and Effector Function of a Human IgG1", Journal of Biological Chemistry, 287(8):5891-5897, Dec. 27, 2011.
Yang H et al: "Cell type-specific targeting with surface-engineered lentiviral vectors co-displaying OKT3 antibody and fusogenic molecule", Pharmaceutical Research, vol. 26, No. 6, Mar. 4, 2009, pp. 1432-1445.
Yang L et al: "Targeting lentiviral vectors to specific cell types in vivo", Proceedings of the National Academy of Sciences, 103(31):11479-11484, Jul. 24, 2006.
Yokoyama K et al: "In vivo leukemogenic potential of an interleukin 7 receptor ? chain mutant in hematopoietic stem and progenitor cells", Blood, 122(26):4259-4263, Oct. 30, 2013.
Yoon H et al: "An efficient strategy for cell-based antibody library selection using an integrated vector system", BMC Biotechnology, 12:62, Sep. 18, 2012.
Zapata G et al: "Engineering linear F(ab')2 fragments for efficient production in *Escherichia coli* and enhanced antiproliferative activity", "Protein Engineering, Design and Selection", 8(10):4 057-1062, Oct. 1995.
Zenatti PP et al: "Oncogenic IL7R gain-of-function mutations in childhood T-cell acute lymphoblastic leukemia", Nature Genetics, 43(10):932-939, Sep. 4, 2011.
Zeng S et al: "Exploration on the mechanism of DNA adsorption on graphene and graphene oxide via molecular simulations", Journal of Physics D: Applied Physics, 48(27):275402, Oct. 10, 2015.
Zhang X et al: "Tumor pH and Its Measurement", Journal of Nuclear Medicine, 51(8):1167-1170, Jul. 21, 2010.
Zhao Y et al: "Multiple Injections of Electroporated Autologous T Cells Expressing a Chimeric Antigen Receptor Mediate Regression of Human Disseminated Tumor", Cancer Research, 70(22):9053-9061, Nov. 15, 2010.
Zichel R et al: "Aptamers as a sensitive tool to detect subtle modifications in therapeutic proteins", PloS One, 7(2):e31948, Feb. 27, 2012.
Zuker M: "Mfold web server for nucleic acid folding and hybridization prediction", Nucleic Acids Research, 31(13):3406-3415, Jul. 1, 2003.
International Application No. PCT/US2018/020818, International Search Report dated Jul. 9, 2018, 10 pages.
Adachi K et al: "IL-7 and CCL19 expression in CAR-T cells improves immune cell infiltration and CAR-T cell survival in the tumor", Nature Biotechnology, 36(4):346-351, Mar. 5, 2018.
Ahn H-J et al: "Requirement for Distinct Janus Kinases and STAT Proteins in T Cell Proliferation Versus IFN-gamma Production Following IL-12 Stimulation", Journal of Immunology, 161(11):5893-5900, Dec. 1, 1998.
Ali RR et al: "Adeno-Associated Virus Gene Transfer to Mouse Retina", Human Gene Therapy, 9(1):81-86, Jan. 1, 1998.
Alpuche Aranda CM et al: "*Salmonella typhimurium* activates virulence gene transcription within acidified macrophage phagosomes.", Proceedings of the National Academy of Sciences, 89(21):10079-10083, Nov. 1, 1992.
Anthony PC et al: "Folding energy landscape of the thiamine pyrophosphate riboswitch aptamer", Proceedings of the National Academy of Sciences, 109(5):1485-1489, Jan. 4, 2012.
Armstrong AJ et al: "ATP-Binding Cassette Transporter G1 Negatively Regulates Thymocyte and Peripheral Lymphocyte Proliferation", Journal of Immunology, 184(1):173-183, Jan. 1, 2010.
Beisel CL et al: "Design of small molecule-responsive microRNAs based on structural requirements for Drosha processing", Nucleic acids research, 39(7):2981-2994, Dec. 11, 2010.
Bennett J et al: "Real-time, noninvasive in vivo assessment of adeno-associated virus-mediated retinal transduction", Investigative Ophthalmology & Visual Science, 38(13):2857-2863, Dec. 1, 1997.
Berens C et al: "RNA aptamers as genetic control devices: The potential of riboswitches as synthetic elements for regulating gene expression", Biotechnology Journal, 10(2):246-257, Feb. 10, 2015.
Biosettia; pLV-miRNA Expression Vector System; Manual; May 2011.
Blø M et al: "Enhanced gene expression from retroviral vectors", BMC Biotechnology, 8:19, Feb. 25, 2008.
Borrás T et al: "Adenoviral reporter gene transfer to the human trabecular meshwork does not alter aqueous humor outflow. Relevance for potential gene therapy of glaucoma", Gene Therapy, 6(4):515-524, Apr. 7, 1999.
Brown RJ et al: "Model for growth hormone receptor activation based on subunit rotation within a receptor dimer", Mature Structural & Molecular Biology, 12(9):814-821, Aug. 21, 2005.
Budde LE et al: "Combining a CD20 chimeric antigen receptor and an inducible caspase 9 suicide switch to improve the efficacy and safety of T cell adoptive immunotherapy for lymphoma", PLOS One, vol. 8, No. 12, Dec. 17, 2013, e82742, pp. 1-10.
Burns JC et al: "Vesicular Stomatitis Virus G glycoprotein pseudotyped retroviral vectors: concentration to very high titer and efficient gene transfer into mammalian and nonmammalian cells", Proceedings National Academy of Sciences, vol. 90, Sep. 1, 1993, pp. 8033-8037.
Burton DR: "Immunoglobulin G: Functional sites", Molecular Immunology, 22(3):161-206, Mar. 1, 1985.
Carneiro M et al: "Co-expression of chimeric antigen receptor (CAR) and miRNAs to T cell therapy", European Journal of Cancer, 50(5):S219, 2014.
Chen YY et al: "Genetic control of mammalian T-cell proliferation with synthetic RNA regulatory systems", Proceedings of the National Academy of Sciences, 107(19):8531-8536, Apr. 26, 2010.
Chinnasamy D et al: "Lentiviral-mediated gene transfer into human lymphocytes: role of HIV-1 accessory proteins", Blood, 96(4):1309-1316, Aug. 15, 2000.
Chmielewski M et al: "Of CARs and TRUCKs: chimeric antigen receptor (CAR) T cells engineered with an inducible cytokine to modulate the tumor stroma", Immunological Reviews, 257(1):83-90, Jan. 2014.
Colby DW et al: "Engineering Antibody Affinity by Yeast Surface Display", Methods in Enzymology, 388:348-358, 2004.
Cooper LJN et al: "T-cell clones can be rendered specific for CD19: toward the selective augmentation of the graft-versus-B—lineage leukemia effect", Blood, 101(4):1637-1644, Feb. 15, 2003.
Cruz CR et al: "Adverse events following infusion of T cells for adoptive immunotherapy: a 10-year experience", Cytotherapy, 12(6):743-749, Oct. 2010.

(56) References Cited

OTHER PUBLICATIONS

Dambach MD et al: "Expanding roles for metabolite-sensing regulatory RNAs", Current opinion in microbiology, 12(2):161-169, Feb. 26, 2009.
Desai SK et al: "Genetic Screens and Selections for Small Molecules Based on a Synthetic Riboswitch That Activates Protein Translation", Journal of the American Chemical Society, 126(41):13247-13254, Oct. 20, 2004.
Dunstan SJ et al: "Use of In Vivo-Regulated Promoters To Deliver Antigens from Attenuated *Salmonella enterica* var. *typhimurium*", Infection and Immunity, 67(10):5133-5141, Oct. 1, 1999.
Durand S et al: "Tailored HIV-1 Vectors for Genetic Modification of Primary Human Dendritic Cells and Monocytes", Journal of Virology, 87(1):234-242, Oct. 17, 2012.
Durum SK: "IL-7 and TSLP receptors: twisted sisters", Blood, 124(1):4-5, Jul. 3, 2014.
Eckelhart E et al: "A novel Ncr1-Cre mouse reveals the essential role of STAT5 for NK-cell survival and development", Blood, 117(5):1565-1573, Dec. 2, 2010.
Edwards A et al: "A structural basis for the recognition of 2'-deoxyguanosine by the purine riboswitch", Journal of molecular biology, 385(3):938-948, Nov. 5, 2008.
Fischer UM et al: "Pulmonary Passage is a Major Obstacle for Intravenous Stem Cell Delivery: The Pulmonary First-Pass Effect", Stem Cells and Development, 18(5):683-692, Jun. 2009.
Flannery JG et al: "Efficient photoreceptor-targeted gene expression in vivo by recombinant adeno-associated virus", Proceedings of the National Academy of Sciences, 94(13):6916-6921, Jun. 24, 1997.
Floss DM et al: "Naturally occurring and synthetic constitutive-active cytokine receptors in disease and therapy", Cytokine & Growth Factor Reviews, 47:1-20, Jun. 2019.
Flotte TR et al: "Stable in vivo expression of the cystic fibrosis transmembrane conductance regulator with an adeno-associated virus vector", Proceedings of the National Academy of Sciences, 90(22):10613-10617, Nov. 15, 1993.
Frecha C et al: "Stable transduction of quiescent T cells without induction of cycle progression by a novel lentiviral vector pseudotyped with measles virus glycoproteins", Blood, 112(13):4843-4852, Dec. 15, 2008.
Freitas AA et al: "Population Biology of Lymphocytes: The Flight for Survival", Annual Review of Immunology, 18(1):83-111, Apr. 2000.
Garst AD et al: "Riboswitches: structures and mechanisms", Cold Spring Harbor perspectives in biology, 3(6):a003533, Oct. 18, 2010.
Geron I: "The role of TSLP pathway in the development of B-cell Acute Lymphoblastic Leukemia", Thesis, Dec. 31, 2018.
Ghosh A et al: "CAR T-Cell Therapies: Current Limitations & Future Opportunities", Cell & Gene, Sep. 26, 2010.
Grindley NDF et al: "Mechanisms of Site-Specific Recombination", Annual Review of Biochemistry, 75:567-605, Jun. 2006.
Groher F et al: "Synthetic riboswitches—A tool comes of age", Biochimica et Biophysica Acta, 1839(10):964-973, May 17, 2014.
Harborne NR et al: "Transcriptional control, translation and function of the products of the five open reading frames of the *Escherichia coli* nir operon", Molecular Microbiology, 6(19):2805-2813, Oct. 1992.
Harris KA et al: "Biochemical analysis of pistol self-cleaving ribozymes", RNA, 21 (11):1852-1858, Sep. 18, 2015.
Hinrichs CS and Rosenberg SA: "Exploiting the curative potential of adoptive T-cell therapy for cancer", Immunological Reviews, vol. 257, No. 1, Jan. 13, 2014, pp. 56-71.
Hoyos V et al: "Engineering CD19-specific T lymphocytes with interleukin-15 and a suicide gene to enhance their anti-lymphoma/leukemia effects and safety", Leukemia, 24(6):1160-1170, Apr. 29, 2010.
Hsieh C et al: "Development of TH1 CD4+ T cells through IL-12 produced by Listeria-induced macrophages", Science, 260(5107):547-549, Apr. 23, 1993.
International Application No. PCT/US2017/041277, International Search Report dated Oct. 27, 2017, 10 pages.
Mao Y. et al: "A Graphene-Based Biosensing Platform Based on Regulated Release of an Aptameric DNA Biosensor", Sensors (Basel), 15(11):28244-28256, Nov. 9, 2015.
Abe et al: "A novel MPL point mutation resulting in thrombopoietin-independent activation", Leukemia 16(8):1500-1506, Aug. 2002.
Alexander et al. "Tyrosine-599 of the c-Mpl receptor is required for Shc phosphorylation and the induction of cellular differentiation", EMBO J. 15(23):6531-40, Dec. 2, 1996.
Benit et al: "Characterization of mpl cytoplasmic domain sequences required for myeloproliferative leukemia virus pathogenicity", J Virol. 68(8): 5270-5274, Aug. 1994.
Blau C A et al: "A proliferation switch for genetically modified cells", Proceedings of the National Academy of Sciences 94(7):3076-3081, Apr. 1997.
Constantinescu et al: "The erythropoietin receptor cytosolic juxtamembrane domain contains an essential, precisely oriented, hydrophobic motif", Mol Cell. 7(2):377-85, Feb. 2001.
Cui et al: "Tuning MPL signaling to influence hematopoietic stem cell differentiation and inhibit essential thrombocythemia progenitors", Proceedings of the National Academy of Sciences 118(2), Jan. 12, 2021.
Dardalhon et al: "Highly efficient gene transfer in naive human T cells with a murine leukemia virus-based vector", Blood. Aug. 1, 2000;96(3):885-93.
Drachman et al: "Thrombopoietin Signal Transduction Requires Functional JAK2, Not TYK2", Journal of Biological Chemistry 274(19): 13480-13484, May 1999.
Fukunaga et al: "Functional domains of the granulocyte colony-stimulating factor receptor", EMBO J. 10(10):2855-65, Oct. 1991.
Gotthardt et al: "JAK/STAT Cytokine Signaling at the Crossroad of NK Cell Development and Maturation", Frontiers in Immunology 10:2590, Nov. 12, 2019.
Gurney ei al: "Distinct regions of c-Mpl cytoplasmic domain are coupled to the JAK-STAT signal transduction pathway and Shc phosphorylation", Proceedings of the National Academy of Sciences 92(12):5292-5296, Jun. 6, 1995.
Hitchcock et al: "YRRL motifs in the cytoplasmic domain of the thrombopoietin receptor regulate receptor internalization and degradation", Blood 112(6):2222-31, Sep. 15, 2008.
Huang et al: "The N-terminal domain of Janus kinase 2 is required for Golgi processing and cell surface expression of erythropoietin receptor", Mol Cell.8(6) :1327-38, Dec. 2001.
Koppikar et al: "Heterodimeric JAK-STAT activation as a mechanism of persistence to JAK2 inhibitor therapy", Nature 489(7414):155-159, Sep. 2012.
Laminet et al: "Affinity, specificity, and kinetics of the interaction of the SHC phosphotyrosine binding domain with asparagine-X-X-phosphotyrosine motifs of growth factor receptors", J Biol Chem. 271(1):264-9, Jan. 5, 1996.
Lee, TaiSung et al: "Effects of clinically relevant MPL mutations in the transmembrane domain revealed at the atomic level through computational modeling", PLoS One. 6(8): e23396, Aug. 2017.
Lin et al: "Allogene—CAR T with Temporally-Controlled, Programmable Cytokine Signaling Outputs", Poster Presentation 2020.
May et al: "Comparative study on the phosphotyrosine motifs of different cytokine receptors involved in STAT5 activation", FEBS Lett. 394(2):221-6, Sep. 30, 1996.
Morizono et al: "Antibody-directed targeting of retroviral vectors via cell surface antigens", J Virol. Sep. 2001;75(17):8016-20.
Murakami et al: "Critical cytoplasmic region of the interleukin 6 signal transducer gp130 is conserved in the cytokine receptor family", Proc Natl Acad Sci U S A 88(24):11349-53, Dec. 15, 1991.
Richard et al: "Differences in F36VMpl-Based in Vivo Selection among Large Animal Models", Molecular Therapy 10(4):730-740, Oct. 2004.
Rommel et al: "Signaling properties of murine MPL and MPL mutants after stimulation with thrombopoietin and romiplostim", Experimental Hematology 85, 33-46.e6, May 2020.
Royer et al: "Kinases Affect Thrombopoietin Receptor Cell Surface Localization and Stability", Journal of Biological Chemistry 280(29):27251-27261, Jul. 2005.

(56) References Cited

OTHER PUBLICATIONS

Saur et al: "Ubiquitination and degradation of the thrombopoietin receptor c-Mpl", Blood 115(6):1254-63, Feb. 11, 2010.
Stahl et al: "Choice of STATs and other substrates specified by modular tyrosine-based motifs in cytokine receptors", Science 267(5202):1349-53, Mar. 3, 1995.
Tong et al: "The Membrane-proximal Region of the Thrombopoietin Receptor Confers Its High Surface Expression by JAK2-dependent and -independent Mechanisms", Journal of Biological Chemistry 281(50): 38930-38940, Dec. 2006.
U.S. Appl. No. 15/644,778, Office Action dated Apr. 16, 2020, 16 pages.
U.S. Appl. No. 15/644,778, Office Action dated Jan. 19, 2021, 15 pages.
Van Der Geer et al: "Identification of residues that control specific binding of the Shc phosphotyrosine-binding domain to phosphotyrosine sites", Proc Natl Acad Sci U S A. 93(3):963-8, Feb. 6, 1996.
Varghese et al: "The Thrombopoietin Receptor: Structural Basis of Traffic and Activation by Ligand, Mutations, Agonists, and Mutated Calreticulin", Front Endocrinol (Lausanne); 8:59, Mar. 31, 2017.
Goyvaerts et al. "Development of the Nanobody display technology to target lentiviral vectors to antigen-presenting cells", Gene Therapy (12) 1133-1140, 2012.
Goyvaerts C et al.; "Development of the Nanobody display technology to target lentiviral vectors to antigen-presenting cells". Gene Ther. Dec. 2012;19(12):1133-40.
International Application No. PCT/US2017/023112, International Search Report dated Sep. 27, 2017.
International Application No. PCT/US2018/051392, International Search Report dated Dec. 20, 2018.
International Application No. PCT/US2019/049259, International Search Report dated Apr. 24, 2020.
International Application No. PCT/US2020/048843, International Search Report dated Jan. 26, 2021.
International Application No. PCT/US2021/020922, International Search Report dated May 13, 2021.

* cited by examiner

SEQUENCE LISTING

```
<160> NUMBER OF SEQ ID NOS: 462

<210> SEQ ID NO 1
<211> LENGTH: 3
<212> TYPE: PRT
<213> ORGANISM: Homo sapiens
<220> FEATURE:
<221> NAME/KEY: misc_feature
<222> LOCATION: (1)..(3)
<223> OTHER INFORMATION: integrin-binding peptide segment

<400> SEQUENCE: 1

Arg Gly Asp
1


<210> SEQ ID NO 2
<211> LENGTH: 43
<212> TYPE: PRT
<213> ORGANISM: Homo sapiens
<220> FEATURE:
<221> NAME/KEY: misc_feature
<222> LOCATION: (1)..(43)
<223> OTHER INFORMATION: wild-type CD8 Stalk

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala
        35                  40


<210> SEQ ID NO 3
<211> LENGTH: 42
<212> TYPE: PRT
<213> ORGANISM: Homo sapiens
<220> FEATURE:
<221> NAME/KEY: misc_feature
<222> LOCATION: (1)..(42)
<223> OTHER INFORMATION: wild-type CD28 Stalk

<400> SEQUENCE: 3

Phe Cys Lys Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
            20                  25                  30

Ser Pro Leu Phe Pro Gly Pro Ser Lys Pro
        35                  40
```

<210> SEQ ID NO 4
<211> LENGTH: 4
<212> TYPE: PRT
<213> ORGANISM: Artificial Sequence
<220> FEATURE:
<223> OTHER INFORMATION: Synthetic: Hinge

<400> SEQUENCE: 4

Cys Pro Pro Cys
1

<210> SEQ ID NO 5
<211> LENGTH: 5
<212> TYPE: PRT
<213> ORGANISM: Artificial Sequence
<220> FEATURE:
<223> OTHER INFORMATION: Synthetic: Hinge

<400> SEQUENCE: 5

Asp Lys Thr His Thr
1 5

<210> SEQ ID NO 6
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 6

Cys Pro Glu Pro Lys Ser Cys Asp Thr Pro Pro Pro Cys Pro Arg
1 5 10 15

<210> SEQ ID NO 7
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 7

Glu Leu Lys Thr Pro Leu Gly Asp Thr Thr His Thr
1 5 10

<210> SEQ ID NO 8
<211> LENGTH: 10
<212> TYPE: PRT
<213> ORGANISM: Artificial Sequence
<220> FEATURE:
<223> OTHER INFORMATION: Synthetic: Hinge

<400> SEQUENCE: 8

Lys Ser Cys Asp Lys Thr His Thr Cys Pro
1 5 10

<210> SEQ ID NO 9
<211> LENGTH: 7
<212> TYPE: PRT
<213> ORGANISM: Artificial Sequence
<220> FEATURE:
<223> OTHER INFORMATION: Synthetic: Hinge

<400> SEQUENCE: 9

Lys Cys Cys Val Asp Cys Pro
1 5

<210> SEQ ID NO 10
<211> LENGTH: 7
<212> TYPE: PRT
<213> ORGANISM: Artificial Sequence
<220> FEATURE:
<223> OTHER INFORMATION: Synthetic: Hinge

<400> SEQUENCE: 10

Lys Tyr Gly Pro Pro Cys Pro
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 11

Glu Pro Lys Ser Cys Asp Lys Thr His Thr Cys Pro Pro Cys Pro
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 12

Glu Arg Lys Cys Cys Val Glu Cys Pro Pro Cys Pro
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic: Hinge

<400> SEQUENCE: 13

Glu Leu Lys Thr Pro Leu Gly Asp Thr Thr His Thr Cys Pro Arg Cys
1               5                   10                  15

Pro

<210> SEQ ID NO 14
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 14

Ser Pro Asn Met Val Pro His Ala His His Ala Gln
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 15

Glu Pro Lys Ser Cys Asp Lys Thr Tyr Thr Cys Pro Pro Cys Pro
1               5                   10                  15

<210> SEQ ID NO 16
<211> LENGTH: 45
<212> TYPE: PRT
<213> ORGANISM: Artificial Sequence
<220> FEATURE:
<223> OTHER INFORMATION: Synthetic: Hinge

<400> SEQUENCE: 16

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 17
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CD* alpha Transmembrane domain

<400> SEQUENCE: 17

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 18
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CD8 beta Transmembrane domain

<400> SEQUENCE: 18

```
Leu Gly Leu Leu Val Ala Gly Val Leu Val Leu Leu Val Ser Leu Gly
1               5                   10                  15

Val Ala Ile His Leu Cys Cys
            20
```

<210> SEQ ID NO 19
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: CD4 Transmembrane domain

<400> SEQUENCE: 19

```
Ala Leu Ile Val Leu Gly Gly Val Ala Gly Leu Leu Leu Phe Ile Gly
1               5                   10                  15

Leu Gly Ile Phe Phe Cys Val Arg Cys
            20                  25
```

<210> SEQ ID NO 20
<211> LENGTH: 23
<212> TYPE: PRT
<213> ORGANISM: Homo sapiens
<220> FEATURE:

<221> NAME/KEY: misc_feature
<222> LOCATION: (1)..(23)
<223> OTHER INFORMATION: CD3 zeta Transmembrane domain

<400> SEQUENCE: 20

Leu Cys Tyr Leu Leu Asp Gly Ile Leu Phe Ile Tyr Gly Val Ile Leu
1 5 10 15

Thr Ala Leu Phe Leu Arg Val
20

<210> SEQ ID NO 21
<211> LENGTH: 27
<212> TYPE: PRT
<213> ORGANISM: Homo sapiens
<220> FEATURE:
<221> NAME/KEY: misc_feature
<222> LOCATION: (1)..(27)
<223> OTHER INFORMATION: CD28 Transmembrane domain

<400> SEQUENCE: 21

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 22
<211> LENGTH: 26
<212> TYPE: PRT
<213> ORGANISM: Homo sapiens
<220> FEATURE:
<221> NAME/KEY: misc_feature
<222> LOCATION: (1)..(26)
<223> OTHER INFORMATION: OX40 Transmembrane domain

<400> SEQUENCE: 22

Val Ala Ala Ile Leu Gly Leu Gly Leu Val Leu Gly Leu Leu Gly Pro
1 5 10 15

Leu Ala Ile Leu Leu Ala Leu Tyr Leu Leu
20 25

<210> SEQ ID NO 23
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CD7 Transmembrane domain

<400> SEQUENCE: 23

Ala Leu Pro Ala Ala Leu Ala Val Ile Ser Phe Leu Leu Gly Leu Gly
1 5 10 15

Leu Gly Val Ala Cys Val Leu Ala
20

<210> SEQ ID NO 24
<211> LENGTH: 69
<212> TYPE: PRT
<213> ORGANISM: Homo sapiens
<220> FEATURE:
<221> NAME/KEY: misc_feature
<222> LOCATION: (1)..(69)
<223> OTHER INFORMATION: CD8a Stalk and Transmembrane domain

<400> SEQUENCE: 24

Thr Thr Thr Pro Ala Pro Arg Pro Pro Thr Pro Ala Pro Thr Ile Ala

-continued

```
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 25
<211> LENGTH: 66
<212> TYPE: PRT
<213> ORGANISM: Homo sapiens
<220> FEATURE:
<221> NAME/KEY: misc_feature
<222> LOCATION: (1)..(66)
<223> OTHER INFORMATION: CD28 Stalk and Transmembrane domain

<400> SEQUENCE: 25

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65
```

<210> SEQ ID NO 26
<211> LENGTH: 163
<212> TYPE: PRT
<213> ORGANISM: Homo sapiens
<220> FEATURE:
<221> NAME/KEY: misc_feature
<222> LOCATION: (1)..(163)
<223> OTHER INFORMATION: CD3Z Activating domain isoform 1

<400> SEQUENCE: 26

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140
```

Ser Thr Ala Thr Lys Asp Thr Tyr Asp Ala Leu His Met Gln Ala Leu
145 150 155 160

Pro Pro Arg

<210> SEQ ID NO 27
<211> LENGTH: 164
<212> TYPE: PRT
<213> ORGANISM: Homo sapiens
<220> FEATURE:
<221> NAME/KEY: misc_feature
<222> LOCATION: (1)..(164)
<223> OTHER INFORMATION: CD3Z Activating domain isoform 2

<400> SEQUENCE: 27

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Gln Arg Arg Lys Asn Pro Gln Glu Gly Leu Tyr Asn
100 105 110

Glu Leu Gln Lys Asp Lys Met Ala Glu Ala Tyr Ser Glu Ile Gly Met
115 120 125

Lys Gly Glu Arg Arg Arg Gly Lys Gly His Asp Gly Leu Tyr Gln Gly
130 135 140

Leu Ser Thr Ala Thr Lys Asp Thr Tyr Asp Ala Leu His Met Gln Ala
145 150 155 160

Leu Pro Pro Arg

<210> SEQ ID NO 28
<211> LENGTH: 112
<212> TYPE: PRT
<213> ORGANISM: Homo sapiens
<220> FEATURE:
<221> NAME/KEY: misc_feature
<222> LOCATION: (1)..(112)
<223> OTHER INFORMATION: CD3Z Activating domain isoform 3

<400> SEQUENCE: 28

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 29
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: CD3Z Activating domain isoform

<400> SEQUENCE: 29

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Gln Arg Arg Lys Asn Pro Gln Glu Gly Leu Tyr Asn Glu Leu Gln
50 55 60

Lys Asp Lys Met Ala Glu Ala Tyr Ser Glu Ile Gly Met Lys Gly Glu
65 70 75 80

Arg Arg Arg Gly Lys Gly His Asp Gly Leu Tyr Gln Gly Leu Ser Thr
85 90 95

Ala Thr Lys Asp Thr Tyr Asp Ala Leu His Met Gln Ala Leu Pro Pro
100 105 110

Arg

<210> SEQ ID NO 30
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3Z Activating domain isoform 4

<400> SEQUENCE: 30

Asn Gln Leu Tyr Asn Glu Leu Asn Leu Gly Arg Arg Glu Glu Tyr Asp
1 5 10 15

Val Leu Asp Lys Arg
20

<210> SEQ ID NO 31
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: CD3Z Activating domain isoform 5

<400> SEQUENCE: 31

Glu Gly Leu Tyr Asn Glu Leu Gln Lys Asp Lys Met Ala Glu Ala Tyr
1 5 10 15

Ser Glu Ile Gly Met Lys
20

<210> SEQ ID NO 32
<211> LENGTH: 21
<212> TYPE: PRT

<213> ORGANISM: Homo sapiens
<220> FEATURE:
<221> NAME/KEY: misc_feature
<222> LOCATION: (1)..(21)
<223> OTHER INFORMATION: CD3Z Activating domain isoform 6

<400> SEQUENCE: 32

```
Asp Gly Leu Tyr Gln Gly Leu Ser Thr Ala Thr Lys Asp Thr Tyr Asp
1               5                   10                  15

Ala Leu His Met Gln
            20
```

<210> SEQ ID NO 33
<211> LENGTH: 171
<212> TYPE: PRT
<213> ORGANISM: Homo sapiens
<220> FEATURE:
<221> NAME/KEY: misc_feature
<222> LOCATION: (1)..(171)
<223> OTHER INFORMATION: CD3D Activating domain isoform 1

<400> SEQUENCE: 33

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 34
<211> LENGTH: 127
<212> TYPE: PRT
<213> ORGANISM: Homo sapiens
<220> FEATURE:
<221> NAME/KEY: misc_feature
<222> LOCATION: (1)..(127)
<223> OTHER INFORMATION: CD3D Activating domain isoform 2

<400> SEQUENCE: 34

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45
```

```
Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125


<210> SEQ ID NO 35
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3D Activating domain isoform 3

<400> SEQUENCE: 35

Asp Gln Val Tyr Gln Pro Leu Arg Asp Arg Asp Asp Ala Gln Tyr Ser
1               5                   10                  15

His Leu Gly Gly Asn
            20


<210> SEQ ID NO 36
<211> LENGTH: 206
<212> TYPE: PRT
<213> ORGANISM: Homo sapiens
<220> FEATURE:
<221> NAME/KEY: misc_feature
<222> LOCATION: (1)..(206)
<223> OTHER INFORMATION: CD3E Activating domain isoform 1

<400> SEQUENCE: 36

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Met Ser
        115                 120                 125

Val Ala Thr Ile Val Ile Val Asp Ile Cys Ile Thr Gly Gly Leu Leu
    130                 135                 140

Leu Leu Val Tyr Tyr Trp Ser Lys Asn Arg Lys Ala Lys Ala Lys Pro
145                 150                 155                 160

Val Thr Arg Gly Ala Gly Ala Gly Gly Arg Gln Arg Gly Gln Asn Lys
                165                 170                 175
```

```
Glu Arg Pro Pro Pro Val Pro Asn Pro Asp Tyr Glu Pro Ile Arg Lys
            180                 185                 190

Gly Gln Arg Asp Leu Tyr Ser Gly Leu Asn Gln Arg Arg Ile
        195                 200                 205


<210> SEQ ID NO 37
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3E Activating domain isoform 2

<400> SEQUENCE: 37

Asn Pro Asp Tyr Glu Pro Ile Arg Lys Gly Gln Arg Asp Leu Tyr Ser
1               5                   10                  15

Gly Leu Asn Gln Arg
            20


<210> SEQ ID NO 38
<211> LENGTH: 182
<212> TYPE: PRT
<213> ORGANISM: Homo sapiens
<220> FEATURE:
<221> NAME/KEY: misc_feature
<222> LOCATION: (1)..(182)
<223> OTHER INFORMATION: CD3G Activating domain isoform 1

<400> SEQUENCE: 38

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180


<210> SEQ ID NO 39
<211> LENGTH: 21
<212> TYPE: PRT
<213> ORGANISM: Homo sapiens
<220> FEATURE:
<221> NAME/KEY: misc_feature
```

<222> LOCATION: (1)..(21)
<223> OTHER INFORMATION: CD3G Activating domain isoform 2

<400> SEQUENCE: 39

Asp Gln Leu Tyr Gln Pro Leu Lys Asp Arg Glu Asp Asp Gln Tyr Ser
1 5 10 15

His Leu Gln Gly Asn
20

<210> SEQ ID NO 40
<211> LENGTH: 226
<212> TYPE: PRT
<213> ORGANISM: Homo sapiens
<220> FEATURE:
<221> NAME/KEY: misc_feature
<222> LOCATION: (1)..(226)
<223> OTHER INFORMATION: CD79A Activating domain isoform 1

<400> SEQUENCE: 40

Met Pro Gly Gly Pro Gly Val Leu Gln Ala Leu Pro Ala Thr Ile Phe
1 5 10 15

Leu Leu Phe Leu Leu Ser Ala Val Tyr Leu Gly Pro Gly Cys Gln Ala
20 25 30

Leu Trp Met His Lys Val Pro Ala Ser Leu Met Val Ser Leu Gly Glu
35 40 45

Asp Ala His Phe Gln Cys Pro His Asn Ser Ser Asn Asn Ala Asn Val
50 55 60

Thr Trp Trp Arg Val Leu His Gly Asn Tyr Thr Trp Pro Pro Glu Phe
65 70 75 80

Leu Gly Pro Gly Glu Asp Pro Asn Gly Thr Leu Ile Ile Gln Asn Val
85 90 95

Asn Lys Ser His Gly Gly Ile Tyr Val Cys Arg Val Gln Glu Gly Asn
100 105 110

Glu Ser Tyr Gln Gln Ser Cys Gly Thr Tyr Leu Arg Val Arg Gln Pro
115 120 125

Pro Pro Arg Pro Phe Leu Asp Met Gly Glu Gly Thr Lys Asn Arg Ile
130 135 140

Ile Thr Ala Glu Gly Ile Ile Leu Leu Phe Cys Ala Val Val Pro Gly
145 150 155 160

Thr Leu Leu Leu Phe Arg Lys Arg Trp Gln Asn Glu Lys Leu Gly Leu
165 170 175

Asp Ala Gly Asp Glu Tyr Glu Asp Glu Asn Leu Tyr Glu Gly Leu Asn
180 185 190

Leu Asp Asp Cys Ser Met Tyr Glu Asp Ile Ser Arg Gly Leu Gln Gly
195 200 205

Thr Tyr Gln Asp Val Gly Ser Leu Asn Ile Gly Asp Val Gln Leu Glu
210 215 220

Lys Pro
225

<210> SEQ ID NO 41
<211> LENGTH: 188
<212> TYPE: PRT
<213> ORGANISM: Homo sapiens
<220> FEATURE:
<221> NAME/KEY: misc_feature
<222> LOCATION: (1)..(188)
<223> OTHER INFORMATION: CD79A Activating domain isoform 2

<400> SEQUENCE: 41

```
Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Glu Pro Pro Pro Arg Pro Phe Leu
                85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
        115                 120                 125

Lys Arg Trp Gln Asn Glu Lys Leu Gly Leu Asp Ala Gly Asp Glu Tyr
    130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 42
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD79A Activating domain isoform 3

<400> SEQUENCE: 42

```
Glu Asn Leu Tyr Glu Gly Leu Asn Leu Asp Asp Cys Ser Met Tyr Glu
1               5                   10                  15

Asp Ile Ser Arg Gly
            20
```

<210> SEQ ID NO 43
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: DAP12 Activating domain isoform 1

<400> SEQUENCE: 43

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60
```

```
Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys


<210> SEQ ID NO 44
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: DAP12 Activating domain isoform 2

<400> SEQUENCE: 44

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln
            100                 105


<210> SEQ ID NO 45
<211> LENGTH: 102
<212> TYPE: PRT
<213> ORGANISM: Homo sapiens
<220> FEATURE:
<221> NAME/KEY: misc_feature
<222> LOCATION: (1)..(102)
<223> OTHER INFORMATION: DAP12 Activating domain isoform 3

<400> SEQUENCE: 45

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
            100


<210> SEQ ID NO 46
```

<211> LENGTH: 101
<212> TYPE: PRT
<213> ORGANISM: Homo sapiens
<220> FEATURE:
<221> NAME/KEY: misc_feature
<222> LOCATION: (1)..(101)
<223> OTHER INFORMATION: DAP12 Activating domain isoform 4

<400> SEQUENCE: 46

```
Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Gln Arg Ile Thr Glu Thr Glu Ser Pro Tyr Gln
65                  70                  75                  80

Glu Leu Gln Gly Gln Arg Ser Asp Val Tyr Ser Asp Leu Asn Thr Gln
                85                  90                  95

Arg Pro Tyr Tyr Lys
            100
```

<210> SEQ ID NO 47
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: DAP12 Activating domain isoform 5

<400> SEQUENCE: 47

```
Glu Ser Pro Tyr Gln Glu Leu Gln Gly Gln Arg Ser Asp Val Tyr Ser
1               5                   10                  15

Asp Leu Asn Thr Gln
            20
```

<210> SEQ ID NO 48
<211> LENGTH: 86
<212> TYPE: PRT
<213> ORGANISM: Homo sapiens
<220> FEATURE:
<221> NAME/KEY: misc_feature
<222> LOCATION: (1)..(86)
<223> OTHER INFORMATION: FCER1G Activating domain isoform 1

<400> SEQUENCE: 48

```
Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```

<210> SEQ ID NO 49
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: FCER1G Activating domain isoform 2

<400> SEQUENCE: 49

Asp Gly Val Tyr Thr Gly Leu Ser Thr Arg Asn Gln Glu Thr Tyr Glu
1               5                   10                  15

Thr Leu Lys His Glu
            20

<210> SEQ ID NO 50
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: DAP10 Activating domain

<400> SEQUENCE: 50

Arg Pro Arg Arg Ser Pro Ala Gln Asp Gly Lys Val Tyr Ile Asn Met
1               5                   10                  15

Pro Gly Arg Gly
            20

<210> SEQ ID NO 51
<211> LENGTH: 68
<212> TYPE: PRT
<213> ORGANISM: Homo sapiens
<220> FEATURE:
<221> NAME/KEY: misc_feature
<222> LOCATION: (1)..(68)
<223> OTHER INFORMATION: CD28 Activating domain

<400> SEQUENCE: 51

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 52
<211> LENGTH: 619
<212> TYPE: PRT
<213> ORGANISM: Homo sapiens
<220> FEATURE:
<221> NAME/KEY: misc_feature
<222> LOCATION: (1)..(619)
<223> OTHER INFORMATION: ZAP70 Activating domain

<400> SEQUENCE: 52

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly

-continued

```
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445
```

```
Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615


<210> SEQ ID NO 53
<211> LENGTH: 42
<212> TYPE: PRT
<213> ORGANISM: Homo sapiens
<220> FEATURE:
<221> NAME/KEY: misc_feature
<222> LOCATION: (1)..(42)
<223> OTHER INFORMATION: CD137 Co-stimulatory domain

<400> SEQUENCE: 53

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 54
<211> LENGTH: 41
<212> TYPE: PRT
<213> ORGANISM: Homo sapiens
<220> FEATURE:
<221> NAME/KEY: misc_feature
<222> LOCATION: (1)..(41)
<223> OTHER INFORMATION: CD28 Co-stimulatory domain

<400> SEQUENCE: 54

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 55
<211> LENGTH: 41
```

<212> TYPE: PRT
<213> ORGANISM: Homo sapiens
<220> FEATURE:
<221> NAME/KEY: misc_feature
<222> LOCATION: (1)..(41)
<223> OTHER INFORMATION: IC? Co-stimulatory domain

<400> SEQUENCE: 55

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser
        35                  40

<210> SEQ ID NO 56
<211> LENGTH: 35
<212> TYPE: PRT
<213> ORGANISM: Homo sapiens
<220> FEATURE:
<221> NAME/KEY: misc_feature
<222> LOCATION: (1)..(35)
<223> OTHER INFORMATION: ICOS Co-stimulatory domain

<400> SEQUENCE: 56

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 57
<211> LENGTH: 37
<212> TYPE: PRT
<213> ORGANISM: Homo sapiens
<220> FEATURE:
<221> NAME/KEY: misc_feature
<222> LOCATION: (1)..(37)
<223> OTHER INFORMATION: OX40 Co-stimulatory domain

<400> SEQUENCE: 57

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 58
<211> LENGTH: 49
<212> TYPE: PRT
<213> ORGANISM: Homo sapiens
<220> FEATURE:
<221> NAME/KEY: misc_feature
<222> LOCATION: (1)..(49)
<223> OTHER INFORMATION: CD27 Co-stimulatory domain

<400> SEQUENCE: 58

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser

```
        35                  40                  45

Pro


<210> SEQ ID NO 59
<211> LENGTH: 114
<212> TYPE: PRT
<213> ORGANISM: Homo sapiens
<220> FEATURE:
<221> NAME/KEY: misc_feature
<222> LOCATION: (1)..(114)
<223> OTHER INFORMATION: BLTA Co-stimulatory domain

<400> SEQUENCE: 59

Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser


<210> SEQ ID NO 60
<211> LENGTH: 187
<212> TYPE: PRT
<213> ORGANISM: Homo sapiens
<220> FEATURE:
<221> NAME/KEY: misc_feature
<222> LOCATION: (1)..(187)
<223> OTHER INFORMATION: CD30 Co-stimulatory domain

<400> SEQUENCE: 60

Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
```

```
145                 150                 155                 160

Leu Gly Ser Cys Ser Asp Val Met Leu Ser Val Glu Glu Glu Gly Lys
                165                 170                 175

Glu Asp Pro Leu Pro Thr Ala Ala Ser Gly Lys
            180                 185


<210> SEQ ID NO 61
<211> LENGTH: 54
<212> TYPE: PRT
<213> ORGANISM: Homo sapiens
<220> FEATURE:
<221> NAME/KEY: misc_feature
<222> LOCATION: (1)..(54)
<223> OTHER INFORMATION: GITR Co-stimulatory domain

<400> SEQUENCE: 61

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50


<210> SEQ ID NO 62
<211> LENGTH: 60
<212> TYPE: PRT
<213> ORGANISM: Homo sapiens
<220> FEATURE:
<221> NAME/KEY: misc_feature
<222> LOCATION: (1)..(60)
<223> OTHER INFORMATION: HVEM Co-stimulatory domain

<400> SEQUENCE: 62

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60


<210> SEQ ID NO 63
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 63

Gly Gly Gly Gly Ser Gly Gly Gly Gly Ser Gly Gly Gly Gly Ser
1               5                   10                  15


<210> SEQ ID NO 64
<211> LENGTH: 30
<212> TYPE: PRT
<213> ORGANISM: Artificial Sequence
<220> FEATURE:
<223> OTHER INFORMATION: Synthetic: Linker

<400> SEQUENCE: 64
```

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 65
<211> LENGTH: 14
<212> TYPE: PRT
<213> ORGANISM: Artificial Sequence
<220> FEATURE:
<223> OTHER INFORMATION: Synthetic: Linker

<400> SEQUENCE: 65

Gly Gly Gly Gly Ser Gly Gly Gly Ser Gly Gly Gly Gly Ser
1 5 10

<210> SEQ ID NO 66
<211> LENGTH: 4
<212> TYPE: PRT
<213> ORGANISM: Artificial Sequence
<220> FEATURE:
<223> OTHER INFORMATION: Synthetic: Linker

<400> SEQUENCE: 66

Gly Gly Ser Gly
1

<210> SEQ ID NO 67
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 67

Gly Gly Ser Gly Gly
1 5

<210> SEQ ID NO 68
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 68

Gly Ser Gly Ser Gly
1 5

<210> SEQ ID NO 69
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 69

Gly Ser Gly Gly Gly
1 5

<210> SEQ ID NO 70
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 70

Gly Gly Gly Ser Gly
1 5

<210> SEQ ID NO 71
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 71

Gly Ser Ser Ser Gly
1 5

<210> SEQ ID NO 72
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD8 Signal peptide

<400> SEQUENCE: 72

Met Ala Leu Pro Val Thr Ala Leu Leu Leu Pro Leu Ala Leu Leu Leu
1 5 10 15

His Ala Ala Arg Pro
20

<210> SEQ ID NO 73
<211> LENGTH: 9
<212> TYPE: PRT
<213> ORGANISM: Artificial Sequence
<220> FEATURE:
<223> OTHER INFORMATION: Synthetic: HA Epitope

<400> SEQUENCE: 73

Tyr Pro Tyr Asp Val Pro Asp Tyr Ala
1 5

<210> SEQ ID NO 74
<211> LENGTH: 8
<212> TYPE: PRT
<213> ORGANISM: Artificial Sequence
<220> FEATURE:
<223> OTHER INFORMATION: Synthetic: FLAG epitope

<400> SEQUENCE: 74

Asp Tyr Lys Asp Asp Asp Asp Lys
1 5

<210> SEQ ID NO 75
<211> LENGTH: 10
<212> TYPE: PRT
<213> ORGANISM: Artificial Sequence
<220> FEATURE:
<223> OTHER INFORMATION: Synthetic: c-myc Epitope

<400> SEQUENCE: 75

Glu Gln Lys Leu Ile Ser Glu Glu Asp Leu
1 5 10

<210> SEQ ID NO 76
<211> LENGTH: 5
<212> TYPE: PRT

<213> ORGANISM: Artificial Sequence
<220> FEATURE:
<223> OTHER INFORMATION: Synthetic: His5 Affinity

<400> SEQUENCE: 76

His His His His His
1 5

<210> SEQ ID NO 77
<211> LENGTH: 6
<212> TYPE: PRT
<213> ORGANISM: Artificial Sequence
<220> FEATURE:
<223> OTHER INFORMATION: Synthetic: HisX6 Affinity

<400> SEQUENCE: 77

His His His His His His
1 5

<210> SEQ ID NO 78
<211> LENGTH: 8
<212> TYPE: PRT
<213> ORGANISM: Artificial Sequence
<220> FEATURE:
<223> OTHER INFORMATION: Synthetic: Strep Tag Affinity

<400> SEQUENCE: 78

Trp Ser His Pro Gln Phe Glu Lys
1 5

<210> SEQ ID NO 79
<211> LENGTH: 5
<212> TYPE: PRT
<213> ORGANISM: Artificial Sequence
<220> FEATURE:
<223> OTHER INFORMATION: Synthetic: Affinity tag

<400> SEQUENCE: 79

Arg Tyr Ile Arg Ser
1 5

<210> SEQ ID NO 80
<211> LENGTH: 4
<212> TYPE: PRT
<213> ORGANISM: Artificial Sequence
<220> FEATURE:
<223> OTHER INFORMATION: Synthetic: Affinity tag

<400> SEQUENCE: 80

Phe His His Thr
1

<210> SEQ ID NO 81
<211> LENGTH: 17
<212> TYPE: PRT
<213> ORGANISM: Artificial Sequence
<220> FEATURE:
<223> OTHER INFORMATION: Synthetic: Affinity tag

<400> SEQUENCE: 81

Trp Glu Ala Ala Ala Arg Glu Ala Cys Cys Arg Glu Cys Cys Ala Arg
1 5 10 15

Ala

<210> SEQ ID NO 82
<211> LENGTH: 357

<212> TYPE: PRT
<213> ORGANISM: Homo sapiens
<220> FEATURE:
<221> NAME/KEY: misc_feature
<222> LOCATION: (1)..(357)
<223> OTHER INFORMATION: EGFR Truncation

<400> SEQUENCE: 82

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 83
<211> LENGTH: 21
<212> TYPE: PRT
<213> ORGANISM: Artificial Sequence
<220> FEATURE:
<223> OTHER INFORMATION: Synthetic: Cleavage signal

<400> SEQUENCE: 83

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 84
<211> LENGTH: 368
<212> TYPE: PRT
<213> ORGANISM: Artificial Sequence
<220> FEATURE:
<223> OTHER INFORMATION: Synthetic: eTAG IL7RA Ins PPCL (interleukin 7 receptor)

<400> SEQUENCE: 84

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285
```

```
Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Glu Ile Asn Asn Ser Ser
                325                 330                 335

Gly Glu Met Asp Pro Ile Leu Leu Pro Pro Cys Leu Thr Ile Ser Ile
            340                 345                 350

Leu Ser Phe Phe Ser Val Ala Leu Leu Val Ile Leu Ala Cys Val Leu
        355                 360                 365


<210> SEQ ID NO 85
<211> LENGTH: 232
<212> TYPE: PRT
<213> ORGANISM: Artificial Sequence
<220> FEATURE:
<223> OTHER INFORMATION: Synthetic: eTAG IL7RA Ins PPCL (interleukin 7
      receptor)

<400> SEQUENCE: 85

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Pro Glu Ile Asn Asn Ser Ser Gly Glu Met Asp Pro Ile Leu Leu
        195                 200                 205

Pro Pro Cys Leu Thr Ile Ser Ile Leu Ser Phe Phe Ser Val Ala Leu
    210                 215                 220

Leu Val Ile Leu Ala Cys Val Leu
225                 230


<210> SEQ ID NO 86
<211> LENGTH: 194
<212> TYPE: PRT
<213> ORGANISM: Artificial Sequence
<220> FEATURE:
<223> OTHER INFORMATION: Synthetic: Myc Tag LMP1 NC_007605_1
```

<400> SEQUENCE: 86

```
Met Glu Gln Lys Leu Ile Ser Glu Glu Asp Leu Glu His Asp Leu Glu
1               5                   10                  15

Arg Gly Pro Pro Gly Pro Arg Arg Pro Pro Arg Gly Pro Pro Leu Ser
            20                  25                  30

Ser Ser Leu Gly Leu Ala Leu Leu Leu Leu Leu Leu Ala Leu Leu Phe
        35                  40                  45

Trp Leu Tyr Ile Val Met Ser Asp Trp Thr Gly Gly Ala Leu Leu Val
    50                  55                  60

Leu Tyr Ser Phe Ala Leu Met Leu Ile Ile Ile Ile Leu Ile Ile Phe
65                  70                  75                  80

Ile Phe Arg Arg Asp Leu Leu Cys Pro Leu Gly Ala Leu Cys Ile Leu
                85                  90                  95

Leu Leu Met Ile Thr Leu Leu Leu Ile Ala Leu Trp Asn Leu His Gly
            100                 105                 110

Gln Ala Leu Phe Leu Gly Ile Val Leu Phe Ile Phe Gly Cys Leu Leu
        115                 120                 125

Val Leu Gly Ile Trp Ile Tyr Leu Leu Glu Met Leu Trp Arg Leu Gly
    130                 135                 140

Ala Thr Ile Trp Gln Leu Leu Ala Phe Phe Leu Ala Phe Phe Leu Asp
145                 150                 155                 160

Leu Ile Leu Leu Ile Ile Ala Leu Tyr Leu Gln Gln Asn Trp Trp Thr
                165                 170                 175

Leu Leu Val Asp Leu Leu Trp Leu Leu Leu Phe Leu Ala Ile Leu Ile
            180                 185                 190

Trp Met
```

<210> SEQ ID NO 87
<211> LENGTH: 174
<212> TYPE: PRT
<213> ORGANISM: Artificial Sequence
<220> FEATURE:
<223> OTHER INFORMATION: Synthetic: Myc LMP1 NC_007605_1

<400> SEQUENCE: 87

```
Met Glu Gln Lys Leu Ile Ser Glu Glu Asp Leu Ser Ser Ser Leu Gly
1               5                   10                  15

Leu Ala Leu Leu Leu Leu Leu Leu Ala Leu Leu Phe Trp Leu Tyr Ile
            20                  25                  30

Val Met Ser Asp Trp Thr Gly Gly Ala Leu Leu Val Leu Tyr Ser Phe
        35                  40                  45

Ala Leu Met Leu Ile Ile Ile Ile Leu Ile Ile Phe Ile Phe Arg Arg
    50                  55                  60

Asp Leu Leu Cys Pro Leu Gly Ala Leu Cys Ile Leu Leu Leu Met Ile
65                  70                  75                  80

Thr Leu Leu Leu Ile Ala Leu Trp Asn Leu His Gly Gln Ala Leu Phe
                85                  90                  95

Leu Gly Ile Val Leu Phe Ile Phe Gly Cys Leu Leu Val Leu Gly Ile
            100                 105                 110

Trp Ile Tyr Leu Leu Glu Met Leu Trp Arg Leu Gly Ala Thr Ile Trp
        115                 120                 125

Gln Leu Leu Ala Phe Phe Leu Ala Phe Phe Leu Asp Leu Ile Leu Leu
    130                 135                 140

Ile Ile Ala Leu Tyr Leu Gln Gln Asn Trp Trp Thr Leu Leu Val Asp
```

145 150 155 160

Leu Leu Trp Leu Leu Leu Phe Leu Ala Ile Leu Ile Trp Met
165 170

<210> SEQ ID NO 88
<211> LENGTH: 184
<212> TYPE: PRT
<213> ORGANISM: Artificial Sequence
<220> FEATURE:
<223> OTHER INFORMATION: Synthetic: LMP1 NC_007605_1

<400> SEQUENCE: 88

Met Glu His Asp Leu Glu Arg Gly Pro Pro Gly Pro Arg Arg Pro Pro
1 5 10 15

Arg Gly Pro Pro Leu Ser Ser Ser Leu Gly Leu Ala Leu Leu Leu Leu
20 25 30

Leu Leu Ala Leu Leu Phe Trp Leu Tyr Ile Val Met Ser Asp Trp Thr
35 40 45

Gly Gly Ala Leu Leu Val Leu Tyr Ser Phe Ala Leu Met Leu Ile Ile
50 55 60

Ile Ile Leu Ile Ile Phe Ile Phe Arg Arg Asp Leu Leu Cys Pro Leu
65 70 75 80

Gly Ala Leu Cys Ile Leu Leu Leu Met Ile Thr Leu Leu Leu Ile Ala
85 90 95

Leu Trp Asn Leu His Gly Gln Ala Leu Phe Leu Gly Ile Val Leu Phe
100 105 110

Ile Phe Gly Cys Leu Leu Val Leu Gly Ile Trp Ile Tyr Leu Leu Glu
115 120 125

Met Leu Trp Arg Leu Gly Ala Thr Ile Trp Gln Leu Leu Ala Phe Phe
130 135 140

Leu Ala Phe Phe Leu Asp Leu Ile Leu Leu Ile Ile Ala Leu Tyr Leu
145 150 155 160

Gln Gln Asn Trp Trp Thr Leu Leu Val Asp Leu Leu Trp Leu Leu Leu
165 170 175

Phe Leu Ala Ile Leu Ile Trp Met
180

<210> SEQ ID NO 89
<211> LENGTH: 162
<212> TYPE: PRT
<213> ORGANISM: Artificial Sequence
<220> FEATURE:
<223> OTHER INFORMATION: Synthetic: LMP1 NC_007605_1

<400> SEQUENCE: 89

Met Ser Leu Gly Leu Ala Leu Leu Leu Leu Leu Leu Ala Leu Leu Phe
1 5 10 15

Trp Leu Tyr Ile Val Met Ser Asp Trp Thr Gly Gly Ala Leu Leu Val
20 25 30

Leu Tyr Ser Phe Ala Leu Met Leu Ile Ile Ile Ile Leu Ile Ile Phe
35 40 45

Ile Phe Arg Arg Asp Leu Leu Cys Pro Leu Gly Ala Leu Cys Ile Leu
50 55 60

Leu Leu Met Ile Thr Leu Leu Leu Ile Ala Leu Trp Asn Leu His Gly
65 70 75 80

Gln Ala Leu Phe Leu Gly Ile Val Leu Phe Ile Phe Gly Cys Leu Leu
85 90 95

```
Val Leu Gly Ile Trp Ile Tyr Leu Leu Glu Met Leu Trp Arg Leu Gly
            100                 105                 110

Ala Thr Ile Trp Gln Leu Leu Ala Phe Phe Leu Ala Phe Phe Leu Asp
        115                 120                 125

Leu Ile Leu Leu Ile Ile Ala Leu Tyr Leu Gln Gln Asn Trp Trp Thr
    130                 135                 140

Leu Leu Val Asp Leu Leu Trp Leu Leu Leu Phe Leu Ala Ile Leu Ile
145                 150                 155                 160

Trp Met


<210> SEQ ID NO 90
<211> LENGTH: 363
<212> TYPE: PRT
<213> ORGANISM: Artificial Sequence
<220> FEATURE:
<223> OTHER INFORMATION: Synthetic: eTAG CRLF2 transcript variant 1
      NM_022148_3

<400> SEQUENCE: 90

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285
```

-continued

```
Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Ala Glu Thr Pro Thr Pro Pro
                325                 330                 335

Lys Pro Lys Leu Ser Lys Cys Ile Leu Ile Ser Ser Leu Ala Ile Leu
            340                 345                 350

Leu Met Val Ser Leu Leu Leu Leu Ser Leu Trp
        355                 360


<210> SEQ ID NO 91
<211> LENGTH: 227
<212> TYPE: PRT
<213> ORGANISM: Artificial Sequence
<220> FEATURE:
<223> OTHER INFORMATION: Synthetic: eTAG CRLF2 transcript variant 1
      NM_022148_3

<400> SEQUENCE: 91

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Ala Glu Thr Pro Thr Pro Pro Lys Pro Lys Leu Ser Lys Cys Ile
        195                 200                 205

Leu Ile Ser Ser Leu Ala Ile Leu Leu Met Val Ser Leu Leu Leu Leu
    210                 215                 220

Ser Leu Trp
225


<210> SEQ ID NO 92
<211> LENGTH: 354
<212> TYPE: PRT
<213> ORGANISM: Artificial Sequence
<220> FEATURE:
<223> OTHER INFORMATION: Synthetic: eTAG CSF2RB NM_000395_2
```

<400> SEQUENCE: 92

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Thr Glu Ser Val Leu Pro Met
                325                 330                 335

Trp Val Leu Ala Leu Ile Glu Ile Phe Leu Thr Ile Ala Val Leu Leu
            340                 345                 350

Ala Leu
```

<210> SEQ ID NO 93
<211> LENGTH: 218
<212> TYPE: PRT
<213> ORGANISM: Artificial Sequence
<220> FEATURE:
<223> OTHER INFORMATION: Synthetic: eTAG CSF2RB NM_000395_2

<400> SEQUENCE: 93

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Thr Glu Ser Val Leu Pro Met Trp Val Leu Ala Leu Ile Glu Ile
        195                 200                 205

Phe Leu Thr Ile Ala Val Leu Leu Ala Leu
    210                 215
```

<210> SEQ ID NO 94
<211> LENGTH: 360
<212> TYPE: PRT
<213> ORGANISM: Artificial Sequence
<220> FEATURE:
<223> OTHER INFORMATION: Synthetic: eTAG CSF3R transcript variant 1 NM_000760_3

<400> SEQUENCE: 94

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
```

-continued

```
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Thr Pro Glu Gly Ser Glu Leu
                325                 330                 335

His Ile Ile Leu Gly Leu Phe Gly Leu Leu Leu Leu Leu Asn Cys Leu
            340                 345                 350

Cys Gly Thr Ala Trp Leu Cys Cys
        355                 360


<210> SEQ ID NO 95
<211> LENGTH: 224
<212> TYPE: PRT
<213> ORGANISM: Artificial Sequence
<220> FEATURE:
<223> OTHER INFORMATION: Synthetic: eTAG CSF3R transcript variant 1
      NM_000760_3

<400> SEQUENCE: 95

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125
```

```
Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Thr Pro Glu Gly Ser Glu Leu His Ile Ile Leu Gly Leu Phe Gly
        195                 200                 205

Leu Leu Leu Leu Leu Asn Cys Leu Cys Gly Thr Ala Trp Leu Cys Cys
    210                 215                 220


<210> SEQ ID NO 96
<211> LENGTH: 359
<212> TYPE: PRT
<213> ORGANISM: Artificial Sequence
<220> FEATURE:
<223> OTHER INFORMATION: Synthetic: eTAG EPOR transcript variant 1
      NM_000121_3

<400> SEQUENCE: 96

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270
```

```
His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Thr Pro Ser Asp Leu Asp Pro
                325                 330                 335

Cys Cys Leu Thr Leu Ser Leu Ile Leu Val Val Ile Leu Val Leu Leu
            340                 345                 350

Thr Val Leu Ala Leu Leu Ser
        355


<210> SEQ ID NO 97
<211> LENGTH: 223
<212> TYPE: PRT
<213> ORGANISM: Artificial Sequence
<220> FEATURE:
<223> OTHER INFORMATION: Synthetic: eTAG EPOR transcript variant 1
      NM_000121_3

<400> SEQUENCE: 97

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Thr Pro Ser Asp Leu Asp Pro Cys Cys Leu Thr Leu Ser Leu Ile
        195                 200                 205

Leu Val Val Ile Leu Val Leu Leu Thr Val Leu Ala Leu Leu Ser
    210                 215                 220


<210> SEQ ID NO 98
<211> LENGTH: 368
<212> TYPE: PRT
<213> ORGANISM: Artificial Sequence
<220> FEATURE:
<223> OTHER INFORMATION: Synthetic: eTAG GHR transcript variant 1
```

NM_000163_4

<400> SEQUENCE: 98

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Thr Leu Pro Gln Met Ser Gln
                325                 330                 335

Phe Thr Cys Cys Glu Asp Phe Tyr Phe Pro Trp Leu Leu Cys Ile Ile
            340                 345                 350

Phe Gly Ile Phe Gly Leu Thr Val Met Leu Phe Val Phe Leu Phe Ser
        355                 360                 365
```

<210> SEQ ID NO 99
<211> LENGTH: 232
<212> TYPE: PRT
<213> ORGANISM: Artificial Sequence
<220> FEATURE:

<223> OTHER INFORMATION: Synthetic: eTAG GHR transcript variant 1
NM_000163_4

<400> SEQUENCE: 99

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Thr Leu Pro Gln Met Ser Gln Phe Thr Cys Cys Glu Asp Phe Tyr
195 200 205

Phe Pro Trp Leu Leu Cys Ile Ile Phe Gly Ile Phe Gly Leu Thr Val
210 215 220

Met Leu Phe Val Phe Leu Phe Ser
225 230

<210> SEQ ID NO 100
<211> LENGTH: 360
<212> TYPE: PRT
<213> ORGANISM: Artificial Sequence
<220> FEATURE:
<223> OTHER INFORMATION: Synthetic: eTAG truncated after Fn F523C IL27RA
NM_004843_3

<400> SEQUENCE: 100

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

```
Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly His Leu Pro Asp Asn Thr Leu
                325                 330                 335

Arg Trp Lys Val Leu Pro Gly Ile Leu Cys Leu Trp Gly Leu Phe Leu
            340                 345                 350

Leu Gly Cys Gly Leu Ser Leu Ala
        355                 360
```

<210> SEQ ID NO 101
<211> LENGTH: 224
<212> TYPE: PRT
<213> ORGANISM: Artificial Sequence
<220> FEATURE:
<223> OTHER INFORMATION: Synthetic: eTAG truncated after Fn F523C IL27RA NM_004843_3

<400> SEQUENCE: 101

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95
```

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln His Leu Pro Asp Asn Thr Leu Arg Trp Lys Val Leu Pro Gly Ile
195 200 205

Leu Cys Leu Trp Gly Leu Phe Leu Leu Gly Cys Gly Leu Ser Leu Ala
210 215 220

<210> SEQ ID NO 102
<211> LENGTH: 359
<212> TYPE: PRT
<213> ORGANISM: Artificial Sequence
<220> FEATURE:
<223> OTHER INFORMATION: Synthetic: eTAG truncated after Fn S505N MPL NM_005373_2

<400> SEQUENCE: 102

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Val Cys His Ala Leu Cys Ser Pro Glu Gly Cys Trp Gly Pro Glu
195 200 205

Pro Arg Asp Cys Val Ser Cys Arg Asn Val Ser Arg Gly Arg Glu Cys
210 215 220

Val Asp Lys Cys Asn Leu Leu Glu Gly Glu Pro Arg Glu Phe Val Glu

```
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Glu Thr Ala Thr Glu Thr Ala
                325                 330                 335

Trp Ile Ser Leu Val Thr Ala Leu His Leu Val Leu Gly Leu Asn Ala
            340                 345                 350

Val Leu Gly Leu Leu Leu Leu
        355


<210> SEQ ID NO 103
<211> LENGTH: 223
<212> TYPE: PRT
<213> ORGANISM: Artificial Sequence
<220> FEATURE:
<223> OTHER INFORMATION: Synthetic: eTAG truncated after Fn S505N MPL
      NM_005373_2

<400> SEQUENCE: 103

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Glu Thr Ala Thr Glu Thr Ala Trp Ile Ser Leu Val Thr Ala Leu
        195                 200                 205

His Leu Val Leu Gly Leu Asn Ala Val Leu Gly Leu Leu Leu Leu
    210                 215                 220
```

<210> SEQ ID NO 104
<211> LENGTH: 368
<212> TYPE: PRT
<213> ORGANISM: Artificial Sequence
<220> FEATURE:
<223> OTHER INFORMATION: Synthetic: eTag 0A JUN NM_002228_3

<400> SEQUENCE: 104

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Leu Glu Arg Ile Ala Arg Leu
                325                 330                 335

Glu Glu Lys Val Lys Thr Leu Lys Ala Gln Asn Ser Glu Leu Ala Ser
            340                 345                 350

Thr Ala Asn Met Leu Arg Glu Gln Val Ala Gln Leu Lys Gln Lys Val
        355                 360                 365
```

<210> SEQ ID NO 105
<211> LENGTH: 369
<212> TYPE: PRT
<213> ORGANISM: Artificial Sequence
<220> FEATURE:
<223> OTHER INFORMATION: Synthetic: eTag 1A JUN NM_002228_3

<400> SEQUENCE: 105

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Leu Glu Arg Ile Ala Arg Leu
                325                 330                 335

Glu Glu Lys Val Lys Thr Leu Lys Ala Gln Asn Ser Glu Leu Ala Ser
            340                 345                 350

Thr Ala Asn Met Leu Arg Glu Gln Val Ala Gln Leu Lys Gln Lys Val
        355                 360                 365
```

Ala

<210> SEQ ID NO 106
<211> LENGTH: 369
<212> TYPE: PRT
<213> ORGANISM: Artificial Sequence
<220> FEATURE:
<223> OTHER INFORMATION: Synthetic: eTag 2A JUN NM_002228_3

<400> SEQUENCE: 106

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Phe Gly Thr Ser Gly Gln Lys Thr
                165                 170                 175

Lys Ile Ile Ser Asn Arg Gly Glu Asn Ser Cys Lys Ala Thr Gly Gln
            180                 185                 190

Val Cys His Ala Leu Cys Ser Pro Glu Gly Cys Trp Gly Pro Glu Pro
        195                 200                 205

Arg Asp Cys Val Ser Cys Arg Asn Val Ser Arg Gly Arg Glu Cys Val
    210                 215                 220

Asp Lys Cys Asn Leu Leu Glu Gly Glu Pro Arg Glu Phe Val Glu Asn
225                 230                 235                 240

Ser Glu Cys Ile Gln Cys His Pro Glu Cys Leu Pro Gln Ala Met Asn
                245                 250                 255

Ile Thr Cys Thr Gly Arg Gly Pro Asp Asn Cys Ile Gln Cys Ala His
            260                 265                 270

Tyr Ile Asp Gly Pro His Cys Val Lys Thr Cys Pro Ala Gly Val Met
        275                 280                 285

Gly Glu Asn Asn Thr Leu Val Trp Lys Tyr Ala Asp Ala Gly His Val
    290                 295                 300

Cys His Leu Cys His Pro Asn Cys Thr Tyr Gly Cys Thr Gly Pro Gly
305                 310                 315                 320

Leu Glu Gly Cys Pro Thr Asn Gly Leu Glu Arg Ile Ala Arg Leu Glu
                325                 330                 335

Glu Lys Val Lys Thr Leu Lys Ala Gln Asn Ser Glu Leu Ala Ser Thr
            340                 345                 350

Ala Asn Met Leu Arg Glu Gln Val Ala Gln Leu Lys Gln Lys Val Ala
```

355 360 365

Ala

<210> SEQ ID NO 107
<211> LENGTH: 371
<212> TYPE: PRT
<213> ORGANISM: Artificial Sequence
<220> FEATURE:
<223> OTHER INFORMATION: Synthetic: eTag 3A JUN NM_002228_3

<400> SEQUENCE: 107

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Val Cys His Ala Leu Cys Ser Pro Glu Gly Cys Trp Gly Pro Glu
195 200 205

Pro Arg Asp Cys Val Ser Cys Arg Asn Val Ser Arg Gly Arg Glu Cys
210 215 220

Val Asp Lys Cys Asn Leu Leu Glu Gly Glu Pro Arg Glu Phe Val Glu
225 230 235 240

Asn Ser Glu Cys Ile Gln Cys His Pro Glu Cys Leu Pro Gln Ala Met
245 250 255

Asn Ile Thr Cys Thr Gly Arg Gly Pro Asp Asn Cys Ile Gln Cys Ala
260 265 270

His Tyr Ile Asp Gly Pro His Cys Val Lys Thr Cys Pro Ala Gly Val
275 280 285

Met Gly Glu Asn Asn Thr Leu Val Trp Lys Tyr Ala Asp Ala Gly His
290 295 300

Val Cys His Leu Cys His Pro Asn Cys Thr Tyr Gly Cys Thr Gly Pro
305 310 315 320

Gly Leu Glu Gly Cys Pro Thr Asn Gly Leu Glu Arg Ile Ala Arg Leu
325 330 335

Glu Glu Lys Val Lys Thr Leu Lys Ala Gln Asn Ser Glu Leu Ala Ser
340 345 350

Thr Ala Asn Met Leu Arg Glu Gln Val Ala Gln Leu Lys Gln Lys Val
355 360 365

Ala Ala Ala
370

<210> SEQ ID NO 108
<211> LENGTH: 372
<212> TYPE: PRT
<213> ORGANISM: Artificial Sequence
<220> FEATURE:
<223> OTHER INFORMATION: Synthetic: eTag 4A JUN NM_002228_3

<400> SEQUENCE: 108

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Val Cys His Ala Leu Cys Ser Pro Glu Gly Cys Trp Gly Pro Glu
195 200 205

Pro Arg Asp Cys Val Ser Cys Arg Asn Val Ser Arg Gly Arg Glu Cys
210 215 220

Val Asp Lys Cys Asn Leu Leu Glu Gly Glu Pro Arg Glu Phe Val Glu
225 230 235 240

Asn Ser Glu Cys Ile Gln Cys His Pro Glu Cys Leu Pro Gln Ala Met
245 250 255

Asn Ile Thr Cys Thr Gly Arg Gly Pro Asp Asn Cys Ile Gln Cys Ala
260 265 270

His Tyr Ile Asp Gly Pro His Cys Val Lys Thr Cys Pro Ala Gly Val
275 280 285

Met Gly Glu Asn Asn Thr Leu Val Trp Lys Tyr Ala Asp Ala Gly His
290 295 300

Val Cys His Leu Cys His Pro Asn Cys Thr Tyr Gly Cys Thr Gly Pro
305 310 315 320

Gly Leu Glu Gly Cys Pro Thr Asn Gly Leu Glu Arg Ile Ala Arg Leu
325 330 335

Glu Glu Lys Val Lys Thr Leu Lys Ala Gln Asn Ser Glu Leu Ala Ser
            340                 345                 350

Thr Ala Asn Met Leu Arg Glu Gln Val Ala Gln Leu Lys Gln Lys Val
        355                 360                 365

Ala Ala Ala Ala
    370

<210> SEQ ID NO 109
<211> LENGTH: 69
<212> TYPE: PRT
<213> ORGANISM: Artificial Sequence
<220> FEATURE:
<223> OTHER INFORMATION: Synthetic: Myc Tag 0A JUN NM_002228_3

<400> SEQUENCE: 109

Met Thr Ile Leu Gly Thr Thr Phe Gly Met Val Phe Ser Leu Leu Gln
1               5                   10                  15

Val Val Ser Gly Glu Gln Lys Leu Ile Ser Glu Glu Asp Leu Leu Glu
            20                  25                  30

Arg Ile Ala Arg Leu Glu Glu Lys Val Lys Thr Leu Lys Ala Gln Asn
        35                  40                  45

Ser Glu Leu Ala Ser Thr Ala Asn Met Leu Arg Glu Gln Val Ala Gln
    50                  55                  60

Leu Lys Gln Lys Val
65

<210> SEQ ID NO 110
<211> LENGTH: 70
<212> TYPE: PRT
<213> ORGANISM: Artificial Sequence
<220> FEATURE:
<223> OTHER INFORMATION: Synthetic: Myc Tag 1A JUN NM_002228_3

<400> SEQUENCE: 110

Met Thr Ile Leu Gly Thr Thr Phe Gly Met Val Phe Ser Leu Leu Gln
1               5                   10                  15

Val Val Ser Gly Glu Gln Lys Leu Ile Ser Glu Glu Asp Leu Leu Glu
            20                  25                  30

Arg Ile Ala Arg Leu Glu Glu Lys Val Lys Thr Leu Lys Ala Gln Asn
        35                  40                  45

Ser Glu Leu Ala Ser Thr Ala Asn Met Leu Arg Glu Gln Val Ala Gln
    50                  55                  60

Leu Lys Gln Lys Val Ala
65                  70

<210> SEQ ID NO 111
<211> LENGTH: 71
<212> TYPE: PRT
<213> ORGANISM: Artificial Sequence
<220> FEATURE:
<223> OTHER INFORMATION: Synthetic: Myc Tag 2A JUN NM_002228_3

<400> SEQUENCE: 111

Met Thr Ile Leu Gly Thr Thr Phe Gly Met Val Phe Ser Leu Leu Gln
1               5                   10                  15

Val Val Ser Gly Glu Gln Lys Leu Ile Ser Glu Glu Asp Leu Leu Glu
            20                  25                  30

Arg Ile Ala Arg Leu Glu Glu Lys Val Lys Thr Leu Lys Ala Gln Asn
        35                  40                  45

```
Ser Glu Leu Ala Ser Thr Ala Asn Met Leu Arg Glu Gln Val Ala Gln
    50                  55                  60

Leu Lys Gln Lys Val Ala Ala
65                  70


<210> SEQ ID NO 112
<211> LENGTH: 72
<212> TYPE: PRT
<213> ORGANISM: Artificial Sequence
<220> FEATURE:
<223> OTHER INFORMATION: Synthetic: Myc Tag 3A JUN NM_002228_3

<400> SEQUENCE: 112

Met Thr Ile Leu Gly Thr Thr Phe Gly Met Val Phe Ser Leu Leu Gln
1               5                   10                  15

Val Val Ser Gly Glu Gln Lys Leu Ile Ser Glu Glu Asp Leu Leu Glu
            20                  25                  30

Arg Ile Ala Arg Leu Glu Glu Lys Val Lys Thr Leu Lys Ala Gln Asn
        35                  40                  45

Ser Glu Leu Ala Ser Thr Ala Asn Met Leu Arg Glu Gln Val Ala Gln
    50                  55                  60

Leu Lys Gln Lys Val Ala Ala Ala
65                  70


<210> SEQ ID NO 113
<211> LENGTH: 73
<212> TYPE: PRT
<213> ORGANISM: Artificial Sequence
<220> FEATURE:
<223> OTHER INFORMATION: Synthetic: Myc Tag 4A JUN NM_002228_3

<400> SEQUENCE: 113

Met Thr Ile Leu Gly Thr Thr Phe Gly Met Val Phe Ser Leu Leu Gln
1               5                   10                  15

Val Val Ser Gly Glu Gln Lys Leu Ile Ser Glu Glu Asp Leu Leu Glu
            20                  25                  30

Arg Ile Ala Arg Leu Glu Glu Lys Val Lys Thr Leu Lys Ala Gln Asn
        35                  40                  45

Ser Glu Leu Ala Ser Thr Ala Asn Met Leu Arg Glu Gln Val Ala Gln
    50                  55                  60

Leu Lys Gln Lys Val Ala Ala Ala Ala
65                  70


<210> SEQ ID NO 114
<211> LENGTH: 23
<212> TYPE: PRT
<213> ORGANISM: Artificial Sequence
<220> FEATURE:
<223> OTHER INFORMATION: Synthetic: CD2 transcript variant 1
      NM_001328609_1

<400> SEQUENCE: 114

Leu Ile Ile Gly Ile Cys Gly Gly Gly Ser Leu Leu Met Val Phe Val
1               5                   10                  15

Ala Leu Leu Val Phe Tyr Ile
            20


<210> SEQ ID NO 115
<211> LENGTH: 21
<212> TYPE: PRT
<213> ORGANISM: Artificial Sequence
<220> FEATURE:
```

```
<223> OTHER INFORMATION: Synthetic: CD3D transcript variant 1
      NM_000732_4

<400> SEQUENCE: 115

Gly Ile Ile Val Thr Asp Val Ile Ala Thr Leu Leu Leu Ala Leu Gly
1               5                   10                  15

Val Phe Cys Phe Ala
            20


<210> SEQ ID NO 116
<211> LENGTH: 26
<212> TYPE: PRT
<213> ORGANISM: Artificial Sequence
<220> FEATURE:
<223> OTHER INFORMATION: Synthetic: CD3E NM_000733_3

<400> SEQUENCE: 116

Val Met Ser Val Ala Thr Ile Val Ile Val Asp Ile Cys Ile Thr Gly
1               5                   10                  15

Gly Leu Leu Leu Leu Val Tyr Tyr Trp Ser
            20                  25


<210> SEQ ID NO 117
<211> LENGTH: 21
<212> TYPE: PRT
<213> ORGANISM: Artificial Sequence
<220> FEATURE:
<223> OTHER INFORMATION: Synthetic: CD3G NM_000073_2

<400> SEQUENCE: 117

Gly Phe Leu Phe Ala Glu Ile Val Ser Ile Phe Val Leu Ala Val Gly
1               5                   10                  15

Val Tyr Phe Ile Ala
            20


<210> SEQ ID NO 118
<211> LENGTH: 21
<212> TYPE: PRT
<213> ORGANISM: Artificial Sequence
<220> FEATURE:
<223> OTHER INFORMATION: Synthetic: CD3Z CD247 transcript variant 1
      NM_198053_2

<400> SEQUENCE: 118

Leu Cys Tyr Leu Leu Asp Gly Ile Leu Phe Ile Tyr Gly Val Ile Leu
1               5                   10                  15

Thr Ala Leu Phe Leu
            20


<210> SEQ ID NO 119
<211> LENGTH: 22
<212> TYPE: PRT
<213> ORGANISM: Artificial Sequence
<220> FEATURE:
<223> OTHER INFORMATION: Synthetic: CD4 transcript variant 1 and 2
      NM_000616_4

<400> SEQUENCE: 119

Met Ala Leu Ile Val Leu Gly Gly Val Ala Gly Leu Leu Leu Phe Ile
1               5                   10                  15

Gly Leu Gly Ile Phe Phe
            20


<210> SEQ ID NO 120
```

<211> LENGTH: 21
<212> TYPE: PRT
<213> ORGANISM: Artificial Sequence
<220> FEATURE:
<223> OTHER INFORMATION: Synthetic: CD8A transcript variant 1
      NM_001768_6

<400> SEQUENCE: 120

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 121
<211> LENGTH: 23
<212> TYPE: PRT
<213> ORGANISM: Artificial Sequence
<220> FEATURE:
<223> OTHER INFORMATION: Synthetic: CD8B transcript variant 2
      NM_172213_3

<400> SEQUENCE: 121

```
Leu Gly Leu Leu Val Ala Gly Val Leu Val Leu Leu Val Ser Leu Gly
1               5                   10                  15

Val Ala Ile His Leu Cys Cys
            20
```

<210> SEQ ID NO 122
<211> LENGTH: 21
<212> TYPE: PRT
<213> ORGANISM: Artificial Sequence
<220> FEATURE:
<223> OTHER INFORMATION: Synthetic: CD27 NM_001242_4

<400> SEQUENCE: 122

```
Ile Leu Val Ile Phe Ser Gly Met Phe Leu Val Phe Thr Leu Ala Gly
1               5                   10                  15

Ala Leu Phe Leu His
            20
```

<210> SEQ ID NO 123
<211> LENGTH: 27
<212> TYPE: PRT
<213> ORGANISM: Artificial Sequence
<220> FEATURE:
<223> OTHER INFORMATION: Synthetic: CD28 transcript variant 1
      NM_006139_3

<400> SEQUENCE: 123

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 124
<211> LENGTH: 22
<212> TYPE: PRT
<213> ORGANISM: Artificial Sequence
<220> FEATURE:
<223> OTHER INFORMATION: Synthetic: CD40 transcript variant 1 and 6
      NM_001250_5

<400> SEQUENCE: 124

```
Ala Leu Val Val Ile Pro Ile Ile Phe Gly Ile Leu Phe Ala Ile Leu
1               5                   10                  15
```

```
Leu Val Leu Val Phe Ile
            20


<210> SEQ ID NO 125
<211> LENGTH: 22
<212> TYPE: PRT
<213> ORGANISM: Artificial Sequence
<220> FEATURE:
<223> OTHER INFORMATION: Synthetic: CD79A transcript variant 1
      NM_001783_3

<400> SEQUENCE: 125

Ile Ile Thr Ala Glu Gly Ile Ile Leu Leu Phe Cys Ala Val Val Pro
1               5                   10                  15

Gly Thr Leu Leu Leu Phe
            20


<210> SEQ ID NO 126
<211> LENGTH: 22
<212> TYPE: PRT
<213> ORGANISM: Artificial Sequence
<220> FEATURE:
<223> OTHER INFORMATION: Synthetic: CD79B transcript variant 3
      NM_001039933_2

<400> SEQUENCE: 126

Gly Ile Ile Met Ile Gln Thr Leu Leu Ile Ile Leu Phe Ile Ile Val
1               5                   10                  15

Pro Ile Phe Leu Leu Leu
            20


<210> SEQ ID NO 127
<211> LENGTH: 21
<212> TYPE: PRT
<213> ORGANISM: Artificial Sequence
<220> FEATURE:
<223> OTHER INFORMATION: Synthetic: CRLF2 transcript variant 1
      NM_022148_3

<400> SEQUENCE: 127

Phe Ile Leu Ile Ser Ser Leu Ala Ile Leu Leu Met Val Ser Leu Leu
1               5                   10                  15

Leu Leu Ser Leu Trp
            20


<210> SEQ ID NO 128
<211> LENGTH: 21
<212> TYPE: PRT
<213> ORGANISM: Artificial Sequence
<220> FEATURE:
<223> OTHER INFORMATION: Synthetic: CRLF2 transcript variant 1
      NM_022148_3

<400> SEQUENCE: 128

Cys Ile Leu Ile Ser Ser Leu Ala Ile Leu Leu Met Val Ser Leu Leu
1               5                   10                  15

Leu Leu Ser Leu Trp
            20


<210> SEQ ID NO 129
<211> LENGTH: 26
<212> TYPE: PRT
<213> ORGANISM: Artificial Sequence
<220> FEATURE:
<223> OTHER INFORMATION: Synthetic: CSF2RA transcript variant 7 and 8
      NM_001161529_1
```

```
<400> SEQUENCE: 129

Asn Leu Gly Ser Val Tyr Ile Tyr Val Leu Leu Ile Val Gly Thr Leu
1               5                   10                  15

Val Cys Gly Ile Val Leu Gly Phe Leu Phe
            20                  25


<210> SEQ ID NO 130
<211> LENGTH: 19
<212> TYPE: PRT
<213> ORGANISM: Artificial Sequence
<220> FEATURE:
<223> OTHER INFORMATION: Synthetic: CSF2RB NM_000395_2

<400> SEQUENCE: 130

Met Trp Val Leu Ala Leu Ile Val Ile Phe Leu Thr Ile Ala Val Leu
1               5                   10                  15

Leu Ala Leu


<210> SEQ ID NO 131
<211> LENGTH: 19
<212> TYPE: PRT
<213> ORGANISM: Artificial Sequence
<220> FEATURE:
<223> OTHER INFORMATION: Synthetic: CSF2RB NM_000395_2

<400> SEQUENCE: 131

Met Trp Val Leu Ala Leu Ile Glu Ile Phe Leu Thr Ile Ala Val Leu
1               5                   10                  15

Leu Ala Leu


<210> SEQ ID NO 132
<211> LENGTH: 23
<212> TYPE: PRT
<213> ORGANISM: Artificial Sequence
<220> FEATURE:
<223> OTHER INFORMATION: Synthetic: CSF3R transcript variant 1
      NM_000760_3

<400> SEQUENCE: 132

Ile Ile Leu Gly Leu Phe Gly Leu Leu Leu Leu Leu Thr Cys Leu Cys
1               5                   10                  15

Gly Thr Ala Trp Leu Cys Cys
            20


<210> SEQ ID NO 133
<211> LENGTH: 23
<212> TYPE: PRT
<213> ORGANISM: Artificial Sequence
<220> FEATURE:
<223> OTHER INFORMATION: Synthetic: CSF3R transcript variant 1
      NM_000760_3

<400> SEQUENCE: 133

Ile Ile Leu Gly Leu Phe Gly Leu Leu Leu Leu Leu Asn Cys Leu Cys
1               5                   10                  15

Gly Thr Ala Trp Leu Cys Cys
            20


<210> SEQ ID NO 134
<211> LENGTH: 23
<212> TYPE: PRT
<213> ORGANISM: Artificial Sequence
<220> FEATURE:
```

<223> OTHER INFORMATION: Synthetic: EPOR transcript variant 1
      NM_000121_3

<400> SEQUENCE: 134

Leu Ile Leu Thr Leu Ser Leu Ile Leu Val Val Ile Leu Val Leu Leu
1               5                   10                  15

Thr Val Leu Ala Leu Leu Ser
            20

<210> SEQ ID NO 135
<211> LENGTH: 23
<212> TYPE: PRT
<213> ORGANISM: Artificial Sequence
<220> FEATURE:
<223> OTHER INFORMATION: Synthetic: EPOR transcript variant 1
      NM_000121_3

<400> SEQUENCE: 135

Cys Cys Leu Thr Leu Ser Leu Ile Leu Val Val Ile Leu Val Leu Leu
1               5                   10                  15

Thr Val Leu Ala Leu Leu Ser
            20

<210> SEQ ID NO 136
<211> LENGTH: 21
<212> TYPE: PRT
<213> ORGANISM: Artificial Sequence
<220> FEATURE:
<223> OTHER INFORMATION: Synthetic: FCER1G NM_004106_1

<400> SEQUENCE: 136

Leu Cys Tyr Ile Leu Asp Ala Ile Leu Phe Leu Tyr Gly Ile Val Leu
1               5                   10                  15

Thr Leu Leu Tyr Cys
            20

<210> SEQ ID NO 137
<211> LENGTH: 23
<212> TYPE: PRT
<213> ORGANISM: Artificial Sequence
<220> FEATURE:
<223> OTHER INFORMATION: Synthetic: FCGR2C NM_201563_5

<400> SEQUENCE: 137

Ile Ile Val Ala Val Val Thr Gly Ile Ala Val Ala Ala Ile Val Ala
1               5                   10                  15

Ala Val Val Ala Leu Ile Tyr
            20

<210> SEQ ID NO 138
<211> LENGTH: 23
<212> TYPE: PRT
<213> ORGANISM: Artificial Sequence
<220> FEATURE:
<223> OTHER INFORMATION: Synthetic: FCGRA2 transcript variant 1
      NM_001136219_1

<400> SEQUENCE: 138

Ile Ile Val Ala Val Val Ile Ala Thr Ala Val Ala Ala Ile Val Ala
1               5                   10                  15

Ala Val Val Ala Leu Ile Tyr
            20

<210> SEQ ID NO 139

<211> LENGTH: 24
<212> TYPE: PRT
<213> ORGANISM: Artificial Sequence
<220> FEATURE:
<223> OTHER INFORMATION: Synthetic: GHR transcript variant 1 NM_000163_4

<400> SEQUENCE: 139

Phe Pro Trp Leu Leu Ile Ile Ile Phe Gly Ile Phe Gly Leu Thr Val
1 5 10 15

Met Leu Phe Val Phe Leu Phe Ser
20

<210> SEQ ID NO 140
<211> LENGTH: 24
<212> TYPE: PRT
<213> ORGANISM: Artificial Sequence
<220> FEATURE:
<223> OTHER INFORMATION: Synthetic: GHR transcript variant 1 NM_000163_4

<400> SEQUENCE: 140

Phe Pro Trp Leu Leu Cys Ile Ile Phe Gly Ile Phe Gly Leu Thr Val
1 5 10 15

Met Leu Phe Val Phe Leu Phe Ser
20

<210> SEQ ID NO 141
<211> LENGTH: 21
<212> TYPE: PRT
<213> ORGANISM: Artificial Sequence
<220> FEATURE:
<223> OTHER INFORMATION: Synthetic: ICOS NM_012092.3

<400> SEQUENCE: 141

Phe Trp Leu Pro Ile Gly Cys Ala Ala Phe Val Val Val Cys Ile Leu
1 5 10 15

Gly Cys Ile Leu Ile
20

<210> SEQ ID NO 142
<211> LENGTH: 21
<212> TYPE: PRT
<213> ORGANISM: Artificial Sequence
<220> FEATURE:
<223> OTHER INFORMATION: Synthetic: IFNAR1 NM_000629_2

<400> SEQUENCE: 142

Ile Trp Leu Ile Val Gly Ile Cys Ile Ala Leu Phe Ala Leu Pro Phe
1 5 10 15

Val Ile Tyr Ala Ala
20

<210> SEQ ID NO 143
<211> LENGTH: 21
<212> TYPE: PRT
<213> ORGANISM: Artificial Sequence
<220> FEATURE:
<223> OTHER INFORMATION: Synthetic: IFNAR2 transcript variant 1
NM_207585_2

<400> SEQUENCE: 143

Ile Gly Gly Ile Ile Thr Val Phe Leu Ile Ala Leu Val Leu Thr Ser
1 5 10 15

Thr Ile Val Thr Leu
20

```
<210> SEQ ID NO 144
<211> LENGTH: 21
<212> TYPE: PRT
<213> ORGANISM: Artificial Sequence
<220> FEATURE:
<223> OTHER INFORMATION: Synthetic: IFNGR1 NM_000416_2

<400> SEQUENCE: 144

Ser Leu Trp Ile Pro Val Val Ala Ala Leu Leu Leu Phe Leu Val Leu
1               5                   10                  15

Ser Leu Val Phe Ile
            20


<210> SEQ ID NO 145
<211> LENGTH: 21
<212> TYPE: PRT
<213> ORGANISM: Artificial Sequence
<220> FEATURE:
<223> OTHER INFORMATION: Synthetic: IFNGR2 transcript variant 1
      NM_001329128_1

<400> SEQUENCE: 145

Val Ile Leu Ile Ser Val Gly Thr Phe Ser Leu Leu Ser Val Leu Ala
1               5                   10                  15

Gly Ala Cys Phe Phe
            20


<210> SEQ ID NO 146
<211> LENGTH: 21
<212> TYPE: PRT
<213> ORGANISM: Artificial Sequence
<220> FEATURE:
<223> OTHER INFORMATION: Synthetic: IFNLR1 NM_170743_3

<400> SEQUENCE: 146

Phe Leu Val Leu Pro Ser Leu Leu Ile Leu Leu Leu Val Ile Ala Ala
1               5                   10                  15

Gly Gly Val Ile Trp
            20


<210> SEQ ID NO 147
<211> LENGTH: 23
<212> TYPE: PRT
<213> ORGANISM: Artificial Sequence
<220> FEATURE:
<223> OTHER INFORMATION: Synthetic: IL1R1 transcript variant 2
      NM_001288706_1

<400> SEQUENCE: 147

His Met Ile Gly Ile Cys Val Thr Leu Thr Val Ile Ile Val Cys Ser
1               5                   10                  15

Val Phe Ile Tyr Lys Ile Phe
            20


<210> SEQ ID NO 148
<211> LENGTH: 21
<212> TYPE: PRT
<213> ORGANISM: Artificial Sequence
<220> FEATURE:
<223> OTHER INFORMATION: Synthetic: IL1RAP transcript variant 1
      NM_002182_3

<400> SEQUENCE: 148

Val Leu Leu Val Val Ile Leu Ile Val Val Tyr His Val Tyr Trp Leu
1               5                   10                  15
```

Glu Met Val Leu Phe
20

<210> SEQ ID NO 149
<211> LENGTH: 21
<212> TYPE: PRT
<213> ORGANISM: Artificial Sequence
<220> FEATURE:
<223> OTHER INFORMATION: Synthetic: IL1RL1 transcript variant 1 NM_016232.4

<400> SEQUENCE: 149

Ile Tyr Cys Ile Ile Ala Val Cys Ser Val Phe Leu Met Leu Ile Asn
1 5 10 15

Val Leu Val Ile Ile
20

<210> SEQ ID NO 150
<211> LENGTH: 21
<212> TYPE: PRT
<213> ORGANISM: Artificial Sequence
<220> FEATURE:
<223> OTHER INFORMATION: Synthetic: IL1RL2 NM_003854.2

<400> SEQUENCE: 150

Ala Tyr Leu Ile Gly Gly Leu Ile Ala Leu Val Ala Val Ala Val Ser
1 5 10 15

Val Val Tyr Ile Tyr
20

<210> SEQ ID NO 151
<211> LENGTH: 19
<212> TYPE: PRT
<213> ORGANISM: Artificial Sequence
<220> FEATURE:
<223> OTHER INFORMATION: Synthetic: IL2RA transcript variant 1 NM_000417_2

<400> SEQUENCE: 151

Val Ala Val Ala Gly Cys Val Phe Leu Leu Ile Ser Val Leu Leu Leu
1 5 10 15

Ser Gly Leu

<210> SEQ ID NO 152
<211> LENGTH: 25
<212> TYPE: PRT
<213> ORGANISM: Artificial Sequence
<220> FEATURE:
<223> OTHER INFORMATION: Synthetic: IL2RB transcript variant 1 NM_000878_4

<400> SEQUENCE: 152

Ile Pro Trp Leu Gly His Leu Leu Val Gly Leu Ser Gly Ala Phe Gly
1 5 10 15

Phe Ile Ile Leu Val Tyr Leu Leu Ile
20 25

<210> SEQ ID NO 153
<211> LENGTH: 21
<212> TYPE: PRT
<213> ORGANISM: Artificial Sequence
<220> FEATURE:
<223> OTHER INFORMATION: Synthetic: IL2RG NM_000206_2

<400> SEQUENCE: 153

Val Val Ile Ser Val Gly Ser Met Gly Leu Ile Ile Ser Leu Leu Cys
1 5 10 15

Val Tyr Phe Trp Leu
20

<210> SEQ ID NO 154
<211> LENGTH: 20
<212> TYPE: PRT
<213> ORGANISM: Artificial Sequence
<220> FEATURE:
<223> OTHER INFORMATION: Synthetic: IL3RA transcript variant 1 and 2
NM_002183_3

<400> SEQUENCE: 154

Thr Ser Leu Leu Ile Ala Leu Gly Thr Leu Leu Ala Leu Val Cys Val
1 5 10 15

Phe Val Ile Cys
20

<210> SEQ ID NO 155
<211> LENGTH: 24
<212> TYPE: PRT
<213> ORGANISM: Artificial Sequence
<220> FEATURE:
<223> OTHER INFORMATION: Synthetic: IL4R transcript variant 1
NM_000418_3

<400> SEQUENCE: 155

Leu Leu Leu Gly Val Ser Val Ser Cys Ile Val Ile Leu Ala Val Cys
1 5 10 15

Leu Leu Cys Tyr Val Ser Ile Thr
20

<210> SEQ ID NO 156
<211> LENGTH: 20
<212> TYPE: PRT
<213> ORGANISM: Artificial Sequence
<220> FEATURE:
<223> OTHER INFORMATION: Synthetic: IL5RA transcript variant 1
NM_000564_4

<400> SEQUENCE: 156

Phe Val Ile Val Ile Met Ala Thr Ile Cys Phe Ile Leu Leu Ile Leu
1 5 10 15

Ser Leu Ile Cys
20

<210> SEQ ID NO 157
<211> LENGTH: 21
<212> TYPE: PRT
<213> ORGANISM: Artificial Sequence
<220> FEATURE:
<223> OTHER INFORMATION: Synthetic: IL6R transcript variant 1
NM_000565_3

<400> SEQUENCE: 157

Thr Phe Leu Val Ala Gly Gly Ser Leu Ala Phe Gly Thr Leu Leu Cys
1 5 10 15

Ile Ala Ile Val Leu
20

<210> SEQ ID NO 158
<211> LENGTH: 22
<212> TYPE: PRT

<213> ORGANISM: Artificial Sequence
<220> FEATURE:
<223> OTHER INFORMATION: Synthetic: IL6ST transcript variant 1 and 3
NM_002184_3

<400> SEQUENCE: 158

Ala Ile Val Val Pro Val Cys Leu Ala Phe Leu Leu Thr Thr Leu Leu
1 5 10 15

Gly Val Leu Phe Cys Phe
20

<210> SEQ ID NO 159
<211> LENGTH: 23
<212> TYPE: PRT
<213> ORGANISM: Artificial Sequence
<220> FEATURE:
<223> OTHER INFORMATION: Synthetic: IL7RA NM_002185_3

<400> SEQUENCE: 159

Ile Leu Leu Thr Ile Ser Ile Leu Ser Phe Phe Ser Val Ala Leu Leu
1 5 10 15

Val Ile Leu Ala Cys Val Leu
20

<210> SEQ ID NO 160
<211> LENGTH: 27
<212> TYPE: PRT
<213> ORGANISM: Artificial Sequence
<220> FEATURE:
<223> OTHER INFORMATION: Synthetic: IL7RA Ins PPCL (interleukin 7
receptor)

<400> SEQUENCE: 160

Ile Leu Leu Pro Pro Cys Leu Thr Ile Ser Ile Leu Ser Phe Phe Ser
1 5 10 15

Val Ala Leu Leu Val Ile Leu Ala Cys Val Leu
20 25

<210> SEQ ID NO 161
<211> LENGTH: 21
<212> TYPE: PRT
<213> ORGANISM: Artificial Sequence
<220> FEATURE:
<223> OTHER INFORMATION: Synthetic: IL9R transcript variant 1
NM_002186_2

<400> SEQUENCE: 161

Gly Asn Thr Leu Val Ala Val Ser Ile Phe Leu Leu Leu Thr Gly Pro
1 5 10 15

Thr Tyr Leu Leu Phe
20

<210> SEQ ID NO 162
<211> LENGTH: 21
<212> TYPE: PRT
<213> ORGANISM: Artificial Sequence
<220> FEATURE:
<223> OTHER INFORMATION: Synthetic: IL10RA transcript variant 1
NM_001558_3

<400> SEQUENCE: 162

Val Ile Ile Phe Phe Ala Phe Val Leu Leu Leu Ser Gly Ala Leu Ala
1 5 10 15

Tyr Cys Leu Ala Leu
20

<210> SEQ ID NO 163
<211> LENGTH: 22
<212> TYPE: PRT
<213> ORGANISM: Artificial Sequence
<220> FEATURE:
<223> OTHER INFORMATION: Synthetic: IL10RB NM_000628_4

<400> SEQUENCE: 163

Trp Met Val Ala Val Ile Leu Met Ala Ser Val Phe Met Val Cys Leu
1 5 10 15

Ala Leu Leu Gly Cys Phe
20

<210> SEQ ID NO 164
<211> LENGTH: 21
<212> TYPE: PRT
<213> ORGANISM: Artificial Sequence
<220> FEATURE:
<223> OTHER INFORMATION: Synthetic: IL11RA NM_001142784_2

<400> SEQUENCE: 164

Ser Leu Gly Ile Leu Ser Phe Leu Gly Leu Val Ala Gly Ala Leu Ala
1 5 10 15

Leu Gly Leu Trp Leu
20

<210> SEQ ID NO 165
<211> LENGTH: 25
<212> TYPE: PRT
<213> ORGANISM: Artificial Sequence
<220> FEATURE:
<223> OTHER INFORMATION: Synthetic: IL12RB1 transcript variant 1 and 4
NM_005535_2

<400> SEQUENCE: 165

Trp Leu Ile Phe Phe Ala Ser Leu Gly Ser Phe Leu Ser Ile Leu Leu
1 5 10 15

Val Gly Val Leu Gly Tyr Leu Gly Leu
20 25

<210> SEQ ID NO 166
<211> LENGTH: 21
<212> TYPE: PRT
<213> ORGANISM: Artificial Sequence
<220> FEATURE:
<223> OTHER INFORMATION: Synthetic: IL12RB2 transcript variant 1 and 3
NM_001559_2

<400> SEQUENCE: 166

Trp Met Ala Phe Val Ala Pro Ser Ile Cys Ile Ala Ile Ile Met Val
1 5 10 15

Gly Ile Phe Ser Thr
20

<210> SEQ ID NO 167
<211> LENGTH: 24
<212> TYPE: PRT
<213> ORGANISM: Artificial Sequence
<220> FEATURE:
<223> OTHER INFORMATION: Synthetic: IL13RA1 NM_001560_2

<400> SEQUENCE: 167

Leu Tyr Ile Thr Met Leu Leu Ile Val Pro Val Ile Val Ala Gly Ala
1 5 10 15

Ile Ile Val Leu Leu Leu Tyr Leu
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic: IL13RA2 NM_000640_2

<400> SEQUENCE: 168

Phe Trp Leu Pro Phe Gly Phe Ile Leu Ile Leu Val Ile Phe Val Thr
1               5                   10                  15

Gly Leu Leu Leu
            20

<210> SEQ ID NO 169
<211> LENGTH: 23
<212> TYPE: PRT
<213> ORGANISM: Artificial Sequence
<220> FEATURE:
<223> OTHER INFORMATION: Synthetic: IL15RA transcript variant 4
      NM_001256765_1

<400> SEQUENCE: 169

Val Ala Ile Ser Thr Ser Thr Val Leu Leu Cys Gly Leu Ser Ala Val
1               5                   10                  15

Ser Leu Leu Ala Cys Tyr Leu
            20

<210> SEQ ID NO 170
<211> LENGTH: 21
<212> TYPE: PRT
<213> ORGANISM: Artificial Sequence
<220> FEATURE:
<223> OTHER INFORMATION: Synthetic: IL17RA NM_014339_6

<400> SEQUENCE: 170

Val Tyr Trp Phe Ile Thr Gly Ile Ser Ile Leu Leu Val Gly Ser Val
1               5                   10                  15

Ile Leu Leu Ile Val
            20

<210> SEQ ID NO 171
<211> LENGTH: 21
<212> TYPE: PRT
<213> ORGANISM: Artificial Sequence
<220> FEATURE:
<223> OTHER INFORMATION: Synthetic: IL17RB NM_018725_3

<400> SEQUENCE: 171

Leu Leu Leu Leu Ser Leu Leu Val Ala Thr Trp Val Leu Val Ala Gly
1               5                   10                  15

Ile Tyr Leu Met Trp
            20

<210> SEQ ID NO 172
<211> LENGTH: 21
<212> TYPE: PRT
<213> ORGANISM: Artificial Sequence
<220> FEATURE:
<223> OTHER INFORMATION: Synthetic: IL17RC transcript variant 1
      NM_153460_3

<400> SEQUENCE: 172

Trp Ala Leu Val Trp Leu Ala Cys Leu Leu Phe Ala Ala Ala Leu Ser
1 5 10 15

Leu Ile Leu Leu Leu
20

<210> SEQ ID NO 173
<211> LENGTH: 21
<212> TYPE: PRT
<213> ORGANISM: Artificial Sequence
<220> FEATURE:
<223> OTHER INFORMATION: Synthetic: IL17RD transcript variant 2
NM_017563_4

<400> SEQUENCE: 173

Ala Val Ala Ile Thr Val Pro Leu Val Val Ile Ser Ala Phe Ala Thr
1 5 10 15

Leu Phe Thr Val Met
20

<210> SEQ ID NO 174
<211> LENGTH: 21
<212> TYPE: PRT
<213> ORGANISM: Artificial Sequence
<220> FEATURE:
<223> OTHER INFORMATION: Synthetic: IL17RE transcript variant 1
NM_153480_1

<400> SEQUENCE: 174

Leu Gly Leu Leu Ile Leu Ala Leu Leu Ala Leu Leu Thr Leu Leu Gly
1 5 10 15

Val Val Leu Ala Leu
20

<210> SEQ ID NO 175
<211> LENGTH: 21
<212> TYPE: PRT
<213> ORGANISM: Artificial Sequence
<220> FEATURE:
<223> OTHER INFORMATION: Synthetic: IL18R1 transcript variant 1
NM_003855_3

<400> SEQUENCE: 175

Gly Met Ile Ile Ala Val Leu Ile Leu Val Ala Val Val Cys Leu Val
1 5 10 15

Thr Val Cys Val Ile
20

<210> SEQ ID NO 176
<211> LENGTH: 21
<212> TYPE: PRT
<213> ORGANISM: Artificial Sequence
<220> FEATURE:
<223> OTHER INFORMATION: Synthetic: IL18RAP NM_003853_3

<400> SEQUENCE: 176

Gly Val Val Leu Leu Tyr Ile Leu Leu Gly Thr Ile Gly Thr Leu Val
1 5 10 15

Ala Val Leu Ala Ala
20

<210> SEQ ID NO 177
<211> LENGTH: 21
<212> TYPE: PRT
<213> ORGANISM: Artificial Sequence
<220> FEATURE:
<223> OTHER INFORMATION: Synthetic: IL20RA transcript variant 1
NM_014432_3

<400> SEQUENCE: 177

Ile Ile Phe Trp Tyr Val Leu Pro Ile Ser Ile Thr Val Phe Leu Phe
1 5 10 15

Ser Val Met Gly Tyr
20

<210> SEQ ID NO 178
<211> LENGTH: 21
<212> TYPE: PRT
<213> ORGANISM: Artificial Sequence
<220> FEATURE:
<223> OTHER INFORMATION: Synthetic: IL20RB NM_144717_3

<400> SEQUENCE: 178

Val Leu Ala Leu Phe Ala Phe Val Gly Phe Met Leu Ile Leu Val Val
1 5 10 15

Val Pro Leu Phe Val
20

<210> SEQ ID NO 179
<211> LENGTH: 21
<212> TYPE: PRT
<213> ORGANISM: Artificial Sequence
<220> FEATURE:
<223> OTHER INFORMATION: Synthetic: IL21R transcript variant 2
NM_181078_2

<400> SEQUENCE: 179

Gly Trp Asn Pro His Leu Leu Leu Leu Leu Leu Leu Val Ile Val Phe
1 5 10 15

Ile Pro Ala Phe Trp
20

<210> SEQ ID NO 180
<211> LENGTH: 21
<212> TYPE: PRT
<213> ORGANISM: Artificial Sequence
<220> FEATURE:
<223> OTHER INFORMATION: Synthetic: IL22RA1 NM_021258_3

<400> SEQUENCE: 180

Tyr Ser Phe Ser Gly Ala Phe Leu Phe Ser Met Gly Phe Leu Val Ala
1 5 10 15

Val Leu Cys Tyr Leu
20

<210> SEQ ID NO 181
<211> LENGTH: 21
<212> TYPE: PRT
<213> ORGANISM: Artificial Sequence
<220> FEATURE:
<223> OTHER INFORMATION: Synthetic: IL23R NM_144701_2

<400> SEQUENCE: 181

Leu Leu Leu Gly Met Ile Val Phe Ala Val Met Leu Ser Ile Leu Ser
1 5 10 15

Leu Ile Gly Ile Phe
20

<210> SEQ ID NO 182

```
<211> LENGTH: 21
<212> TYPE: PRT
<213> ORGANISM: Artificial Sequence
<220> FEATURE:
<223> OTHER INFORMATION: Synthetic: IL27RA NM_004843_3

<400> SEQUENCE: 182

Val Leu Pro Gly Ile Leu Phe Leu Trp Gly Leu Phe Leu Leu Gly Cys
1               5                   10                  15

Gly Leu Ser Leu Ala
            20


<210> SEQ ID NO 183
<211> LENGTH: 21
<212> TYPE: PRT
<213> ORGANISM: Artificial Sequence
<220> FEATURE:
<223> OTHER INFORMATION: Synthetic: IL27RA NM_004843_3

<400> SEQUENCE: 183

Val Leu Pro Gly Ile Leu Cys Leu Trp Gly Leu Phe Leu Leu Gly Cys
1               5                   10                  15

Gly Leu Ser Leu Ala
            20


<210> SEQ ID NO 184
<211> LENGTH: 24
<212> TYPE: PRT
<213> ORGANISM: Artificial Sequence
<220> FEATURE:
<223> OTHER INFORMATION: Synthetic: IL31RA transcript variant 1
      NM_139017_5

<400> SEQUENCE: 184

Ile Ile Leu Ile Thr Ser Leu Ile Gly Gly Gly Leu Leu Ile Leu Ile
1               5                   10                  15

Ile Leu Thr Val Ala Tyr Gly Leu
            20


<210> SEQ ID NO 185
<211> LENGTH: 23
<212> TYPE: PRT
<213> ORGANISM: Artificial Sequence
<220> FEATURE:
<223> OTHER INFORMATION: Synthetic: LEPR transcript variant 1
      NM_002303_5

<400> SEQUENCE: 185

Ala Gly Leu Tyr Val Ile Val Pro Val Ile Ile Ser Ser Ser Ile Leu
1               5                   10                  15

Leu Leu Gly Thr Leu Leu Ile
            20


<210> SEQ ID NO 186
<211> LENGTH: 25
<212> TYPE: PRT
<213> ORGANISM: Artificial Sequence
<220> FEATURE:
<223> OTHER INFORMATION: Synthetic: LIFR NM_001127671_1

<400> SEQUENCE: 186

Val Gly Leu Ile Ile Ala Ile Leu Ile Pro Val Ala Val Ala Val Ile
1               5                   10                  15

Val Gly Val Val Thr Ser Ile Leu Cys
            20                  25
```

<210> SEQ ID NO 187
<211> LENGTH: 22
<212> TYPE: PRT
<213> ORGANISM: Artificial Sequence
<220> FEATURE:
<223> OTHER INFORMATION: Synthetic: MPL NM_005373_2

<400> SEQUENCE: 187

```
Ile Ser Leu Val Thr Ala Leu His Leu Val Leu Gly Leu Ser Ala Val
1               5                   10                  15

Leu Gly Leu Leu Leu Leu
            20
```

<210> SEQ ID NO 188
<211> LENGTH: 22
<212> TYPE: PRT
<213> ORGANISM: Artificial Sequence
<220> FEATURE:
<223> OTHER INFORMATION: Synthetic: MPL NM_005373_2

<400> SEQUENCE: 188

```
Ile Ser Leu Val Thr Ala Leu His Leu Val Leu Gly Leu Asn Ala Val
1               5                   10                  15

Leu Gly Leu Leu Leu Leu
            20
```

<210> SEQ ID NO 189
<211> LENGTH: 21
<212> TYPE: PRT
<213> ORGANISM: Artificial Sequence
<220> FEATURE:
<223> OTHER INFORMATION: Synthetic: OSMR transcript variant 4
      NM_001323505_1

<400> SEQUENCE: 189

```
Leu Ile His Ile Leu Leu Pro Met Val Phe Cys Val Leu Leu Ile Met
1               5                   10                  15

Val Met Cys Tyr Leu
            20
```

<210> SEQ ID NO 190
<211> LENGTH: 24
<212> TYPE: PRT
<213> ORGANISM: Artificial Sequence
<220> FEATURE:
<223> OTHER INFORMATION: Synthetic: PRLR transcript variant 1
      NM_000949_6

<400> SEQUENCE: 190

```
Thr Thr Val Trp Ile Ser Val Ala Val Leu Ser Ala Val Ile Cys Leu
1               5                   10                  15

Ile Ile Val Trp Ala Val Ala Leu
            20
```

<210> SEQ ID NO 191
<211> LENGTH: 21
<212> TYPE: PRT
<213> ORGANISM: Artificial Sequence
<220> FEATURE:
<223> OTHER INFORMATION: Synthetic: TNFRSF4 NM_003327_3

<400> SEQUENCE: 191

```
Val Ala Ala Ile Leu Gly Leu Gly Leu Val Leu Gly Leu Leu Gly Pro
1               5                   10                  15
```

Leu Ala Ile Leu Leu
20

<210> SEQ ID NO 192
<211> LENGTH: 28
<212> TYPE: PRT
<213> ORGANISM: Artificial Sequence
<220> FEATURE:
<223> OTHER INFORMATION: Synthetic: TNFRSF8 transcript variant 1 NM_001243_4

<400> SEQUENCE: 192

Pro Val Leu Asp Ala Gly Pro Val Leu Phe Trp Val Ile Leu Val Leu
1 5 10 15

Val Val Val Val Gly Ser Ser Ala Phe Leu Leu Cys
20 25

<210> SEQ ID NO 193
<211> LENGTH: 27
<212> TYPE: PRT
<213> ORGANISM: Artificial Sequence
<220> FEATURE:
<223> OTHER INFORMATION: Synthetic: TNFRSF9 NM_001561_5

<400> SEQUENCE: 193

Ile Ile Ser Phe Phe Leu Ala Leu Thr Ser Thr Ala Leu Leu Phe Leu
1 5 10 15

Leu Phe Phe Leu Thr Leu Arg Phe Ser Val Val
20 25

<210> SEQ ID NO 194
<211> LENGTH: 21
<212> TYPE: PRT
<213> ORGANISM: Artificial Sequence
<220> FEATURE:
<223> OTHER INFORMATION: Synthetic: TNFRSF14 transcript variant 1 NM_003820_3

<400> SEQUENCE: 194

Trp Trp Phe Leu Ser Gly Ser Leu Val Ile Val Ile Val Cys Ser Thr
1 5 10 15

Val Gly Leu Ile Ile
20

<210> SEQ ID NO 195
<211> LENGTH: 21
<212> TYPE: PRT
<213> ORGANISM: Artificial Sequence
<220> FEATURE:
<223> OTHER INFORMATION: Synthetic: TNFRSF18 transcript variant 1 NM_004195_2

<400> SEQUENCE: 195

Leu Gly Trp Leu Thr Val Val Leu Leu Ala Val Ala Ala Cys Val Leu
1 5 10 15

Leu Leu Thr Ser Ala
20

<210> SEQ ID NO 196
<211> LENGTH: 117
<212> TYPE: PRT
<213> ORGANISM: Artificial Sequence
<220> FEATURE:
<223> OTHER INFORMATION: Synthetic: CD2 transcript variant 1 NM_001328609_1

<400> SEQUENCE: 196

Thr Lys Arg Lys Lys Gln Arg Ser Arg Arg Asn Asp Glu Glu Leu Glu
1               5                   10                  15

Thr Arg Ala His Arg Val Ala Thr Glu Glu Arg Gly Arg Lys Pro His
            20                  25                  30

Gln Ile Pro Ala Ser Thr Pro Gln Asn Pro Ala Thr Ser Gln His Pro
        35                  40                  45

Pro Pro Pro Pro Gly His Arg Ser Gln Ala Pro Ser His Arg Pro Pro
    50                  55                  60

Pro Pro Gly His Arg Val Gln His Gln Pro Gln Lys Arg Pro Pro Ala
65                  70                  75                  80

Pro Ser Gly Thr Gln Val His Gln Gln Lys Gly Pro Pro Leu Pro Arg
                85                  90                  95

Pro Arg Val Gln Pro Lys Pro Pro His Gly Ala Ala Glu Asn Ser Leu
            100                 105                 110

Ser Pro Ser Ser Asn
        115

<210> SEQ ID NO 197
<211> LENGTH: 45
<212> TYPE: PRT
<213> ORGANISM: Artificial Sequence
<220> FEATURE:
<223> OTHER INFORMATION: Synthetic: CD3D transcript variant 1
      NM_000732_4

<400> SEQUENCE: 197

Gly His Glu Thr Gly Arg Leu Ser Gly Ala Ala Asp Thr Gln Ala Leu
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys
        35                  40                  45

<210> SEQ ID NO 198
<211> LENGTH: 55
<212> TYPE: PRT
<213> ORGANISM: Artificial Sequence
<220> FEATURE:
<223> OTHER INFORMATION: Synthetic: CD3E NM_000733_3

<400> SEQUENCE: 198

Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55

<210> SEQ ID NO 199
<211> LENGTH: 45
<212> TYPE: PRT
<213> ORGANISM: Artificial Sequence
<220> FEATURE:
<223> OTHER INFORMATION: Synthetic: CD3G NM_000073_2

<400> SEQUENCE: 199

-continued

```
Gly Gln Asp Gly Val Arg Gln Ser Arg Ala Ser Asp Lys Gln Thr Leu
1               5                   10                  15

Leu Pro Asn Asp Gln Leu Tyr Gln Pro Leu Lys Asp Arg Glu Asp Asp
            20                  25                  30

Gln Tyr Ser His Leu Gln Gly Asn Gln Leu Arg Arg Asn
        35                  40                  45


<210> SEQ ID NO 200
<211> LENGTH: 40
<212> TYPE: PRT
<213> ORGANISM: Artificial Sequence
<220> FEATURE:
<223> OTHER INFORMATION: Synthetic: CD4 transcript variant 1 and 2
      NM_000616_4

<400> SEQUENCE: 200

Cys Val Arg Cys Arg His Arg Arg Arg Gln Ala Glu Arg Met Ser Gln
1               5                   10                  15

Ile Lys Arg Leu Leu Ser Glu Lys Lys Thr Cys Gln Cys Pro His Arg
            20                  25                  30

Phe Gln Lys Thr Cys Ser Pro Ile
        35                  40


<210> SEQ ID NO 201
<211> LENGTH: 32
<212> TYPE: PRT
<213> ORGANISM: Artificial Sequence
<220> FEATURE:
<223> OTHER INFORMATION: Synthetic: CD8A transcript variant 1
      NM_001768_6

<400> SEQUENCE: 201

Leu Tyr Cys Asn His Arg Asn Arg Arg Arg Val Cys Lys Cys Pro Arg
1               5                   10                  15

Pro Val Val Lys Ser Gly Asp Lys Pro Ser Leu Ser Ala Arg Tyr Val
            20                  25                  30


<210> SEQ ID NO 202
<211> LENGTH: 48
<212> TYPE: PRT
<213> ORGANISM: Artificial Sequence
<220> FEATURE:
<223> OTHER INFORMATION: Synthetic: CD8B transcript variant 2
      NM_172213_3

<400> SEQUENCE: 202

Arg Arg Arg Arg Ala Arg Leu Arg Phe Met Lys Gln Pro Gln Gly Glu
1               5                   10                  15

Gly Ile Ser Gly Thr Phe Val Pro Gln Cys Leu His Gly Tyr Tyr Ser
            20                  25                  30

Asn Thr Thr Thr Ser Gln Lys Leu Leu Asn Pro Trp Ile Leu Lys Thr
        35                  40                  45


<210> SEQ ID NO 203
<211> LENGTH: 26
<212> TYPE: PRT
<213> ORGANISM: Artificial Sequence
<220> FEATURE:
<223> OTHER INFORMATION: Synthetic: CD8B transcript variant 3
      NM_172101_3

<400> SEQUENCE: 203

Arg Arg Arg Arg Ala Arg Leu Arg Phe Met Lys Gln Leu Arg Leu His
1               5                   10                  15
```

```
Pro Leu Glu Lys Cys Ser Arg Met Asp Tyr
            20                  25


<210> SEQ ID NO 204
<211> LENGTH: 15
<212> TYPE: PRT
<213> ORGANISM: Artificial Sequence
<220> FEATURE:
<223> OTHER INFORMATION: Synthetic: CD8B transcript variant 5
      NM_004931_4

<400> SEQUENCE: 204

Arg Arg Arg Arg Ala Arg Leu Arg Phe Met Lys Gln Phe Tyr Lys
1               5                   10                  15


<210> SEQ ID NO 205
<211> LENGTH: 48
<212> TYPE: PRT
<213> ORGANISM: Artificial Sequence
<220> FEATURE:
<223> OTHER INFORMATION: Synthetic: CD27 NM_001242_4

<400> SEQUENCE: 205

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 206
<211> LENGTH: 41
<212> TYPE: PRT
<213> ORGANISM: Artificial Sequence
<220> FEATURE:
<223> OTHER INFORMATION: Synthetic: mutated Delta Lck CD28 transcript
      variant 1 NM_006139_3

<400> SEQUENCE: 206

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser
        35                  40


<210> SEQ ID NO 207
<211> LENGTH: 41
<212> TYPE: PRT
<213> ORGANISM: Artificial Sequence
<220> FEATURE:
<223> OTHER INFORMATION: Synthetic: CD28 transcript variant 1
      NM_006139_3

<400> SEQUENCE: 207

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 208
```

```
<211> LENGTH: 62
<212> TYPE: PRT
<213> ORGANISM: Artificial Sequence
<220> FEATURE:
<223> OTHER INFORMATION: Synthetic: CD40 transcript variant 1 and 6
      NM_001250_5

<400> SEQUENCE: 208

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60


<210> SEQ ID NO 209
<211> LENGTH: 66
<212> TYPE: PRT
<213> ORGANISM: Artificial Sequence
<220> FEATURE:
<223> OTHER INFORMATION: Synthetic: CD40 transcript variant 5
      NM_001322421_1

<400> SEQUENCE: 209

Ser Glu Ser Ser Glu Lys Val Ala Lys Lys Pro Thr Asn Lys Ala Pro
1               5                   10                  15

His Pro Lys Gln Glu Pro Gln Glu Ile Asn Phe Pro Asp Asp Leu Pro
            20                  25                  30

Gly Ser Asn Thr Ala Ala Pro Val Gln Glu Thr Leu His Gly Cys Gln
        35                  40                  45

Pro Val Thr Gln Glu Asp Gly Lys Glu Ser Arg Ile Ser Val Gln Glu
    50                  55                  60

Arg Gln
65


<210> SEQ ID NO 210
<211> LENGTH: 61
<212> TYPE: PRT
<213> ORGANISM: Artificial Sequence
<220> FEATURE:
<223> OTHER INFORMATION: Synthetic: CD79A transcript variant 1
      NM_001783_3

<400> SEQUENCE: 210

Arg Lys Arg Trp Gln Asn Glu Lys Leu Gly Leu Asp Ala Gly Asp Glu
1               5                   10                  15

Tyr Glu Asp Glu Asn Leu Tyr Glu Gly Leu Asn Leu Asp Asp Cys Ser
            20                  25                  30

Met Tyr Glu Asp Ile Ser Arg Gly Leu Gln Gly Thr Tyr Gln Asp Val
        35                  40                  45

Gly Ser Leu Asn Ile Gly Asp Val Gln Leu Glu Lys Pro
    50                  55                  60


<210> SEQ ID NO 211
<211> LENGTH: 49
<212> TYPE: PRT
<213> ORGANISM: Artificial Sequence
<220> FEATURE:
<223> OTHER INFORMATION: Synthetic: CD79B transcript variant 3
      NM_001039933_2
```

<400> SEQUENCE: 211

Leu Asp Lys Asp Asp Ser Lys Ala Gly Met Glu Glu Asp His Thr Tyr
1 5 10 15

Glu Gly Leu Asp Ile Asp Gln Thr Ala Thr Tyr Glu Asp Ile Val Thr
20 25 30

Leu Arg Thr Gly Glu Val Lys Trp Ser Val Gly Glu His Pro Gly Gln
35 40 45

Glu

<210> SEQ ID NO 212
<211> LENGTH: 119
<212> TYPE: PRT
<213> ORGANISM: Artificial Sequence
<220> FEATURE:
<223> OTHER INFORMATION: Synthetic: CRLF2 transcript variant 1
NM_022148_3

<400> SEQUENCE: 212

Lys Leu Trp Arg Val Lys Lys Phe Leu Ile Pro Ser Val Pro Asp Pro
1 5 10 15

Lys Ser Ile Phe Pro Gly Leu Phe Glu Ile His Gln Gly Asn Phe Gln
20 25 30

Glu Trp Ile Thr Asp Thr Gln Asn Val Ala His Leu His Lys Met Ala
35 40 45

Gly Ala Glu Gln Glu Ser Gly Pro Glu Glu Pro Leu Val Val Gln Leu
50 55 60

Ala Lys Thr Glu Ala Glu Ser Pro Arg Met Leu Asp Pro Gln Thr Glu
65 70 75 80

Glu Lys Glu Ala Ser Gly Gly Ser Leu Gln Leu Pro His Gln Pro Leu
85 90 95

Gln Gly Gly Asp Val Val Thr Ile Gly Gly Phe Thr Phe Val Met Asn
100 105 110

Asp Arg Ser Tyr Val Ala Leu
115

<210> SEQ ID NO 213
<211> LENGTH: 437
<212> TYPE: PRT
<213> ORGANISM: Artificial Sequence
<220> FEATURE:
<223> OTHER INFORMATION: Synthetic: CSF2RB NM_000395_2

<400> SEQUENCE: 213

Arg Phe Cys Gly Ile Tyr Gly Tyr Arg Leu Arg Arg Lys Trp Glu Glu
1 5 10 15

Lys Ile Pro Asn Pro Ser Lys Ser His Leu Phe Gln Asn Gly Ser Ala
20 25 30

Glu Leu Trp Pro Pro Gly Ser Met Ser Ala Phe Thr Ser Gly Ser Pro
35 40 45

Pro His Gln Gly Pro Trp Gly Ser Arg Phe Pro Glu Leu Glu Gly Val
50 55 60

Phe Pro Val Gly Phe Gly Asp Ser Glu Val Ser Pro Leu Thr Ile Glu
65 70 75 80

Asp Pro Lys His Val Cys Asp Pro Pro Ser Gly Pro Asp Thr Thr Pro
85 90 95

Ala Ala Ser Asp Leu Pro Thr Glu Gln Pro Pro Ser Pro Gln Pro Gly
100 105 110

```
Pro Pro Ala Ala Ser His Thr Pro Glu Lys Gln Ala Ser Ser Phe Asp
        115                 120                 125

Phe Asn Gly Pro Tyr Leu Gly Pro Pro His Ser Arg Ser Leu Pro Asp
    130                 135                 140

Ile Leu Gly Gln Pro Glu Pro Pro Gln Glu Gly Gly Ser Gln Lys Ser
145                 150                 155                 160

Pro Pro Pro Gly Ser Leu Glu Tyr Leu Cys Leu Pro Ala Gly Gly Gln
                165                 170                 175

Val Gln Leu Val Pro Leu Ala Gln Ala Met Gly Pro Gly Gln Ala Val
            180                 185                 190

Glu Val Glu Arg Arg Pro Ser Gln Gly Ala Ala Gly Ser Pro Ser Leu
        195                 200                 205

Glu Ser Gly Gly Gly Pro Ala Pro Pro Ala Leu Gly Pro Arg Val Gly
    210                 215                 220

Gly Gln Asp Gln Lys Asp Ser Pro Val Ala Ile Pro Met Ser Ser Gly
225                 230                 235                 240

Asp Thr Glu Asp Pro Gly Val Ala Ser Gly Tyr Val Ser Ser Ala Asp
                245                 250                 255

Leu Val Phe Thr Pro Asn Ser Gly Ala Ser Ser Val Ser Leu Val Pro
            260                 265                 270

Ser Leu Gly Leu Pro Ser Asp Gln Thr Pro Ser Leu Cys Pro Gly Leu
        275                 280                 285

Ala Ser Gly Pro Pro Gly Ala Pro Gly Pro Val Lys Ser Gly Phe Glu
    290                 295                 300

Gly Tyr Val Glu Leu Pro Pro Ile Glu Gly Arg Ser Pro Arg Ser Pro
305                 310                 315                 320

Arg Asn Asn Pro Val Pro Pro Glu Ala Lys Ser Pro Val Leu Asn Pro
                325                 330                 335

Gly Glu Arg Pro Ala Asp Val Ser Pro Thr Ser Pro Gln Pro Glu Gly
            340                 345                 350

Leu Leu Val Leu Gln Gln Val Gly Asp Tyr Cys Phe Leu Pro Gly Leu
        355                 360                 365

Gly Pro Gly Pro Leu Ser Leu Arg Ser Lys Pro Ser Ser Pro Gly Pro
    370                 375                 380

Gly Pro Glu Ile Lys Asn Leu Asp Gln Ala Phe Gln Val Lys Lys Pro
385                 390                 395                 400

Pro Gly Gln Ala Val Pro Gln Val Pro Val Ile Gln Leu Phe Lys Ala
                405                 410                 415

Leu Lys Gln Gln Asp Tyr Leu Ser Leu Pro Pro Trp Glu Val Asn Lys
            420                 425                 430

Pro Gly Glu Val Cys
        435


<210> SEQ ID NO 214
<211> LENGTH: 54
<212> TYPE: PRT
<213> ORGANISM: Artificial Sequence
<220> FEATURE:
<223> OTHER INFORMATION: Synthetic: CSF2RA transcript variant 7 and 8
      NM_001161529_1

<400> SEQUENCE: 214

Lys Arg Phe Leu Arg Ile Gln Arg Leu Phe Pro Pro Val Pro Gln Ile
1               5                   10                  15

Lys Asp Lys Leu Asn Asp Asn His Glu Val Glu Asp Glu Ile Ile Trp
            20                  25                  30
```

```
Glu Glu Phe Thr Pro Glu Glu Gly Lys Gly Tyr Arg Glu Glu Val Leu
        35                  40                  45

Thr Val Lys Glu Ile Thr
    50


<210> SEQ ID NO 215
<211> LENGTH: 64
<212> TYPE: PRT
<213> ORGANISM: Artificial Sequence
<220> FEATURE:
<223> OTHER INFORMATION: Synthetic: CSF2RA transcript variant 9
      NM_001161531_1

<400> SEQUENCE: 215

Lys Arg Phe Leu Arg Ile Gln Arg Leu Phe Pro Pro Val Pro Gln Ile
1               5                   10                  15

Lys Asp Lys Leu Asn Asp Asn His Glu Val Glu Asp Glu Met Gly Pro
            20                  25                  30

Gln Arg His His Arg Cys Gly Trp Asn Leu Tyr Pro Thr Pro Gly Pro
        35                  40                  45

Ser Pro Gly Ser Gly Ser Ser Pro Arg Leu Gly Ser Glu Ser Ser Leu
    50                  55                  60


<210> SEQ ID NO 216
<211> LENGTH: 186
<212> TYPE: PRT
<213> ORGANISM: Artificial Sequence
<220> FEATURE:
<223> OTHER INFORMATION: Synthetic: CSF3R transcript variant 1
      NM_000760_3

<400> SEQUENCE: 216

Ser Pro Asn Arg Lys Asn Pro Leu Trp Pro Ser Val Pro Asp Pro Ala
1               5                   10                  15

His Ser Ser Leu Gly Ser Trp Val Pro Thr Ile Met Glu Glu Asp Ala
            20                  25                  30

Phe Gln Leu Pro Gly Leu Gly Thr Pro Pro Ile Thr Lys Leu Thr Val
        35                  40                  45

Leu Glu Glu Asp Glu Lys Lys Pro Val Pro Trp Glu Ser His Asn Ser
    50                  55                  60

Ser Glu Thr Cys Gly Leu Pro Thr Leu Val Gln Thr Tyr Val Leu Gln
65                  70                  75                  80

Gly Asp Pro Arg Ala Val Ser Thr Gln Pro Gln Ser Gln Ser Gly Thr
                85                  90                  95

Ser Asp Gln Val Leu Tyr Gly Gln Leu Leu Gly Ser Pro Thr Ser Pro
            100                 105                 110

Gly Pro Gly His Tyr Leu Arg Cys Asp Ser Thr Gln Pro Leu Leu Ala
        115                 120                 125

Gly Leu Thr Pro Ser Pro Lys Ser Tyr Glu Asn Leu Trp Phe Gln Ala
    130                 135                 140

Ser Pro Leu Gly Thr Leu Val Thr Pro Ala Pro Ser Gln Glu Asp Asp
145                 150                 155                 160

Cys Val Phe Gly Pro Leu Leu Asn Phe Pro Leu Leu Gln Gly Ile Arg
                165                 170                 175

Val His Gly Met Glu Ala Leu Gly Ser Phe
            180                 185


<210> SEQ ID NO 217
```

<211> LENGTH: 213
<212> TYPE: PRT
<213> ORGANISM: Artificial Sequence
<220> FEATURE:
<223> OTHER INFORMATION: Synthetic: CSF3R transcript variant 3
NM_156039_3

<400> SEQUENCE: 217

```
Ser Pro Asn Arg Lys Asn Pro Leu Trp Pro Ser Val Pro Asp Pro Ala
1               5                   10                  15

His Ser Ser Leu Gly Ser Trp Val Pro Thr Ile Met Glu Glu Leu Pro
            20                  25                  30

Gly Pro Arg Gln Gly Gln Trp Leu Gly Gln Thr Ser Glu Met Ser Arg
        35                  40                  45

Ala Leu Thr Pro His Pro Cys Val Gln Asp Ala Phe Gln Leu Pro Gly
    50                  55                  60

Leu Gly Thr Pro Pro Ile Thr Lys Leu Thr Val Leu Glu Glu Asp Glu
65                  70                  75                  80

Lys Lys Pro Val Pro Trp Glu Ser His Asn Ser Ser Glu Thr Cys Gly
                85                  90                  95

Leu Pro Thr Leu Val Gln Thr Tyr Val Leu Gln Gly Asp Pro Arg Ala
            100                 105                 110

Val Ser Thr Gln Pro Gln Ser Gln Ser Gly Thr Ser Asp Gln Val Leu
        115                 120                 125

Tyr Gly Gln Leu Leu Gly Ser Pro Thr Ser Pro Gly Pro Gly His Tyr
    130                 135                 140

Leu Arg Cys Asp Ser Thr Gln Pro Leu Leu Ala Gly Leu Thr Pro Ser
145                 150                 155                 160

Pro Lys Ser Tyr Glu Asn Leu Trp Phe Gln Ala Ser Pro Leu Gly Thr
                165                 170                 175

Leu Val Thr Pro Ala Pro Ser Gln Glu Asp Asp Cys Val Phe Gly Pro
            180                 185                 190

Leu Leu Asn Phe Pro Leu Leu Gln Gly Ile Arg Val His Gly Met Glu
        195                 200                 205

Ala Leu Gly Ser Phe
    210
```

<210> SEQ ID NO 218
<211> LENGTH: 133
<212> TYPE: PRT
<213> ORGANISM: Artificial Sequence
<220> FEATURE:
<223> OTHER INFORMATION: Synthetic: CSF3R transcript variant 4
NM_172313_2

<400> SEQUENCE: 218

```
Ser Pro Asn Arg Lys Asn Pro Leu Trp Pro Ser Val Pro Asp Pro Ala
1               5                   10                  15

His Ser Ser Leu Gly Ser Trp Val Pro Thr Ile Met Glu Glu Asp Ala
            20                  25                  30

Phe Gln Leu Pro Gly Leu Gly Thr Pro Pro Ile Thr Lys Leu Thr Val
        35                  40                  45

Leu Glu Glu Asp Glu Lys Lys Pro Val Pro Trp Glu Ser His Asn Ser
    50                  55                  60

Ser Glu Thr Cys Gly Leu Pro Thr Leu Val Gln Thr Tyr Val Leu Gln
65                  70                  75                  80

Gly Asp Pro Arg Ala Val Ser Thr Gln Pro Gln Ser Gln Ser Gly Thr
                85                  90                  95
```

```
Ser Asp Gln Ala Gly Pro Pro Arg Arg Ser Ala Tyr Phe Lys Asp Gln
            100                 105                 110

Ile Met Leu His Pro Ala Pro Pro Asn Gly Leu Leu Cys Leu Phe Pro
        115                 120                 125

Ile Thr Ser Val Leu
    130
```

<210> SEQ ID NO 219
<211> LENGTH: 235
<212> TYPE: PRT
<213> ORGANISM: Artificial Sequence
<220> FEATURE:
<223> OTHER INFORMATION: Synthetic: EPOR transcript variant 1 NM_000121_3

<400> SEQUENCE: 219

```
His Arg Arg Ala Leu Lys Gln Lys Ile Trp Pro Gly Ile Pro Ser Pro
1               5                   10                  15

Glu Ser Glu Phe Glu Gly Leu Phe Thr Thr His Lys Gly Asn Phe Gln
            20                  25                  30

Leu Trp Leu Tyr Gln Asn Asp Gly Cys Leu Trp Trp Ser Pro Cys Thr
        35                  40                  45

Pro Phe Thr Glu Asp Pro Pro Ala Ser Leu Glu Val Leu Ser Glu Arg
    50                  55                  60

Cys Trp Gly Thr Met Gln Ala Val Glu Pro Gly Thr Asp Asp Glu Gly
65                  70                  75                  80

Pro Leu Leu Glu Pro Val Gly Ser Glu His Ala Gln Asp Thr Tyr Leu
                85                  90                  95

Val Leu Asp Lys Trp Leu Leu Pro Arg Asn Pro Pro Ser Glu Asp Leu
            100                 105                 110

Pro Gly Pro Gly Gly Ser Val Asp Ile Val Ala Met Asp Glu Gly Ser
        115                 120                 125

Glu Ala Ser Ser Cys Ser Ser Ala Leu Ala Ser Lys Pro Ser Pro Glu
    130                 135                 140

Gly Ala Ser Ala Ala Ser Phe Glu Tyr Thr Ile Leu Asp Pro Ser Ser
145                 150                 155                 160

Gln Leu Leu Arg Pro Trp Thr Leu Cys Pro Glu Leu Pro Pro Thr Pro
                165                 170                 175

Pro His Leu Lys Tyr Leu Tyr Leu Val Val Ser Asp Ser Gly Ile Ser
            180                 185                 190

Thr Asp Tyr Ser Ser Gly Asp Ser Gln Gly Ala Gln Gly Gly Leu Ser
        195                 200                 205

Asp Gly Pro Tyr Ser Asn Pro Tyr Glu Asn Ser Leu Ile Pro Ala Ala
    210                 215                 220

Glu Pro Leu Pro Pro Ser Tyr Val Ala Cys Ser
225                 230                 235
```

<210> SEQ ID NO 220
<211> LENGTH: 235
<212> TYPE: PRT
<213> ORGANISM: Artificial Sequence
<220> FEATURE:
<223> OTHER INFORMATION: Synthetic: EPOR transcript variant 1 NM_000121_3

<400> SEQUENCE: 220

```
His Arg Arg Ala Leu Lys Gln Lys Ile Trp Pro Gly Ile Pro Ser Pro
1               5                   10                  15
```

```
Glu Ser Glu Phe Glu Gly Leu Phe Thr Thr His Lys Gly Asn Phe Gln
            20                  25                  30

Leu Trp Leu Tyr Gln Asn Asp Gly Cys Leu Trp Trp Ser Pro Cys Thr
        35                  40                  45

Pro Phe Thr Glu Asp Pro Pro Ala Ser Leu Glu Val Leu Ser Glu Arg
    50                  55                  60

Cys Trp Gly Thr Met Gln Ala Val Glu Pro Gly Thr Asp Asp Glu Gly
65                  70                  75                  80

Pro Leu Leu Glu Pro Val Gly Ser Glu His Ala Gln Asp Thr Tyr Leu
                85                  90                  95

Val Leu Asp Lys Trp Leu Leu Pro Arg Asn Pro Pro Ser Glu Asp Leu
            100                 105                 110

Pro Gly Pro Gly Gly Ser Val Asp Ile Val Ala Met Asp Glu Gly Ser
        115                 120                 125

Glu Ala Ser Ser Cys Ser Ser Ala Leu Ala Ser Lys Pro Ser Pro Glu
    130                 135                 140

Gly Ala Ser Ala Ala Ser Phe Glu Tyr Thr Ile Leu Asp Pro Ser Ser
145                 150                 155                 160

Gln Leu Leu Arg Pro Trp Thr Leu Cys Pro Glu Leu Pro Pro Thr Pro
                165                 170                 175

Pro His Leu Lys Phe Leu Phe Leu Val Val Ser Asp Ser Gly Ile Ser
            180                 185                 190

Thr Asp Tyr Ser Ser Gly Asp Ser Gln Gly Ala Gln Gly Gly Leu Ser
        195                 200                 205

Asp Gly Pro Tyr Ser Asn Pro Tyr Glu Asn Ser Leu Ile Pro Ala Ala
    210                 215                 220

Glu Pro Leu Pro Pro Ser Tyr Val Ala Cys Ser
225                 230                 235


<210> SEQ ID NO 221
<211> LENGTH: 42
<212> TYPE: PRT
<213> ORGANISM: Artificial Sequence
<220> FEATURE:
<223> OTHER INFORMATION: Synthetic: FCER1G NM_004106_1

<400> SEQUENCE: 221

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40


<210> SEQ ID NO 222
<211> LENGTH: 77
<212> TYPE: PRT
<213> ORGANISM: Artificial Sequence
<220> FEATURE:
<223> OTHER INFORMATION: Synthetic: FCGR2C NM_201563_5

<400> SEQUENCE: 222

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Pro Glu Glu Thr Asn Asn Asp Tyr Glu Thr Ala Asp Gly Gly Tyr
```

```
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75


<210> SEQ ID NO 223
<211> LENGTH: 77
<212> TYPE: PRT
<213> ORGANISM: Artificial Sequence
<220> FEATURE:
<223> OTHER INFORMATION: Synthetic: FCGRA2 transcript variant 1
      NM_001136219_1

<400> SEQUENCE: 223

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Leu Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75


<210> SEQ ID NO 224
<211> LENGTH: 350
<212> TYPE: PRT
<213> ORGANISM: Artificial Sequence
<220> FEATURE:
<223> OTHER INFORMATION: Synthetic: GHR transcript variant 1
      NM_000163_4

<400> SEQUENCE: 224

Lys Gln Gln Arg Ile Lys Met Leu Ile Leu Pro Pro Val Pro Val Pro
1               5                   10                  15

Lys Ile Lys Gly Ile Asp Pro Asp Leu Leu Lys Glu Gly Lys Leu Glu
            20                  25                  30

Glu Val Asn Thr Ile Leu Ala Ile His Asp Ser Tyr Lys Pro Glu Phe
        35                  40                  45

His Ser Asp Asp Ser Trp Val Glu Phe Ile Glu Leu Asp Ile Asp Glu
    50                  55                  60

Pro Asp Glu Lys Thr Glu Glu Ser Asp Thr Asp Arg Leu Leu Ser Ser
65                  70                  75                  80

Asp His Glu Lys Ser His Ser Asn Leu Gly Val Lys Asp Gly Asp Ser
                85                  90                  95

Gly Arg Thr Ser Cys Cys Glu Pro Asp Ile Leu Glu Thr Asp Phe Asn
            100                 105                 110

Ala Asn Asp Ile His Glu Gly Thr Ser Glu Val Ala Gln Pro Gln Arg
        115                 120                 125

Leu Lys Gly Glu Ala Asp Leu Leu Cys Leu Asp Gln Lys Asn Gln Asn
    130                 135                 140

Asn Ser Pro Tyr His Asp Ala Cys Pro Ala Thr Gln Gln Pro Ser Val
145                 150                 155                 160

Ile Gln Ala Glu Lys Asn Lys Pro Gln Pro Leu Pro Thr Glu Gly Ala
                165                 170                 175

Glu Ser Thr His Gln Ala Ala His Ile Gln Leu Ser Asn Pro Ser Ser
```

```
            180                 185                 190

Leu Ser Asn Ile Asp Phe Tyr Ala Gln Val Ser Asp Ile Thr Pro Ala
        195                 200                 205

Gly Ser Val Val Leu Ser Pro Gly Gln Lys Asn Lys Ala Gly Met Ser
    210                 215                 220

Gln Cys Asp Met His Pro Glu Met Val Ser Leu Cys Gln Glu Asn Phe
225                 230                 235                 240

Leu Met Asp Asn Ala Tyr Phe Cys Glu Ala Asp Ala Lys Lys Cys Ile
                245                 250                 255

Pro Val Ala Pro His Ile Lys Val Glu Ser His Ile Gln Pro Ser Leu
            260                 265                 270

Asn Gln Glu Asp Ile Tyr Ile Thr Thr Glu Ser Leu Thr Thr Ala Ala
        275                 280                 285

Gly Arg Pro Gly Thr Gly Glu His Val Pro Gly Ser Glu Met Pro Val
    290                 295                 300

Pro Asp Tyr Thr Ser Ile His Ile Val Gln Ser Pro Gln Gly Leu Ile
305                 310                 315                 320

Leu Asn Ala Thr Ala Leu Pro Leu Pro Asp Lys Glu Phe Leu Ser Ser
                325                 330                 335

Cys Gly Tyr Val Ser Thr Asp Gln Leu Asn Lys Ile Met Pro
            340                 345                 350


<210> SEQ ID NO 225
<211> LENGTH: 38
<212> TYPE: PRT
<213> ORGANISM: Artificial Sequence
<220> FEATURE:
<223> OTHER INFORMATION: Synthetic: ICOS NM_012092.3

<400> SEQUENCE: 225

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35


<210> SEQ ID NO 226
<211> LENGTH: 100
<212> TYPE: PRT
<213> ORGANISM: Artificial Sequence
<220> FEATURE:
<223> OTHER INFORMATION: Synthetic: IFNAR1 NM_000629_2

<400> SEQUENCE: 226

Lys Val Phe Leu Arg Cys Ile Asn Tyr Val Phe Phe Pro Ser Leu Lys
1               5                   10                  15

Pro Ser Ser Ser Ile Asp Glu Tyr Phe Ser Glu Gln Pro Leu Lys Asn
            20                  25                  30

Leu Leu Leu Ser Thr Ser Glu Glu Gln Ile Glu Lys Cys Phe Ile Ile
        35                  40                  45

Glu Asn Ile Ser Thr Ile Ala Thr Val Glu Glu Thr Asn Gln Thr Asp
    50                  55                  60

Glu Asp His Lys Lys Tyr Ser Ser Gln Thr Ser Gln Asp Ser Gly Asn
65                  70                  75                  80

Tyr Ser Asn Glu Asp Glu Ser Glu Ser Lys Thr Ser Glu Glu Leu Gln
                85                  90                  95
```

Gln Asp Phe Val
100

<210> SEQ ID NO 227
<211> LENGTH: 251
<212> TYPE: PRT
<213> ORGANISM: Artificial Sequence
<220> FEATURE:
<223> OTHER INFORMATION: Synthetic: IFNAR2 transcript variant 1
NM_207585_2

<400> SEQUENCE: 227

Lys Trp Ile Gly Tyr Ile Cys Leu Arg Asn Ser Leu Pro Lys Val Leu
1 5 10 15

Asn Phe His Asn Phe Leu Ala Trp Pro Phe Pro Asn Leu Pro Pro Leu
20 25 30

Glu Ala Met Asp Met Val Glu Val Ile Tyr Ile Asn Arg Lys Lys Lys
35 40 45

Val Trp Asp Tyr Asn Tyr Asp Asp Glu Ser Asp Ser Asp Thr Glu Ala
50 55 60

Ala Pro Arg Thr Ser Gly Gly Gly Tyr Thr Met His Gly Leu Thr Val
65 70 75 80

Arg Pro Leu Gly Gln Ala Ser Ala Thr Ser Thr Glu Ser Gln Leu Ile
85 90 95

Asp Pro Glu Ser Glu Glu Glu Pro Asp Leu Pro Glu Val Asp Val Glu
100 105 110

Leu Pro Thr Met Pro Lys Asp Ser Pro Gln Gln Leu Glu Leu Leu Ser
115 120 125

Gly Pro Cys Glu Arg Arg Lys Ser Pro Leu Gln Asp Pro Phe Pro Glu
130 135 140

Glu Asp Tyr Ser Ser Thr Glu Gly Ser Gly Gly Arg Ile Thr Phe Asn
145 150 155 160

Val Asp Leu Asn Ser Val Phe Leu Arg Val Leu Asp Asp Glu Asp Ser
165 170 175

Asp Asp Leu Glu Ala Pro Leu Met Leu Ser Ser His Leu Glu Glu Met
180 185 190

Val Asp Pro Glu Asp Pro Asp Asn Val Gln Ser Asn His Leu Leu Ala
195 200 205

Ser Gly Glu Gly Thr Gln Pro Thr Phe Pro Ser Pro Ser Ser Glu Gly
210 215 220

Leu Trp Ser Glu Asp Ala Pro Ser Asp Gln Ser Asp Thr Ser Glu Ser
225 230 235 240

Asp Val Asp Leu Gly Asp Gly Tyr Ile Met Arg
245 250

<210> SEQ ID NO 228
<211> LENGTH: 67
<212> TYPE: PRT
<213> ORGANISM: Artificial Sequence
<220> FEATURE:
<223> OTHER INFORMATION: Synthetic: IFNAR2 transcript variant 2
NM_000874_4

<400> SEQUENCE: 228

Lys Trp Ile Gly Tyr Ile Cys Leu Arg Asn Ser Leu Pro Lys Val Leu
1 5 10 15

Arg Gln Gly Leu Ala Lys Gly Trp Asn Ala Val Ala Ile His Arg Cys
20 25 30

Ser His Asn Ala Leu Gln Ser Glu Thr Pro Glu Leu Lys Gln Ser Ser
35 40 45

Cys Leu Ser Phe Pro Ser Ser Trp Asp Tyr Lys Arg Ala Ser Leu Cys
50 55 60

Pro Ser Asp
65

<210> SEQ ID NO 229
<211> LENGTH: 223
<212> TYPE: PRT
<213> ORGANISM: Artificial Sequence
<220> FEATURE:
<223> OTHER INFORMATION: Synthetic: IFNGR1 NM_000416_2

<400> SEQUENCE: 229

Cys Phe Tyr Ile Lys Lys Ile Asn Pro Leu Lys Glu Lys Ser Ile Ile
1 5 10 15

Leu Pro Lys Ser Leu Ile Ser Val Val Arg Ser Ala Thr Leu Glu Thr
20 25 30

Lys Pro Glu Ser Lys Tyr Val Ser Leu Ile Thr Ser Tyr Gln Pro Phe
35 40 45

Ser Leu Glu Lys Glu Val Val Cys Glu Glu Pro Leu Ser Pro Ala Thr
50 55 60

Val Pro Gly Met His Thr Glu Asp Asn Pro Gly Lys Val Glu His Thr
65 70 75 80

Glu Glu Leu Ser Ser Ile Thr Glu Val Val Thr Thr Glu Glu Asn Ile
85 90 95

Pro Asp Val Val Pro Gly Ser His Leu Thr Pro Ile Glu Arg Glu Ser
100 105 110

Ser Ser Pro Leu Ser Ser Asn Gln Ser Glu Pro Gly Ser Ile Ala Leu
115 120 125

Asn Ser Tyr His Ser Arg Asn Cys Ser Glu Ser Asp His Ser Arg Asn
130 135 140

Gly Phe Asp Thr Asp Ser Ser Cys Leu Glu Ser His Ser Ser Leu Ser
145 150 155 160

Asp Ser Glu Phe Pro Pro Asn Asn Lys Gly Glu Ile Lys Thr Glu Gly
165 170 175

Gln Glu Leu Ile Thr Val Ile Lys Ala Pro Thr Ser Phe Gly Tyr Asp
180 185 190

Lys Pro His Val Leu Val Asp Leu Leu Val Asp Asp Ser Gly Lys Glu
195 200 205

Ser Leu Ile Gly Tyr Arg Pro Thr Glu Asp Ser Lys Glu Phe Ser
210 215 220

<210> SEQ ID NO 230
<211> LENGTH: 69
<212> TYPE: PRT
<213> ORGANISM: Artificial Sequence
<220> FEATURE:
<223> OTHER INFORMATION: Synthetic: IFNGR2 transcript variant 1
NM_001329128_1

<400> SEQUENCE: 230

Leu Val Leu Lys Tyr Arg Gly Leu Ile Lys Tyr Trp Phe His Thr Pro
1 5 10 15

Pro Ser Ile Pro Leu Gln Ile Glu Glu Tyr Leu Lys Asp Pro Thr Gln
20 25 30

Pro Ile Leu Glu Ala Leu Asp Lys Asp Ser Ser Pro Lys Asp Asp Val 35 40 45

Trp Asp Ser Val Ser Ile Ile Ser Phe Pro Glu Lys Glu Gln Glu Asp
50 55 60

Val Leu Gln Thr Leu
65

<210> SEQ ID NO 231
<211> LENGTH: 271
<212> TYPE: PRT
<213> ORGANISM: Artificial Sequence
<220> FEATURE:
<223> OTHER INFORMATION: Synthetic: IFNLR1 NM_170743_3

<400> SEQUENCE: 231

Lys Thr Leu Met Gly Asn Pro Trp Phe Gln Arg Ala Lys Met Pro Arg
1 5 10 15

Ala Leu Asp Phe Ser Gly His Thr His Pro Val Ala Thr Phe Gln Pro
20 25 30

Ser Arg Pro Glu Ser Val Asn Asp Leu Phe Leu Cys Pro Gln Lys Glu
35 40 45

Leu Thr Arg Gly Val Arg Pro Thr Pro Arg Val Arg Ala Pro Ala Thr
50 55 60

Gln Gln Thr Arg Trp Lys Lys Asp Leu Ala Glu Asp Glu Glu Glu Glu
65 70 75 80

Asp Glu Glu Asp Thr Glu Asp Gly Val Ser Phe Gln Pro Tyr Ile Glu
85 90 95

Pro Pro Ser Phe Leu Gly Gln Glu His Gln Ala Pro Gly His Ser Glu
100 105 110

Ala Gly Gly Val Asp Ser Gly Arg Pro Arg Ala Pro Leu Val Pro Ser
115 120 125

Glu Gly Ser Ser Ala Trp Asp Ser Ser Asp Arg Ser Trp Ala Ser Thr
130 135 140

Val Asp Ser Ser Trp Asp Arg Ala Gly Ser Ser Gly Tyr Leu Ala Glu
145 150 155 160

Lys Gly Pro Gly Gln Gly Pro Gly Gly Asp Gly His Gln Glu Ser Leu
165 170 175

Pro Pro Pro Glu Phe Ser Lys Asp Ser Gly Phe Leu Glu Glu Leu Pro
180 185 190

Glu Asp Asn Leu Ser Ser Trp Ala Thr Trp Gly Thr Leu Pro Pro Glu
195 200 205

Pro Asn Leu Val Pro Gly Gly Pro Pro Val Ser Leu Gln Thr Leu Thr
210 215 220

Phe Cys Trp Glu Ser Ser Pro Glu Glu Glu Glu Glu Ala Arg Glu Ser
225 230 235 240

Glu Ile Glu Asp Ser Asp Ala Gly Ser Trp Gly Ala Glu Ser Thr Gln
245 250 255

Arg Thr Glu Asp Arg Gly Arg Thr Leu Gly His Tyr Met Ala Arg
260 265 270

<210> SEQ ID NO 232
<211> LENGTH: 242
<212> TYPE: PRT
<213> ORGANISM: Artificial Sequence
<220> FEATURE:
<223> OTHER INFORMATION: Synthetic: IFNLR1 transcript variant 2
NM_173064_2

<400> SEQUENCE: 232

```
Lys Thr Leu Met Gly Asn Pro Trp Phe Gln Arg Ala Lys Met Pro Arg
1               5                   10                  15

Ala Leu Glu Leu Thr Arg Gly Val Arg Pro Thr Pro Arg Val Arg Ala
            20                  25                  30

Pro Ala Thr Gln Gln Thr Arg Trp Lys Lys Asp Leu Ala Glu Asp Glu
        35                  40                  45

Glu Glu Glu Asp Glu Glu Asp Thr Glu Asp Gly Val Ser Phe Gln Pro
    50                  55                  60

Tyr Ile Glu Pro Pro Ser Phe Leu Gly Gln Glu His Gln Ala Pro Gly
65                  70                  75                  80

His Ser Glu Ala Gly Gly Val Asp Ser Gly Arg Pro Arg Ala Pro Leu
                85                  90                  95

Val Pro Ser Glu Gly Ser Ser Ala Trp Asp Ser Ser Asp Arg Ser Trp
            100                 105                 110

Ala Ser Thr Val Asp Ser Ser Trp Asp Arg Ala Gly Ser Ser Gly Tyr
        115                 120                 125

Leu Ala Glu Lys Gly Pro Gly Gln Gly Pro Gly Gly Asp Gly His Gln
    130                 135                 140

Glu Ser Leu Pro Pro Pro Glu Phe Ser Lys Asp Ser Gly Phe Leu Glu
145                 150                 155                 160

Glu Leu Pro Glu Asp Asn Leu Ser Ser Trp Ala Thr Trp Gly Thr Leu
                165                 170                 175

Pro Pro Glu Pro Asn Leu Val Pro Gly Gly Pro Pro Val Ser Leu Gln
            180                 185                 190

Thr Leu Thr Phe Cys Trp Glu Ser Ser Pro Glu Glu Glu Glu Glu Ala
        195                 200                 205

Arg Glu Ser Glu Ile Glu Asp Ser Asp Ala Gly Ser Trp Gly Ala Glu
    210                 215                 220

Ser Thr Gln Arg Thr Glu Asp Arg Gly Arg Thr Leu Gly His Tyr Met
225                 230                 235                 240

Ala Arg


<210> SEQ ID NO 233
<211> LENGTH: 179
<212> TYPE: PRT
<213> ORGANISM: Artificial Sequence
<220> FEATURE:
<223> OTHER INFORMATION: Synthetic: IL1R1 transcript variant 2
      NM_001288706_1

<400> SEQUENCE: 233

Lys Ile Asp Ile Val Leu Trp Tyr Arg Asp Ser Cys Tyr Asp Phe Leu
1               5                   10                  15

Pro Ile Lys Val Leu Pro Glu Val Leu Glu Lys Gln Cys Gly Tyr Lys
            20                  25                  30

Leu Phe Ile Tyr Gly Arg Asp Asp Tyr Val Gly Glu Asp Ile Val Glu
        35                  40                  45

Val Ile Asn Glu Asn Val Lys Lys Ser Arg Arg Leu Ile Ile Ile Leu
    50                  55                  60

Val Arg Glu Thr Ser Gly Phe Ser Trp Leu Gly Gly Ser Ser Glu Glu
65                  70                  75                  80

Gln Ile Ala Met Tyr Asn Ala Leu Val Gln Asp Gly Ile Lys Val Val
                85                  90                  95

Leu Leu Glu Leu Glu Lys Ile Gln Asp Tyr Glu Lys Met Pro Glu Ser
            100                 105                 110
```

Ile Lys Phe Ile Lys Gln Lys His Gly Ala Ile Arg Trp Ser Gly Asp
115 120 125

Phe Thr Gln Gly Pro Gln Ser Ala Lys Thr Arg Phe Trp Lys Asn Val
130 135 140

Arg Tyr His Met Pro Val Gln Arg Arg Ser Pro Ser Ser Lys His Gln
145 150 155 160

Leu Leu Ser Pro Ala Thr Lys Glu Lys Leu Gln Arg Glu Ala His Val
165 170 175

Pro Leu Gly

<210> SEQ ID NO 234
<211> LENGTH: 210
<212> TYPE: PRT
<213> ORGANISM: Artificial Sequence
<220> FEATURE:
<223> OTHER INFORMATION: Synthetic: IL1R1 transcript variant 3 NM_001320978_1

<400> SEQUENCE: 234

Lys Ile Asp Ile Val Leu Trp Tyr Arg Asp Ser Cys Tyr Asp Phe Leu
1 5 10 15

Pro Ile Lys Ala Ser Asp Gly Lys Thr Tyr Asp Ala Tyr Ile Leu Tyr
20 25 30

Pro Lys Thr Val Gly Glu Gly Ser Thr Ser Asp Cys Asp Ile Phe Val
35 40 45

Phe Lys Val Leu Pro Glu Val Leu Glu Lys Gln Cys Gly Tyr Lys Leu
50 55 60

Phe Ile Tyr Gly Arg Asp Asp Tyr Val Gly Glu Asp Ile Val Glu Val
65 70 75 80

Ile Asn Glu Asn Val Lys Lys Ser Arg Arg Leu Ile Ile Ile Leu Val
85 90 95

Arg Glu Thr Ser Gly Phe Ser Trp Leu Gly Gly Ser Ser Glu Glu Gln
100 105 110

Ile Ala Met Tyr Asn Ala Leu Val Gln Asp Gly Ile Lys Val Val Leu
115 120 125

Leu Glu Leu Glu Lys Ile Gln Asp Tyr Glu Lys Met Pro Glu Ser Ile
130 135 140

Lys Phe Ile Lys Gln Lys His Gly Ala Ile Arg Trp Ser Gly Asp Phe
145 150 155 160

Thr Gln Gly Pro Gln Ser Ala Lys Thr Arg Phe Trp Lys Asn Val Arg
165 170 175

Tyr His Met Pro Val Gln Arg Arg Ser Pro Ser Ser Lys His Gln Leu
180 185 190

Leu Ser Pro Ala Thr Lys Glu Lys Leu Gln Arg Glu Ala His Val Pro
195 200 205

Leu Gly
210

<210> SEQ ID NO 235
<211> LENGTH: 182
<212> TYPE: PRT
<213> ORGANISM: Artificial Sequence
<220> FEATURE:
<223> OTHER INFORMATION: Synthetic: IL1RAP transcript variant 1 NM_002182_3

<400> SEQUENCE: 235

```
Tyr Arg Ala His Phe Gly Thr Asp Glu Thr Ile Leu Asp Gly Lys Glu
1               5                   10                  15

Tyr Asp Ile Tyr Val Ser Tyr Ala Arg Asn Ala Glu Glu Glu Glu Phe
            20                  25                  30

Val Leu Leu Thr Leu Arg Gly Val Leu Glu Asn Glu Phe Gly Tyr Lys
        35                  40                  45

Leu Cys Ile Phe Asp Arg Asp Ser Leu Pro Gly Gly Ile Val Thr Asp
    50                  55                  60

Glu Thr Leu Ser Phe Ile Gln Lys Ser Arg Arg Leu Leu Val Val Leu
65                  70                  75                  80

Ser Pro Asn Tyr Val Leu Gln Gly Thr Gln Ala Leu Leu Glu Leu Lys
                85                  90                  95

Ala Gly Leu Glu Asn Met Ala Ser Arg Gly Asn Ile Asn Val Ile Leu
            100                 105                 110

Val Gln Tyr Lys Ala Val Lys Glu Thr Lys Val Lys Glu Leu Lys Arg
        115                 120                 125

Ala Lys Thr Val Leu Thr Val Ile Lys Trp Lys Gly Glu Lys Ser Lys
    130                 135                 140

Tyr Pro Gln Gly Arg Phe Trp Lys Gln Leu Gln Val Ala Met Pro Val
145                 150                 155                 160

Lys Lys Ser Pro Arg Arg Ser Ser Ser Asp Glu Gln Gly Leu Ser Tyr
                165                 170                 175

Ser Ser Leu Lys Asn Val
            180


<210> SEQ ID NO 236
<211> LENGTH: 299
<212> TYPE: PRT
<213> ORGANISM: Artificial Sequence
<220> FEATURE:
<223> OTHER INFORMATION: Synthetic: IL1RAP transcript variant 6
      NM_001167931_1

<400> SEQUENCE: 236

Tyr Arg Ala His Phe Gly Thr Asp Glu Thr Ile Leu Asp Gly Lys Glu
1               5                   10                  15

Tyr Asp Ile Tyr Val Ser Tyr Ala Arg Asn Ala Glu Glu Glu Glu Phe
            20                  25                  30

Val Leu Leu Thr Leu Arg Gly Val Leu Glu Asn Glu Phe Gly Tyr Lys
        35                  40                  45

Leu Cys Ile Phe Asp Arg Asp Ser Leu Pro Gly Gly Asn Thr Val Glu
    50                  55                  60

Ala Val Phe Asp Phe Ile Gln Arg Ser Arg Arg Met Ile Val Val Leu
65                  70                  75                  80

Ser Pro Asp Tyr Val Thr Glu Lys Ser Ile Ser Met Leu Glu Phe Lys
                85                  90                  95

Leu Gly Val Met Cys Gln Asn Ser Ile Ala Thr Lys Leu Ile Val Val
            100                 105                 110

Glu Tyr Arg Pro Leu Glu His Pro His Pro Gly Ile Leu Gln Leu Lys
        115                 120                 125

Glu Ser Val Ser Phe Val Ser Trp Lys Gly Glu Lys Ser Lys His Ser
    130                 135                 140

Gly Ser Lys Phe Trp Lys Ala Leu Arg Leu Ala Leu Pro Leu Arg Ser
145                 150                 155                 160

Leu Ser Ala Ser Ser Gly Trp Asn Glu Ser Cys Ser Ser Gln Ser Asp
                165                 170                 175
```

```
Ile Ser Leu Asp His Val Gln Arg Arg Arg Ser Arg Leu Lys Glu Pro
            180                 185                 190

Pro Glu Leu Gln Ser Ser Glu Arg Ala Ala Gly Ser Pro Pro Ala Pro
        195                 200                 205

Gly Thr Met Ser Lys His Arg Gly Lys Ser Ser Ala Thr Cys Arg Cys
    210                 215                 220

Cys Val Thr Tyr Cys Glu Gly Glu Asn His Leu Arg Asn Lys Ser Arg
225                 230                 235                 240

Ala Glu Ile His Asn Gln Pro Gln Trp Glu Thr His Leu Cys Lys Pro
                245                 250                 255

Val Pro Gln Glu Ser Glu Thr Gln Trp Ile Gln Asn Gly Thr Arg Leu
            260                 265                 270

Glu Pro Pro Ala Pro Gln Ile Ser Ala Leu Ala Leu His His Phe Thr
        275                 280                 285

Asp Leu Ser Asn Asn Asn Asp Phe Tyr Ile Leu
    290                 295


<210> SEQ ID NO 237
<211> LENGTH: 207
<212> TYPE: PRT
<213> ORGANISM: Artificial Sequence
<220> FEATURE:
<223> OTHER INFORMATION: Synthetic: IL1RL1 transcript variant 1
      NM_016232.4

<400> SEQUENCE: 237

Leu Lys Met Phe Trp Ile Glu Ala Thr Leu Leu Trp Arg Asp Ile Ala
1               5                   10                  15

Lys Pro Tyr Lys Thr Arg Asn Asp Gly Lys Leu Tyr Asp Ala Tyr Val
            20                  25                  30

Val Tyr Pro Arg Asn Tyr Lys Ser Ser Thr Asp Gly Ala Ser Arg Val
        35                  40                  45

Glu His Phe Val His Gln Ile Leu Pro Asp Val Leu Glu Asn Lys Cys
    50                  55                  60

Gly Tyr Thr Leu Cys Ile Tyr Gly Arg Asp Met Leu Pro Gly Glu Asp
65                  70                  75                  80

Val Val Thr Ala Val Glu Thr Asn Ile Arg Lys Ser Arg Arg His Ile
                85                  90                  95

Phe Ile Leu Thr Pro Gln Ile Thr His Asn Lys Glu Phe Ala Tyr Glu
            100                 105                 110

Gln Glu Val Ala Leu His Cys Ala Leu Ile Gln Asn Asp Ala Lys Val
        115                 120                 125

Ile Leu Ile Glu Met Glu Ala Leu Ser Glu Leu Asp Met Leu Gln Ala
    130                 135                 140

Glu Ala Leu Gln Asp Ser Leu Gln His Leu Met Lys Val Gln Gly Thr
145                 150                 155                 160

Ile Lys Trp Arg Glu Asp His Ile Ala Asn Lys Arg Ser Leu Asn Ser
                165                 170                 175

Lys Phe Trp Lys His Val Arg Tyr Gln Met Pro Val Pro Ser Lys Ile
            180                 185                 190

Pro Arg Lys Ala Ser Ser Leu Thr Pro Leu Ala Ala Gln Lys Gln
        195                 200                 205


<210> SEQ ID NO 238
<211> LENGTH: 219
<212> TYPE: PRT
```

```
<213> ORGANISM: Artificial Sequence
<220> FEATURE:
<223> OTHER INFORMATION: Synthetic: IL1RL2 NM_003854.2

<400> SEQUENCE: 238

Asn Ile Phe Lys Ile Asp Ile Val Leu Trp Tyr Arg Ser Ala Phe His
1               5                   10                  15

Ser Thr Glu Thr Ile Val Asp Gly Lys Leu Tyr Asp Ala Tyr Val Leu
            20                  25                  30

Tyr Pro Lys Pro His Lys Glu Ser Gln Arg His Ala Val Asp Ala Leu
        35                  40                  45

Val Leu Asn Ile Leu Pro Glu Val Leu Glu Arg Gln Cys Gly Tyr Lys
    50                  55                  60

Leu Phe Ile Phe Gly Arg Asp Glu Phe Pro Gly Gln Ala Val Ala Asn
65                  70                  75                  80

Val Ile Asp Glu Asn Val Lys Leu Cys Arg Arg Leu Ile Val Ile Val
                85                  90                  95

Val Pro Glu Ser Leu Gly Phe Gly Leu Leu Lys Asn Leu Ser Glu Glu
            100                 105                 110

Gln Ile Ala Val Tyr Ser Ala Leu Ile Gln Asp Gly Met Lys Val Ile
        115                 120                 125

Leu Ile Glu Leu Glu Lys Ile Glu Asp Tyr Thr Val Met Pro Glu Ser
    130                 135                 140

Ile Gln Tyr Ile Lys Gln Lys His Gly Ala Ile Arg Trp His Gly Asp
145                 150                 155                 160

Phe Thr Glu Gln Ser Gln Cys Met Lys Thr Lys Phe Trp Lys Thr Val
                165                 170                 175

Arg Tyr His Met Pro Pro Arg Arg Cys Arg Pro Phe Pro Pro Val Gln
            180                 185                 190

Leu Leu Gln His Thr Pro Cys Tyr Arg Thr Ala Gly Pro Glu Leu Gly
        195                 200                 205

Ser Arg Arg Lys Lys Cys Thr Leu Thr Thr Gly
    210                 215


<210> SEQ ID NO 239
<211> LENGTH: 13
<212> TYPE: PRT
<213> ORGANISM: Artificial Sequence
<220> FEATURE:
<223> OTHER INFORMATION: Synthetic: IL2RA transcript variant 1
      NM_000417_2

<400> SEQUENCE: 239

Thr Trp Gln Arg Arg Gln Arg Lys Ser Arg Arg Thr Ile
1               5                   10


<210> SEQ ID NO 240
<211> LENGTH: 286
<212> TYPE: PRT
<213> ORGANISM: Artificial Sequence
<220> FEATURE:
<223> OTHER INFORMATION: Synthetic: IL2RB transcript variant 1
      NM_000878_4

<400> SEQUENCE: 240

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30
```

```
Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Leu Gln Gln Asp Lys Val Pro Glu
65                  70                  75                  80

Pro Ala Ser Leu Ser Ser Asn His Ser Leu Thr Ser Cys Phe Thr Asn
                85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
        115                 120                 125

Glu Gly Val Ala Gly Ala Pro Thr Gly Ser Ser Pro Gln Pro Leu Gln
    130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
        195                 200                 205

Pro Pro Thr Pro Gly Val Pro Asp Leu Val Asp Phe Gln Pro Pro Pro
    210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
            260                 265                 270

Ser Leu Gln Glu Leu Gln Gly Gln Asp Pro Thr His Leu Val
        275                 280                 285


<210> SEQ ID NO 241
<211> LENGTH: 86
<212> TYPE: PRT
<213> ORGANISM: Artificial Sequence
<220> FEATURE:
<223> OTHER INFORMATION: Synthetic: IL2RG NM_000206_2

<400> SEQUENCE: 241

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
    50                  55                  60

Ala Ser Pro Cys Asn Gln His Ser Pro Tyr Trp Ala Pro Pro Cys Tyr
65                  70                  75                  80

Thr Leu Lys Pro Glu Thr
                85


<210> SEQ ID NO 242
<211> LENGTH: 53
```

```
<212> TYPE: PRT
<213> ORGANISM: Artificial Sequence
<220> FEATURE:
<223> OTHER INFORMATION: Synthetic: IL3RA transcript variant 1 and 2
      NM_002183_3

<400> SEQUENCE: 242

Arg Arg Tyr Leu Val Met Gln Arg Leu Phe Pro Arg Ile Pro His Met
1               5                   10                  15

Lys Asp Pro Ile Gly Asp Ser Phe Gln Asn Asp Lys Leu Val Val Trp
            20                  25                  30

Glu Ala Gly Lys Ala Gly Leu Glu Glu Cys Leu Val Thr Glu Val Gln
        35                  40                  45

Val Val Gln Lys Thr
    50


<210> SEQ ID NO 243
<211> LENGTH: 569
<212> TYPE: PRT
<213> ORGANISM: Artificial Sequence
<220> FEATURE:
<223> OTHER INFORMATION: Synthetic: IL4R transcript variant 1
      NM_000418_3

<400> SEQUENCE: 243

Lys Ile Lys Lys Glu Trp Trp Asp Gln Ile Pro Asn Pro Ala Arg Ser
1               5                   10                  15

Arg Leu Val Ala Ile Ile Ile Gln Asp Ala Gln Gly Ser Gln Trp Glu
            20                  25                  30

Lys Arg Ser Arg Gly Gln Glu Pro Ala Lys Cys Pro His Trp Lys Asn
        35                  40                  45

Cys Leu Thr Lys Leu Leu Pro Cys Phe Leu Glu His Asn Met Lys Arg
    50                  55                  60

Asp Glu Asp Pro His Lys Ala Ala Lys Glu Met Pro Phe Gln Gly Ser
65                  70                  75                  80

Gly Lys Ser Ala Trp Cys Pro Val Glu Ile Ser Lys Thr Val Leu Trp
                85                  90                  95

Pro Glu Ser Ile Ser Val Val Arg Cys Val Glu Leu Phe Glu Ala Pro
            100                 105                 110

Val Glu Cys Glu Glu Glu Glu Glu Val Glu Glu Glu Lys Gly Ser Phe
        115                 120                 125

Cys Ala Ser Pro Glu Ser Ser Arg Asp Asp Phe Gln Glu Gly Arg Glu
    130                 135                 140

Gly Ile Val Ala Arg Leu Thr Glu Ser Leu Phe Leu Asp Leu Leu Gly
145                 150                 155                 160

Glu Glu Asn Gly Gly Phe Cys Gln Gln Asp Met Gly Glu Ser Cys Leu
                165                 170                 175

Leu Pro Pro Ser Gly Ser Thr Ser Ala His Met Pro Trp Asp Glu Phe
            180                 185                 190

Pro Ser Ala Gly Pro Lys Glu Ala Pro Pro Trp Gly Lys Glu Gln Pro
        195                 200                 205

Leu His Leu Glu Pro Ser Pro Pro Ala Ser Pro Thr Gln Ser Pro Asp
    210                 215                 220

Asn Leu Thr Cys Thr Glu Thr Pro Leu Val Ile Ala Gly Asn Pro Ala
225                 230                 235                 240

Tyr Arg Ser Phe Ser Asn Ser Leu Ser Gln Ser Pro Cys Pro Arg Glu
                245                 250                 255
```

```
Leu Gly Pro Asp Pro Leu Leu Ala Arg His Leu Glu Glu Val Glu Pro
            260                 265                 270

Glu Met Pro Cys Val Pro Gln Leu Ser Glu Pro Thr Thr Val Pro Gln
        275                 280                 285

Pro Glu Pro Glu Thr Trp Glu Gln Ile Leu Arg Arg Asn Val Leu Gln
    290                 295                 300

His Gly Ala Ala Ala Ala Pro Val Ser Ala Pro Thr Ser Gly Tyr Gln
305                 310                 315                 320

Glu Phe Val His Ala Val Glu Gln Gly Gly Thr Gln Ala Ser Ala Val
                325                 330                 335

Val Gly Leu Gly Pro Pro Gly Glu Ala Gly Tyr Lys Ala Phe Ser Ser
            340                 345                 350

Leu Leu Ala Ser Ser Ala Val Ser Pro Glu Lys Cys Gly Phe Gly Ala
        355                 360                 365

Ser Ser Gly Glu Glu Gly Tyr Lys Pro Phe Gln Asp Leu Ile Pro Gly
    370                 375                 380

Cys Pro Gly Asp Pro Ala Pro Val Pro Val Pro Leu Phe Thr Phe Gly
385                 390                 395                 400

Leu Asp Arg Glu Pro Pro Arg Ser Pro Gln Ser Ser His Leu Pro Ser
                405                 410                 415

Ser Ser Pro Glu His Leu Gly Leu Glu Pro Gly Glu Lys Val Glu Asp
            420                 425                 430

Met Pro Lys Pro Pro Leu Pro Gln Glu Gln Ala Thr Asp Pro Leu Val
        435                 440                 445

Asp Ser Leu Gly Ser Gly Ile Val Tyr Ser Ala Leu Thr Cys His Leu
    450                 455                 460

Cys Gly His Leu Lys Gln Cys His Gly Gln Glu Asp Gly Gly Gln Thr
465                 470                 475                 480

Pro Val Met Ala Ser Pro Cys Cys Gly Cys Cys Cys Gly Asp Arg Ser
                485                 490                 495

Ser Pro Pro Thr Thr Pro Leu Arg Ala Pro Asp Pro Ser Pro Gly Gly
            500                 505                 510

Val Pro Leu Glu Ala Ser Leu Cys Pro Ala Ser Leu Ala Pro Ser Gly
        515                 520                 525

Ile Ser Glu Lys Ser Lys Ser Ser Ser Ser Phe His Pro Ala Pro Gly
    530                 535                 540

Asn Ala Gln Ser Ser Ser Gln Thr Pro Lys Ile Val Asn Phe Val Ser
545                 550                 555                 560

Val Gly Pro Thr Tyr Met Arg Val Ser
                565
```

<210> SEQ ID NO 244
<211> LENGTH: 569
<212> TYPE: PRT
<213> ORGANISM: Artificial Sequence
<220> FEATURE:
<223> OTHER INFORMATION: Synthetic: IL4R transcript variant 1 NM_000418_3

<400> SEQUENCE: 244

```
Lys Ile Lys Lys Glu Trp Trp Asp Gln Ile Pro Asn Pro Ala Arg Ser
1               5                   10                  15

Arg Leu Val Ala Ile Ile Ile Gln Asp Ala Gln Gly Ser Gln Trp Glu
            20                  25                  30

Lys Arg Ser Arg Gly Gln Glu Pro Ala Lys Cys Pro His Trp Lys Asn
        35                  40                  45
```

-continued

```
Cys Leu Thr Lys Leu Leu Pro Cys Phe Leu Glu His Asn Met Lys Arg
    50                  55                  60

Asp Glu Asp Pro His Lys Ala Ala Lys Glu Met Pro Phe Gln Gly Ser
65                  70                  75                  80

Gly Lys Ser Ala Trp Cys Pro Val Glu Ile Ser Lys Thr Val Leu Trp
                85                  90                  95

Pro Glu Ser Ile Ser Val Val Arg Cys Val Glu Leu Phe Glu Ala Pro
            100                 105                 110

Val Glu Cys Glu Glu Glu Glu Glu Val Glu Glu Glu Lys Gly Ser Phe
        115                 120                 125

Cys Ala Ser Pro Glu Ser Ser Arg Asp Asp Phe Gln Glu Gly Arg Glu
    130                 135                 140

Gly Ile Val Ala Arg Leu Thr Glu Ser Leu Phe Leu Asp Leu Leu Gly
145                 150                 155                 160

Glu Glu Asn Gly Gly Phe Cys Gln Gln Asp Met Gly Glu Ser Cys Leu
                165                 170                 175

Leu Pro Pro Ser Gly Ser Thr Ser Ala His Met Pro Trp Asp Glu Phe
            180                 185                 190

Pro Ser Ala Gly Pro Lys Glu Ala Pro Pro Trp Gly Lys Glu Gln Pro
        195                 200                 205

Leu His Leu Glu Pro Ser Pro Pro Ala Ser Pro Thr Gln Ser Pro Asp
    210                 215                 220

Asn Leu Thr Cys Thr Glu Thr Pro Leu Val Ile Ala Gly Asn Pro Ala
225                 230                 235                 240

Tyr Arg Ser Phe Ser Asn Ser Leu Ser Gln Ser Pro Cys Pro Arg Glu
                245                 250                 255

Leu Gly Pro Asp Pro Leu Leu Ala Arg His Leu Glu Glu Val Glu Pro
            260                 265                 270

Glu Met Pro Cys Val Pro Gln Leu Ser Glu Pro Thr Thr Val Pro Gln
        275                 280                 285

Pro Glu Pro Glu Thr Trp Glu Gln Ile Leu Arg Arg Asn Val Leu Gln
    290                 295                 300

His Gly Ala Ala Ala Ala Pro Val Ser Ala Pro Thr Ser Gly Tyr Gln
305                 310                 315                 320

Glu Phe Val His Ala Val Glu Gln Gly Gly Thr Gln Ala Ser Ala Val
                325                 330                 335

Val Gly Leu Gly Pro Pro Gly Glu Ala Gly Tyr Lys Ala Phe Ser Ser
            340                 345                 350

Leu Leu Ala Ser Ser Ala Val Ser Pro Glu Lys Cys Gly Phe Gly Ala
        355                 360                 365

Ser Ser Gly Glu Glu Gly Tyr Lys Pro Phe Gln Asp Leu Ile Pro Gly
    370                 375                 380

Cys Pro Gly Asp Pro Ala Pro Val Pro Val Pro Leu Phe Thr Phe Gly
385                 390                 395                 400

Leu Asp Arg Glu Pro Pro Arg Ser Pro Gln Ser Ser His Leu Pro Ser
                405                 410                 415

Ser Ser Pro Glu His Leu Gly Leu Glu Pro Gly Glu Lys Val Glu Asp
            420                 425                 430

Met Pro Lys Pro Pro Leu Pro Gln Glu Gln Ala Thr Asp Pro Leu Val
        435                 440                 445

Asp Ser Leu Gly Ser Gly Ile Val Tyr Ser Ala Leu Thr Cys His Leu
    450                 455                 460
```

```
Cys Gly His Leu Lys Gln Cys His Gly Gln Glu Asp Gly Gly Gln Thr
465                 470                 475                 480

Pro Val Met Ala Ser Pro Cys Cys Gly Cys Cys Cys Gly Asp Arg Ser
                485                 490                 495

Ser Pro Pro Thr Thr Pro Leu Arg Ala Pro Asp Pro Ser Pro Gly Gly
            500                 505                 510

Val Pro Leu Glu Ala Ser Leu Cys Pro Ala Ser Leu Ala Pro Ser Gly
        515                 520                 525

Ile Ser Glu Lys Ser Lys Ser Ser Ser Ser Phe His Pro Ala Pro Gly
    530                 535                 540

Asn Ala Gln Ser Ser Ser Gln Thr Pro Lys Ile Val Asn Phe Val Ser
545                 550                 555                 560

Val Gly Pro Thr Tyr Met Arg Val Ser
                565


<210> SEQ ID NO 245
<211> LENGTH: 58
<212> TYPE: PRT
<213> ORGANISM: Artificial Sequence
<220> FEATURE:
<223> OTHER INFORMATION: Synthetic: IL5RA transcript variant 1
      NM_000564_4

<400> SEQUENCE: 245

Lys Ile Cys His Leu Trp Ile Lys Leu Phe Pro Pro Ile Pro Ala Pro
1               5                   10                  15

Lys Ser Asn Ile Lys Asp Leu Phe Val Thr Thr Asn Tyr Glu Lys Ala
            20                  25                  30

Gly Ser Ser Glu Thr Glu Ile Glu Val Ile Cys Tyr Ile Glu Lys Pro
        35                  40                  45

Gly Val Glu Thr Leu Glu Asp Ser Val Phe
    50                  55


<210> SEQ ID NO 246
<211> LENGTH: 82
<212> TYPE: PRT
<213> ORGANISM: Artificial Sequence
<220> FEATURE:
<223> OTHER INFORMATION: Synthetic: IL6R transcript variant 1
      NM_000565_3

<400> SEQUENCE: 246

Arg Phe Lys Lys Thr Trp Lys Leu Arg Ala Leu Lys Glu Gly Lys Thr
1               5                   10                  15

Ser Met His Pro Pro Tyr Ser Leu Gly Gln Leu Val Pro Glu Arg Pro
            20                  25                  30

Arg Pro Thr Pro Val Leu Val Pro Leu Ile Ser Pro Pro Val Ser Pro
        35                  40                  45

Ser Ser Leu Gly Ser Asp Asn Thr Ser Ser His Asn Arg Pro Asp Ala
    50                  55                  60

Arg Asp Pro Arg Ser Pro Tyr Asp Ile Ser Asn Thr Asp Tyr Phe Phe
65                  70                  75                  80

Pro Arg


<210> SEQ ID NO 247
<211> LENGTH: 277
<212> TYPE: PRT
<213> ORGANISM: Artificial Sequence
<220> FEATURE:
<223> OTHER INFORMATION: Synthetic: IL6ST transcript variant 1 and 3
```

NM_002184_3

<400> SEQUENCE: 247

Asn Lys Arg Asp Leu Ile Lys Lys His Ile Trp Pro Asn Val Pro Asp
1 5 10 15

Pro Ser Lys Ser His Ile Ala Gln Trp Ser Pro His Thr Pro Pro Arg
20 25 30

His Asn Phe Asn Ser Lys Asp Gln Met Tyr Ser Asp Gly Asn Phe Thr
35 40 45

Asp Val Ser Val Val Glu Ile Glu Ala Asn Asp Lys Lys Pro Phe Pro
50 55 60

Glu Asp Leu Lys Ser Leu Asp Leu Phe Lys Lys Glu Lys Ile Asn Thr
65 70 75 80

Glu Gly His Ser Ser Gly Ile Gly Gly Ser Ser Cys Met Ser Ser Ser
85 90 95

Arg Pro Ser Ile Ser Ser Ser Asp Glu Asn Glu Ser Ser Gln Asn Thr
100 105 110

Ser Ser Thr Val Gln Tyr Ser Thr Val Val His Ser Gly Tyr Arg His
115 120 125

Gln Val Pro Ser Val Gln Val Phe Ser Arg Ser Glu Ser Thr Gln Pro
130 135 140

Leu Leu Asp Ser Glu Glu Arg Pro Glu Asp Leu Gln Leu Val Asp His
145 150 155 160

Val Asp Gly Gly Asp Gly Ile Leu Pro Arg Gln Gln Tyr Phe Lys Gln
165 170 175

Asn Cys Ser Gln His Glu Ser Ser Pro Asp Ile Ser His Phe Glu Arg
180 185 190

Ser Lys Gln Val Ser Ser Val Asn Glu Glu Asp Phe Val Arg Leu Lys
195 200 205

Gln Gln Ile Ser Asp His Ile Ser Gln Ser Cys Gly Ser Gly Gln Met
210 215 220

Lys Met Phe Gln Glu Val Ser Ala Ala Asp Ala Phe Gly Pro Gly Thr
225 230 235 240

Glu Gly Gln Val Glu Arg Phe Glu Thr Val Gly Met Glu Ala Ala Thr
245 250 255

Asp Glu Gly Met Pro Lys Ser Tyr Leu Pro Gln Thr Val Arg Gln Gly
260 265 270

Gly Tyr Met Pro Gln
275

<210> SEQ ID NO 248
<211> LENGTH: 196
<212> TYPE: PRT
<213> ORGANISM: Artificial Sequence
<220> FEATURE:
<223> OTHER INFORMATION: Synthetic: IL7RA Isoform 1 NM_002185.4

<400> SEQUENCE: 248

Trp Lys Lys Arg Ile Lys Pro Ile Val Trp Pro Ser Leu Pro Asp His
1 5 10 15

Lys Lys Thr Leu Glu His Leu Cys Lys Lys Pro Arg Lys Asn Leu Asn
20 25 30

Val Ser Phe Asn Pro Glu Ser Phe Leu Asp Cys Gln Ile His Arg Val
35 40 45

Asp Asp Ile Gln Ala Arg Asp Glu Val Glu Gly Phe Leu Gln Asp Thr
50 55 60

Phe Pro Gln Gln Leu Glu Glu Ser Glu Lys Gln Arg Leu Gly Gly Asp
65 70 75 80

Val Gln Ser Pro Asn Cys Pro Ser Glu Asp Val Val Ile Thr Pro Glu
85 90 95

Ser Phe Gly Arg Asp Ser Ser Leu Thr Cys Leu Ala Gly Asn Val Ser
100 105 110

Ala Cys Asp Ala Pro Ile Leu Ser Ser Ser Arg Ser Leu Asp Cys Arg
115 120 125

Glu Ser Gly Lys Asn Gly Pro His Val Tyr Gln Asp Leu Leu Leu Ser
130 135 140

Leu Gly Thr Thr Asn Ser Thr Leu Pro Pro Pro Phe Ser Leu Gln Ser
145 150 155 160

Gly Ile Leu Thr Leu Asn Pro Val Ala Gln Gly Gln Pro Ile Leu Thr
165 170 175

Ser Leu Gly Ser Asn Gln Glu Glu Ala Tyr Val Thr Met Ser Ser Phe
180 185 190

Tyr Gln Asn Gln
195

<210> SEQ ID NO 249
<211> LENGTH: 35
<212> TYPE: PRT
<213> ORGANISM: Artificial Sequence
<220> FEATURE:
<223> OTHER INFORMATION: Synthetic: IL7RA Isoform 3 (C-term deletion) (interleukin 7 receptor)

<400> SEQUENCE: 249

Trp Lys Lys Arg Ile Lys Pro Ile Val Trp Pro Ser Leu Pro Asp His
1 5 10 15

Lys Lys Thr Leu Glu His Leu Cys Lys Lys Pro Arg Lys Val Ser Val
20 25 30

Phe Gly Ala
35

<210> SEQ ID NO 250
<211> LENGTH: 230
<212> TYPE: PRT
<213> ORGANISM: Artificial Sequence
<220> FEATURE:
<223> OTHER INFORMATION: Synthetic: IL9R transcript variant 1 NM_002186_2

<400> SEQUENCE: 250

Lys Leu Ser Pro Arg Val Lys Arg Ile Phe Tyr Gln Asn Val Pro Ser
1 5 10 15

Pro Ala Met Phe Phe Gln Pro Leu Tyr Ser Val His Asn Gly Asn Phe
20 25 30

Gln Thr Trp Met Gly Ala His Gly Ala Gly Val Leu Leu Ser Gln Asp
35 40 45

Cys Ala Gly Thr Pro Gln Gly Ala Leu Glu Pro Cys Val Gln Glu Ala
50 55 60

Thr Ala Leu Leu Thr Cys Gly Pro Ala Arg Pro Trp Lys Ser Val Ala
65 70 75 80

Leu Glu Glu Glu Gln Glu Gly Pro Gly Thr Arg Leu Pro Gly Asn Leu
85 90 95

Ser Ser Glu Asp Val Leu Pro Ala Gly Cys Thr Glu Trp Arg Val Gln
100 105 110

```
Thr Leu Ala Tyr Leu Pro Gln Glu Asp Trp Ala Pro Thr Ser Leu Thr
        115                 120                 125

Arg Pro Ala Pro Pro Asp Ser Glu Gly Ser Arg Ser Ser Ser Ser Ser
    130                 135                 140

Ser Ser Ser Asn Asn Asn Asn Tyr Cys Ala Leu Gly Cys Tyr Gly Gly
145                 150                 155                 160

Trp His Leu Ser Ala Leu Pro Gly Asn Thr Gln Ser Ser Gly Pro Ile
                165                 170                 175

Pro Ala Leu Ala Cys Gly Leu Ser Cys Asp His Gln Gly Leu Glu Thr
            180                 185                 190

Gln Gln Gly Val Ala Trp Val Leu Ala Gly His Cys Gln Arg Pro Gly
        195                 200                 205

Leu His Glu Asp Leu Gln Gly Met Leu Leu Pro Ser Val Leu Ser Lys
    210                 215                 220

Ala Arg Ser Trp Thr Phe
225                 230


<210> SEQ ID NO 251
<211> LENGTH: 322
<212> TYPE: PRT
<213> ORGANISM: Artificial Sequence
<220> FEATURE:
<223> OTHER INFORMATION: Synthetic: IL10RA transcript variant 1
      NM_001558_3

<400> SEQUENCE: 251

Gln Leu Tyr Val Arg Arg Arg Lys Lys Leu Pro Ser Val Leu Leu Phe
1               5                   10                  15

Lys Lys Pro Ser Pro Phe Ile Phe Ile Ser Gln Arg Pro Ser Pro Glu
            20                  25                  30

Thr Gln Asp Thr Ile His Pro Leu Asp Glu Glu Ala Phe Leu Lys Val
        35                  40                  45

Ser Pro Glu Leu Lys Asn Leu Asp Leu His Gly Ser Thr Asp Ser Gly
    50                  55                  60

Phe Gly Ser Thr Lys Pro Ser Leu Gln Thr Glu Glu Pro Gln Phe Leu
65                  70                  75                  80

Leu Pro Asp Pro His Pro Gln Ala Asp Arg Thr Leu Gly Asn Arg Glu
                85                  90                  95

Pro Pro Val Leu Gly Asp Ser Cys Ser Ser Gly Ser Ser Asn Ser Thr
            100                 105                 110

Asp Ser Gly Ile Cys Leu Gln Glu Pro Ser Leu Ser Pro Ser Thr Gly
        115                 120                 125

Pro Thr Trp Glu Gln Gln Val Gly Ser Asn Ser Arg Gly Gln Asp Asp
    130                 135                 140

Ser Gly Ile Asp Leu Val Gln Asn Ser Glu Gly Arg Ala Gly Asp Thr
145                 150                 155                 160

Gln Gly Gly Ser Ala Leu Gly His His Ser Pro Pro Glu Pro Glu Val
                165                 170                 175

Pro Gly Glu Glu Asp Pro Ala Ala Val Ala Phe Gln Gly Tyr Leu Arg
            180                 185                 190

Gln Thr Arg Cys Ala Glu Glu Lys Ala Thr Lys Thr Gly Cys Leu Glu
        195                 200                 205

Glu Glu Ser Pro Leu Thr Asp Gly Leu Gly Pro Lys Phe Gly Arg Cys
    210                 215                 220

Leu Val Asp Glu Ala Gly Leu His Pro Pro Ala Leu Ala Lys Gly Tyr
```

```
225                 230                 235                 240

Leu Lys Gln Asp Pro Leu Glu Met Thr Leu Ala Ser Ser Gly Ala Pro
                245                 250                 255

Thr Gly Gln Trp Asn Gln Pro Thr Glu Glu Trp Ser Leu Leu Ala Leu
            260                 265                 270

Ser Ser Cys Ser Asp Leu Gly Ile Ser Asp Trp Ser Phe Ala His Asp
        275                 280                 285

Leu Ala Pro Leu Gly Cys Val Ala Ala Pro Gly Gly Leu Leu Gly Ser
    290                 295                 300

Phe Asn Ser Asp Leu Val Thr Leu Pro Leu Ile Ser Ser Leu Gln Ser
305                 310                 315                 320

Ser Glu


<210> SEQ ID NO 252
<211> LENGTH: 83
<212> TYPE: PRT
<213> ORGANISM: Artificial Sequence
<220> FEATURE:
<223> OTHER INFORMATION: Synthetic: IL10RB NM_000628_4

<400> SEQUENCE: 252

Ala Leu Leu Trp Cys Val Tyr Lys Lys Thr Lys Tyr Ala Phe Ser Pro
1               5                   10                  15

Arg Asn Ser Leu Pro Gln His Leu Lys Glu Phe Leu Gly His Pro His
            20                  25                  30

His Asn Thr Leu Leu Phe Phe Ser Phe Pro Leu Ser Asp Glu Asn Asp
        35                  40                  45

Val Phe Asp Lys Leu Ser Val Ile Ala Glu Asp Ser Glu Ser Gly Lys
    50                  55                  60

Gln Asn Pro Gly Asp Ser Cys Ser Leu Gly Thr Pro Pro Gly Gln Gly
65                  70                  75                  80

Pro Gln Ser


<210> SEQ ID NO 253
<211> LENGTH: 31
<212> TYPE: PRT
<213> ORGANISM: Artificial Sequence
<220> FEATURE:
<223> OTHER INFORMATION: Synthetic: IL11RA NM_001142784_2

<400> SEQUENCE: 253

Arg Leu Arg Arg Gly Gly Lys Asp Gly Ser Pro Lys Pro Gly Phe Leu
1               5                   10                  15

Ala Ser Val Ile Pro Val Asp Arg Arg Pro Gly Ala Pro Asn Leu
            20                  25                  30


<210> SEQ ID NO 254
<211> LENGTH: 92
<212> TYPE: PRT
<213> ORGANISM: Artificial Sequence
<220> FEATURE:
<223> OTHER INFORMATION: Synthetic: IL12RB1 transcript variant 1 and 4
      NM_005535_2

<400> SEQUENCE: 254

Asn Arg Ala Ala Arg His Leu Cys Pro Pro Leu Pro Thr Pro Cys Ala
1               5                   10                  15

Ser Ser Ala Ile Glu Phe Pro Gly Gly Lys Glu Thr Trp Gln Trp Ile
            20                  25                  30
```

```
Asn Pro Val Asp Phe Gln Glu Glu Ala Ser Leu Gln Glu Ala Leu Val
        35                  40                  45

Val Glu Met Ser Trp Asp Lys Gly Glu Arg Thr Glu Pro Leu Glu Lys
    50                  55                  60

Thr Glu Leu Pro Glu Gly Ala Pro Glu Leu Ala Leu Asp Thr Glu Leu
65                  70                  75                  80

Ser Leu Glu Asp Gly Asp Arg Cys Lys Ala Lys Met
                85                  90


<210> SEQ ID NO 255
<211> LENGTH: 90
<212> TYPE: PRT
<213> ORGANISM: Artificial Sequence
<220> FEATURE:
<223> OTHER INFORMATION: Synthetic: IL12RB1 transcript variant 3
      NM_001290023_1

<400> SEQUENCE: 255

Asn Arg Ala Ala Arg His Leu Cys Pro Pro Leu Pro Thr Pro Cys Ala
1               5                   10                  15

Ser Ser Ala Ile Glu Phe Pro Gly Gly Lys Glu Thr Trp Gln Trp Ile
            20                  25                  30

Asn Pro Val Asp Phe Gln Glu Glu Ala Ser Leu Gln Glu Ala Leu Val
        35                  40                  45

Val Glu Met Ser Trp Asp Lys Gly Glu Arg Thr Glu Pro Leu Glu Lys
    50                  55                  60

Thr Glu Leu Pro Glu Gly Ala Pro Glu Leu Ala Leu Asp Thr Glu Leu
65                  70                  75                  80

Ser Leu Glu Asp Gly Asp Arg Cys Asp Arg
                85                  90


<210> SEQ ID NO 256
<211> LENGTH: 219
<212> TYPE: PRT
<213> ORGANISM: Artificial Sequence
<220> FEATURE:
<223> OTHER INFORMATION: Synthetic: IL12RB2 transcript variant 1 and 3
      NM_001559_2

<400> SEQUENCE: 256

His Tyr Phe Gln Gln Lys Val Phe Val Leu Leu Ala Ala Leu Arg Pro
1               5                   10                  15

Gln Trp Cys Ser Arg Glu Ile Pro Asp Pro Ala Asn Ser Thr Cys Ala
            20                  25                  30

Lys Lys Tyr Pro Ile Ala Glu Glu Lys Thr Gln Leu Pro Leu Asp Arg
        35                  40                  45

Leu Leu Ile Asp Trp Pro Thr Pro Glu Asp Pro Glu Pro Leu Val Ile
    50                  55                  60

Ser Glu Val Leu His Gln Val Thr Pro Val Phe Arg His Pro Pro Cys
65                  70                  75                  80

Ser Asn Trp Pro Gln Arg Glu Lys Gly Ile Gln Gly His Gln Ala Ser
                85                  90                  95

Glu Lys Asp Met Met His Ser Ala Ser Ser Pro Pro Pro Pro Arg Ala
            100                 105                 110

Leu Gln Ala Glu Ser Arg Gln Leu Val Asp Leu Tyr Lys Val Leu Glu
        115                 120                 125

Ser Arg Gly Ser Asp Pro Lys Pro Glu Asn Pro Ala Cys Pro Trp Thr
    130                 135                 140
```

Val Leu Pro Ala Gly Asp Leu Pro Thr His Asp Gly Tyr Leu Pro Ser
145 150 155 160

Asn Ile Asp Asp Leu Pro Ser His Glu Ala Pro Leu Ala Asp Ser Leu
165 170 175

Glu Glu Leu Glu Pro Gln His Ile Ser Leu Ser Val Phe Pro Ser Ser
180 185 190

Ser Leu His Pro Leu Thr Phe Ser Cys Gly Asp Lys Leu Thr Leu Asp
195 200 205

Gln Leu Lys Met Arg Cys Asp Ser Leu Met Leu
210 215

<210> SEQ ID NO 257
<211> LENGTH: 60
<212> TYPE: PRT
<213> ORGANISM: Artificial Sequence
<220> FEATURE:
<223> OTHER INFORMATION: Synthetic: IL13RA1 NM_001560_2

<400> SEQUENCE: 257

Lys Arg Leu Lys Ile Ile Ile Phe Pro Pro Ile Pro Asp Pro Gly Lys
1 5 10 15

Ile Phe Lys Glu Met Phe Gly Asp Gln Asn Asp Asp Thr Leu His Trp
20 25 30

Lys Lys Tyr Asp Ile Tyr Glu Lys Gln Thr Lys Glu Glu Thr Asp Ser
35 40 45

Val Val Leu Ile Glu Asn Leu Lys Lys Ala Ser Gln
50 55 60

<210> SEQ ID NO 258
<211> LENGTH: 17
<212> TYPE: PRT
<213> ORGANISM: Artificial Sequence
<220> FEATURE:
<223> OTHER INFORMATION: Synthetic: IL13RA2 NM_000640_2

<400> SEQUENCE: 258

Arg Lys Pro Asn Thr Tyr Pro Lys Met Ile Pro Glu Phe Phe Cys Asp
1 5 10 15

Thr

<210> SEQ ID NO 259
<211> LENGTH: 39
<212> TYPE: PRT
<213> ORGANISM: Artificial Sequence
<220> FEATURE:
<223> OTHER INFORMATION: Synthetic: IL15RA transcript variant 4
NM_001256765_1

<400> SEQUENCE: 259

Lys Ser Arg Gln Thr Pro Pro Leu Ala Ser Val Glu Met Glu Ala Met
1 5 10 15

Glu Ala Leu Pro Val Thr Trp Gly Thr Ser Ser Arg Asp Glu Asp Leu
20 25 30

Glu Asn Cys Ser His His Leu
35

<210> SEQ ID NO 260
<211> LENGTH: 525
<212> TYPE: PRT
<213> ORGANISM: Artificial Sequence
<220> FEATURE:
<223> OTHER INFORMATION: Synthetic: IL17RA NM_014339_6

<400> SEQUENCE: 260

Cys Met Thr Trp Arg Leu Ala Gly Pro Gly Ser Glu Lys Tyr Ser Asp
1 5 10 15

Asp Thr Lys Tyr Thr Asp Gly Leu Pro Ala Ala Asp Leu Ile Pro Pro
20 25 30

Pro Leu Lys Pro Arg Lys Val Trp Ile Ile Tyr Ser Ala Asp His Pro
35 40 45

Leu Tyr Val Asp Val Val Leu Lys Phe Ala Gln Phe Leu Leu Thr Ala
50 55 60

Cys Gly Thr Glu Val Ala Leu Asp Leu Leu Glu Glu Gln Ala Ile Ser
65 70 75 80

Glu Ala Gly Val Met Thr Trp Val Gly Arg Gln Lys Gln Glu Met Val
85 90 95

Glu Ser Asn Ser Lys Ile Ile Val Leu Cys Ser Arg Gly Thr Arg Ala
100 105 110

Lys Trp Gln Ala Leu Leu Gly Arg Gly Ala Pro Val Arg Leu Arg Cys
115 120 125

Asp His Gly Lys Pro Val Gly Asp Leu Phe Thr Ala Ala Met Asn Met
130 135 140

Ile Leu Pro Asp Phe Lys Arg Pro Ala Cys Phe Gly Thr Tyr Val Val
145 150 155 160

Cys Tyr Phe Ser Glu Val Ser Cys Asp Gly Asp Val Pro Asp Leu Phe
165 170 175

Gly Ala Ala Pro Arg Tyr Pro Leu Met Asp Arg Phe Glu Glu Val Tyr
180 185 190

Phe Arg Ile Gln Asp Leu Glu Met Phe Gln Pro Gly Arg Met His Arg
195 200 205

Val Gly Glu Leu Ser Gly Asp Asn Tyr Leu Arg Ser Pro Gly Gly Arg
210 215 220

Gln Leu Arg Ala Ala Leu Asp Arg Phe Arg Asp Trp Gln Val Arg Cys
225 230 235 240

Pro Asp Trp Phe Glu Cys Glu Asn Leu Tyr Ser Ala Asp Asp Gln Asp
245 250 255

Ala Pro Ser Leu Asp Glu Glu Val Phe Glu Glu Pro Leu Leu Pro Pro
260 265 270

Gly Thr Gly Ile Val Lys Arg Ala Pro Leu Val Arg Glu Pro Gly Ser
275 280 285

Gln Ala Cys Leu Ala Ile Asp Pro Leu Val Gly Glu Glu Gly Gly Ala
290 295 300

Ala Val Ala Lys Leu Glu Pro His Leu Gln Pro Arg Gly Gln Pro Ala
305 310 315 320

Pro Gln Pro Leu His Thr Leu Val Leu Ala Ala Glu Glu Gly Ala Leu
325 330 335

Val Ala Ala Val Glu Pro Gly Pro Leu Ala Asp Gly Ala Ala Val Arg
340 345 350

Leu Ala Leu Ala Gly Glu Gly Glu Ala Cys Pro Leu Leu Gly Ser Pro
355 360 365

Gly Ala Gly Arg Asn Ser Val Leu Phe Leu Pro Val Asp Pro Glu Asp
370 375 380

Ser Pro Leu Gly Ser Ser Thr Pro Met Ala Ser Pro Asp Leu Leu Pro
385 390 395 400

Glu Asp Val Arg Glu His Leu Glu Gly Leu Met Leu Ser Leu Phe Glu

```
                405                 410                 415

Gln Ser Leu Ser Cys Gln Ala Gln Gly Gly Cys Ser Arg Pro Ala Met
            420                 425                 430

Val Leu Thr Asp Pro His Thr Pro Tyr Glu Glu Glu Gln Arg Gln Ser
        435                 440                 445

Val Gln Ser Asp Gln Gly Tyr Ile Ser Arg Ser Ser Pro Gln Pro Pro
    450                 455                 460

Glu Gly Leu Thr Glu Met Glu Glu Glu Glu Glu Glu Glu Gln Asp Pro
465                 470                 475                 480

Gly Lys Pro Ala Leu Pro Leu Ser Pro Glu Asp Leu Glu Ser Leu Arg
                485                 490                 495

Ser Leu Gln Arg Gln Leu Leu Phe Arg Gln Leu Gln Lys Asn Ser Gly
            500                 505                 510

Trp Asp Thr Met Gly Ser Glu Ser Glu Gly Pro Ser Ala
        515                 520                 525


<210> SEQ ID NO 261
<211> LENGTH: 189
<212> TYPE: PRT
<213> ORGANISM: Artificial Sequence
<220> FEATURE:
<223> OTHER INFORMATION: Synthetic: IL17RB NM_018725_3

<400> SEQUENCE: 261

Arg His Glu Arg Ile Lys Lys Thr Ser Phe Ser Thr Thr Thr Leu Leu
1               5                   10                  15

Pro Pro Ile Lys Val Leu Val Val Tyr Pro Ser Glu Ile Cys Phe His
            20                  25                  30

His Thr Ile Cys Tyr Phe Thr Glu Phe Leu Gln Asn His Cys Arg Ser
        35                  40                  45

Glu Val Ile Leu Glu Lys Trp Gln Lys Lys Lys Ile Ala Glu Met Gly
    50                  55                  60

Pro Val Gln Trp Leu Ala Thr Gln Lys Lys Ala Ala Asp Lys Val Val
65                  70                  75                  80

Phe Leu Leu Ser Asn Asp Val Asn Ser Val Cys Asp Gly Thr Cys Gly
                85                  90                  95

Lys Ser Glu Gly Ser Pro Ser Glu Asn Ser Gln Asp Leu Phe Pro Leu
            100                 105                 110

Ala Phe Asn Leu Phe Cys Ser Asp Leu Arg Ser Gln Ile His Leu His
        115                 120                 125

Lys Tyr Val Val Val Tyr Phe Arg Glu Ile Asp Thr Lys Asp Asp Tyr
    130                 135                 140

Asn Ala Leu Ser Val Cys Pro Lys Tyr His Leu Met Lys Asp Ala Thr
145                 150                 155                 160

Ala Phe Cys Ala Glu Leu Leu His Val Lys Gln Gln Val Ser Ala Gly
                165                 170                 175

Lys Arg Ser Gln Ala Cys His Asp Gly Cys Cys Ser Leu
            180                 185


<210> SEQ ID NO 262
<211> LENGTH: 232
<212> TYPE: PRT
<213> ORGANISM: Artificial Sequence
<220> FEATURE:
<223> OTHER INFORMATION: Synthetic: IL17RC transcript variant 1
      NM_153460_3

<400> SEQUENCE: 262
```

```
Lys Lys Asp His Ala Lys Gly Trp Leu Arg Leu Leu Lys Gln Asp Val
1               5                   10                  15

Arg Ser Gly Ala Ala Ala Arg Gly Arg Ala Ala Leu Leu Leu Tyr Ser
            20                  25                  30

Ala Asp Asp Ser Gly Phe Glu Arg Leu Val Gly Ala Leu Ala Ser Ala
        35                  40                  45

Leu Cys Gln Leu Pro Leu Arg Val Ala Val Asp Leu Trp Ser Arg Arg
    50                  55                  60

Glu Leu Ser Ala Gln Gly Pro Val Ala Trp Phe His Ala Gln Arg Arg
65                  70                  75                  80

Gln Thr Leu Gln Glu Gly Gly Val Val Val Leu Leu Phe Ser Pro Gly
                85                  90                  95

Ala Val Ala Leu Cys Ser Glu Trp Leu Gln Asp Gly Val Ser Gly Pro
            100                 105                 110

Gly Ala His Gly Pro His Asp Ala Phe Arg Ala Ser Leu Ser Cys Val
        115                 120                 125

Leu Pro Asp Phe Leu Gln Gly Arg Ala Pro Gly Ser Tyr Val Gly Ala
    130                 135                 140

Cys Phe Asp Arg Leu Leu His Pro Asp Ala Val Pro Ala Leu Phe Arg
145                 150                 155                 160

Thr Val Pro Val Phe Thr Leu Pro Ser Gln Leu Pro Asp Phe Leu Gly
                165                 170                 175

Ala Leu Gln Gln Pro Arg Ala Pro Arg Ser Gly Arg Leu Gln Glu Arg
            180                 185                 190

Ala Glu Gln Val Ser Arg Ala Leu Gln Pro Ala Leu Asp Ser Tyr Phe
        195                 200                 205

His Pro Pro Gly Thr Pro Ala Pro Gly Arg Gly Val Gly Pro Gly Ala
    210                 215                 220

Gly Pro Gly Ala Gly Asp Gly Thr
225                 230
```

<210> SEQ ID NO 263
<211> LENGTH: 219
<212> TYPE: PRT
<213> ORGANISM: Artificial Sequence
<220> FEATURE:
<223> OTHER INFORMATION: Synthetic: IL17RC transcript variant 4 NM_001203263_1

<400> SEQUENCE: 263

```
Lys Lys Asp His Ala Lys Ala Ala Ala Arg Gly Arg Ala Ala Leu Leu
1               5                   10                  15

Leu Tyr Ser Ala Asp Asp Ser Gly Phe Glu Arg Leu Val Gly Ala Leu
            20                  25                  30

Ala Ser Ala Leu Cys Gln Leu Pro Leu Arg Val Ala Val Asp Leu Trp
        35                  40                  45

Ser Arg Arg Glu Leu Ser Ala Gln Gly Pro Val Ala Trp Phe His Ala
    50                  55                  60

Gln Arg Arg Gln Thr Leu Gln Glu Gly Gly Val Val Val Leu Leu Phe
65                  70                  75                  80

Ser Pro Gly Ala Val Ala Leu Cys Ser Glu Trp Leu Gln Asp Gly Val
                85                  90                  95

Ser Gly Pro Gly Ala His Gly Pro His Asp Ala Phe Arg Ala Ser Leu
            100                 105                 110

Ser Cys Val Leu Pro Asp Phe Leu Gln Gly Arg Ala Pro Gly Ser Tyr
```

```
        115                 120                 125

Val Gly Ala Cys Phe Asp Arg Leu Leu His Pro Asp Ala Val Pro Ala
    130                 135                 140

Leu Phe Arg Thr Val Pro Val Phe Thr Leu Pro Ser Gln Leu Pro Asp
145                 150                 155                 160

Phe Leu Gly Ala Leu Gln Gln Pro Arg Ala Pro Arg Ser Gly Arg Leu
                165                 170                 175

Gln Glu Arg Ala Glu Gln Val Ser Arg Ala Leu Gln Pro Ala Leu Asp
            180                 185                 190

Ser Tyr Phe His Pro Pro Gly Thr Pro Ala Pro Gly Arg Gly Val Gly
        195                 200                 205

Pro Gly Ala Gly Pro Gly Ala Gly Asp Gly Thr
    210                 215


<210> SEQ ID NO 264
<211> LENGTH: 419
<212> TYPE: PRT
<213> ORGANISM: Artificial Sequence
<220> FEATURE:
<223> OTHER INFORMATION: Synthetic: IL17RD transcript variant 2
      NM_017563_4

<400> SEQUENCE: 264

Cys Arg Lys Lys Gln Gln Glu Asn Ile Tyr Ser His Leu Asp Glu Glu
1               5                   10                  15

Ser Ser Glu Ser Ser Thr Tyr Thr Ala Ala Leu Pro Arg Glu Arg Leu
            20                  25                  30

Arg Pro Arg Pro Lys Val Phe Leu Cys Tyr Ser Ser Lys Asp Gly Gln
        35                  40                  45

Asn His Met Asn Val Val Gln Cys Phe Ala Tyr Phe Leu Gln Asp Phe
    50                  55                  60

Cys Gly Cys Glu Val Ala Leu Asp Leu Trp Glu Asp Phe Ser Leu Cys
65                  70                  75                  80

Arg Glu Gly Gln Arg Glu Trp Val Ile Gln Lys Ile His Glu Ser Gln
                85                  90                  95

Phe Ile Ile Val Val Cys Ser Lys Gly Met Lys Tyr Phe Val Asp Lys
            100                 105                 110

Lys Asn Tyr Lys His Lys Gly Gly Gly Arg Gly Ser Gly Lys Gly Glu
        115                 120                 125

Leu Phe Leu Val Ala Val Ser Ala Ile Ala Glu Lys Leu Arg Gln Ala
    130                 135                 140

Lys Gln Ser Ser Ser Ala Ala Leu Ser Lys Phe Ile Ala Val Tyr Phe
145                 150                 155                 160

Asp Tyr Ser Cys Glu Gly Asp Val Pro Gly Ile Leu Asp Leu Ser Thr
                165                 170                 175

Lys Tyr Arg Leu Met Asp Asn Leu Pro Gln Leu Cys Ser His Leu His
            180                 185                 190

Ser Arg Asp His Gly Leu Gln Glu Pro Gly Gln His Thr Arg Gln Gly
        195                 200                 205

Ser Arg Arg Asn Tyr Phe Arg Ser Lys Ser Gly Arg Ser Leu Tyr Val
    210                 215                 220

Ala Ile Cys Asn Met His Gln Phe Ile Asp Glu Glu Pro Asp Trp Phe
225                 230                 235                 240

Glu Lys Gln Phe Val Pro Phe His Pro Pro Pro Leu Arg Tyr Arg Glu
                245                 250                 255
```

```
Pro Val Leu Glu Lys Phe Asp Ser Gly Leu Val Leu Asn Asp Val Met
            260                 265                 270

Cys Lys Pro Gly Pro Glu Ser Asp Phe Cys Leu Lys Val Glu Ala Ala
        275                 280                 285

Val Leu Gly Ala Thr Gly Pro Ala Asp Ser Gln His Glu Ser Gln His
    290                 295                 300

Gly Gly Leu Asp Gln Asp Gly Glu Ala Arg Pro Ala Leu Asp Gly Ser
305                 310                 315                 320

Ala Ala Leu Gln Pro Leu Leu His Thr Val Lys Ala Gly Ser Pro Ser
                325                 330                 335

Asp Met Pro Arg Asp Ser Gly Ile Tyr Asp Ser Ser Val Pro Ser Ser
            340                 345                 350

Glu Leu Ser Leu Pro Leu Met Glu Gly Leu Ser Thr Asp Gln Thr Glu
        355                 360                 365

Thr Ser Ser Leu Thr Glu Ser Val Ser Ser Ser Ser Gly Leu Gly Glu
    370                 375                 380

Glu Glu Pro Pro Ala Leu Pro Ser Lys Leu Leu Ser Ser Gly Ser Cys
385                 390                 395                 400

Lys Ala Asp Leu Gly Cys Arg Ser Tyr Thr Asp Glu Leu His Ala Val
                405                 410                 415

Ala Pro Leu


<210> SEQ ID NO 265
<211> LENGTH: 192
<212> TYPE: PRT
<213> ORGANISM: Artificial Sequence
<220> FEATURE:
<223> OTHER INFORMATION: Synthetic: IL17RE transcript variant 1
      NM_153480_1

<400> SEQUENCE: 265

Thr Cys Arg Arg Pro Gln Ser Gly Pro Gly Pro Ala Arg Pro Val Leu
1               5                   10                  15

Leu Leu His Ala Ala Asp Ser Glu Ala Gln Arg Arg Leu Val Gly Ala
            20                  25                  30

Leu Ala Glu Leu Leu Arg Ala Ala Leu Gly Gly Gly Arg Asp Val Ile
        35                  40                  45

Val Asp Leu Trp Glu Gly Arg His Val Ala Arg Val Gly Pro Leu Pro
    50                  55                  60

Trp Leu Trp Ala Ala Arg Thr Arg Val Ala Arg Glu Gln Gly Thr Val
65                  70                  75                  80

Leu Leu Leu Trp Ser Gly Ala Asp Leu Arg Pro Val Ser Gly Pro Asp
                85                  90                  95

Pro Arg Ala Ala Pro Leu Leu Ala Leu Leu His Ala Ala Pro Arg Pro
            100                 105                 110

Leu Leu Leu Leu Ala Tyr Phe Ser Arg Leu Cys Ala Lys Gly Asp Ile
        115                 120                 125

Pro Pro Pro Leu Arg Ala Leu Pro Arg Tyr Arg Leu Leu Arg Asp Leu
    130                 135                 140

Pro Arg Leu Leu Arg Ala Leu Asp Ala Arg Pro Phe Ala Glu Ala Thr
145                 150                 155                 160

Ser Trp Gly Arg Leu Gly Ala Arg Gln Arg Arg Gln Ser Arg Leu Glu
                165                 170                 175

Leu Cys Ser Arg Leu Glu Arg Glu Ala Ala Arg Leu Ala Asp Leu Gly
            180                 185                 190
```

<210> SEQ ID NO 266
<211> LENGTH: 191
<212> TYPE: PRT
<213> ORGANISM: Artificial Sequence
<220> FEATURE:
<223> OTHER INFORMATION: Synthetic: IL18R1 transcript variant 1
NM_003855_3

<400> SEQUENCE: 266

```
Tyr Arg Val Asp Leu Val Leu Phe Tyr Arg His Leu Thr Arg Arg Asp
1               5                   10                  15

Glu Thr Leu Thr Asp Gly Lys Thr Tyr Asp Ala Phe Val Ser Tyr Leu
            20                  25                  30

Lys Glu Cys Arg Pro Glu Asn Gly Glu Glu His Thr Phe Ala Val Glu
        35                  40                  45

Ile Leu Pro Arg Val Leu Glu Lys His Phe Gly Tyr Lys Leu Cys Ile
    50                  55                  60

Phe Glu Arg Asp Val Val Pro Gly Gly Ala Val Val Asp Glu Ile His
65                  70                  75                  80

Ser Leu Ile Glu Lys Ser Arg Arg Leu Ile Ile Val Leu Ser Lys Ser
                85                  90                  95

Tyr Met Ser Asn Glu Val Arg Tyr Glu Leu Glu Ser Gly Leu His Glu
            100                 105                 110

Ala Leu Val Glu Arg Lys Ile Lys Ile Ile Leu Ile Glu Phe Thr Pro
        115                 120                 125

Val Thr Asp Phe Thr Phe Leu Pro Gln Ser Leu Lys Leu Leu Lys Ser
    130                 135                 140

His Arg Val Leu Lys Trp Lys Ala Asp Lys Ser Leu Ser Tyr Asn Ser
145                 150                 155                 160

Arg Phe Trp Lys Asn Leu Leu Tyr Leu Met Pro Ala Lys Thr Val Lys
                165                 170                 175

Pro Gly Arg Asp Glu Pro Glu Val Leu Pro Val Leu Ser Glu Ser
            180                 185                 190
```

<210> SEQ ID NO 267
<211> LENGTH: 222
<212> TYPE: PRT
<213> ORGANISM: Artificial Sequence
<220> FEATURE:
<223> OTHER INFORMATION: Synthetic: IL18RAP NM_003853_3

<400> SEQUENCE: 267

```
Ser Ala Leu Leu Tyr Arg His Trp Ile Glu Ile Val Leu Leu Tyr Arg
1               5                   10                  15

Thr Tyr Gln Ser Lys Asp Gln Thr Leu Gly Asp Lys Lys Asp Phe Asp
            20                  25                  30

Ala Phe Val Ser Tyr Ala Lys Trp Ser Ser Phe Pro Ser Glu Ala Thr
        35                  40                  45

Ser Ser Leu Ser Glu Glu His Leu Ala Leu Ser Leu Phe Pro Asp Val
    50                  55                  60

Leu Glu Asn Lys Tyr Gly Tyr Ser Leu Cys Leu Leu Glu Arg Asp Val
65                  70                  75                  80

Ala Pro Gly Gly Val Tyr Ala Glu Asp Ile Val Ser Ile Ile Lys Arg
                85                  90                  95

Ser Arg Arg Gly Ile Phe Ile Leu Ser Pro Asn Tyr Val Asn Gly Pro
            100                 105                 110

Ser Ile Phe Glu Leu Gln Ala Ala Val Asn Leu Ala Leu Asp Asp Gln
```

115 120 125

Thr Leu Lys Leu Ile Leu Ile Lys Phe Cys Tyr Phe Gln Glu Pro Glu
130 135 140

Ser Leu Pro His Leu Val Lys Lys Ala Leu Arg Val Leu Pro Thr Val
145 150 155 160

Thr Trp Arg Gly Leu Lys Ser Val Pro Pro Asn Ser Arg Phe Trp Ala
165 170 175

Lys Met Arg Tyr His Met Pro Val Lys Asn Ser Gln Gly Phe Thr Trp
180 185 190

Asn Gln Leu Arg Ile Thr Ser Arg Ile Phe Gln Trp Lys Gly Leu Ser
195 200 205

Arg Thr Glu Thr Thr Gly Arg Ser Ser Gln Pro Lys Glu Trp
210 215 220

<210> SEQ ID NO 268
<211> LENGTH: 282
<212> TYPE: PRT
<213> ORGANISM: Artificial Sequence
<220> FEATURE:
<223> OTHER INFORMATION: Synthetic: IL20RA transcript variant 1 NM_014432_3

<400> SEQUENCE: 268

Ser Ile Tyr Arg Tyr Ile His Val Gly Lys Glu Lys His Pro Ala Asn
1 5 10 15

Leu Ile Leu Ile Tyr Gly Asn Glu Phe Asp Lys Arg Phe Phe Val Pro
20 25 30

Ala Glu Lys Ile Val Ile Asn Phe Ile Thr Leu Asn Ile Ser Asp Asp
35 40 45

Ser Lys Ile Ser His Gln Asp Met Ser Leu Leu Gly Lys Ser Ser Asp
50 55 60

Val Ser Ser Leu Asn Asp Pro Gln Pro Ser Gly Asn Leu Arg Pro Pro
65 70 75 80

Gln Glu Glu Glu Glu Val Lys His Leu Gly Tyr Ala Ser His Leu Met
85 90 95

Glu Ile Phe Cys Asp Ser Glu Glu Asn Thr Glu Gly Thr Ser Leu Thr
100 105 110

Gln Gln Glu Ser Leu Ser Arg Thr Ile Pro Pro Asp Lys Thr Val Ile
115 120 125

Glu Tyr Glu Tyr Asp Val Arg Thr Thr Asp Ile Cys Ala Gly Pro Glu
130 135 140

Glu Gln Glu Leu Ser Leu Gln Glu Glu Val Ser Thr Gln Gly Thr Leu
145 150 155 160

Leu Glu Ser Gln Ala Ala Leu Ala Val Leu Gly Pro Gln Thr Leu Gln
165 170 175

Tyr Ser Tyr Thr Pro Gln Leu Gln Asp Leu Asp Pro Leu Ala Gln Glu
180 185 190

His Thr Asp Ser Glu Glu Gly Pro Glu Glu Glu Pro Ser Thr Thr Leu
195 200 205

Val Asp Trp Asp Pro Gln Thr Gly Arg Leu Cys Ile Pro Ser Leu Ser
210 215 220

Ser Phe Asp Gln Asp Ser Glu Gly Cys Glu Pro Ser Glu Gly Asp Gly
225 230 235 240

Leu Gly Glu Glu Gly Leu Leu Ser Arg Leu Tyr Glu Glu Pro Ala Pro
245 250 255

```
Asp Arg Pro Pro Gly Glu Asn Glu Thr Tyr Leu Met Gln Phe Met Glu
            260                 265                 270

Glu Trp Gly Leu Tyr Val Gln Met Glu Asn
        275                 280


<210> SEQ ID NO 269
<211> LENGTH: 57
<212> TYPE: PRT
<213> ORGANISM: Artificial Sequence
<220> FEATURE:
<223> OTHER INFORMATION: Synthetic: IL20RB NM_144717_3

<400> SEQUENCE: 269

Trp Lys Met Gly Arg Leu Leu Gln Tyr Ser Cys Cys Pro Val Val Val
1               5                   10                  15

Leu Pro Asp Thr Leu Lys Ile Thr Asn Ser Pro Gln Lys Leu Ile Ser
            20                  25                  30

Cys Arg Arg Glu Glu Val Asp Ala Cys Ala Thr Ala Val Met Ser Pro
        35                  40                  45

Glu Glu Leu Leu Arg Ala Trp Ile Ser
    50                  55


<210> SEQ ID NO 270
<211> LENGTH: 285
<212> TYPE: PRT
<213> ORGANISM: Artificial Sequence
<220> FEATURE:
<223> OTHER INFORMATION: Synthetic: IL21R transcript variant 2
      NM_181078_2

<400> SEQUENCE: 270

Ser Leu Lys Thr His Pro Leu Trp Arg Leu Trp Lys Lys Ile Trp Ala
1               5                   10                  15

Val Pro Ser Pro Glu Arg Phe Phe Met Pro Leu Tyr Lys Gly Cys Ser
            20                  25                  30

Gly Asp Phe Lys Lys Trp Val Gly Ala Pro Phe Thr Gly Ser Ser Leu
        35                  40                  45

Glu Leu Gly Pro Trp Ser Pro Glu Val Pro Ser Thr Leu Glu Val Tyr
    50                  55                  60

Ser Cys His Pro Pro Arg Ser Pro Ala Lys Arg Leu Gln Leu Thr Glu
65                  70                  75                  80

Leu Gln Glu Pro Ala Glu Leu Val Glu Ser Asp Gly Val Pro Lys Pro
                85                  90                  95

Ser Phe Trp Pro Thr Ala Gln Asn Ser Gly Gly Ser Ala Tyr Ser Glu
            100                 105                 110

Glu Arg Asp Arg Pro Tyr Gly Leu Val Ser Ile Asp Thr Val Thr Val
        115                 120                 125

Leu Asp Ala Glu Gly Pro Cys Thr Trp Pro Cys Ser Cys Glu Asp Asp
    130                 135                 140

Gly Tyr Pro Ala Leu Asp Leu Asp Ala Gly Leu Glu Pro Ser Pro Gly
145                 150                 155                 160

Leu Glu Asp Pro Leu Leu Asp Ala Gly Thr Thr Val Leu Ser Cys Gly
                165                 170                 175

Cys Val Ser Ala Gly Ser Pro Gly Leu Gly Gly Pro Leu Gly Ser Leu
            180                 185                 190

Leu Asp Arg Leu Lys Pro Pro Leu Ala Asp Gly Glu Asp Trp Ala Gly
        195                 200                 205

Gly Leu Pro Trp Gly Gly Arg Ser Pro Gly Gly Val Ser Glu Ser Glu
```

```
    210                 215                 220

Ala Gly Ser Pro Leu Ala Gly Leu Asp Met Asp Thr Phe Asp Ser Gly
225                 230                 235                 240

Phe Val Gly Ser Asp Cys Ser Ser Pro Val Glu Cys Asp Phe Thr Ser
                245                 250                 255

Pro Gly Asp Glu Gly Pro Pro Arg Ser Tyr Leu Arg Gln Trp Val Val
            260                 265                 270

Ile Pro Pro Pro Leu Ser Ser Pro Gly Pro Gln Ala Ser
        275                 280                 285


<210> SEQ ID NO 271
<211> LENGTH: 325
<212> TYPE: PRT
<213> ORGANISM: Artificial Sequence
<220> FEATURE:
<223> OTHER INFORMATION: Synthetic: IL22RA1 NM_021258_3

<400> SEQUENCE: 271

Ser Tyr Arg Tyr Val Thr Lys Pro Pro Ala Pro Pro Asn Ser Leu Asn
1               5                   10                  15

Val Gln Arg Val Leu Thr Phe Gln Pro Leu Arg Phe Ile Gln Glu His
            20                  25                  30

Val Leu Ile Pro Val Phe Asp Leu Ser Gly Pro Ser Ser Leu Ala Gln
        35                  40                  45

Pro Val Gln Tyr Ser Gln Ile Arg Val Ser Gly Pro Arg Glu Pro Ala
    50                  55                  60

Gly Ala Pro Gln Arg His Ser Leu Ser Glu Ile Thr Tyr Leu Gly Gln
65                  70                  75                  80

Pro Asp Ile Ser Ile Leu Gln Pro Ser Asn Val Pro Pro Pro Gln Ile
                85                  90                  95

Leu Ser Pro Leu Ser Tyr Ala Pro Asn Ala Ala Pro Glu Val Gly Pro
            100                 105                 110

Pro Ser Tyr Ala Pro Gln Val Thr Pro Glu Ala Gln Phe Pro Phe Tyr
        115                 120                 125

Ala Pro Gln Ala Ile Ser Lys Val Gln Pro Ser Ser Tyr Ala Pro Gln
    130                 135                 140

Ala Thr Pro Asp Ser Trp Pro Pro Ser Tyr Gly Val Cys Met Glu Gly
145                 150                 155                 160

Ser Gly Lys Asp Ser Pro Thr Gly Thr Leu Ser Ser Pro Lys His Leu
                165                 170                 175

Arg Pro Lys Gly Gln Leu Gln Lys Glu Pro Pro Ala Gly Ser Cys Met
            180                 185                 190

Leu Gly Gly Leu Ser Leu Gln Glu Val Thr Ser Leu Ala Met Glu Glu
        195                 200                 205

Ser Gln Glu Ala Lys Ser Leu His Gln Pro Leu Gly Ile Cys Thr Asp
    210                 215                 220

Arg Thr Ser Asp Pro Asn Val Leu His Ser Gly Glu Glu Gly Thr Pro
225                 230                 235                 240

Gln Tyr Leu Lys Gly Gln Leu Pro Leu Leu Ser Ser Val Gln Ile Glu
                245                 250                 255

Gly His Pro Met Ser Leu Pro Leu Gln Pro Pro Ser Arg Pro Cys Ser
            260                 265                 270

Pro Ser Asp Gln Gly Pro Ser Pro Trp Gly Leu Leu Glu Ser Leu Val
        275                 280                 285

Cys Pro Lys Asp Glu Ala Lys Ser Pro Ala Pro Glu Thr Ser Asp Leu
```

```
    290                 295                 300

Glu Gln Pro Thr Glu Leu Asp Ser Leu Phe Arg Gly Leu Ala Leu Thr
305                 310                 315                 320

Val Gln Trp Glu Ser
                325


<210> SEQ ID NO 272
<211> LENGTH: 253
<212> TYPE: PRT
<213> ORGANISM: Artificial Sequence
<220> FEATURE:
<223> OTHER INFORMATION: Synthetic: IL23R NM_144701_2

<400> SEQUENCE: 272

Asn Arg Ser Phe Arg Thr Gly Ile Lys Arg Arg Ile Leu Leu Leu Ile
1               5                   10                  15

Pro Lys Trp Leu Tyr Glu Asp Ile Pro Asn Met Lys Asn Ser Asn Val
            20                  25                  30

Val Lys Met Leu Gln Glu Asn Ser Glu Leu Met Asn Asn Asn Ser Ser
        35                  40                  45

Glu Gln Val Leu Tyr Val Asp Pro Met Ile Thr Glu Ile Lys Glu Ile
    50                  55                  60

Phe Ile Pro Glu His Lys Pro Thr Asp Tyr Lys Lys Glu Asn Thr Gly
65                  70                  75                  80

Pro Leu Glu Thr Arg Asp Tyr Pro Gln Asn Ser Leu Phe Asp Asn Thr
                85                  90                  95

Thr Val Val Tyr Ile Pro Asp Leu Asn Thr Gly Tyr Lys Pro Gln Ile
            100                 105                 110

Ser Asn Phe Leu Pro Glu Gly Ser His Leu Ser Asn Asn Asn Glu Ile
        115                 120                 125

Thr Ser Leu Thr Leu Lys Pro Pro Val Asp Ser Leu Asp Ser Gly Asn
    130                 135                 140

Asn Pro Arg Leu Gln Lys His Pro Asn Phe Ala Phe Ser Val Ser Ser
145                 150                 155                 160

Val Asn Ser Leu Ser Asn Thr Ile Phe Leu Gly Glu Leu Ser Leu Ile
                165                 170                 175

Leu Asn Gln Gly Glu Cys Ser Ser Pro Asp Ile Gln Asn Ser Val Glu
            180                 185                 190

Glu Glu Thr Thr Met Leu Leu Glu Asn Asp Ser Pro Ser Glu Thr Ile
        195                 200                 205

Pro Glu Gln Thr Leu Leu Pro Asp Glu Phe Val Ser Cys Leu Gly Ile
    210                 215                 220

Val Asn Glu Glu Leu Pro Ser Ile Asn Thr Tyr Phe Pro Gln Asn Ile
225                 230                 235                 240

Leu Glu Ser His Phe Asn Arg Ile Ser Leu Leu Glu Lys
                245                 250


<210> SEQ ID NO 273
<211> LENGTH: 99
<212> TYPE: PRT
<213> ORGANISM: Artificial Sequence
<220> FEATURE:
<223> OTHER INFORMATION: Synthetic: IL27RA NM_004843_3

<400> SEQUENCE: 273

Thr Ser Gly Arg Cys Tyr His Leu Arg His Lys Val Leu Pro Arg Trp
1               5                   10                  15
```

```
Val Trp Glu Lys Val Pro Asp Pro Ala Asn Ser Ser Ser Gly Gln Pro
            20                  25                  30

His Met Glu Gln Val Pro Glu Ala Gln Pro Leu Gly Asp Leu Pro Ile
        35                  40                  45

Leu Glu Val Glu Glu Met Glu Pro Pro Pro Val Met Glu Ser Ser Gln
    50                  55                  60

Pro Ala Gln Ala Thr Ala Pro Leu Asp Ser Gly Tyr Glu Lys His Phe
65                  70                  75                  80

Leu Pro Thr Pro Glu Glu Leu Gly Leu Leu Gly Pro Pro Arg Pro Gln
                85                  90                  95

Val Leu Ala


<210> SEQ ID NO 274
<211> LENGTH: 86
<212> TYPE: PRT
<213> ORGANISM: Artificial Sequence
<220> FEATURE:
<223> OTHER INFORMATION: Synthetic: IL27RA NM_004843_3

<400> SEQUENCE: 274

Thr Ser Trp Val Trp Glu Lys Val Pro Asp Pro Ala Asn Ser Ser Ser
1               5                   10                  15

Gly Gln Pro His Met Glu Gln Val Pro Glu Ala Gln Pro Leu Gly Asp
            20                  25                  30

Leu Pro Ile Leu Glu Val Glu Glu Met Glu Pro Pro Pro Val Met Glu
        35                  40                  45

Ser Ser Gln Pro Ala Gln Ala Thr Ala Pro Leu Asp Ser Gly Tyr Glu
    50                  55                  60

Lys His Phe Leu Pro Thr Pro Glu Glu Leu Gly Leu Leu Gly Pro Pro
65                  70                  75                  80

Arg Pro Gln Val Leu Ala
                85


<210> SEQ ID NO 275
<211> LENGTH: 189
<212> TYPE: PRT
<213> ORGANISM: Artificial Sequence
<220> FEATURE:
<223> OTHER INFORMATION: Synthetic: IL31RA transcript variant 1
      NM_139017_5

<400> SEQUENCE: 275

Lys Lys Pro Asn Lys Leu Thr His Leu Cys Trp Pro Thr Val Pro Asn
1               5                   10                  15

Pro Ala Glu Ser Ser Ile Ala Thr Trp His Gly Asp Asp Phe Lys Asp
            20                  25                  30

Lys Leu Asn Leu Lys Glu Ser Asp Asp Ser Val Asn Thr Glu Asp Arg
        35                  40                  45

Ile Leu Lys Pro Cys Ser Thr Pro Ser Asp Lys Leu Val Ile Asp Lys
    50                  55                  60

Leu Val Val Asn Phe Gly Asn Val Leu Gln Glu Ile Phe Thr Asp Glu
65                  70                  75                  80

Ala Arg Thr Gly Gln Glu Asn Asn Leu Gly Gly Glu Lys Asn Gly Tyr
                85                  90                  95

Val Thr Cys Pro Phe Arg Pro Asp Cys Pro Leu Gly Lys Ser Phe Glu
            100                 105                 110

Glu Leu Pro Val Ser Pro Glu Ile Pro Pro Arg Lys Ser Gln Tyr Leu
        115                 120                 125
```

```
Arg Ser Arg Met Pro Glu Gly Thr Arg Pro Glu Ala Lys Glu Gln Leu
    130                 135                 140

Leu Phe Ser Gly Gln Ser Leu Val Pro Asp His Leu Cys Glu Glu Gly
145                 150                 155                 160

Ala Pro Asn Pro Tyr Leu Lys Asn Ser Val Thr Ala Arg Glu Phe Leu
                165                 170                 175

Val Ser Glu Lys Leu Pro Glu His Thr Lys Gly Glu Val
            180                 185


<210> SEQ ID NO 276
<211> LENGTH: 106
<212> TYPE: PRT
<213> ORGANISM: Artificial Sequence
<220> FEATURE:
<223> OTHER INFORMATION: Synthetic: IL31RA transcript variant 4
      NM_001242638_1

<400> SEQUENCE: 276

Lys Lys Pro Asn Lys Leu Thr His Leu Cys Trp Pro Thr Val Pro Asn
1               5                   10                  15

Pro Ala Glu Ser Ser Ile Ala Thr Trp His Gly Asp Asp Phe Lys Asp
            20                  25                  30

Lys Leu Asn Leu Lys Glu Ser Asp Asp Ser Val Asn Thr Glu Asp Arg
        35                  40                  45

Ile Leu Lys Pro Cys Ser Thr Pro Ser Asp Lys Leu Val Ile Asp Lys
    50                  55                  60

Leu Val Val Asn Phe Gly Asn Val Leu Gln Glu Ile Phe Thr Asp Glu
65                  70                  75                  80

Ala Arg Thr Gly Gln Glu Asn Asn Leu Gly Gly Glu Lys Asn Gly Thr
                85                  90                  95

Arg Ile Leu Ser Ser Cys Pro Thr Ser Ile
            100                 105


<210> SEQ ID NO 277
<211> LENGTH: 303
<212> TYPE: PRT
<213> ORGANISM: Artificial Sequence
<220> FEATURE:
<223> OTHER INFORMATION: Synthetic: LEPR transcript variant 1
      NM_002303_5

<400> SEQUENCE: 277

Ser His Gln Arg Met Lys Lys Leu Phe Trp Glu Asp Val Pro Asn Pro
1               5                   10                  15

Lys Asn Cys Ser Trp Ala Gln Gly Leu Asn Phe Gln Lys Pro Glu Thr
            20                  25                  30

Phe Glu His Leu Phe Ile Lys His Thr Ala Ser Val Thr Cys Gly Pro
        35                  40                  45

Leu Leu Leu Glu Pro Glu Thr Ile Ser Glu Asp Ile Ser Val Asp Thr
    50                  55                  60

Ser Trp Lys Asn Lys Asp Glu Met Met Pro Thr Thr Val Val Ser Leu
65                  70                  75                  80

Leu Ser Thr Thr Asp Leu Glu Lys Gly Ser Val Cys Ile Ser Asp Gln
                85                  90                  95

Phe Asn Ser Val Asn Phe Ser Glu Ala Glu Gly Thr Glu Val Thr Tyr
            100                 105                 110

Glu Asp Glu Ser Gln Arg Gln Pro Phe Val Lys Tyr Ala Thr Leu Ile
        115                 120                 125
```

```
Ser Asn Ser Lys Pro Ser Glu Thr Gly Glu Glu Gln Gly Leu Ile Asn
    130                 135                 140

Ser Ser Val Thr Lys Cys Phe Ser Ser Lys Asn Ser Pro Leu Lys Asp
145                 150                 155                 160

Ser Phe Ser Asn Ser Ser Trp Glu Ile Glu Ala Gln Ala Phe Phe Ile
                165                 170                 175

Leu Ser Asp Gln His Pro Asn Ile Ile Ser Pro His Leu Thr Phe Ser
            180                 185                 190

Glu Gly Leu Asp Glu Leu Leu Lys Leu Glu Gly Asn Phe Pro Glu Glu
        195                 200                 205

Asn Asn Asp Lys Lys Ser Ile Tyr Tyr Leu Gly Val Thr Ser Ile Lys
    210                 215                 220

Lys Arg Glu Ser Gly Val Leu Leu Thr Asp Lys Ser Arg Val Ser Cys
225                 230                 235                 240

Pro Phe Pro Ala Pro Cys Leu Phe Thr Asp Ile Arg Val Leu Gln Asp
                245                 250                 255

Ser Cys Ser His Phe Val Glu Asn Asn Ile Asn Leu Gly Thr Ser Ser
            260                 265                 270

Lys Lys Thr Phe Ala Ser Tyr Met Pro Gln Phe Gln Thr Cys Ser Thr
        275                 280                 285

Gln Thr His Lys Ile Met Glu Asn Lys Met Cys Asp Leu Thr Val
    290                 295                 300


<210> SEQ ID NO 278
<211> LENGTH: 96
<212> TYPE: PRT
<213> ORGANISM: Artificial Sequence
<220> FEATURE:
<223> OTHER INFORMATION: Synthetic: LEPR transcript variant 2
      NM_001003680_3

<400> SEQUENCE: 278

Ser His Gln Arg Met Lys Lys Leu Phe Trp Glu Asp Val Pro Asn Pro
1               5                   10                  15

Lys Asn Cys Ser Trp Ala Gln Gly Leu Asn Phe Gln Lys Met Leu Glu
            20                  25                  30

Gly Ser Met Phe Val Lys Ser His His His Ser Leu Ile Ser Ser Thr
        35                  40                  45

Gln Gly His Lys His Cys Gly Arg Pro Gln Gly Pro Leu His Arg Lys
    50                  55                  60

Thr Arg Asp Leu Cys Ser Leu Val Tyr Leu Leu Thr Leu Pro Pro Leu
65                  70                  75                  80

Leu Ser Tyr Asp Pro Ala Lys Ser Pro Ser Val Arg Asn Thr Gln Glu
                85                  90                  95


<210> SEQ ID NO 279
<211> LENGTH: 34
<212> TYPE: PRT
<213> ORGANISM: Artificial Sequence
<220> FEATURE:
<223> OTHER INFORMATION: Synthetic: LEPR transcript variant 3
      NM_001003679_3

<400> SEQUENCE: 279

Ser His Gln Arg Met Lys Lys Leu Phe Trp Glu Asp Val Pro Asn Pro
1               5                   10                  15

Lys Asn Cys Ser Trp Ala Gln Gly Leu Asn Phe Gln Lys Arg Thr Asp
            20                  25                  30
```

Ile Leu

<210> SEQ ID NO 280
<211> LENGTH: 44
<212> TYPE: PRT
<213> ORGANISM: Artificial Sequence
<220> FEATURE:
<223> OTHER INFORMATION: Synthetic: LEPR transcript variant 5
NM_001198688_1

<400> SEQUENCE: 280

```
Ser His Gln Arg Met Lys Lys Leu Phe Trp Glu Asp Val Pro Asn Pro
1               5                   10                  15

Lys Asn Cys Ser Trp Ala Gln Gly Leu Asn Phe Gln Lys Lys Met Pro
            20                  25                  30

Gly Thr Lys Glu Leu Leu Gly Gly Gly Trp Leu Thr
        35                  40
```

<210> SEQ ID NO 281
<211> LENGTH: 239
<212> TYPE: PRT
<213> ORGANISM: Artificial Sequence
<220> FEATURE:
<223> OTHER INFORMATION: Synthetic: LIFR NM_001127671_1

<400> SEQUENCE: 281

```
Tyr Arg Lys Arg Glu Trp Ile Lys Glu Thr Phe Tyr Pro Asp Ile Pro
1               5                   10                  15

Asn Pro Glu Asn Cys Lys Ala Leu Gln Phe Gln Lys Ser Val Cys Glu
            20                  25                  30

Gly Ser Ser Ala Leu Lys Thr Leu Glu Met Asn Pro Cys Thr Pro Asn
        35                  40                  45

Asn Val Glu Val Leu Glu Thr Arg Ser Ala Phe Pro Lys Ile Glu Asp
    50                  55                  60

Thr Glu Ile Ile Ser Pro Val Ala Glu Arg Pro Glu Asp Arg Ser Asp
65                  70                  75                  80

Ala Glu Pro Glu Asn His Val Val Val Ser Tyr Cys Pro Pro Ile Ile
                85                  90                  95

Glu Glu Glu Ile Pro Asn Pro Ala Ala Asp Glu Ala Gly Gly Thr Ala
            100                 105                 110

Gln Val Ile Tyr Ile Asp Val Gln Ser Met Tyr Gln Pro Gln Ala Lys
        115                 120                 125

Pro Glu Glu Glu Gln Glu Asn Asp Pro Val Gly Gly Ala Gly Tyr Lys
    130                 135                 140

Pro Gln Met His Leu Pro Ile Asn Ser Thr Val Glu Asp Ile Ala Ala
145                 150                 155                 160

Glu Glu Asp Leu Asp Lys Thr Ala Gly Tyr Arg Pro Gln Ala Asn Val
                165                 170                 175

Asn Thr Trp Asn Leu Val Ser Pro Asp Ser Pro Arg Ser Ile Asp Ser
            180                 185                 190

Asn Ser Glu Ile Val Ser Phe Gly Ser Pro Cys Ser Ile Asn Ser Arg
        195                 200                 205

Gln Phe Leu Ile Pro Pro Lys Asp Glu Asp Ser Pro Lys Ser Asn Gly
    210                 215                 220

Gly Gly Trp Ser Phe Thr Asn Phe Phe Gln Asn Lys Pro Asn Asp
225                 230                 235
```

<210> SEQ ID NO 282
<211> LENGTH: 202
<212> TYPE: PRT
<213> ORGANISM: Artificial Sequence
<220> FEATURE:
<223> OTHER INFORMATION: Synthetic: LMP1 NC_007605_1

<400> SEQUENCE: 282

```
Tyr Tyr His Gly Gln Arg His Ser Asp Glu His His His Asp Asp Ser
1               5                   10                  15

Leu Pro His Pro Gln Gln Ala Thr Asp Asp Ser Gly His Glu Ser Asp
            20                  25                  30

Ser Asn Ser Asn Glu Gly Arg His His Leu Leu Val Ser Gly Ala Gly
        35                  40                  45

Asp Gly Pro Pro Leu Cys Ser Gln Asn Leu Gly Ala Pro Gly Gly Gly
    50                  55                  60

Pro Asp Asn Gly Pro Gln Asp Pro Asp Asn Thr Asp Asp Asn Gly Pro
65                  70                  75                  80

Gln Asp Pro Asp Asn Thr Asp Asp Asn Gly Pro His Asp Pro Leu Pro
                85                  90                  95

Gln Asp Pro Asp Asn Thr Asp Asp Asn Gly Pro Gln Asp Pro Asp Asn
            100                 105                 110

Thr Asp Asp Asn Gly Pro His Asp Pro Leu Pro His Ser Pro Ser Asp
        115                 120                 125

Ser Ala Gly Asn Asp Gly Gly Pro Pro Gln Leu Thr Glu Glu Val Glu
    130                 135                 140

Asn Lys Gly Gly Asp Gln Gly Pro Pro Leu Met Thr Asp Gly Gly Gly
145                 150                 155                 160

Gly His Ser His Asp Ser Gly His Gly Gly Gly Asp Pro His Leu Pro
                165                 170                 175

Thr Leu Leu Leu Gly Ser Ser Gly Ser Gly Gly Asp Asp Asp Asp Pro
            180                 185                 190

His Gly Pro Val Gln Leu Ser Tyr Tyr Asp
        195                 200
```

<210> SEQ ID NO 283
<211> LENGTH: 122
<212> TYPE: PRT
<213> ORGANISM: Artificial Sequence
<220> FEATURE:
<223> OTHER INFORMATION: Synthetic: MPL NM_005373_2

<400> SEQUENCE: 283

```
Arg Trp Gln Phe Pro Ala His Tyr Arg Arg Leu Arg His Ala Leu Trp
1               5                   10                  15

Pro Ser Leu Pro Asp Leu His Arg Val Leu Gly Gln Tyr Leu Arg Asp
            20                  25                  30

Thr Ala Ala Leu Ser Pro Pro Lys Ala Thr Val Ser Asp Thr Cys Glu
        35                  40                  45

Glu Val Glu Pro Ser Leu Leu Glu Ile Leu Pro Lys Ser Ser Glu Arg
    50                  55                  60

Thr Pro Leu Pro Leu Cys Ser Ser Gln Ala Gln Met Asp Tyr Arg Arg
65                  70                  75                  80

Leu Gln Pro Ser Cys Leu Gly Thr Met Pro Leu Ser Val Cys Pro Pro
                85                  90                  95

Met Ala Glu Ser Gly Ser Cys Cys Thr Thr His Ile Ala Asn His Ser
            100                 105                 110
```

```
Tyr Leu Pro Leu Ser Tyr Trp Gln Gln Pro
        115                 120


<210> SEQ ID NO 284
<211> LENGTH: 304
<212> TYPE: PRT
<213> ORGANISM: Artificial Sequence
<220> FEATURE:
<223> OTHER INFORMATION: Synthetic: MYD88 transcript variant 1
      NM_001172567_1

<400> SEQUENCE: 284

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Leu Ala Arg Arg Pro Arg Gly Gly Cys
    210                 215                 220

Arg Arg Met Val Val Val Val Ser Asp Asp Tyr Leu Gln Ser Lys Glu
225                 230                 235                 240

Cys Asp Phe Gln Thr Lys Phe Ala Leu Ser Leu Ser Pro Gly Ala His
                245                 250                 255

Gln Lys Arg Leu Ile Pro Ile Lys Tyr Lys Ala Met Lys Lys Glu Phe
            260                 265                 270

Pro Ser Ile Leu Arg Phe Ile Thr Val Cys Asp Tyr Thr Asn Pro Cys
        275                 280                 285

Thr Lys Ser Trp Phe Trp Thr Arg Leu Ala Lys Ala Leu Ser Leu Pro
    290                 295                 300


<210> SEQ ID NO 285
<211> LENGTH: 296
<212> TYPE: PRT
<213> ORGANISM: Artificial Sequence
<220> FEATURE:
<223> OTHER INFORMATION: Synthetic: MYD88 transcript variant 2
      NM_002468_4
```

<400> SEQUENCE: 285

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
    290                 295

<210> SEQ ID NO 286
<211> LENGTH: 251
<212> TYPE: PRT
<213> ORGANISM: Artificial Sequence
<220> FEATURE:
<223> OTHER INFORMATION: Synthetic: MYD88 transcript variant 3
      NM_001172568_1

<400> SEQUENCE: 286

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

```
Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Gly His Met
            100                 105                 110

Pro Glu Arg Phe Asp Ala Phe Ile Cys Tyr Cys Pro Ser Asp Ile Gln
        115                 120                 125

Phe Val Gln Glu Met Ile Arg Gln Leu Glu Gln Thr Asn Tyr Arg Leu
    130                 135                 140

Lys Leu Cys Val Ser Asp Arg Asp Val Leu Pro Gly Thr Cys Val Trp
145                 150                 155                 160

Ser Ile Ala Ser Glu Leu Ile Glu Lys Arg Cys Arg Arg Met Val Val
                165                 170                 175

Val Val Ser Asp Asp Tyr Leu Gln Ser Lys Glu Cys Asp Phe Gln Thr
            180                 185                 190

Lys Phe Ala Leu Ser Leu Ser Pro Gly Ala His Gln Lys Arg Leu Ile
        195                 200                 205

Pro Ile Lys Tyr Lys Ala Met Lys Lys Glu Phe Pro Ser Ile Leu Arg
    210                 215                 220

Phe Ile Thr Val Cys Asp Tyr Thr Asn Pro Cys Thr Lys Ser Trp Phe
225                 230                 235                 240

Trp Thr Arg Leu Ala Lys Ala Leu Ser Leu Pro
                245                 250
```

<210> SEQ ID NO 287
<211> LENGTH: 191
<212> TYPE: PRT
<213> ORGANISM: Artificial Sequence
<220> FEATURE:
<223> OTHER INFORMATION: Synthetic: MYD88 transcript variant 4 NM_001172569_1

<400> SEQUENCE: 287

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly Ala Ala Gly Trp Trp
```

```
145                 150                 155                 160

Trp Leu Ser Leu Met Ile Thr Cys Arg Ala Arg Asn Val Thr Ser Arg
                165                 170                 175

Pro Asn Leu His Ser Ala Ser Leu Gln Val Pro Ile Arg Ser Asp
            180                 185                 190


<210> SEQ ID NO 288
<211> LENGTH: 146
<212> TYPE: PRT
<213> ORGANISM: Artificial Sequence
<220> FEATURE:
<223> OTHER INFORMATION: Synthetic: MYD88 transcript variant 5
      NM_001172566_1

<400> SEQUENCE: 288

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Gly Ala Ala
            100                 105                 110

Gly Trp Trp Trp Leu Ser Leu Met Ile Thr Cys Arg Ala Arg Asn Val
        115                 120                 125

Thr Ser Arg Pro Asn Leu His Ser Ala Ser Leu Gln Val Pro Ile Arg
    130                 135                 140

Ser Asp
145


<210> SEQ ID NO 289
<211> LENGTH: 172
<212> TYPE: PRT
<213> ORGANISM: Artificial Sequence
<220> FEATURE:
<223> OTHER INFORMATION: Synthetic: MYD88 transcript variant 1
      NM_001172567_1

<400> SEQUENCE: 289

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
```

```
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170


<210> SEQ ID NO 290
<211> LENGTH: 127
<212> TYPE: PRT
<213> ORGANISM: Artificial Sequence
<220> FEATURE:
<223> OTHER INFORMATION: Synthetic: MYD88 transcript variant 3
      NM_001172568_1

<400> SEQUENCE: 290

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Gly His Met
            100                 105                 110

Pro Glu Arg Phe Asp Ala Phe Ile Cys Tyr Cys Pro Ser Asp Ile
        115                 120                 125


<210> SEQ ID NO 291
<211> LENGTH: 304
<212> TYPE: PRT
<213> ORGANISM: Artificial Sequence
<220> FEATURE:
<223> OTHER INFORMATION: Synthetic: MYD88 transcript variant 1
      NM_001172567_1

<400> SEQUENCE: 291

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
```

```
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Leu Ala Arg Arg Pro Arg Gly Gly Cys
    210                 215                 220

Arg Arg Met Val Val Val Val Ser Asp Asp Tyr Leu Gln Ser Lys Glu
225                 230                 235                 240

Cys Asp Phe Gln Thr Lys Phe Ala Leu Ser Leu Ser Pro Gly Ala His
                245                 250                 255

Gln Lys Arg Pro Ile Pro Ile Lys Tyr Lys Ala Met Lys Lys Glu Phe
            260                 265                 270

Pro Ser Ile Leu Arg Phe Ile Thr Val Cys Asp Tyr Thr Asn Pro Cys
        275                 280                 285

Thr Lys Ser Trp Phe Trp Thr Arg Leu Ala Lys Ala Leu Ser Leu Pro
    290                 295                 300


<210> SEQ ID NO 292
<211> LENGTH: 296
<212> TYPE: PRT
<213> ORGANISM: Artificial Sequence
<220> FEATURE:
<223> OTHER INFORMATION: Synthetic: MYD88 transcript variant 2
      NM_002468_4

<400> SEQUENCE: 292

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160
```

```
Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Pro Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
    290                 295


<210> SEQ ID NO 293
<211> LENGTH: 251
<212> TYPE: PRT
<213> ORGANISM: Artificial Sequence
<220> FEATURE:
<223> OTHER INFORMATION: Synthetic: MYD88 transcript variant 3
      NM_001172568_1

<400> SEQUENCE: 293

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Gly His Met
            100                 105                 110

Pro Glu Arg Phe Asp Ala Phe Ile Cys Tyr Cys Pro Ser Asp Ile Gln
        115                 120                 125

Phe Val Gln Glu Met Ile Arg Gln Leu Glu Gln Thr Asn Tyr Arg Leu
    130                 135                 140

Lys Leu Cys Val Ser Asp Arg Asp Val Leu Pro Gly Thr Cys Val Trp
145                 150                 155                 160

Ser Ile Ala Ser Glu Leu Ile Glu Lys Arg Cys Arg Arg Met Val Val
                165                 170                 175

Val Val Ser Asp Asp Tyr Leu Gln Ser Lys Glu Cys Asp Phe Gln Thr
            180                 185                 190

Lys Phe Ala Leu Ser Leu Ser Pro Gly Ala His Gln Lys Arg Pro Ile
        195                 200                 205

Pro Ile Lys Tyr Lys Ala Met Lys Lys Glu Phe Pro Ser Ile Leu Arg
    210                 215                 220
```

```
Phe Ile Thr Val Cys Asp Tyr Thr Asn Pro Cys Thr Lys Ser Trp Phe
225                 230                 235                 240

Trp Thr Arg Leu Ala Lys Ala Leu Ser Leu Pro
                245                 250


<210> SEQ ID NO 294
<211> LENGTH: 218
<212> TYPE: PRT
<213> ORGANISM: Artificial Sequence
<220> FEATURE:
<223> OTHER INFORMATION: Synthetic: OSMR transcript variant 4
      NM_001323505_1

<400> SEQUENCE: 294

Lys Ser Gln Trp Ile Lys Glu Thr Cys Tyr Pro Asp Ile Pro Asp Pro
1               5                   10                  15

Tyr Lys Ser Ser Ile Leu Ser Leu Ile Lys Phe Lys Glu Asn Pro His
            20                  25                  30

Leu Ile Ile Met Asn Val Ser Asp Cys Ile Pro Asp Ala Ile Glu Val
        35                  40                  45

Val Ser Lys Pro Glu Gly Thr Lys Ile Gln Phe Leu Gly Thr Arg Lys
    50                  55                  60

Ser Leu Thr Glu Thr Glu Leu Thr Lys Pro Asn Tyr Leu Tyr Leu Leu
65                  70                  75                  80

Pro Thr Glu Lys Asn His Ser Gly Pro Gly Pro Cys Ile Cys Phe Glu
                85                  90                  95

Asn Leu Thr Tyr Asn Gln Ala Ala Ser Asp Ser Gly Ser Cys Gly His
            100                 105                 110

Val Pro Val Ser Pro Lys Ala Pro Ser Met Leu Gly Leu Met Thr Ser
        115                 120                 125

Pro Glu Asn Val Leu Lys Ala Leu Glu Lys Asn Tyr Met Asn Ser Leu
    130                 135                 140

Gly Glu Ile Pro Ala Gly Glu Thr Ser Leu Asn Tyr Val Ser Gln Leu
145                 150                 155                 160

Ala Ser Pro Met Phe Gly Asp Lys Asp Ser Leu Pro Thr Asn Pro Val
                165                 170                 175

Glu Ala Pro His Cys Ser Glu Tyr Lys Met Gln Met Ala Val Ser Leu
            180                 185                 190

Arg Leu Ala Leu Pro Pro Pro Thr Glu Asn Ser Ser Leu Ser Ser Ile
        195                 200                 205

Thr Leu Leu Asp Pro Gly Glu His Tyr Cys
    210                 215


<210> SEQ ID NO 295
<211> LENGTH: 364
<212> TYPE: PRT
<213> ORGANISM: Artificial Sequence
<220> FEATURE:
<223> OTHER INFORMATION: Synthetic: PRLR transcript variant 1
      NM_000949_6

<400> SEQUENCE: 295

Lys Gly Tyr Ser Met Val Thr Cys Ile Phe Pro Pro Val Pro Gly Pro
1               5                   10                  15

Lys Ile Lys Gly Phe Asp Ala His Leu Leu Glu Lys Gly Lys Ser Glu
            20                  25                  30

Glu Leu Leu Ser Ala Leu Gly Cys Gln Asp Phe Pro Pro Thr Ser Asp
        35                  40                  45
```

```
Tyr Glu Asp Leu Leu Val Glu Tyr Leu Glu Val Asp Asp Ser Glu Asp
    50                  55                  60

Gln His Leu Met Ser Val His Ser Lys Glu His Pro Ser Gln Gly Met
65                  70                  75                  80

Lys Pro Thr Tyr Leu Asp Pro Asp Thr Asp Ser Gly Arg Gly Ser Cys
                85                  90                  95

Asp Ser Pro Ser Leu Leu Ser Glu Lys Cys Glu Glu Pro Gln Ala Asn
            100                 105                 110

Pro Ser Thr Phe Tyr Asp Pro Glu Val Ile Glu Lys Pro Glu Asn Pro
        115                 120                 125

Glu Thr Thr His Thr Trp Asp Pro Gln Cys Ile Ser Met Glu Gly Lys
    130                 135                 140

Ile Pro Tyr Phe His Ala Gly Gly Ser Lys Cys Ser Thr Trp Pro Leu
145                 150                 155                 160

Pro Gln Pro Ser Gln His Asn Pro Arg Ser Ser Tyr His Asn Ile Thr
                165                 170                 175

Asp Val Cys Glu Leu Ala Val Gly Pro Ala Gly Ala Pro Ala Thr Leu
            180                 185                 190

Leu Asn Glu Ala Gly Lys Asp Ala Leu Lys Ser Ser Gln Thr Ile Lys
        195                 200                 205

Ser Arg Glu Glu Gly Lys Ala Thr Gln Gln Arg Glu Val Glu Ser Phe
    210                 215                 220

His Ser Glu Thr Asp Gln Asp Thr Pro Trp Leu Leu Pro Gln Glu Lys
225                 230                 235                 240

Thr Pro Phe Gly Ser Ala Lys Pro Leu Asp Tyr Val Glu Ile His Lys
                245                 250                 255

Val Asn Lys Asp Gly Ala Leu Ser Leu Leu Pro Lys Gln Arg Glu Asn
            260                 265                 270

Ser Gly Lys Pro Lys Lys Pro Gly Thr Pro Glu Asn Asn Lys Glu Tyr
        275                 280                 285

Ala Lys Val Ser Gly Val Met Asp Asn Asn Ile Leu Val Leu Val Pro
    290                 295                 300

Asp Pro His Ala Lys Asn Val Ala Cys Phe Glu Glu Ser Ala Lys Glu
305                 310                 315                 320

Ala Pro Pro Ser Leu Glu Gln Asn Gln Ala Glu Lys Ala Leu Ala Asn
                325                 330                 335

Phe Thr Ala Thr Ser Ser Lys Cys Arg Leu Gln Leu Gly Gly Leu Asp
            340                 345                 350

Tyr Leu Asp Pro Ala Cys Phe Thr His Ser Phe His
        355                 360
```

<210> SEQ ID NO 296
<211> LENGTH: 42
<212> TYPE: PRT
<213> ORGANISM: Artificial Sequence
<220> FEATURE:
<223> OTHER INFORMATION: Synthetic: TNFRSF4 NM_003327_3

<400> SEQUENCE: 296

```
Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40
```

<210> SEQ ID NO 297
<211> LENGTH: 188
<212> TYPE: PRT
<213> ORGANISM: Artificial Sequence
<220> FEATURE:
<223> OTHER INFORMATION: Synthetic: TNFRSF8 transcript variant 1
NM_001243_4

<400> SEQUENCE: 297

```
His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Glu Thr
    50                  55                  60

Cys His Ser Val Gly Ala Ala Tyr Leu Glu Ser Leu Pro Leu Gln Asp
65                  70                  75                  80

Ala Ser Pro Ala Gly Gly Pro Ser Ser Pro Arg Asp Leu Pro Glu Pro
                85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
        115                 120                 125

Glu Gly Arg Gly Leu Ala Gly Pro Ala Glu Pro Glu Leu Glu Glu Glu
    130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185
```

<210> SEQ ID NO 298
<211> LENGTH: 42
<212> TYPE: PRT
<213> ORGANISM: Artificial Sequence
<220> FEATURE:
<223> OTHER INFORMATION: Synthetic: TNFRSF9 NM_001561_5

<400> SEQUENCE: 298

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 299
<211> LENGTH: 60
<212> TYPE: PRT
<213> ORGANISM: Artificial Sequence
<220> FEATURE:
<223> OTHER INFORMATION: Synthetic: TNFRSF14 transcript variant 1
NM_003820_3

<400> SEQUENCE: 299

```
Cys Val Lys Arg Arg Lys Pro Arg Gly Asp Val Val Lys Val Ile Val
```

```
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60


<210> SEQ ID NO 300
<211> LENGTH: 58
<212> TYPE: PRT
<213> ORGANISM: Artificial Sequence
<220> FEATURE:
<223> OTHER INFORMATION: Synthetic: TNFRSF18 transcript variant 1
      NM_004195_2

<400> SEQUENCE: 300

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55


<210> SEQ ID NO 301
<211> LENGTH: 51
<212> TYPE: PRT
<213> ORGANISM: Artificial Sequence
<220> FEATURE:
<223> OTHER INFORMATION: Synthetic: TNFRSF18 transcript variant
      3_NM_148902_1

<400> SEQUENCE: 301

Gln Leu Gly Leu His Ile Trp Gln Leu Arg Lys Thr Gln Leu Leu Leu
1               5                   10                  15

Glu Val Pro Pro Ser Thr Glu Asp Ala Arg Ser Cys Gln Phe Pro Glu
            20                  25                  30

Glu Glu Arg Gly Glu Arg Ser Ala Glu Glu Lys Gly Arg Leu Gly Asp
        35                  40                  45

Leu Trp Val
    50


<210> SEQ ID NO 302
<211> LENGTH: 23
<212> TYPE: PRT
<213> ORGANISM: Artificial Sequence
<220> FEATURE:
<223> OTHER INFORMATION: Synthetic: Linker

<400> SEQUENCE: 302

Gly Ser Gly Gly Ser Glu Gly Gly Gly Ser Glu Gly Gly Ala Ala Thr
1               5                   10                  15

Ala Gly Ser Gly Ser Gly Ser
            20


<210> SEQ ID NO 303
<211> LENGTH: 5
<212> TYPE: PRT
<213> ORGANISM: Artificial Sequence
<220> FEATURE:
```

<223> OTHER INFORMATION: Synthetic: TRAF1, TRAF2, and TRAF3 consensus binding sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 303

Pro Xaa Gln Xaa Thr
1               5

<210> SEQ ID NO 304
<211> LENGTH: 4
<212> TYPE: PRT
<213> ORGANISM: Artificial Sequence
<220> FEATURE:
<223> OTHER INFORMATION: Synthetic: TRAF2 consensus binding sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 304

Ser Xaa Xaa Glu
1

<210> SEQ ID NO 305
<211> LENGTH: 6
<212> TYPE: PRT
<213> ORGANISM: Artificial Sequence
<220> FEATURE:
<223> OTHER INFORMATION: Synthetic: TRAF6 consensus binding sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 305

Gln Xaa Pro Xaa Glu Xaa
1               5

<210> SEQ ID NO 306
<211> LENGTH: 4
<212> TYPE: PRT
<213> ORGANISM: Artificial Sequence
<220> FEATURE:
<223> OTHER INFORMATION: Synthetic: Box1 motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 306

Pro Xaa Xaa Pro
1

<210> SEQ ID NO 307
<211> LENGTH: 4
<212> TYPE: PRT

<213> ORGANISM: Artificial Sequence
<220> FEATURE:
<223> OTHER INFORMATION: Synthetic: Shc phosphotyrosine-binding binding motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 307

Asn Xaa Xaa Tyr
1

<210> SEQ ID NO 308
<211> LENGTH: 4
<212> TYPE: PRT
<213> ORGANISM: Artificial Sequence
<220> FEATURE:
<223> OTHER INFORMATION: Synthetic: STAT3 consensus binding sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 308

Tyr Xaa Xaa Gln
1

<210> SEQ ID NO 309
<211> LENGTH: 4
<212> TYPE: PRT
<213> ORGANISM: Artificial Sequence
<220> FEATURE:
<223> OTHER INFORMATION: Synthetic: STAT5 recruitment sequence

<400> SEQUENCE: 309

Tyr Leu Pro Leu
1

<210> SEQ ID NO 310
<211> LENGTH: 4
<212> TYPE: PRT
<213> ORGANISM: Artificial Sequence
<220> FEATURE:
<223> OTHER INFORMATION: Synthetic: STAT5 consensus recruitment sequence
<220> FEATURE:
<221> NAME/KEY: misc_feature
<222> LOCATION: (1)..(1)
<223> OTHER INFORMATION: Xaa is phosphorylated tyrosine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 310

Xaa Leu Xaa Leu
1

<210> SEQ ID NO 311
<211> LENGTH: 570
<212> TYPE: PRT
<213> ORGANISM: Influenza virus
<220> FEATURE:
<221> NAME/KEY: misc_feature
<222> LOCATION: (1)..(570)
<223> OTHER INFORMATION: Influenze A HA from H1N1

<400> SEQUENCE: 311

```
Met Lys Ala Asn Leu Leu Val Leu Leu Cys Ala Leu Ala Ala Ala Asp
1               5                   10                  15
```

-continued

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Arg Arg Lys Lys Arg Gly Leu Phe Gly
            340                 345                 350

Ala Ile Ala Gly Phe Ile Glu Gly Gly Trp Thr Gly Met Ile Asp Gly
        355                 360                 365

Trp Tyr Gly Tyr His His Gln Asn Glu Gln Gly Ser Gly Tyr Ala Ala
    370                 375                 380

Asp Gln Lys Ser Thr Gln Asn Ala Ile Asn Gly Ile Thr Asn Lys Val
385                 390                 395                 400

Asn Thr Val Ile Glu Lys Met Asn Ile Gln Phe Thr Ala Val Gly Lys
                405                 410                 415

Glu Phe Asn Lys Leu Glu Lys Arg Met Glu Asn Leu Asn Lys Lys Val
            420                 425                 430
```

```
Asp Asp Gly Phe Leu Asp Ile Trp Thr Tyr Asn Ala Glu Leu Leu Val
        435                 440                 445

Leu Leu Glu Asn Glu Arg Thr Leu Asp Phe His Asp Ser Asn Val Lys
    450                 455                 460

Asn Leu Tyr Glu Lys Val Lys Ser Gln Leu Lys Asn Asn Ala Lys Glu
465                 470                 475                 480

Ile Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Lys Tyr Ser Glu
            500                 505                 510

Glu Ser Lys Leu Asn Arg Glu Lys Val Asp Gly Val Lys Leu Glu Ser
        515                 520                 525

Met Gly Ile Tyr Gln Ile Leu Ala Ile Tyr Ser Thr Val Ala Ser Ser
    530                 535                 540

Leu Val Leu Leu Val Ser Leu Gly Ala Ile Ser Phe Trp Met Cys Ser
545                 550                 555                 560

Asn Gly Ser Leu Gln Cys Arg Ile Cys Ile
                565                 570


<210> SEQ ID NO 312
<211> LENGTH: 470
<212> TYPE: PRT
<213> ORGANISM: Influenza virus
<220> FEATURE:
<221> NAME/KEY: misc_feature
<222> LOCATION: (1)..(470)
<223> OTHER INFORMATION: Influenze A NA from H10N7

<400> SEQUENCE: 312

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asn Lys Gly Thr Gly Thr Thr Lys Gln
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asn Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
```

```
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala His Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Asp Asn Thr Trp Leu Gly Arg Thr Ile Ser Pro Arg
        355                 360                 365

Ser Arg Ser Gly Phe Glu Met Leu Lys Ile Pro Asn Ala Gly Thr Asp
    370                 375                 380

Pro Asn Ser Arg Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Val Cys Tyr Asn Pro Cys Phe Tyr Val Glu Leu Ile Arg Gly Arg Pro
            420                 425                 430

Glu Glu Ala Lys Tyr Val Trp Trp Thr Ser Asn Ser Leu Val Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470


<210> SEQ ID NO 313
<211> LENGTH: 523
<212> TYPE: PRT
<213> ORGANISM: Artificial Sequence
<220> FEATURE:
<223> OTHER INFORMATION: Synthetic: MV(ed)-F-delta-30

<400> SEQUENCE: 313

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
```

-continued

```
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg
        515                 520
```

<210> SEQ ID NO 314
<211> LENGTH: 599
<212> TYPE: PRT
<213> ORGANISM: Artificial Sequence
<220> FEATURE:
<223> OTHER INFORMATION: Synthetic: MV(ed)-H-delta-18

<400> SEQUENCE: 314

```
Met Gly Ser Arg Ile Val Ile Asn Arg Glu His Leu Met Ile Asp Arg
1               5                   10                  15

Pro Tyr Val Leu Leu Ala Val Leu Phe Val Met Ser Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Ser Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365
```

Lys Gly Lys Ile Gln Ala Leu Cys Glu Asn Pro Glu Trp Ala Pro Leu
370 375 380

Lys Asp Asn Arg Ile Pro Ser Tyr Gly Val Leu Ser Val Asp Leu Ser
385 390 395 400

Leu Thr Val Glu Leu Lys Ile Lys Ile Ala Ser Gly Phe Gly Pro Leu
405 410 415

Ile Thr His Gly Ser Gly Met Asp Leu Tyr Lys Ser Asn His Asn Asn
420 425 430

Val Tyr Trp Leu Thr Ile Pro Pro Met Lys Asn Leu Ala Leu Gly Val
435 440 445

Ile Asn Thr Leu Glu Trp Ile Pro Arg Phe Lys Val Ser Pro Asn Leu
450 455 460

Phe Thr Val Pro Ile Lys Glu Ala Gly Glu Asp Cys His Ala Pro Thr
465 470 475 480

Tyr Leu Pro Ala Glu Val Asp Gly Asp Val Lys Leu Ser Ser Asn Leu
485 490 495

Val Ile Leu Pro Gly Gln Asp Leu Gln Tyr Val Leu Ala Thr Tyr Asp
500 505 510

Thr Ser Arg Val Glu His Ala Val Val Tyr Tyr Val Tyr Ser Pro Gly
515 520 525

Arg Ser Phe Ser Tyr Phe Tyr Pro Phe Arg Leu Pro Ile Lys Gly Val
530 535 540

Pro Ile Glu Leu Gln Val Glu Cys Phe Thr Trp Asp Gln Lys Leu Trp
545 550 555 560

Cys Arg His Phe Cys Val Leu Ala Asp Ser Glu Ser Gly Gly His Ile
565 570 575

Thr His Ser Gly Met Val Gly Met Gly Val Ser Cys Thr Val Thr Arg
580 585 590

Glu Asp Gly Thr Asn Arg Arg
595

<210> SEQ ID NO 315
<211> LENGTH: 593
<212> TYPE: PRT
<213> ORGANISM: Artificial Sequence
<220> FEATURE:
<223> OTHER INFORMATION: Synthetic: MV(ed)-H-delta-24

<400> SEQUENCE: 315

Met Asn Arg Glu His Leu Met Ile Asp Arg Pro Tyr Val Leu Leu Ala
1 5 10 15

Val Leu Phe Val Met Ser Leu Ser Leu Ile Gly Leu Leu Ala Ile Ala
20 25 30

Gly Ile Arg Leu His Arg Ala Ala Ile Tyr Thr Ala Glu Ile His Lys
35 40 45

Ser Leu Ser Thr Asn Leu Asp Val Thr Asn Ser Ile Glu His Gln Val
50 55 60

Lys Asp Val Leu Thr Pro Leu Phe Lys Ile Ile Gly Asp Glu Val Gly
65 70 75 80

Leu Arg Thr Pro Gln Arg Phe Thr Asp Leu Val Lys Phe Ile Ser Asp
85 90 95

Lys Ile Lys Phe Leu Asn Pro Asp Arg Glu Tyr Asp Phe Arg Asp Leu
100 105 110

Thr Trp Cys Ile Asn Pro Pro Glu Arg Ile Lys Leu Asp Tyr Asp Gln
115 120 125

```
Tyr Cys Ala Asp Val Ala Ala Glu Glu Leu Met Asn Ala Leu Val Asn
    130                 135                 140

Ser Thr Leu Leu Glu Thr Arg Thr Thr Asn Gln Phe Leu Ala Val Ser
145                 150                 155                 160

Lys Gly Asn Cys Ser Gly Pro Thr Thr Ile Arg Gly Gln Phe Ser Asn
                165                 170                 175

Met Ser Leu Ser Leu Leu Asp Leu Tyr Leu Ser Arg Gly Tyr Asn Val
            180                 185                 190

Ser Ser Ile Val Thr Met Thr Ser Gln Gly Met Tyr Gly Gly Thr Tyr
        195                 200                 205

Leu Val Glu Lys Pro Asn Leu Ser Ser Lys Arg Ser Glu Leu Ser Gln
    210                 215                 220

Leu Ser Met Tyr Arg Val Phe Glu Val Gly Val Ile Arg Asn Pro Gly
225                 230                 235                 240

Leu Gly Ala Pro Val Phe His Met Thr Asn Tyr Leu Glu Gln Pro Val
                245                 250                 255

Ser Asn Asp Leu Ser Asn Cys Met Val Ala Leu Gly Glu Leu Lys Leu
            260                 265                 270

Ala Ala Leu Cys His Gly Glu Asp Ser Ile Thr Ile Pro Tyr Gln Gly
        275                 280                 285

Ser Gly Lys Gly Val Ser Phe Gln Leu Val Lys Leu Gly Val Trp Lys
    290                 295                 300

Ser Pro Thr Asp Met Gln Ser Trp Val Pro Leu Ser Thr Asp Asp Pro
305                 310                 315                 320

Val Ile Asp Arg Leu Tyr Leu Ser Ser His Arg Gly Val Ile Ala Asp
                325                 330                 335

Asn Gln Ala Lys Trp Ala Val Pro Thr Thr Arg Thr Asp Asp Lys Leu
            340                 345                 350

Arg Met Glu Thr Cys Phe Gln Gln Ala Cys Lys Gly Lys Ile Gln Ala
        355                 360                 365

Leu Cys Glu Asn Pro Glu Trp Ala Pro Leu Lys Asp Asn Arg Ile Pro
    370                 375                 380

Ser Tyr Gly Val Leu Ser Val Asp Leu Ser Leu Thr Val Glu Leu Lys
385                 390                 395                 400

Ile Lys Ile Ala Ser Gly Phe Gly Pro Leu Ile Thr His Gly Ser Gly
                405                 410                 415

Met Asp Leu Tyr Lys Ser Asn His Asn Asn Val Tyr Trp Leu Thr Ile
            420                 425                 430

Pro Pro Met Lys Asn Leu Ala Leu Gly Val Ile Asn Thr Leu Glu Trp
        435                 440                 445

Ile Pro Arg Phe Lys Val Ser Pro Asn Leu Phe Thr Val Pro Ile Lys
    450                 455                 460

Glu Ala Gly Glu Asp Cys His Ala Pro Thr Tyr Leu Pro Ala Glu Val
465                 470                 475                 480

Asp Gly Asp Val Lys Leu Ser Ser Asn Leu Val Ile Leu Pro Gly Gln
                485                 490                 495

Asp Leu Gln Tyr Val Leu Ala Thr Tyr Asp Thr Ser Arg Val Glu His
            500                 505                 510

Ala Val Val Tyr Tyr Val Tyr Ser Pro Gly Arg Ser Phe Ser Tyr Phe
        515                 520                 525

Tyr Pro Phe Arg Leu Pro Ile Lys Gly Val Pro Ile Glu Leu Gln Val
    530                 535                 540
```

```
Glu Cys Phe Thr Trp Asp Gln Lys Leu Trp Cys Arg His Phe Cys Val
545                 550                 555                 560

Leu Ala Asp Ser Glu Ser Gly Gly His Ile Thr His Ser Gly Met Val
                565                 570                 575

Gly Met Gly Val Ser Cys Thr Val Thr Arg Glu Asp Gly Thr Asn Arg
            580                 585                 590

Arg


<210> SEQ ID NO 316
<211> LENGTH: 477
<212> TYPE: DNA
<213> ORGANISM: Artificial Sequence
<220> FEATURE:
<223> OTHER INFORMATION: Synthetic: hGH polyA

<400> SEQUENCE: 316

gggtggcatc cctgtgaccc ctccccagtg cctctcctgg ccctggaagt tgccactcca     60

gtgcccacca gccttgtcct aataaaatta agttgcatca ttttgtctga ctaggtgtcc    120

ttctataata ttatggggtg gaggggggtg gtatggagca aggggcaagt tgggaagaca    180

acctgtaggg cctgcggggt ctgttgggaa ccaagctgga gtgcagtggc acaatcttgg    240

ctcactgcaa tctccgcctc ctgggttcaa gcgattctcc tgcctcagcc tcccgagttg    300

ttgggattcc aggcatgcat gaccaggctc agctaatttt tgtttttttg gtagagacgg    360

ggtttcacca tattggccag gctggtctcc aactcctaat ctcaggtgat ctacccacct    420

tggcctccca aattgctggg attacaggcg tgaaccactg ctcccttccc tgtcctt       477


<210> SEQ ID NO 317
<211> LENGTH: 49
<212> TYPE: DNA
<213> ORGANISM: Artificial Sequence
<220> FEATURE:
<223> OTHER INFORMATION: Synthetic: SPA1

<400> SEQUENCE: 317

aataaaagat ctttattttc attagatctg tgtgttggtt ttttgtgtg                 49


<210> SEQ ID NO 318
<211> LENGTH: 120
<212> TYPE: DNA
<213> ORGANISM: Artificial Sequence
<220> FEATURE:
<223> OTHER INFORMATION: Synthetic: SPA2

<400> SEQUENCE: 318

aataaaatat ctcagagctc tagacatctg tgtgttggtt ttttgtgtgt agtaatgagg     60

atctggagat attgaagtat cttccggacg actaacagct gtcattggcg gatcttaata    120


<210> SEQ ID NO 319
<211> LENGTH: 295
<212> TYPE: DNA
<213> ORGANISM: Artificial Sequence
<220> FEATURE:
<223> OTHER INFORMATION: Synthetic: b-globin polyA spacer B

<400> SEQUENCE: 319

atctcaagag tggcagcggt cttgagtggc agcggcggta tacggcagcg gcatgtaact     60

agctcctcag tggcagcgat gaggaggcaa taaaggaaat tgattttcat tgcaatagtg    120

tgttggaatt ttttgtgtct ctcaaggttc tgttaagtaa ctgaacccaa tgtcgttagt    180
```

gacgcttagc tcttaagagg tcactgacct aacaatctca agagtggcag cggtcttgag 240
tggcagcggc ggtatacggc agcgctatct aagtagtaac aagtagcgtg gggca 295

<210> SEQ ID NO 320
<211> LENGTH: 512
<212> TYPE: DNA
<213> ORGANISM: Artificial Sequence
<220> FEATURE:
<223> OTHER INFORMATION: Synthetic: b-globin polyA spacer A

<400> SEQUENCE: 320
acgcgccctg tagcggcgca ttaagcgcgg cgggtgtggt ggttacgcgc agcgtgaccg 60
ctacacttgc cagcgcccta gcgcccgctc ctttcgcttt cttcccttcc tttctcgcca 120
cgttcgccgg ctttccccgt caagctctaa atcgggggct ccctttaggg ttccgattta 180
gtgctttacg gcacctcgac cccaaaaaac ttgattaggg tgatggttaa taaaggaaat 240
tgattttcat tgcaatagtg tgttggaatt ttttgtgtct ctcacacgta gtgggccatc 300
gccctgatag acggtttttc gccctttgac gttggagtcc acgttcttcg atagtggact 360
cttgttccaa actggaacaa cactcaaccc tatctcggtc tattcttttg atttataagg 420
gattttgccg atttcggcct attggttaaa aaatgagctg atttaacaaa aatttaacgc 480
gaattttaac aaaatattaa cgcttagaat tt 512

<210> SEQ ID NO 321
<211> LENGTH: 243
<212> TYPE: DNA
<213> ORGANISM: Artificial Sequence
<220> FEATURE:
<223> OTHER INFORMATION: Synthetic: 250 cHS4 insulator v1

<400> SEQUENCE: 321
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagcc tgcagacacg tggggggata cggggaaaag 240
ctt 243

<210> SEQ ID NO 322
<211> LENGTH: 243
<212> TYPE: DNA
<213> ORGANISM: Artificial Sequence
<220> FEATURE:
<223> OTHER INFORMATION: Synthetic: 250 cHS4 insulator v2

<400> SEQUENCE: 322
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagcg tgcagacacg tggggggata cggggaaaag 240
ctt 243

<210> SEQ ID NO 323
<211> LENGTH: 650
<212> TYPE: DNA
<213> ORGANISM: Artificial Sequence
<220> FEATURE:
<223> OTHER INFORMATION: Synthetic: 650 cHS4 insulator

<400> SEQUENCE: 323
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagca tgcagacaca tggggggata cggggaaaaa 240
gctttaggct ctgcatgttt gatggtgtat ggatgcaagc agaaggggtg gaagagcttg 300
cctggagaga tacagctggg tcagtaggac tgggacaggc agctggagaa ttgccatgta 360
gatgttcata caatcgtcaa atcatgaagg ctggaaaagc cctccaagat ccccaagacc 420
aaccccaacc cacccagcgt gcccactggc catgtccctc agtgccacat ccccacagtt 480
cttcatcacc tccagggacg gtgacccccc cacctccgtg ggcagctgtg ccactgcagc 540
accgctcttt ggagaagata aatcttgcta aatccagccc gaccctcccc tggcacaaca 600
taaggccatt atctctcatc caactccagg acggagtcag tgagaatatt 650

<210> SEQ ID NO 324
<211> LENGTH: 420
<212> TYPE: DNA
<213> ORGANISM: Artificial Sequence
<220> FEATURE:
<223> OTHER INFORMATION: Synthetic: 400 cHS4 insulator

<400> SEQUENCE: 324
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagca tgcagacaca tggggggata cggggaaaaa 240
gctttaggct gaaagagaga tttagaatga cagaatcata gaacggcctg ggttgcaaag 300
gagcacagtg ctcatccaga tccaaccccc tgctatgtgc agggtcatca accagcagcc 360
caggctgccc agagccacat ccagcctggc cttgaatgcc tgcagggatg gggcatccac 420

<210> SEQ ID NO 325
<211> LENGTH: 949
<212> TYPE: DNA
<213> ORGANISM: Artificial Sequence
<220> FEATURE:
<223> OTHER INFORMATION: Synthetic: 650 cHS4 insulator and b-globin
polyA spacer B

<400> SEQUENCE: 325
gagctcacgg ggacagcccc cccccaaagc ccccagggat gtaattacgt ccctcccccg 60
ctagggggca gcagcgagcc gcccggggct ccgctccggt ccggcgctcc ccccgcatcc 120
ccgagccggc agcgtgcggg gacagcccgg gcacggggaa ggtggcacgg gatcgctttc 180
ctctgaacgc ttctcgctgc tctttgagca tgcagacaca tggggggata cggggaaaaa 240
gctttaggct ctgcatgttt gatggtgtat ggatgcaagc agaaggggtg gaagagcttg 300
cctggagaga tacagctggg tcagtaggac tgggacaggc agctggagaa ttgccatgta 360
gatgttcata caatcgtcaa atcatgaagg ctggaaaagc cctccaagat ccccaagacc 420
aaccccaacc cacccagcgt gcccactggc catgtccctc agtgccacat ccccacagtt 480
cttcatcacc tccagggacg gtgacccccc cacctccgtg ggcagctgtg ccactgcagc 540
accgctcttt ggagaagata aatcttgcta aatccagccc gaccctcccc tggcacaaca 600
taaggccatt atctctcatc caactccagg acggagtcag tgagaatatt gcgatgcccc 660
acgctacttg ttactactta gatagcgctg ccgtataccg ccgctgccac tcaagaccgc 720
tgccactctt gagattgtta ggtcagtgac ctcttaagag ctaagcgtca ctaacgacat 780
tgggttcagt tacttaacag aaccttgaga gacacaaaaa attccaacac actattgcaa 840
tgaaaatcaa tttcctttat tgcctcctca tcgctgccac tgaggagcta gttacatgcc 900
gctgccgtat accgccgctg ccactcaaga ccgctgccac tcttgagat 949

<210> SEQ ID NO 326
<211> LENGTH: 949
<212> TYPE: DNA
<213> ORGANISM: Artificial Sequence
<220> FEATURE:
<223> OTHER INFORMATION: Synthetic: b-globin polyA spacer B and 650 cHS4 insulator

<400> SEQUENCE: 326
atctcaagag tggcagcggt cttgagtggc agcggcggta tacggcagcg gcatgtaact 60
agctcctcag tggcagcgat gaggaggcaa taaaggaaat tgattttcat tgcaatagtg 120
tgttggaatt ttttgtgtct ctcaaggttc tgttaagtaa ctgaacccaa tgtcgttagt 180
gacgcttagc tcttaagagg tcactgacct aacaatctca agagtggcag cggtcttgag 240
tggcagcggc ggtatacggc agcgctatct aagtagtaac aagtagcgtg gggcatcgcg 300
agctcacggg gacagccccc ccccaaagcc cccagggatg gtcgtacgtc cctcccccgc 360
tagggggcag cagcgagccg cccggggctc cgctccggtc cggcgctccc cccgcatccc 420
cgagccggca gcgtgcgggg acagcccggg cacggggaag gtggcacggg atcgctttcc 480
tctgaacgct tctcgctgct ctttgagcat gcagacacat gggggggatac ggggaaaaag 540 ctttaggctc tgcatgtttg atggtgtatg gatgcaagca gaaggggtgg aagagcttgc 600
ctggagagat acagctgggt cagtaggact gggacaggca gctggagaat tgccatgtag 660
atgttcatac aatcgtcaaa tcatgaaggc tggaaaagcc ctccaagatc cccaagacca 720
accccaaccc acccagcgtg cccactggcc atgtccctca gtgccacatc cccacagttc 780
ttcatcacct ccagggacgg tgaccccccc acctccgtgg gcagctgtgc cactgcagca 840
ccgctctttg gagaagataa atcttgctaa atccagcccg accctcccct ggcacaacat 900
aaggccatta tctctcatcc aactccagga cggagtcagt gagaatatt 949

<210> SEQ ID NO 327
<211> LENGTH: 15
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (1)..(3)
<223> OTHER INFORMATION: nnn, if present, is GCC
<220> FEATURE:
<221> NAME/KEY: misc_feature
<222> LOCATION: (10)..(10)
<223> OTHER INFORMATION: n is A or G

<400> SEQUENCE: 327
nnngccgccn ccatg 15

<210> SEQ ID NO 328
<211> LENGTH: 9

<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (7)..(7)
<223> OTHER INFORMATION: n is T or U
<220> FEATURE:
<221> NAME/KEY: misc_feature
<222> LOCATION: (9)..(9)
<223> OTHER INFORMATION: n, if present, is G

<400> SEQUENCE: 328 ccaccangn 9

<210> SEQ ID NO 329
<211> LENGTH: 9
<212> TYPE: DNA
<213> ORGANISM: Artificial Sequence
<220> FEATURE:
<223> OTHER INFORMATION: Synthetic: Kozak-type sequence 2
<220> FEATURE:
<221> NAME/KEY: misc_feature
<222> LOCATION: (7)..(7)
<223> OTHER INFORMATION: n is T or U
<220> FEATURE:
<221> NAME/KEY: misc_feature
<222> LOCATION: (9)..(9)
<223> OTHER INFORMATION: n, if present, is G

<400> SEQUENCE: 329 ccgccangn 9

<210> SEQ ID NO 330
<211> LENGTH: 13
<212> TYPE: DNA
<213> ORGANISM: Artificial Sequence
<220> FEATURE:
<223> OTHER INFORMATION: Synthetic: Kozak-type sequence 3
<220> FEATURE:
<221> NAME/KEY: misc_feature
<222> LOCATION: (11)..(11)
<223> OTHER INFORMATION: n is T or U
<220> FEATURE:
<221> NAME/KEY: misc_feature
<222> LOCATION: (13)..(13)
<223> OTHER INFORMATION: n, if present, is G

<400> SEQUENCE: 330
gccgccgcca ngn 13

<210> SEQ ID NO 331
<211> LENGTH: 13
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (11)..(11)
<223> OTHER INFORMATION: n is T or U
<220> FEATURE:
<221> NAME/KEY: misc_feature
<222> LOCATION: (13)..(13)
<223> OTHER INFORMATION: n, if present, is G

<400> SEQUENCE: 331
gccgccacca ngn 13

<210> SEQ ID NO 332

<211> LENGTH: 12
<212> TYPE: RNA
<213> ORGANISM: Artificial Sequence
<220> FEATURE:
<223> OTHER INFORMATION: Synthetic: Kozak sequence

<400> SEQUENCE: 332
gccgccacca ug 12

<210> SEQ ID NO 333
<211> LENGTH: 28
<212> TYPE: DNA
<213> ORGANISM: Mus musculus
<220> FEATURE:
<221> NAME/KEY: misc_feature
<222> LOCATION: (1)..(28)
<223> OTHER INFORMATION: SIBR (synthetic inhibitory BIC-derived RNA)

<400> SEQUENCE: 333
ctggaggctt gctgaaggct gtatgctg 28

<210> SEQ ID NO 334
<211> LENGTH: 45
<212> TYPE: DNA
<213> ORGANISM: Mus musculus
<220> FEATURE:
<221> NAME/KEY: misc_feature
<222> LOCATION: (1)..(45)
<223> OTHER INFORMATION: 3? microRNA flanking sequence of miR-155

<400> SEQUENCE: 334
caggacacaa ggcctgttac tagcactcac atggaacaaa tggcc 45

<210> SEQ ID NO 335
<211> LENGTH: 19
<212> TYPE: DNA
<213> ORGANISM: Artificial Sequence
<220> FEATURE:
<223> OTHER INFORMATION: Synthetic: synthetic DNA encoding stem

<400> SEQUENCE: 335
gttttggcca ctgactgac 19

<210> SEQ ID NO 336
<211> LENGTH: 511
<212> TYPE: PRT
<213> ORGANISM: Artificial Sequence
<220> FEATURE:
<223> OTHER INFORMATION: Synthetic: VSV-G envelope protein

<400> SEQUENCE: 336

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
```

```
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```

<210> SEQ ID NO 337

<211> LENGTH: 563
<212> TYPE: PRT
<213> ORGANISM: Artificial Sequence
<220> FEATURE:
<223> OTHER INFORMATION: Synthetic: Baboon retroviral envelope glycoprotein

<400> SEQUENCE: 337

```
Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
```

```
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala Met Val Leu Thr Gln Gln Tyr Gln Val Leu Arg Thr Asp Glu Glu
545                 550                 555                 560

Ala Gln Asp


<210> SEQ ID NO 338
<211> LENGTH: 654
<212> TYPE: PRT
<213> ORGANISM: Artificial Sequence
<220> FEATURE:
<223> OTHER INFORMATION: Synthetic: MuLV envelope protein

<400> SEQUENCE: 338

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175
```

```
Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
    370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445

Gln Leu Glu Gln Arg Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590
```

```
Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650


<210> SEQ ID NO 339
<211> LENGTH: 545
<212> TYPE: PRT
<213> ORGANISM: Artificial Sequence
<220> FEATURE:
<223> OTHER INFORMATION: Synthetic: Baboon retroviral envelope
      glycoprotein -delta-R (HA)

<400> SEQUENCE: 339

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300
```

```
Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala
545


<210> SEQ ID NO 340
<211> LENGTH: 546
<212> TYPE: PRT
<213> ORGANISM: Artificial Sequence
<220> FEATURE:
<223> OTHER INFORMATION: Synthetic: Baboon retroviral envelope
      glycoprotein -delta-R (HAM)

<400> SEQUENCE: 340

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
```

```
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525
```

```
Phe Asn Arg Leu Thr Ala Phe Ile Asn Asp Lys Leu Asn Ile Ile His
    530                 535                 540

Ala Met
545


<210> SEQ ID NO 341
<211> LENGTH: 905
<212> TYPE: PRT
<213> ORGANISM: Artificial Sequence
<220> FEATURE:
<223> OTHER INFORMATION: Synthetic: Fusion of anti-CD3 scFV from UCHT1
      to MuLV envelope protein

<400> SEQUENCE: 341

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Asp Ile
            20                  25                  30

Gln Met Thr Gln Ser Pro Ser Ser Leu Ser Ala Ser Val Gly Asp Arg
        35                  40                  45

Val Thr Ile Thr Cys Arg Ala Ser Gln Asp Ile Arg Asn Tyr Leu Asn
    50                  55                  60

Trp Tyr Gln Gln Lys Pro Gly Lys Ala Pro Lys Leu Leu Ile Tyr Tyr
65                  70                  75                  80

Thr Ser Arg Leu Glu Ser Gly Val Pro Ser Arg Phe Ser Gly Ser Gly
                85                  90                  95

Ser Gly Thr Asp Tyr Thr Leu Thr Ile Ser Ser Leu Gln Pro Glu Asp
            100                 105                 110

Phe Ala Thr Tyr Tyr Cys Gln Gln Gly Asn Thr Leu Pro Trp Thr Phe
        115                 120                 125

Gly Gln Gly Thr Lys Val Glu Ile Lys Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ser Phe Thr Gly Tyr Thr Met Asn Trp Val Arg Gln Ala
            180                 185                 190

Pro Gly Lys Gly Leu Glu Trp Val Ala Leu Ile Asn Pro Tyr Lys Gly
        195                 200                 205

Val Ser Thr Tyr Asn Gln Lys Phe Lys Asp Arg Phe Thr Ile Ser Val
    210                 215                 220

Asp Lys Ser Lys Asn Thr Ala Tyr Leu Gln Met Asn Ser Leu Arg Ala
225                 230                 235                 240

Glu Asp Thr Ala Val Tyr Tyr Cys Ala Arg Ser Gly Tyr Tyr Gly Asp
                245                 250                 255

Ser Asp Trp Tyr Phe Asp Val Trp Gly Gln Gly Thr Leu Val Thr Val
            260                 265                 270

Ser Ser Ala Ala Ala Ile Glu Gly Arg Met Ala Glu Ser Pro His Gln
        275                 280                 285

Val Phe Asn Val Thr Trp Arg Val Thr Asn Leu Met Thr Gly Arg Thr
    290                 295                 300

Ala Asn Ala Thr Ser Leu Leu Gly Thr Val Gln Asp Ala Phe Pro Lys
305                 310                 315                 320

Leu Tyr Phe Asp Leu Cys Asp Leu Val Gly Glu Glu Trp Asp Pro Ser
```

-continued

```
                325                 330                 335

Asp Gln Glu Pro Tyr Val Gly Tyr Gly Cys Lys Tyr Pro Ala Gly Arg
            340                 345                 350

Gln Arg Thr Arg Thr Phe Asp Phe Tyr Val Cys Pro Gly His Thr Val
        355                 360                 365

Lys Ser Gly Cys Gly Gly Pro Gly Glu Gly Tyr Cys Gly Lys Trp Gly
    370                 375                 380

Cys Glu Thr Thr Gly Gln Ala Tyr Trp Lys Pro Thr Ser Ser Trp Asp
385                 390                 395                 400

Leu Ile Ser Leu Lys Arg Gly Asn Thr Pro Trp Asp Thr Gly Cys Ser
                405                 410                 415

Lys Val Ala Cys Gly Pro Cys Tyr Asp Leu Ser Lys Val Ser Asn Ser
            420                 425                 430

Phe Gln Gly Ala Thr Arg Gly Gly Arg Cys Asn Pro Leu Val Leu Glu
        435                 440                 445

Phe Thr Asp Ala Gly Lys Lys Ala Asn Trp Asp Gly Pro Lys Ser Trp
    450                 455                 460

Gly Leu Arg Leu Tyr Arg Thr Gly Thr Asp Pro Ile Thr Met Phe Ser
465                 470                 475                 480

Leu Thr Arg Gln Val Leu Asn Val Gly Pro Arg Val Pro Ile Gly Pro
                485                 490                 495

Asn Pro Val Leu Pro Asp Gln Arg Leu Pro Ser Ser Pro Ile Glu Ile
            500                 505                 510

Val Pro Ala Pro Gln Pro Pro Ser Pro Leu Asn Thr Ser Tyr Pro Pro
        515                 520                 525

Ser Thr Thr Ser Thr Pro Ser Thr Ser Pro Thr Ser Pro Ser Val Pro
    530                 535                 540

Gln Pro Pro Pro Gly Thr Gly Asp Arg Leu Leu Ala Leu Val Lys Gly
545                 550                 555                 560

Ala Tyr Gln Ala Leu Asn Leu Thr Asn Pro Asp Lys Thr Gln Glu Cys
                565                 570                 575

Trp Leu Cys Leu Val Ser Gly Pro Pro Tyr Tyr Glu Gly Val Ala Val
            580                 585                 590

Val Gly Thr Tyr Thr Asn His Ser Thr Ala Pro Ala Asn Cys Thr Ala
        595                 600                 605

Thr Ser Gln His Lys Leu Thr Leu Ser Glu Val Thr Gly Gln Gly Leu
    610                 615                 620

Cys Met Gly Ala Val Pro Lys Thr His Gln Ala Leu Cys Asn Thr Thr
625                 630                 635                 640

Gln Ser Ala Gly Ser Gly Ser Tyr Tyr Leu Ala Ala Pro Ala Gly Thr
                645                 650                 655

Met Trp Ala Cys Ser Thr Gly Leu Thr Pro Cys Leu Ser Thr Thr Val
            660                 665                 670

Leu Asn Leu Thr Thr Asp Tyr Cys Val Leu Val Glu Leu Trp Pro Arg
        675                 680                 685

Val Ile Tyr His Ser Pro Asp Tyr Met Tyr Gly Gln Leu Glu Gln Arg
    690                 695                 700

Thr Lys Tyr Lys Arg Glu Pro Val Ser Leu Thr Leu Ala Leu Leu Leu
705                 710                 715                 720

Gly Gly Leu Thr Met Gly Gly Ile Ala Ala Gly Ile Gly Thr Gly Thr
                725                 730                 735

Thr Ala Leu Ile Lys Thr Gln Gln Phe Glu Gln Leu His Ala Ala Ile
            740                 745                 750
```

```
Gln Thr Asp Leu Asn Glu Val Glu Lys Ser Ile Thr Asn Leu Glu Lys
        755                 760                 765

Ser Leu Thr Ser Leu Ser Glu Val Val Leu Gln Asn Arg Arg Gly Leu
    770                 775                 780

Asp Leu Leu Phe Leu Lys Glu Gly Gly Leu Cys Ala Ala Leu Lys Glu
785                 790                 795                 800

Glu Cys Cys Phe Tyr Ala Asp His Thr Gly Leu Val Arg Asp Ser Met
                805                 810                 815

Ala Lys Leu Arg Glu Arg Leu Asn Gln Arg Gln Lys Leu Phe Glu Thr
            820                 825                 830

Gly Gln Gly Trp Phe Glu Gly Leu Phe Asn Arg Ser Pro Trp Phe Thr
        835                 840                 845

Thr Leu Ile Ser Thr Ile Met Gly Pro Leu Ile Val Leu Leu Leu Ile
    850                 855                 860

Leu Leu Phe Gly Pro Cys Ile Leu Asn Arg Leu Val Gln Phe Val Lys
865                 870                 875                 880

Asp Arg Ile Ser Val Val Gln Ala Leu Val Leu Thr Gln Gln Tyr His
                885                 890                 895

Gln Leu Lys Pro Ile Glu Tyr Glu Pro
            900                 905
```

```
<210> SEQ ID NO 342
<211> LENGTH: 223
<212> TYPE: DNA
<213> ORGANISM: Artificial Sequence
<220> FEATURE:
<223> OTHER INFORMATION: Synthetic: cCBL miRNA at P1

<400> SEQUENCE: 342

cggcacctgc gctgccgttg gatcggggat gaaagctggc gctggaggct tgctgaaggc      60

tgtatgctgt aataactccc aactcactgg gttttggcca ctgactgacc cagtgagggg     120

agttattaca ggacacaagg cctgttacta gcactcacat ggaacaaatg gcccacattg     180

gtgccggatg aagctcttat gttgcgtccc atcgcaggtg cct                       223


<210> SEQ ID NO 343
<211> LENGTH: 204
<212> TYPE: DNA
<213> ORGANISM: Artificial Sequence
<220> FEATURE:
<223> OTHER INFORMATION: Synthetic: cCBL miRNA at P2

<400> SEQUENCE: 343

cctcacctgc ttgcgtccca ttctggaggc ttgctgaagg ctgtatgctg tttagtaatc      60

cgaaatgtgt cgttttggcc actgactgac gacacattgg attactaaac aggacacaag     120

gcctgttact agcactcaca tggaacaaat ggccgttgcc tgagtcttgg cagcgagaga     180

tcactaactg ctaagcaggt gctt                                            204


<210> SEQ ID NO 344
<211> LENGTH: 204
<212> TYPE: DNA
<213> ORGANISM: Artificial Sequence
<220> FEATURE:
<223> OTHER INFORMATION: Synthetic: cCBL miRNA at P3

<400> SEQUENCE: 344

tgtcacctgc actaactgct aactggaggc ttgctgaagg ctgtatgctg taatcattgc      60
```

-continued aggtcagatc agttttggcc actgactgac tgatctgatg caatgattac aggacacaag 120
gcctgttact agcactcaca tggaacaaat ggccgtgtta attgtccatg tagcgaggca 180
tccttatggc gtgggcaggt gtcc 204

<210> SEQ ID NO 345
<211> LENGTH: 200
<212> TYPE: DNA
<213> ORGANISM: Artificial Sequence
<220> FEATURE:
<223> OTHER INFORMATION: Synthetic: cCBL miRNA at P4

<400> SEQUENCE: 345
ccttcacctg ccttatggcg tggctggagg cttgctgaag gctgtatgct gtttgtgaat 60
gaatttctgg aggttttggc cactgactga cctccagaat cattcacaaa caggacacaa 120
ggcctgttac tagcactcac atggaacaaa tggccggtgt ccgttatcgg ggaagaaggt 180
cgcgcacata gcaggtgtcc 200

<210> SEQ ID NO 346
<211> LENGTH: 223
<212> TYPE: DNA
<213> ORGANISM: Artificial Sequence
<220> FEATURE:
<223> OTHER INFORMATION: Synthetic: CD3Z miRNA at P1

<400> SEQUENCE: 346
cggcacctgc gctgccgttg gatcggggat gaaagctggc gctggaggct tgctgaaggc 60
tgtatgctga catggtacag ttcaatggtg gttttggcca ctgactgacc accattgctg 120
taccatgtca ggacacaagg cctgttacta gcactcacat ggaacaaatg gcccacattg 180
gtgccggatg aagctcttat gttgcgtccc atcgcaggtg cct 223

<210> SEQ ID NO 347
<211> LENGTH: 204
<212> TYPE: DNA
<213> ORGANISM: Artificial Sequence
<220> FEATURE:
<223> OTHER INFORMATION: Synthetic: CD3Z miRNA at P2

<400> SEQUENCE: 347
cctcacctgc ttgcgtccca ttctggaggc ttgctgaagg ctgtatgctg tcagtctgtt 60
catcttctgg cgttttggcc actgactgac gccagaagga acagactgac aggacacaag 120
gcctgttact agcactcaca tggaacaaat ggccgttgcc tgagtcttgg cagcgagaga 180
tcactaactg ctaagcaggt gctt 204

<210> SEQ ID NO 348
<211> LENGTH: 204
<212> TYPE: DNA
<213> ORGANISM: Artificial Sequence
<220> FEATURE:
<223> OTHER INFORMATION: Synthetic: CD3Z miRNA at P3

<400> SEQUENCE: 348
tgtcacctgc actaactgct aactggaggc ttgctgaagg ctgtatgctg aagcgtgaag 60
tgaatcaacg ggttttggcc actgactgac ccgttgatac ttcacgcttc aggacacaag 120
gcctgttact agcactcaca tggaacaaat ggccgtgtta attgtccatg tagcgaggca 180
tccttatggc gtgggcaggt gtcc 204

<210> SEQ ID NO 349
<211> LENGTH: 200
<212> TYPE: DNA
<213> ORGANISM: Artificial Sequence
<220> FEATURE:
<223> OTHER INFORMATION: Synthetic: CD3Z miRNA at P4

<400> SEQUENCE: 349
ccttcacctg ccttatggcg tggctggagg cttgctgaag gctgtatgct ggcagtatcc 60
tagtacattg acgttttggc cactgactga cgtcaatgtt aggatactgc caggacacaa 120
ggcctgttac tagcactcac atggaacaaa tggccggtgt ccgttatcgg ggaagaaggt 180
cgcgcacata gcaggtgtcc 200

<210> SEQ ID NO 350
<211> LENGTH: 223
<212> TYPE: DNA
<213> ORGANISM: Artificial Sequence
<220> FEATURE:
<223> OTHER INFORMATION: Synthetic: PD1 miRNA at P1

<400> SEQUENCE: 350
cggcacctgc gctgccgttg gatcggggat gaaagctggc gctggaggct tgctgaaggc 60
tgtatgctga atgggttcca aggagagctc gttttggcca ctgactgacg agctctctgg 120
aacccattca ggacacaagg cctgttacta gcactcacat ggaacaaatg gcccacattg 180
gtgccggatg aagctcttat gttgcgtccc atcgcaggtg cct 223

<210> SEQ ID NO 351
<211> LENGTH: 204
<212> TYPE: DNA
<213> ORGANISM: Artificial Sequence
<220> FEATURE:
<223> OTHER INFORMATION: Synthetic: PD1 miRNA at P2

<400> SEQUENCE: 351
cctcacctgc ttgcgtccca ttctggaggc ttgctgaagg ctgtatgctg ttctctcgcc 60
actggaaatc cgttttggcc actgactgac ggatttcctg gcgagagaac aggacacaag 120
gcctgttact agcactcaca tggaacaaat ggccgttgcc tgagtcttgg cagcgagaga 180
tcactaactg ctaagcaggt gctt 204

<210> SEQ ID NO 352
<211> LENGTH: 204
<212> TYPE: DNA
<213> ORGANISM: Artificial Sequence
<220> FEATURE:
<223> OTHER INFORMATION: Synthetic: PD1 miRNA at P3

<400> SEQUENCE: 352
tgtcacctgc actaactgct aactggaggc ttgctgaagg ctgtatgctg tttagcacga 60
agctctccga tgttttggcc actgactgac atcggagatt cgtgctaaac aggacacaag 120
gcctgttact agcactcaca tggaacaaat ggccgtgtta attgtccatg tagcgaggca 180
tccttatggc gtgggcaggt gtcc 204

<210> SEQ ID NO 353
<211> LENGTH: 200
<212> TYPE: DNA
<213> ORGANISM: Artificial Sequence
<220> FEATURE:
<223> OTHER INFORMATION: Synthetic: PD1 miRNA at P4

<400> SEQUENCE: 353
ccttcacctg ccttatggcg tggctggagg cttgctgaag gctgtatgct gttgtccgtc 60
tggttgctgg gggttttggc cactgactga cccccagcac agacggacaa caggacacaa 120
ggcctgttac tagcactcac atggaacaaa tggccggtgt ccgttatcgg ggaagaaggt 180
cgcgcacata gcaggtgtcc 200

<210> SEQ ID NO 354
<211> LENGTH: 223
<212> TYPE: DNA
<213> ORGANISM: Artificial Sequence
<220> FEATURE:
<223> OTHER INFORMATION: Synthetic: CTLA4 miRNA at P1

<400> SEQUENCE: 354
cggcacctgc gctgccgttg gatcggggat gaaagctggc gctggaggct tgctgaaggc 60
tgtatgctga ttacataaat ctgggttccg gttttggcca ctgactgacc ggaacccatt 120
tatgtaatca ggacacaagg cctgttacta gcactcacat ggaacaaatg gcccacattg 180
gtgccggatg aagctcttat gttgcgtccc atcgcaggtg cct 223

<210> SEQ ID NO 355
<211> LENGTH: 204
<212> TYPE: DNA
<213> ORGANISM: Artificial Sequence
<220> FEATURE:
<223> OTHER INFORMATION: Synthetic: CTLA4 miRNA at P2

<400> SEQUENCE: 355
cctcacctgc ttgcgtccca ttctggaggc ttgctgaagg ctgtatgctg atactcacac 60
acaaagctgg cgttttggcc actgactgac gccagctttg tgtgagtatc aggacacaag 120
gcctgttact agcactcaca tggaacaaat ggccgttgcc tgagtcttgg cagcgagaga 180
tcactaactg ctaagcaggt gctt 204

<210> SEQ ID NO 356
<211> LENGTH: 204
<212> TYPE: DNA
<213> ORGANISM: Artificial Sequence
<220> FEATURE:
<223> OTHER INFORMATION: Synthetic: CTLA4 miRNA at P3

<400> SEQUENCE: 356
tgtcacctgc actaactgct aactggaggc ttgctgaagg ctgtatgctg taaatctggg 60
ttccgttgcc tgttttggcc actgactgac aggcaacgac ccagatttac aggacacaag 120
gcctgttact agcactcaca tggaacaaat ggccgtgtta attgtccatg tagcgaggca 180
tccttatggc gtgggcaggt gtcc 204

<210> SEQ ID NO 357
<211> LENGTH: 200
<212> TYPE: DNA
<213> ORGANISM: Artificial Sequence
<220> FEATURE:
<223> OTHER INFORMATION: Synthetic: CTLA4 miRNA at P4

<400> SEQUENCE: 357
ccttcacctg ccttatggcg tggctggagg cttgctgaag gctgtatgct gtaacttaat 60
tccttgaccc acgttttggc cactgactga cgtgggtcag aattaagtta caggacacaa 120
ggcctgttac tagcactcac atggaacaaa tggccggtgt ccgttatcgg ggaagaaggt 180
cgcgcacata gcaggtgtcc 200

<210> SEQ ID NO 358
<211> LENGTH: 223
<212> TYPE: DNA
<213> ORGANISM: Artificial Sequence
<220> FEATURE:
<223> OTHER INFORMATION: Synthetic: TIM3 miRNA at P1

<400> SEQUENCE: 358
cggcacctgc gctgccgttg gatcggggat gaaagctggc gctggaggct tgctgaaggc 60
tgtatgctgt ttgatgacca acttcaggtt gttttggcca ctgactgaca acctgaatgg 120
tcatcaaaca ggacacaagg cctgttacta gcactcacat ggaacaaatg gcccacattg 180
gtgccggatg aagctcttat gttgcgtccc atcgcaggtg cct 223

<210> SEQ ID NO 359
<211> LENGTH: 204
<212> TYPE: DNA
<213> ORGANISM: Artificial Sequence
<220> FEATURE:
<223> OTHER INFORMATION: Synthetic: TIM3 miRNA at P2

<400> SEQUENCE: 359
cctcacctgc ttgcgtccca ttctggaggc ttgctgaagg ctgtatgctg tttatctgaa 60
gtttcatgga cgttttggcc actgactgac gtccatgact tcagataaac aggacacaag 120
gcctgttact agcactcaca tggaacaaat ggccgttgcc tgagtcttgg cagcgagaga 180
tcactaactg ctaagcaggt gctt 204

<210> SEQ ID NO 360
<211> LENGTH: 204
<212> TYPE: DNA
<213> ORGANISM: Artificial Sequence
<220> FEATURE:
<223> OTHER INFORMATION: Synthetic: TIM3 miRNA at P3

<400> SEQUENCE: 360
tgtcacctgc actaactgct aactggaggc ttgctgaagg ctgtatgctg tatagcttca 60
gtttggtcca cgttttggcc actgactgac gtggaccact gaagctatac aggacacaag 120
gcctgttact agcactcaca tggaacaaat ggccgtgtta attgtccatg tagcgaggca 180
tccttatggc gtgggcaggt gtcc 204

<210> SEQ ID NO 361
<211> LENGTH: 200
<212> TYPE: DNA
<213> ORGANISM: Artificial Sequence
<220> FEATURE:
<223> OTHER INFORMATION: Synthetic: TIM3 miRNA at P4

<400> SEQUENCE: 361
ccttcacctg ccttatggcg tggctggagg cttgctgaag gctgtatgct gtatgcctgg 60
gatttggatc cggttttggc cactgactga ccggatccat cccaggcata caggacacaa 120
ggcctgttac tagcactcac atggaacaaa tggccggtgt ccgttatcgg ggaagaaggt 180
cgcgcacata gcaggtgtcc 200

<210> SEQ ID NO 362
<211> LENGTH: 223
<212> TYPE: DNA

<213> ORGANISM: Artificial Sequence
<220> FEATURE:
<223> OTHER INFORMATION: Synthetic: LAG3 miRNA at P1

<400> SEQUENCE: 362
cggcacctgc gctgccgttg gatcggggat gaaagctggc gctggaggct tgctgaaggc 60
tgtatgctgt tatacatgat ggagacgttg gttttggcca ctgactgacc aacgtctatc 120
atgtataaca ggacacaagg cctgttacta gcactcacat ggaacaaatg gcccacattg 180
gtgccggatg aagctcttat gttgcgtccc atcgcaggtg cct 223

<210> SEQ ID NO 363
<211> LENGTH: 204
<212> TYPE: DNA
<213> ORGANISM: Artificial Sequence
<220> FEATURE:
<223> OTHER INFORMATION: Synthetic: LAG3 miRNA at P2

<400> SEQUENCE: 363
cctcacctgc ttgcgtccca ttctggaggc ttgctgaagg ctgtatgctg taaagtcgcc 60
attgtctcca ggttttggcc actgactgac ctggagactg gcgactttac aggacacaag 120
gcctgttact agcactcaca tggaacaaat ggccgttgcc tgagtcttgg cagcgagaga 180
tcactaactg ctaagcaggt gctt 204

<210> SEQ ID NO 364
<211> LENGTH: 204
<212> TYPE: DNA
<213> ORGANISM: Artificial Sequence
<220> FEATURE:
<223> OTHER INFORMATION: Synthetic: LAG3 miRNA at P3

<400> SEQUENCE: 364
tgtcacctgc actaactgct aactggaggc ttgctgaagg ctgtatgctg attgccaatg 60
tgacagtggc agttttggcc actgactgac tgccactgac attggcaatc aggacacaag 120
gcctgttact agcactcaca tggaacaaat ggccgtgtta attgtccatg tagcgaggca 180
tccttatggc gtgggcaggt gtcc 204

<210> SEQ ID NO 365
<211> LENGTH: 200
<212> TYPE: DNA
<213> ORGANISM: Artificial Sequence
<220> FEATURE:
<223> OTHER INFORMATION: Synthetic: LAG3 miRNA at P4

<400> SEQUENCE: 365
ccttcacctg ccttatggcg tggctggagg cttgctgaag gctgtatgct gattgtctcc 60
agtcaccagg aggttttggc cactgactga cctcctggtc tggagacaat caggacacaa 120
ggcctgttac tagcactcac atggaacaaa tggccggtgt ccgttatcgg ggaagaaggt 180
cgcgcacata gcaggtgtcc 200

<210> SEQ ID NO 366
<211> LENGTH: 223
<212> TYPE: DNA
<213> ORGANISM: Artificial Sequence
<220> FEATURE:
<223> OTHER INFORMATION: Synthetic: SMAD2 miRNA at P1

<400> SEQUENCE: 366
cggcacctgc gctgccgttg gatcggggat gaaagctggc gctggaggct tgctgaaggc 60
tgtatgctga agattgcact atcacttagg gttttggcca ctgactgacc ctaagtgagt 120
gcaatcttca ggacacaagg cctgttacta gcactcacat ggaacaaatg gcccacattg 180
gtgccggatg aagctcttat gttgcgtccc atcgcaggtg cct 223

<210> SEQ ID NO 367
<211> LENGTH: 204
<212> TYPE: DNA
<213> ORGANISM: Artificial Sequence
<220> FEATURE:
<223> OTHER INFORMATION: Synthetic: SMAD2 miRNA at P2

<400> SEQUENCE: 367
cctcacctgc ttgcgtccca ttctggaggc ttgctgaagg ctgtatgctg tatgacatgc 60
ttgagcaacg cgttttggcc actgactgac gcgttgctag catgtcatac aggacacaag 120
gcctgttact agcactcaca tggaacaaat ggccgttgcc tgagtcttgg cagcgagaga 180
tcactaactg ctaagcaggt gctt 204

<210> SEQ ID NO 368
<211> LENGTH: 204
<212> TYPE: DNA
<213> ORGANISM: Artificial Sequence
<220> FEATURE:
<223> OTHER INFORMATION: Synthetic: SMAD2 miRNA at P3

<400> SEQUENCE: 368
tgtcacctgc actaactgct aactggaggc ttgctgaagg ctgtatgctg ttaagtagta 60
ctgatgtggt ggttttggcc actgactgac caccacatgt actacttaac aggacacaag 120
gcctgttact agcactcaca tggaacaaat ggccgtgtta attgtccatg tagcgaggca 180
tccttatggc gtgggcaggt gtcc 204

<210> SEQ ID NO 369
<211> LENGTH: 200
<212> TYPE: DNA
<213> ORGANISM: Artificial Sequence
<220> FEATURE:
<223> OTHER INFORMATION: Synthetic: SMAD2 miRNA at P4

<400> SEQUENCE: 369
ccttcacctg ccttatggcg tggctggagg cttgctgaag gctgtatgct gttacctagg 60
acatttactc tggttttggc cactgactga ccagagtaag tcctaggtaa caggacacaa 120
ggcctgttac tagcactcac atggaacaaa tggccggtgt ccgttatcgg ggaagaaggt 180
cgcgcacata gcaggtgtcc 200

<210> SEQ ID NO 370
<211> LENGTH: 223
<212> TYPE: DNA
<213> ORGANISM: Artificial Sequence
<220> FEATURE:
<223> OTHER INFORMATION: Synthetic: TNFRSF10B miRNA at P1

<400> SEQUENCE: 370
cggcacctgc gctgccgttg gatcggggat gaaagctggc gctggaggct tgctgaaggc 60
tgtatgctga aaggaggtca ttccagtgag gttttggcca ctgactgacc tcactggtga 120
cctcctttca ggacacaagg cctgttacta gcactcacat ggaacaaatg gcccacattg 180
gtgccggatg aagctcttat gttgcgtccc atcgcaggtg cct 223

<210> SEQ ID NO 371
<211> LENGTH: 204
<212> TYPE: DNA
<213> ORGANISM: Artificial Sequence
<220> FEATURE:
<223> OTHER INFORMATION: Synthetic: TNFRSF10B miRNA at P2

<400> SEQUENCE: 371
cctcacctgc ttgcgtccca ttctggaggc ttgctgaagg ctgtatgctg tatgggtgca 60
aatgagactg cgttttggcc actgactgac gcagtctctt gcacccatac aggacacaag 120
gcctgttact agcactcaca tggaacaaat ggccgttgcc tgagtcttgg cagcgagaga 180
tcactaactg ctaagcaggt gctt 204

<210> SEQ ID NO 372
<211> LENGTH: 204
<212> TYPE: DNA
<213> ORGANISM: Artificial Sequence
<220> FEATURE:
<223> OTHER INFORMATION: Synthetic: TNFRSF10B miRNA at P3

<400> SEQUENCE: 372
tgtcacctgc actaactgct aactggaggc ttgctgaagg ctgtatgctg tagtcctgtc 60
catatttgca ggttttggcc actgactgac ctgcaaatgg acaggactac aggacacaag 120
gcctgttact agcactcaca tggaacaaat ggccgtgtta attgtccatg tagcgaggca 180
tccttatggc gtgggcaggt gtcc 204

<210> SEQ ID NO 373
<211> LENGTH: 200
<212> TYPE: DNA
<213> ORGANISM: Artificial Sequence
<220> FEATURE:
<223> OTHER INFORMATION: Synthetic: TNFRSF10B miRNA at P4

<400> SEQUENCE: 373
ccttcacctg ccttatggcg tggctggagg cttgctgaag gctgtatgct gatactcacg 60
atctcattga gggttttggc cactgactga ccctcaatga tcgtgagtat caggacacaa 120
ggcctgttac tagcactcac atggaacaaa tggccggtgt ccgttatcgg ggaagaaggt 180
cgcgcacata gcaggtgtcc 200

<210> SEQ ID NO 374
<211> LENGTH: 223
<212> TYPE: DNA
<213> ORGANISM: Artificial Sequence
<220> FEATURE:
<223> OTHER INFORMATION: Synthetic: PPP2CA miRNA at P1

<400> SEQUENCE: 374
cggcacctgc gctgccgttg gatcggggat gaaagctggc gctggaggct tgctgaaggc 60
tgtatgctga aatcgttact acattccggt gttttggcca ctgactgaca ccggaatagt 120
aacgatttca ggacacaagg cctgttacta gcactcacat ggaacaaatg gcccacattg 180
gtgccggatg aagctcttat gttgcgtccc atcgcaggtg cct 223

<210> SEQ ID NO 375
<211> LENGTH: 204
<212> TYPE: DNA
<213> ORGANISM: Artificial Sequence
<220> FEATURE:
<223> OTHER INFORMATION: Synthetic: PPP2CA miRNA at P2

<400> SEQUENCE: 375
cctcacctgc ttgcgtccca ttctggaggc ttgctgaagg ctgtatgctg aataacaaag 60
aacaacatgg ggttttggcc actgactgac cccatgtttc tttgttattc aggacacaag 120
gcctgttact agcactcaca tggaacaaat ggccgttgcc tgagtcttgg cagcgagaga 180
tcactaactg ctaagcaggt gctt 204

<210> SEQ ID NO 376
<211> LENGTH: 204
<212> TYPE: DNA
<213> ORGANISM: Artificial Sequence
<220> FEATURE:
<223> OTHER INFORMATION: Synthetic: PPP2CA miRNA at P3

<400> SEQUENCE: 376
tgtcacctgc actaactgct aactggaggc ttgctgaagg ctgtatgctg tttgtatctg 60
gtgatttgcc agttttggcc actgactgac tggcaaatcc agatacaaac aggacacaag 120
gcctgttact agcactcaca tggaacaaat ggccgtgtta attgtccatg tagcgaggca 180
tccttatggc gtgggcaggt gtcc 204

<210> SEQ ID NO 377
<211> LENGTH: 200
<212> TYPE: DNA
<213> ORGANISM: Artificial Sequence
<220> FEATURE:
<223> OTHER INFORMATION: Synthetic: PPP2CA miRNA at P4

<400> SEQUENCE: 377
ccttcacctg ccttatggcg tggctggagg cttgctgaag gctgtatgct gtttgccacc 60
aattctaaac aggttttggc cactgactga cctgtttagt tggtggcaaa caggacacaa 120
ggcctgttac tagcactcac atggaacaaa tggccggtgt ccgttatcgg ggaagaaggt 180
cgcgcacata gcaggtgtcc 200

<210> SEQ ID NO 378
<211> LENGTH: 223
<212> TYPE: DNA
<213> ORGANISM: Artificial Sequence
<220> FEATURE:
<223> OTHER INFORMATION: Synthetic: TNFRSF6 miRNA at P1

<400> SEQUENCE: 378
cggcacctgc gctgccgttg gatcggggat gaaagctggc gctggaggct tgctgaaggc 60
tgtatgctgt ttaatcaatg tgtcatacgc gttttggcca ctgactgacg cgtatgacat 120
tgattaaaca ggacacaagg cctgttacta gcactcacat ggaacaaatg gcccacattg 180
gtgccggatg aagctcttat gttgcgtccc atcgcaggtg cct 223

<210> SEQ ID NO 379
<211> LENGTH: 204
<212> TYPE: DNA
<213> ORGANISM: Artificial Sequence
<220> FEATURE:
<223> OTHER INFORMATION: Synthetic: TNFRSF6 miRNA at P2

<400> SEQUENCE: 379
cctcacctgc ttgcgtccca ttctggaggc ttgctgaagg ctgtatgctg tttacagcca 60
gctattaaga agttttggcc actgactgac ttcttaatct ggctgtaaac aggacacaag 120
gcctgttact agcactcaca tggaacaaat ggccgttgcc tgagtcttgg cagcgagaga 180
tcactaactg ctaagcaggt gctt 204

<210> SEQ ID NO 380
<211> LENGTH: 204
<212> TYPE: DNA
<213> ORGANISM: Artificial Sequence
<220> FEATURE:
<223> OTHER INFORMATION: Synthetic: TNFRSF6 miRNA at P3

<400> SEQUENCE: 380
tgtcacctgc actaactgct aactggaggc ttgctgaagg ctgtatgctg tttaacttga 60
cttagtgtca tgttttggcc actgactgac atgacactgt caagttaaac aggacacaag 120
gcctgttact agcactcaca tggaacaaat ggccgtgtta attgtccatg tagcgaggca 180
tccttatggc gtgggcaggt gtcc 204

<210> SEQ ID NO 381
<211> LENGTH: 200
<212> TYPE: DNA
<213> ORGANISM: Artificial Sequence
<220> FEATURE:
<223> OTHER INFORMATION: Synthetic: TNFRSF6 miRNA at P4

<400> SEQUENCE: 381
ccttcacctg ccttatggcg tggctggagg cttgctgaag gctgtatgct gttagtatct 60
ccaaaccagg ctgttttggc cactgactga cagcctggtg gagatactaa caggacacaa 120
ggcctgttac tagcactcac atggaacaaa tggccggtgt ccgttatcgg ggaagaaggt 180
cgcgcacata gcaggtgtcc 200

<210> SEQ ID NO 382
<211> LENGTH: 223
<212> TYPE: DNA
<213> ORGANISM: Artificial Sequence
<220> FEATURE:
<223> OTHER INFORMATION: Synthetic: BTLA miRNA at P1

<400> SEQUENCE: 382
cggcacctgc gctgccgttg gatcggggat gaaagctggc gctggaggct tgctgaaggc 60
tgtatgctgt ttaaacgttc tactattctg gttttggcca ctgactgacc agaataggaa 120
cgtttaaaca ggacacaagg cctgttacta gcactcacat ggaacaaatg gcccacattg 180
gtgccggatg aagctcttat gttgcgtccc atcgcaggtg cct 223

<210> SEQ ID NO 383
<211> LENGTH: 204
<212> TYPE: DNA
<213> ORGANISM: Artificial Sequence
<220> FEATURE:
<223> OTHER INFORMATION: Synthetic: BTLA miRNA at P2

<400> SEQUENCE: 383
cctcacctgc ttgcgtccca ttctggaggc ttgctgaagg ctgtatgctg ttaatttccc 60
ttcctgctgt ggttttggcc actgactgac cacagcagag ggaaattaac aggacacaag 120
gcctgttact agcactcaca tggaacaaat ggccgttgcc tgagtcttgg cagcgagaga 180
tcactaactg ctaagcaggt gctt 204

<210> SEQ ID NO 384
<211> LENGTH: 204

<212> TYPE: DNA
<213> ORGANISM: Artificial Sequence
<220> FEATURE:
<223> OTHER INFORMATION: Synthetic: BTLA miRNA at P3

<400> SEQUENCE: 384
tgtcacctgc actaactgct aactggaggc ttgctgaagg ctgtatgctg aattccagtt 60
tctgatagca ggttttggcc actgactgac ctgctatcaa actggaattc aggacacaag 120
gcctgttact agcactcaca tggaacaaat ggccgtgtta attgtccatg tagcgaggca 180
tccttatggc gtgggcaggt gtcc 204

<210> SEQ ID NO 385
<211> LENGTH: 200
<212> TYPE: DNA
<213> ORGANISM: Artificial Sequence
<220> FEATURE:
<223> OTHER INFORMATION: Synthetic: BTLA miRNA at P4

<400> SEQUENCE: 385
ccttcacctg ccttatggcg tggctggagg cttgctgaag gctgtatgct gttagaataa 60
acttcagacc ctgttttggc cactgactga cagggtctgg tttattctaa caggacacaa 120
ggcctgttac tagcactcac atggaacaaa tggccggtgt ccgttatcgg ggaagaaggt 180
cgcgcacata gcaggtgtcc 200

<210> SEQ ID NO 386
<211> LENGTH: 223
<212> TYPE: DNA
<213> ORGANISM: Artificial Sequence
<220> FEATURE:
<223> OTHER INFORMATION: Synthetic: TIGIT miRNA at P1

<400> SEQUENCE: 386
cggcacctgc gctgccgttg gatcggggat gaaagctggc gctggaggct tgctgaaggc 60
tgtatgctgt taactgtaag ttcttgaggg gttttggcca ctgactgacc cctcaagctt 120
acagttaaca ggacacaagg cctgttacta gcactcacat ggaacaaatg gcccacattg 180
gtgccggatg aagctcttat gttgcgtccc atcgcaggtg cct 223

<210> SEQ ID NO 387
<211> LENGTH: 204
<212> TYPE: DNA
<213> ORGANISM: Artificial Sequence
<220> FEATURE:
<223> OTHER INFORMATION: Synthetic: TIGIT miRNA at P2

<400> SEQUENCE: 387
cctcacctgc ttgcgtccca ttctggaggc ttgctgaagg ctgtatgctg tattgtgcct 60
gtcatcattc cgttttggcc actgactgac ggaatgatca ggcacaatac aggacacaag 120
gcctgttact agcactcaca tggaacaaat ggccgttgcc tgagtcttgg cagcgagaga 180
tcactaactg ctaagcaggt gctt 204

<210> SEQ ID NO 388
<211> LENGTH: 204
<212> TYPE: DNA
<213> ORGANISM: Artificial Sequence
<220> FEATURE:
<223> OTHER INFORMATION: Synthetic: TIGIT miRNA at P3

<400> SEQUENCE: 388

-continued

```
tgtcacctgc actaactgct aactggaggc ttgctgaagg ctgtatgctg aagtagtcat     60

gcagctcggc agttttggcc actgactgac tgccgagcca tgactacttc aggacacaag    120

gcctgttact agcactcaca tggaacaaat ggccgtgtta attgtccatg tagcgaggca    180

tccttatggc gtgggcaggt gtcc                                           204


<210> SEQ ID NO 389
<211> LENGTH: 200
<212> TYPE: DNA
<213> ORGANISM: Artificial Sequence
<220> FEATURE:
<223> OTHER INFORMATION: Synthetic: TIGIT miRNA at P4

<400> SEQUENCE: 389

ccttcacctg ccttatggcg tggctggagg cttgctgaag gctgtatgct gtttcctaca     60

agttccctag acgttttggc cactgactga cgtctagggc ttgtaggaaa caggacacaa    120

ggcctgttac tagcactcac atggaacaaa tggccggtgt ccgttatcgg ggaagaaggt    180

cgcgcacata gcaggtgtcc                                                200


<210> SEQ ID NO 390
<211> LENGTH: 223
<212> TYPE: DNA
<213> ORGANISM: Artificial Sequence
<220> FEATURE:
<223> OTHER INFORMATION: Synthetic: A2AR miRNA at P1

<400> SEQUENCE: 390

cggcacctgc gctgccgttg gatcggggat gaaagctggc gctggaggct tgctgaaggc     60

tgtatgctgt tgttccaacc tagcatggga gttttggcca ctgactgact cccatgcggt    120

tggaacaaca ggacacaagg cctgttacta gcactcacat ggaacaaatg gcccacattg    180

gtgccggatg aagctcttat gttgcgtccc atcgcaggtg cct                      223


<210> SEQ ID NO 391
<211> LENGTH: 204
<212> TYPE: DNA
<213> ORGANISM: Artificial Sequence
<220> FEATURE:
<223> OTHER INFORMATION: Synthetic: A2AR miRNA at P2

<400> SEQUENCE: 391

cctcacctgc ttgcgtccca ttctggaggc ttgctgaagg ctgtatgctg taaagatctc     60

cttcccttag ggttttggcc actgactgac cctaaggggg agatctttac aggacacaag    120

gcctgttact agcactcaca tggaacaaat ggccgttgcc tgagtcttgg cagcgagaga    180

tcactaactg ctaagcaggt gctt                                           204


<210> SEQ ID NO 392
<211> LENGTH: 204
<212> TYPE: DNA
<213> ORGANISM: Artificial Sequence
<220> FEATURE:
<223> OTHER INFORMATION: Synthetic: A2AR miRNA at P3

<400> SEQUENCE: 392

tgtcacctgc actaactgct aactggaggc ttgctgaagg ctgtatgctg aatagacacc     60

cagcatgagc agttttggcc actgactgac tgctcatggg gtgtctattc aggacacaag    120

gcctgttact agcactcaca tggaacaaat ggccgtgtta attgtccatg tagcgaggca    180

tccttatggc gtgggcaggt gtcc                                           204
```

<210> SEQ ID NO 393
<211> LENGTH: 200
<212> TYPE: DNA
<213> ORGANISM: Artificial Sequence
<220> FEATURE:
<223> OTHER INFORMATION: Synthetic: A2AR miRNA at P4

<400> SEQUENCE: 393
ccttcacctg ccttatggcg tggctggagg cttgctgaag gctgtatgct gaattggtgt 60
gggagaggac gagttttggc cactgactga ctcgtcctcc cacaccaatt caggacacaa 120
ggcctgttac tagcactcac atggaacaaa tggccggtgt ccgttatcgg ggaagaaggt 180
cgcgcacata gcaggtgtcc 200

<210> SEQ ID NO 394
<211> LENGTH: 223
<212> TYPE: DNA
<213> ORGANISM: Artificial Sequence
<220> FEATURE:
<223> OTHER INFORMATION: Synthetic: AHR miRNA at P1

<400> SEQUENCE: 394
cggcacctgc gctgccgttg gatcggggat gaaagctggc gctggaggct tgctgaaggc 60
tgtatgctgt taagtcggtc tctatgccgc gttttggcca ctgactgacg cggcatagac 120
cgacttaaca ggacacaagg cctgttacta gcactcacat ggaacaaatg gcccacattg 180
gtgccggatg aagctcttat gttgcgtccc atcgcaggtg cct 223

<210> SEQ ID NO 395
<211> LENGTH: 204
<212> TYPE: DNA
<213> ORGANISM: Artificial Sequence
<220> FEATURE:
<223> OTHER INFORMATION: Synthetic: AHR miRNA at P2

<400> SEQUENCE: 395
cctcacctgc ttgcgtccca ttctggaggc ttgctgaagg ctgtatgctg ttaataccaa 60
ctttaagcag tgttttggcc actgactgac actgcttagt tggtattaac aggacacaag 120
gcctgttact agcactcaca tggaacaaat ggccgttgcc tgagtcttgg cagcgagaga 180
tcactaactg ctaagcaggt gctt 204

<210> SEQ ID NO 396
<211> LENGTH: 204
<212> TYPE: DNA
<213> ORGANISM: Artificial Sequence
<220> FEATURE:
<223> OTHER INFORMATION: Synthetic: AHR miRNA at P3

<400> SEQUENCE: 396
tgtcacctgc actaactgct aactggaggc ttgctgaagg ctgtatgctg ttaatgcaac 60
atcaaagaag cgttttggcc actgactgac gcttcttttg ttgcattaac aggacacaag 120
gcctgttact agcactcaca tggaacaaat ggccgtgtta attgtccatg tagcgaggca 180
tccttatggc gtgggcaggt gtcc 204

<210> SEQ ID NO 397
<211> LENGTH: 200
<212> TYPE: DNA
<213> ORGANISM: Artificial Sequence
<220> FEATURE:

<223> OTHER INFORMATION: Synthetic: AHR miRNA at P4

<400> SEQUENCE: 397
ccttcacctg ccttatggcg tggctggagg cttgctgaag gctgtatgct gtttcgtaaa 60
tgctctgttc ctgttttggc cactgactga caggaacagc atttacgaaa caggacacaa 120
ggcctgttac tagcactcac atggaacaaa tggccggtgt ccgttatcgg ggaagaaggt 180
cgcgcacata gcaggtgtcc 200

<210> SEQ ID NO 398
<211> LENGTH: 223
<212> TYPE: DNA
<213> ORGANISM: Artificial Sequence
<220> FEATURE:
<223> OTHER INFORMATION: Synthetic: EOMES miRNA at P1

<400> SEQUENCE: 398
cggcacctgc gctgccgttg gatcggggat gaaagctggc gctggaggct tgctgaaggc 60
tgtatgctgt aatgtcctca cactttatgg gttttggcca ctgactgacc cataaagtga 120
ggacattaca ggacacaagg cctgttacta gcactcacat ggaacaaatg gcccacattg 180
gtgccggatg aagctcttat gttgcgtccc atcgcaggtg cct 223

<210> SEQ ID NO 399
<211> LENGTH: 204
<212> TYPE: DNA
<213> ORGANISM: Artificial Sequence
<220> FEATURE:
<223> OTHER INFORMATION: Synthetic: EOMES miRNA at P2

<400> SEQUENCE: 399
cctcacctgc ttgcgtccca ttctggaggc ttgctgaagg ctgtatgctg aaatgtctcc 60
ttctgaaacg ggttttggcc actgactgac ccgtttcaag gagacatttc aggacacaag 120
gcctgttact agcactcaca tggaacaaat ggccgttgcc tgagtcttgg cagcgagaga 180
tcactaactg ctaagcaggt gctt 204

<210> SEQ ID NO 400
<211> LENGTH: 204
<212> TYPE: DNA
<213> ORGANISM: Artificial Sequence
<220> FEATURE:
<223> OTHER INFORMATION: Synthetic: EOMES miRNA at P3

<400> SEQUENCE: 400
tgtcacctgc actaactgct aactggaggc ttgctgaagg ctgtatgctg tttgcgcctt 60
tgttattggt ggttttggcc actgactgac caccaataaa aggcgcaaac aggacacaag 120
gcctgttact agcactcaca tggaacaaat ggccgtgtta attgtccatg tagcgaggca 180
tccttatggc gtgggcaggt gtcc 204

<210> SEQ ID NO 401
<211> LENGTH: 200
<212> TYPE: DNA
<213> ORGANISM: Artificial Sequence
<220> FEATURE:
<223> OTHER INFORMATION: Synthetic: EOMES miRNA at P4

<400> SEQUENCE: 401
ccttcacctg ccttatggcg tggctggagg cttgctgaag gctgtatgct gtttgttggt 60
cccaggttgc tggttttggc cactgactga ccagcaaccg gaccaacaaa caggacacaa 120
ggcctgttac tagcactcac atggaacaaa tggccggtgt ccgttatcgg ggaagaaggt 180
cgcgcacata gcaggtgtcc 200

<210> SEQ ID NO 402
<211> LENGTH: 223
<212> TYPE: DNA
<213> ORGANISM: Artificial Sequence
<220> FEATURE:
<223> OTHER INFORMATION: Synthetic: SMAD3 miRNA at P1

<400> SEQUENCE: 402
cggcacctgc gctgccgttg gatcggggat gaaagctggc gctggaggct tgctgaaggc 60
tgtatgctga aatagcgctg tcactgaggc gttttggcca ctgactgacg cctcagtcag 120
cgctatttca ggacacaagg cctgttacta gcactcacat ggaacaaatg gcccacattg 180
gtgccggatg aagctcttat gttgcgtccc atcgcaggtg cct 223

<210> SEQ ID NO 403
<211> LENGTH: 204
<212> TYPE: DNA
<213> ORGANISM: Artificial Sequence
<220> FEATURE:
<223> OTHER INFORMATION: Synthetic: SMAD3 miRNA at P2

<400> SEQUENCE: 403
cctcacctgc ttgcgtccca ttctggaggc ttgctgaagg ctgtatgctg ttcaggtgca 60
gctcaatcca ggttttggcc actgactgac ctggattgct gcacctgaac aggacacaag 120
gcctgttact agcactcaca tggaacaaat ggccgttgcc tgagtcttgg cagcgagaga 180
tcactaactg ctaagcaggt gctt 204

<210> SEQ ID NO 404
<211> LENGTH: 204
<212> TYPE: DNA
<213> ORGANISM: Artificial Sequence
<220> FEATURE:
<223> OTHER INFORMATION: Synthetic: SMAD3 miRNA at P3

<400> SEQUENCE: 404
tgtcacctgc actaactgct aactggaggc ttgctgaagg ctgtatgctg tttcagcttg 60
cagaagtgct ggttttggcc actgactgac cagcacttgc aagctgaaac aggacacaag 120
gcctgttact agcactcaca tggaacaaat ggccgtgtta attgtccatg tagcgaggca 180
tccttatggc gtgggcaggt gtcc 204

<210> SEQ ID NO 405
<211> LENGTH: 200
<212> TYPE: DNA
<213> ORGANISM: Artificial Sequence
<220> FEATURE:
<223> OTHER INFORMATION: Synthetic: SMAD3 miRNA at P4

<400> SEQUENCE: 405
ccttcacctg ccttatggcg tggctggagg cttgctgaag gctgtatgct gaatactacc 60
tgttctgctc acgttttggc cactgactga cgtgagcagc aggtagtatt caggacacaa 120
ggcctgttac tagcactcac atggaacaaa tggccggtgt ccgttatcgg ggaagaaggt 180
cgcgcacata gcaggtgtcc 200

<210> SEQ ID NO 406

<211> LENGTH: 223
<212> TYPE: DNA
<213> ORGANISM: Artificial Sequence
<220> FEATURE:
<223> OTHER INFORMATION: Synthetic: SMAD4 miRNA at P1

<400> SEQUENCE: 406
cggcacctgc gctgccgttg gatcggggat gaaagctggc gctggaggct tgctgaaggc 60
tgtatgctga attaggtgtg tatggtgcag gttttggcca ctgactgacc tgcaccacac 120
acctaattca ggacacaagg cctgttacta gcactcacat ggaacaaatg gcccacattg 180
gtgccggatg aagctcttat gttgcgtccc atcgcaggtg cct 223

<210> SEQ ID NO 407
<211> LENGTH: 204
<212> TYPE: DNA
<213> ORGANISM: Artificial Sequence
<220> FEATURE:
<223> OTHER INFORMATION: Synthetic: SMAD4 miRNA at P2

<400> SEQUENCE: 407
cctcacctgc ttgcgtccca ttctggaggc ttgctgaagg ctgtatgctg aagtacttcg 60
tctaggagct ggttttggcc actgactgac cagctcctac gaagtacttc aggacacaag 120
gcctgttact agcactcaca tggaacaaat ggccgttgcc tgagtcttgg cagcgagaga 180
tcactaactg ctaagcaggt gctt 204

<210> SEQ ID NO 408
<211> LENGTH: 204
<212> TYPE: DNA
<213> ORGANISM: Artificial Sequence
<220> FEATURE:
<223> OTHER INFORMATION: Synthetic: SMAD4 miRNA at P3

<400> SEQUENCE: 408
tgtcacctgc actaactgct aactggaggc ttgctgaagg ctgtatgctg tatcccacga 60
tctactcccc ggttttggcc actgactgac cggggagtat cgtgggatac aggacacaag 120
gcctgttact agcactcaca tggaacaaat ggccgtgtta attgtccatg tagcgaggca 180
tccttatggc gtgggcaggt gtcc 204

<210> SEQ ID NO 409
<211> LENGTH: 200
<212> TYPE: DNA
<213> ORGANISM: Artificial Sequence
<220> FEATURE:
<223> OTHER INFORMATION: Synthetic: SMAD4 miRNA at P4

<400> SEQUENCE: 409
ccttcacctg ccttatggcg tggctggagg cttgctgaag gctgtatgct gttatgatgg 60
taagtagctg gcgttttggc cactgactga cgccagctat accatcataa caggacacaa 120
ggcctgttac tagcactcac atggaacaaa tggccggtgt ccgttatcgg ggaagaaggt 180
cgcgcacata gcaggtgtcc 200

<210> SEQ ID NO 410
<211> LENGTH: 223
<212> TYPE: DNA
<213> ORGANISM: Artificial Sequence
<220> FEATURE:
<223> OTHER INFORMATION: Synthetic: TGFBR2 miRNA at P1

<400> SEQUENCE: 410
cggcacctgc gctgccgttg gatcggggat gaaagctggc gctggaggct tgctgaaggc 60
tgtatgctgt tattaaccga cttctgaacg gttttggcca ctgactgacc gttcagatcg 120
gttaataaca ggacacaagg cctgttacta gcactcacat ggaacaaatg gcccacattg 180
gtgccggatg aagctcttat gttgcgtccc atcgcaggtg cct 223

<210> SEQ ID NO 411
<211> LENGTH: 204
<212> TYPE: DNA
<213> ORGANISM: Artificial Sequence
<220> FEATURE:
<223> OTHER INFORMATION: Synthetic: TGFBR2 miRNA at P2

<400> SEQUENCE: 411
cctcacctgc ttgcgtccca ttctggaggc ttgctgaagg ctgtatgctg taaacacgat 60
aaagcctaga ggttttggcc actgactgac ctctaggcta tcgtgtttac aggacacaag 120
gcctgttact agcactcaca tggaacaaat ggccgttgcc tgagtcttgg cagcgagaga 180
tcactaactg ctaagcaggt gctt 204

<210> SEQ ID NO 412
<211> LENGTH: 204
<212> TYPE: DNA
<213> ORGANISM: Artificial Sequence
<220> FEATURE:
<223> OTHER INFORMATION: Synthetic: TGFBR2 miRNA at P3

<400> SEQUENCE: 412
tgtcacctgc actaactgct aactggaggc ttgctgaagg ctgtatgctg attctaggac 60
ttctggagcc agttttggcc actgactgac tggctccaag tcctagaatc aggacacaag 120
gcctgttact agcactcaca tggaacaaat ggccgtgtta attgtccatg tagcgaggca 180
tccttatggc gtgggcaggt gtcc 204

<210> SEQ ID NO 413
<211> LENGTH: 200
<212> TYPE: DNA
<213> ORGANISM: Artificial Sequence
<220> FEATURE:
<223> OTHER INFORMATION: Synthetic: TGFBR2 miRNA at P4

<400> SEQUENCE: 413
ccttcacctg ccttatggcg tggctggagg cttgctgaag gctgtatgct gttcttcacg 60
aggatattgg aggttttggc cactgactga cctccaatac tcgtgaagaa caggacacaa 120
ggcctgttac tagcactcac atggaacaaa tggccggtgt ccgttatcgg ggaagaaggt 180
cgcgcacata gcaggtgtcc 200

<210> SEQ ID NO 414
<211> LENGTH: 223
<212> TYPE: DNA
<213> ORGANISM: Artificial Sequence
<220> FEATURE:
<223> OTHER INFORMATION: Synthetic: PPP2R2D miRNA at P1

<400> SEQUENCE: 414
cggcacctgc gctgccgttg gatcggggat gaaagctggc gctggaggct tgctgaaggc 60
tgtatgctga aatgtccggc ttaactatgc gttttggcca ctgactgacg catagttgcc 120
ggacatttca ggacacaagg cctgttacta gcactcacat ggaacaaatg gcccacattg 180
gtgccggatg aagctcttat gttgcgtccc atcgcaggtg cct 223

<210> SEQ ID NO 415
<211> LENGTH: 204
<212> TYPE: DNA
<213> ORGANISM: Artificial Sequence
<220> FEATURE:
<223> OTHER INFORMATION: Synthetic: PPP2R2D miRNA at P2

<400> SEQUENCE: 415
cctcacctgc ttgcgtccca ttctggaggc ttgctgaagg ctgtatgctg attaattctc 60
aggtcatctg cgttttggcc actgactgac gcagatgatg agaattaatc aggacacaag 120
gcctgttact agcactcaca tggaacaaat ggccgttgcc tgagtcttgg cagcgagaga 180
tcactaactg ctaagcaggt gctt 204

<210> SEQ ID NO 416
<211> LENGTH: 204
<212> TYPE: DNA
<213> ORGANISM: Artificial Sequence
<220> FEATURE:
<223> OTHER INFORMATION: Synthetic: PPP2R2D miRNA at P3

<400> SEQUENCE: 416
tgtcacctgc actaactgct aactggaggc ttgctgaagg ctgtatgctg tttgaagcta 60
ctttaaacca ggttttggcc actgactgac ctggtttagt agcttcaaac aggacacaag 120
gcctgttact agcactcaca tggaacaaat ggccgtgtta attgtccatg tagcgaggca 180
tccttatggc gtgggcaggt gtcc 204

<210> SEQ ID NO 417
<211> LENGTH: 200
<212> TYPE: DNA
<213> ORGANISM: Artificial Sequence
<220> FEATURE:
<223> OTHER INFORMATION: Synthetic: PPP2R2D miRNA at P4

<400> SEQUENCE: 417
ccttcacctg ccttatggcg tggctggagg cttgctgaag gctgtatgct gttcaccgac 60
aggtagtctc tggttttggc cactgactga ccagagactc tgtcggtgaa caggacacaa 120
ggcctgttac tagcactcac atggaacaaa tggccggtgt ccgttatcgg ggaagaaggt 180
cgcgcacata gcaggtgtcc 200

<210> SEQ ID NO 418
<211> LENGTH: 223
<212> TYPE: DNA
<213> ORGANISM: Artificial Sequence
<220> FEATURE:
<223> OTHER INFORMATION: Synthetic: TNFSF6 miRNA at P1

<400> SEQUENCE: 418
cggcacctgc gctgccgttg gatcggggat gaaagctggc gctggaggct tgctgaaggc 60
tgtatgctgt tattatgcaa gcctctagtc gttttggcca ctgactgacg actagagttg 120
cataataaca ggacacaagg cctgttacta gcactcacat ggaacaaatg gcccacattg 180
gtgccggatg aagctcttat gttgcgtccc atcgcaggtg cct 223

<210> SEQ ID NO 419
<211> LENGTH: 204
<212> TYPE: DNA
<213> ORGANISM: Artificial Sequence
<220> FEATURE:
<223> OTHER INFORMATION: Synthetic: TNFSF6 miRNA at P2

<400> SEQUENCE: 419
cctcacctgc ttgcgtccca ttctggaggc ttgctgaagg ctgtatgctg aaattgacca 60
gagagagctc agttttggcc actgactgac tgagctctct ggtcaatttc aggacacaag 120
gcctgttact agcactcaca tggaacaaat ggccgttgcc tgagtcttgg cagcgagaga 180
tcactaactg ctaagcaggt gctt 204

<210> SEQ ID NO 420
<211> LENGTH: 204
<212> TYPE: DNA
<213> ORGANISM: Artificial Sequence
<220> FEATURE:
<223> OTHER INFORMATION: Synthetic: TNFSF6 miRNA at P3

<400> SEQUENCE: 420
tgtcacctgc actaactgct aactggaggc ttgctgaagg ctgtatgctg tattcctcca 60
tttgtctggc tgttttggcc actgactgac agccagacat ggaggaatac aggacacaag 120
gcctgttact agcactcaca tggaacaaat ggccgtgtta attgtccatg tagcgaggca 180
tccttatggc gtgggcaggt gtcc 204

<210> SEQ ID NO 421
<211> LENGTH: 200
<212> TYPE: DNA
<213> ORGANISM: Artificial Sequence
<220> FEATURE:
<223> OTHER INFORMATION: Synthetic: TNFSF6 miRNA at P4

<400> SEQUENCE: 421
ccttcacctg ccttatggcg tggctggagg cttgctgaag gctgtatgct gtttcaatct 60
gcctaaatac tcgttttggc cactgactga cgagtatttg cagattgaaa caggacacaa 120
ggcctgttac tagcactcac atggaacaaa tggccggtgt ccgttatcgg ggaagaaggt 180
cgcgcacata gcaggtgtcc 200

<210> SEQ ID NO 422
<211> LENGTH: 223
<212> TYPE: DNA
<213> ORGANISM: Artificial Sequence
<220> FEATURE:
<223> OTHER INFORMATION: Synthetic: CASP3 miRNA at P1

<400> SEQUENCE: 422
cggcacctgc gctgccgttg gatcggggat gaaagctggc gctggaggct tgctgaaggc 60
tgtatgctgt ttcagcatgg cacaaagcga gttttggcca ctgactgact cgctttgcca 120
tgctgaaaca ggacacaagg cctgttacta gcactcacat ggaacaaatg gcccacattg 180
gtgccggatg aagctcttat gttgcgtccc atcgcaggtg cct 223

<210> SEQ ID NO 423
<211> LENGTH: 204
<212> TYPE: DNA
<213> ORGANISM: Artificial Sequence
<220> FEATURE:
<223> OTHER INFORMATION: Synthetic: CASP3 miRNA at P2

<400> SEQUENCE: 423
cctcacctgc ttgcgtccca ttctggaggc ttgctgaagg ctgtatgctg tttgagcctt 60
tgaccatgcc cgttttggcc actgactgac gggcatggaa aggctcaaac aggacacaag 120
gcctgttact agcactcaca tggaacaaat ggccgttgcc tgagtcttgg cagcgagaga 180
tcactaactg ctaagcaggt gctt 204

<210> SEQ ID NO 424
<211> LENGTH: 204
<212> TYPE: DNA
<213> ORGANISM: Artificial Sequence
<220> FEATURE:
<223> OTHER INFORMATION: Synthetic: CASP3 miRNA at P3

<400> SEQUENCE: 424
tgtcacctgc actaactgct aactggaggc ttgctgaagg ctgtatgctg ttattgcctc 60
accaccttta ggttttggcc actgactgac ctaaaggttg aggcaataac aggacacaag 120
gcctgttact agcactcaca tggaacaaat ggccgtgtta attgtccatg tagcgaggca 180
tccttatggc gtgggcaggt gtcc 204

<210> SEQ ID NO 425
<211> LENGTH: 200
<212> TYPE: DNA
<213> ORGANISM: Artificial Sequence
<220> FEATURE:
<223> OTHER INFORMATION: Synthetic: CASP3 miRNA at P4

<400> SEQUENCE: 425
ccttcacctg ccttatggcg tggctggagg cttgctgaag gctgtatgct gaaggactca 60
aattctgttg ccgttttggc cactgactga cggcaacagt ttgagtcctt caggacacaa 120
ggcctgttac tagcactcac atggaacaaa tggccggtgt ccgttatcgg ggaagaaggt 180
cgcgcacata gcaggtgtcc 200

<210> SEQ ID NO 426
<211> LENGTH: 223
<212> TYPE: DNA
<213> ORGANISM: Artificial Sequence
<220> FEATURE:
<223> OTHER INFORMATION: Synthetic: SOCS2 miRNA at P1

<400> SEQUENCE: 426
cggcacctgc gctgccgttg gatcggggat gaaagctggc gctggaggct tgctgaaggc 60
tgtatgctgt aatcaagaaa gttccttctg gttttggcca ctgactgacc agaaggattt 120
cttgattaca ggacacaagg cctgttacta gcactcacat ggaacaaatg gcccacattg 180
gtgccggatg aagctcttat gttgcgtccc atcgcaggtg cct 223

<210> SEQ ID NO 427
<211> LENGTH: 204
<212> TYPE: DNA
<213> ORGANISM: Artificial Sequence
<220> FEATURE:
<223> OTHER INFORMATION: Synthetic: SOCS2 miRNA at P2

<400> SEQUENCE: 427
cctcacctgc ttgcgtccca ttctggaggc ttgctgaagg ctgtatgctg tttagtcttg 60
ttggtaaagg cgttttggcc actgactgac gcctttacac aagactaaac aggacacaag 120
gcctgttact agcactcaca tggaacaaat ggccgttgcc tgagtcttgg cagcgagaga 180
tcactaactg ctaagcaggt gctt 204

<210> SEQ ID NO 428
<211> LENGTH: 204
<212> TYPE: DNA
<213> ORGANISM: Artificial Sequence
<220> FEATURE:
<223> OTHER INFORMATION: Synthetic: SOCS2 miRNA at P3

<400> SEQUENCE: 428
tgtcacctgc actaactgct aactggaggc ttgctgaagg ctgtatgctg atatgataga 60
gtccaatctg agttttggcc actgactgac tcagattgct ctatcatatc aggacacaag 120
gcctgttact agcactcaca tggaacaaat ggccgtgtta attgtccatg tagcgaggca 180
tccttatggc gtgggcaggt gtcc 204

<210> SEQ ID NO 429
<211> LENGTH: 200
<212> TYPE: DNA
<213> ORGANISM: Artificial Sequence
<220> FEATURE:
<223> OTHER INFORMATION: Synthetic: SOCS2 miRNA at P4

<400> SEQUENCE: 429
ccttcacctg ccttatggcg tggctggagg cttgctgaag gctgtatgct gttagtaggt 60
agtctgaatg cggttttggc cactgactga ccgcattcac tacctactaa caggacacaa 120
ggcctgttac tagcactcac atggaacaaa tggccggtgt ccgttatcgg ggaagaaggt 180
cgcgcacata gcaggtgtcc 200

<210> SEQ ID NO 430
<211> LENGTH: 223
<212> TYPE: DNA
<213> ORGANISM: Artificial Sequence
<220> FEATURE:
<223> OTHER INFORMATION: Synthetic: TIEG1 miRNA at P1

<400> SEQUENCE: 430
cggcacctgc gctgccgttg gatcggggat gaaagctggc gctggaggct tgctgaaggc 60
tgtatgctga tttagcttgc tcacttccat gttttggcca ctgactgaca tggaagtgca 120
agctaaatca ggacacaagg cctgttacta gcactcacat ggaacaaatg gcccacattg 180
gtgccggatg aagctcttat gttgcgtccc atcgcaggtg cct 223

<210> SEQ ID NO 431
<211> LENGTH: 204
<212> TYPE: DNA
<213> ORGANISM: Artificial Sequence
<220> FEATURE:
<223> OTHER INFORMATION: Synthetic: TIEG1 miRNA at P2

<400> SEQUENCE: 431
cctcacctgc ttgcgtccca ttctggaggc ttgctgaagg ctgtatgctg atttgacact 60
tgagagggtt cgttttggcc actgactgac gaaccctcaa gtgtcaaatc aggacacaag 120
gcctgttact agcactcaca tggaacaaat ggccgttgcc tgagtcttgg cagcgagaga 180
tcactaactg ctaagcaggt gctt 204

<210> SEQ ID NO 432
<211> LENGTH: 204
<212> TYPE: DNA
<213> ORGANISM: Artificial Sequence
<220> FEATURE:
<223> OTHER INFORMATION: Synthetic: TIEG1 miRNA at P3

<400> SEQUENCE: 432
tgtcacctgc actaactgct aactggaggc ttgctgaagg ctgtatgctg aaatcagata 60
ctggtgtaac agttttggcc actgactgac tgttacacgt atctgatttc aggacacaag 120
gcctgttact agcactcaca tggaacaaat ggccgtgtta attgtccatg tagcgaggca 180
tccttatggc gtgggcaggt gtcc 204

<210> SEQ ID NO 433
<211> LENGTH: 200
<212> TYPE: DNA
<213> ORGANISM: Artificial Sequence
<220> FEATURE:
<223> OTHER INFORMATION: Synthetic: TIEG1 miRNA at P4

<400> SEQUENCE: 433
ccttcacctg ccttatggcg tggctggagg cttgctgaag gctgtatgct gtttctctca 60
catttggatc tggttttggc cactgactga ccagatccat gtgagagaaa caggacacaa 120
ggcctgttac tagcactcac atggaacaaa tggccggtgt ccgttatcgg ggaagaaggt 180
cgcgcacata gcaggtgtcc 200

<210> SEQ ID NO 434
<211> LENGTH: 223
<212> TYPE: DNA
<213> ORGANISM: Artificial Sequence
<220> FEATURE:
<223> OTHER INFORMATION: Synthetic: JunB miRNA at P1

<400> SEQUENCE: 434
cggcacctgc gctgccgttg gatcggggat gaaagctggc gctggaggct tgctgaaggc 60
tgtatgctgg tttcaggagt ttgtagtcgt gttttggcca ctgactgaca cgactacact 120
cctgaaacca ggacacaagg cctgttacta gcactcacat ggaacaaatg gcccacattg 180
gtgccggatg aagctcttat gttgcgtccc atcgcaggtg cct 223

<210> SEQ ID NO 435
<211> LENGTH: 204
<212> TYPE: DNA
<213> ORGANISM: Artificial Sequence
<220> FEATURE:
<223> OTHER INFORMATION: Synthetic: JunB miRNA at P2

<400> SEQUENCE: 435
cctcacctgc ttgcgtccca ttctggaggc ttgctgaagg ctgtatgctg atatgaatcg 60
agtctgtttc cgttttggcc actgactgac ggaaacagtc gattcatatc aggacacaag 120
gcctgttact agcactcaca tggaacaaat ggccgttgcc tgagtcttgg cagcgagaga 180
tcactaactg ctaagcaggt gctt 204

<210> SEQ ID NO 436
<211> LENGTH: 204
<212> TYPE: DNA
<213> ORGANISM: Artificial Sequence
<220> FEATURE:
<223> OTHER INFORMATION: Synthetic: JunB miRNA at P3

<400> SEQUENCE: 436
tgtcacctgc actaactgct aactggaggc ttgctgaagg ctgtatgctg taaacgtcga 60
ggtggaagga cgttttggcc actgactgac gtccttccct cgacgtttac aggacacaag 120
gcctgttact agcactcaca tggaacaaat ggccgtgtta attgtccatg tagcgaggca 180
tccttatggc gtgggcaggt gtcc 204

<210> SEQ ID NO 437
<211> LENGTH: 200
<212> TYPE: DNA
<213> ORGANISM: Artificial Sequence
<220> FEATURE:
<223> OTHER INFORMATION: Synthetic: JunB miRNA at P4

<400> SEQUENCE: 437
ccttcacctg ccttatggcg tggctggagg cttgctgaag gctgtatgct gttgcgctcc 60
actttgatgc gcgttttggc cactgactga cgcgcatcag tggagcgcaa caggacacaa 120
ggcctgttac tagcactcac atggaacaaa tggccggtgt ccgttatcgg ggaagaaggt 180
cgcgcacata gcaggtgtcc 200

<210> SEQ ID NO 438
<211> LENGTH: 223
<212> TYPE: DNA
<213> ORGANISM: Artificial Sequence
<220> FEATURE:
<223> OTHER INFORMATION: Synthetic: Cbx3 miRNA at P1

<400> SEQUENCE: 438
cggcacctgc gctgccgttg gatcggggat gaaagctggc gctggaggct tgctgaaggc 60
tgtatgctgt aatgactatg gacatttccc gttttggcca ctgactgacg ggaaatgcat 120
agtcattaca ggacacaagg cctgttacta gcactcacat ggaacaaatg gcccacattg 180
gtgccggatg aagctcttat gttgcgtccc atcgcaggtg cct 223

<210> SEQ ID NO 439
<211> LENGTH: 204
<212> TYPE: DNA
<213> ORGANISM: Artificial Sequence
<220> FEATURE:
<223> OTHER INFORMATION: Synthetic: Cbx3 miRNA at P2

<400> SEQUENCE: 439
cctcacctgc ttgcgtccca ttctggaggc ttgctgaagg ctgtatgctg ataatccaat 60
gagtgtgggc agttttggcc actgactgac tgcccacaca ttggattatc aggacacaag 120
gcctgttact agcactcaca tggaacaaat ggccgttgcc tgagtcttgg cagcgagaga 180
tcactaactg ctaagcaggt gctt 204

<210> SEQ ID NO 440
<211> LENGTH: 204
<212> TYPE: DNA
<213> ORGANISM: Artificial Sequence
<220> FEATURE:
<223> OTHER INFORMATION: Synthetic: Cbx3 miRNA at P3

<400> SEQUENCE: 440
tgtcacctgc actaactgct aactggaggc ttgctgaagg ctgtatgctg aaatcctctt 60
ggtttgtcag cgttttggcc actgactgac gctgacaaca agaggatttc aggacacaag 120
gcctgttact agcactcaca tggaacaaat ggccgtgtta attgtccatg tagcgaggca 180
tccttatggc gtgggcaggt gtcc 204

<210> SEQ ID NO 441
<211> LENGTH: 200
<212> TYPE: DNA

<213> ORGANISM: Artificial Sequence
<220> FEATURE:
<223> OTHER INFORMATION: Synthetic: Cbx3 miRNA at P4

<400> SEQUENCE: 441
ccttcacctg ccttatggcg tggctggagg cttgctgaag gctgtatgct gttcatattt 60
gcctctttcg ccgttttggc cactgactga cggcgaaagg caaatatgaa caggacacaa 120
ggcctgttac tagcactcac atggaacaaa tggccggtgt ccgttatcgg ggaagaaggt 180
cgcgcacata gcaggtgtcc 200

<210> SEQ ID NO 442
<211> LENGTH: 223
<212> TYPE: DNA
<213> ORGANISM: Artificial Sequence
<220> FEATURE:
<223> OTHER INFORMATION: Synthetic: Tet2 miRNA at P1

<400> SEQUENCE: 442
cggcacctgc gctgccgttg gatcggggat gaaagctggc gctggaggct tgctgaaggc 60
tgtatgctga aataacgact tggcgtgaaa gttttggcca ctgactgact ttcacgcagt 120
cgttatttca ggacacaagg cctgttacta gcactcacat ggaacaaatg gcccacattg 180
gtgccggatg aagctcttat gttgcgtccc atcgcaggtg cct 223

<210> SEQ ID NO 443
<211> LENGTH: 204
<212> TYPE: DNA
<213> ORGANISM: Artificial Sequence
<220> FEATURE:
<223> OTHER INFORMATION: Synthetic: Tet2 miRNA at P2

<400> SEQUENCE: 443
cctcacctgc ttgcgtccca ttctggaggc ttgctgaagg ctgtatgctg tttcatggtc 60
tgactataag ggttttggcc actgactgac ccttatagag accatgaaac aggacacaag 120
gcctgttact agcactcaca tggaacaaat ggccgttgcc tgagtcttgg cagcgagaga 180
tcactaactg ctaagcaggt gctt 204

<210> SEQ ID NO 444
<211> LENGTH: 204
<212> TYPE: DNA
<213> ORGANISM: Artificial Sequence
<220> FEATURE:
<223> OTHER INFORMATION: Synthetic: Tet2 miRNA at P3

<400> SEQUENCE: 444
tgtcacctgc actaactgct aactggaggc ttgctgaagg ctgtatgctg ataccctcta 60
ctttcttgtg tgttttggcc actgactgac acacaagagt agagggtatc aggacacaag 120
gcctgttact agcactcaca tggaacaaat ggccgtgtta attgtccatg tagcgaggca 180
tccttatggc gtgggcaggt gtcc 204

<210> SEQ ID NO 445
<211> LENGTH: 200
<212> TYPE: DNA
<213> ORGANISM: Artificial Sequence
<220> FEATURE:
<223> OTHER INFORMATION: Synthetic: Tet2 miRNA at P4

<400> SEQUENCE: 445
ccttcacctg ccttatggcg tggctggagg cttgctgaag gctgtatgct gttgtcctgt 60
agctctccac tggttttggc cactgactga ccagtggagc tacaggacaa caggacacaa 120
ggcctgttac tagcactcac atggaacaaa tggccggtgt ccgttatcgg ggaagaaggt 180
cgcgcacata gcaggtgtcc 200

<210> SEQ ID NO 446
<211> LENGTH: 223
<212> TYPE: DNA
<213> ORGANISM: Artificial Sequence
<220> FEATURE:
<223> OTHER INFORMATION: Synthetic: HK2 miRNA at P1

<400> SEQUENCE: 446
cggcacctgc gctgccgttg gatcggggat gaaagctggc gctggaggct tgctgaaggc 60
tgtatgctga atactactga ctgccctaag gttttggcca ctgactgacc ttagggctca 120
gtagtattca ggacacaagg cctgttacta gcactcacat ggaacaaatg gcccacattg 180
gtgccggatg aagctcttat gttgcgtccc atcgcaggtg cct 223

<210> SEQ ID NO 447
<211> LENGTH: 204
<212> TYPE: DNA
<213> ORGANISM: Artificial Sequence
<220> FEATURE:
<223> OTHER INFORMATION: Synthetic: HK2 miRNA at P2

<400> SEQUENCE: 447
cctcacctgc ttgcgtccca ttctggaggc ttgctgaagg ctgtatgctg aaatcgatga 60
gaatgttacg ggttttggcc actgactgac ccgtaacact catcgatttc aggacacaag 120
gcctgttact agcactcaca tggaacaaat ggccgttgcc tgagtcttgg cagcgagaga 180
tcactaactg ctaagcaggt gctt 204

<210> SEQ ID NO 448
<211> LENGTH: 204
<212> TYPE: DNA
<213> ORGANISM: Artificial Sequence
<220> FEATURE:
<223> OTHER INFORMATION: Synthetic: HK2 miRNA at P3

<400> SEQUENCE: 448
tgtcacctgc actaactgct aactggaggc ttgctgaagg ctgtatgctg caatgtcgat 60
atcaaagtcc cgttttggcc actgactgac gggactttta tcgacattgc aggacacaag 120
gcctgttact agcactcaca tggaacaaat ggccgtgtta attgtccatg tagcgaggca 180
tccttatggc gtgggcaggt gtcc 204

<210> SEQ ID NO 449
<211> LENGTH: 200
<212> TYPE: DNA
<213> ORGANISM: Artificial Sequence
<220> FEATURE:
<223> OTHER INFORMATION: Synthetic: HK2 miRNA at P4

<400> SEQUENCE: 449
ccttcacctg ccttatggcg tggctggagg cttgctgaag gctgtatgct gttatccatg 60
aagttagcca gggttttggc cactgactga ccctggctat tcatggataa caggacacaa 120
ggcctgttac tagcactcac atggaacaaa tggccggtgt ccgttatcgg ggaagaaggt 180
cgcgcacata gcaggtgtcc 200

<210> SEQ ID NO 450
<211> LENGTH: 9
<212> TYPE: DNA
<213> ORGANISM: Artificial Sequence
<220> FEATURE:
<223> OTHER INFORMATION: Synthetic: Kozak-typesequence

<400> SEQUENCE: 450 gccgccacc 9

<210> SEQ ID NO 451
<211> LENGTH: 9
<212> TYPE: DNA
<213> ORGANISM: Artificial Sequence
<220> FEATURE:
<223> OTHER INFORMATION: Synthetic: triple stopsequence

<400> SEQUENCE: 451 taatagtga 9

<210> SEQ ID NO 452
<211> LENGTH: 191
<212> TYPE: DNA
<213> ORGANISM: Artificial Sequence
<220> FEATURE:
<223> OTHER INFORMATION: Synthetic: WPRE

<400> SEQUENCE: 452
gtcctttcca tggctgctcg cctgtgttgc cacctggatt ctgcgcggga cgtccttctg 60
ctacgtccct tcggccctca atccagcgga ccttccttcc cgcggcctgc tgccggctct 120
gcggcctctt ccgcgtcttc gccttcgccc tcagacgagt cggatctccc tttgggccgc 180
ctccccgcct g 191

<210> SEQ ID NO 453
<211> LENGTH: 654
<212> TYPE: PRT
<213> ORGANISM: Artificial Sequence
<220> FEATURE:
<223> OTHER INFORMATION: Synthetic: MuLVSUx

<400> SEQUENCE: 453

Met Ala Arg Ser Thr Leu Ser Lys Pro Pro Gln Asp Lys Ile Asn Pro
1 5 10 15

Trp Lys Pro Leu Ile Val Met Gly Val Leu Leu Gly Val Gly Met Ala
20 25 30

Glu Ser Pro His Gln Val Phe Asn Val Thr Trp Arg Val Thr Asn Leu
35 40 45

Met Thr Gly Arg Thr Ala Asn Ala Thr Ser Leu Leu Gly Thr Val Gln
50 55 60

Asp Ala Phe Pro Lys Leu Tyr Phe Asp Leu Cys Asp Leu Val Gly Glu
65 70 75 80

Glu Trp Asp Pro Ser Asp Gln Glu Pro Tyr Val Gly Tyr Gly Cys Lys
85 90 95

Tyr Pro Ala Gly Arg Gln Arg Thr Arg Thr Phe Asp Phe Tyr Val Cys
100 105 110

Pro Gly His Thr Val Lys Ser Gly Cys Gly Gly Pro Gly Glu Gly Tyr
115 120 125

Cys Gly Lys Trp Gly Cys Glu Thr Thr Gly Gln Ala Tyr Trp Lys Pro
130 135 140

-continued

```
Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
    370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445

Gln Leu Glu Gln Arg Thr Ile Glu Gly Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
```

```
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650


<210> SEQ ID NO 454
<211> LENGTH: 905
<212> TYPE: PRT
<213> ORGANISM: Artificial Sequence
<220> FEATURE:
<223> OTHER INFORMATION: Synthetic: UMuLVSUx

<400> SEQUENCE: 454

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Asp Ile
            20                  25                  30

Gln Met Thr Gln Ser Pro Ser Ser Leu Ser Ala Ser Val Gly Asp Arg
        35                  40                  45

Val Thr Ile Thr Cys Arg Ala Ser Gln Asp Ile Arg Asn Tyr Leu Asn
    50                  55                  60

Trp Tyr Gln Gln Lys Pro Gly Lys Ala Pro Lys Leu Leu Ile Tyr Tyr
65                  70                  75                  80

Thr Ser Arg Leu Glu Ser Gly Val Pro Ser Arg Phe Ser Gly Ser Gly
                85                  90                  95

Ser Gly Thr Asp Tyr Thr Leu Thr Ile Ser Ser Leu Gln Pro Glu Asp
            100                 105                 110

Phe Ala Thr Tyr Tyr Cys Gln Gln Gly Asn Thr Leu Pro Trp Thr Phe
        115                 120                 125

Gly Gln Gly Thr Lys Val Glu Ile Lys Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ser Phe Thr Gly Tyr Thr Met Asn Trp Val Arg Gln Ala
            180                 185                 190

Pro Gly Lys Gly Leu Glu Trp Val Ala Leu Ile Asn Pro Tyr Lys Gly
        195                 200                 205

Val Ser Thr Tyr Asn Gln Lys Phe Lys Asp Arg Phe Thr Ile Ser Val
    210                 215                 220

Asp Lys Ser Lys Asn Thr Ala Tyr Leu Gln Met Asn Ser Leu Arg Ala
225                 230                 235                 240

Glu Asp Thr Ala Val Tyr Tyr Cys Ala Arg Ser Gly Tyr Tyr Gly Asp
                245                 250                 255

Ser Asp Trp Tyr Phe Asp Val Trp Gly Gln Gly Thr Leu Val Thr Val
            260                 265                 270

Ser Ser Ala Ala Ala Ile Glu Gly Arg Met Ala Glu Ser Pro His Gln
```

275 280 285

Val Phe Asn Val Thr Trp Arg Val Thr Asn Leu Met Thr Gly Arg Thr
290 295 300

Ala Asn Ala Thr Ser Leu Leu Gly Thr Val Gln Asp Ala Phe Pro Lys
305 310 315 320

Leu Tyr Phe Asp Leu Cys Asp Leu Val Gly Glu Glu Trp Asp Pro Ser
325 330 335

Asp Gln Glu Pro Tyr Val Gly Tyr Gly Cys Lys Tyr Pro Ala Gly Arg
340 345 350

Gln Arg Thr Arg Thr Phe Asp Phe Tyr Val Cys Pro Gly His Thr Val
355 360 365

Lys Ser Gly Cys Gly Gly Pro Gly Glu Gly Tyr Cys Gly Lys Trp Gly
370 375 380

Cys Glu Thr Thr Gly Gln Ala Tyr Trp Lys Pro Thr Ser Ser Trp Asp
385 390 395 400

Leu Ile Ser Leu Lys Arg Gly Asn Thr Pro Trp Asp Thr Gly Cys Ser
405 410 415

Lys Val Ala Cys Gly Pro Cys Tyr Asp Leu Ser Lys Val Ser Asn Ser
420 425 430

Phe Gln Gly Ala Thr Arg Gly Gly Arg Cys Asn Pro Leu Val Leu Glu
435 440 445

Phe Thr Asp Ala Gly Lys Lys Ala Asn Trp Asp Gly Pro Lys Ser Trp
450 455 460

Gly Leu Arg Leu Tyr Arg Thr Gly Thr Asp Pro Ile Thr Met Phe Ser
465 470 475 480

Leu Thr Arg Gln Val Leu Asn Val Gly Pro Arg Val Pro Ile Gly Pro
485 490 495

Asn Pro Val Leu Pro Asp Gln Arg Leu Pro Ser Ser Pro Ile Glu Ile
500 505 510

Val Pro Ala Pro Gln Pro Pro Ser Pro Leu Asn Thr Ser Tyr Pro Pro
515 520 525

Ser Thr Thr Ser Thr Pro Ser Thr Ser Pro Thr Ser Pro Ser Val Pro
530 535 540

Gln Pro Pro Pro Gly Thr Gly Asp Arg Leu Leu Ala Leu Val Lys Gly
545 550 555 560

Ala Tyr Gln Ala Leu Asn Leu Thr Asn Pro Asp Lys Thr Gln Glu Cys
565 570 575

Trp Leu Cys Leu Val Ser Gly Pro Pro Tyr Tyr Glu Gly Val Ala Val
580 585 590

Val Gly Thr Tyr Thr Asn His Ser Thr Ala Pro Ala Asn Cys Thr Ala
595 600 605

Thr Ser Gln His Lys Leu Thr Leu Ser Glu Val Thr Gly Gln Gly Leu
610 615 620

Cys Met Gly Ala Val Pro Lys Thr His Gln Ala Leu Cys Asn Thr Thr
625 630 635 640

Gln Ser Ala Gly Ser Gly Ser Tyr Tyr Leu Ala Ala Pro Ala Gly Thr
645 650 655

Met Trp Ala Cys Ser Thr Gly Leu Thr Pro Cys Leu Ser Thr Thr Val
660 665 670

Leu Asn Leu Thr Thr Asp Tyr Cys Val Leu Val Glu Leu Trp Pro Arg
675 680 685

Val Ile Tyr His Ser Pro Asp Tyr Met Tyr Gly Gln Leu Glu Gln Arg
690 695 700

Thr Ile Glu Gly Arg Glu Pro Val Ser Leu Thr Leu Ala Leu Leu Leu
705 710 715 720

Gly Gly Leu Thr Met Gly Gly Ile Ala Ala Gly Ile Gly Thr Gly Thr
725 730 735

Thr Ala Leu Ile Lys Thr Gln Gln Phe Glu Gln Leu His Ala Ala Ile
740 745 750

Gln Thr Asp Leu Asn Glu Val Glu Lys Ser Ile Thr Asn Leu Glu Lys
755 760 765

Ser Leu Thr Ser Leu Ser Glu Val Val Leu Gln Asn Arg Arg Gly Leu
770 775 780

Asp Leu Leu Phe Leu Lys Glu Gly Gly Leu Cys Ala Ala Leu Lys Glu
785 790 795 800

Glu Cys Cys Phe Tyr Ala Asp His Thr Gly Leu Val Arg Asp Ser Met
805 810 815

Ala Lys Leu Arg Glu Arg Leu Asn Gln Arg Gln Lys Leu Phe Glu Thr
820 825 830

Gly Gln Gly Trp Phe Glu Gly Leu Phe Asn Arg Ser Pro Trp Phe Thr
835 840 845

Thr Leu Ile Ser Thr Ile Met Gly Pro Leu Ile Val Leu Leu Leu Ile
850 855 860

Leu Leu Phe Gly Pro Cys Ile Leu Asn Arg Leu Val Gln Phe Val Lys
865 870 875 880

Asp Arg Ile Ser Val Val Gln Ala Leu Val Leu Thr Gln Gln Tyr His
885 890 895

Gln Leu Lys Pro Ile Glu Tyr Glu Pro
900 905

<210> SEQ ID NO 455
<211> LENGTH: 770
<212> TYPE: PRT
<213> ORGANISM: Artificial Sequence
<220> FEATURE:
<223> OTHER INFORMATION: Synthetic: UCHT1-(G4S)3-VSVG

<400> SEQUENCE: 455

Met Lys Cys Leu Leu Tyr Leu Ala Phe Leu Phe Ile Gly Val Asn Cys
1 5 10 15

Asp Ile Gln Met Thr Gln Ser Pro Ser Ser Leu Ser Ala Ser Val Gly
20 25 30

Asp Arg Val Thr Ile Thr Cys Arg Ala Ser Gln Asp Ile Arg Asn Tyr
35 40 45

Leu Asn Trp Tyr Gln Gln Lys Pro Gly Lys Ala Pro Lys Leu Leu Ile
50 55 60

Tyr Tyr Thr Ser Arg Leu Glu Ser Gly Val Pro Ser Arg Phe Ser Gly
65 70 75 80

Ser Gly Ser Gly Thr Asp Tyr Thr Leu Thr Ile Ser Ser Leu Gln Pro
85 90 95

Glu Asp Phe Ala Thr Tyr Tyr Cys Gln Gln Gly Asn Thr Leu Pro Trp
100 105 110

Thr Phe Gly Gln Gly Thr Lys Val Glu Ile Lys Gly Gly Gly Gly Ser
115 120 125

Gly Gly Gly Gly Ser Gly Gly Gly Gly Ser Glu Val Gln Leu Val Glu
130 135 140

Ser Gly Gly Gly Leu Val Gln Pro Gly Gly Ser Leu Arg Leu Ser Cys
145 150 155 160

-continued

```
Ala Ala Ser Gly Tyr Ser Phe Thr Gly Tyr Thr Met Asn Trp Val Arg
                165                 170                 175

Gln Ala Pro Gly Lys Gly Leu Glu Trp Val Ala Leu Ile Asn Pro Tyr
            180                 185                 190

Lys Gly Val Ser Thr Tyr Asn Gln Lys Phe Lys Asp Arg Phe Thr Ile
        195                 200                 205

Ser Val Asp Lys Ser Lys Asn Thr Ala Tyr Leu Gln Met Asn Ser Leu
    210                 215                 220

Arg Ala Glu Asp Thr Ala Val Tyr Tyr Cys Ala Arg Ser Gly Tyr Tyr
225                 230                 235                 240

Gly Asp Ser Asp Trp Tyr Phe Asp Val Trp Gly Gln Gly Thr Leu Val
                245                 250                 255

Thr Val Ser Ser Gly Gly Gly Gly Ser Gly Gly Gly Gly Ser Gly Gly
            260                 265                 270

Gly Gly Ser Lys Phe Thr Ile Val Phe Pro His Asn Gln Lys Gly Asn
        275                 280                 285

Trp Lys Asn Val Pro Ser Asn Tyr His Tyr Cys Pro Ser Ser Ser Asp
    290                 295                 300

Leu Asn Trp His Asn Asp Leu Ile Gly Thr Ala Leu Gln Val Lys Met
305                 310                 315                 320

Pro Lys Ser His Lys Ala Ile Gln Ala Asp Gly Trp Met Cys His Ala
                325                 330                 335

Ser Lys Trp Val Thr Thr Cys Asp Phe Arg Trp Tyr Gly Pro Lys Tyr
            340                 345                 350

Ile Thr His Ser Ile Arg Ser Phe Thr Pro Ser Val Glu Gln Cys Lys
        355                 360                 365

Glu Ser Ile Glu Gln Thr Lys Gln Gly Thr Trp Leu Asn Pro Gly Phe
    370                 375                 380

Pro Pro Gln Ser Cys Gly Tyr Ala Thr Val Thr Asp Ala Glu Ala Val
385                 390                 395                 400

Ile Val Gln Val Thr Pro His His Val Leu Val Asp Glu Tyr Thr Gly
                405                 410                 415

Glu Trp Val Asp Ser Gln Phe Ile Asn Gly Lys Cys Ser Asn Tyr Ile
            420                 425                 430

Cys Pro Thr Val His Asn Ser Thr Thr Trp His Ser Asp Tyr Lys Val
        435                 440                 445

Lys Gly Leu Cys Asp Ser Asn Leu Ile Ser Met Asp Ile Thr Phe Phe
    450                 455                 460

Ser Glu Asp Gly Glu Leu Ser Ser Leu Gly Lys Glu Gly Thr Gly Phe
465                 470                 475                 480

Arg Ser Asn Tyr Phe Ala Tyr Glu Thr Gly Gly Lys Ala Cys Lys Met
                485                 490                 495

Gln Tyr Cys Lys His Trp Gly Val Arg Leu Pro Ser Gly Val Trp Phe
            500                 505                 510

Glu Met Ala Asp Lys Asp Leu Phe Ala Ala Ala Arg Phe Pro Glu Cys
        515                 520                 525

Pro Glu Gly Ser Ser Ile Ser Ala Pro Ser Gln Thr Ser Val Asp Val
    530                 535                 540

Ser Leu Ile Gln Asp Val Glu Arg Ile Leu Asp Tyr Ser Leu Cys Gln
545                 550                 555                 560

Glu Thr Trp Ser Lys Ile Arg Ala Gly Leu Pro Ile Ser Pro Val Asp
                565                 570                 575
```

```
Leu Ser Tyr Leu Ala Pro Lys Asn Pro Gly Thr Gly Pro Ala Phe Thr
            580                 585                 590

Ile Ile Asn Gly Thr Leu Lys Tyr Phe Glu Thr Arg Tyr Ile Arg Val
        595                 600                 605

Asp Ile Ala Ala Pro Ile Leu Ser Arg Met Val Gly Met Ile Ser Gly
    610                 615                 620

Thr Thr Thr Glu Arg Glu Leu Trp Asp Asp Trp Ala Pro Tyr Glu Asp
625                 630                 635                 640

Val Glu Ile Gly Pro Asn Gly Val Leu Arg Thr Ser Ser Gly Tyr Lys
                645                 650                 655

Phe Pro Leu Tyr Met Ile Gly His Gly Met Leu Asp Ser Asp Leu His
            660                 665                 670

Leu Ser Ser Lys Ala Gln Val Phe Glu His Pro His Ile Gln Asp Ala
        675                 680                 685

Ala Ser Gln Leu Pro Asp Asp Glu Ser Leu Phe Phe Gly Asp Thr Gly
    690                 695                 700

Leu Ser Lys Asn Pro Ile Glu Leu Val Glu Gly Trp Phe Ser Ser Trp
705                 710                 715                 720

Lys Ser Ser Ile Ala Ser Phe Phe Phe Ile Ile Gly Leu Ile Ile Gly
                725                 730                 735

Leu Phe Leu Val Leu Arg Val Gly Ile His Leu Cys Ile Lys Leu Lys
            740                 745                 750

His Thr Lys Lys Arg Gln Ile Tyr Thr Asp Ile Glu Met Asn Arg Leu
        755                 760                 765

Gly Lys
    770
```

<210> SEQ ID NO 456
<211> LENGTH: 767
<212> TYPE: PRT
<213> ORGANISM: Artificial Sequence
<220> FEATURE:
<223> OTHER INFORMATION: Synthetic: UCHT1-hinge-VSVG

<400> SEQUENCE: 456

```
Met Lys Cys Leu Leu Tyr Leu Ala Phe Leu Phe Ile Gly Val Asn Cys
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Ile Arg Asn Tyr
        35                  40                  45

Leu Asn Trp Tyr Gln Gln Lys Pro Gly Lys Ala Pro Lys Leu Leu Ile
    50                  55                  60

Tyr Tyr Thr Ser Arg Leu Glu Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Phe Ala Thr Tyr Tyr Cys Gln Gln Gly Asn Thr Leu Pro Trp
            100                 105                 110

Thr Phe Gly Gln Gly Thr Lys Val Glu Ile Lys Gly Gly Gly Gly Ser
        115                 120                 125

Gly Gly Gly Gly Ser Gly Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160
```

```
Ala Ala Ser Gly Tyr Ser Phe Thr Gly Tyr Thr Met Asn Trp Val Arg
                165                 170                 175

Gln Ala Pro Gly Lys Gly Leu Glu Trp Val Ala Leu Ile Asn Pro Tyr
            180                 185                 190

Lys Gly Val Ser Thr Tyr Asn Gln Lys Phe Lys Asp Arg Phe Thr Ile
        195                 200                 205

Ser Val Asp Lys Ser Lys Asn Thr Ala Tyr Leu Gln Met Asn Ser Leu
    210                 215                 220

Arg Ala Glu Asp Thr Ala Val Tyr Tyr Cys Ala Arg Ser Gly Tyr Tyr
225                 230                 235                 240

Gly Asp Ser Asp Trp Tyr Phe Asp Val Trp Gly Gln Gly Thr Leu Val
                245                 250                 255

Thr Val Ser Ser Glu Pro Lys Ser Cys Asp Lys Thr His Thr Cys Pro
            260                 265                 270

Lys Phe Thr Ile Val Phe Pro His Asn Gln Lys Gly Asn Trp Lys Asn
        275                 280                 285

Val Pro Ser Asn Tyr His Tyr Cys Pro Ser Ser Ser Asp Leu Asn Trp
    290                 295                 300

His Asn Asp Leu Ile Gly Thr Ala Leu Gln Val Lys Met Pro Lys Ser
305                 310                 315                 320

His Lys Ala Ile Gln Ala Asp Gly Trp Met Cys His Ala Ser Lys Trp
                325                 330                 335

Val Thr Thr Cys Asp Phe Arg Trp Tyr Gly Pro Lys Tyr Ile Thr His
            340                 345                 350

Ser Ile Arg Ser Phe Thr Pro Ser Val Glu Gln Cys Lys Glu Ser Ile
        355                 360                 365

Glu Gln Thr Lys Gln Gly Thr Trp Leu Asn Pro Gly Phe Pro Pro Gln
    370                 375                 380

Ser Cys Gly Tyr Ala Thr Val Thr Asp Ala Glu Ala Val Ile Val Gln
385                 390                 395                 400

Val Thr Pro His His Val Leu Val Asp Glu Tyr Thr Gly Glu Trp Val
                405                 410                 415

Asp Ser Gln Phe Ile Asn Gly Lys Cys Ser Asn Tyr Ile Cys Pro Thr
            420                 425                 430

Val His Asn Ser Thr Thr Trp His Ser Asp Tyr Lys Val Lys Gly Leu
        435                 440                 445

Cys Asp Ser Asn Leu Ile Ser Met Asp Ile Thr Phe Phe Ser Glu Asp
    450                 455                 460

Gly Glu Leu Ser Ser Leu Gly Lys Glu Gly Thr Gly Phe Arg Ser Asn
465                 470                 475                 480

Tyr Phe Ala Tyr Glu Thr Gly Gly Lys Ala Cys Lys Met Gln Tyr Cys
                485                 490                 495

Lys His Trp Gly Val Arg Leu Pro Ser Gly Val Trp Phe Glu Met Ala
            500                 505                 510

Asp Lys Asp Leu Phe Ala Ala Ala Arg Phe Pro Glu Cys Pro Glu Gly
        515                 520                 525

Ser Ser Ile Ser Ala Pro Ser Gln Thr Ser Val Asp Val Ser Leu Ile
    530                 535                 540

Gln Asp Val Glu Arg Ile Leu Asp Tyr Ser Leu Cys Gln Glu Thr Trp
545                 550                 555                 560

Ser Lys Ile Arg Ala Gly Leu Pro Ile Ser Pro Val Asp Leu Ser Tyr
                565                 570                 575

Leu Ala Pro Lys Asn Pro Gly Thr Gly Pro Ala Phe Thr Ile Ile Asn
```

```
            580                 585                 590

Gly Thr Leu Lys Tyr Phe Glu Thr Arg Tyr Ile Arg Val Asp Ile Ala
        595                 600                 605

Ala Pro Ile Leu Ser Arg Met Val Gly Met Ile Ser Gly Thr Thr Thr
    610                 615                 620

Glu Arg Glu Leu Trp Asp Asp Trp Ala Pro Tyr Glu Asp Val Glu Ile
625                 630                 635                 640

Gly Pro Asn Gly Val Leu Arg Thr Ser Ser Gly Tyr Lys Phe Pro Leu
                645                 650                 655

Tyr Met Ile Gly His Gly Met Leu Asp Ser Asp Leu His Leu Ser Ser
            660                 665                 670

Lys Ala Gln Val Phe Glu His Pro His Ile Gln Asp Ala Ala Ser Gln
        675                 680                 685

Leu Pro Asp Asp Glu Ser Leu Phe Phe Gly Asp Thr Gly Leu Ser Lys
    690                 695                 700

Asn Pro Ile Glu Leu Val Glu Gly Trp Phe Ser Ser Trp Lys Ser Ser
705                 710                 715                 720

Ile Ala Ser Phe Phe Phe Ile Ile Gly Leu Ile Ile Gly Leu Phe Leu
                725                 730                 735

Val Leu Arg Val Gly Ile His Leu Cys Ile Lys Leu Lys His Thr Lys
            740                 745                 750

Lys Arg Gln Ile Tyr Thr Asp Ile Glu Met Asn Arg Leu Gly Lys
        755                 760                 765
```

<210> SEQ ID NO 457
<211> LENGTH: 1823
<212> TYPE: DNA
<213> ORGANISM: Artificial Sequence
<220> FEATURE:
<223> OTHER INFORMATION: Synthetic: synthetic EF-1a promoter with miRs

<400> SEQUENCE: 457

```
ggctccggtg cccgtcagtg ggcagagcgc acatcgccca cagtccccga gaagttgggg      60

ggaggggtcg gcaattgaac cggtgcctag agaaggtggc gcggggtaaa ctgggaaagt     120

gatgtcgtgt actggctccg cctttttccc gagggtgggg gagaaccgta tataagtgca     180

gtagtcgccg tgaacgttct ttttcgcaac gggtttgccg ccagaacaca ggtaagtgcc     240

gtgtgtggtt cccgcgggcc tggcctcttt acgggttatg gcccttgcgt gccttgaatt     300

acttccacct ggctgcagta cgtgattctt gatcccgagc ttcgggttgg aagtgggtgg     360

gagagttcga ggccttgcgc ttaaggagcc ccttcgcctc gtgcttgagt tgaggcctgg     420

cctgggcgct ggggccgccg cgtgcgaatc tggtggcacc ttcgcgcctg tctcgctgct     480

ttcgataagt ctctagccat ttaaaatttt tgatgacctg ctgcgacgct ttttttctgg     540

caagatagtc ttgtaaatgc gggccaagat ctgcacactg gtatttcggt ttttggggcc     600

gcgggcggcg acggggcccg tgcgtcccag cgcacatgtt cggcgaggcg gggcctgcga     660

gcgcggccac cgagaatcgg acgggggtag tctcaagctg gccggcctgc tctggtgcct     720

ggcctcgcgc cgccgtgtat cgccccgccc tgggcggcaa ggctggcccg gtcggcacca     780

gttgcgtgag cggaaagatg gccgcttccc ggccctgctg cagggagctc aaaatggagg     840

acgcggcgct cgggagagcg ggcgggtgag tcacccacac aaaggaaaag ggcctttccg     900

tcctcagccg tcgcttcatg tgactccact gagtaccggg cgccgtccag gcacctcgat     960

tagttcctgg aggcttgctg aaggctgtat gctgacatgg tacagttcaa tggtggtttt    1020
```

```
ggccactgac tgaccaccat tgctgtacca tgtcaggaca caaggcctgt tactagcact   1080

cacatggaac aaatggccca cattggtgcc ggatgaagct cttatgttgc acggtcatct   1140

ggaggcttgc tgaaggctgt atgctgtcag tctgttcatc ttctggcgtt ttggccactg   1200

actgacgcca gaaggaacag actgacagga cacaaggcct gttactagca ctcacatgga   1260

acaaatggcc gttgccggag tcttggcagc gagagatcac tatcaactaa ctggaggctt   1320

gctgaaggct gtatgctgaa gcgtgaagtg aatcaacggg ttttggccac tgactgaccc   1380

gttgatactt cacgcttcag gacacaaggc ctgttactag cactcacatg gaacaaatgg   1440

ccgtgttaat tgtccatgta gcgaggcatc cttatggcgt ggctggaggc ttgctgaagg   1500

ctgtatgctg gcagtatcct agtacattga cgttttggcc actgactgac gtcaatgtta   1560

ggatactgcc aggacacaag gcctgttact agcactcaca tggaacaaat ggccgctttt   1620

ggagtacgtc gtctttaggt tggggggagg ggttttatgc gatggagttt ccccacactg   1680

agtgggtgga gactgaagtt aggccagctt ggcacttgat gtaattctcc ttggaatttg   1740

ccctttttga gtttggatct tggttcattc tcaagcctca gacagtggtt caaagttttt   1800

ttcttccatt tcaggtgtcg tga                                            1823
```

<210> SEQ ID NO 458
<211> LENGTH: 152
<212> TYPE: PRT
<213> ORGANISM: Artificial sequence
<220> FEATURE:
<223> OTHER INFORMATION: synthetic polypeptide IL7

<400> SEQUENCE: 458

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 459
<211> LENGTH: 458
<212> TYPE: PRT
<213> ORGANISM: Homo sapiens

<400> SEQUENCE: 459

```
Met Thr Ile Leu Gly Thr Thr Phe Gly Met Val Phe Ser Leu Leu Gln
1               5                   10                  15
```

-continued

```
Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
```

```
        435                 440                 445

Tyr Val Thr Met Ser Ser Phe Tyr Gln Asn
    450                 455


<210> SEQ ID NO 460
<211> LENGTH: 244
<212> TYPE: PRT
<213> ORGANISM: Artificial sequence
<220> FEATURE:
<223> OTHER INFORMATION: synthetic polypeptide IL7RA ECD and TM

<400> SEQUENCE: 460

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Ile Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Val Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp Pro Ile Leu Leu Thr
    210                 215                 220

Ile Ser Ile Leu Ser Phe Phe Ser Val Ala Leu Leu Val Ile Leu Ala
225                 230                 235                 240

Cys Val Leu Trp


<210> SEQ ID NO 461
<211> LENGTH: 286
<212> TYPE: PRT
<213> ORGANISM: Artificial sequence
<220> FEATURE:
<223> OTHER INFORMATION: synthetic polypeptide IL2RB ICD

<400> SEQUENCE: 461

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
```

```
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Leu Gln Gln Asp Lys Val Pro Glu
65                  70                  75                  80

Pro Ala Ser Leu Ser Ser Asn His Ser Leu Thr Ser Cys Phe Thr Asn
                85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
        115                 120                 125

Glu Gly Val Ala Gly Ala Pro Thr Gly Ser Ser Pro Gln Pro Leu Gln
    130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
        195                 200                 205

Pro Pro Thr Pro Gly Val Pro Asp Leu Val Asp Phe Gln Pro Pro Pro
    210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
            260                 265                 270

Ser Leu Gln Glu Leu Gln Gly Gln Asp Pro Thr His Leu Val
        275                 280                 285


<210> SEQ ID NO 462
<211> LENGTH: 532
<212> TYPE: PRT
<213> ORGANISM: Artificial sequence
<220> FEATURE:
<223> OTHER INFORMATION: Synthetic DAFss-IL7-DAF fusion

<400> SEQUENCE: 462

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Val
            20                  25                  30

Trp Gly Asp Cys Asp Ile Glu Gly Lys Asp Gly Lys Gln Tyr Glu Ser
        35                  40                  45

Val Leu Met Val Ser Ile Asp Gln Leu Leu Asp Ser Met Lys Glu Ile
    50                  55                  60

Gly Ser Asn Cys Leu Asn Asn Glu Phe Asn Phe Phe Lys Arg His Ile
65                  70                  75                  80

Cys Asp Ala Asn Lys Glu Gly Met Phe Leu Phe Arg Ala Ala Arg Lys
                85                  90                  95

Leu Arg Gln Phe Leu Lys Met Asn Ser Thr Gly Asp Phe Asp Leu His
            100                 105                 110

Leu Leu Lys Val Ser Glu Gly Thr Thr Ile Leu Leu Asn Cys Thr Gly
```

```
        115                 120                 125

Gln Val Lys Gly Arg Lys Pro Ala Ala Leu Gly Glu Ala Gln Pro Thr
    130                 135                 140

Lys Ser Leu Glu Glu Asn Lys Ser Leu Lys Glu Gln Lys Lys Leu Asn
145                 150                 155                 160

Asp Leu Cys Phe Leu Lys Arg Leu Leu Gln Glu Ile Lys Thr Cys Trp
                165                 170                 175

Asn Lys Ile Leu Met Gly Thr Lys Glu His Cys Gly Leu Pro Pro Asp
            180                 185                 190

Val Pro Asn Ala Gln Pro Ala Leu Glu Gly Arg Thr Ser Phe Pro Glu
        195                 200                 205

Asp Thr Val Ile Thr Tyr Lys Cys Glu Glu Ser Phe Val Lys Ile Pro
    210                 215                 220

Gly Glu Lys Asp Ser Val Ile Cys Leu Lys Gly Ser Gln Trp Ser Asp
225                 230                 235                 240

Ile Glu Glu Phe Cys Asn Arg Ser Cys Glu Val Pro Thr Arg Leu Asn
                245                 250                 255

Ser Ala Ser Leu Lys Gln Pro Tyr Ile Thr Gln Asn Tyr Phe Pro Val
            260                 265                 270

Gly Thr Val Val Glu Tyr Glu Cys Arg Pro Gly Tyr Arg Arg Glu Pro
        275                 280                 285

Ser Leu Ser Pro Lys Leu Thr Cys Leu Gln Asn Leu Lys Trp Ser Thr
    290                 295                 300

Ala Val Glu Phe Cys Lys Lys Lys Ser Cys Pro Asn Pro Gly Glu Ile
305                 310                 315                 320

Arg Asn Gly Gln Ile Asp Val Pro Gly Gly Ile Leu Phe Gly Ala Thr
                325                 330                 335

Ile Ser Phe Ser Cys Asn Thr Gly Tyr Lys Leu Phe Gly Ser Thr Ser
            340                 345                 350

Ser Phe Cys Leu Ile Ser Gly Ser Ser Val Gln Trp Ser Asp Pro Leu
        355                 360                 365

Pro Glu Cys Arg Glu Ile Tyr Cys Pro Ala Pro Pro Gln Ile Asp Asn
    370                 375                 380

Gly Ile Ile Gln Gly Glu Arg Asp His Tyr Gly Tyr Arg Gln Ser Val
385                 390                 395                 400

Thr Tyr Ala Cys Asn Lys Gly Phe Thr Met Ile Gly Glu His Ser Ile
                405                 410                 415

Tyr Cys Thr Val Asn Asn Asp Glu Gly Glu Trp Ser Gly Pro Pro Pro
            420                 425                 430

Glu Cys Arg Gly Lys Ser Leu Thr Ser Lys Val Pro Pro Thr Val Gln
        435                 440                 445

Lys Pro Thr Thr Val Asn Val Pro Thr Thr Glu Val Ser Pro Thr Ser
    450                 455                 460

Gln Lys Thr Thr Thr Lys Thr Thr Thr Pro Asn Ala Gln Ala Thr Arg
465                 470                 475                 480

Ser Thr Pro Val Ser Arg Thr Thr Lys His Phe His Glu Thr Thr Pro
                485                 490                 495
```

-continued

```
Asn Lys Gly Ser Gly Thr Thr Ser Gly Thr Thr Arg Leu Leu Ser Gly
            500                 505                 510

His Thr Cys Phe Thr Leu Thr Gly Leu Leu Gly Thr Leu Val Thr Met
        515                 520                 525

Gly Leu Leu Thr
    530
```

METHODS AND COMPOSITIONS FOR GENETICALLY MODIFYING LYMPHOCYTES TO EXPRESS POLYPEPTIDES COMPRISING THE INTRACELLULAR DOMAIN OF MPL

CROSS-REFERENCE TO RELATED APPLICATIONS

This application is a continuation-in-part of International Application No. PCT/US2019/049259 filed Sep. 2, 2019, and U.S. application Ser. No. 16/490,201 filed Aug. 30, 2019; International Application No. PCT/US2019/049259 is a continuation-in-part of International Application No. PCT/US2018/051392 filed Sep. 17, 2018; and claims the benefit of U.S. Provisional Application No. 62/726,293, filed Sep. 2, 2018; U.S. Provisional Application No. 62/726,294, filed Sep. 2, 2018; U.S. Provisional Application No. 62/728,056 filed Sep. 6, 2018; U.S. Provisional Application No. 62/732,528, filed Sep. 17, 2018; U.S. Provisional Application No. 62/821,434, filed Mar. 20, 2019; and U.S. Provisional Application No. 62/894,853, filed Sep. 1, 2019; and International Application No. PCT/US2018/051392 is a continuation-in-part of International Application No. PCT/US2018/020818, filed Mar. 3, 2018; and claims the benefit of U.S. Provisional Application No. 62/560,176, filed Sep. 18, 2017; U.S. Provisional Application No. 62/564,253, filed Sep. 27, 2017; U.S. Provisional Application No. 62/564,991, filed Sep. 28, 2017; and U.S. Provisional Application No. 62/728,056, filed Sep. 6, 2018; International Application No. PCT/US2018/020818 is a continuation-in-part of International Application No. PCT/US2017/023112 filed Mar. 19, 2017; a continuation-in-part of International Application No. PCT/US2017/041277 filed Jul. 8, 2017; a continuation-in-part of U.S. application Ser. No. 15/462,855 filed Mar. 19, 2017, now U.S. Pat. No. 10,596,274; and a continuation-in-part of U.S. application Ser. No. 15/644,778 filed Jul. 8, 2017; and claims the benefit of U.S. Provisional Application No. 62/467,039 filed Mar. 3, 2017; U.S. Provisional Application No. 62/560,176 filed Sep. 18, 2017; U.S. Provisional Application No. 62/564,253 filed Sep. 27, 2017; and U.S. Provisional Application No. 62/564,991 filed Sep. 28, 2017; International Application No. PCT/US2017/023112 claims the benefit of U.S. Provisional Application No. 62/390,093, filed Mar. 19, 2016; U.S. Provisional Application No. 62/360,041, filed Jul. 8, 2016; and U.S. Provisional Application No. 62/467,039, filed Mar. 3, 2017; International Application No. PCT/US2017/041277 claims the benefit of International Application No. PCT/US2017/023112, filed Mar. 19, 2017; U.S. patent application Ser. No. 15/462,855, filed Mar. 19, 2017, now U.S. Pat. No. 10,596,274; U.S. Provisional Application No. 62/360,041, filed Jul. 8, 2016; and U.S. Provisional Application No. 62/467,039, filed Mar. 3, 2017; U.S. application Ser. No. 15/462,855 claims the benefit of U.S. Provisional Application No. 62/390,093, filed Mar. 19, 2016; U.S. Provisional Application No. 62/360,041, filed Jul. 8, 2016; and U.S. Provisional Application No. 62/467,039, filed Mar. 3, 2017; and U.S. application Ser. No. 15/644,778 is a continuation-in-part of International Application No. PCT/US2017/023112, filed Mar. 19, 2017; and a continuation-in-part of U.S. patent application Ser. No. 15/462,855, filed Mar. 19, 2017, now U.S. Pat. No. 10,596,274; and claims the benefit of U.S. Provisional Application No. 62/360,041, filed Jul. 8, 2016, U.S. Provisional Application No. 62/467,039, filed Mar. 3, 2017; and U.S. application Ser. No. 16/490,201 is a 35 U.S.C. § 371 of International Application No. PCT/US2018/020818 filed Mar. 3, 2018. These applications are incorporated by reference herein in their entireties.

SEQUENCE LISTING

This application hereby incorporates by reference the material of the electronic Sequencing Listing filed concurrently herewith. The materials in the electronic Sequence Listing is submitted as a text (.txt) file entitled "F1_001_US_05_Sequence_Listing_November_23_2021.txt" created on Nov. 23, 2021, which has a file size of 464 KB, and is herein incorporated by reference in its entirety.

FIELD OF INVENTION

This disclosure relates to the field of immunology, or more specifically, to the genetic modification of T lymphocytes or other immune cells, and methods of controlling proliferation of such cells.

BACKGROUND OF THE DISCLOSURE

Lymphocytes isolated from a subject (e.g. patient) can be activated in vitro and genetically modified to express synthetic proteins that enable redirected engagement with other cells and environments based upon the genetic programs incorporated. Examples of such synthetic proteins include recombinant T cell receptors (TCRs) and chimeric antigen receptors (CARs). One CAR that is currently used is a fusion of an extracellular recognition domain (e.g., an antigen-binding domain), a transmembrane domain, and one or more intracellular signaling domains encoded by a replication incompetent recombinant retrovirus.

While recombinant retroviruses have shown efficacy in infecting non-dividing cells, resting CD4 and CD8 lymphocytes are refractory to genetic transduction by these vectors. To overcome this difficulty, these cells are typically activated in vitro using stimulation reagents before genetic modification with the CAR gene vector can occur. Following stimulation and transduction, the genetically modified cells are expanded in vitro and subsequently reintroduced into a lymphodepleted patient. Upon antigen engagement in vivo, the intracellular signaling portion of the CAR can initiate an activation-related response in an immune cell and release of cytolytic molecules to induce target cell death.

Such current methods require extensive manipulation and manufacturing of proliferating T cells outside the body prior to their reinfusion into the patient, as well as lymphodepleting chemotherapy to free cytokines and deplete competing receptors to facilitate T cell engraftment. Such CAR therapies further cannot be controlled for propagation rate in vivo once introduced into the body, nor safely directed towards targets that are also expressed outside the tumor. As a result, CAR therapies today are typically infused from cells expanded ex vivo from 12 to 28 days using doses from $1\times10^5$ to $1\times10^8$ cells/kg and are directed towards targets, for example tumor targets, for which off tumor on target toxicity is generally acceptable. These relatively long ex vivo expansion times create issues of cell viability and sterility, as well as sample identity in addition to challenges of scalability. Thus, there are significant needs for a safer, more effective scalable T cell or NK cell therapy.

Since our understanding of processes that drive transduction, proliferation and survival of lymphocytes is central to various potential commercial uses that involve immunological processes, there is a need for improved methods and compositions for studying lymphocytes. For example, it would be helpful to identify methods and compositions that can be used to better characterize and understand how lymphocytes can be genetically modified and the factors that influence their survival and proliferation. Furthermore, it would be helpful to identify compositions that drive lymphocyte proliferation and survival. Such compositions could be used to study the regulation of such processes. In addition to methods and compositions for studying lymphocytes, there is a need for improved viral packaging cell lines and methods of making and using the same. For example, such cell lines and methods would be useful in analyzing different components of recombinant viruses, such as recombinant retroviral particles, and for methods that use packaging cells lines for the production of recombinant retroviral particles.

More recent methods have been developed that can be performed without pre-activation and ex vivo expansion. However, further reduction in the complexity and time required for such methods would be highly desirable, especially if such methods allow a subject to have their blood collected, for example within an infusion center, and then reintroduced into the subject that same day. Furthermore, simpler and quicker methods alone or methods that require fewer specialized instruments, could democratize these cell therapy processes, which are currently performed regularly only at highly specialized medical centers.

Some groups have attempted to simplify ex-vivo processing for cell therapy by eliminating ex-vivo transduction expansion, by infusion viral particles intravenously, to transduce cells in vivo. However, such methods require large quantities of vector and the methods have the risk of inactivation of the retroviral particles by clotting factors, and/or other enzymes present in vivo. Finally, such methods risk a high level of transduction of non-target cells/organs.

SUMMARY

Provided herein are methods, compositions, and kits that help overcome issues related to the effectiveness and safety of methods for transducing and/or genetically modifying lymphocytes such as T cells and/or NK cells. Certain embodiments of such methods are useful for performing adoptive cell therapy with these cells. Accordingly, in some aspects, provided herein are methods, compositions, and kits for genetically modifying lymphocytes, especially T cell and/or NK cells, and/or for regulating the activity of transduced and/or genetically modified T cells and/or NK cells. Such methods, compositions, and kits provide improved efficacy and safety over current technologies, especially with respect to T cells and/or NK cells that express recombinant T cell receptors (TCRs), chimeric antigen receptors (CARs), and in illustrative embodiments microenvironment restricted biologic ("MRB") CARs. Transduced and/or genetically modified T cells and/or NK cells that are produced by and/or used in methods provided herein, include functionality and combinations of functionality, in illustrative embodiments delivered from retroviral (e.g. lentiviral) genomes via retroviral (e.g. lentiviral) particles, that provide improved features for such cells and for methods that utilize such cells, such as research methods, commercial production methods, and adoptive cellular therapy. For example, such cells can be produced in less time ex vivo, and that have improved growth properties that can be better regulated.

In some aspects, methods are provided for transducing and/or genetically modifying lymphocytes such as T cells and/or NK cells, and in illustrative embodiments, ex vivo methods for transducing and/or genetically modifying resting T cells and/or NK cells. Some of these aspects can be performed much more quickly than previous methods, which can facilitate more efficient research, more effective commercial production, and improved methods of patient care. Methods, compositions, and kits provided herein, can be used as research tools, in commercial production, and in adoptive cellular therapy with transduced and/or genetically modified T cells and/or NK cells expressing a TCR or a CAR.

With respect to methods, uses and compositions provided herein that relate to transduction of lymphocytes such as T cells and/or NK cells, methods, and associated uses and compositions, are provide herein that include transduction reactions of enriched PBMCs or transduction reactions without prior PBMC enrichment, such as in whole blood that are simplified and quicker methods for performing ex-vivo cell processing, for example for CAR-T therapy. Such methods require less specialized instrumentation and training. Furthermore, such methods reduce the risk of non-targeted cell transduction compared to in vivo transduction methods. Furthermore, provided herein are methods, uses, and compositions, including embodiments of the methods immediately above, that include certain target inhibitory RNAs, polypeptide lymphoproliferative elements, and pseudotyping elements that can be optionally be combined with any other aspects provided herein to provide powerful methods, uses, and compositions for driving expansion of lymphocytes, especially T cells and/or NK cells in vitro, ex vivo, and in vivo.

Further details regarding aspects and embodiments of the present disclosure are provided throughout this patent application. Sections and section headers are for ease of reading and are not intended to limit combinations of disclosure, such as methods, compositions, and kits or functional elements therein across sections.

BRIEF DESCRIPTION OF THE DRAWINGS

FIG. 1A is a flow chart of a process that uses a system with PBMC enrichment before the contacting of T cells and NK cells in the PBMCs with retroviral particles. FIG. 1B is a flow chart of a process in which no blood cell fractionation or enrichment is performed before T cells and NK cells in the whole blood are contacted with retroviral particles, and a PBMC enrichment is performed after transduction.

FIG. 3A shows a histogram of the total number of live cells per well on Day 6 following transduction. FIG. 3B shows a histogram of the percent of CD3+ cells transduced as measured by eTAG expression.

FIG. 4A shows a histogram of the absolute cell number per uL of the live lymphocyte population. FIG. 4B shows a histogram of the percentage (%) CD3+eTag+ cells in the live lymphocyte population at Day 6 post-transduction.

DEFINITIONS

Figure 1A:
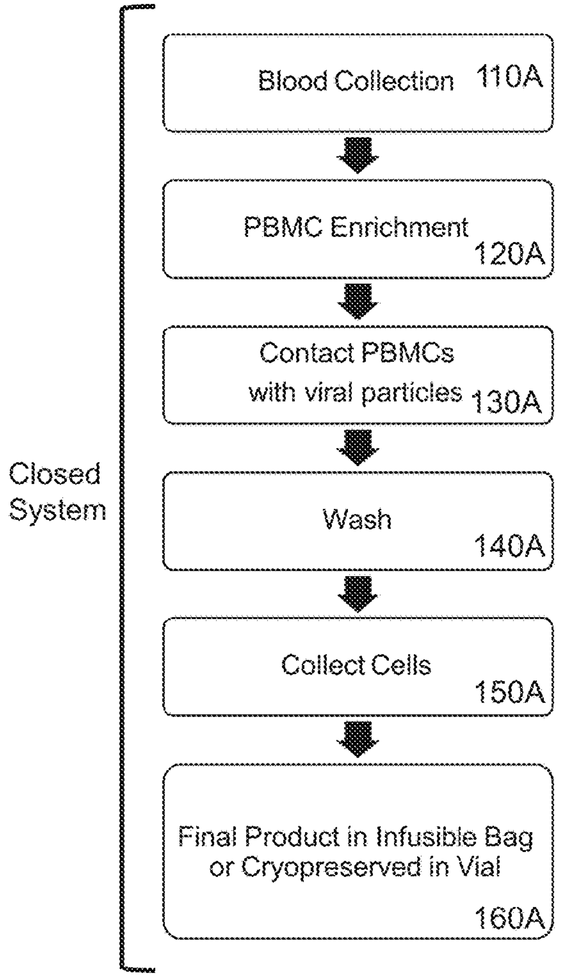
FIGS. 1A-1B are flowcharts of non-limiting exemplary cell processing workflows.

As used herein, the term "chimeric antigen receptor" or "CAR" or "CARs" refers to engineered receptors, which graft an antigen specificity onto cells, for example T cells, NK cells, macrophages, and stem cells. The CARs of the invention include at least one antigen-specific targeting region (ASTR), a transmembrane domain (TM), and an intracellular activating domain (IAD) and can include a stalk, and one or more co-stimulatory domains (CSDs). In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

As used herein, the term "microenvironment" means any portion or region of a tissue or body that has constant or temporal, physical, or chemical differences from other regions of the tissue or regions of the body. For example, a "tumor microenvironment" as used herein refers to the environment in which a tumor exists, which is the non-cellular area within the tumor and the area directly outside the tumorous tissue but does not pertain to the intracellular compartment of the cancer cell itself. The tumor microenvironment can refer to any and all conditions of the tumor milieu including conditions that create a structural and or functional environment for the malignant process to survive and/or expand and/or spread. For example, the tumor microenvironment can include alterations in conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions a skilled artisan will understand.

As used interchangeably herein, the terms "polynucleotide" and "nucleic acid" refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the term "antibody" includes polyclonal and monoclonal antibodies, including intact antibodies and fragments of antibodies which retain specific binding to antigen. The antibody fragments can be, but are not limited to, fragment antigen binding (Fab) fragments, Fab' fragments, $F(ab')_2$ fragments, Fv fragments, Fab'-SH fragments, $(Fab')_2$ Fv fragments, Fd fragments, recombinant IgG (rIgG) fragments, single-chain antibody fragments, including single-chain variable fragments (scFv), divalent scFv's, trivalent scFv's, and single domain antibody fragments (e.g., sdAb, sdFv, nanobody). The term includes genetically engineered and/or otherwise modified forms of immunoglobulins, such as intrabodies, peptibodies, chimeric antibodies, single-chain antibodies, fully human antibodies, humanized antibodies, fusion proteins including an antigen-specific targeting region of an antibody and a non-antibody protein, heteroconjugate antibodies, multispecific, e.g., bispecific, antibodies, diabodies, triabodies, and tetrabodies, tandem di-scFv's, and tandem tri-scFv's. Unless otherwise stated, the term "antibody" should be understood to include functional antibody fragments thereof. The term also includes intact or full-length antibodies, including antibodies of any class or sub-class, including IgG and sub-classes thereof, IgM, IgE, IgA, and IgD.

As used herein, the term "antibody fragment" includes a portion of an intact antibody, for example, the antigen binding or variable region of an intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fe" fragment, a designation reflecting the ability to crystallize readily. Pepsin treatment yields an $F(ab')_2$ fragment that has two antigen combining sites and is still capable of cross-linking antigen.

As used interchangeably herein, the terms "single-chain Fv," "scFv," or "sFv" antibody fragments include the $V_H$ and $V_L$ domains of antibody, wherein these domains are present in a single polypeptide chain. In some embodiments, the Fv polypeptide further includes a polypeptide linker or spacer between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

As used herein, "naturally occurring" VH and VL domains refer to VH and VL domains that have been isolated from a host without further molecular evolution to change their affinities when generated in an scFv format under specific conditions such as those disclosed in U.S. Pat. No. 8,709,755 B2 and application WO/2016/033331A1.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

As used herein, the term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, reference to a "cell surface expression system" or "cell surface display system" refers to the display or expression of a protein or portion thereof on the surface of a cell. Typically, a cell is generated that expresses proteins of interest fused to a cell-surface protein. For example, a protein is expressed as a fusion protein with a transmembrane domain.

As used herein, the term "element" includes polypeptides, including fusions of polypeptides, regions of polypeptides, and functional mutants or fragments thereof and polynucleotides, including microRNAs and shRNAs, and functional mutants or fragments thereof.

As used herein, the term "region" is any segment of a polypeptide or polynucleotide.

As used herein, a "domain" is a region of a polypeptide or polynucleotide with a functional and/or structural property.

As used herein, the terms "stalk" or "stalk domain" refer to a flexible polypeptide connector region providing structural flexibility and spacing to flanking polypeptide regions and can consist of natural or synthetic polypeptides. A stalk can be derived from a hinge or hinge region of an immunoglobulin (e.g., IgG1) that is generally defined as stretching from Glu216 to Pro230 of human IgG1 (Burton (1985) Molec. Immunol., 22:161-206). Hinge regions of other IgG isotypes may be aligned with the IgG1 sequence by placing the first and last cysteine residues forming inter-heavy chain disulfide (S—S) bonds in the same positions. The stalk may be of natural occurrence or non-natural occurrence, including but not limited to an altered hinge region, as disclosed in U.S. Pat. No. 5,677,425. The stalk can include a complete hinge region derived from an antibody of any class or subclass. The stalk can also include regions derived from CD8, CD28, or other receptors that provide a similar function in providing flexibility and spacing to flanking regions.

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "polypeptide" is a single chain of amino acid residues linked by peptide bonds. A polypeptide does not fold into a fixed structure nor does it have any post-translational modification. A "protein" is a polypeptide that folds into a fixed structure. "Polypeptides" and "proteins" are used interchangeably herein.

As used herein, a polypeptide may be "purified" to remove contaminant components of a polypeptide's natural environment, e.g. materials that would interfere with diagnostic or therapeutic uses for the polypeptide such as, for example, enzymes, hormones, and other proteinaceous or nonproteinaceous solutes. A polypeptide can be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

As used herein, "T cell" includes all types of immune cells expressing CD3 including T-helper cells (CD4+ cells), cytotoxic T cells (CD8+ cells), T-regulatory cells (Treg) and gamma-delta T cells.

As used herein, a "cytotoxic cell" includes CD8+ T cells, natural-killer (NK) cells, NK-T cells, γδ T cells, a subpopulation of CD4+ cells, and neutrophils, which are cells capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoietic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used interchangeably herein, the terms "individual", "subject", "host", and "patient" refer to a mammal, including, but not limited to, humans, murines (e.g., rats, mice), lagomorphs (e.g., rabbits), non-human primates, humans, canines, felines, ungulates (e.g., equines, bovines, ovines, porcines, caprines), etc.

As used herein, the terms "therapeutically effective amount" or "efficacious amount" refers to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

As used herein, the term "evolution" or "evolving" refers to using one or more methods of mutagenesis to generate a different polynucleotide encoding a different polypeptide, which is itself an improved biological molecule and/or contributes to the generation of another improved biological molecule. "Physiological" or "normal" or "normal physiological" conditions are conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions, that would be considered within a normal range at the site of administration, or at the tissue or organ at the site of action, to a subject.

As used herein, a "genetically modified cell" is a cell that contain an exogenous nucleic acid(s) regardless of whether the exogenous nucleic acid(s) is integrated into the genome of the cell. As used herein, a "transduced cell" is a cell that contains an exogenous nucleic acid(s) that is integrated into the genome of the cell.

A "polypeptide" as used herein can include part of or an entire protein molecule as well as any posttranslational or other modifications.

A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. The "binding polypeptide" as used herein, can also be referred to as a "T cell and/or NK cell binding polypeptide" or a "target engagement element," and the "fusogenic polypeptide" can also be referred to as a "fusogenic element".

A "resting" lymphocyte, such as for example, a resting T cell, is a lymphocyte in the GO stage of the cell cycle that does not express activation markers such as Ki-67. Resting lymphocytes can include naïve T cells that have never encountered specific antigen and memory T cells that have been altered by a previous encounter with an antigen. A "resting" lymphocyte can also be referred to as a "quiescent" lymphocyte.

As used herein, "lymphodepletion" involves methods that reduce the number of lymphocytes in a subject, for example by administration of a lymphodepletion agent. Lymphodepletion can also be attained by partial body or whole body fractioned radiation therapy. A lymphodepletion agent can be a chemical compound or composition capable of decreasing the number of functional lymphocytes in a mammal when administered to the mammal One example of such an agent is one or more chemotherapeutic agents. Such agents and dosages are known, and can be selected by a treating physician depending on the subject to be treated. Examples of lymphodepletion agents include, but are not limited to, fludarabine, cyclophosphamide, cladribine, denileukin diftitox, or combinations thereof.

RNA interference (RNAi) is a biological process in which RNA molecules inhibit gene expression or translation by neutralizing targeted RNA molecules. The RNA target may be mRNA, or it may be any other RNA susceptible to functional inhibition by RNAi. As used herein, an "inhibitory RNA molecule" refers to an RNA molecule whose presence within a cell results in RNAi and leads to reduced expression of a transcript to which the inhibitory RNA molecule is targeted. An inhibitory RNA molecule as used herein has a 5' stem and a 3' stem that is capable of forming an RNA duplex. The inhibitory RNA molecule can be, for example, a miRNA (either endogenous or artificial) or a shRNA, a precursor of a miRNA (i.e. a Pri-miRNA or Pre-miRNA) or shRNA, or a dsRNA that is either transcribed or introduced directly as an isolated nucleic acid, to a cell or subject.

As used herein, "double stranded RNA" or "dsRNA" or "RNA duplex" refers to RNA molecules that are comprised of two strands. Double-stranded molecules include those comprised of two RNA strands that hybridize to form the duplex RNA structure or a single RNA strand that doubles back on itself to form a duplex structure. Most, but not necessarily all of the bases in the duplex regions are base-paired. The duplex region comprises a sequence complementary to a target RNA. The sequence complementary to a target RNA is an antisense sequence, and is frequently from 18 to 29, from 19 to 29, from 19 to 21, or from 25 to 28 nucleotides long, or in some embodiments between 18, 19, 20, 21, 22, 23, 24, 25 on the low end and 21, 22, 23, 24, 25, 26, 27, 28 29, or 30 on the high end, where a given range always has a low end lower than a high end. Such structures typically include a 5' stem, a loop, and a 3' stem connected by a loop which is contiguous with each stem and which is not part of the duplex. The loop comprises, in certain embodiments, at least 3, 4, 5, 6, 7, 8, 9, or 10 nucleotides. In other embodiments the loop comprises from 2 to 40, from 3 to 40, from 3 to 21, or from 19 to 21 nucleotides, or in some embodiments between 2, 3, 4, 5, 6, 7, 8, 9, 10, 11, 12, 13, 14, 15, 16, 17, 18, 19, or 20 on the low end and 10, 11, 12, 13, 14, 15, 16, 17, 18, 19, 20, 25, 30, 35, or 40 on the high end, where a given range always has a low end lower than a high end.

The term "microRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure.

The term "linker" when used in reference to a multiplex inhibitory RNA molecule refers to a connecting means that joins two inhibitory RNA molecules.

As used herein, a "recombinant retrovirus" refers to a non-replicable, or "replication incompetent", retrovirus unless it is explicitly noted as a replicable retrovirus. The terms "recombinant retrovirus" and "recombinant retroviral particle" are used interchangeably herein. Such retrovirus/retroviral particle can be any type of retroviral particle including, for example, gamma retrovirus, and in illustrative embodiments, lentivirus. As is known, such retroviral particles, for example lentiviral particles, typically are formed in packaging cells by transfecting the packing cells with plasmids that include packaging components such as Gag, Pol and Rev, an envelope or pseudotyping plasmid that encodes a pseudotyping element, and a transfer, genomic, or retroviral (e.g. lentiviral) expression vector, which is typically a plasmid on which a gene(s) or other coding sequence of interest is encoded. Accordingly, a retroviral (e.g. lentiviral) expression vector includes sequences (e.g. a 5' LTR and a 3' LTR flanking e.g. a psi packaging element and a target heterologous coding sequence) that promote expression and packaging after transfection into a cell. The terms "lentivirus" and "lentiviral particle" are used interchangeably herein.

A "framework" of a miRNA consists of "5' microRNA flanking sequence" and/or "3' microRNA flanking sequence" surrounding a miRNA and, in some cases, a loop sequence that separates the stems of a stem-loop structure in a miRNA. In some examples, the "framework" is derived from naturally occurring miRNAs, such as, for example, miR-155. The terms "5' microRNA flanking sequence" and "5' arm" are used interchangeably herein. The terms "3' microRNA flanking sequence" and "3' arm" are used interchangeably herein.

As used herein, the term "miRNA precursor" refers to an RNA molecule of any length which can be enzymatically processed into an miRNA, such as a primary RNA transcript, a pri-miRNA, or a pre-miRNA.

As used herein, the term "construct" refers to an isolated polypeptide or an isolated polynucleotide encoding a polypeptide. A polynucleotide construct can encode a polypeptide, for example, a lymphoproliferative element. A skilled artisan will understand whether a construct refers to an isolated polynucleotide or an isolated polypeptide depending on the context.

As used herein, "MOI", refers to Multiplicity of Infection ratio where the MOI is equal to the ratio of the number of virus particles used for infection per number of cells. Functional titering of the number of virus particles can be performed using FACS and reporter expression.

"Peripheral blood mononuclear cells" (PBMCs) include peripheral blood cells having a round nucleus and include lymphocytes (e.g. T cells, NK cells, and B cells) and monocytes. Some blood cell types that are not PBMCs include red blood cells, platelets and granulocytes (i.e. neutrophils, eosinophils, and basophils).

It is to be understood that the present disclosure and the aspects and embodiments provided herein, are not limited to particular examples disclosed, as such may, of course, vary. It is also to be understood that the terminology used herein is for the purpose of disclosing particular examples and embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. When multiple low and multiple high values for ranges are given that overlap, a skilled artisan will recognize that a selected range will include a low value that is less than the high value. All headings in this specification are for the convenience of the reader and are not limiting.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

DETAILED DESCRIPTION

The present disclosure overcomes prior art challenges by providing improved methods and compositions for genetically modifying lymphocytes, for example NK cells and in illustrative embodiments, T cells. Some of the methods and compositions herein, provide simplified and more rapid processes for transducing lymphocytes that avoid some steps that require specialized devices. Furthermore, the methods provide better control of post-transduction processing since any such processing is done ex vivo, which therefore allows the option of removing various unwanted cells. Thus, the methods provide an important step toward democratization of cell therapy methods.

Illustrative methods and compositions for genetically modifying lymphocytes, for example NK cells and in illustrative embodiments, T cells, are performed in less time than prior methods. Furthermore, compositions that have many uses, including their use in these improved methods, are provided. Some of these compositions are genetically modified lymphocytes that have improved proliferative and survival qualities, including in in vitro culturing, for example in the absence of growth factors. Such genetically modified lymphocytes will have utility for example, as research tools to better understand factors that influence T cell proliferation and survival, and for commercial production, for example for the production of certain factors, such as growth factors and immunomodulatory agents, that can be harvested and tested or used in commercial products.

Methods for Transducing and/or Genetically Modifying Lymphocytes

Provided herein in certain aspects, is a method of transducing and/or genetically modifying a lymphocyte, such as a (typically a population of) peripheral blood mononuclear cell (PBMC), typically a T cell and/or an NK cell, and in certain illustrative embodiments a resting T cell and/or resting NK cell, that includes contacting the lymphocyte with a (typically a population of) replication incompetent recombinant retroviral particle, wherein the replication incompetent recombinant retroviral particle typically comprises a pseudotyping element on its surface, wherein said contacting (and incubation under contacting conditions) facilitates membrane association, membrane fusion, and optionally transduction of the resting T cell and/or NK cell by the replication incompetent recombinant retroviral particle, thereby producing the genetically modified T cell and/or NK cell. In illustrative embodiments, pre-activation of the T cell and/or NK cell is not required, and an activation element, which can be any activation element provided herein, is present in a reaction mixture in which the contacting takes place. In further illustrative embodiments, the activation element is present on a surface of the replication incompetent recombinant retroviral particle. In illustrative embodiments, the activation element is anti-CD3, such as anti-CD3 scFv, or anti-CD3 scFvFc.

In some embodiments, the contacting step and an optional incubation thereafter, which includes a step to remove retroviral particles not associated with cells, in a method provided herein of transducing and/or genetically modifying a PBMC or a lymphocyte, typically a T cell and/or an NK cell, can be performed (or can occur), for 72, 48, or 24 hours or less or for any of the contacting time ranges provided herein. However, in illustrative embodiments, the contacting is performed for less than 2 hours, less than 1 hour, less than 30 minutes or less than 15 minutes, but in each case there is at least an initial contacting step in which retroviral particles and cells are brought into contact in suspension in a transduction reaction mixture. This contacting typically includes an initial step in which retroviral particles that are not associated with a cell of the reaction mixture are separated from the cells, which are then further processed. Such suspension can include allowing cells and retroviral particles to settle or causing such settling through application of a force, such as a centrifugal force, to the bottom of a vessel or chamber, as discussed in further detail herein. In illustrative embodiments, such g force is lower than the g forces used successfully in spinoculation procedures. Further contacting times and discussions regarding contacting and the optional incubation, are discussed further herein. In further illustrative embodiments, the contacting is performed for between an initial contacting step only (without any further incubating in the reaction mixture including the retroviral particles free in suspension and cells in suspension) without any further incubation in the reaction mixture, or a 5 minute, 10 minute, 15 minute, 30 minute, or 1 hour incubation in the reaction mixture, which can be a step of separating free retroviral particles in a reaction mixture from those associated with cells.

Various embodiments of this method, as well as other aspects, such as use and NK cells and T cells made by such a method, are disclosed in detail herein. Furthermore, various elements or steps of such method aspects for transducing and/or genetically modifying a PBMC, lymphocyte, T cell and/or NK cell, are provided herein, for example in this section and the Exemplary Embodiments section, and such methods include embodiments that are provided throughout this specification, as further discussed herein, For example, embodiments of any of the aspects for transducing and/or genetically modifying a PBMC or a lymphocyte, for example an NK cell or in illustrative embodiments, a T cell, provided for example in this section and in the Exemplary Embodiments section, can include any of the embodiments of replication incompetent recombinant retroviral particles provided herein, including those that include one or more lymphoproliferative element, CAR, pseudotyping element, riboswitch, activation element, membrane-bound cytokine, miRNA, Kozak-type sequence, WPRE element, triple stop codon, and/or other element disclosed herein, and can be combined with methods herein for producing retroviral particles using a packaging cell. In certain illustrative embodiments, the retroviral particle is a lentiviral particle. Such a method for genetically modifying and/or transducing a PBMC or a lymphocyte, such as a T cell and/or NK cell can be performed in vitro or ex vivo. A skilled artisan will recognize that details provided herein for transducing and/or genetically modifying PBMCs or lymphocytes, such as T cell(s) and/or NK cell(s) can apply to any aspect that includes such step(s).

In certain illustrative embodiments, the cell is genetically modified and/or transduced without requiring prior activation or stimulation, whether in vivo, in vitro, or ex vivo. In certain illustrative embodiments, the cell is activated during the contacting and is not activated at all or for more than 15 minutes, 30 minutes, 1, 2, 4, or 8 hours before the contacting. In certain illustrative embodiments, activation by elements that are not present on the retroviral particle surface is not required for genetically modifying and/or transducing the cell. Accordingly, such activation or stimulation elements are not required other than on the retroviral particle, before, during, or after the contacting. Thus, as discussed in more detail herein, these illustrative embodiments that do not require pre-activation or stimulation provide the ability to rapidly perform in vitro experiments aimed at better understanding T cells and the biologicals mechanisms, therein. Furthermore, such methods provide for much more efficient commercial production of biological products produced using PBMCs, lymphocytes, T cells, or NK cells, and development of such commercial production methods. Finally, such methods provide for more rapid ex vivo processing of PBMCs for adoptive cell therapy, fundamentally simplifying the delivery of such therapies, for example by providing point of care methods.

Compositions and Methods for Transducing Lymphocytes in Whole Blood Lymphocytes in Whole Blood Provided herein in certain aspects, is a method of transducing and/or genetically modifying peripheral blood mononuclear cells (PBMCs), or lymphocytes, typically T cells and/or NK cells, and in certain illustrative embodiments resting T cells and/or resting NK cells, in a reaction mixture comprising blood, or a component thereof, and/or an anticoagulant, that includes contacting the lymphocytes with replication incompetent recombinant retroviral particles in the reaction mixture that itself represents a separate aspect provided herein, The reaction mixture in illustrative embodiments comprises the lymphocytes and the replication incompetent recombinant retroviral particles, a T cell activation element and one or more additional blood components set out below that in illustrative embodiments are present because the reaction mixture comprises at least 10% whole blood, wherein the replication incompetent recombinant retroviral particles typically comprises a pseudotyping element on its surface. In such methods, the contacting (and incubation under contacting conditions) facilitates association of the lymphocytes with the replication incompetent recombinant retroviral particles, wherein the recombinant retroviral particles genetically modify and/or transduce the lymphocytes. The reaction mixture of this aspect comprises at least 10% whole blood (e.g. at least 10%, 20%, 25%, 50%, 60%, 70%, 80%, 90%, 95%, or 99% whole blood) and optionally an effective amount of an anticoagulant, or the reaction mixture further comprises at least one additional blood or blood preparation component that is not a PBMC, for example the reaction mixture comprises an effective amount of an anti-coagulant and one or more blood preparation component that is not a PBMC. In illustrative embodiments such blood or blood preparation component that is not a PBMC is one or more (e.g. at least one, two, three, four, or five) or all of the following additional components:

a) erythrocytes, wherein the erythrocytes comprise between 1 and 60% of the volume of the reaction mixture;
b) neutrophils, wherein the neutrophils comprise at least 10% of the white blood cells in the reaction mixture, or wherein the reaction mixture comprises at least 10% as many neutrophils as T cells;
c) basophils, wherein the basophils comprise at least 0.05% of the white blood cells in the reaction mixture;
d) eosinophils, wherein the reaction mixture comprises at least 0.1% of the white blood cells in the reaction mixture;
e) plasma, wherein the plasma comprises at least 1% of the volume of the reaction mixture; and
f) an anti-coagulant (such blood or blood preparation components a-f above referred to herein as ("Noteworthy Non-PBMC Blood or Blood Preparation Components")).

The one or more additional blood components are present in certain illustrative embodiments of the reaction mixture (including related use, genetically modified T cell or NK cell, or method for genetically modifying T cells and/or NK cells aspects provided herein) because in these illustrative embodiments the reaction mixture comprises at least 10% whole blood, and in certain illustrative embodiments, at least 25%, 50%, 75%, 90%, or 95% whole blood, or for example between 25% and 95% whole blood. In these illustrative embodiments, such reaction mixtures are formed by combining whole blood with an anticoagulant (for example by collecting whole blood into a blood collection tube comprising an anti-coagulant), and adding a solution of recombinant retroviruses to the blood with anticoagulant. Thus, in illustrative embodiments, the reaction mixture comprises an anti-coagulant as set out in more detail herein. In some embodiments, the whole blood is not, or does not comprise, cord blood.

The reaction mixture in these aspects, typically does not include a PBMC enrichment procedure before the transduction reaction mixture is formed. Thus, typically such reaction mixtures include additional components listed in a)-f) above, which are not PBMCs. Furthermore, in illustrative embodiments, the reaction mixture comprises all of the additional components listed in a) to e) above, because the reaction mixture comprises substantially whole blood, or whole blood. "Substantially whole blood" is blood that was isolated from an individual(s), has not been subjected to a PBMC enrichment procedure, and is diluted by less than 50% with other solutions. For example, this dilution can be from addition of an anti-coagulant as well as addition of a volume of fluid comprising retroviral particles. Further reaction mixture embodiments for methods and compositions that relate to transducing lymphocytes in whole blood, are provided herein.

In another aspect, provided herein are genetically modified lymphocytes, in illustrative embodiments genetically modified T cells and/or NK cells made by the above method of transducing and/or genetically modifying lymphocytes in whole blood. In yet another aspect provided herein, is use of replication incompetent recombinant retroviral particles in the manufacture of a kit for genetically modifying lymphocytes, in illustrative embodiments T cells and/or NK cells of a subject, wherein the use of the kit comprises the above method of transducing and/or genetically modifying lymphocytes in whole blood. In another aspect, provided herein are methods for administering genetically modified lymphocytes to a subject, wherein the genetically modified lymphocytes are produced by the above method of transducing and/or genetically modifying lymphocytes in whole blood. Aspects provided herein that include such methods of transducing and/or genetically modifying lymphocytes in whole blood, uses of such a method in the manufacture of a kit, reaction mixtures formed in such a method, genetically modified lymphocytes made by such a method, and methods for administering a genetically modified lymphocyte made by such a method, are referred to herein as "composition and method aspects for transducing lymphocytes in whole blood." It should be noted that although illustrative embodiments for such aspects involve contacting T cells and/or NK cells with retroviral particles in whole blood, such aspects also include other embodiments, where one or more of additional components a-f above, are present in transduction reaction mixtures at higher concentrations than is typical after a PBMC enrichment procedure.

Various elements or steps of such method aspects for transducing lymphocytes in whole blood, are provided herein, for example in this section and the Exemplary Embodiments section, and such methods include embodiments that are provided throughout this specification, as further discussed herein. A skilled artisan will recognize that many embodiments provided herein anywhere in this specification can be applied to any of the aspects of the composition and method aspects for transducing lymphocytes in whole blood. For example, embodiments of any of the composition and method aspects for transducing lymphocytes in whole blood provided for example in this section and/or in the Exemplary Embodiments section, can include any of the embodiments of replication incompetent recombinant retroviral particles provided herein, including those that include one or more polypeptide lymphoproliferative element, inhibitory RNA, CAR, pseudotyping element, riboswitch, activation element, membrane-bound cytokine, miRNA, Kozak-type sequence, WPRE element, triple stop codon, and/or other element disclosed herein, and can be combined with methods herein for producing retroviral particles using a packaging cell.

As non-limiting examples of embodiments that can be used in many aspects herein, as discussed in more detail herein, the pseudotyping element is typically capable of binding lymphocytes (e.g. T cells and/or NK cells) in illustrative embodiments resting T cells and/or resting NK cells and facilitating membrane fusion on its own or in conjunction with other protein(s) of the replication incompetent recombinant retroviral particles. In certain illustrative embodiments, the retroviral particle is a lentiviral particle. Such a method for genetically modifying a lymphocyte, such as a T cell and/or NK cell in whole blood, can be performed in vitro or ex vivo.

Anticoagulants are included in reaction mixtures for certain embodiments of the composition and method aspects for transducing lymphocytes in whole blood provided herein. In some illustrative embodiments, blood is collected with the anti-coagulant present in the collection vessel (e.g. tube or bag), for example using standard blood collection protocols known in the art. Anticoagulants that can be used in composition and method aspects for transducing lymphocytes in whole blood provided herein include compounds or biologics that block or limit the thrombin blood clotting cascade. The anti-coagulants include: metal chelating agents, preferably calcium ion chelating agents, such as citrate (e.g. containing free citrate ion), including solutions of citrate that contain one or more components such as citric acid, sodium citrate, phosphate, adenine and mono or polysaccharides, for example dextrose, oxalate, and EDTA; heparin and heparin analogues, such as unfractionated heparin, low molecular weight heparins, and other synthetic saccharides; and vitamin K antagonists such as coumarins. Exemplary citrate compositions include: acid citrate dextrose (ACD) (also called anticoagulant citrate dextrose solution A and solution B (United States Pharmacopeia 26, 2002, pp 158)); and a citrate phosphate dextrose (CPD) solution, which can also be prepared as CPD-A1 as is known in the art. Accordingly, the anticoagulant composition may also include phosphate ions or monobasic phosphate ion, adenine, and mono or polysaccharides.

Such anti-coagulants can be present in a reaction mixture at concentrations that are effective for preventing coagulation of blood (i.e. effective amounts) as known in the art, or at a concentration that is, for example, 2 times, 1.5 times, 1.25 times, 1.2 times, 1.1 times, or 9⁄10, 4⁄5, 7⁄10, 3⁄5, 1⁄2, 2⁄5, 3⁄10, 1⁄5, or 1⁄10 the effective concentration. The effective concentrations of many different anticoagulants is known and can be readily determined empirically by analyzing different concentrations for their ability to prevent blood coagulation, which can be physically observed. Numerous coagulometers are available commercially that measure coagulation, and various sensor technologies can be used, for example QCM sensors (See e.g., Yao et al., "Blood Coagulation Testing Smartphone Platform Using Quartz Crystal Microbalance Dissipation Method," Sensors (Basel). 2018 September; 18(9): 3073). The effective concentration includes the concentration of any commercially available anti-coagulant in a commercially available tube or bag after the anti-coagulant is diluted in the volume of blood intended for the tube or bag. For example, the concentration of acid citrate dextrose (ACD) in a reaction mixture in certain embodiments of the composition and method aspects for transducing lymphocytes in whole blood provided herein, can be between 0.1 and 5×, or between 0.25 and 2.5×, between 0.5 and 2×, between 0.75 and 1.5×, between 0.8 and 1.2×, between 0.9 and 1.1×, about 1×, or 1× the concentration of ACD in a commercially available ACD blood collection tube or bag. For example, in a standard process, blood can be collected into tubes or bags containing 3.2% (109 mM) sodium citrate (109 mM) at a ratio of 9 parts blood and 1 part anticoagulant. Thus, in certain illustrative embodiments with a reaction mixture made by adding 1-2 parts of a retroviral particle solution to this mixture of 1 part anticoagulant to 9 parts blood, the citrate concentration can be between for example, 0.25% to 0.4%, or 0.30% to 0.35%. In an illustrative standard blood collection embodiment, 15 mls of ACD Solution A are present in a blood bag for collecting 100 mL of blood. The ACD before addition of blood contains Citric acid (anhydrous) 7.3 g/L (0.73%), Sodium citrate (dihydrate) 22.0 g/L (2.2%), and Dextrose (monohydrate) 24.5 g/L [USP] (2.4%). After addition of 100 ml of blood to the bag that contains ACD, a volume of for example, between 5 and 20 mls of the genetically modified retroviral particles is added. Thus, in some embodiments, the concentration of ACD components in a reaction mixture can be between 0.05 and 0.1%, or 0.06 and 0.08% Citric acid (anhydrous), 0.17 and 0.27, or 0.20 and 0.24 Sodium citrate (dihydrate), 0.2 and 0.3, or 0.20 and 0.28, or 0.22 and 0.26% Dextrose (monohydrate). In certain embodiments, sodium citrate is used at a concentration of between 0.001 and 0.02 M in the reaction mixture.

In some embodiments, heparin is present in the reaction mixtures, for example at a concentration between 0.1 and 5×, or between 0.25 and 2.5×, between 0.5 and 2×, between 0.75 and 1.5×, between 0.8 and 1.2×, between 0.9 and 1.1×, about 1×, or 1× the concentration of heparin in a commercially available heparin blood collection tube. Heparin is a glycosaminoglycan anticoagulant with a molecular weight ranging from 5,000-30,000 daltons. In some embodiments, heparin is used at a concentration of about 1.5 to 45, 5 to 30, 10 to 20, or 15 USP units/ml of reaction mixture. In some embodiments, the effective concentration for EDTA, for example as $K_2EDTA$, in the reaction mixtures herein can be between 0.15 and 5 mg/ml, between 1 and 3 mg/ml between 1.5-2.2 mg/ml of blood, or between 1 and 2 mg/ml, or about 1.5 mg/ml. The reaction mixtures in composition and method aspects for transducing lymphocytes in whole blood provided herein, can include two or more anticoagulants whose combined effective dose prevents coagulation of the blood prior to formation of the reaction mixture and/or of the reaction mixture itself.

In some embodiments, the anti-coagulant can be administered to a subject before blood is collected from the subject for ex vivo transduction, such that coagulation of the blood when it is collected in inhibited, at least partially and at least through a contacting step and optional incubation period thereafter. In such embodiments, for example acid citrate dextrose can be administered to the subject at between 80 mg/kg/day and 5 mg/kg/day (mg refer to the mg of citric acid and kg applies to the mammal to be treated). Heparin, can be delivered for example, at a dose of between 5 units/kg/hr to 30 units/kg/hr.

In addition to, or instead of an anti-coagulant, composition and method aspects for transducing lymphocytes in whole blood provided herein, can include at least one additional component selected from one or more of the following components:

a) erythrocytes, wherein the erythrocytes comprise between 0.1 and 75% of the volume of the reaction mixture;
b) neutrophils, wherein the neutrophils comprise at least 10% of the white blood cells in the reaction mixture, or wherein the reaction mixture comprises at least 10% as many neutrophils as T cells;
c) basophils, wherein the basophils comprise at least 0.05% of the white blood cells in the reaction mixture;
d) eosinophils, wherein the reaction mixture comprises at least 0.1% of the white blood cells in the reaction mixture;
e) plasma, wherein the plasma comprises at least 1% of the volume of the reaction mixture; and
f) platelets, wherein the platelets comprise at least $1\times10^6$ platelets/liter of the reaction mixture.

With respect to erythrocytes, in some embodiments, erythrocytes can comprise between 0.1, 0.5, 1, 5, 10, 25, 35 or 40% of the volume of the reaction mixture on the low end of the range, and between 25, 50, 60, or 75% of the volume of the reaction mixture on the high end of the range. In illustrative embodiments, erythrocytes comprise between 1 and 60%, between 10 and 60%, between 20 and 60%, between 30 and 60%, between 40 and 60%, between 40 and 50%, between 42 and 48%, between 44 and 46%, about 45% or 45%.

With respect to neutrophils, in some embodiments, neutrophils can comprise between 0.1, 0.5, 1, 5, 10, 20, 25, 35 or 40% of the white blood cells of the reaction mixture on the low end of the range, and between 25, 50, 60, 70, 75 and 80% of the white blood cells of the reaction mixture on the high end of the range, for example between 25% and 70%, or between 30% and 60%, or between 40% and 60% of the white blood cells of the reaction mixture. In some embodiments, more neutrophils are present than T cells and/or NK cells, in reaction mixtures herein.

With respect to eosinophils in some embodiments, eosinophils can comprise between 0.05, 0.1, 0.2, 0.4, 0.6, 0.8, 1.0, 1.2, 1.4, 1.6, and 1.8% of the white blood cells of the reaction mixture on the low end of the range, and between 2.0, 2.2, 2.4, 2.6, 2.8, 3.0, 3.5, 4, 5, 6, 8 and 10% of the white blood cells of the reaction mixture on the high end of the range. In illustrative embodiments, eosinophils comprise between 0.05 and 10.0%, between 0.1 and 9%, between 0.2 and 8%, between 0.2 and 6%, between 0.5 and 4%, between 0.8 and 4%, or between 1 and 4% of the white blood cells of the reaction mixture.

With respect to basophils in some embodiments, basophils can comprise between 0.05, 0.1, 0.2, 0.4, 0.45 and 0.5% of the white blood cells of the reaction mixture on the low end of the range, and between 0.8, 0.9, 1.0, 1.1, 1.2, 1.5 and 2.0% of the white blood cells of the reaction mixture on the high end of the range. In illustrative embodiments, basophils comprise between 0.05 and 1.4%, between 0.1 and 1.4%, between 0.2 and 1.4%, between 0.3 and 1.4%, between 0.4 and 1.4%, between 0.5 and 1.4%, between 0.5 and 1.2%, between 0.5 and 1.1%, or between 0.5 and 1.0% of the white blood cells of the reaction mixture.

With respect to plasma, in some embodiments, plasma can comprise between 0.1, 0.5, 1, 5, 10, 25, 35 or 45% of the volume of the reaction mixture on the low end of the range, and between 25, 50, 60, 70 and 80% of the volume of the reaction mixture on the high end of the range. In illustrative embodiments, plasma comprise between 0.1 and 80%, between 1 and 80%, between 5 and 80%, between 10 and 80%, between 30 and 80%, between 40 and 80%, between 45 and 70%, between 50 and 60%, between 52 and 58%, between 54 and 56%, about 55% or 55% of the reaction mixture.

With respect to platelets, in some embodiments, platelets can comprise between $1\times10^5$, $1\times10^6$, $1\times10^7$, or $1\times10^8$ platelets/mL of the reaction mixture on the low end of the range, and between $1\times10^9$, $1\times10^{10}$, $1\times10^{11}$, $1\times10^{12}$, $2\times10^{13}$, or $2\times10^{14}$ platelets/mL of the reaction mixture on the high end of the range. In illustrative embodiments, platelets comprise between $1\times10^5$ and $1\times10^{12}$ platelets, between $1\times10^6$ and $1\times10^{11}$ platelets, between $1\times10^7$ and $1\times10^{10}$ platelets, between $1\times10^8$, and $1\times10^9$ platelets/mL, or between $1\times10^8$ and $5\times10^8$ platelets/ml of the reaction mixture.

Figure 1B:
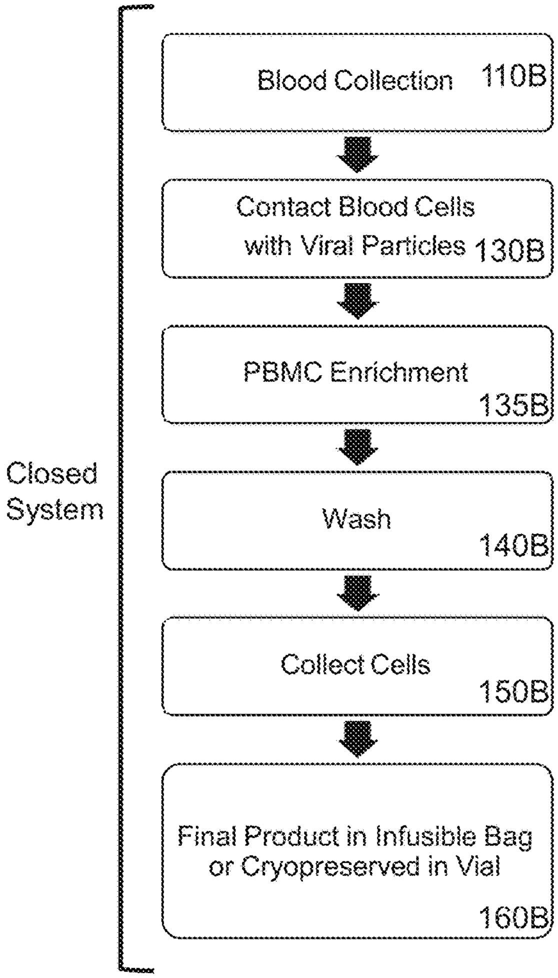

Illustrative Cell Processing Methods for Genetically Modifying T Cells and/or NK Cells in the Presence of Blood, or a Component Thereof It is noteworthy that some embodiments of methods for genetically modifying provided herein do not include a step of collecting blood from a subject. However, as shown in FIG. 1, some of the methods provided herein include a step where blood is collected (110) from a subject. Blood can be collected or obtained from a subject by any suitable method known in the art as discussed in more detail herein. For example, the blood can be collected by venipuncture or any other blood collection method by which a sample of blood is collected. In some embodiments, the volume of blood collected is between 25 ml and 250 ml, for example, between 25 ml and 60 ml, between 50 ml and 90 ml, between 75 ml and 125 ml, or between 90 ml and 120 ml, or between 95 and 110 ml.

Regardless of whether blood is collected from a subject, in any of the method aspects provided herein for genetically modifying lymphocytes (e.g. T cells and/or NK cells), the lymphocytes are contacted with replication incompetent retroviral particles in a reaction mixture. In illustrative embodiments, this contacting, and the reaction mixture in which the contacting occurs, takes place within a closed cell processing system, as discussed in more detail herein. In traditional closed cell processing methods that involve genetic modification and/or transductions of lymphocytes ex vivo, especially in methods for autologous cell therapy, many steps occur over days, such as PBMC enrichment(s), washing(s), cell activation, transduction, expansion, collection, and optionally reintroduction. In more recent methods (See FIG. 1A), some of the steps and time involved in this ex vivo cell processing have been reduced (See e.g. WO2019/055946). These more recent methods (as well as the further improved cell processing methods provided herein), furthermore use a rapid ex vivo transduction process, for example that includes no or minimal preactivation (e.g. less than 30, 15, 10, or 5 minutes of contacting lymphocytes such as T cells and/or NK cells with an activation agent before they are contacted with retroviral particles). In certain embodiments of such methods, a T cell and/or NK cell activation element is present in the reaction mixture in which the contacting step occurs. In illustrative embodiments, the T cell and/or NK cell activation element is associated with surfaces of retroviral particles present in the reaction mixture. In illustrative embodiments, such a method is used in a point of care autologous cell therapy method. However, such more recent methods still involve a PBMC enrichment step/procedure (120), which typically takes at least around 1 hour within the closed system, followed by cell counting, transfer and media addition, which takes at least around 45 additional minutes before lymphocytes are contacted with retroviral particles to form a transduction reaction mixture (130A). Following the "viral transduction" step, which typically is a contacting step with incubating as discussed in detail herein, lymphocytes are typically washed away from retroviral particles that remain in suspension (140A), for example using a Sepax, and collected (150A), with the final product typically in an infusion bag for reinfusion or cryopreservation vial for storage (160A). As discussed in further detail herein, traditional PBMC enrichment procedures typically involve ficoll density gradients and centrifugal (e.g. centrifugation) or centripetal (e.g. Sepax) forces or use leukophoresis to enrich PBMCs.

As demonstrated in the Examples provided herein, it was surprisingly found that lymphocytes (e.g. T cells and/or NK cells) can be contacted with replication incompetent retroviral particles in a reaction mixture of whole blood that contains an anti-coagulant, and a significant percentage of the lymphocytes can be genetically modified and transduced. Thus, it was discovered that effective genetic modification of lymphocytes by recombinant retroviral particles can be carried out in the presence of blood components and blood cells in addition to PBMCs. Furthermore, based on the surprising finding discussed immediately above regarding effective genetic modification of T cells and optionally NK cells by retroviral particles even when contacting is performed in whole blood, provided herein in an illustrative embodiment, is a further simplified method in which lymphocytes are genetically modified and/or transduced by adding replication incompetent retroviral particles directly to whole blood to form a reaction mixture (130B), and cells in the whole blood are contacted by the replication incompetent retroviral particles for contacting times with optional incubations provided herein. Such a further improved method in this illustrative embodiment, thus includes no lymphocyte enrichment steps before lymphocytes in whole blood, typically containing an anti-coagulant, are contacted with retroviral particles. This further improved method, like other cell processing methods herein, is typically carried out within a closed cell processing system and can include no or minimal preactivation before lymphocytes are contacted with retroviral particles. In these further simplified methods lymphocytes in whole blood can be contacted with retroviral particles directly in a blood bag. After the contacting step (130B) in such methods, lymphocytes that were contacted with retroviral particles, are washed and concentrated using a PBMC enrichment procedure (135B), which also reduces neutrophils to facilitate reintroduction into a subject. Thus, in such embodiments, no PBMC enrichment procedure and no lymphocyte-enriching filtration is performed before cells in whole blood, and typically comprising an anticoagulant, are contacted with recombinant retroviral particles. However, in the embodiment of FIG. 1B, such a PBMC enrichment method is performed (135B) for example using a Sepax with a ficoll gradient, after the contacting with optional incubation (130B) is carried out. Following the PBMC enrichment, lymphocytes optionally can be washed further away from any retroviral particles that remain (140B), for example using a Sepax, and collected (150B), with the final product typically in an infusion bag for reinfusion or cryopreservation vial for storage (160B).

Figure 2:
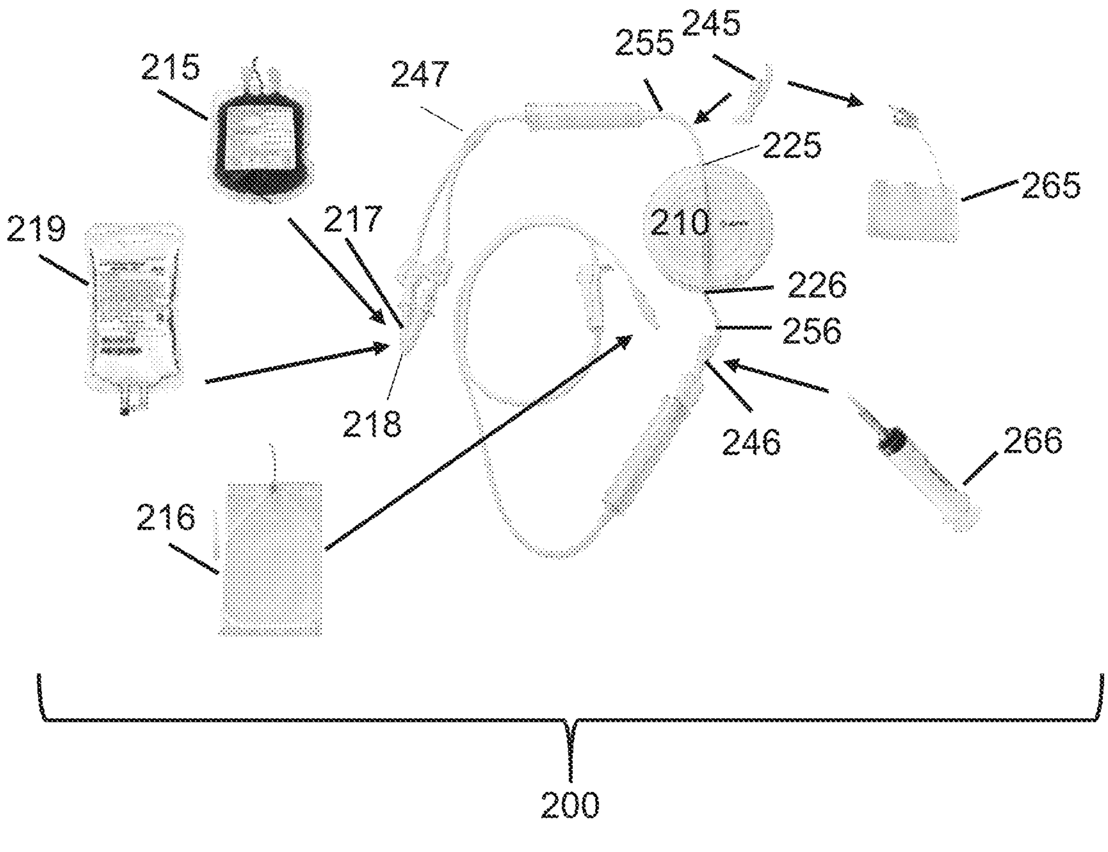
FIG. 2 is a diagram of a non-limiting exemplary leukodepletion filter assembly (200) with associated blood processing bags, tubes, valves, and filter enclosure (210) comprising a leukodepletion filter set.

FIG. 2 provides a non-limiting illustrative example of a cell processing leukodepletion filtration assembly (200) that enriches nucleated cells that can be used as the leukodepletion filter in the methods of FIG. 1. The illustrative leukodepletion filtration assembly (200), which in illustrative embodiments is a single-use filtration assembly, comprises a leukocyte depletion media (e.g. filter set) within a filter enclosure (210), that has an inlet (225), and an outlet (226), and a configuration of bags, valves and/or channels/tubes that provide the ability to concentrate, enrich, wash and collect retained white blood cells or nucleated blood cells using perfusion and reverse perfusion (see e.g. EP2602315A1, incorporated by reference herein, in its entirety). In an illustrative embodiment, the leukodepletion filtration assembly (200) is a commercially available HemaTrate filter (Cook Regenetec, Indianapolis, Ind.). Leukodepletion filtration assemblies can be used, to concentrate total nucleated cells (TNC) including granulocytes, which are removed in PBMC enrichment procedures in a closed cell processing system. Since a filter assembly comprising leukocyte depletion media of EP2602315A1 such as a HemaTrate filter and the illustrative leukodepletion filter assembly of FIG. 2 do not remove granulocytes, they are not considered PBMC enrichment assemblies or filters herein, and methods that incorporate them are not considered PBMC enrichment procedures or steps herein.

The leukodepletion filter assembly (200) of FIG. 2 is a single-use sterile assembly that includes various tubes and valves, typically needle-free valves, that allow isolation of white blood cells from whole blood and blood cell preparations that include leukocytes, as well as rapid washing and concentrating of white blood cells. In this illustrative assembly, a blood bag (215), for example a 500 ml PVC bag containing about 120 ml of a transduction/contacting reaction mixture comprising whole blood, an anti-coagulant, and retroviral particles is connected to the assembly (200) at a first assembly opening (217) of an inlet tubing (255), after the reaction mixture is subjected to a contacting step with optional incubation, as disclosed in detail herein. Lymphocytes, including some T cells and/or NK cells with associated retroviral particles, and some that could be genetically modified at this point, as well as other blood cells and components in the whole blood reaction mixture as well as the anti-coagulant enter the inlet tubing (255) through the first assembly opening (217) by gravitational force when a clamp on the first inlet tubing (255) is released. The genetically modified T cells and/or NK cells pass through a inlet valve (247) and a collection valve (245), to enter a filter enclosure (210) through a filter enclosure inlet (225) to contact a leukodepletion IV filter set (e.g. SKU J1472A Jorgensen Labs) within the filter enclosure (210). Nucleated blood cells including leukocytes are retained by the filter, but other blood components pass through the filter and out the filter enclosure outlet (226) into the outlet tubing (256), then through an outlet valve (247) and are collected in a waste collection bag (216), which for example can be a 2 L PVC waste collection bag.

An optional buffer wash step can be performed by switching inlet valve (247) to a wash position. In this optional wash step, a buffer bag (219), for example a 500 ml saline wash bag, is connected to a second assembly opening (218) of inlet tubing (255). The buffer moves into the inlet tubing (255) through the second assembly opening (218) by gravitational force when a clamp on the inlet tubing (255) is released. The buffer passes through inlet valve (247) and collection valve (245), to enter filter enclosure (210) through the filter enclosure inlet (225) and passes through the leukodepletion filter set within the filter enclosure (210) to rinse the lymphocytes retained on the filter. The buffer moves out the filter enclosure outlet (226) into the outlet tubing (256), then through an outlet valve (247) and is collected in a waste collection bag (216), which can be the same waste collection bag as used to collect reaction mixture components that passed through the filter in the previous step, or a new waste collection bag swapped in place of the first waste collection bag before the buffer was allowed to enter the second assembly opening (218). The optional wash step can be optionally performed multiple times by repeating the above process with additional buffer.

Once the entire or substantially the entire volume of the reaction mixture in the blood bag (215) passes over the filter (210), and the optional washing step(s) is optionally performed, a reverse perfusion process is initiated to move fluid in an opposite direction in the assembly (200) to collect lymphocytes retained on the filter set within the filter enclosure (210). Illustrative embodiments of leukodepletion filter assemblies herein are adaptable for reperfusion. Before initiating the reverse perfusion process in the illustrative assembly (200), the outlet valve (247) is switched to a reperfusion position and the collection valve (245) is switched to a collection position. To initiate reperfusion, a buffer (e.g. PBS) in syringe (266), which for example can be a 25 ml syringe, is passed into outlet tubing (256) by injection using syringe (266). The buffer then enters the filter enclosure (210) through the filter enclosure outlet (226) and moves lymphocytes retained on the filter set out of the filter enclosure (210) through the filter enclosure inlet (225) and into the inlet tubing (255). Then lymphocytes, including some T cells and/or NK cells with associated retroviral particles, some of which could be genetically modified and/or transduced at this point, are collected in a cell sample collection bag (265), which for example can be a 25 ml cryopreservation bag, after the pass through the collection valve (245).

In some aspects, provided herein is a kit for genetically modifying NK cells and/or in illustrative embodiments, T cells. The kit includes a leukodepletion filtration assembly and any of the replication incompetent retroviral vector embodiments disclosed herein, typically contained in a tube or vial. The leukodepletion filtration assembly in such a kit typically includes a leukodepletion filter or a leukodepletion filter set, typically within a filter enclosure, as exemplified by the illustrative assembly of FIG. 2, as well as a plurality of connected sterile tubes and a plurality of valves connected thereto, that are adapted for use in a single-use closed blood processing system. Such a kit optionally includes a blood collection bag, in illustrative embodiments comprising an anti-coagulant, a blood processing buffer bag, a blood processing waste collection bag, a blood processing cell sample collection bag, and a sterile syringe. In illustrative embodiments, the kit includes a T cell activation element as disclosed in detail herein, for example anti-CD3. Such activation element can be provided in solution in the tube or vial containing the retroviral particle, or in a separate tube or vial. In illustrative embodiments, the activation element is an anti-CD3 associated with a surface of the replication incompetent retroviral particle. In illustrative embodiments, the replication incompetent recombinant retroviral particles in the kit comprise a polynucleotide comprising one or more transcriptional units operatively linked to a promoter active in T cells and/or NK cells, wherein the one or more transcriptional units encode a first polypeptide comprising a chimeric antigen receptor (CAR) and optionally a lymphoproliferative element, according to any of the embodiments provided herein.

Steps and Reaction Mixtures for Methods for Genetically Modifying Lymphocytes

Some embodiments of any methods used in any aspects provided herein, which are typically methods for genetically modifying lymphocytes, PBMCs, and in illustrative embodiments NK cells and/or in further illustrative embodiments, T cells, can include a step of collecting blood from a subject. The blood includes blood components including blood cells such as lymphocytes (e.g. T cells and NK cells) that can be used in methods and compositions provided herein. In certain illustrative embodiments, the subject is a human subject afflicted with cancer (i.e. a human cancer subject). It is noteworthy that certain embodiments, do not include such a step. However, in embodiments that include collecting blood from a subject, blood can be collected or obtained from a subject by any suitable method known in the art as discussed in more detail herein. For example, the blood can be collected by venipuncture or any other blood collection method by which a sample of blood is collected. In some embodiments, the volume of blood collected is between 50 ml and 250 ml, for example, between 75 ml and 125 ml, or between 90 ml and 120 ml, or between 95 and 110 ml. In some embodiments, the volume of blood collected can be between 25, 30, 35, 40, 45, 50, 55, 60, 65, 70, 75, 80, 85, 90, 95, 100, 110, 120, 130, 140, 150, 175, 200, 225, 250, 275, 300, 350, 400, 450, 500, 600, 700, 800, or 900 ml on the low end of the range and 30, 35, 40, 45, 50, 55, 60, 65, 70, 75, 80, 85, 90, 95, 100, 110, 120, 130, 140, 150, 175, 200, 225, 250, 275, 300, 350, 400, 450, 500, 600, 700, 800, or 900 ml or 1 L on the high end of the range. In some embodiments, lymphocytes (e.g. T cells and/or NK cells) can be obtained by apheresis. In some embodiments, the volume of blood taken and processed during apheresis can be between 0.5, 0.6, 0.7, 0.75, 0.8, 0.9, 1, 1.25, or 1.5 total blood volumes of a subject on the low end of the range and 0.6, 0.7, 0.75, 0.8, 0.9, 1, 1.25, 1.5 1.75, 2, 2.25, or 2.5 total blood volumes of a subject on the high end of the range. The total blood volume of a human typically ranges from 4.5 to 6 L and thus much more blood is taken and processed during apheresis than if the blood is collected and then lymphocytes therein are genetically modified and/or transduced, as in illustrative embodiments herein.

Regardless of whether blood is collected from a subject, in any of the method aspects provided herein for genetically modifying lymphocytes (e.g. T cells and/or NK cells), the lymphocytes are contacted with replication incompetent retroviral particles in a reaction mixture. The contacting in any embodiment provided herein, can be performed for example in a chamber of a closed system adapted for processing of blood cells, for example within a blood bag, as discussed in more detail herein. The transduction reaction mixture can include one or more buffers, ions, and a culture media. With respect to retroviral particles, and in illustrative embodiments, lentiviral particles, in certain exemplary reaction mixtures provided herein, between 0.1 and 50, 0.5 and 50, 0.5 and 20, 0.5 and 10, 1 and 25, 1 and 15, 1 and 10, 1 and 5, 2 and 15, 2 and 10, 2 and 7, 2 and 3, 3 and 10, 3 and 15, or 5 and 15, multiplicity of infection (MOI); or at least 1 and less than 6, 11, or 51 MOI; or in some embodiments, between 5 and 10 MOI units of replication incompetent recombinant retroviral particles are present. In some embodiments, the MOI can be at least 0.1, 0.5, 1, 2, 2.5, 3, 5, 10 or 15. With respect to composition and method for transducing lymphocytes in blood, in certain embodiments higher MOI can be used than in methods wherein PBMCs are isolated and used in the reaction mixtures. For example, illustrative embodiments of compositions and methods for transducing lymphocytes in whole blood, assuming $1\times10^6$ PBMCs/ml of blood, can use retroviral particles with an MOI of between 1 and 50, 2 and 25, 2.5 and 20, 2.5 and 10, 4 and 6, or about 5, and in some embodiments between 5 and 20, 5 and 15, 10 and 20, or 10 and 15.

In illustrative embodiments, this contacting, and the reaction mixture in which the contacting occurs, takes place within a closed cell processing system, as discussed in more detail herein. A packaging cell, and in illustrative embodiments a packaging cell line, and in particularly illustrative embodiments a packaging cell provided in certain aspects herein, can be used to produce the replication incompetent recombinant retroviral particles. The lymphocytes in the reaction mixture can be PBMCs, or in aspects herein that provide compositions and methods for transducing lymphocytes in whole blood, an anti-coagulant and/or an additional blood component, including additional types of blood cells that are not PBMCs, as discussed herein. In fact, in illustrative embodiments of these composition and method aspects for transducing lymphocytes in whole blood, the reaction mixture can essentially be whole blood, and typically an anti-coagulant, retroviral particles, and a small amount of the solution in which the retroviral particles were delivered to the whole blood.

In some reaction mixture provided herein, T-cells can be present for example, between 10, 20, 30, or 40% of the lymphocytes of the reaction mixture on the low end of the range, and between 40, 50, 60, 70, 80, or 90% of the lymphocytes of the reaction mixture on the high end of the range. In illustrative embodiments, T-cells comprise between 10 and 90%, between 20 and 90%, between 30 and 90%, between 40 and 90%, between 40 and 80%, between 45% to 75% or of the lymphocytes. In such embodiments, for example, NK cells can be present at between 1, 2, 3, 4, or 5% of the lymphocytes of the reaction mixture on the low end of the range, and between 5, 6, 7, 8, 9, 10, 11, 12, 13, or 14% of the lymphocytes of the reaction mixture on the high end of the range. In illustrative embodiments, T-cells comprise between 1 and 14%, between 2 and 14%, between 3 and 14%, between 4 and 14%, between 5 and 14%, between 5 to 13%, between 5 to 12%, between 5 to 11% or, between 5 to 10% of the lymphocytes of the reaction mixture.

In reaction mixtures that relate to composition and method aspects for genetically modifying lymphocytes in whole blood provided herein, lymphocytes, including NK cells and T cells, can be present at a lower percent of blood cells, and at a lower percentage of white blood cells, in the reaction mixture than methods that involve a PBMC enrichment procedure before forming the reaction mixture. For example, in some embodiments of these aspects, more granulocytes or neutrophils are present in the reaction mixture than NK cells or even T cells. Details regarding compositions of anti-coagulants and one or more additional blood components present in the reaction mixtures of aspects for genetically modifying lymphocytes in whole blood, are provided in detail in other sections herein.

As disclosed herein, composition and method aspects for transducing lymphocytes in whole blood typically do not involve a PBMC enrichment step of a blood sample, before lymphocytes from the blood sample are contacted with retroviral particles in the reaction mixtures disclosed herein for those aspects. However, in some embodiments, neutrophils/granulocytes are separated away from other blood cells before the cells are contacted with replication incompetent recombinant retroviral particles. In some embodiments, peripheral blood mononuclear cells (PBMCs) including peripheral blood lymphocytes (PBLs) such as T cell and/or NK cells, are isolated away from other components of a blood sample using for example, a PBMC enrichment procedure, before they are combined into a reaction mixture with retroviral particles.

A PBMC enrichment procedure is a procedure in which PBMCs are enriched at least 25-fold, and typically at least 50-fold from other blood cell types. For example, it is believed that PBMCs make up less than 1% of blood cells in whole blood. After a PBMC enrichment procedure, at least 30%, and in some examples as many as 70% of cells isolated in the PBMC fraction are PBMCs. It is possible that even higher enrichment of PBMCs is achieved using some PBMC enrichment procedures. Various different PBMC enrichment procedures are known in the art. For example, a PBMC enrichment procedure is a ficoll density gradient centrifugation process that separates the main cell populations, such as lymphocytes, monocytes, granulocytes, and red blood cells, throughout a density gradient medium. In such a method the aqueous medium includes ficoll, a hydrophilic polysaccharide that forms the high density solution. Layering of whole blood over or under a density medium without mixing of the two layers followed by centrifugation will disperse the cells according to their densities with the PBMC fraction forming a thin white layer at the interface between the plasma and the density gradient medium (see e.g. Panda and Ravindran (2013) Isolation of Human PBMCs. BioProtoc. Vol. 3(3)). Furthermore, centripetal forces can be used to separate PBMCs from other blood components, in ficoll using the spinning force of a Sepax cell processing system.

In another PBMC enrichment method, an automated leukapheresis collection system (such as SPECTRA OPTIA® APHERESIS SYSTEM form TERUMO BCT, INC. Lakewood Colo. 80215, USA) is used to separate the inflow of whole blood from the target PBMC fraction using high-speed centrifugation while typically returning the outflow material, such as plasma, red blood cells, and granulocytes, back to the donor, although this returning would be optional in methods provided herein. Further processing may be necessary to remove residual red blood cells and granulocytes. Both methods include a time intensive purification of the PBMCs, and the leukapheresis method requires the presence and participation of the patient during the PBMC enrichment step.

As further non-limiting examples of PBMC enrichment procedures, in some embodiments for methods of transducing or genetically modifying herein, PBMCs are isolated using a Sepax or Sepax 2 cell processing system (BioSafe). In some embodiments, the PBMCs are isolated using a CliniMACS Prodigy cell processor (Miltenyi Biotec). In some embodiments, an automated apheresis separator is used which takes blood from the subject, passes the blood through an apparatus that sorts out a particular cell type (such as, for example, PBMCs), and returns the remainder back into the subject. Density gradient centrifugation can be performed after apheresis. In some embodiments, the PBMCs are isolated using a leukodepletion filter assembly. In some embodiments, magnetic bead activated cell sorting is then used for purifying a specific cell population from PBMCs, such as, for example, PBLs or a subset thereof, according to a cellular phenotype (i.e. positive selection), before they are used in a reaction mixture herein.

Other methods for purification can also be used, such as, for example, substrate adhesion, which utilizes a substrate that mimics the environment that a T cell encounters during recruitment, to purify T cells before adding them to a reaction mixture, or negative selection can be used, in which unwanted cells are targeted for removal with antibody complexes that target the unwanted cells for removal before a reaction mixture for a contacting step is formed. In some embodiments, red blood cell rosetting can be used to remove red blood cells before forming a reaction mixture. In other embodiments, hematopoietic stem cells can be removed before a contacting step, and thus in these embodiments, are not present during the contacting step. In some embodiments herein, especially for compositions and methods for transducing lymphocytes in whole blood, an ABC transporter inhibitor and/or substrate is not present before, during, or both before and during the contacting (i.e. not present in the reaction mixture in which contacting takes place) with or without optional incubating, or any step of the method.

In certain illustrative embodiments for any aspects provided herein, lymphocytes are genetically modified and/or transduced without prior activation or stimulation, and/or without requiring prior activation or stimulation, whether in vivo, in vitro, or ex-vivo; and/or furthermore, in some embodiments, without ex vivo or in vitro activation or stimulation after an initial contacting with or without an optional incubation, or without requiring ex vivo or in vitro activation or stimulation after an initial contacting with or without an optional incubation. Thus, in illustrative embodiments, some, most, at least 25%, 50%, 60%, 70%, 75%, 80%, 90%, at least 95%, at least 99%, or all of the lymphocytes are resting when they are combined with retroviral particles to form a reaction mixture, and typically are resting when they are contacted with retroviral viral particles in a reaction mixture. In methods for genetically modifying lymphocytes such as T cells and/or NK cells in blood or a component thereof, lymphocytes can be contacted in the typically resting state they were in when present in the collected blood in vivo immediately before collection. In some embodiments, the T cells and/or NK cells consist of between 95 and 100% resting cells (Ki-67). In some embodiments, the T cell and/or NK cells that are contacted by replication incompetent recombinant retroviral particles include between 90, 91, 92, 93, 94, and 95% resting cells on the low end of the range and 96, 97, 98, 99, or 100% resting cells on the high end of the range. In some embodiments, the T cells and/or NK cells include naïve cells. In some illustrative embodiments, the subembodiments in this paragraph are included in composition and method aspects for transducing lymphocytes in whole blood.

Contact between the T cells and/or NK cells and the replication incompetent recombinant retroviral particles can facilitate transduction of the T cells and/or NK cells by the replication incompetent recombinant retroviral particles. Not to be limited by theory, during the period of contact, the replication incompetent recombinant retroviral particles identify and bind to T cells and/or NK cells at which point the retroviral and host cell membranes start to fuse. Then, as a next step in the process of transduction, genetic material from the replication incompetent recombinant retroviral particles enters the T cells and/or NK cells at which time the T cells and/or NK cells are "genetically modified" as the phrase is used herein. It is noteworthy that such process might occur hours or even days after the contacting is initiated, and even after non-associated retroviral particles are rinsed away. Then the genetic material is typically integrated into the genomic DNA of the T cells and/or NK cells, at which time the T cells and/or NK cells are now "transduced" as the term is used herein. Accordingly, in illustrative embodiments, any method for genetically modifying lymphocytes (e.g. T cells and/or NK cells) herein, is a method for transducing lymphocytes (e.g. T cells and/or NK cells). It is believed that by day 6 in vivo or ex vivo, after contacting is initiated, the vast majority of genetically modified cells have been transduced. Methods of lentiviral transduction are known. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. Throughout this disclosure, a transduced T cell and/or NK cell includes progeny of ex vivo transduced cells that retain at least some of the nucleic acids or polynucleotides that are incorporated into the genome of a cell during the ex vivo transduction. In methods herein that recite "reintroducing" a transduced cell, it will be understood that such cell is typically not in a transduced state when it is collected from the blood of a subject.

Many of the methods provided herein include genetic modification and transduction of T cells and/or NK cells. Methods are known in the art for genetically modifying and transducing T cells and/or NK cells ex vivo with replication incompetent recombinant retroviral particles, such as replication incompetent recombinant lentiviral particles. Methods provided herein, in illustrative embodiments, do not require ex vivo stimulation or activation. Thus, this common step in prior methods can be avoided in the present method, although ex vivo stimulatory molecule(s) such as anti-CD3 and/or anti-CD28 beads, can be present during the contacting and optional incubation thereafter. However, with illustrative methods provided herein, ex vivo stimulation is not required.

In certain illustrative embodiments for any aspects herein, the blood cells, such as lymphocytes, and especially T cells and/or NK cells are activated during the contacting or an optional incubation thereafter, and are not activated at all or for more than 15 minutes, 30 minutes, 1, 2, 4, or 8 hours before the contacting. In certain illustrative embodiments, activation by elements that are not present on the retroviral particle surface is not required for genetically modifying the lymphocytes. Accordingly, such activation or stimulation elements are not required other than on the retroviral particle, before, during, or after the contacting. Thus, as discussed in more detail herein, these illustrative embodiments that do not require pre-activation or stimulation provide the ability to rapidly perform in vitro experiments aimed at better understanding T cells and the biologicals mechanisms, therein. Furthermore, such methods provide for much more efficient commercial production of biological products produced using PBMCs, lymphocytes, T cells, or NK cells, and development of such commercial production methods. Finally, such methods provide for more rapid ex vivo processing of lymphocytes (e.g. NK cells and especially T cells) for adoptive cell therapy, fundamentally simplifying the delivery of such therapies, for example by providing point of care methods.

Although in illustrative embodiments, T cells and/or NK cells are not activated prior to being contacted with a recombinant retrovirus in methods herein, a T cell activation element in illustrative embodiments is present in the reaction mixture where initial contacting of a recombinant retrovirus and lymphocytes occurs. For example, such T cell activation element can be in solution in the reaction mixture. For example, soluble anti-CD3 antibodies can be present in the reaction mixture during the contacting and optional incubation thereafter, at 25-200, 50-150, 75-125, or 100 ng/ml. In illustrative embodiments, the T cell activation element is associated with the retroviral surface. The T cell activation element can be any T cell activation element provided herein. In illustrative embodiments, the T cell activation element can be anti-CD3, such as anti-CD3 scFv, or anti-CD3 scFvFc. Accordingly, in some embodiments, the replication incompetent recombinant retroviral particle can further include a T cell activation element, which in further illustrative examples is associated with the external side of the surface of the retrovirus.

The contacting step of a method for transducing and/or a method for genetically modifying lymphocytes in whole blood, provided herein, typically includes an initial step in which the retroviral particle, typically a population of retroviral particles, are brought into contact with blood cells, typically a population of blood cells that includes an anticoagulant and/or additional blood components other than PBMCs, that are not present after a PBMC enrichment procedure, while in suspension in a liquid buffer and/or media to form a transduction reaction mixture. This contacting, as in other aspects provided herein, can be followed by an optional incubating period in this reaction mixture that includes the retroviral particles and the blood cells comprising lymphocytes (e.g. T cells and/or NK cells) in suspension. In methods for genetically modifying T cells and/or NK cells in blood or a component thereof, the reaction mixture can include at least one, two, three, four, five, or all additional blood components as disclosed herein, and in illustrative embodiments includes one or more anticoagulants.

The transduction reaction mixture in any of the aspects provided herein can be incubated at between 23 and 39° C., and in some illustrative embodiments at 37° C., in an optional incubation step after the initial contacting of retroviral particles and lymphocytes. In certain embodiments, the transduction reaction can be carried out at 37-39° C. for faster fusion/transduction. The cells and retroviral particles when brought into contact in the transduction reaction mixture can be immediately processed to remove the retroviral particles that remain free in suspension and not associated with cells, from the cells. Optionally, the cells in suspension and retroviral particles whether free in suspension or associated with the cells in suspension, can be incubated for various lengths of time, as provided herein for a contacting step in a method provided herein. Before further steps, a wash can be performed, regardless of whether such cells will be studied in vitro, ex vivo or introduced into a subject.

Illustrative methods are disclosed herein for genetically modifying lymphocytes, especially NK cells and in illustrative embodiments, T cells, that are much shorter and simpler than prior methods. Accordingly, in some embodiments, the contacting step in any method provided herein of transducing and/or genetically modifying a PBMC or a lymphocyte, typically a T cell and/or an NK cell, can be performed (or can occur) for any of the time periods provided in this specification, included, but not limited to those provided in the Exemplary Embodiments section. For example, said contacting can be for less than 24 hours, for example, less than 12 hours, less than 8 hours, less than 4 hours, less than 2 hours, less than 1 hour, less than 30 minutes or less than 15 minutes, but in each case there is at least an initial contacting step in which retroviral particles and cells come into contact in suspension in a transduction reaction mixture before retroviral particles that remain in suspension not associated with a cell, are separated from cells and typically discarded, as discussed in further detail herein. It should be noted, but not intending to be limited by theory, that it is believed that contacting begins at the time that retroviral particles and lymphocytes are combined together, typically by adding a solution containing the retroviral particles into a solution containing lymphocytes (e.g. T cells and/or NK cells).

After such initial contacting, in some embodiments there is an incubating of the reaction mixture containing cells and retroviral particles in suspension for a specified time period without removing retroviral particles that remain free in solution and not associated with cells. This incubating is sometimes referred to herein as an optional incubation. Thus, In illustrative embodiments, the contacting (including initial contacting and optional incubation) can be performed (or can occur) (where as indicated in general herein the low end of a selected range is less than the high end of the selected range) for between 30 seconds or 1, 2, 5, 10, 15, 30 or 45 minutes, or 1, 2, 3, 4, 5, 6, 7, or 8 hours on the low end of the range, and between 10 minutes, 15 minutes, 30 minutes, or 1, 2, 4, 6, 8, 10, 12, 18, 24, 36, 48, and 72 hours on the high end of the range. In certain illustrative embodiments, the contacting step can be performed for between 30 seconds, 1 minute, 5 minutes, 10 minutes, 15 minutes, or 30 minutes on the low end of the range and 1 hour, 2 hours, 4 hours, 6 hours, 8 hours, 10 hours, or 12 hours on the high end of the range. In some embodiments, the contacting step is performed for between 30 seconds, 1 minute, and 5 minutes on the low end of the range, and 10 minutes, 15 minutes, 30 minutes, 1 hour, 2 hours, 4 hours, or 8 hours on the high end of the range. Thus, in some embodiments, after the time when a reaction mixture is formed by adding retroviral particles to lymphocytes, the reaction mixture can be incubated for between 5 minutes and 12 hours, between 5 minutes and 10 hours, between 5 minutes and 8 hours, between 5 minutes and 6 hours, between 5 minutes and 4 hours, between 5 minutes and 2 hours, between 5 minutes and 1 hour, between 5 minutes and 30 minutes, or between 5 minutes and 15 minutes. In other embodiments, the reaction mixture can be incubated for between 15 minutes and 12 hours, between 15 minutes and 10 hours, between 15 minutes and 8 hours, between 15 minutes and 6 hours, between 15 minutes and 4 hours, between 15 minutes and 2 hours, between 15 minutes and 1 hour, between 15 minutes and 45 minutes, or between 15 minutes and 30 minutes. In other embodiments, the reaction mixture can be incubated for between 30 minutes and 12 hours, between 30 minutes and 10 hours, between 30 minutes and 8 hours, between 30 minutes and 6 hours, between 30 minutes and 4 hours, between 30 minutes and 2 hours, between 30 minutes and 1 hour, between 30 minutes and 45 minutes. In other embodiments, the reaction mixture can be incubated for between 1 hour and 12 hours, between 1 hour and 8 hours, between 1 hour and 4 hours, or between/hour and 2 hours. In another illustrative embodiment, the contacting is performed for between an initial contacting step only (without any further incubating in the reaction mixture including the retroviral particles free in suspension and cells in suspension) without any further incubation in the reaction mixture, or a 5 minute, 10 minute, 15 minute, 30 minute, or 1 hour incubation in the reaction mixture.

After the indicated time period for the initial contacting and optional incubation that can be part of the contacting step, blood cells or a T cell and/or NK cell-containing fraction thereof in the reaction mixture, are separated from retroviral particles that are not associated with such cells. For example, this can be performed using a PBMC enrichment procedure (e.g. a Ficoll gradient in a Sepax unit), or in certain illustrative embodiments provided herein, by filtering the reaction mixture over a leukocyte depletion filter set assembly, and then collecting the leukocytes, which include T cells and NK cells. In another embodiment, this can be performed by centrifugation of the reaction mixture at a relative centrifugal force less than 500 g, for example 400 g, or between 300 and 490 g, or between 350 and 450 g. Such centrifugation to separate retroviral particles from cells can be performed for example, for between 5 minutes and 15 minutes, or between 5 minutes and 10 minutes. In illustrative embodiments where centrifugal force is used to separate cells from retroviral particles that are not associated with cells, such g force is typically lower than the g forces used successfully in spinoculation procedures.

In some illustrative embodiments, a method provided herein in any aspect, does not involve performing a spinoculation. In some embodiments, spinoculation is included as part of a contacting step. In illustrative embodiments, when spinoculation is performed there is no additional incubating as part of the contacting, as the time of the spinoculation provides the incubation time of the optional incubation discussed above. In other embodiments, there is an additional incubation after the spinoculating of between 15 minutes and 4 hours, or between 15 minutes and 2 hours, or between 15 minutes and 1 hour. The spinoculation can be performed for example, for 30 minutes to 120 minutes, typically for at least 60 minutes, for example for 60 minutes to 180 minutes, or 60 minutes to 90 minutes. The spinoculation is typically performed in a centrifuge with a relative centrifugal force of at least 800 g, and more typically at least 1,200 g, for example between 800 g and 2400 g, or between 800 g and 1800 g, or between 1200 g and 2400 g, or between 1200 g and 1800 g. After the spinoculation, such methods typically involve an additional step of resuspending the pelleted cells and retroviral particles, and then removing retroviral particles that are not associated with cells according to steps discussed above when spinoculation is not performed.

The contacting step including the optional incubation therein, and the spinoculation, in embodiments that include spinoculation, can be performed at between 4 C and 42 C, or between 20 C and 37 C. In certain illustrative embodiments, spinoculation is not performed and the contacting and associated optional incubation are carried out at 20-25 C for 4 hours or less, 2 hours or less, 1 hour or less, 30 minutes or less, 15 minutes or less, or 15 minutes to 2 hours, 15 minutes to 1 hour, or 15 minutes to 30 minutes.

In some embodiments of the methods and compositions disclosed herein, between 5% and 85% of the total lymphocytes collected from the blood are genetically modified. In some embodiments, the percent of lymphocytes that are genetically modified and/or transduced is between 1, 5, and 10% on the low end of the range, and 15, 20, 25, 30, 40, 50, 60, 70, 80, and 85% on the high end of the range. In some embodiments, the percent of T cells and NK cells that are genetically modified and/or transduced is at least 5%, at least 10%, at least 15%, or at least 20%. As illustrated in the Examples herein, in exemplary methods provided herein for transducing lymphocytes in whole blood, between 1% and 20%, or between 1% and 15%, or between 5% and 15%, or between 7% and 12% or about 10% of lymphocytes are genetically modified and/or transduced.

Methods of genetically modifying lymphocytes provided according to any method herein, typically include insertion into the cell, of a polynucleotide comprising one or more transcriptional units encoding a CAR or a lymphoproliferative element, or in illustrative embodiments encoding both a CAR and a lymphoproliferative element according to any of the CAR and lymphoproliferative element embodiments provided herein. Such CAR and lymphoproliferative elements can be provided to support the shorter and more simplified methods provided herein, which can support expansion of genetically modified and/or transduced T cells and/or NK cells after the contacting and optional incubation. Accordingly, in exemplary embodiments of any methods provided herein, lymphoproliferative elements can be delivered from the genome of the retroviral particles inside genetically modified and/or transduced T cells and/or NK cells, such that those cells have the characteristics of increased proliferation and/or survival disclosed in the Lymphoproliferative Elements section herein. In exemplary embodiments of any methods provided herein, the genetically modified T cell or NK cell is capable of engraftment in vivo in mice and/or enrichment in vivo in mice for at least 7, 14, or 28 days. A skilled artisan will recognize that such mice may be treated or otherwise genetically modified so that any immunological differences between the genetically modified T cell and/or NK cell do not result in an immune response being elicited in the mice against any component of the lymphocyte transduced by the replication incompetent recombinant retroviral particle.

Media that can be included in a contacting step, for example when the cells and retroviral particles are initially brought into contact, or in any aspects provided herein, during optional incubation periods with the reaction mixture thereafter that include retroviral particles and cells in suspension in the media, or media that can be used during cell culturing and/or during various wash steps in any aspects provided herein, can include base media such as commercially available media for ex vivo T cell and/or NK cell culture. Non-limiting examples of such media include, X-VIVO™ 15 Chemically Defined, Serum-free Hematopoietic Cell Medium (Lonza) (2018 catalog numbers BE02-060F, BE02-00Q, BE-02-061Q, 04-744Q, or 04-418Q), ImmunoCult™-XF T Cell Expansion Medium (STEMCELL Technologies) (2018 catalog number 10981), PRIME-XV® T Cell Expansion XSFM (Irvine Scientific) (2018 catalog number 91141), AIM V® Medium CTS™ (Therapeutic Grade) (Thermo Fisher Scientific (Referred to herein as "Thermo Fisher"), or CTS™ Optimizer™ media (Thermo Fisher) (2018 catalog numbers A10221-01 (basal media (bottle)), and A10484-02 (supplement), A10221-03 (basal media (bag)), A1048501 (basal media and supplement kit (bottle)) and, A1048503 (basal media and supplement kit (bag)). Such media can be a chemically defined, serum-free formulation manufactured in compliance with cGMP. The media can be xeno-free and complete. In some embodiments, the base media has been cleared by regulatory agencies for use in ex vivo cell processing, such as an FDA 510(k) cleared device. In some embodiments, the media is the basal media with or without the supplied T cell expansion supplement of 2018 catalog number A1048501 (CTS™ OpTmizer™ T Cell Expansion SFM, bottle format) or A1048503 (CTS™ OpTmizer™ T Cell Expansion SFM, bag format) both available from Thermo Fisher (Waltham, Mass.). Additives such as human serum albumin, human AB+ serum, and/or serum derived from the subject can be added to the transduction reaction mixture. Supportive cytokines can be added to the transduction reaction mixture, such as IL2, IL7, or IL15, or those found in human sera. dGTP can be added to the transduction reaction in certain embodiments.

In some embodiments of any method herein that includes a step of genetically modifying lymphocytes (e.g. T cells and/or NK cells), the cells can be contacted with a retroviral particle without prior activation. In some embodiments of any method herein that includes a step of genetically modifying T cells and/or NK cells, the T cells and/or NK cells have not been incubated on a substrate that adheres to monocytes for more than 4 hours in one embodiment, or for more than 6, hours in another embodiment, or for more than 8 hours in another embodiment before the transduction. In one illustrative embodiment, the T cells and/or NK cells have been incubated overnight on an adherent substrate to remove monocytes before the transduction. In another embodiment, the method can include incubating the T cells and/or NK cells on an adherent substrate that binds monocytes for no more than 30 minutes, 1 hour, or 2 hours before the transduction. In another embodiment, the T cells and/or NK cells are exposed to no step of removing monocytes by an incubation on an adherent substrate before said transduction step. In another embodiment, the T cells and/or NK cells are not incubated with or exposed to a bovine serum, such as a cell culturing bovine serum, for example fetal bovine serum before or during a contacting step and/or a genetically modifying and/or transduction step.

Some or all of the steps of the methods for genetically modifying provided herein, or uses of such methods, are performed in a closed system. Thus, reaction mixtures formed in such methods, and genetically modified and/or transduced lymphocytes (e.g. T cells and/or NK cells) made by such methods, can be contained within such a closed system. A closed system is a cell processing system that is generally closed or fully closed to an environment, such as an environment within a room or even the environment within a hood, outside of the conduits such as tubes, and chambers, of the system in which cells are processed and/or transported. One of the greatest risks to safety and regulatory control in the cell processing procedure is the risk of contamination through frequent exposure to the environment as is found in traditional open cell culture systems. To mitigate this risk, particularly in the absence of antibiotics, some commercial processes have been developed that focus on the use of disposable (single-use) equipment. However, even with their use under aseptic conditions, there is always a risk of contamination from the opening of flasks to sample or add additional growth media. To overcome this problem, methods provided herein, which are typically ex vivo methods, are typically performed within a closed-system. Such a process is designed and can be operated such that the product is not exposed to the outside environment. Material transfer occurs via sterile connections, such as sterile tubing and sterile welded connections. Air for gas exchange can occur via a gas permeable membrane, via 0.2 μm filter to prevent environmental exposure. In some illustrative embodiments, the methods are performed on T cells, for example to provide genetically modified T cells.

Such closed system methods can be performed with commercially available devices. Different closed system devices can be used at different steps within a method and the cells can be transferred between these devices using tubing and connections such as welded, luer, spike, or clave ports to prevent exposure of the cells or media to the environment. For example, blood can be collected into an IV bag or syringe, optionally including an anti-coagulant, and transferred to a Sepax 2 device (Biosafe) for PBMC enrichment and isolation. In other embodiments, whole blood can be filtered to collect leukocytes using a leukodepletion filter assembly. The isolated PBMCs or isolated leukocytes can be transferred to a chamber of a G-Rex device for an optional activation, a transduction and optional expansion. Alternatively, collected blood can be transduced in a blood bag, for example, the bag in which it was collected. Finally, the cells can be harvested and collected into another bag using a Sepax 2 device. The methods can be carried out in any device or combination of devices adapted for closed system T cell and/or NK cell production. Non-limiting examples of such devices include G-Rex devices (Wilson Wolf), GatheRex (Wilson Wolf), Sepax 2 (Biosafe), WAVE Bioreactors (General Electric), a CultiLife Cell Culture bag (Takara), a PermaLife bag (OriGen), CliniMACS Prodigy (Miltenyi Biotec), and VueLife bags (Saint-Gobain). In illustrative embodiments, the optional activating, the transducing and optional expanding can be performed in the same chamber or vessel in the closed system. For example, in illustrative embodiments, the chamber can be a chamber of a G-Rex device and PBMCs or leukocytes can be transferred to the chamber of the G-Rex device after they are enriched and isolated, and can remain in the same chamber of the G-Rex device until harvesting.

Methods provided herein can include transferring blood and cells therein and/or fractions thereof, as well as lymphocytes before or after they are contacted with retroviral particles, between vessels within a closed system, which thus is without environmental exposure. Vessels used in the closed system, for example, can be a tube, bag, syringe, or other container. In some embodiments, the vessel is a vessel that is used in a research facility. In some embodiments, the vessel is a vessel used in commercial production. In other embodiments, the vessel can be a collection vessel used in a blood collection process. Methods for genetically modifying herein, typically involve a contacting step wherein lymphocytes are contacted with a replication incompetent recombinant retroviral particle. The contacting in some embodiments, can be performed in the vessel, for example, within a blood bag. Blood and various lymphocyte-containing fractions thereof, can be transferred from the vessel to another vessel (for example from a first vessel to a second vessel) within the closed system for the contacting. The second vessel can be a cell processing compartment of a closed device, such as a G-Rex device. In some embodiments, after the contacting the genetically modified (e.g. transduced) cells can be transferred to a different vessel within the closed system (i.e. without exposure to the environment). Either before or after this transfer the cells are typically washed within the closed system to remove substantially all or all of the retroviral particles. In some embodiments, a process disclosed herein, from collection of blood, to contacting (e.g. transduction), optional incubating, and post-incubation isolation and optional washing, is performed for between 15 minutes, 30 minutes, or 1, 2, 3, or 4 hours on the low end of the range, and 4, 8, 10, or 12 hours on the high end of the range.

Not to be limited by theory, in non-limiting illustrative methods, the delivery of a polynucleotide encoding a lymphoproliferative element, to a resting T cell and/or NK cell ex vivo, which can integrate into the genome of the T cell or NK cell, provides that cell with a driver for in vivo expansion without the need for lymphodepleting the host. Thus, in illustrative embodiments, the subject is not exposed to a lymphodepleting agent within 1, 2, 3, 4, 5, 6, 7, 10, 14, 21, or 28 days, or within 1 month, 2 months, 3 months or 6 months of performing the contacting, during the contacting, and/or within 1, 2, 3, 4, 5, 6, 7, 10, 14, 21, or 28 days, or within 1 month, 2 months, 3 months or 6 months after the modified T cells and/or NK cells are reintroduced back into the subject. Furthermore, in non-limiting illustrative embodiments, methods provided herein can be performed without exposing the subject to a lymphodepleting agent during a step wherein a replication incompetent recombinant retroviral particle is in contact with resting T cells and/or resting NK cells of the subject and/or during the entire ex vivo method. Hence, methods of expanding genetically modified T cells and/or NK cells in a subject in vivo is a feature of some embodiments of the present disclosure. In illustrative embodiments, such methods are ex vivo propagation-free or substantially propagation-free.

This entire method/process from blood draw from a subject to reintroduction of blood back into the subject after ex vivo transduction of T cells and/or NK cells, in non-limiting illustrative embodiments of any aspects provided herein, can occur over a time period less than 48 hours, less than 36 hours, less than 24 hours, less than 12 hours, less than 11 hours, less than 10 hours, less than 9 hours, less than 8 hours, less than 7 hours, less than 6 hours, less than 5 hours, less than 4 hours, less than 3 hours, 2 hours, or less than 2 hours. In other embodiments, the entire method/process from blood draw/collection from a subject to reintroduction of blood back into the subject after ex vivo transduction of T cells and/or NK cells, in non-limiting illustrative embodiments herein, occurs over a time period between 1 hour and 12 hours, or between 2 hours and 8 hours, or between 1 hour and 3 hours, or between 2 hours and 4 hours, or between 2 hours and 6 hours, or between 4 hours and 12 hours, or between 4 hours and 24 hours, or between 8 hours and 24 hours, or between 8 hours and 36 hours, or between 8 hours and 48 hours, or between 12 hours and 24 hours, or between 12 hours and 36 hours, or between 12 hours and 48 hours, or over a time period between 15, 30, 60, 90, 120, 180, and 240 minutes on the low end of the range, and 120, 180, and 240, 300, 360, 420, and 480 minutes on the high end of the range. In other embodiments, the entire method/process from blood draw/collection from a subject to reintroduction of blood back into the subject after ex vivo transduction of T cells and/or NK cells, occurs over a time period between 1, 2, 3, 4, 6, 8, 10, and 12 hours on the low end of the range, and 8, 9, 10, 11, 12, 18, 24, 36, or 48 hours on the high end of the range. In some embodiments, the genetically modified T cells and/or NK cells are separated from the replication incompetent recombinant retroviral particles after the time period in which contact occurs.

Because methods provided herein for genetically modifying lymphocytes, and associated methods for performing adoptive cell therapy can be performed in significantly less time than prior methods, fundamental improvements in patient care and safety as well as product manufacturability are made possible. Therefore, such processes are expected to be favorable in the view of regulatory agencies responsible for approving such processes when carried out in vivo for therapeutic purposes. For example, the subject in non-limiting examples of any aspects provided herein that include a subject, can remain in the same building (e.g. infusion clinic) or room as the instrument processing their blood or sample for the entire time that the sample is being processed before modified T cells and/or NK cells are reintroduced into the patient. In non-limiting illustrative embodiments, a subject remains within line of site and/or within 100, 50, 25, or 12 feet or arm's distance of their blood or cells that are being processed, for the entire method/process from blood draw/collection from the subject to reintroduction of blood to the subject after ex vivo transduction of T cells and/or NK cells. In other non-limiting illustrative embodiments, a subject remains awake and/or at least one person can continue to monitor the blood or cells of the subject that are being processed, throughout and/or continuously for the entire method/process from blood draw/collection from the subject to reintroduction of blood to the subject after ex vivo transduction of T cells and/or NK cells. Because of improvements provided herein, the entire method/process for adoptive cell therapy and/or for transducing resting T cells and/or NK cells from blood draw/collection from the subject to reintroduction of blood to the subject after ex vivo transduction of T cells and/or NK cells can be performed with continuous monitoring by a human. In other non-limiting illustrative embodiments, at no point the entire method/process from blood draw/collection from the subject to reintroduction of blood to the subject after ex vivo transduction of T cells and/or NK cells, are blood cells incubated in a room that does not have a person present. In other non-limiting illustrative embodiments, the entire method/process from blood draw/collection from the subject to reintroduction of blood to the subject after ex vivo transduction of T cells and/or NK cells, is performed next to the subject and/or in the same room as the subject and/or next to the bed or chair of the subject. Thus, sample identity mix-ups can be avoided, as well as long and expensive incubations over periods of days or weeks. This is further provided by the fact that methods provided herein are readily adaptable to closed and automated blood processing systems, where a blood sample and its components that will be reintroduced into the subject, only make contact with disposable, single-use components.

Methods for genetically modifying and/or transducing lymphocytes such as T cells and/or NK cells provided herein, can be part of a method for performing adoptive cell therapy. Typically, methods for performing adoptive cell therapy include steps of collecting blood from a subject, and returning genetically modified and/or transduced lymphocytes (e.g T cells and/or NK cells) to the subject. The present disclosure provides various treatment methods using a CAR. A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The ASTR of the CAR binds to an antigen present on the surface of a target cell. The present disclosure provides methods of killing, or inhibiting the growth of, a target cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cell, and mediates killing of the target cell. The target cell can be a cancer cell, for example, and autologous cell therapy methods herein, can be methods for treating cancer, in some illustrative embodiments. In these embodiments, the subject can be a an animal or human suspected of having cancer, or more typically, a subject that is known to have cancer.

In some embodiments of any of the methods provided herein for genetically modifying lymphocytes (e.g. T cells and/or NK cells), and aspects directed to use of replication incompetent recombinant retroviral particles in the manufacture of a kit for genetically modifying T cells and/or NK cells of a subject, the genetically modified and/or transduced lymphocyte (e.g. T cell and/or NK cell) or population thereof, are introduced or reintroduced into the subject. Introduction or reintroduction of the genetically modified lymphocytes into a subject can be via any route known in the art. For example, introduction or reintroduction can be delivery via infusion into a blood vessel of the subject. In some embodiments, the genetically modified and/or transduced lymphocyte (e.g. T cell and/or NK cell) or population thereof, undergo 4 or fewer cell divisions ex vivo prior to being introduced or reintroduced into the subject. In some embodiments, the lymphocyte(s) used in such a method are resting T cells and/or resting NK cells that are in contact with the replication incompetent recombinant retroviral particles for between 1 hour and 12 hours. In some embodiments, no more than 12 hours, 10 hours, 8 hours, 6 hours, 4 hours, 2 hours, or 1 hour pass(es) between the time blood is collected from the subject and the time the genetically modified T cells and/or NK cells are reintroduced into the subject. In some embodiments, all steps after the blood is collected and before the blood is reintroduced, are performed in a closed system in which a person monitors the closed system throughout the processing.

In some embodiments of the methods and compositions disclosed herein, the genetically modified T cells and/or NK cells are introduced back, reintroduced, reinfused or otherwise delivered into the subject without additional ex vivo manipulation, such as stimulation and/or activation of T cells and/or NKs. In the prior art methods, ex vivo manipulation is used for stimulation/activation of T cells and/or NK cells and for expansion of genetically modified T cells and/or NK cells prior to introducing the genetically modified T cells and/or NK cells into the subject. In prior art methods, this generally takes days or weeks and requires a subject to return to a clinic for a blood infusion days or weeks after an initial blood draw. In some embodiments of the methods and compositions disclosed herein, T cells and/or NK cells are not stimulated ex vivo by exposure to anti-CD3/anti-CD28 solid supports such as, for example, beads coated with anti-CD3/anti-CD28, prior to contacting the T cells and/or NK cells with the replication incompetent recombinant retroviral particles. As such provided herein is an ex vivo propagation-free method. In other embodiments, genetically modified T cells and/or NK cells are not expanded ex vivo, or only expanded for a small number of cell divisions (e.g. 1, 2, 3, 4, 5, 6, 7, 8, 9, or 10 rounds of cell division), but are rather expanded, or predominantly expanded, in vivo, i.e. within the subject. In some embodiments, no additional media is added to allow for further expansion of the cells. In some embodiments, no cell manufacturing of the primary blood lymphocytes (PBLs) occurs while the PBLs are contacted with the replication incompetent recombinant retroviral particles. In illustrative embodiments, no cell manufacturing of the PBLs occurs while the PBLs are ex vivo. In traditional methods of adoptive cell therapy, subjects are lymphodepleted prior to reinfusion with genetically modified T cells and or NK cells. In some embodiments, patients or subjects are not lymphodepleted prior to blood being withdrawn. In some embodiments, patients or subjects are not lymphodepleted prior to reinfusion with genetically modified T cells and or NK cells. However, the embodiments of the methods and compositions disclosed herein can be used on pre-activated or pre-stimulated T cells and/or NK cells as well. In some embodiments, T cells and/or NK cells can be stimulated ex vivo by exposure to anti-CD3/anti-CD28 solid supports prior to contacting the T cells and/or NK cells with the replication incompetent recombinant retroviral particles. In some embodiments, the T cells and/or NK cells can be exposed to anti-CD3/anti-CD28 solid supports for less than 1, 2, 3, 4, 6, 8, 10, 12, 14, 16, 18, or 24 hours, including no exposure, before the T cells and/or NK cells are contacted the replication incompetent recombinant retroviral particles. In illustrative embodiments, the T cells and/or NK cells can be exposed to anti-CD3/anti-CD28 solid supports for less than 1, 2, 3, 4, 6, or 8 hours before the T cells and/or NK cells are contacted the replication incompetent recombinant retroviral particles.

In some illustrative embodiments, cells are introduced or reintroduced into the subject by infusion into a vein or artery. In any of the embodiments disclosed herein, the number of T cells and/or NK cells to be reinfused into a subject can be between $1\times10^3$, $2.5\times10^3$, $5\times10^3$, $1\times10^4$, $2.5\times10^4$, $5\times10^4$, $1\times10^5$, $2.5\times10^5$, $5\times10^5$, $1\times10^6$, $2.5\times10^6$, $5\times10^6$, and $1\times10^7$ cells/kg on the low end of the range and $5\times10^4$, $1\times10^5$, $2.5\times10^5$, $5\times10^5$, $1\times10^6$, $2.5\times10^6$, $5\times10^6$, $1\times10^7$, $2.5\times10^7$, $5\times10^7$, and $1\times10^8$ cells/kg on the high end of the range. In illustrative embodiments, the number of T cells and/or NK cells to be reinfused or otherwise delivered into a subject can be between $1\times10^4$, $2.5\times10^4$, $5\times10^4$, and $1\times10^5$ cells/kg on the low end of the range and $2.5\times10^4$, $5\times10^4$, $1\times10^5$, $2.5\times10^5$, $5\times10^5$, and $1\times10^6$ cells/kg on the high end of the range. In some embodiments, the number of PBLs to be reinfused or otherwise delivered into a subject can be fewer than $5\times10^5$, $1\times10^6$, $2.5\times10^6$, $5\times10^6$, $1\times10^7$, $2.5\times10^7$, $5\times10^7$, and $1\times10^8$ cells and the low end of the range and $2.5\times10^6$, $5\times10^6$, $1\times10^7$, $2.5\times10^7$, $5\times10^7$, $1\times10^8$, $2.5\times10^8$, $5\times10^8$, and $1\times10^9$ cells on the high end of the range. In some embodiments, the number of T cells and/or NK cells available for infusion or reinfusion into a 70 kg subject or patient is between $7\times10^5$ and $2.5\times10^8$ cells. In other embodiments, the number of T cells and/or NK cells available for transduction is approximately $7\times10^6$ plus or minus 10%.

Engineered Signaling Polypeptide(S)

In some embodiments, the replication incompetent recombinant retroviral particles used to contact T cells and/or NK cells have a polynucleotide or nucleic acid having one or more transcriptional units that encode one or more engineered signaling polypeptides. In some embodiments, an engineered signaling polypeptide includes any combination of an extracellular domain (e.g. an antigen-specific targeting region or ASTR), a stalk and a transmembrane domain, combined with one or more intracellular activating domains, optionally one or more modulatory domains (such as a co-stimulatory domain), and optionally one or more T cell survival motifs. In illustrative embodiments, at least one, two, or all of the engineered signaling polypeptides is a chimeric antigen receptor (CAR) or a lymphoproliferative element (LE) such as a chimeric lymphoproliferative element (CLE). In some embodiments, at least one, two, or all of the engineered signaling polypeptides is a recombinant T cell receptor (TCR). In some embodiments, when two signaling polypeptides are utilized, one encodes a lymphoproliferative element and the other encodes a chimeric antigen receptor (CAR) that includes an antigen-specific targeting region (ASTR), a transmembrane domain, and an intracellular activating domain. For any domain of an engineered signaling polypeptide disclosed herein, exemplary sequences can be found in WO2019/055946, incorporated herein in its entirety by reference. A skilled artisan will recognize that such engineered polypeptides can also be referred to as recombinant polypeptides. The engineered signaling polypeptides, such as CARs, recombinant TCRs, LEs, and CLEs provided herein, are typically transgenes with respect to lymphocytes, especially T cells and NK cells, and most especially T cells and/or NK cells that are engineered using methods and compositions provided herein, to express such signaling polypeptides.

Extracellular Domain

In some embodiments, an engineered signaling polypeptide includes an extracellular domain that is a member of a specific binding pair. For example, in some embodiments, the extracellular domain can be the extracellular domain of a cytokine receptor, or a mutant thereof, or a hormone receptor, or a mutant thereof. Such mutant extracellular domains in some embodiments have been reported to be constitutively active when expressed at least in some cell types. In illustrative embodiments, such extracellular and transmembrane domains do not include a ligand binding region. It is believed that such domains do not bind a ligand when present in an engineered signaling polypeptide and expressed in B cells, T cells, and/or NK cells. Mutations in such receptor mutants can occur in the extracellular juxtamembrane region. Not to be limited by theory, a mutation in at least some extracellular domains (and some extracellular-transmembrane domains) of engineered signaling polypeptides provided herein, are responsible for signaling of the engineered signaling polypeptide in the absence of ligand, by bringing activating chains together that are not normally together. Further embodiments regarding extracellular domains that comprise mutations in extracellular domains can be found, for example, in the Lymphoproliferative Element section herein.

In certain illustrative embodiments, the extracellular domain comprises a dimerizing motif. In an illustrative embodiment the dimerizing motif comprises a leucine zipper. In some embodiments, the leucine zipper is from a jun polypeptide, for example c-jun. Further embodiments regarding extracellular domains that comprise a dimerizing motif can be found, for example, in the Lymphoproliferative Element section herein.

In certain embodiments, the extracellular domain is an antigen-specific targeting region (ASTR), sometimes called an antigen binding domain herein. Specific binding pairs include, but are not limited to, antigen-antibody binding pairs; ligand-receptor binding pairs; and the like. Thus, a member of a specific binding pair suitable for use in an engineered signaling polypeptide of the present disclosure includes an ASTR that is an antibody, an antigen, a ligand, a receptor binding domain of a ligand, a receptor, a ligand binding domain of a receptor, and an affibody.

An ASTR suitable for use in an engineered signaling polypeptide of the present disclosure can be any antigen-binding polypeptide. In certain embodiments, the ASTR is an antibody such as a full-length antibody, a single-chain antibody, an Fab fragment, an Fab' fragment, an (Fab')2 fragment, an Fv fragment, and a divalent single-chain antibody or a diabody.

In some embodiments, the ASTR is a single chain Fv (scFv). In some embodiments, the heavy chain is positioned N-terminal of the light chain in the engineered signaling polypeptide. In other embodiments, the light chain is positioned N-terminal of the heavy chain in the engineered signaling polypeptide. In any of the disclosed embodiments, the heavy and light chains can be separated by a linker as discussed in more detail herein. In any of the disclosed embodiments, the heavy or light chain can be at the N-terminus of the engineered signaling polypeptide and is typically C-terminal of another domain, such as a signal sequence or peptide.

Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use with the engineered signaling polypeptides and methods using the engineered signaling polypeptides of the present disclosure. In some instances, T cell receptor (TCR) based recognition domains.

Certain embodiments for any aspect or embodiment herein that includes a CAR, include CARs having extracellular domains engineered to co-opt the endogenous TCR signaling complex and CD3Z signaling pathway. In one embodiment, a chimeric antigen receptor ASTR is fused to one of the endogenous TCR complex chains (e.g. TCR alpha, CD3E etc) to promote incorporation into the TCR complex and signaling through the endogenous CD3Z chains. In other embodiments, a CAR contains a first scFv or protein that binds to the TCR complex and a second scFv or protein that binds to the target antigen (e.g. tumor antigen). In another embodiment, the TCR can be a single chain TCR (scTv, single chain two-domain TCR containing $V\alpha V\beta$). Finally, scFv's may also be generated to recognize the specific MHC/peptide complex, thereby acting as a surrogate TCR. Such peptide/MHC scFv-binders may be used in many similar configurations as CAR's.

In some embodiments, the ASTR can be multispecific, e.g. bispecific antibodies. Multispecific antibodies have binding specificities for at least two different sites. In certain embodiments, one of the binding specificities is for one target antigen and the other is for another target antigen. In certain embodiments, bispecific antibodies may bind to two different epitopes of a target antigen. Bispecific antibodies may also be used to localize cytotoxic agents to cells which express a target antigen. Bispecific antibodies can be prepared as full-length antibodies or antibody fragments.

An ASTR suitable for use in an engineered signaling polypeptide of the present disclosure can have a variety of antigen-binding specificities. In some cases, the antigen-binding domain is specific for an epitope present in an antigen that is expressed by (synthesized by) a target cell. In one example, the target cell is a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an ASTR of an engineered signaling polypeptide can bind include, e.g., CD19, CD20, CD38, CD30, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, Ax1, Ror2, and the like.

In some embodiments, a member of a specific binding pair suitable for use in an engineered signaling polypeptide is an ASTR that is a ligand for a receptor. Ligands include, but are not limited to, hormones (e.g. erythropoietin, growth hormone, leptin, etc.); cytokines (e.g., interferons, interleukins, certain hormones, etc.); growth factors (e.g., heregulin; vascular endothelial growth factor (VEGF); and the like); an integrin-binding peptide (e.g., a peptide comprising the sequence Arg-Gly-Asp (SEQ ID NO:1); and the like.

Where the member of a specific binding pair in an engineered signaling polypeptide is a ligand, the engineered signaling polypeptide can be activated in the presence of a second member of the specific binding pair, where the second member of the specific binding pair is a receptor for the ligand. For example, where the ligand is VEGF, the second member of the specific binding pair can be a VEGF receptor, including a soluble VEGF receptor.

As noted above, in some cases, the member of a specific binding pair that is included in an engineered signaling polypeptide is an ASTR that is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); CD27; a natural cytotoxicity receptor (NCR) (e.g., NKP30 (NCR3/CD337) polypeptide (receptor for HLA-B-associated transcript 3 (BAT3) and B7-H6); etc.); etc.

In certain embodiments of any of the aspects provided herein that include an ASTR, the ASTR can be directed to an intermediate protein that links the ASTR with a target molecule expressed on a target cell. The intermediate protein may be endogenously expressed or introduced exogenously and may be natural, engineered, or chemically modified. In certain embodiments the ASTR can be an anti-tag ASTR such that at least one tagged intermediate, typically an antibody-tag conjugate, is included between a tag recognized by the ASTR and a target molecule, typically a protein target, expressed on a target cell. Accordingly, in such embodiments, the ASTR binds a tag and the tag is conjugated to an antibody directed against an antigen on a target cell, such as a cancer cell. Non-limiting examples of tags include fluorescein isothiocyanate (FITC), streptavidin, biotin, histidine, dinitrophenol, peridinin chlorophyll protein complex, green fluorescent protein, phycoerythrin (PE), horse radish peroxidase, palmitoylation, nitrosylation, alkaline phosphatase, glucose oxidase, and maltose binding protein. As such, the ASTR comprises a molecule that binds the tag.

Stalk

In some embodiments, the engineered signaling polypeptide includes a stalk which is located in the portion of the engineered signaling polypeptide lying outside the cell and interposed between the ASTR and the transmembrane domain. In some embodiments, the stalk has at least 85, 90, 95, 96, 97, 98, 99, or 100% identity to a wild-type CD8 stalk region (TTTPAPRPPTPAPTIASQPLSLRPEACRPAAGGAVHTRGLDFA (SEQ ID NO:2), has at least 85, 90, 95, 96, 97, 98, 99, or 100% identity to a wild-type CD28 stalk region (FCKIEVMYPPPYLD-NEKSNGTIIHVKGKHLCPSPLFPGPSKP (SEQ ID NO:3), or has at least 85, 90, 95, 96, 97, 98, 99, or 100% identity to a wild-type immunoglobulin heavy chain stalk region. In an engineered signaling polypeptide, the stalk employed allows the antigen-specific targeting region, and typically the entire engineered signaling polypeptide, to retain increased binding to a target antigen.

The stalk region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

In some embodiments, the stalk of an engineered signaling polypeptide includes at least one cysteine. For example, In some embodiments, the stalk can include the sequence Cys-Pro-Pro-Cys (SEQ ID NO:4). If present, a cysteine in the stalk of a first engineered signaling polypeptide can be available to form a disulfide bond with a stalk in a second engineered signaling polypeptide.

Stalks can include immunoglobulin hinge region amino acid sequences that are known in the art; see, e.g., Tan et al. (1990) *Proc. Natl. Acad. Sci. USA* 87:162; and Huck et al. (1986) *Nucl. Acids Res.* 14:1779. As non-limiting examples, an immunoglobulin hinge region can include a domain with at least 50, 60, 70, 75, 80, 85, 90, 95, 96, 97, 98, 99 or 100% sequence identity to a stretch of at least 10, 15, 20, or all of the amino acids of any of the following amino acid sequences: DKTHT (SEQ ID NO:5); CPPC (SEQ ID NO:4); CPEPKSCDTPPPCPR (SEQ ID NO:6) (see, e.g., Glaser et al. (2005) *J. Biol. Chem.* 280:41494); ELKTPLGDTTHT (SEQ ID NO:7); KSCDKTHTCP (SEQ ID NO:8); KCCVDCP (SEQ ID NO:9); KYGPPCP (SEQ ID NO:10); EPKSCDKTHTCPPCP (SEQ ID NO:11) (human IgG1 hinge); ERKCCVECPPCP (SEQ ID NO:12) (human IgG2 hinge); ELKTPLGDTTHTCPRCP (SEQ ID NO:13) (human IgG3 hinge); SPNMVPHAHHAQ (SEQ ID NO:14) (human IgG4 hinge); and the like. The stalk can include a hinge region with an amino acid sequence of a human IgG1, IgG2, IgG3, or IgG4, hinge region. The stalk can include one or more amino acid substitutions and/or insertions and/or deletions compared to a wild-type (naturally-occurring) hinge region. For example, His229 of human IgG 1 hinge can be substituted with Tyr, so that the stalk includes the sequence EPKSCDKTYTCPPCP (SEQ ID NO:15), (see, e.g., Yan et al. (2012) *J. Biol. Chem.* 287:5891). The stalk can include an amino acid sequence derived from human CD8; e.g., the stalk can include the amino acid sequence: TTTPAPRPPTPAPTIASQPLSLRPEACRPAAGGAVHTR-GLDFACD (SEQ ID NO:16), or a variant thereof.

Transmembrane Domain

An engineered signaling polypeptide of the present disclosure can include transmembrane domains for insertion into a eukaryotic cell membrane. The transmembrane domain can be interposed between the ASTR and the co-stimulatory domain. The transmembrane domain can be interposed between the stalk and the co-stimulatory domain, such that the chimeric antigen receptor includes, in order from the amino terminus (N-terminus) to the carboxyl terminus (C-terminus): an ASTR; a stalk; a transmembrane domain; and an activating domain.

Any transmembrane (TM) domain that provides for insertion of a polypeptide into the cell membrane of a eukaryotic (e.g., mammalian) cell is suitable for use in aspects and embodiments disclosed herein.

Non-limiting examples of (TM) domains suitable for any of the aspects or embodiments provided herein, include a domain with at least 50, 60, 70, 75, 80, 85, 90, 95, 96, 97, 98, 99 or 100% sequence identity to a stretch of at least 10, 15, 20, or all of the amino acids of any of the following (TM) domains or combined stalk and TM domains: a) CD8 alpha (TM) (SEQ ID NO:17); b) CD8 beta (TM) (SEQ ID NO:18); c) CD4 stalk (SEQ ID NO:19); d) CD3Z TM (SEQ ID NO:20); e) CD28 TM (SEQ ID NO:21); f) CD134 (OX40) TM: (SEQ ID NO:22); g) CD7 TM (SEQ ID NO:23); h) CD8 stalk and TM (SEQ ID NO:24); and i) CD28 stalk and TM (SEQ ID NO:25).

As non-limiting examples, a transmembrane domain of an aspect of the invention can have at least 80%, 90%, or 95% or can have 100% sequence identity to the SEQ ID NO:17 transmembrane domain, or can have 100% sequence identity to any of the transmembrane domains from the following genes respectively: the CD8 beta transmembrane domain, the CD4 transmembrane domain, the CD3 zeta transmembrane domain, the CD28 transmembrane domain, the CD134 transmembrane domain, or the CD7 transmembrane domain Intracellular Activating Domain Intracellular activating domains suitable for use in an engineered signaling polypeptide of the present disclosure when activated, typically induce the production of one or more cytokines; increase cell death; and/or increase proliferation of $CD8^+$ T cells, $CD4^+$ T cells, NKT cells, γδT cells, and/or neutrophils. Activating domains can also be referred to as activation domains herein. Activating domains can be used in CARs or in lymphoproliferative elements provided herein.

In some embodiments, the intracellular activating domain includes at least one (e.g., one, two, three, four, five, six, etc.) ITAM motifs as described below. In some embodiments, an intracellular activating domain of an aspect of the invention can have at least 80%, 90%, or 95% or can have 100% sequence identity to the CD3Z, CD3D, CD3E, CD3G, CD79A, CD79B, DAP12, FCER1G, FCGR2A, FCGR2C, DAP10/CD28, or ZAP70 domains as described below.

Intracellular activating domains suitable for use in an engineered signaling polypeptide of the present disclosure include immunoreceptor tyrosine-based activation motif (ITAM)-containing intracellular signaling polypeptides. An ITAM motif is $YX_1X_2L/I$, where $X_1$ and $X_2$ are independently any amino acid. In some embodiments, the intracellular activating domain of an engineered signaling polypeptide includes 1, 2, 3, 4, or 5 ITAM motifs. In some embodiments, an ITAM motif is repeated twice in an intracellular activating domain, where the first and second instances of the ITAM motif are separated from one another by 6 to 8 amino acids, e.g., $(YX_1X_2L/I)(X_3)_n(YX_1X_2L/I)$, where n is an integer from 6 to 8, and each of the 6-8 $X_3$ can be any amino acid. In some embodiments, the intracellular activating domain of an engineered signaling polypeptide includes 3 ITAM motifs.

A suitable intracellular activating domain can be an ITAM motif-containing portion that is derived from a polypeptide that contains an ITAM motif. For example, a suitable intracellular activating domain can be an ITAM motif-containing domain from any ITAM motif-containing protein. Thus, a suitable intracellular activating domain need not contain the entire sequence of the entire protein from which it is derived. Examples of suitable ITAM motif-containing polypeptides include, but are not limited to: CD3Z (CD3 zeta); CD3D (CD3 delta); CD3E (CD3 epsilon); CD3G (CD3 gamma); CD79A (antigen receptor complex-associated protein alpha chain); CD79B (antigen receptor complex-associated protein beta chain) DAP12; and FCER1G (Fc epsilon receptor I gamma chain).

In some embodiments, the intracellular activating domain is derived from T cell surface glycoprotein CD3 zeta chain (also known as CD3Z, T cell receptor T3 zeta chain, CD247, CD3-ZETA, CD3H, CD3Q, T3Z, TCRZ, etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms): MKWKA-LFTAAILQAQLPITEAQSFGLLDPKLCYLLDGIL-FIYGVILTALFLRVKFSRSADAPAYQQ GQNQL [YNELNLGRREEYDVL] DKRRGRDPEMGGKPRRKNPQEGL [YNELQKDKMAEAYSEI]G MKGERRRGKGHDGL [YQGLSTATKDTYDAL]HMQALPPR (SEQ ID NO:26) or MKWKALFTAAILQAQLPITEAQSFGLLDPKLCYLL-DGILFIYGVILTALFLRVKFSRSADAPAYQQ GQNQL [YNELNLGRREEYDVL]DKRR-GRDPEMGGKPQRRKNPQEGL [YNELQKDKMAEAYSEI] GMKGERRRGKGHDGL [YQGLSTATKDTYDAL]HMQALPPR (SEQ ID NO:27), where the ITAM motifs are set out with brackets.

Likewise, a suitable intracellular activating domain polypeptide can include an ITAM motif-containing a portion of the full length CD3 zeta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: RVKFSRSADAPAYQQGQNQL[YNELNLGRREEYDVL]DKRRGRDPEMGGKPRRKNPQEGL[YNE LQKDKMAEAYSEI]GMKGERRRGKGHDGL[YQGLSTATKDTYDAL] HMQALPPR (SEQ ID NO:28); RVKFSRSADAPAYQQGQNQL[YNELNLGRREEYDVL]DKRRGRDPEMGGKPQRRKNPQEGL[YN ELQKDKMAEAYSEI]GMKGERRRGKGHDGL[YQGLSTATKDTYDAL]HMQALPPR (SEQ ID NO:29); NQL[YNELNLGRREEYDVL]DKR SEQ ID NO:30); EGL [YNELQKDKMAEAYSEI]GMK (SEQ ID NO:31); or DGL[YQGLSTATKDTYDAL]HMQ (SEQ ID NO:32), where the ITAM motifs are set out in brackets.

In some embodiments, the intracellular activating domain is derived from T cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T cell receptor T3 delta chain; T cell surface glycoprotein CD3 delta chain; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MEHSTFLSGLVLATLLSQVSPFKIPIEELEDRVFVNCNTSITWVEGTVGTLLSDITRLDLGKRILDP RGIYRCNGTDIYKDKESTVQVHYRMCQSCVELDPATVAGIIVTDVIATLLLALGVFCFAGHETGR LSGAADTQALLRNDQV [YQPLRDRDDAQYSHL]GGNWARNK (SEQ ID NO:33) or MEHSTFLSGLVLATLLSQVSPFKIPIEELEDRVFVNCNTSITWVEGTVGTLLSDITRLDLGKRILDP RGIYRCNGTDIYKDKESTVQVHYRTADTQALLRNDQV[YQPLRDRDDAQYSHL]GGNWARNK (SEQ ID NO:34), where the ITAM motifs are set out in brackets.

Likewise, a suitable intracellular activating domain polypeptide can comprise an ITAM motif-containing portion of the full length CD3 delta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQV[YQPLRDRDDAQYSHL]GGN (SEQ ID NO:35), where the ITAM motifs are set out in brackets.

In some embodiments, the intracellular activating domain is derived from T cell surface glycoprotein CD3 epsilon chain (also known as CD3e, T cell surface antigen T3/Leu-4 epsilon chain, T cell surface glycoprotein CD3 epsilon chain, AI504783, CD3, CD3epsilon, T3e, etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MQSGTHWRVLGLCLLSVGVWGQDGNEEMGGITQTPYKVSISGTTVILTCPQYPGSEILWQHNDK NIGGDEDDKNIGSDEDHLSLKEFSELEQSGYYVCYPRGSKPEDANFYLYLRARVCENCMEMDMS VATIVIVDICITGGLLLLVYYWSKNRKAKAKPVTRGAGAGGRQRGQNKERPPPVPNPD[YEPIRK GQRDLYSGL]NQRRI (SEQ ID NO:36), where the ITAM motifs are set out in brackets.

Likewise, a suitable intracellular activating domain polypeptide can comprise an ITAM motif-containing portion of the full length CD3 epsilon amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: NPD[YEPIRKGQRDLYSGL]NQR (SEQ ID NO:37), where the ITAM motifs are set out in brackets.

In some embodiments, the intracellular activating domain is derived from T cell surface glycoprotein CD3 gamma chain (also known as CD3G, T cell receptor T3 gamma chain, CD3-GAMMA, T3G, gamma polypeptide (TiT3 complex), etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MEQGKGLAVLILAIILLQGTLAQSIKGNHLVKVYDYQEDGSVLLTCDAEAKNITWFKDGKMIGF LTEDKKKWNLGSNAKDPRGMYQCKGSQNKSKPLQVYYRMCQNCIELNAATISGFLFAEIVSIFV LAVGVYFIAGQDGVRQSRASDKQTLLPNDQL [YQPLKDREDDQYSHL]QGNQLRRN (SEQ ID NO:38), where the ITAM motifs are set out in brackets.

Likewise, a suitable intracellular activating domain polypeptide can comprise an ITAM motif-containing portion of the full length CD3 gamma amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQL[YQPLKDREDDQYSHL]QGN (SEQ ID NO:39), where the ITAM motifs are set out in brackets.

In some embodiments, the intracellular activating domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MPGGPGVLQALPATIFLLFLL-SAVYLGPGCQALWMHKVPASLMVSLGE-DAHFQCPHNSSNNAN VTWWRVLHGNYTWPPE-FLGPGEDPNGTLIIQNVNKSHGGIYVCRVQEGNES-YQQSCGTYLRVR QPPPRPFLDMGEGTKNRIITAE-GIILLFCAVVPGTLLL-FRKRWQNEKLGLDAGDEYEDENL[YEGL NLDDCSMYEDI]SRGLQGTYQDVGSLNIGDVQLEKP (SEQ ID NO:40) or MPGGPGVLQALPATIFLLFLL-SAVYLGPGCQALWMHKVPASLMVSLGE-DAHFQCPHNSSNNAN VTWWRVLHGNYTWPPE-FLGPGEDPNEPPPRPFLDMGEGTKNRIITAEGIILLF-CAVVPGTLLLFRK RWQNEKLGLDAGDEYEDENL[Y-EGLNLDDCSMYEDI]SR-GLQGTYQDVGSLNIGDVQLEKP (SEQ ID NO:41), where the ITAM motifs are set out in brackets.

Likewise, a suitable intracellular activating domain polypeptide can comprise an ITAM motif-containing portion of the full length CD79A amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ENL[YEGLNLDDCSMYEDI]SRG (SEQ ID NO:42), where the ITAM motifs are set out in brackets.

In some embodiments, the intracellular activating domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (4 isoforms): MGGLEPCSRLLLLPLL-LAVSGLRPVQAQAQSDCSCSTVSPGVLA-GIVMGDLVLTVLIALAVYFLG RLVPRGR-GAAEAATRKQRITETESP[YQELQGQRSDVYSDL] NTQRPYYK (SEQ ID NO:43), MGGLEPCSRLLLLPLLLAVSGLRPVQAQAQSDCSC-STVSPGVLAGIVMGDLVLTVLIALAVYFLG RLVPR-GRGAAEATRKQRITETESP[YQELQGQRSDVYSDL] NTQ (SEQ ID NO:44), MGGLEPCSRLLLLPLLLAVSDCSCSTVSPGVLA-GIVMGDLVLTVLIALAVYFLGRLVPRGRGAAE AATRKQRITETESP[YQELQGQRSDVYSDL] NTQRPYYK (SEQ ID NO:45), or MGGLEPCSRLLLLPLLLAVSDCSCSTVSPGVLA-GIVMGDLVLTVLIALAVYFLGRLVPRGRGAAE ATRKQRITETESP[YQELQGQRSDVYSDL] NTQRPYYK (SEQ ID NO:46), where the ITAM motifs are set out in brackets.

Likewise, a suitable intracellular activating domain polypeptide can comprise an ITAM motif-containing portion of the full length DAP12 amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ESP[YQELQGQRSDVYSDL]NTQ (SEQ ID NO:47), where the ITAM motifs are set out in brackets.

In some embodiments, the intracellular activating domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 50 amino acids to about 60 amino acids (aa), from about 60 aa to about 70 aa, from about 70 aa to about 80 aa, or from about 80 aa to about 88 aa, of the following amino acid sequence: MIPAVVLLLLLLVEQAAALGEPQL-CYILDAILFLYGIVLTLLYCRLKIQVRKAAIT-SYEKSDGV[YT GLSTRNQETYETL]KHEKPPQ (SEQ ID NO:48), where the ITAM motifs are set out in brackets.

Likewise, a suitable intracellular activating domain polypeptide can comprise an ITAM motif-containing portion of the full length FCER1G amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DGV[YTGLSTRNQETYETL]KHE (SEQ ID NO:49), where the ITAM motifs are set out in brackets.

Intracellular activating domains suitable for use in an engineered signaling polypeptide of the present disclosure include a DAP10/CD28 type signaling chain. An example of a DAP10 signaling chain is the amino acid SEQ ID NO:50. In some embodiments, a suitable intracellular activating domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in SEQ ID NO:50.

An example of a CD28 signaling chain is the amino acid sequence is SEQ ID NO:51. In some embodiments, a suitable intracellular domain includes a domain with at least 50%, 60%, 70%, 75%, 80%, 85%, 90%, 95%, 96%, 97%, 98%, 99% or 100% sequence identity to a stretch of at least 10, 15, 20, or all amino acids of SEQ ID NO:51.

Intracellular activating domains suitable for use in an engineered signaling polypeptide of the present disclosure include a ZAP70 polypeptide, For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 300 amino acids to about 400 amino acids, from about 400 amino acids to about 500 amino acids, or from about 500 amino acids to 619 amino acids, of SEQ ID NO:52.

Modulatory Domains

Modulatory domains can change the effect of the intracellular activating domain in the engineered signaling polypeptide, including enhancing or dampening the downstream effects of the activating domain or changing the nature of the response. Modulatory domains suitable for use in an engineered signaling polypeptide of the present disclosure include co-stimulatory domains. A modulatory domain suitable for inclusion in the engineered signaling polypeptide can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains typically enhance and/or change the nature of the response to an activation domain Co-stimulatory domains suitable for use in an engineered signaling polypeptide of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD27, CD28, CD28 deleted for Lck binding (ICA), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICA), ICOS, OX40, BTLA, CD27, CD30, GITR, or HVEM. For example, a co-stimulatory domain of an aspect of the invention can have at least 80%, 90%, or 95% sequence identity to the co-stimulatory domain of non-limiting examples of suitable co-stimulatory polypeptides include, but are not limited to, 4-1BB (CD137), CD27, CD28, CD28 deleted for Lck binding (ICA), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICA), ICOS, OX40, BTLA, CD27, CD30, GITR, or HVEM.

A co-stimulatory domain suitable for inclusion in an engineered signaling polypeptide can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some embodiments, the co-stimulatory domain is derived from an intracellular portion of the transmembrane protein CD137 (also known as TNFRSF9; CD137; 4-1BB; CDw137; ILA; etc.). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:53. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein CD28 (also known as Tp44). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:54. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein CD28 deleted for Lck binding (ICA). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:55. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein ICOS (also known as AILIM, CD278, and CVID1). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:56. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein OX40 (also known as TNFRSF4, RP5-902P8.3, ACT35, CD134, OX-40, TXGP1L). OX40 contains a p85 PI3K binding motif at residues 34-57 and a TRAF binding motif at residues 76-102, each of SEQ ID NO: 296 (of Table 1). In some embodiments, the costimulatory domain can include the p85 PI3K binding motif of OX40. In some embodiments, the costimulatory domain can include the TRAF binding motif of OX40. Lysines corresponding to amino acids 17 and 41 of SEQ ID NO: 296 are potentially negative regulatory sites that function as parts of ubiquitin targeting motifs. In some embodiments, one or both of these Lysines in the costimulatory domain of OX40 are mutated Arginines or another amino acid. In some embodiments, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:57. In some of these embodiments, the co-stimulatory domain has a length of from about 20 aa to about 25 aa, about 25 aa to about 30 aa, 30 aa to about 35 aa, from about 35 aa to about 40 aa, from about 40 aa to about 45 aa, or from about 45 aa to about 50 aa. In illustrative embodiments, the co-stimulatory domain has a length of from about 20 aa to about 50 aa, for example 20 aa to 45 aa, or 20 aa to 42 aa.

In some embodiments, the co-stimulatory domain is derived from an intracellular portion of the transmembrane protein CD27 (also known as S 152, T 14, TNFRSF7, and Tp55). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:58. In some of these embodiments, the co-stimulatory domain has a length of from about 30 aa to about 35 aa, from about 35 aa to about 40 aa, from about 40 aa to about 45 aa, or from about 45 aa to about 50 aa.

In some embodiments, the co-stimulatory domain is derived from an intracellular portion of the transmembrane protein BTLA (also known as BTLA1 and CD272). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:59.

In some embodiments, the co-stimulatory domain is derived from an intracellular portion of the transmembrane protein CD30 (also known as TNFRSF8, D1S166E, and Ki-1). For example, a suitable co-stimulatory domain can include a domain with at least 50%, 60%, 70%, 75%, 80%, 85%, 90%, 95%, 96%, 97%, 98%, 99% or 100% sequence identity to a stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of SEQ ID NO:60.

In some embodiments, the co-stimulatory domain is derived from an intracellular portion of the transmembrane protein GITR (also known as TNFRSF18, RP5-902P8.2, AITR, CD357, and GITR-D). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:61. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:62. In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Linker

In some embodiments, the engineered signaling polypeptide includes a linker between any two adjacent domains. For example, a linker can be between the transmembrane domain and the first co-stimulatory domain. As another example, the ASTR can be an antibody and a linker can be between the heavy chain and the light chain. As another example, a linker can be between the ASTR and the transmembrane domain and a co-stimulatory domain. As another example, a linker can be between the co-stimulatory domain and the intracellular activating domain of the second polypeptide. As another example, the linker can be between the ASTR and the intracellular signaling domain.

The linker peptide may have any of a variety of amino acid sequences. Proteins can be joined by a spacer peptide, generally of a flexible nature, although other chemical linkages are not excluded. A linker can be a peptide of between about 1 and about 100 amino acids in length, or between about 1 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$, $GGGS_n$, and $GGGGS_n$ where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGGGSGGGGSGGGGS (SEQ ID NO:63), GGGGSGGGGSGGGGSGGGGSGGGGSGGGGS (SEQ ID NO:64), GGGGSGGGSGGGGS (SEQ ID NO:65), GGSG (SEQ ID NO:66), GGSGG (SEQ ID NO:67), GSGSG (SEQ ID NO:68), GSGGG (SEQ ID NO:69), GGGSG (SEQ ID NO:70), GSSSG (SEQ ID NO:71), and the like. The ordinarily skilled artisan will recognize that design of a peptide conjugated to any elements described above can include linkers that are all or partially flexible, such that the linker can include a flexible linker as well as one or more portions that confer less flexible structure.

Combinations

In some embodiments, a polynucleotide provided by the replication incompetent recombinant retroviral particles has one or more transcriptional units that encode certain combinations of the one or more engineered signaling polypeptides. In some methods and compositions provided herein, genetically modified T cells include the combinations of the one or more engineered signaling polypeptides after transduction of T cells by the replication incompetent recombinant retroviral particles. It will be understood that the reference of a first polypeptide, a second polypeptide, a third polypeptide, etc. is for convenience and elements on a "first polypeptide" and those on a "second polypeptide" means that the elements are on different polypeptides that are referenced as first or second for reference and convention only, typically in further elements or steps to that specific polypeptide.

In some embodiments, the first engineered signaling polypeptide includes an extracellular antigen binding domain, which is capable of binding an antigen, and an intracellular signaling domain. In other embodiments, the first engineered signaling polypeptide also includes a T cell survival motif and/or a transmembrane domain. In some embodiments, the first engineered signaling polypeptide does not include a co-stimulatory domain, while in other embodiments, the first engineered signaling polypeptide does include a co-stimulatory domain.

In some embodiments, a second engineered signaling polypeptide includes a lymphoproliferative gene product and optionally an extracellular antigen binding domain. In some embodiments, the second engineered signaling polypeptide also includes one or more of the following: a T cell survival motif, an intracellular signaling domain, and one or more co-stimulatory domains. In other embodiments, when two engineered signaling polypeptides are used, at least one is a CAR.

In one embodiment, the one or more engineered signaling polypeptides are expressed under a T cell specific promoter or a general promoter under the same transcript wherein in the transcript, nucleic acids encoding the engineered signaling polypeptides are separated by nucleic acids that encode one or more internal ribosomal entry sites (IREs) or one or more protease cleavage peptides.

In certain embodiments, the polynucleotide encodes two engineered signaling polypeptides wherein the first engineered signaling polypeptide includes a first extracellular antigen binding domain, which is capable of binding to a first antigen, and a first intracellular signaling domain but not a co-stimulatory domain, and the second polypeptide includes a second extracellular antigen binding domain, which is capable of binding VEGF, and a second intracellular signaling domain, such as for example, the signaling domain of a co-stimulatory molecule. In a certain embodiment, the first antigen is PSCA, PSMA, or BCMA. In a certain embodiment, the first extracellular antigen binding domain comprises an antibody or fragment thereof (e.g., scFv), e.g., an antibody or fragment thereof specific to PSCA, PSMA, or BCMA. In a certain embodiment, the second extracellular antigen binding domain that binds VEGF is a receptor for VEGF, i.e., VEGFR. In certain embodiments, the VEGFR is VEGFR1, VEGFR2, or VEGFR3. In a certain embodiment, the VEGFR is VEGFR2.

In certain embodiments, the polynucleotide encodes two engineered signaling polypeptides wherein the first engineered signaling polypeptide includes an extracellular tumor antigen binding domain and a CD3ζ signaling domain, and the second engineered signaling polypeptide includes an antigen-binding domain, wherein the antigen is an angiogenic or vasculogenic factor, and one or more co-stimulatory molecule signaling domains. The angiogenic factor can be, e.g., VEGF. The one or more co-stimulatory molecule signaling motifs can comprise, e.g., co-stimulatory signaling domains from each of CD27, CD28, OX40, ICOS, and 4-1BB.

In certain embodiments, the polynucleotide encodes two engineered signaling polypeptides wherein the first engineered signaling polypeptide includes an extracellular tumor antigen-binding domain and a CD3ζ signaling domain, the second polypeptide comprises an antigen-binding domain, which is capable of binding to VEGF, and co-stimulatory signaling domains from each of CD27, CD28, OX40, ICOS, and 4-1BB. In a further embodiment, the first signaling polypeptide or second signaling polypeptide also has a T cell survival motif. In some embodiments, the T cell survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor or the TGFβ decoy receptor (TGF-β-dominant-negative receptor II (DNRII)).

In certain embodiments, the polynucleotide encodes two engineered signaling polypeptides wherein the first engineered signaling polypeptide includes an extracellular tumor antigen-binding domain and a CD3 signaling domain, and the second engineered signaling polypeptide includes an antigen-binding domain, which is capable of binding to VEGF, an IL-7 receptor intracellular T cell survival motif, and co-stimulatory signaling domains from each of CD27, CD28, OX40, ICOS, and 4-1BB.

In some embodiments, more than two signaling polypeptides are encoded by the polynucleotide. In certain embodiments, only one of the engineered signaling polypeptides includes an antigen binding domain that binds to a tumor-associated antigen or a tumor-specific antigen; each of the remainder of the engineered signaling polypeptides comprises an antigen binding domain that binds to an antigen that is not a tumor-associated antigen or a tumor-specific antigen. In other embodiments, two or more of the engineered signaling polypeptides include antigen binding domains that bind to one or more tumor-associated antigens or tumor-specific antigens, wherein at least one of the engineered signaling polypeptides comprises an antigen binding domain that does not bind to a tumor-associated antigen or a tumor-specific antigen.

In some embodiments, the tumor-associated antigen or tumor-specific antigen is Her2, prostate stem cell antigen (PSCA), PSMA (prostate-specific membrane antigen), B cell maturation antigen (BCMA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EphA2, CSPG4, CD138, FAP (Fibroblast Activation Protein), CD171, kappa, lambda, 5T4, αvβ6 integrin, integrin αvβ3 (CD61), galactin, K-Ras (V-Ki-ras2 Kirsten rat sarcoma viral oncogene), Ral-B, B7-H3, B7-H6, CAIX, CD20, CD33, CD44, CD44v6, CD44v7/8, CD123, EGFR, EGP2, EGP40, EpCAM, fetal AchR, FRα, GD3, HLA-A1+MAGE1, HLA-A1+NY-ESO-1, IL-11Rα, IL-13Rα2, Lewis-Y, Muc16, NCAM, NKG2D Ligands, NY-ESO-1, PRAME, ROR1, Survivin, TAG72, TEMs, VEGFR2, EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein.

In some embodiments, the first engineered signaling polypeptide includes a first extracellular antigen binding domain that binds a first antigen, and a first intracellular signaling domain; and a second engineered signaling polypeptide includes a second extracellular antigen binding domain that binds a second antigen, or a receptor that binds the second antigen; and a second intracellular signaling domain, wherein the second engineered signaling polypeptide does not comprise a co-stimulatory domain. In a certain embodiment, the first antigen-binding domain and the second antigen-binding domain are independently an antigen-binding portion of a receptor or an antigen-binding portion of an antibody. In a certain embodiment, either or both of the first antigen binding domain or the second antigen binding domain are scFv antibody fragments. In certain embodiments, the first engineered signaling polypeptide and/or the second engineered signaling polypeptide additionally comprises a transmembrane domain. In a certain embodiment, the first engineered signaling polypeptide or the second engineered signaling polypeptide comprises a T cell survival motif, e.g., any of the T cell survival motifs described herein.

In another embodiment, the first engineered signaling polypeptide includes a first extracellular antigen binding domain that binds HER2 and the second engineered signaling polypeptide includes a second extracellular antigen binding domain that binds MUC-1.

In another embodiment, the second extracellular antigen binding domain of the second engineered signaling polypeptide binds an interleukin.

In another embodiment, the second extracellular antigen binding domain of the second engineered signaling polypeptide binds a damage associated molecular pattern molecule (DAMP; also known as an alarmin). In other embodiments, a DAMP is a heat shock protein, chromatin-associated protein high mobility group box 1 (HMGB1), S100A8 (also known as MRP8, or calgranulin A), S100A9 (also known as MRP14, or calgranulin B), serum amyloid A (SAA), deoxyribonucleic acid, adenosine triphosphate, uric acid, or heparin sulfate.

In certain embodiments, said second antigen is an antigen on an antibody that binds to an antigen presented by a tumor cell.

In some embodiments, signal transduction activation through the second engineered signaling polypeptide is non-antigenic, but is associated with hypoxia. In certain embodiments, hypoxia is induced by activation of hypoxia-inducible factor-1α (HIF-1α), HIF-1β, HIF-2α, HIF-2β, HIF-3α, or HIF-3β.

In some embodiments, expression of the one or more engineered signaling polypeptides is regulated by a control element, which is disclosed in more detail herein.

Additional Sequences

The engineered signaling polypeptides, such as CARs, can further include one or more additional polypeptide domains, where such domains include, but are not limited to, a signal sequence; an epitope tag; an affinity domain; and a polypeptide whose presence or activity can be detected (detectable marker), for example by an antibody assay or because it is a polypeptide that produces a detectable signal. Non-limiting examples of additional domains for any of the aspects or embodiments provided herein, include a domain with at least 50%, 60%, 70%, 75%, 80%, 85%, 90%, 95%, 96%, 97%, 98%, 99% or 100% sequence identity to any of the following sequences as described below: a signal sequence, an epitope tag, an affinity domain, or a polypeptide that produces a detectable signal.

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc. In some embodiments, for example, the signal sequence can be the CD8 signal sequence MALPVTALLLPLALLLHAARP (SEQ ID NO:72).

Suitable epitope tags include, but are not limited to, hemagglutinin (HA; e.g., YPYDVPDYA; SEQ ID NO:73); FLAG (e.g., DYKDDDDK; SEQ ID NO:74); c-myc (e.g., EQKLISEEDL; SEQ ID NO:75), and the like.

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH; SEQ ID NO:76), HisX6 (HHHHHH; SEQ ID NO:77), c-myc (EQKLISEEDL; SEQ ID NO:75), Flag (DYKDDDDK; SEQ ID NO:74), Strep Tag (WSHPQFEK; SEQ ID NO:78), hemagglutinin, e.g., HA Tag (YPYDVPDYA; SEQ ID NO:73), GST, thioredoxin, cellulose binding domain, RYIRS (SEQ ID NO:79), Phe-His-His-Thr (SEQ ID NO:80), chitin binding domain, S-peptide, T7 peptide, SH2 domain, C-end RNA tag, WEAAAREACCRECCARA (SEQ ID NO:81), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recognition and/or Elimination Domain

Any of the replication incompetent recombinant retroviral particles provided herein can include nucleic acids that encode a recognition or elimination domain as part of, or separate from, nucleic acids encoding any of the engineered signaling polypeptides provided herein. Thus, any of the engineered signaling polypeptides provided herein, can include a recognition or elimination domain. For example, any of the CARs disclosed herein can include a recognition or elimination domain. Moreover, a recognition or elimination domain can be expressed together with, or even fused with any of the lymphoproliferative elements disclosed herein. The recognition or elimination domains are expressed on the T cell and/or NK cell but are not expressed on the replication incompetent recombinant retroviral particles.

In some embodiments, the recognition or elimination domain can be derived from herpes simplex virus-derived enzyme thymidine kinase (HSV-tk) or inducible caspase-9. In some embodiments, the recognition or elimination domain can include a modified endogenous cell-surface molecule, for example as disclosed in U.S. Pat. No. 8,802,374. The modified endogenous cell-surface molecule can be any cell-surface related receptor, ligand, glycoprotein, cell adhesion molecule, antigen, integrin, or cluster of differentiation (CD) that is modified. In some embodiments, the modified endogenous cell-surface molecule is a truncated tyrosine kinase receptor. In one aspect, the truncated tyrosine kinase receptor is a member of the epidermal growth factor receptor (EGFR) family (e.g., ErbB1, ErbB2, ErbB3, and ErbB4). In some embodiments, the recognition domain can be a polypeptide that is recognized by an antibody that recognizes the extracellular domain of an EGFR member. In some embodiments, the recognition domain can be at least 20 contiguous amino acids of an EGFR family member, or for example, between 20 and 50 contiguous amino acids of an EGFR family member. For example, SEQ ID NO:82, is an exemplary polypeptide that is recognized by, and under the appropriate conditions bound by an antibody that recognizes the extracellular domain of an EGFR member. Such extracellular EGFR epitopes are sometimes referred to herein as eTags. In illustrative embodiments, such epitopes are recognized by commercially available anti-EGFR monoclonal antibodies.

Epidermal growth factor receptor, also known as EGFR, ErbB1 and HER1, is a cell-surface receptor for members of the epidermal growth factor family of extracellular ligands. Alterations in EGFR activity have been implicated in certain cancers. In some embodiments, a gene encoding an EGFR polypeptide including human epidermal growth factor receptor (EGFR) is constructed by removal of nucleic acid sequences that encode polypeptides including the membrane distal EGF-binding domain and the cytoplasmic signaling tail, but retains the extracellular membrane proximal epitope recognized by an anti-EGFR antibody. Preferably, the antibody is a known, commercially available anti-EGFR monoclonal antibody, such as cetuximab, matuzumab, necitumumab or panitumumab.

Others have shown that application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Furthermore, others have shown that constitutive expression of this inert EGFR molecule does not affect T cell phenotype or effector function as directed by the coordinately expressed chimeric antigen receptor (CAR), CD19R. In addition, others have shown that through flow cytometric analysis, EGFR was successfully utilized as an in vivo tracking marker for T cell engraftment in mice. Furthermore, EGFR was demonstrated to have suicide gene potential through Erbitux® mediated antibody dependent cellular cytotoxicity (ADCC) pathways. The inventors of the present disclosure have successfully expressed eTag in PBMCs using lentiviral vectors, and have found that expression of eTag in vitro by PBMCs exposed to Cetuximab, provided an effective elimination mechanism for PBMCs. Thus, EGFR may be used as a non-immunogenic selection tool, tracking marker, and suicide gene for transduced T cells that have immunotherapeutic potential. The EGFR nucleic acid may also be detected by means well known in the art.

In some embodiments provided herein, EGFR is expressed as part of a single polypeptide that also includes the CAR or as part of a single polypeptide that includes the lymphoproliferative element. In some embodiments, the amino acid sequence encoding the EGFR recognition domain can be separated from the amino acid sequence encoding the chimeric antigen receptor by a cleavage signal and/or a ribosomal skip sequence. The ribosomal skip and/or cleavage signal can be any ribosomal skip and/or cleavage signal known in the art. Not to be limited by theory, the ribosomal skip sequence can be, for example T2A (also referred to as 2A-1 herein) with amino acid sequence GSGEGRGSLLTCGDVEENPGP (SEQ ID NO:83). Not to be limited by theory, other examples of cleavage signals and ribosomal skip sequences include FMDV 2A (F2A); equine rhinitis A virus 2A (abbreviated as E2A); porcine teschovirus-1 2A (P2A); and *Thoseaasigna* virus 2A (T2A). In some embodiments, the polynucleotide sequence encoding the recognition domain can be on the same transcript as the CAR or lymphoproliferative element but separated from the polynucleotide sequence encoding the CAR or lymphoproliferative element by an internal ribosome entry site.

In other embodiments as exemplified empirically herein, a recognition domain can be expressed as part of a fusion polypeptide, fused to a lymphoproliferative element. Such constructs provide the advantage, especially in combination with other "space saving" elements provided herein, of taking up less genomic space on an RNA genome compared to separate polypeptides. In one illustrative embodiment, an eTag is expressed as a fusion polypeptide, fused to an IL7Rα mutant, as experimentally demonstrated herein.

Chimeric Antigen Receptor

In some aspects of the present invention, an engineered signaling polypeptide is a chimeric antigen receptor (CAR) or a polynucleotide encoding a CAR, which, for simplicity, is referred to herein as "CAR." A CAR of the present disclosure includes: a) at least one antigen-specific targeting region (ASTR); b) a transmembrane domain; and c) an intracellular activating domain. In illustrative embodiments, the antigen-specific targeting region of the CAR is an scFv portion of an antibody to the target antigen. In illustrative embodiments, the intracellular activating domain is from CD3Z, CD3D, CD3E, CD3G, CD79A, CD79B, DAP12, FCER1G, FCGR2A, FCGR2C, DAP10/CD28, or ZAP70, and some further illustrative embodiments, from CD3z. In illustrative embodiments, the CAR further comprises a co-stimulatory domain, for example any of the co-stimulatory domains provided above in the Modulatory Domains section, and in further illustrative embodiments the co-stimulatory domain is the intracellular co-stimulatory domain of 4-1BB (CD137), CD28, ICOS, OX-40, BTLA, CD27, CD30, GITR, and HVEM. In some embodiments, the CAR includes any of the transmembrane domains listed in the Transmembrane Domain section above.

A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell, an NK-T cell, and a macrophage. When present in the plasma membrane of a eukaryotic cell, a CAR of the present disclosure is active in the presence of one or more target antigens that, in certain conditions, binds the ASTR. The target antigen is the second member of the specific binding pair. The target antigen of the specific binding pair can be a soluble (e.g., not bound to a cell) factor; a factor present on the surface of a cell such as a target cell; a factor presented on a solid surface; a factor present in a lipid bilayer; and the like. Where the ASTR is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by one or more target antigens, increases expression of at least one nucleic acid in the cell. For example, in some cases, a CAR of the present disclosure, when present in the plasma membrane of a eukaryotic cell, and when activated by the one or more target antigens, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of the one or more target antigens.

As an example, the CAR of the present disclosure can include an immunoreceptor tyrosine-based activation motif (ITAM)-containing intracellular signaling polypeptide.

A CAR of the present disclosure, when present in the plasma membrane of a eukaryotic cell, and when activated by one or more target antigens, can, in some instances, result in increased production of one or more cytokines by the cell. For example, a CAR of the present disclosure, when present in the plasma membrane of a eukaryotic cell, and when activated by the one or more target antigens, can increase production of a cytokine by the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the cell in the absence of the one or more target antigens. Cytokines whose production can be increased include, but are not limited to interferon gamma (IFN-$\gamma$), tumor necrosis factor-alpha (TNF-$\alpha$), IL-2, IL-15, IL-12, IL-4, IL-5, IL-10; a chemokine; a growth factor; and the like.

In some embodiments, a CAR of the present disclosure, when present in the plasma membrane of a eukaryotic cell, and when activated by one or more target antigens, can result in both an increase in transcription of a nucleic acid in the cell and an increase in production of a cytokine by the cell.

In some instances, a CAR of the present disclosure, when present in the plasma membrane of a eukaryotic cell, and when activated by one or more target antigens, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by the one or more target antigens, increases cytotoxic activity of the cell toward a target cell that expresses on its cell surface the one or more target antigens. For example, where the eukaryotic cell is an NK cell or a T lymphocyte, a CAR of the present disclosure, when present in the plasma membrane of the cell, and when activated by the one or more target antigens, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the one or more target antigens.

In some embodiments, a CAR of the present disclosure, when present in the plasma membrane of a eukaryotic cell, and when activated by one or more target antigens, can result in other CAR activation related events such as proliferation and expansion (either due to increased cellular division or anti-apoptotic responses).

In some embodiments, a CAR of the present disclosure, when present in the plasma membrane of a eukaryotic cell, and when activated by one or more target antigens, can result in other CAR activation related events such as intracellular signaling modulation, cellular differentiation, or cell death.

In some embodiments, CARs of the present disclosure are microenvironment restricted. This property is typically the result of the microenvironment restricted nature of the ASTR domain of the CAR. Thus, CARs of the present disclosure can have a lower binding affinity or, in illustrative embodiments, can have a higher binding affinity to one or more target antigens under a condition(s) in a microenvironment than under a condition in a normal physiological environment.

In certain illustrative embodiments, CARs provided herein comprise a co-stimulatory domain in addition to an intracellular activating domain, wherein the co-stimulatory domain is any of the intracellular signaling domains provided herein for lymphoproliferative elements (LEs), such as, for example, intracellular domains of CLEs. In certain illustrative embodiments, the co-stimulatory domains of CARs herein are first intracellular domains (P3 domains) identified herein for CLEs or P4 domains that are shown as effective intracellular signaling domains of CLEs herein in the absence of a P3 domain. Furthermore, in certain illustrative embodiments, co-stimulatory domains of CARs can comprise both a P3 and a P4 intracellular signaling domain identified herein for CLEs. Certain illustrative subembodiments include especially effective P3 and P4 partner intracellular signaling domains as identified herein for CLEs. In illustrative embodiments, the co-stimulatory domain is other than an ITAM-containing intracellular domain of a CAR either as part of the co-stimulatory domain, or in further illustrative embodiments as the only co-stimulatory domain.

In these embodiments that include a CAR with a co-stimulatory domain identified herein as an effective intracellular domain of an LE, the co-stimulatory domain of a CAR can be any intracellular signaling domain in Table 1 provided herein. Active fragments of any of the intracellular domains in Table 1 can be a co-stimulatory domain of a CAR. In illustrative embodiments, the ASTR of the CAR comprises an scFV. In illustrative embodiments, in addition to the c-stimulatory intracellular domain of a CLE, these CARs comprise an intracellular activating domain that in illustrative embodiments is a CD3Z, CD3D, CD3E, CD3G, CD79A, CD79B, DAP12, FCER1G, FCGR2A, FCGR2C. DAP10/CD28, or ZAP70 intracellular activating domain, or in further illustrative embodiments is a CD3z intracellular activating domain.

In these illustrative embodiments, the co-stimulatory domain of a CAR can comprise an intracellular domain or a functional signaling fragment thereof that includes a signaling domain from CSF2RB, CRLF2, CSF2RA, CSF3R, EPOR, GHR, IFNAR1, IFNAR2, IFNGR1, IFNGR2, IFNLR1, IL1R1, IL1RAP, IL1RL1, IL1RL2, IL2RA, IL2RB, IL2RG, IL3RA, IL5RA, IL6R, IL6ST, IL7RA, IL9R, IL10RA, IL10RB, IL11RA, IL12RB1, IL12RB2, IL13RA1, IL13RA2, IL15RA, IL17RB, IL17RC, IL17RD, IL18R1, IL18RAP, IL20RA, IL20RB, IL21R, IL22RA1, IL23R, IL27RA, IL31RA, LEPR, LIFR, LMP1, MPL, MyD88, OSMR, or PRLR. In some embodiments, the co-stimulatory domain of a CAR can include an intracellular domain or a functional signaling fragment thereof that includes a signaling domain from CSF2RB, CRLF2, CSF2RA, CSF3R, EPOR, GHR, IFNAR1, IFNAR2, IFNGR1, IFNGR2, IFNLR1, IL1R1, IL1RAP, IL1RL1, IL1RL2, IL2RA, IL2RB, IL2RG, IL3RA, IL5RA, IL6R, IL6ST, IL9R, IL10RA, IL10RB, IL11RA, IL13RA1, IL13RA2, IL17RB, IL17RC, IL17RD, IL18R1, IL18RAP, IL20RA, IL20RB, IL22RA1, IL31RA, LEPR, LIFR, LMP1, MPL, MyD88, OSMR, or PRLR. In some embodiments, the co-stimulatory domain of a CAR can include an intracellular domain or a functional fragment thereof that includes a signaling domain from CSF2RB, CSF2RA, CSF3R, EPOR, IFNGR1, IFNGR2, IL1R1, IL1RAP, IL1RL1, IL2RA, IL2RG, IL5RA, IL6R, IL9R, IL10RB, IL11RA, IL12RB1, IL12RB2, IL13RA2, IL15RA, IL17RD, IL21R, IL23R, IL27RA, IL31RA, LEPR, MPL, MyD88, or OSMR. In some embodiments, the co-stimulatory domain of a CAR can include an intracellular domain or a fragment thereof that includes a signaling domain from CSF2RB, CSF2RA, CSF3R, EPOR, IFNGR1, IFNGR2, IL1R1, IL1RAP, IL1RL1, IL2RA, IL2RG, IL5RA, IL6R, IL9R, IL10RB, IL11RA, IL13RA2, IL17RD, IL31RA, LEPR, MPL, MyD88, or OSMR. In some embodiments, the co-stimulatory domain of a CAR can include an intracellular domain or a functional signaling fragment thereof that includes a signaling domain from CSF2RB, CSF3R, IFNAR1, IFNGR1, IL2RB, IL2RG, IL6ST, IL10RA, IL12RB2, IL17RC, IL17RE, IL18R1, IL27RA, IL31RA, MPL, MyD88, OSMR, or PRLR. In some embodiments, the co-stimulatory domain of a CAR can include an intracellular domain or a functional signaling fragment thereof that includes a signaling domain from CSF2RB, CSF3R, IFNGR1, IL2RB, IL2RG, IL6ST, IL10RA, IL17RE, IL31RA, MPL, or MyD88.

In some embodiments, the co-stimulatory domain of a CAR can include an intracellular domain or a fragment thereof that includes a signaling domain from CSF3R, IL6ST, IL27RA, MPL, and MyD88. In certain illustrative subembodiments, the intracellular activating domain of the CAR is derived from CD3z.

Recombinant T Cell Receptors (TCRs)

T Cell Receptors (TCRs) recognize specific protein fragments derived from intracellular and well as extracellular proteins. When proteins are broken into peptide fragments, they are presented on the cell surface with another protein called major histocompatibility complex, or MHC, which is called the HLA (human leukocyte antigen) complex in humans. Three different T cell antigen receptors combinations in vertebrates are αβ TCR, γδTCR and pre-TCR. Such combinations are formed by dimerization between members of dimerizing subtypes, such as an α TCR subunit and a β TCR subunit, a γ TCR subunit and a δ TCR subunit, and for pre-TCRs, a pTα subunit and a β TCR subunit. A set of TCR subunits dimerize and recognize a target peptide fragment presented in the context of an MHC. The pre-TCR is expressed only on the surface of immature αβ T cells while the αβ TCR is expressed on the surface of mature αβ T cells and NK T cells, and γδTCR is expressed on the surface of γδT cells. αβTCRs on the surface of a T cell recognize the peptide presented by MHCI or MHCII and the αβ TCR on the surface of NK T cells recognize lipid antigens presented by CD1. γδTCRs can recognize MHC and MHC-like molecules, and can also recognize non-MHC molecules such as viral glycoproteins. Upon ligand recognition, αβTCRs and γδTCRs transmit activation signals through the CD3zeta chain that stimulate T cell proliferation and cytokine secretion.

TCR molecules belong to the immunoglobulin superfamily with its antigen-specific presence in the V region, where CDR3 has more variability than CDR1 and CDR2, directly determining the antigen binding specificity of the TCR. When the MHC-antigen peptide complex is recognized by a TCR, the CDR1 and CDR2 recognize and bind the sidewall of the MHC molecule antigen binding channel, and the CDR3 binds directly to the antigenic peptide. Recombinant TCRs may thus be engineered that recognize a tumor-specific protein fragment presented on MHC.

Recombinant TCR's such as those derived from human TCRα and TCRβ pairs that recognize specific peptides with common HLAs can thus be generated with specificity to a tumor specific protein (Schmitt, T M et al., 2009). The target of recombinant TCRs may be peptides derived from any of the antigen targets for CAR ASTRs provided herein, but are more commonly derived from intracellular tumor specific proteins such as oncofetal antigens, or mutated variants of normal intracellular proteins or other cancer specific neoepitopes. Libraries of TCR subunits may be screened for their selectivity to a target antigen. Screens of natural and/or recombinant TCR subunits can identify sets of TCR subunits with high avidities and/or reactivities towards a target antigen. Members of such sets of TCR subunits can be selected and cloned to produce one or more polynucleotide encoding the TCR subunit.

Polynucleotides encoding such a set of TCR subunits can be included in a replication incompetent recombinant retroviral particle to genetically modify a lymphocyte, or in illustrative embodiments, a T cell or an NK cell, such that the lymphocyte expresses the recombinant TCR. Accordingly, in any aspect or embodiment provided herein that includes an engineered signaling polypeptide, such as embodiments that include one more CARs and/or lymphoproliferative elements, the engineered signaling polypeptide(s) can include or can be one or more sets of recombinant γδTCR chains, or in illustrative embodiments αβTCR chains. TCR chains that form a set may be co-expressed using a number of different techniques to co-express the two TCR chains as is disclosed herein for expressing two or more other engineered signaling polypeptides such as CARs and lymphoproliferative elements. For example, protease cleavage epitopes such as 2A protease, internal ribosomal entry sites (IRES), and separate promoters may be used.

Several strategies have been employed to reduce the likelihood of mixed TCR dimer formation. In general, this involves modification of the constant (C) domains of the TCRα and TCRβ chains to promote the preferential pairing of the introduced TCR chains with each other, while rendering them less likely to successfully pair with endogenous TCR chains. One approach that has shown some promise in vitro involves replacement of the C domain of human TCRα and TCRβ chains with their mouse counterparts. Another approach involves mutation of the human TCRα common domain and TCRβ chain common regions to promote self-pairing, or the expression of an endogenous TCR alpha and TCR beta miRNA within the viral gene construct. Accordingly, in some embodiments provided herein that include one or more sets of TCR chains as engineered signaling polypeptides, each member of the set of TCR chains, in illustrative embodiments αβTCR chains, comprises a modified constant domain that promotes preferential pairing with each other. In some subembodiments, each member of a set of TCR chains, in illustrative embodiments αβTCR chains, comprises a mouse constant domain from the same TCR chain type, or a constant domain from the same TCR chain subtype with enough sequences derived from a mouse constant domain from the same TCR chain subtype, such that dimerization of the set of TCR chains to each other is preferred over, or occurs to the exclusion of, dimerization with human TCR chains. In other subembodiments, each member of a set of TCR chains, in illustrative embodiments αβTCR chains, comprises corresponding mutations in its constant domain, such that dimerization of the set of TCR chains to each other is preferred over, or occurs to the exclusion of, dimerization with TCR chains that have human constant domains. Such preferred or exclusive dimerization in illustrative embodiments, is under physiological conditions.

Lymphoproliferative Elements

Peripheral T lymphocyte numbers are maintained at remarkably stable levels throughout adulthood, despite the continuing addition of cells, due to emigration from the thymus and proliferation in response to antigen encounter, and loss of cells owing to the removal of antigen-specific effectors after antigen clearance (Marrak, P. et al. 2000. *Nat Immunol* 1:107-111; Freitas, A. A. et al. 2000. *Annu Rev Immunol* 18:83-111). The size of the peripheral T cell compartment is regulated by multiple factors that influence both proliferation and survival. However, in a lymphopenic environment, T lymphocytes divide independently of cognate antigen, due to "acute homeostatic proliferation" mechanisms that maintain the size of the peripheral T cell compartment. Conditions for lymphopenia have been established in subjects or patients during adoptive cell therapy by proliferating T cells in vitro and introducing them into lymphodepleted subjects, resulting in enhanced engraftment and antitumor function of transferred T cells. However, lymphodepletion of a subject is not desirable because it can cause serious side effects, including immune dysfunction and death.

Studies have shown that lymphodepletion removes endogenous lymphocytes functioning as cellular sinks for homeostatic cytokines, thereby freeing cytokines to induce survival and proliferation of adoptively transferred cells. Some cytokines, such as for example, IL-7 and IL-15, are known to mediate antigen-independent proliferation of T cells and are thus capable of eliciting homeostatic proliferation in non-lymphopenic environments. However, these cytokines and their receptors have intrinsic control mechanisms that prevent lymphoproliferative disorders at homeostasis.

Many of the embodiments provided herein include a lymphoproliferative element, or a nucleic acid encoding the same, typically as part of an engineered signaling polypeptide. Accordingly, in some aspects of the present invention, an engineered signaling polypeptide is a lymphoproliferative element (LE) such as a chimeric lymphoproliferative element (CLE). Typically, the LE comprises an extracellular domain, a transmembrane domain, and at least one intracellular signaling domain that drives proliferation, and in illustrative embodiments a second intracellular signaling domain.

In some embodiments, the lymphoproliferative element can include a first and/or second intracellular signaling domain. In some embodiments, the first and/or second intracellular signaling domain can include CD2, CD3D, CD3E, CD3G, CD4, CD8A, CD8B, CD27, mutated Delta Lck CD28, CD28, CD40, CD79A, CD79B, CRLF2, CSF2RB, CSF2RA, CSF3R, EPOR, FCER1G, FCGR2C, FCGRA2, GHR, ICOS, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL7RA, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL31RA, LEPR, LIFR, LMP1, MPL, MYD88, OSMR, PRLR, TNFRSF4, TNFRSF8, TNFRSF9, TNFRSF14, or TNFRSF18, or functional mutants and/or fragments thereof. In illustrative embodiments, the first intracellular signaling domain can include MyD88, or a functional mutant and/or fragment thereof. In further illustrative embodiments, the first intracellular signaling domain can include MyD88, or a functional mutant and/or fragment thereof, and the second intracellular signaling domain can include ICOS, TNFRSF4, or TNSFR18, or functional mutants and/or fragments thereof. In some embodiments, the first intracellular domain is MyD88 and the second intracellular domain is an ITAM-containing intracellular domain, for example, an intracellular domain from CD3Z, CD3D, CD3E, CD3G, CD79A, CD79B, DAP12, FCER1G, FCGR2A, FCGR2C, DAP10/CD28, or ZAP70. In some embodiments, the second intracellular signaling domain can include TNFRSF18, or a functional mutant and/or fragment thereof.

In some embodiments, the lymphoproliferative element can include a fusion of an extracellular domain and a transmembrane domain. In some embodiments, the fusion of an extracellular domain and a transmembrane domain can include eTAG IL7RA Ins PPCL (interleukin 7 receptor), Myc LMP1, LMP1, eTAG CRLF2, eTAG CSF2RB, eTAG CSF3R, eTAG EPOR, eTAG GHR, eTAG truncated after Fn F523C IL27RA, or eTAG truncated after Fn S505N MPL, or functional mutants and/or fragments thereof. In some embodiments, the lymphoproliferative element can include an extracellular domain. In some embodiments, the extracellular domain can include eTag with 0, 1, 2, 3, or 4 additional alanines at the carboxy terminus. In some embodiments, the extracellular domain can include Myc with 0, 1, 2, 3, or 4 additional alanines at the carboxy terminus, or functional mutants and/or fragments thereof. In some embodiments, the lymphoproliferative element can include a transmembrane domain. In some embodiments, the transmembrane domain can include CD2, CD3D, CD3E, CD3G, CD3Z CD247, CD4, CD8A, CD8B, CD27, CD28, CD40, CD79A, CD79B, CRLF2, CSF2RA, CSF2RB, CSF3R, EPOR, FCER1G, FCGR2C, FCGRA2, GHR, ICOS, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL7RA, IL7RA Ins PPCL, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL31RA, LEPR, LIFR, MPL, OSMR, PRLR, TNFRSF4, TNFRSF8, TNFRSF9, TNFRSF14, or TNFRSF18, or functional mutants and/or fragments thereof.

CLEs for use in any aspect or embodiment herein can include any CLE disclosed in WO2019/055946 (incorporated by reference herein, in its entirety), the vast majority of which were designed to be and are believed to be constitutively active. As illustrated therein, where there is a first and a second intracellular signaling domain of a CLE, the first intracellular signaling domain is positioned between the membrane associating motif and the second intracellular domain.

In another embodiment, the LE provides, is capable of providing and/or possesses the property of (or a cell genetically modified and/or transduced with the LE is capable of providing, is adapted for, possesses the property of, and/or is modified for) driving T cell expansion in vivo. Methods for performing such an in vivo test are provided in Example 6. For example, as illustrated in Example 6, the in vivo test can utilize a mouse model and measure T cell expansion at 15 to 25 days in vivo, or at 19 to 21 days in vivo, or at approximately 21 days in vivo, after T cells are contacted with lentiviral vectors encoding the LEs, are introduced into the mice.

In some embodiments, the lymphoproliferative element can include any of the sequences listed in Table 1 (SEQ ID NOs: 84-302). Table 1 shows the parts, names (including gene names), and amino acid sequences for domains that were tested in CLEs. Typically, a CLE includes an extracellular domain (denoted P1), a transmembrane domain (denoted P2), a first intracellular domain (denoted P3), and a second intracellular domain (denoted P4). Typically, the lymphoproliferative element includes a first intracellular domain. In illustrative embodiments, the first intracellular domain can include any of the parts listed as 5036 to 50216 or in Table 1, or functional mutants and/or fragments thereof. In some embodiments, the lymphoproliferative element can include a second intracellular domain. In illustrative embodiments, the second intracellular domain can include any of the parts listed as S036 to S0216 or in Table 1, or functional mutants and/or fragments thereof. In some embodiments, the lymphoproliferative element can include an extracellular domain. In illustrative embodiments, the extracellular domain can include any of the sequences of parts listed as M001 to M049 or E006 to E015 in Table 1, or functional mutants and/or fragments thereof. In some embodiments, the lymphoproliferative element can include a transmembrane domain. In illustrative embodiments, the transmembrane domain can include any of the parts listed as M001 to M049 or T001 to T082 in Table 1, or functional mutants and/or fragments thereof. In some embodiments, the lymphoproliferative element can be of fusion of an extracellular/transmembrane domain (M001 to M049 in Table 1), a first intracellular domain (S036 to S0216 in Table 1), and a second intracellular domain (S036 to 5216 in Table 1). In some embodiments, the lymphoproliferative element can be a fusion of an extracellular domain (E006 to E015 in Table 1), a transmembrane domain (T001 to T082 in Table 1), a first intracellular domain (S036 to 50216 in Table 1), and a second intracellular domain (S036 to 50216 in Table 1). For example, the lymphoproliferative element can be a fusion of E006, T001, 5036, and 5216, also written as E006-T001-S036-S216). In illustrative embodiments, the lymphoproliferative element can be the fusion E010-T072-S192-S212, E007-T054-S197-S212, E006-T006-S194-S211, E009-T073-S062-S053, E008-T001-S121-S212, E006-T044-S186-S053, or E006-T016-S186-S050.

In illustrative embodiments, the intracellular domain of an LE, or the first intracellular domain in an LE that has two or more intracellular domains, is other than a functional intracellular activating domain from an ITAM-containing intracellular domain, for example, an intracellular domain from CD3Z, CD3D, CD3E, CD3G, CD79A, CD79B, DAP12, FCER1G, FCGR2A, FCGR2C, DAP10/CD28, or ZAP70, and in a further illustrative subembodiment, CD3z. In illustrative embodiments, a second intracellular domain of an LE is other than a co-stimulatory domain of 4-1BB (CD137), CD28, ICOS, OX-40, BTLA, CD27, CD30, GITR, and HVEM. In illustrative embodiments, the extracellular domain of an LE does not comprise a single-chain variable fragment (scFv). In further illustrative embodiments, the extracellular domain of an LE that upon binding to a binding partner activates an LE, does not comprise a single-chain variable fragment (scFv).

A CLE does not comprise both an ASTR and an activation domain from CD3Z, CD3D, CD3E, CD3G, CD79A, CD79B, DAP12, FCER1G, FCGR2A, FCGR2C, DAP10/CD28, or ZAP70. Not to be limited by theory, the extracellular domain and transmembrane domain are believed to play support roles in LEs, assuring that the intracellular signaling domain(s) is in an effective conformation/orientation/localization for driving proliferation. Thus, the ability of an LE to drive proliferation is believed to be provided by the intracellular domain(s) of the LE, and the extracellular and transmembrane domains are believed to play secondary roles relative to the intracellular domain(s). A lymphoproliferative element includes an intracellular domain that is a signaling polypeptide that is capable of driving proliferation of T cells or NK cells that is associated with a membrane through a membrane-associating motif (e.g. a transmembrane domain) and is oriented in, or capable of being oriented into, an active conformation. The ASTR of an LE in illustrative embodiments, does not include an scFv. Strategies are provided herein for associating an intracellular domain with a membrane, such as by inclusion of a transmembrane domain, a GPI anchor, a myristoylation region, a palmitoylation region, and/or a prenylation region. In some embodiments, a lymphoproliferative element does not include an extracellular domain.

The extracellular domains, transmembrane domains, and intracellular domains of LEs can vary in their respective amino acid lengths. For example, for embodiments that include a replication incompetent retroviral particle, there are limits to the length of a polynucleotide that can be packaged into a retroviral particle so LEs with shorter amino acid sequences can be advantageous in certain illustrative embodiments. In some embodiments, the overall length of the LE can be between 3 and 4000 amino acids, for example between 10 and 3000, 10 and 2000, 50 and 2000, 250 and 2000 amino acids, and, in illustrative embodiments between 50 and 1000, 100 and 1000 or 250 and 1000 amino acids. The extracellular domain, when present to form an extracellular and transmembrane domain, can be between 1 and 1000 amino acids, and is typically between 4 and 400, between 4 and 200, between 4 and 100, between 4 and 50, between 4 and 25, or between 4 and 20 amino acids. In one embodiment, the extracellular region is GGGS for an extracellular and transmembrane domain of this aspect of the invention. The transmembrane domains, or transmembrane regions of extracellular and transmembrane domains, can be between 10 and 250 amino acids, and are more typically at least 15 amino acids in length, and can be, for example, between 15 and 100, 15 and 75, 15 and 50, 15 and 40, or 15 and 30 amino acids in length. The intracellular signaling domains can be, for example, between 10 and 1000, 10 and 750, 10 and 500, 10 and 250, or 10 and 100 amino acids. In illustrative embodiments, the intracellular signaling domain can be at least 30, or between 30 and 500, 30 and 250, 30 and 150, 30 and 100, 50 and 500, 50 and 250, 50 and 150, or 50 and 100 amino acids. In some embodiments, an intracellular signaling domain for a particular gene is at least 90%, 95%, 98%, 99% or 100% identical to at least 10, 25, 30, 40, or 50 amino acids from a sequence of that intracellular signaling domain, such as a sequence provided herein for that intracellular domain, up to the size of the entire intracellular domain sequence, and can include for example, up to an additional 1, 2, 3, 4, 5, 10, 20, or 25 amino acids, provided that such sequence still is capable of providing any of the properties of LEs disclosed herein.

In some embodiments, the lymphoproliferative element is a chimeric cytokine receptor such as but not limited to a cytokine tethered to its receptor that typically constitutively activates the same STAT pathway as a corresponding activated wild-type cytokine receptor such as STAT3, STAT4, and in illustrative embodiments, STAT5. In some embodiments, the chimeric cytokine receptor is an interleukin, or a fragment thereof, tethered to or covalently attached to its cognate receptor, or a fragment thereof, via a linker. In some embodiments, the chimeric cytokine receptor is IL7 tethered to IL7Rα (also known as IL7RA). In other embodiments, the chimeric cytokine receptor is IL-7 tethered to a domain of IL7Rα, such as for example, the extracellular domain of IL-7Rα and/or the transmembrane domain of IL-7Rα. In some embodiments, the lymphoproliferative element is a cytokine receptor that is not tethered to a cytokine, and in fact in illustrative embodiments, provided herein a lymphoproliferative element is a constitutively active cytokine receptor that is not tethered to a cytokine. These chimeric IL-7 receptors typically constitutively activate STAT5 when expressed.

In illustrative embodiments of any of the methods and compositions provided herein that include a lymphoproliferative element, wherein the lymphoproliferative element is a cytokine or cytokine receptor polypeptide, or a fragment thereof comprising a signaling domain, the lymphoproliferative element can comprise an interleukin polypeptide covalently attached to a portion of its cognate interleukin receptor polypeptide via a linker. Typically, this portion of the cognate interleukin receptor includes a functional portion of the extracellular domain capable of binding the interleukin cytokine and the transmembrane domain. In some embodiments, the intracellular domain is an intracellular portion of the cognate interleukin receptor. In some embodiments, the intracellular domain is an intracellular portion of a different cytokine receptor that is capable of promoting lymphocyte proliferation. In some embodiments the lymphoproliferative element is an interleukin polypeptide covalently attached to its full length cognate interleukin receptor polypeptide via a linker.

In illustrative embodiments of any of the methods and compositions provided herein that include a lymphoproliferative element, the intracellular domain can be derived from a portion of the protein IL7RA. The domains, motifs, and point mutations of IL7RA that induce proliferation and/or survival of T cells and/or NK cells are known in the art and a skilled artisan can identify corresponding domains, motifs, and point mutations in IL7RA polypeptides, some of which are discussed in this paragraph. The IL7RA protein has an S region rich in serine residues (359-394 of full-length IL7RA, corresponding to residues 96-133 of SEQ ID NO:248), a T region with three tyrosine residues (residues Y401, Y449, and Y456 of full-length IL7RA, corresponding to residues Y138, Y18, and Y193 of SEQ ID NO:248), and a Box1 motif that can bind the signaling kinase Jak1 (residues 272-280 of full-length IL7RA corresponding to residues 9-17 of SEQ ID NO:248 and 249) (Jiang, Qiong et al. Mol. and Cell. Biol. Vol. 24(14):6501-13 (2004)). In some embodiments, a lymphoproliferative element herein can include one or more, for example all of the domains and motifs of IL7RA disclosed herein or otherwise known to induce proliferation and/or survival of T cells and/or NK cells. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:248 or 249. In some embodiments, the intracellular domain derived from IL7RA has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, or from about 175 aa to about 200 aa. In illustrative embodiments, the intracellular domain derived from IL7RA has a length of from about 30 aa to about 200 aa. In illustrative embodiments of lymphoproliferative elements that include a first intracellular domain derived from IL7RA, the second intracellular domain can be derived from TNFRSF8.

In illustrative embodiments of any of the methods and compositions provided herein that include a lymphoproliferative element, the intracellular domain can be derived from a portion of the protein IL12RB. The domains, motifs, and point mutations of IL12RB that induce proliferation and/or survival of T cells and/or NK cells are known in the art and a skilled artisan can identify corresponding domains, motifs, and point mutations in IL12RB polypeptides, some of which are discussed in this paragraph. Full-length IL12RB contains at least one Box1 motif PXXP (SEQ ID NO:306) where each X can be any amino acid (residues 10-12 of SEQ ID NOs:254 and 255; and residues 107-110 and 139-142 of SEQ ID NO:256) (Presky D H et al. Proc Natl Acad Sci USA. 1996 Nov. 26; 93(24)). In some embodiments, a lymphoproliferative element that includes an IL12RB intracellular domain can include one or more of the above Box1 motifs or other motifs, domains, or mutations of IL12RB known to induce proliferation and/or survival of T cells and/or NK cells. The Box1 motifs of IL12RB are known in the art and a skilled artisan can identify corresponding motifs in IL12RB polypeptides. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:254-256. In some embodiments, the intracellular domain derived from IL12RB has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, or from about 200 aa to about 219 aa. In illustrative embodiments, the intracellular domain derived from IL12RB has a length of from about 30 aa to about 219 aa, for example, 30 aa to 92 aa, or 30 aa to 90 aa.

In illustrative embodiments of any of the methods and compositions provided herein that include a lymphoproliferative element, the intracellular domain can be derived from a portion of the protein IL31RA. The domains, motifs, and point mutations of IL31RA that induce proliferation and/or survival of T cells and/or NK cells are known in the art and a skilled artisan can identify corresponding domains, motifs, and point mutations in IL31RA polypeptides, some of which are discussed in this paragraph. Full-length IL31RA contains the Box1 motif PXXP (SEQ ID NO:306) where each X can be any amino acid (corresponding to residues 12-15 of SEQ ID NOs:275 and 276) (Cornelissen C et al. Eur J Cell Biol. 2012 June-July; 91(6-7):552-66). In some embodiments, a lymphoproliferative element that includes an IL31RA intracellular domain can include the Box1 motif. Full-length IL31RA also contains three phosphorylatable tyrosine residues that are important for downstream signaling, Y652, Y683, and Y721 (corresponding to residues Y96, Y237, and Y165 of SEQ ID NO:275; these tyrosine residues are not present in SEQ ID NO:276) (Cornelissen C et al. Eur J Cell Biol. 2012 June-July; 91(6-7): 552-66). All three tyrosine residues contribute to the activation of STAT1, while Y652 is required for STAT5 activation and Y721 recruits STAT3. In some embodiments, a lymphoproliferative element with an IL31RA intracellular domain includes the Box1 motif and/or the known phosphorylation sites disclosed herein. The Box1 motif and phosphorylatable tyrosines of IL31RA are known in the art and a skilled artisan will be able to identify corresponding motifs and phosphorylatable tyrosines in similar IL31RA polypeptides. In other embodiments, a lymphoproliferative element with an IL31RA intracellular domain does not include the known phosphorylation sites disclosed herein. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:275 or 276. In some embodiments, the intracellular domain derived from IL31RA has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, or from about 175 aa to about 189 aa. In illustrative embodiments, the intracellular domain derived from IL31RA has a length of from about 30 aa to about 200 aa, for example, 30 aa to 189 aa, 30 aa to 106 aa.

In illustrative embodiments of any of the methods and compositions provided herein that include a lymphoproliferative element, the intracellular domain can be derived from an intracellular portion of the transmembrane protein CD40. The domains, motifs, and point mutations of CD40 that induce proliferation and/or survival of T cells and/or NK cells are known in the art and a skilled artisan can identify corresponding domains, motifs, and point mutations in CD40 polypeptides, some of which are discussed in this paragraph. The CD40 protein contains several binding sites for TRAF proteins. Not to be limited by theory, binding sites for TRAF1, TRAF2, and TRAF3 are located at the membrane distal domain of the intracellular portion of CD40 and include the amino acid sequence PXQXT (SEQ ID NO:303) where each X can be any amino acid, (corresponding to amino acids 35-39 of SEQ ID NO:208) (Elgueta et al. Immunol Rev. 2009 May; 229(1):152-72). TRAF2 has also been shown to bind to the consensus sequence SXXE (SEQ ID NO:304) where each X can be any amino acid, (corresponding to amino acids 57-60 of SEQ ID NO:208) (Elgueta et al. Immunol Rev. 2009 May; 229(1):152-72). A distinct binding site for TRAF6 is situated at the membrane proximal domain of intracellular portion of CD40 and includes the consensus sequence QXPXEX (SEQ ID NO:305) where each X can be any amino acid (corresponding to amino acids 16-21 of SEQ ID NO:208) (Lu et al. J Biol Chem. 2003 Nov. 14; 278(46):45414-8). In illustrative embodiments, the intracellular portion of the transmembrane protein CD40 can include all the binding sites for the TRAF proteins. The TRAF binding sites are known in the art and a skilled artisan will be able to identify corresponding TRAF binding sites in similar CD40 polypeptides. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:208 or SEQ ID NO:209. In some embodiments, the intracellular domain derived from CD40 has a length of from about 30 amino acids (aa) to about 35 aa, from about 35 aa to about 40 aa, from about 40 aa to about 45 aa, from about 45 aa to about 50 aa, from about 50 aa to about 55 aa, from about 55 aa to about 60 aa, or from about 60 aa to about 65 aa. In illustrative embodiments, the intracellular domain derived from CD40 has a length of from about 30 aa to about 66 aa, for example, 30 aa to 65 aa, or 50 aa to 66 aa. In illustrative embodiments of lymphoproliferative elements that include a first intracellular domain derived from CD40, the second intracellular domain can be other than an intracellular domain derived from MyD88, a CD28 family member (e.g. CD28, ICOS), Pattern Recognition Receptor, a C-reactive protein receptor (i.e., Nodi, Nod2, PtX3-R), a TNF receptor, CD40, RANK/TRANCE-R, OX40, 4-1BB), an HSP receptor (Lox-1 and CD91), or CD28. Pattern Recognition Receptors include, but are not limited to endocytic pattern-recognition receptors (i.e., mannose receptors, scavenger receptors (i.e., Mac-1, LRP, peptidoglycan, techoic acids, toxins, CD11c/CR4)); external signal pattern-recognition receptors (Toll-like receptors (TLR1, TLR2, TLR3, TLR4, TLR5, TLR6, TLR7, TLR8, TLR9, TLR10), peptidoglycan recognition protein, (PGRPs bind bacterial peptidoglycan, and CD14); internal signal pattern-recognition receptors (i.e., NOD-receptors 1 & 2), and RIG1

In illustrative embodiments of any of the methods and compositions provided herein that include a lymphoproliferative element, the intracellular domain can be derived from an intracellular portion of CD27. The domains, motifs, and point mutations of CD27 that induce proliferation and/or survival of T cells and/or NK cells are known in the art and a skilled artisan can identify corresponding domains, motifs, and point mutations in CD27 polypeptides, some of which are discussed in this paragraph. The serine at amino acid 219 of full-length CD27 (corresponding to the serine at amino acid 6 of SEQ ID NO:205) has been shown to be phosphorylated. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:205. In some embodiments, the intracellular domain derived from CD27 has a length of from about 30 amino acids (aa) to about 35 aa, from about 35 aa to about 40 aa, from about 40 aa to about 45 aa, or from about 45 aa to about 50 aa.

In illustrative embodiments of any of the methods and compositions provided herein that include a lymphoproliferative element, the intracellular domain can be derived from an intracellular portion of CSF2RB. The domains, motifs, and point mutations of CSF2RB that induce proliferation and/or survival of T cells and/or NK cells are known in the art and a skilled artisan can identify corresponding domains, motifs, and point mutations in CSF2RB polypeptides, some of which are discussed in this paragraph. Full-length CSF2RB contains a Box1 motif at amino acids 474-482 (corresponding to amino acids 14-22 of SEQ ID NO:213). The tyrosine at amino acid 766 of full-length CSF2RB (corresponding to the tyrosine at amino acid 306 of SEQ ID NO: 213) has been shown to be phosphorylated. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO: 213. In some embodiments, the intracellular domain derived from CSF2RB has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, from about 250 aa to 300 aa, from about 300 aa to 350 aa, from about 350 aa to about 400 aa, or from about 400 aa to about 450 aa.

In illustrative embodiments of any of the methods and compositions provided herein that include a lymphoproliferative element, the intracellular domain can be derived from an intracellular portion of IL2RB. The domains, motifs, and point mutations of IL2RB that induce proliferation and/or survival of T cells and/or NK cells are known in the art and a skilled artisan can identify corresponding domains, motifs, and point mutations in IL2RB polypeptides, some of which are discussed in this paragraph. Full-length IL2RB contains a Box1 motif at amino acids 278-286 (corresponding to amino acids 13-21 of SEQ ID NO:240). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:240. In some embodiments, the intracellular domain derived from IL2RB has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, or from about 250 aa to 300 aa.

In illustrative embodiments of any of the methods and compositions provided herein that include a lymphoproliferative element, the intracellular domain can be derived from an intracellular portion of IL6ST. The domains, motifs, and point mutations of IL6ST that induce proliferation and/or survival of T cells and/or NK cells are known in the art and a skilled artisan can identify corresponding domains, motifs, and point mutations in IL6ST polypeptides, some of which are discussed in this paragraph. Full-length IL6ST contains a Box1 motif at amino acids 651-659 (corresponding to amino acids 10-18 of SEQ ID NO:247). The serines at amino acids 661, 667, 782, 789, 829, and 839 of full-length IL6ST (corresponding to serines at amino acids 20, 26, 141, 148, 188, and 198, respectively, of SEQ ID NO:247) have been shown to be phosphorylated. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:246 or SEQ ID NO:247. In some embodiments, the intracellular domain derived from IL6ST has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, or from about 250 aa to 300 aa.

In illustrative embodiments of any of the methods and compositions provided herein that include a lymphoproliferative element, the intracellular domain can be derived from an intracellular portion of IL17RE. The domains, motifs, and point mutations of IL17RE that induce proliferation and/or survival of T cells and/or NK cells are known in the art and a skilled artisan can identify corresponding domains, motifs, and point mutations in IL17RE polypeptides, some of which are discussed in this paragraph. Full-length IL17RE contains a TIR domain at amino acids 372-495 (corresponding to amino acids 13-136 of SEQ ID NO:265). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:265. In some embodiments, the intracellular domain derived from IL17RE has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, or from about 175 aa to about 200 aa.

In illustrative embodiments of any of the methods and compositions provided herein that include a lymphoproliferative element, the intracellular domain can be derived from an intracellular portion of IL2RG. The domains, motifs, and point mutations of IL2RG that induce proliferation and/or survival of T cells and/or NK cells are known in the art and a skilled artisan can identify corresponding domains, motifs, and point mutations in IL2RG polypeptides, some of which are discussed in this paragraph. Full-length IL2RG contains a Box1 motif at amino acids 286-294 (corresponding to amino acids 3-11 of SEQ ID NO:241). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:241. In some embodiments, the intracellular domain derived from IL2RG has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, or from about 70 aa to about 100 aa.

In illustrative embodiments of any of the methods and compositions provided herein that include a lymphoproliferative element, the intracellular domain can be derived from an intracellular portion of IL18R1. The domains, motifs, and point mutations of IL18R1 that induce proliferation and/or survival of T cells and/or NK cells are known in the art and a skilled artisan can identify corresponding domains, motifs, and point mutations in IL18R1 polypeptides, some of which are discussed in this paragraph. Full-length IL18R1 contains a TIR domain at amino acids 222-364 (corresponding to amino acids 28-170 of SEQ ID NO:266). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:266. In some embodiments, the intracellular domain derived from IL18R1 has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, or from about 70 aa to about 100 aa.

In illustrative embodiments of any of the methods and compositions provided herein that include a lymphoproliferative element, the intracellular domain can be derived from an intracellular portion of IL27RA. The domains, motifs, and point mutations of IL27RA that induce proliferation and/or survival of T cells and/or NK cells are known in the art and a skilled artisan can identify corresponding domains, motifs, and point mutations in IL27RA polypeptides, some of which are discussed in this paragraph. Full-length IL27RA contains a Box1 motif at amino acids 554-562 (corresponding to amino acids 17-25 of SEQ ID NO:273). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:273 or SEQ ID NO:274. In some embodiments, the intracellular domain derived from IL27RA has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, or from about 70 aa to about 100 aa.

In illustrative embodiments of any of the methods and compositions provided herein that include a lymphoproliferative element, the intracellular domain can be derived from an intracellular portion of IFNGR2. The domains, motifs, and point mutations of IFNGR2 that induce proliferation and/or survival of T cells and/or NK cells are known in the art and a skilled artisan can identify corresponding domains, motifs, and point mutations in IFNGR2 polypeptides, some of which are discussed in this paragraph. Full-length IFNGR2 contains a dileucine internalization motif at amino acids 276-277 (corresponding to amino acids 8-9 of SEQ ID NO:230). In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:230. In some embodiments, the intracellular domain derived from IFNGR2 has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In illustrative embodiments of any of the methods and compositions provided herein that include a lymphoproliferative element, the intracellular domain can be derived from a portion of the protein MyD88. The domains, motifs, and point mutations of MyD88 that induce proliferation and/or survival of T cells and/or NK cells are known in the art and a skilled artisan can identify corresponding domains, motifs, and point mutations in MyD88 polypeptides, some of which are discussed in this paragraph. The MyD88 protein has an N-terminal death domain that mediates interactions with other death domain-containing proteins (corresponding to amino acids 29-106 of SEQ ID NO:284), an intermediate domain that interacts with IL-1R associated kinase (corresponding to amino acids 107-156 of SEQ ID NO:284), and a C-terminal TIR domain (corresponding to amino acids 160-304 of SEQ ID NO:284) that associates with the TLR-TIR domain (Biol Res. 2007; 40(2):97-112). MyD88 also has canonical nuclear localization and export motifs. Point mutations have been identified in MyD88 and include the loss-of-function mutations L93P and R193C (corresponding to L93P and R196C in SEQ ID NO:284), and the gain-of-function mutation L265P (corresponding to L260P in SEQ ID NO:284) (Deguine and Barton. F1000Prime Rep. 2014 Nov. 4; 6:97). In some embodiments, a lymophoproliferative element herein can include one or more, for example all of the domains and motifs of MyD88 disclosed herein. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:284-293, and in illustrative embodiments includes one or more, in illustrative embodiments all, of the following MyD88 domains/motifs: the death domain, the intermediate domain, the TIR domain, the nuclear localization and export motifs, an amino acid corresponding to position L93, R193, and L265 or P265. In some embodiments, the intracellular domain derived from MyD88 has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, from about 250 aa to 300 aa, or from about 300 aa to 350 aa. In illustrative embodiments, the intracellular domain derived from MyD88 has a length of from about 30 aa to about 350 aa, for example, 50 aa to 350 aa, or 100 aa to 350 aa, 100 aa to 304 aa, 100 aa to 296 aa, 100 aa to 251 aa, 100 aa to 191 aa, 100 aa to 172 aa, 100 aa to 146 aa, or 100 aa to 127 aa. In illustrative embodiments of lymphoproliferative elements that include a first intracellular domain derived from MyD88, the second intracellular domain can be derived from TNFRSF4 or TNFRSF8. In other illustrative embodiments of lymphoproliferative elements that include a first intracellular domain derived from MyD88, the second intracellular domain can be other than an intracellular domain derived from a CD28 family member (e.g. CD28, ICOS), Pattern Recognition Receptor, a C-reactive protein receptor (i.e., Nodi, Nod2, PtX3-R), a TNF receptor (i.e., CD40, RANK/TRANCE-R, OX40, 4-1BB), an HSP receptor (Lox-1 and CD91), or CD28.

In illustrative embodiments of any of the methods and compositions provided herein that include a lymphoproliferative element, the intracellular domain can be derived from a portion of the transmembrane protein MPL. The domains, motifs, and point mutations of MPL that induce proliferation and/or survival of T cells and/or NK cells are known in the art and a skilled artisan can identify corresponding domains, motifs, and point mutations in MPL polypeptides, some of which are discussed in this paragraph. The transmembrane MPL protein contains the Box1 motif PXXP (SEQ ID NO:306) where each X can be any amino acid (corresponding to amino acids 17-20 in SEQ ID NO:283) and the Box2 motif, a region with increased serine and glutamic acid content (corresponding to amino acids 46-64 in SEQ ID NO:283) (Drachman and Kaushansky. Proc Natl Acad Sci USA. 1997 Mar. 18; 94(6):2350-5). The Box1 and Box2 motifs are involved in binding to JAKs and signal transduction, although the Box2 motif presence is not always required for a proliferative signal (Murakami et al. Proc Natl Acad Sci USA. 1991 Dec. 15; 88(24):11349-53; Fukunaga et al. EMBO J. 1991 October; 10(10):2855-65; and O'Neal and Lee. Lymphokine Cytokine Res. 1993 October; 12(5):309-12). Many cytokine receptors have hydrophobic residues at positions −1, −2, and −6 relative to the Box1 motif (corresponding to amino acids 16, 15, and 11, respectively, of SEQ ID NO:283), that form a "switch motif," which is required for cytokine-induced JAK2 activation but not for JAK2 binding (Constantinescu et al. Mol Cell. 2001 February; 7(2):377-85; and Huang et al. Mol Cell. 2001 December; 8(6):1327-38). Deletion of the region encompassing amino acids 70-95 in SEQ ID NO:283 was shown to support viral transformation in the context of v-mpl (Benit et al. J Virol. 1994 August; 68(8):5270-4), thus indicating that this region is not necessary for the function of mpl in this context. Morello et al. Blood 1995 July; 86(8):557-71 used the same deletion to show that this region was not required for stimulating transcription for a hematopoietin receptor-responsive CAT reporter gene construct and furthermore saw that this deletion resulted in slightly enhanced transcription expected for removal of a nonessential and negative element in this region as suggested by Drachman and Kaushansky. Thus, in some embodiments, a MPL intracellular signaling domain does not comprise the region comprising amino acids 70-95 in SEQ ID NO:283. In full-length MPL, the lysines K553 (corresponding to K40 of SEQ ID NO: 283) and K573 (corresponding to K60 of SEQ ID NO: 283) have been shown to be negative regulatory sites that function as part of a ubiquitination targeting motif (Saur et al. Blood 2010 Feb. 11; 115(6):1254-63). Thus, in some embodiments herein, a MPL intracellular signaling domain does not comprise these ubiquitination targeting motif residues. In full-length MPL, the tyrosines Y521 (corresponding to Y8 of SEQ ID NO: 283), Y542 (corresponding to Y29 of SEQ ID NO:283), Y591 (corresponding to Y78 of SEQ ID NO: 283), Y626 (corresponding to Y113 of SEQ ID NO: 283), and Y631 (corresponding to Y118 of SEQ ID NO: 283) have been shown to be phosphorylated (Varghese et al. Front Endocrinol (Lausanne). 2017 Mar. 31; 8:59). Y521 and Y591 of full-length MPL are negative regulatory sites that function either as part of a lysosomal targeting motif (Y521) or via an interaction with adaptor protein AP2 (Y591) (Drachman and Kaushansky. Proc Natl Acad Sci USA. 1997 Mar. 18; 94(6):2350-5; and Hitchcock et al. Blood. 2008 Sep. 15; 112(6):2222-31). Y626 and Y631 of full-length MPL are positive regulatory sites (Drachman and Kaushansky. Proc Natl Acad Sci USA. 1997 Mar. 18; 94(6):2350-5) and the murine homolog of Y626 is required for cellular differentiation and the phosphorylation of Shc (Alexander et al. EMBO J. 1996 Dec. 2; 15(23):6531-40) and Y626 is also required for constitutive signaling in MPL with the W515A mutation described below (Pecquet et al. Blood. 2010 Feb. 4; 115(5):1037-48). MPL contains the Shc phosphotyrosine-binding binding motif NXXY (SEQ ID NO:307) where each X can be any amino acid (corresponding to amino acids 110-113 of SEQ ID NO: 283), and this tyrosine is phosphorylated and important for the TPO-dependent phosphorylation of Shc, SHIP, and STAT3 (Laminet et al. J Biol Chem. 1996 Jan. 5; 271(1):264-9; and van der Geer et al. Proc Natl Acad Sci USA. 1996 Feb. 6; 93(3):963-8). MPL also contains the STAT3 consensus binding sequence YXXQ (SEQ ID NO:308) where each X can be any amino acid (corresponding to amino acids 118-121 of SEQ ID NO: 283) (Stahl et al. Science. 1995 Mar. 3; 267(5202):1349-53). The tyrosine of this sequence can be phosphorylated and MPL is capable of partial STAT3 recruitment (Drachman and Kaushansky. Proc Natl Acad Sci USA. 1997 Mar. 18; 94(6):2350-5). MPL also contains the sequence YLPL (SEQ ID NO: 309) (corresponding to amino acid 113-116 of SEQ ID NO: 283), which is similar to the consensus binding site for STAT5 recruitment pYLXL (SEQ ID NO:310) where pY is phosphotyrosine and X can be any amino acid (May et al. FEBS Lett. 1996 Sep. 30; 394(2):221-6). Using computer simulations, Lee et al. found clinically relevant mutations in the transmembrane domain of MPL should activate MPL with the following order of activating effects: W515K (corresponding to the amino acid substitution W2K of SEQ ID NO: 283)>5505A (corresponding to the amino acid substitution S14A of SEQ ID NO:187) >W515I (corresponding to the amino acid substitution W2I of SEQ ID NO: 283)>5505N (corresponding to the amino acid substitution S14N of SEQ ID NO:187, which was tested in Example 12 as part T075 (SEQ ID NO:188)) (PLoS One. 2011; 6(8):e23396). The simulations predicted these mutations could cause constitutive activation of JAK2, the kinase partner of MPL. In some embodiments, the intracellular portion of MPL can include one or more, or all the domains and motifs described herein that are present in SEQ ID NO: 283. In some embodiments, a transmembrane portion of MPL can include one or more, or all the domains and motifs described herein that are present in SEQ ID NO:187. The domains, motifs, and point mutations of MPL provided herein are known in the art and a skilled artisan would recognize that MPL intracellular signaling domains herein in illustrative embodiments would include one or more corresponding domains, motifs, and point mutations in that have been shown to promote proliferative activity and would not include that that have been shown to inhibit MPLs proliferative activity. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO: 283. In some embodiments, the intracellular domain derived from MPL has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, from about 250 aa to 300 aa, from about 300 aa to 350 aa, from about 350 aa to about 400 aa, from about 400 aa to about 450 aa, from about 450 aa to about 500 aa, from about 500 aa to about 550 aa, from about 550 aa to about 600 aa, or from about 600 aa to about 635 aa. In illustrative embodiments, the intracellular domain derived from MPL has a length of from about 30 aa to about 200 aa, for example, 30 aa to 150 aa, 30 aa to 119 aa, 30 aa to 121 aa, 30 aa to 122 aa, or 50 aa to 125 aa. In illustrative embodiments of lymphoproliferative elements that include a first intracellular domain derived from MPL, the second intracellular domain can be derived from CD79B.

In illustrative embodiments of any of the methods and compositions provided herein that include a lymphoproliferative element, the intracellular domain can be derived from a portion of the transmembrane protein CD79B, also known as B29; IGB; AGM6. The domains, motifs, and point mutations of CD79B that induce proliferation and/or survival of T cells and/or NK cells are known in the art and a skilled artisan can identify corresponding domains, motifs, and point mutations in CD79B polypeptides, some of which are discussed in this paragraph. CD79B contains an ITAM motif at residues 193-212 (corresponding to amino acids 16-30 of SEQ ID NO:211). CD79B has two tyrosines that are known to be phosphorylated, Y196 and Y207 (corresponding to Y16 and Y27 of SEQ ID NO: 211). In some embodiments, the intracellular portion of the transmembrane protein CD79B includes the ITAM motif and/or the known phosphorylation sites disclosed herein. The motif and phosphorylatable tyrosines of CD79B are known in the art and a skilled artisan will be able to identify corresponding motifs and phosphorylatable tyrosines in similar CD79B polypeptides. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO: 211. In some embodiments, the intracellular domain derived from CD79B has a length of from about 30 aa to about 35 aa, from about 35 aa to about 40 aa, from about 40 aa to about 45 aa, or from about 45 aa to about 50 aa). In illustrative embodiments, the intracellular domain derived from CD79B has a length of from about 30 aa to about 50 aa. For example, a suitable CD79B intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids of the following sequence: LDKDDSKAGMEEDHT[YEGLDIDQTATYEDI]VTLRT-GEVKWSVGEHPGQE (SEQ ID NO: 211), where the ITAM motif is set out in brackets. In illustrative embodiments of lymphoproliferative elements that include a second intracellular domain derived from CD79B, the first intracellular domain can be derived from CSF3R.

In illustrative embodiments of any of the methods and compositions provided herein that include a lymphoproliferative element, the intracellular domain can be derived from a portion of the transmembrane protein OSMR. The domains, motifs, and point mutations of OSMR that induce proliferation and/or survival of T cells and/or NK cells are known in the art and a skilled artisan can identify corresponding domains, motifs, and point mutations in OSMR polypeptides, some of which are discussed in this paragraph. OSMR contains a Box1 motif at amino acids 771-779 of isoform 3 (corresponding to amino acids 16-30 of SEQ ID NO:294). OSMR has two serines at amino acids 829 and 890 of isoform 3 that are known to be phosphorylated (serines at amino acids 65 and 128 of SEQ ID NO:294). In some embodiments, the intracellular portion of the protein OSMR can include the Box1 motif and the known phosphorylation sites disclosed herein. The motif and phosphorylatable serines of OSMR are known in the art and a skilled artisan will be able to identify corresponding motifs and phosphorylatable serines in similar OSMR polypeptides. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:294. In some embodiments, the intracellular domain derived from OSMR has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, or from about 200 aa to about 250 aa.

In illustrative embodiments of any of the methods and compositions provided herein that include a lymphoproliferative element, the intracellular domain can be derived from a portion of the transmembrane protein PRLR. The domains, motifs, and point mutations of PRLR that induce proliferation and/or survival of T cells and/or NK cells are known in the art and a skilled artisan can identify corresponding domains, motifs, and point mutations in PRLR polypeptides, some of which are discussed in this paragraph. PRLR contains a growth hormone receptor binding domain at amino acids 185-261 of isoform 6 (corresponding to amino acids 28-104 of SEQ ID NO:295). The growth hormone receptor binding domain of PRLR is known in the art and a skilled artisan will be able to identify corresponding domain in similar PRLR polypeptides. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:295. In some embodiments, the intracellular domain derived from PRLR has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, from about 200 aa to about 250 aa, from about 250 aa to 300 aa, from about 300 aa to 350 aa, or from about 350 aa to about 400 aa.

In some embodiments, an intracellular domain of a lymphoproliferative element is derived from an intracellular portion of the transmembrane protein CD30 (also known as TNFRSF8, D1S166E, and Ki-1).

In illustrative embodiments of any of the methods and compositions provided herein that include a lymphoproliferative element, the intracellular domain can be derived from a portion of the protein CD28. The domains, motifs, and point mutations of CD28 that induce proliferation and/or survival of T cells and/or NK cells are known in the art and a skilled artisan can identify corresponding domains, motifs, and point mutations in CD28 polypeptides, some of which are discussed in this paragraph. Full-length CD28 contains a PI3-K- and Grb2-binding motif that corresponds to residues 12-15 of SEQ ID NOs:206 and 207 (Harada et al. J Exp Med. 2003 Jan. 20; 197(2):257-62). In some embodiments, a lymphoproliferative element that includes a CD28 intracellular domain can include the PI3-K- and Grb2-binding motif. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:206 or 207. In some embodiments, the intracellular domain derived from CD28 has a length of from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, or from about 35 aa to about 42 aa.

In illustrative embodiments of any of the methods and compositions provided herein that include a lymphoproliferative element, the intracellular domain can be derived from a portion of the protein ICOS. The domains, motifs, and point mutations of ICOS that induce proliferation and/or survival of T cells and/or NK cells are known in the art and a skilled artisan can identify corresponding domains, motifs, and point mutations in ICOS polypeptides, some of which are discussed in this paragraph. Unlike CD28, ICOS binds PI3-K and not Grb2. The PI3-K-binding motif of full-length ICOS corresponds to residues 19-22 of SEQ ID NO:225. A single amino acid substitution in this motif can lead to Grb2 binding by ICOS and increased IL-2 production (Harada et al. J Exp Med. 2003 Jan. 20; 197(2):257-62). This mutation corresponds to mutating phenylalanine 21 of SEQ ID NO:225 to an asparagine. A skilled artisan will understand how to mutate this residue in SEQ ID NO:225 and generate an ICOS intracellular domain that binds Grb2 in addition to PI3-K. In some embodiments, a lymphoproliferative element that includes an ICOS intracellular domain can include the PI3-K-binding motif. In some embodiments, a lymphoproliferative element that includes an ICOS intracellular domain can include the PI3-K-binding motif that has been mutated to additionally bind Grb2. ICOS also contains a membrane proximal motif in the cytoplasmic tail that is essential for ICOS-assisted calcium signaling (Leconte et al. Mol Immunol. 2016 November; 79:38-46). This calcium signaling-motif corresponds to residues 5-8 of SEQ ID NO:225. In some embodiments, a lymphoproliferative element that includes an ICOS intracellular domain can include the calcium-signaling motif. Two other conserved motifs have been identified in full-length ICOS. A first conserved motif at residues 170-179 (corresponding to residues 9-18 of SEQ ID NO:225) and a second conserved motif at residues 185-191 (corresponding to residues 24-30 of SEQ ID NO:225) (Pedros et al. Nat Immunol. 2016 July; 17(7):825-33). These two conserved motifs might have important function(s) in mediating downstream ICOS signaling. In some embodiments, a lymphoproliferative element that includes an ICOS intracellular domain can include at least one of the first or second conserved motifs. In some embodiments, a lymphoproliferative element that includes an ICOS intracellular domain does not include the first conserved motif, does not include the second conserved motif, or does not include the first and second conserved motifs. In some embodiments, a suitable intracellular domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:225. In some embodiments, the intracellular domain derived from ICOS has a length of from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, or from about 35 aa to about 38 aa.

In some embodiments, an intracellular domain of a chimeric lymphoproliferative element is derived from an intracellular portion of the transmembrane protein OX40 (also known as TNFRSF4, RP5-902P8.3, ACT35, CD134, OX-40, TXGP1L). The domains, motifs, and point mutations of OX40 that induce proliferation and/or survival of T cells and/or NK cells are known in the art and a skilled artisan can identify corresponding domains, motifs, and point mutations in OX40 polypeptides, some of which are discussed in this paragraph. OX40 contains a TRAF binding motif at residues 256-263 of full-length OX40 (corresponding to residues 20-27 of SEQ ID NO:296) that are important for binding TRAF1, TRAF2, TRAF3, and TRAF5 (Kawamata, S, et al. J Biol Chem. 1998 Mar. 6; 273(10): 5808-14; Hori, T. Int J Hematol. 2006 January; 83(1):17-22). Full-length OX40 also contains a p85 PI3K binding motif at residues 34-57. In some embodiments, when OX40 is present as an intracellular domain of a lymphoproliferative element, it includes the p85 PI3K binding motif of OX40. In some embodiments, an intracellular domain of OX40 can include the TRAF binding motif of OX40. In some embodiments, an intracellular domain of OX40 can bind TRAF1, TRAF2, TRAF3, and TRAF5. Lysines corresponding to amino acids 17 and 41 of SEQ ID NO: 296 are potentially negative regulatory sites that function as parts of ubiquitin targeting motifs. In some embodiments, one or both of these lysines in the intracellular domain of OX40 are mutated arginines or another amino acid. In some embodiments, a suitable intracellular domain of a lymphoproliferative element can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:57. In some of these embodiments, the intracellular domain of OX40 has a length of from about 20 aa to about 25 aa, about 25 aa to about 30 aa, 30 aa to about 35 aa, from about 35 aa to about 40 aa, from about 40 aa to about 45 aa, or from about 45 aa to about 50 aa. In illustrative embodiments, the intracellular domain of OX40 has a length of from about 20 aa to about 50 aa, for example 20 aa to 45 aa, or 20 aa to 42 aa.

In some embodiments, an intracellular domain of a chimeric lymphoproliferative element is derived from an intracellular portion of the transmembrane protein IFNAR2. The domains, motifs, and point mutations of IFNAR2 that induce proliferation and/or survival of T cells and/or NK cells are known in the art and a skilled artisan can identify corresponding domains, motifs, and point mutations in IFNAR2 polypeptides, some of which are discussed in this paragraph. Full-length IFNAR2 contains a Box1 motif and two Box2 motifs (known as Box2A and Box2B). (Usacheva A et al. J Biol Chem. 2002 Dec. 13; 277(50):48220-6). In some embodiments, a lymphoproliferative element that includes a IFNAR2 intracellular domain can include one or more of the Box1 or Box2 motifs. In illustrative embodiments, the IFNAR2 intracellular domain can include one or more of the Box1, Box2A, or Box2B motifs. IFNAR2 contains a JAK1-binding site (Gauzzi M C et al. Proc Natl Acad Sci USA. 1997 Oct. 28; 94(22):11839-44; Schindler et al. J Biol Chem. 2007 Jul. 13; 282(28):20059-63). In some embodiments, a lymphoproliferative element that includes a IFNAR2 intracellular domain can include the JAK1-binding site. In some embodiments, a suitable intracellular domain of a lymphoproliferative element can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:227 or 228. In some of these embodiments, the intracellular domain of IFNAR2 has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, or from about 200 aa to about 251 aa. In illustrative embodiments, the intracellular domain of OX40 has a length of from about 30 aa to about 251 aa, for example 30 aa to 67 aa.

In some embodiments, an intracellular domain of a chimeric lymphoproliferative element is derived from an intracellular portion of the transmembrane protein CSF3R. The domains, motifs, and point mutations of CSF3R that induce proliferation and/or survival of T cells and/or NK cells are known in the art and a skilled artisan can identify corresponding domains, motifs, and point mutations in CSF3R polypeptides, some of which are discussed in this paragraph. Full-length CSF3R contains a Box1 and Box2 motif as well as a Box3 motif (Nguyen-Jackson H T et al. G-CSF Receptor Structure, Function, and Intracellular Signal Transduction. Twenty Years of G-CSF, (2011) 83-105). In some embodiments, a lymphoproliferative element that includes a CSF3R intracellular domain can include one or more of the Box1, Box2, or Box3 motifs. CSF3R contains four tyrosine residues, Y704, Y729, Y744, and Y764 in full-length CSF3R, that are important for binding STAT3 (Y704 and Y744), SOCS3 (Y729), and Grb2 and p21Ras (Y764). In some embodiments, a lymphoproliferative element that includes a CSF3R intracellular domain can include one, two, three, or all of the tyrosine residues corresponding to Y704, Y729, Y744, and Y764 of full-length CSF3R. CSF3R contains two threonine residues, T615 and T618 in full-length CSF3R, that can increase receptor dimerization and activity when mutated to alanine and isoleucine, respectively (T615A and T618I) (Maxson et al. J Biol Chem. 2014 Feb. 28; 289(9):5820-7). In some embodiments, a lymphoproliferative element that includes a CSF3R intracellular domain can include one or more of the mutations corresponding to T615A and T618I. In some embodiments, a suitable intracellular domain of a lymphoproliferative element can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:216, 217, or 218. In some of these embodiments, the intracellular domain of CSF3R has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, or from about 200 aa to about 213 aa. In illustrative embodiments, the intracellular domain of CSF3R has a length of from about 30 aa to about 213 aa, for example from about 30 aa to about 186 or from about 30 aa to about 133 aa.

In some embodiments, an intracellular domain of a chimeric lymphoproliferative element is derived from an intracellular portion of the transmembrane protein EPOR. The domains, motifs, and point mutations of EPOR that induce proliferation and/or survival of T cells and/or NK cells are known in the art and a skilled artisan can identify corresponding domains, motifs, and point mutations in EPOR polypeptides, some of which are discussed in this paragraph. EPOR contains a Box1 (residues 257-264 of full-length EPOR) and Box2 (residues 303-313 of full-length EPOR) motif (Constantinescu S N. Trends Endocrinol Metab. 1999 December; 10(1):18-23). EPOR also contains an extended Box2 motif (residues 329-372) important for binding tyrosine kinase receptor KIT (Constantinescu S N. Trends Endocrinol Metab. 1999 December; 10(1):18-23). In some embodiments, a lymphoproliferative element that includes an EPOR intracellular domain can include one or more of the Box1, Box2, or extended Box2 motifs. EPOR also contains a short segment important for EPOR internalization (residues 267-276 of full-length EPOR). In some embodiments, a lymphoproliferative element that includes an EPOR intracellular domain does not include the internalization segment. In some embodiments, a suitable intracellular domain of a lymphoproliferative element can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NOs:219 or 220. In some of these embodiments, the intracellular domain of EPOR has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, from about 65 aa to about 70 aa, from about 70 aa to about 100 aa, from about 100 aa to about 125 aa, from about 125 aa to 150 aa, from about 150 to about 175 aa, from about 175 aa to about 200 aa, or from about 200 aa to about 235 aa. In illustrative embodiments, the intracellular domain of EPOR has a length of from about 30 aa to about 235 aa.

In some embodiments, an intracellular domain of a chimeric lymphoproliferative element is derived from an intracellular portion of the transmembrane protein CD3G. The domains, motifs, and point mutations of CD3G that induce proliferation and/or survival of T cells and/or NK cells are known in the art and a skilled artisan can identify corresponding domains, motifs, and point mutations in CD3G polypeptides, some of which are discussed in this paragraph. Two serine residues, 5123 and 5126 of full-length CD3G have been shown to be phosphorylated in T cells in response to ionomycin (Davies et al. J Biol Chem. 1987 Aug. 15; 262(23):10918-21). In some embodiments, a lymphoproliferative element that includes a CD3G intracellular domain can include one or more of the serine residues corresponding to full-length 5123 and 5126. Furthermore, phosphorylation at S126 but not S123 was shown to be required for PKC-mediated down-regulation (Dietrich J et al. EMBO J. 1994 May 1; 13(9):2156-66). In some embodiments, a lymphoproliferative element that includes a CD3G intracellular domain can include the serine residue corresponding to full-length S123 and not include serine residue corresponding to full-length S126. In some embodiments, a lymphoproliferative element that includes a CD3G intracellular domain can include a non-phosphorylatable amino acid substitution at the serine residue corresponding to full-length 5126. In illustrative embodiments, the amino acid substitution can be a serine to alanine mutation. Additionally, leucine to alanine mutations of either leucine of a di-leucine motif, L131 and L132 in full-length CD3G, was shown to prevent PKC-mediated down-regulation (Dietrich J et al. EMBO J. 1994 May 1; 13(9):2156-66). In some embodiments, a lymphoproliferative element that includes a CD3G intracellular domain can include at least one amino acid substitution at the leucine residues corresponding to L131 or L132 of full-length CD3G. In illustrative embodiments, the amino acid substitution can be a leucine to alanine mutation. In some embodiments, a suitable intracellular domain of a lymphoproliferative element can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:199. In some of these embodiments, the intracellular domain of CD3G has a length of from about 20 aa to about 25 aa, from about 25 aa to about 30 aa, from about 30 aa to about 35 aa, from about 35 aa to about 40 aa, or from about 40 aa to about 45 aa. In illustrative embodiments, the intracellular domain of CD3D has a length of from about 30 aa to about 45 aa.

The cytoplasmic domains of TNF receptors (TNFRs), which in illustrative embodiments can be TNFRSF4, TNFRSF8, TNFRSF9, TNFRSF14, or TNFRSF18, can recruit signaling molecules, including TRAFs (TNF receptor-associated factors) and/or "death domain" (DD) molecules. The domains, motifs, and point mutations of TNFRs that induce proliferation and/or survival of T cells and/or NK cells are known in the art and a skilled artisan can identify corresponding domains, motifs, and point mutations in TNFR polypeptides, some of which are discussed in this paragraph. In mammals, there are at least six TRAF molecules and a number of nonreceptor DD molecules. Receptors and adaptor proteins that bind to TRAFs share short consensus TRAF-binding motifs that are known in the art (Meads et al. J Immunol. 2010 Aug. 1; 185(3):1606-15). The DD-binding motif is a roughly 60 amino acid globular bundle of 6 conserved α-helices that is also known in the art (Locksley R M et al. Cell. 2001 Feb. 23; 104(4):487-501). A skilled artisan will be able to identify the TRAF- and/or DD-binding motif in the different TNFR families using, for example, sequence alignments to known binding motifs. TNFRs can recruit TRADD and TRAF2, resulting in the activation of NF-κB, MAPK, and JNK (Sedger and McDermott. Cytokine Growth Factor Rev. 2014 August; 25(4):453-72). In some embodiments, a lymphoproliferative element that includes a TNFR intracellular domain can include one or more TRAF-binding motifs. In some embodiments, a lymphoproliferative element that includes a TNFR intracellular domain does not include a DD-binding motif, or has one or more DD-binding motifs deleted or mutated within the intracellular domain. In some embodiments, a lymphoproliferative element that includes a TNFR intracellular domain can recruit TRADD and/or TRAF2. TNFRs also include cysteine-rich domains (CRDs) that are important for ligand binding (Locksley R M et al. Cell. 2001 Feb. 23; 104(4):487-501). In some embodiments, a lymphoproliferative element that includes a TNFR intracellular domain does not include a TNFR CRD.

Lymphoproliferative elements and CLEs that can be included in any of the aspects disclosed herein, can be any of the LEs or CLEs disclosed in WO2019/055946. CLEs were disclosed therein that promoted proliferation in cell culture of PBMCs that were transduced with lentiviral particles encoding the CLEs between day 7 and day 21, 28, 35 and/or 42 after transduction. Furthermore, CLEs were identified therein, that promoted proliferation in vivo in mice in the presence or absence of an antigen recognized by a CAR, wherein T cells expressing one of the CLEs and the CAR were introduced into the mice. As exemplified therein, tests and/or criteria can be used to identify whether any test polypeptide, including LEs, or test domains of an LE, such as a first intracellular domain, or a second intracellular domain, or both a first and second intracellular domain, are indeed LEs or effective intracellular domains of LEs, or especially effective LEs or intracellular domains of LEs. Thus, in certain embodiments, any aspect or other embodiment provided herein that includes an LE or a polynucleotide or nucleic acid encoding an LE can recite that the LE meets, or provides the property of, or is capable of providing and/or possesses the property of, any one or more of the identified tests or criteria for identifying an LE provided herein, or that a cell genetically modified and/or transduced with a retroviral particle, such as a lentiviral particle encoding the LE, is capable of providing, is adapted for, possesses the property of, and/or is modified for achieving the results of one or more of the recited tests. In one embodiment, the LE provides, is capable of providing and/or possesses the property of, (or a cell genetically modified and/or transduced with a retroviral particle encoding the LE is capable of providing, is adapted for, possesses the property of, and/or is modified for) improved expansion to pre-activated PBMCs transduced with a lentivirus comprising a nucleic acid encoding the LE and an anti-CD19 CAR comprising a CD3 zeta intracellular activating domain but no co-stimulatory domain, between day 7 and day 21, 28, 35, and/or 42 of in vitro culturing post-transduction in the absence of exogenously added cytokines, compared to a control retroviral particle, e.g. lentiviral particle under identical conditions. In some embodiments, a lymphoproliferative element test for improved or enhanced survival, expansion, and/or proliferation of cells transduced with a retroviral particle (e.g. lentiviral particle) having a genome encoding a test construct encoding a putative LE (test cells) can be performed based on a comparison to control cells, which can be, for example, either untransduced cells or cells transduced with a control retroviral (e.g. lentiviral) particle identical to the lentiviral particle comprising the nucleic acid encoding the lymphoproliferative element, but lacking the lymphoproliferative element, or lacking the intracellular domain or domains of the test polypeptide construct but comprising the same extracellular domain, if present, and the same transmembrane region or membrane targeting region of the respective test polypeptide construct. In some embodiments control cells are transduced with a retroviral particle (e.g. lentiviral particle) having a genome encoding a lymphoproliferative element or intracellular domain(s) thereof, identified herein as exemplifying a lymphoproliferative element. In such an embodiment, the test criteria can include that there is at least as much enrichment, survival and/or expansion, or no statistical difference of enrichment, survival, and/or expansion when the test is performed using a retroviral particle (e.g. lentiviral particle) having a genome encoding a test construct versus encoding the control lymphoproliferative element, typically by analyzing cells transcribed therewith. Exemplary or illustrative embodiments of lymphoproliferative elements herein, in some embodiments, are illustrative embodiments of control lymphoproliferative elements for such a test.

In some embodiments, this test for an improved property of a putative or test lymphoproliferative element is performed by performing replicates and/or performing a statistical test. A skilled artisan will recognize that many statistical tests can be used for such a lymphoproliferative element test. Contemplated for such a test in these embodiments would be any such test known in the art. In some embodiments, the statistical test can be a T-test or a Mann-Whitney-Wilcoxon test. In some embodiments, the normalized enrichment level of a test construct is significant at a p-value of less than 0.1, or less than 0.05, or less than 0.01.

In another embodiment, the LE provides, is capable of providing and/or possesses the property of (or a cell genetically modified and/or transduced with the LE is capable of providing, is adapted for, possesses the property of, and/or is modified for) at least a 1.5-fold, 2-fold, 3-fold, 4-fold, 5-fold, 6-fold, 7-fold, 8-fold, 9-fold, or 10-fold expansion, or between 1.5 fold and 25-fold expansion, or between 2-fold and 20-fold expansion, or between 2-fold and 15-fold expansion, or between 5-fold and 25-fold expansion, or between 5-fold and 20-fold expansion, or between 5-fold and 15-fold expansion, of pre-activated PBMCs transduced with a nucleic acid encoding the LE when transduced along with an anti-CD19 CAR comprising a CD3 zeta intracellular activating domain but no co-stimulatory domain, between day 7 and day 21, 28, 35, and/or 42 of in vitro culturing in the absence of exogenously added cytokines. In some embodiments, the test is performed in the presence of PBMCs, for example at a 1:1 ratio of transduced cells to PBMCs, which can be for example, from a matched donor, and in some embodiments, the test is performed in the absence of PBMCs. In some embodiments, the analysis of expansion for any of these tests is performed as illustrated in WO2019/055946. In some embodiments, the test can include a further statistical test and a cut-off such as a P value below 0.1, 0.05, or 0.01, wherein a test polypeptide or nucleic acid encoding the same, needs to meet one or both thresholds (i.e. fold expansion and statistical cutoff).

For any of the lymphoproliferative element tests provided herein, the number of test cells and the number of control cells can be compared between day 7 and day 14, 21, 28, 35, 42 or 60 post-transduction. In some embodiments, the numbers of test and control cells can be determined by sequencing DNA and counting the occurrences of unique identifiers present in each construct. In some embodiments, the numbers of test and control cells can be counted directly, for example with a hemocytometer or a cell counter. In some embodiments, all the test cells and control cells can be grown within the same vessel, well or flask. In some embodiments, the test cells can be seeded in one or more wells, flasks or vessels, and the control cells can be seeded in one or more flasks or vessels. In some embodiments, test and control cells can be seeded individually into wells or flasks, e.g., one cell per well. In some embodiments, the numbers of test cells and control cells can be compared using enrichment levels. In some embodiments, the enrichment level for a test or control construct can be calculated by dividing the number of cells at a later time point (day 14, 21, 28, 35, or day 45) by the number of cells at day 7 for each construct. In some embodiments, the enrichment level for a test or control construct can be calculated by dividing the number of cells at a time point (day 14, 21, 28, 35, or day 45) by the number of cells at that time point for untransduced cells. In some embodiments, the enrichment level of each test construct can be normalized to the enrichment level of the respective control construct to generate a normalized enrichment level. In some embodiments, a LE encoded in the test construct provides (or a cell genetically modified and/or transduced with a retroviral particle (e.g. lentiviral particle) having a genome encoding the LE is capable of providing, is adapted for, possesses the property of, and/or is modified for) at least a 1.5-fold, 2-fold, 3-fold, 4-fold, 5-fold, 6-fold, 7-fold, 8-fold, 9-fold, or 10-fold normalized enrichment level, or between 1.5 fold and 25-fold normalized enrichment level, or between 3-fold and 20-fold normalized enrichment level, or between 5-fold and 25-fold normalized enrichment level, or between 5-fold and 20-fold normalized enrichment level, or between 5-fold and 15-fold normalized enrichment level. Enrichment can be measured, for example, by direct cell counting. Cutoff values can be based on a single test, or two, three, four, or five repeats, or based on many repeats. The cutoff can be met when a lymphoproliferative element meets one or more repeat tests, or meets or exceeds a cutoff for all repeats. In some embodiments, the enrichment is measured as $\log_2$((normalized count data on the test day+1)/(normalized count data on day 7+1)).

As illustrated in WO2019/055946, CLEs were identified from libraries of constructs that included constructs that encoded test chimeric polypeptides that were designed to comprise an intracellular domain believed to induce proliferation and/or survival of lymphoid or myeloid cells, and an anti-CD19 CAR that comprised an intracellular activating domain but not a co-stimulatory domain. Preactivation, which was performed overnight at 37° C., was performed in a preactivation reaction mixture comprising PBMCs, a commercial media for lymphocytes (Complete OpTmizer™ CTS™ T-Cell Expansion SFM), recombinant human interleukin-2 (100 IU/ml) and anti-CD3 Ab (OKT3) (50 ng/ml). Following preactivation, transduction was performed overnight at 37° C. after addition of test and control lentiviral particles to the preactivation reaction mixtures at a multiplicity of infection (MOI) of 5. Some control lentiviral particles contained constructs encoding polypeptides with extracellular and transmembrane domains but no intracellular domains. In contrast, the test lentiviral particles contained constructs encoding polypeptides with extracellular and transmembrane domains and either one or two intracellular domains. Following transduction, Complete OpTmizer™ CTS™ T-Cell Expansion SFM was added to dilute the reaction mixture 5- to 20-fold and the cells were cultured for up to 45 days at 37° C. After day 7 post-transduction, cultures were either "fed" additional untransduced donor matched PBMCs or not ("unfed"). No additional cytokines (e.g. IL-2, IL-7, or IL-15 and no other lymphoid mitogenic agent) were added to these cultures that were not present in the commercial media, after the transduction reaction mixtures were initially formed. Expansion was measured by analyzing enrichment of cell counts actually counted as nucleic acid sequence counts of unique identifiers for each construct in the mixed cultured PBMC cell populations, such that enrichment was positive as calculated as the logarithm in base 2 of the ratio between normalized count at the last day for analysis plus one to the count at day 7 plus one. Additional details regarding the tests performed to identify the LEs are illustrated in WO2019/055946, including experimental conditions.

As illustrated in WO2019/055946, test constructs were identified as CLEs because the CLEs induced proliferation/expansion in these fed or unfed cultures without added cytokines such as IL-2 between days 7 and day 21, 28, 35, and/or 42. For example, as illustrated in WO2019/055946, effective CLEs were identified by identifying test CLEs that provided increased expansion of these in vitro cultures, whether fed or unfed with untransduced PBMCs, between day 7 and day 21, 28, 35, and/or 42 post-transduction, compared to control constructs that did not include any intracellular domains. WO2019/055946 discloses that at least one and typically more than one test CLE that included an intracellular domain from a test gene provided more expansion than every control construct that was present at day 7 post-transduction, that did not include an intracellular domain WO2019/055946 further provides a statistical method that was used to identify exceptionally effective genes with respect to a first intracellular domain, and one or more exemplary intracellular domain(s) from these genes. The method used a Mann-Whitney-Wilcoxon test and a false discovery cutoff rate of less than 0.1 or less than 0.05. WO2019/055946 identified especially effective genes for the first intracellular domain or the second intracellular domain, for example, by analyzing scores for genes calculated as combined score for all constructs with that gene. Such analysis can use a cutoff of greater than 1, or greater than negative control constructs without any intracellular domains, or greater than 2, as shown for some of the tests disclosed in WO2019/055946.

In another embodiment, the LE provides, is capable of providing and/or possesses the property of (or a cell genetically modified and/or transduced with the LE is capable of providing, is adapted for, possesses the property of, and/or is modified for) driving T cell expansion in vivo. For example, the in vivo test can utilize a mouse model and measure T cell expansion at 15 to 25 days in vivo, or at 19 to 21 days in vivo, or at approximately 21 days in vivo, after T cells are contacted with lentiviral vectors encoding the LEs, are introduced into the mice, as disclosed in WO2019/055946, In exemplary aspects and embodiments that include a LE, which typically include a CAR, such as methods provided herein for genetically modifying, genetically modified and/or transduced cells, and uses thereof, the genetically modified cell is modified so as to possess new properties not previously possessed by the cell before genetic modification and/or transduction. Such a property can be provided by genetic modification with a nucleic acid encoding a CAR or a LE, and in illustrative embodiments both a CAR and a LE. For example, in certain embodiments, the genetically modified and/or transduced cell is capable of, is adapted for, possesses the property of, and/or is modified for survival and/or proliferation in ex vivo culture for at least 7, 14, 21, 28, 35, 42, or 60 days or from between day 7 and day 14, 21, 28, 35, 42 or 60 post-transduction, in the absence of added IL-2 or in the absence of added cytokines such as IL-2, IL-15, or IL-7, and in certain illustrative embodiments, in the presence of the antigen recognized by the CAR where the method comprises genetically modifying using a retroviral particle having a pseudotyping element and optionally a separate or fused activation domain on its surface and typically does not require pre-activation.

By capable of enhanced survival and/or proliferation in certain embodiments, it is meant that the genetically modified and/or transduced cell exhibits, is capable of, is adapted for, possesses the property of, and/or is modified for improved survival or expansion in ex vivo or in vitro culture in culture media in the absence of one or more added cytokines such as IL-2, IL-15, or IL-7, or added lymphocyte mitogenic agent, compared to a control cell(s) identical to the genetically modified and/or transduced cell(s) before it was genetically modified and/or transduced or to a control cell that was transduced with a retroviral particle identical to an on-test retroviral particle that comprises an LE or a putative LE, but without the LE or the intracellular domains of the LE, wherein said survival or proliferation of said control cell(s) is promoted by adding said one or more cytokines, such as IL-2, IL-15, or IL-7, or said lymphocyte mitogenic agent to the culture media. By added cytokine or lymphocyte mitogenic agent, it is meant that cytokine or lymphocyte mitogenic agent is added from an exogenous source to a culture media such that the concentration of said cytokine or lymphocyte mitogenic agent is increased in the culture media during culturing of the cell(s) compared to the initial culture media, and in some embodiments can be absent from the initial culture media before said adding. By "added" or "exogenously added", it is meant that such cytokine or lymphocyte mitogenic agent is added to a lymphocyte media used to culture the genetically modified and/or transduced cell after the genetically modifying, where the culture media may or may not already possess the cytokine or lymphocyte mitogenic agent. All or a portion of the media that includes a mixture of multiple media components is typically stored and in illustrative embodiments has been shipped to a site where the culturing takes place, without the exogenously added cytokine(s) or lymphocyte mitogenic agent(s). The lymphocyte media in some embodiments is purchased from a supplier, and a user such as a technician not employed by the supplier and not located within a supplier facility, adds the exogenously added cytokine or lymphocyte mitogenic agent to the lymphocyte media and then the genetically modified and/or transduced cells are cultured in the presence or absence of such exogenously added cytokine or lymphocyte mitogenic agent.

In some embodiments, improved or enhanced survival, expansion, and/or proliferation can be shown as an increase in the number of cells determined by sequencing DNA from cells transduced with retroviral particle (e.g. lentiviral particle) having a genome encoding CLEs and counting the occurrences of sequences present in unique identifiers from each CLE. In some embodiments, improved survival and/or improved expansion can be determined by counting the cells directly, for example with a hemocytometer or a cell counter, at each time point. In some embodiments, improved survival and/or improved expansion and/or enrichment can be calculated by dividing the number of cells at the later time point (day 21, 28, 35, and/or day 45) by the number of cells at day 7 for each construct. In some embodiments, the cells can be counted by hemocytometer or cell counters. In some embodiments, the enrichment level determined using the nucleic acid counts or the cell counts of each specific test construct can be normalized to the enrichment level of the respective control construct, i.e., the construct with the same extracellular domain and transmembrane domain but lacking the intracellular domains present in the test construct. In these embodiments, the LE encoded in the construct provides (or a cell genetically modified and/or transduced with a retroviral particle (e.g. lentiviral particle) having a genome encoding the LE is capable of providing, is adapted for, possesses the property of, and/or is modified for) at least a 1.5-fold, 2-fold, 3-fold, 4-fold, 5-fold, 6-fold, 7-fold, 8-fold, 9-fold, or 10-fold normalized enrichment level, or between 1.5 fold and 25-fold normalized enrichment level, or between 3-fold and 20-fold normalized enrichment level, or between 5-fold and 25-fold normalized enrichment level, or between 5-fold and 20-fold normalized enrichment level, or between 5-fold and 15-fold normalized enrichment level.

In illustrative embodiments of any of the methods, uses, genetically modified T cells and/or NK cells, and other composition aspects provided herein that include a lymphoproliferative element, the lymphoproliferative element can include an intracellular domain or a fragment thereof that includes an intracellular signaling domain from any of the genes having a P3 signaling domain with or without a P4 domain, or from any of the genes having a P4 domain wherein the P3 domain was a linker, in the CLEs identified in Tables 4 to 8 herein, which promote T cell, e.g. CAR-T cell, expansion in vivo. In illustrative embodiments of any of the methods, uses, and composition aspects provided herein that include a lymphoproliferative element having a P3 and P4 domain, the lymphoproliferative element can include at the P4 position, an intracellular domain or a fragment thereof that includes a signaling domain from any of the genes having a P4 signaling domain in constructs having a P3 and a P4 signaling domain in the CLEs identified in Tables 4 to 8 herein, which promote T cell, e.g. CAR-T cell, expansion in vivo. In illustrative embodiments of any of the methods, uses, and composition aspects provided herein that include a lymphoproliferative element, the lymphoproliferative element can include an intracellular domain or a fragment thereof that includes a signaling domain from any of the genes having a P3 signaling domain and a signaling domain from any of the genes having a P4 domain in the same CLE, in illustrative embodiments in the P3 and P4 positions respectively, in any of the CLEs identified in Tables 4 to 8 herein, which promote T cell, e.g. CAR-T cell, expansion in vivo. In any of the CLEs of embodiments provided in this paragraph, the P2 domain can be from any of the genes identified as having a P2 part in CLEs found in Tables 4 to 8 herein. Furthermore, the CLEs can include in some illustrative embodiments a P1 domain from Tables 4 to 8.

In illustrative embodiments of any of the methods, uses, genetically modified T cells and/or NK cells, and other composition aspects provided herein that include a lymphoproliferative element, the lymphoproliferative element can include a P3 signaling domain from any of the CLEs identified in Tables 4 to 8 herein, which promote T cell, e.g. CAR-T cell, expansion in vivo, or a P4 signaling domain in a construct having no P3 signaling domain, from any of the CLEs identified in Tables 4 to 8 herein, which promote T cell, e.g. CAR-T cell, expansion in vivo. In illustrative embodiments of any of the methods, uses, and composition aspects provided herein that include a lymphoproliferative element having a P3 and P4 domain, the lymphoproliferative element can include at the P4 position, a P4 signaling domain in constructs having a P3 and a P4 signaling domain in the CLEs identified in Tables 4 to 8 herein, which promote T cell, e.g. CAR-T cell, expansion in vivo. In illustrative embodiments of any of the methods, uses, and composition aspects provided herein that include a lymphoproliferative element, the lymphoproliferative element can include a P3 signaling domain and a P4 signaling domain in the P3 and P4 positions respectively, from any one of the CLEs identified in Tables 4 to 8 herein, which promote T cell, e.g. CAR-T cell, expansion in vivo. Furthermore, the CLEs can include in some illustrative embodiments, a P1 domain from Tables 4 to 8. In any of the CLEs of embodiments provided in this paragraph, the P2 domain can comprise or be any P2 domain from a CLE found in Tables 4 to 8 herein, or in illustrative embodiments, a lymphoproliferative element can include a P2 domain, P3 domain and P4 domain, and optionally P1 domain, all from the same CLE identified in Tables 4 to 8 herein. In certain illustrative embodiments of any of the methods, uses, genetically modified T cells and/or NK cells, and other composition aspects provided herein that include a lymphoproliferative element, the lymphoproliferative element can have P3 and P4 domains S121-S212 or S186-S053, or P2, P3, and P4 domains T001-S121-S212 or T044-S186-S053 optionally with a P1 domain E008 or E006.

In some embodiments, the lymphoproliferative element can include a cytokine receptor or a fragment that includes a signaling domain thereof. In some embodiments, the cytokine receptor can be CD27, CD40, CRLF2, CSF2RA, CSF2RB, CSF3R, EPOR, GHR, IFNAR1, IFNAR2, IFNGR1, IFNGR2, IFNLR1, IL1R1, IL1RAP, IL1RL1, IL1RL2, IL2R, IL2RA, IL2RB, IL2RG, IL3RA, IL4R, IL5RA, IL6R, IL6ST, IL7R, IL7RA, IL9R, IL10RA, IL10RB, IL11RA, IL12RB1, IL13R, IL13RA1, IL13RA2, IL15R, IL15RA, IL17RA, IL17RB, IL17RC, IL17RE, IL18R1, IL18RAP, IL20RA, IL20RB, IL21R, IL22RA1, IL23R, IL27R, IL27RA, IL31RA, LEPR, LIFR, MPL, OSMR, PRLR, TGFβR, TGFβ decoy receptor, TNFRSF4, TNFRSF8, TNFRSF9, TNFRSF14, or TNFRSF18. In some embodiments, the cytokine receptor can be CD27, CD40, CRLF2, CSF2RA, CSF2RB, CSF3R, EPOR, GHR, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL7RA, IL9R, IL10RA, IL10RB, IL11RA, IL13RA1, IL13RA2, IL15RA, IL17RA, IL17RB, IL17RC, IL17RE, IL18R1, IL18RAP, IL20RA, IL20RB, IL22RA1, IL27RA, IL31RA, LEPR, LIFR, MPL, OSMR, PRLR, TNFRSF4, TNFRSF8, TNFRSF9, TNFRSF14, or TNFRSF18.

In illustrative embodiments, the lymphoproliferative element can comprise an intracellular domain from the cytokine receptors CD27, CD40, CRLF2, CSF2RA, CSF3R, EPOR, GHR, IFNAR1, IFNAR2, IFNGR2, IL1R1, IL1RL1, IL2RA, IL2RG, IL3RA, IL5RA, IL6R, IL7R, IL9R, IL10RB, IL11RA, IL12RB1, IL13RA1, IL13RA2, IL15RA, IL17RB, IL18R1, IL18RAP, IL20RB, IL22RA1, IL27RA, IL31RA, LEPR, MPL, OSMR, PRLR, TNFRSF4, TNFRSF8, TNFRSF9, TNFRSF14, or TNFRSF18 In illustrative embodiments, the intracellular domain in a lymphoproliferative element comprises a domain from CD40, CRLF2, CSF2RA, CSF3R, EPOR, FCGR2A, IFNAR2, IFNGR2, IL1R1, IL3RA, IL7R, IL10RB, IL11RA, IL12RB1, IL13RA2, IL18RAP, IL31RA, MPL, MYD88, TNFRSF14, or TNFRSF18, which were present in constructs that showed particularly noteworthy enrichments in an initial screen and a repeated screen as disclosed in WO2019/055946.

In illustrative embodiments, the lymphoproliferative element can comprise a costimulatory domain from CD27, CD28, OX40 (also referred to as TNFRSF4), GITR (also referred to as TNFRSF18), or HVEM (also referred to as TNFRSF14). In some embodiments, a lymphoproliferative element comprising a costimulatory domain from OX40 does not comprise an intracellular domain from CD3Z, CD28, 4-1BB, ICOS, CD27, BTLA, CD30, GITR, or HVEM. In some embodiments, a lymphoproliferative element comprising a costimulatory domain from GITR does not comprise an intracellular domain from CD3Z, CD28, 4-1BB, ICOS, CD27, BTLA, CD30, or HVEM. In some embodiments, a lymphoproliferative element comprising a costimulatory domain from CD28 does not comprise an intracellular domain from CD3Z, 4-1BB, ICOS, CD27, BTLA, CD30, or HVEM. In some embodiments, a lymphoproliferative element comprising a costimulatory domain from OX40, CD3Z, CD28, 4-1BB, ICOS, CD27, BTLA, CD30, GITR, or HVEM does not comprise a coiled-coil spacer domain N-terminal of the transmembrane domain. In some embodiments, a lymphoproliferative element comprising a costimulatory domain from GITR does not comprise an intracellular domain from CD3Z that is N-terminal of the costimulatory domain of GITR.

In certain illustrative embodiments, the lymphoproliferative element comprises an intracellular domain of CD40, MPL and IL2Rb. In some embodiments, the lymphoproliferative element can be other than a cytokine receptor. In some embodiments, the lymphoproliferative element other than a cytokine receptor can include an intracellular signaling domain from CD2, CD3D, CD3G, CD3Z, CD4, CD8RA, CD8RB, CD28, CD79A, CD79B, FCER1G, FCGR2A, FCGR2C, or ICOS.

In some embodiments, a lymphoproliferative element, including a CLE, comprises an intracellular activating domain as disclosed hereinabove. In some illustrative embodiments a lymphoproliferative element is a CLE comprising an intracellular activating domain comprising an ITAM-containing domain, as such, the CLE can comprise an intracellular activating domain having at least 80%, 90%, 95%, 98%, or 100% sequence identity to the CD3Z, CD3D, CD3E, CD3G, CD79A, CD79B, DAP12, FCER1G, FCGR2A, FCGR2C, DAP10/CD28, or ZAP70 domains provided herein wherein the CLE does not comprise an ASTR. In certain illustrative embodiments, the intracellular activating domain is an ITAM-containing domain from CD3D, CD3G, CD3Z, CD79A, CD79B, FCER1G, FCGR2A, or FCGR2C. CLEs comprising these intracellular activating domains are illustrated in WO2019/055946, as being effective at promoting proliferation of PBMCs ex vivo in cultures in the absence of exogenous cytokines such as exogenous IL-2. In some embodiments, provided herein are CLEs comprising an intracellular domain from CD3D, CD3G, CD3Z, CD79A, FCER1G.

In some embodiments, one or more domains of a lymphoproliferative element is fused to a modulatory domain, such as a co-stimulatory domain, and/or an intracellular activating domain of a CAR. In some embodiments of the composition and method aspects for transducing lymphocytes in whole blood, one or more intracellular domains of a lymphoproliferative element can be part of the same polypeptide as a CAR or can be fused and optionally functionally connected to some components of CARs. In still other embodiments, an engineered signaling polypeptide can include an ASTR, an intracellular activation domain (such as a CD3 zeta signaling domain), a co-stimulatory domain, and a lymphoproliferative domain. Further details regarding co-stimulatory domains, intracellular activating domains, ASTRs and other CAR domains, are disclosed elsewhere herein.

In some embodiments, the lymphoproliferative element is not a polypeptide, but rather comprises an inhibitory RNA. In some embodiments, methods, uses, compositions, and products of processes according to any aspect herein include both a lymphoproliferative element comprising an inhibitory RNA and a lymphoproliferative element that is an engineered signaling polypeptide. In embodiments where a lymphoproliferative element is or includes an inhibitory RNA, or multiple inhibitory RNAs, the inhibitory RNA or multiple inhibitory RNAs, can have any of the structures identified elsewhere herein, for example in the Inhibitory RNA Molecules section herein. In some embodiments, the inhibitory RNA can be a miRNA that stimulates the STAT5 pathway typically by potentiating activation of STAT5 by degrading or causing down-regulation of a negative regulator in the SOCS pathway. Inhibitory RNA lymphoproliferative elements can target any of the mRNAs identified in the Inhibitory RNA Molecules section herein or elsewhere herein.

In illustrative embodiments, as exemplified herein, such inhibitory RNA (e.g. miRNAs) can be located in introns in packaging cells and/or a replication incompetent recombinant retroviral particle genome and/or a retroviral vector, typically with expression driven by a promoter that is active in a T cell and/or NK cell. Not to be limited by theory, inclusion of introns in transcription units are believed to result in higher expression and/or stability of transcripts. As such, the ability to place miRNAs within introns of a retroviral genome adds to the teachings of the present disclosure that overcome challenges in the prior art of trying to get maximum activities into the size restrictions of a retroviral, such as a lentivirus genome. In some embodiments, 1, 2, 3, 4, 5, 6, 7, 8, 9, or 10 miRNAs, in illustrative embodiments between 2 and 5, for example 4 miRNAs, one or more of which each bind nucleic acids encoding one or more of the targets disclosed herein, can be included in the recombinant retroviral genome and delivered to a target cell, for example T cells and/or NK cells, using methods provided herein. In fact, as provided herein 1, 2, 3, or 4 miRNAs can be delivered in a single intron such as the EF1-a intron.

In some embodiments, the lymphoproliferative element comprises MPL, or is MPL, or a variant and/or fragment thereof, including a variant and/or fragment that includes at least 75, 80, 85, 90, 95, 96, 97, 98, 99, or 100% of the intracellular domain of MPL, with or without a transmembrane and/or extracellular domain of MPL, and/or has at least 75, 80, 85, 90, 95, 96, 97, 98, 99, or 100% sequence identity to the intracellular domain of MPL, with or without a transmembrane and/or extracellular domain of MPL, wherein the variant and/or fragment retains the ability to promote cell proliferation of PBMCs, and in some embodiments T cells. In illustrative embodiments, the lymphoproliferative element comprises an intracellular domain of MPL, or a variant or fragment thereof that includes at least 75, 80, 85, 90, 95, 96, 97, 98, 99, or 100% of the intracellular domain of MPL, and the lymphoproliferative element does not comprise a transmembrane domain of MPL. In some embodiments, the lymphoproliferative element comprises an intracellular domain of MPL, or a variant or fragment thereof that includes at least 75, 80, 85, 90, 95, 96, 97, 98, 99, or 100% of the intracellular domain of MPL, and the lymphoproliferative element comprises a transmembrane domain of MPL. In some embodiments, a cell expressing the lymphoproliferative element comprising an intracellular and transmembrane domain of MPL can be contacted with, exposed to, or treated with eltrombopag. Not to be limited by theory, eltrombopag binds to the transmembrane domain of MPL and induces the activation of the intracellular domain of MPL. In some embodiments, an MPL fragment included in the compositions and methods herein has and/or retains a JAK-2 binding domain. In some embodiments, an MPL fragment included herein has or retains the ability to activate a STAT. The full intracellular domain of MPL is SEQ ID NO:283 (part 5186 as illustrated in WO2019/055946). MPL is the receptor for thrombopoietin. Several cytokines such as thrombopoietin and EPO are referred to in the literature and herein as either a hormone or a cytokine.

In some embodiments, which provide separate aspects of the present disclosure, provided herein are chimeric polypeptides that are chimeric lymphoproliferative elements (CLEs), as well as isolated polynucleotides and nucleic acid sequences that encode the same. CLEs can include any of the domains and/or domains derived from specific genes discussed in the section. Similarly, the isolated polynucleotides and nucleic acid sequences encoding CLEs can encode as part of the CLE any of the domains and/or domains derived from specific genes discussed in this section.

Lymphoproliferative elements provided herein typically include a transmembrane domain. For example, the transmembrane domain can have 80%, 85%, 90%, 95%, 97%, 98%, 99% or 100% sequence identity to any one of the transmembrane domains from the following genes and representative sequences disclosed in WO2019/055946: CD8 beta, CD4, CD3 zeta, CD28, CD134, CD7, CD2, CD3D, CD3E, CD3G, CD3Z, CD4, CD8A CD8B, CD27, CD28, CD40, CD79A, CD79B, CRLF2, CRLF2, CSF2RA, CSF2RB, CSF2RB, CSF3R, EPOR, FCER1G, FCGR2C, FCGRA2, GHR, GHR, ICOS, IFNAR, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL7RA, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL27RA, IL31RA, LEPR, LIFR, MPL, OSMR, PRLR, TNFRSF4, TNFRSF8, TNFRSF9, TNFRSF14, and TNFRSF18. Transmembrane™ domains suitable for use in any engineered signaling polypeptide include, but are not limited to, constitutively active cytokine receptors, the TM domain from LMP1, and TM domains from type 1 TM proteins comprising a dimerizing motif, as discussed in more detail herein. In any of the aspects disclosed herein containing the transmembrane domain from a type I transmembrane protein, the transmembrane domain can be a Type I growth factor receptor, a hormone receptor, a T cell receptor, or a TNF-family receptor.

Eltrombopag is a small molecule activator of the thrombopoietin receptor MPL (also known as TPOR). In some aspects a cell expressing an LE comprising a MPL transmembrane domain, can be exposed to or contacted with eltrombopag, or a patient or subject to which such a cell has been infused, can be treated with eltrombopag. Upon said contacting or treating, the proliferative and/or survival properties of the LE are activated and provided to the cell, thereby increasing survival and/or proliferation of the cell compared to the absence of the eltrombopag. Not to be limited by theory, binding of eltrombopag occurs in the transmembrane domain and can activate one or more intracellular domains that are part of the same polypeptide. A skilled artisan will understand the amount of eltrombopag to be used to activate a CLE comprising a MPL transmembrane domain.

In some embodiments, CLEs include both an extracellular portion and a transmembrane portion that is from the same protein, in illustrative embodiments the same receptor, either of which in illustrative embodiments is a mutant, thus forming an extracellular and transmembrane domain. These domains can be from a cytokine receptor, or a mutant thereof, or a hormone receptor, or a mutant thereof in some embodiments that have been reported to be constitutively active when expressed at least in some cell types. In illustrative embodiments, such extracellular and transmembrane domains do not include a ligand binding region. It is believed that such domains do not bind a ligand when present in CLEs and expressed in B cells, T cells, and/or NK cells. Mutations in such receptor mutants can occur in the transmembrane region or in the extracellular juxtamembrane region. Not to be limited by theory, a mutation in at least some extracellular-transmembrane domains of CLEs provided herein, are responsible for signaling of the CLE in the absence of ligand, by bringing activating chains together that are not normally together, or by changing the confirmation of a linked transmembrane and/or intracellular domain.

Exemplary extracellular and transmembrane domains for CLEs of embodiments that include such domains, in illustrative embodiments, are extracellular regions, typically less than 30 amino acids of the membrane-proximal extracellular domains along with transmembrane domains from mutant receptors that have been reported to be constitutive, that is not require ligand binding for activation of an associated intracellular domain. In illustrative embodiments, such extracellular and transmembrane domains include IL7RA Ins PPCL, CRLF2 F232C, CSF2RB V449E, CSF3R T640N, EPOR L251C I252C, GHR E260C I270C, IL27RA F523C, and MPL S505N. In some embodiments, the extracellular and transmembrane domain does not comprise more than 10, 20, 25 30 or 50 consecutive amino acids that are identical in sequence to a portion of the extracellular and/or transmembrane domain of IL7RA, or a mutant thereof. In some embodiments, the extracellular and transmembrane domain is other than IL7RA Ins PPCL. In some embodiments, the extracellular and transmembrane does not comprise more than 10, 20, 25, 30, or 50 consecutive amino acids that are identical in sequence to a portion of the extracellular and/or transmembrane domain of IL15R.

In one embodiment of this aspect, an LE provided herein comprises an extracellular domain, and in illustrative embodiments, the extracellular domain comprises a dimerizing motif. In illustrative embodiments of this aspect, the extracellular domain comprises a leucine zipper. In some embodiments, the leucine zipper is from a jun polypeptide, for example c-jun. In certain embodiments the c-jun polypeptide is the c-jun polypeptide region of ECD-11.

In embodiments of any of these aspects and embodiments wherein the transmembrane domain is a type I transmembrane protein, the transmembrane domain can be a Type I growth factor receptor, a hormone receptor, a T cell receptor, or a TNF-family receptor. In an embodiment of any of the aspects and embodiments wherein the chimeric polypeptide comprises an extracellular domain and wherein the extracellular domain comprises a dimerizing motif, the transmembrane domain can be a Type I cytokine receptor, a hormone receptor, a T cell receptor, or a TNF-family receptor.

Exemplary transmembrane domains include any transmembrane domain that was illustrated in WO2019/055946. In some embodiments, the transmembrane domain is from CD4, CD8RB, CD40, CRLF2, CSF2RA, CSF3R, EPOR, FCGR2C, GHR, ICOS, IFNAR1, IFNGR1, IFNGR2, IL1R1, IL1RAP, IL2RG, IL3RA, IL5RA, IL6ST, IL7RA, IL10RB, IL11RA, IL13RA2, IL17RA, IL17RB, IL17RC, IL17RE, IL18R1, IL18RAP, IL20RA, IL22RA1, IL31RA, LEPR, PRLR, and TNFRSF8, or mutants thereof that are known to promote signaling activity in certain cell types if such mutants are present in the constructs provided in WO2019/055946. In some embodiments, the transmembrane domain is from CD40, ICOS, FCGR2C, PRLR, IL3RA, or IL6ST.

In some embodiments, the extracellular and transmembrane domain is the viral protein LMP1, or a mutant and/or fragment thereof. LMP1 is a multispan transmembrane protein that is known to activate cell signaling independent of ligand when targeted to lipid rafts or when fused to CD40 (Kaykas et al. EMBO J. 20: 2641 (2001)). A fragment of LMP1 is typically long enough to span a plasma membrane and to activate a linked intracellular domain(s). For example, the LMP1 can be between 15 and 386, 15 and 200, 15 and 150, 15 and 100, 18 and 50, 18 and 30, 20 and 200, 20 and 150, 20 and 50, 20 and 30, 20 and 100, 20 and 40, or 20 and 25 amino acids. A mutant and/or fragment of LMP1 when included in a CLE provided herein, retains its ability to activate an intracellular domain. Furthermore, if present, the extracellular domain includes at least 1, but typically at least 4 amino acids and is typically linked to another functional polypeptide, such as a clearance domain, for example, an eTag. In some embodiments, the lymphoproliferative element comprises an LMP1 transmembrane domain. In illustrative embodiments, the lymphoproliferative element comprises an LMP1 transmembrane domain and the one or more intracellular domains do not comprise an intracellular domain from TNFRSF proteins (i.e. CD40, 4-IBB, RANK, TACI, OX40, CD27, GITR, LTR, and BAFFR), TLR1 to TLR13, integrins, FcγRIII, Dectin1, Dectin2, NOD1, NOD2, CD16, IL-2R, Type I II interferon receptor, chemokine receptors such as CCR5 and CCR7, G-protein coupled receptors, TREM1, CD79A, CD79B, Ig-alpha, IPS-1, MyD88, RIG-1, MDA5, CD3Z, MyD88ΔTIR, TRIF, TRAM, TIRAP, MAL, BTK, RTK, RAC1, SYK, NALP3 (NLRP3), NALP3ΔLRR, NALP1, CARDS, DAI, IPAG, STING, Zap70, or LAT.

In other embodiments of CLEs provided herein, the extracellular domain includes a dimerizing moiety. Many different dimerizing moieties disclosed herein can be used for these embodiments. In illustrative embodiments, the dimerizing moieties are capable of homodimerizing. Not to be limited by theory, dimerizing moieties can provide an activating function on intracellular domains connected thereto via transmembrane domains. Such activation can be provided, for example, upon dimerization of a dimerizing moiety, which can cause a change in orientation of intracellular domains connected thereto via a transmembrane domain, or which can cause intracellular domains to come into proximity. An extracellular domain with a dimerizing moiety can also serve a function of connecting a recognition tag to a cell expressing a CLE. In some embodiments, the dimerizing agent can be located intracellularly rather than extracellularly. In some embodiments, more than one or multiples of dimerizing domains can be used.

Extracellular domains for embodiments where extracellular domains have a dimerizing motif, are long enough to form dimers, such as leucine zipper dimers. As such, extracellular domains that include a dimerizing moiety can be from 15 to 100, 20 to 50, 30 to 45, or 35 to 40 amino acids, of in illustrative embodiments is a c-Jun portion of a c-Jun extracellular domain Extracellular domains of polypeptides that include a dimerizing moiety, may not retain other functionalities. For example, for leucine zippers embodiments, such leucine zippers are capable of forming dimers because they retain a motif of leucines spaced 7 residues apart along an alpha helix. However, leucine zipper moieties of certain embodiments of CLEs provided herein, may or may not retain their DNA binding function.

A spacer of between 1 and 4 alanine residues can be included in CLEs between the extracellular domain that has a dimerizing moiety, and the transmembrane domain. Not to be limited by theory, it is believed that the alanine spacer affects signaling of intracellular domains connected to the leucine zipper extracellular region via the transmembrane domain, by changing the orientation of the intracellular domains.

The first and optional second intracellular domains of CLEs provided herein, are intracellular signaling domains of genes that are known in at least some cell types, to promote proliferation, survival (anti-apoptotic), and/or provide a co-stimulatory signal that enhances proliferative potential or resistance to cell death. As such, these intracellular domains can be intracellular domains from lymphoproliferative elements and co-stimulatory domains provided herein. Some of the intracellular domains of candidate chimeric polypeptides are known to activate JAK1/JAK2, JAK3, STAT1, STAT2, STAT3, STAT4, STAT5, and STAT6 signaling. Conserved motifs that are found in intracellular domains of cytokine receptors that are responsible for this signaling are known (see e.g., Morris et al., "The molecular details of cytokine signaling via the JAK/STAT pathway," Protein Science (2018) 27:1984-2009). The Box1 and Box2 motifs are involved in binding to JAKs and signal transduction, although the Box2 motif presence is not always required for a proliferative signal (Murakami et al. Proc Natl Acad Sci USA. 1991 Dec. 15; 88(24):11349-53; Fukunaga et al. EMBO J. 1991 October; 10(10):2855-65; and O'Neal and Lee. Lymphokine Cytokine Res. 1993 October; 12(5):309-12). Accordingly, in some embodiments a lymphoproliferative element herein is a transgenic BOX1-containing cytokine receptor that includes an intracellular domain of a cytokine receptor comprising a Box1 Janus kinase (JAK)-binding motif, optionally a Box2 JAK-binding motif, and a Signal Transducer and Activator of Transcription (STAT) binding motif comprising a tyrosine residue. Many cytokine receptors have hydrophobic residues at positions −1, −2, and −6 relative to the Box1 motif, that form a "switch motif," which is required for cytokine-induced JAK2 activation but not for JAK2 binding (Constantinescu et al. Mol Cell. 2001 February; 7(2):377-85; and Huang et al. Mol Cell. 2001 December; 8(6):1327-38). Accordingly, in certain embodiments of the transgenic BOX1-containing cytokine receptor lymphoproliferative element has a switch motif, which in illustrative embodiments has one or more, and preferably all hydrophobic residues at positions −1, −2, and −6 relative to the Box1 motif. In certain embodiments, the Box1 motif an ICD of a lymphoproliferative element is located proximal to the transmembrane (TM) domain (for example between 5 and 15 or about 10 residues downstream from the TM domain) relative to the Box2 motif, which is located proximal to the transmembrane domain (for example between 10 and 50 residues downstream from the TM domain) relative to the STAT binding motif. The STAT binding motif typically comprising a tyrosine residue, the phosphorylation of which affects binding of a STAT to the STAT binding motif of the lymphoproliferative element. In some embodiments, the ICDs comprising multiple STAT binding motifs where multiple STAT binding motifs are present in a native ICD (e.g. EPO receptor and IL-6 receptor signaling chain (gp130).

Intracellular domains from IFNAR1, IFNGR1, IFNLR1, IL2RB, IL4R, IL5RB, IL6R, IL6ST, IL7RA, IL9R, IL10RA, IL21R, IL27R, IL31RA, LIFR, and OSMR are known in the art to activate JAK1 signaling. Intracellular domains from CRLF2, CSF2RA, CSF2RB, CSF3R, EPOR, GHR, IFNGR2, IL3RA, IL5RA, IL6ST, IL20RA, IL20RB, IL23R, IL27R, LEPR, MPL, and PRLR are known in the art to activate JAK2. Intracellular domains from IL2RG are known in the art to activate JAK3. Intracellular domains from GHR, IFNAR1, IFNAR2, IFNGR1, IFNGR2, IL2RB, IL2RG, IL4R, IL5RA, IL5RB, IL7RA, IL9R, IL21R, IL22RA1, IL31RA, LIFR, MPL, and OSMR are known in the art to activate STAT1. Intracellular domains from IFNAR1 and IFNAR2 are known in the art to activate STAT2. Intracellular domains from GHR, IL2RB, IL2RG, IL6R, IL7RA, IL9R, IL10RA, IL10RB, IL21R, IL22RA1, IL23R, IL27R, IL31RA, LEPR, LIFR, MPL, and OSMR are known in the art to activate STAT3. Intracellular domains from IL12RB1 are known in the art to activate STAT4. Intracellular domains from CSF2RA, CSF2RB, CSF3R, EPOR, GHR, IL2RB, IL2RG, IL3RA, IL4R, IL5RA, IL5RB, IL7RA, IL9R, IL15RA, IL20RA, IL20RB, IL21R, IL22RA1, IL31RA, LIFR, MPL, OSMR, and PRLR are known in the art to activate STAT5. Intracellular domains from IL4R and OSMR are known in the art to activate STATE. The genes and intracellular domains thereof that are found in a first intracellular domain are the same as the optional second intracellular domain, except that if the first and second intracellular domain are identical, then at least one, and typically both the transmembrane domain and the extracellular domain are not from the same gene.

In some embodiments, all domains of a CLE are other than an IL-7 receptor, or a mutant thereof, and/or a fragment thereof that has at least 10, 15, 20, or 25 contiguous amino acids of IL-7 receptor, or other than an IL-15 receptor, or a mutant thereof, and/or a fragment thereof that has at least 10, 15, 20, or 25 contiguous amino acids of IL-15 receptor. In some embodiments, a CLE does not comprise a combination of first intracellular domain and second intracellular domain of CD40 and MyD88.

In illustrative embodiments, CLEs include a recognition and/or elimination domain Details regarding recognition and/or elimination domains are provided in other sections herein. Any of the recognition and/or elimination domains provided herein can be part of a CLE. Typically the recognition domain is linked to the N terminus of the extracellular domain Not to be limited by theory, in some embodiments, the extracellular domain includes the function of providing a linker, in illustrative embodiments a flexible linker, linking a recognition domain to a cell that expresses the CLE.

Furthermore, polynucleotides that include a nucleic acid sequence encoding a CLE provided herein, also typically comprise a signal sequence to direct expression to the plasma membrane. Exemplary signal sequences are provided herein in other sections. Elements can be provided on the transcript such that both a CAR and CLE are expressed from the same transcript in certain embodiments.

In any aspects or embodiments wherein the extracellular domain of a CLE comprises a dimerizing motif, the dimerizing motif can be selected from the group consisting of: a leucine zipper motif-containing polypeptide, CD69, CD71, CD72, CD96, Cd105, Cd161, Cd162, Cd249, CD271, and Cd324, as well as mutants and/or active fragments thereof that retain the ability to dimerize. In any of the aspects and embodiments herein wherein the extracellular domain of a CLE comprises a dimerizing motif, the dimerizing motif can require a dimerizing agent, and the dimerizing motif and associated dimerizing agent can be selected from the group consisting of: FKBP and rapamycin or analogs thereof, GyrB and coumermycin or analogs thereof, DHFR and methotrexate or analogs thereof, or DmrB and AP20187 or analogs thereof, as well as mutants and/or active fragments of the recited dimerizing proteins that retain the ability to dimerize. In some aspects and illustrative embodiments, a lymphoproliferative element is constitutively active, and is other than a lymphoproliferative element that requires a dimerizing agent for activation.

In illustrative embodiments of any aspects or embodiments herein wherein the extracellular domain of a CLE comprises a dimerizing motif, the extracellular domain can comprise a leucine zipper motif. In some embodiments, the leucine zipper motif is from a jun polypeptide, for example c-jun. In certain embodiments the c-jun polypeptide is the c-jun polypeptide region of ECD-11. Internally dimerizing and/or multimerizing lymphoproliferative elements in one embodiment are an integral part of a system that uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 dimerizer drugs for their binding domain, FKBP12 permits specific activation of the recombinant receptor in vivo without the induction of non-specific side effects through endogenous FKBP12. FKBP12 variants having amino acid substitutions and deletions, such as FKBP12V36, that bind to a dimerizer drug, may also be used. In addition, the synthetic ligands are resistant to protease degradation, making them more efficient at activating receptors in vivo than most delivered protein agents.

Pseudotyping Elements

Many of the methods and compositions provided herein include pseudotyping elements. The pseudotyping of replication incompetent recombinant retroviral particles with heterologous envelope glycoproteins typically alters the tropism of a virus and facilitates the transduction of host cells. A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. In some embodiments provided herein, pseudotyping elements are provided as polypeptide(s)/protein(s), or as nucleic acid sequences encoding the polypeptide(s)/protein(s).

In some embodiments, the pseudotyping element is the feline endogenous virus (RD114) envelope protein, an oncoretroviral amphotropic envelope protein, an oncoretroviral ecotropic envelope protein, the vesicular stomatitis virus envelope protein (VSV-G) (SEQ ID NO: 336), the baboon retroviral envelope glycoprotein (BaEV) (SEQ ID NO: 337), the murine leukemia envelope protein (MuLV) (SEQ ID NO: 338), the influenza glycoprotein HA surface glycoprotein (HA), the influenza glycoprotein neurominidase (NA), the paramyxovirus Measles envelope protein H, the paramyxovirus Measles envelope protein F, and/or functional variants or fragments of any of these envelope proteins.

In some embodiments, the pseudotyping element can be wild-type BaEV. Not to be limited by theory, BaEV contains an R peptide that has been shown to inhibit transduction. In some embodiments, the BaEV can contain a deletion of the R peptide. In some embodiments, the BaEV can contain a deletion of the inhibitory R peptide after the nucleotides encoding the amino acid sequence HA, referred to herein as BaEVΔR (HA) (SEQ ID NO: 339). In some embodiments, the BaEV can contain a deletion of the inhibitory R peptide after the nucleotides encoding the amino acid sequence HAM, referred to herein as BaEVΔR (HAM) (SEQ ID NO: 340).

In some embodiments, the pseudotyping element can be wild-type MuLV. In some embodiments, the MuLV can contain one or more mutations to remove the furin-mediated cleavage site located between the transmembrane (TM) and surface (SU) subunits of the envelope glycoprotein. In some embodiments the MuLV contains the SUx mutation (MuLVSUx) (SEQ ID NO: 453) which inhibits furin-mediated cleavage of MuLV envelope protein in packaging cells. In certain embodiments the C-terminus of the cytoplasmic tail of the MuLV or MuLVSUx protein is truncated by 4 to 31 amino acids. In certain embodiments the C-terminus of the cytoplasmic tail of the MuLV or MuLVSUx protein is truncated by 4, 8, 12, 16, 20, 24, 28, or 31 amino acids.

In some embodiments, the pseudotyping elements include a binding polypeptide and a fusogenic polypeptide derived from different proteins. For example, the replication incompetent recombinant retroviral particles of the methods and compositions disclosed herein can be pseudotyped with the fusion (F) and/or hemagglutinin (H) polypeptides of the measles virus (MV), as non-limiting examples, clinical wildtype strains of MV, and vaccine strains including the Edmonston strain (MV-Edm) (GenBank; AF266288.2) or fragments thereof. Not to be limited by theory, both hemagglutinin (H) and fusion (F) polypeptides are believed to play a role in entry into host cells wherein the H protein binds MV to receptors CD46, SLAM, and Nectin-4 on target cells and F mediates fusion of the retroviral and host cell membranes. In an illustrative embodiment, especially where the target cell is a T cell and/or NK cell, the binding polypeptide is a Measles Virus H polypeptide and the fusogenic polypeptide is a Measles Virus F polypeptide.

In some studies, lentiviral particles pseudotyped with truncated F and H polypeptides had a significant increase in titers and transduction efficiency (Funke et al. 2008. *Molecular Therapy.* 16(8):1427-1436), (Frecha et al. 2008. *Blood.* 112(13):4843-4852). The highest titers were obtained when the F cytoplasmic tail was truncated by 30 residues (referred to as MV(Ed)-FΔ30 (SEQ ID NO:313)). For the H variants, optimal truncation occurred when 18 or 19 residues were deleted (MV(Ed)-HΔ18 (SEQ ID NO:314) or MV(Ed)-HΔ19), although variants with a truncation of 24 residues with and without replacement of deleted residues with alanine (MV(Ed)-HΔ24 (SEQ ID NO:315) and MV(Ed)-HΔ24+A) also resulted in optimal titers. Accordingly, in some embodiments, including those directed to transducing T cells and/or NK cells, the replication incompetent recombinant retroviral particles of the methods and compositions disclosed herein are pseudotyped with mutated or variant versions of the measles virus fusion (F) and hemagglutinin (H) polypeptides, in illustrative examples, cytoplasmic domain deletion variants of measles virus F and H polypeptides. In some embodiments, the mutated F and H polypeptides are "truncated H" or "truncated F" polypeptides, whose cytoplasmic portion has been truncated, i.e. amino acid residues (or coding nucleic acids of the corresponding nucleic acid molecule encoding the protein) have been deleted. "HAY" and "FAX" designate such truncated H and F polypeptide, respectively, wherein "Y" refers to 1-34 residues that have been deleted from the amino termini and "X" refers to 1-35 residues that have been deleted from the carboxy termini of the cytoplasmic domains. In a further embodiment, the "truncated F polypeptide" is FΔ24 or FΔ30 and/or the "truncated H protein" is selected from the group consisting of HΔ14, HΔ15, HΔ16, HΔ17, HΔ18, HΔ19, HΔ20, HΔ21+A, HΔ24 and HΔ24+4A, more preferably HΔ18 or HΔ24. In an illustrative embodiment, the truncated F polypeptide is MV(Ed)-FΔ30 and the truncated H polypeptide is MV(Ed)-HΔ18.

In some embodiments, the pseudotyping element includes polypeptides derived from different proteins. For example, the pseudotyping element can comprise an influenza protein hemagglutinin HA and/or a neuraminidase (NA). In certain embodiments the HA is from influenza A virus subtype H1N1. In illustrative embodiments the HA is from H1N1 PR8 1934 in which the monobasic trypsin-dependent cleavage site has been mutated to a more promiscuous multibasic sequence (SEQ ID NO:311). In certain embodiments the NA is from influenza A virus subtype H10N7. In illustrative embodiments the NA is from H10N7-HKWF446C-07 (SEQ ID NO:312).

In some embodiments, the viral particles are copseudotyped with envelope glycoproteins from 2 or more heterologous viruses. In some embodiments, the viral particles are copseudotyped with VSV-G, or a functional variant or fragment thereof, and an envelope protein from RD114, BaEV, MuLV, influenza virus, measles virus, and/or a functional variant or fragment thereof. In some embodiments, the viral particles are copseudotyped with VSV-G and the MV(Ed)-H glycoprotein or the MV(Ed)-H glycoprotein with a truncated cytoplasmic domain. In illustrative embodiments, the viral particles are copseudotyped with VSV-G and MV(Ed)-HΔ24. In certain embodiments, VSV-G is copseudotyped with MuLV or MuLV with a truncated cytoplasmic domain. In other embodiments, VSV-G is copseudotyped with MuLVSUx or MuLVSUx with a truncated cytoplasmic domain. In further illustrative embodiments, VSV-G is copseudotyped with a fusion of an antiCD3scFv to MuLV.

In some embodiments, the fusogenic polypeptide includes multiple elements expressed as one polypeptide. In some embodiments, the binding polypeptide and fusogenic polypeptide are translated from the same transcript but from separate ribosome binding sites; in other embodiments, the binding polypeptide and fusogenic polypeptide are separated by a cleavage peptide site, which not to be bound by theory, is cleaved after translation, as is common in the literature, or a ribosomal skip sequence. In some embodiments, the translation of the binding polypeptide and fusogenic polypeptide from separate ribosome binding sites results in a higher amount of the fusogenic polypeptide as compared to the binding polypeptide. In some embodiments, the ratio of the fusogenic polypeptide to the binding polypeptide is at least 2:1, at least 3:1, at least 4:1, at least 5:1, at least 6:1, at least 7:1, or at least 8:1. In some embodiments, the ratio of the fusogenic polypeptide to the binding polypeptide is between 1.5:1, 2:1, or 3:1, on the low end of the range, and 3:1, 4:1, 5:1, 6:1, 7:1, 8:1.9:1 or 10:1 on the high end of the range.

Activation Elements

Many of the methods and composition aspects of the present disclosure include an activation element, also referred to herein as a T cell activation element, or a nucleic acid encoding an activation element. The restrictions associated with lentiviral (LV) transduction into resting T cells are attributed to a series of pre-entry and post-entry barriers as well as cellular restrictive factors (Strebel et al 2009. *BMC Medicine* 7:48). One restriction is the inability for the envelope pseudotyped-LV particles to recognize potential receptors and mediate fusion with the cellular membrane. However, under certain conditions, the transduction of resting T cells with HIV-1-based lentiviral vectors is possible mostly upon T cell receptor (TCR) CD3 complex and CD28 co-stimulation (Korin & Zack. 1998. *Journal of Virology.* 72:3161-8, Maurice et al. 2002. *Blood* 99:2342-50), as well as through exposure to cytokines (Cavalieri et al. 2003).

Cells of the immune system such as T lymphocytes recognize and interact with specific antigens through receptors or receptor complexes which, upon recognition or an interaction with such antigens, cause activation of the cell and expansion in the body. An example of such a receptor is the antigen-specific T lymphocyte receptor complex (TCR/CD3). The T cell receptor (TCR) is expressed on the surface of T lymphocytes. One component, CD3, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system. Thus, activation elements provided herein, activate T cells by binding to one or more components of the T cell receptor associated complex, for example by binding to CD3. In some embodiments, the activation element can activate alone. In other cases, the activation requires activation through the TCR receptor complex in order to further activate cells.

T lymphocytes also require a second, co-stimulatory signal to become fully active in vivo. Without such a signal, T lymphocytes are either non-responsive to antigen binding to the TCR, or become anergic. However, the second, co-stimulatory signal is not required for the transduction and expansion of T cells. Such a co-stimulatory signal, for example, is provided by CD28, a T lymphocyte protein, which interacts with CD80 and CD86 on antigen-producing cells. As used herein, a functional extracellular fragment of CD80 retains its ability to interact with CD28. OX40, 4-1BB, and ICOS (Inducible COStimulator), other T lymphocyte proteins, and provides a co-stimulatory signal when bound to one or more of its respective ligands: OX40L, 4-1BBL, and ICOSLG.

Activation of the T cell receptor (TCR) CD3 complex and co-stimulation with CD28 can occur by ex vivo exposure to solid surfaces (e.g. beads) coated with anti-CD3 and anti-CD28. In some embodiments of the methods and compositions disclosed herein, resting T cells are activated by exposure to solid surfaces coated with anti-CD3 and anti-CD28 ex vivo. In other embodiments, resting T cells or NK cells, and in illustrative embodiments resting T cells, are activated by exposure to soluble anti-CD3 antibodies (e.g. at 50-150, or 75-125, or 100 ng/ml). In such embodiments, which can be part of methods for genetically modifying or transducing, in illustrative embodiments without prior activation, such activation and/or contacting can be carried out by including anti-CD3 in a transduction reaction mixture and contacting with optional incubating for any of the times provided herein. Furthermore, such activation with soluble anti-CD3 can occur by incubating lymphocytes, such as PBMCs, and in illustrative embodiments NK cells and in more illustrative embodiments, T cells, after they are contacted with retroviral particles in a media containing an anti-CD3. Such incubation can be for example, for between 5, 10, 15, 30, 45, 60, or 120 minutes on the low end of the range, and 15, 30, 45, 60, 120, 180, or 240 minutes on the high end of the range, for example, between 15 and 1 hours or 2 hours.

In certain illustrative embodiments of the methods and compositions provided herein, polypeptides that are capable of binding to an activating T cell surface protein are presented as "activation elements" on the surface of replication incompetent recombinant retroviral particles of the methods and compositions disclosed herein, which are also aspects of the invention. In illustrative embodiments, the activation elements on the surfaces of the replication incompetent recombinant retroviral particles can include one or more polypeptides capable of binding CD3. In illustrative embodiments, the activation elements on the surfaces of the replication incompetent recombinant retroviral particles can include one or more polypeptides capable of binding the epsilon chain of CD3 (CD3 epsilon). In other embodiments, the activation element on the surfaces of the replication incompetent recombinant retroviral particles can include one or more polypeptides capable of binding CD28, OX40, 4-1BB, ICOS, CD9, CD53, CD63, CD81, and/or CD82 and optionally one or more polypeptides capable of binding CD3. In illustrative embodiments, the activation element can be a T cell surface protein agonist. The activation element can include a polypeptide that acts as a ligand for a T cell surface protein. In some embodiments, the polypeptide that acts as a ligand for a T cell surface protein is, or includes, one or more of OX40L, 4-1BBL, or ICOSLG.

In some embodiments, one or typically more copies of one or more of these activation elements can be expressed on the surfaces of the replication incompetent recombinant retroviral particles as polypeptides separate and distinct from the pseudotyping elements. In some embodiments, the activation elements can be expressed on the surfaces of the replication incompetent recombinant retroviral particles as fusion polypeptides. In illustrative embodiments, the fusion polypeptides include one or more activation elements and one or more pseudotyping elements. In further illustrative embodiments, the fusion polypeptide includes anti-CD3, for example an anti-CD3scFv, or an anti-CD3scFvFc, and a viral envelope protein. In one example the fusion polypeptide is the OKT-3scFv fused to the amino terminal end of a viral envelope protein such as the MuLV envelope protein, as shown in Maurice et al. (2002). In some embodiments, the fusion polypeptide is UCHT1scFv fused to a viral envelope protein, for example the MuLV envelope protein (SEQ ID NO:341), the MuLVSUx envelope protein (SEQ ID NO:454), VSV-G (SEQ ID NO:455 or SEQ ID NO:456), or functional variants or fragments thereof, including any of the membrane protein truncations provided herein. In such fusion constructs, and any other constructs wherein an activation element is tethered to the surface of a retroviral particle, illustrative embodiments especially for compositions and methods herein for transducing lymphocytes in whole blood, do not include any blood protein (e.g. blood Factor (e.g. Factor X)) cleavage sites in the portion of the fusion protein that resides outside the retroviral particle. In some embodiments, the fusion constructs do not include any furin cleavage sites. Furin is a membrane bound protease expressed in all mammalian cells examined, some of which is secreted and active in blood plasma (See e.g. C. Fernandez et al. J. Internal. Medicine (2018) 284; 377-387). Mutations can be made to fusion constructs using known methods to remove such protease cleavage sites.

Polypeptides that bind CD3, CD28, OX40, 4-1BB, or ICOS are referred to as activation elements because of their ability to activate resting T cells. In certain embodiments, nucleic acids encoding such an activating element are found in the genome of a replication incompetent recombinant retroviral particle that contains the activating element on its surface. In other embodiments, nucleic acids encoding an activating element are not found in the replication incompetent recombinant retroviral particle genome. In still other embodiments, the nucleic acids encoding an activating element are found in the genome of a virus packaging cell.

In some embodiments, the activation element is a polypeptide capable of binding to CD3. In certain embodiments the polypeptide capable of binding to CD3, binds to CD3D, CD3E, CD3G, or CD3Z. In illustrative embodiments the activation element is a polypeptide capable of binding to CD3E. In some embodiments, the polypeptide capable of binding to CD3 is an anti-CD3 antibody, or a fragment thereof that retains the ability to bind to CD3. In illustrative embodiments, the anti-CD3 antibody or fragment thereof is a single chain anti-CD3 antibody, such as but not limited to, an anti-CD3 scFv. In another illustrative embodiment, the polypeptide capable of binding to CD3 is anti-CD3scFvFc.

A number of anti-human CD3 monoclonal antibodies and antibody fragments thereof are available, and can be used in the present invention, including but not limited to UCHT1, OKT-3, HIT3A, TRX4, X35-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XIII46, XIII-87, 12F6, T3/RW2-8C8, T3/RW24B6, OKT3D, M-T301, SMC2 and F101.01.

In some embodiments, the activation element is a polypeptide capable of binding to CD28. In some embodiments, the polypeptide capable of binding to CD28 is an anti-CD28 antibody, or a fragment thereof that retains the ability to bind to CD28. In other embodiments, the polypeptide capable of binding to CD28 is CD80, CD86, or a functional fragment thereof that is capable of binding CD28 and inducing CD28-mediated activation of Akt, such as an external fragment of CD80. In some aspects herein, an external fragment of CD80 means a fragment that is typically present on the outside of a cell in the normal cellular location of CD80, that retains the ability to bind to CD28. In illustrative embodiments, the anti-CD28 antibody or fragment thereof is a single chain anti-CD28 antibody, such as, but not limited to, an anti-CD28 scFv. In another illustrative embodiment, the polypeptide capable of binding to CD28 is CD80, or a fragment of CD80 such as an external fragment of CD80.

Anti-CD28 antibodies are known in the art and can include, as non-limiting examples, monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody.

In an illustrative embodiment, an activation element includes two polypeptides, a polypeptide capable of binding to CD3 and a polypeptide capable of binding to CD28.

In certain embodiments, the polypeptide capable of binding to CD3 or CD28 is an antibody, a single chain monoclonal antibody or an antibody fragment, for example a single chain antibody fragment. Accordingly, the antibody fragment can be, for example, a single chain fragment variable region (scFv), an antibody binding (Fab) fragment of an antibody, a single chain antigen-binding fragment (scFab), a single chain antigen-binding fragment without cysteines (scFabΔC), a fragment variable region (Fv), a construct specific to adjacent epitopes of an antigen (CRAb), or a single domain antibody (VH or VL).

In any of the embodiments disclosed herein, an activation element, or a nucleic acid encoding the same, can include a dimerizing or higher order multimerizing motif. Dimerizing and multimerizing motifs are well-known in the art and a skilled artisan will understand how to incorporate them into the polypeptides for effective dimerization or multimerization. For example, in some embodiments, the activation element that includes a dimerizing motif can be one or more polypeptides capable of binding to CD3 and/or CD28. In some embodiments, the polypeptide capable of binding to CD3 is an anti-CD3 antibody, or a fragment thereof that retains the ability to bind to CD3. In illustrative embodiments, the anti-CD3 antibody or fragment thereof is a single chain anti-CD3 antibody, such as but not limited to, an anti-CD3 scFv. In another illustrative embodiment, the polypeptide capable of binding to CD3 is anti-CD3scFvFc, which in some embodiments is considered an anti-CD3 with a dimerizing motif without any additional dimerizing motif, since anti-CD3scFvFc constructs are known to be capable of dimerizing without the need for a separate dimerizing motif.

In some embodiments, the dimerizing or multimerizing motif, or a nucleic acid sequence encoding the same, can be an amino acid sequence from transmembrane polypeptides that naturally exist as homodimers or multimers. In some embodiments, the dimerizing or multimerizing motif, or a nucleic acid sequence encoding the same, can be an amino acid sequence from a fragment of a natural protein or an engineered protein. In one embodiment, the homodimeric polypeptide is a leucine zipper motif-containing polypeptide (leucine zipper polypeptide). For example, a leucine zipper polypeptide derived from c-JUN, non-limiting examples of which are disclosed related to chimeric lymphoproliferative elements (CLEs) herein.

In some embodiments, these transmembrane homodimeric polypeptides can include early activation antigen CD69 (CD69), Transferrin receptor protein 1 (CD71), B-cell differentiation antigen (CD72), T-cell surface protein tactile (CD96), Endoglin (Cd105), Killer cell lectin-like receptor subfamily B member 1 (Cd161), P-selectin glycoprotein ligand 1 (Cd162), Glutamyl aminopeptidase (Cd249), Tumor necrosis factor receptor superfamily member 16 (CD271), Cadherin-1 (E-Cadherin) (Cd324), or active fragments thereof. In some embodiments, the dimerizing motif, and nucleic acid encoding the same, can include an amino acid sequence from transmembrane proteins that dimerize upon ligand (also referred to herein as a dimerizer or dimerizing agent) binding. In some embodiments, the dimerizing motif and dimerizer can include (where the dimerizer is in parentheses following the dimerizer-binding pair): FKBP and FKBP (rapamycin); GyrB and GyrB (coumermycin); DHFR and DHFR (methotrexate); or DmrB and DmrB (AP20187). As noted above, rapamycin can serve as a dimerizer. Alternatively, a rapamycin derivative or analog can be used (see, e.g., WO96/41865; WO 99/36553; WO 01/14387; and Ye et al (1999) Science 283:88-91). For example, analogs, homologs, derivatives, and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional information is presented in, e.g., U.S. Pat. Nos. 5,525,610; 5,310,903 5,362,718; and 5,527,907. Selective epimerization of the C-28 hydroxyl group has been described (see, e.g., WO 01/14387). Additional synthetic dimerizing agents suitable for use as an alternative to rapamycin include those described in U.S. Patent Publication No. 2012/0130076. As noted above, coumermycin can serve as a dimerizing agent. Alternatively, a coumermycin analog can be used (see, e.g., Farrar et al. (1996) Nature 383:178-181; and U.S. Pat. No. 6,916,846). As noted above, in some cases, the dimerizing agent is methotrexate, e.g., a non-cytotoxic, homo-bifunctional methotrexate dimer (see, e.g., U.S. Pat. No. 8,236, 925). Although some embodiments of lymphoproliferative elements include a dimerizing agent, in some aspects and illustrative embodiments, a lymphoproliferative element is constitutively active, and is other than a lymphoproliferative element that requires a dimerizing agent for activation.

In some embodiments, when present on the surface of replication incompetent recombinant retroviral particles, an activation element including a dimerizing motif can be active in the absence of a dimerizing agent. For example, activation elements including a dimerizing motif from transmembrane homodimeric polypeptides including CD69, CD71, CD72, CD96, Cd105, Cd161, Cd162, Cd249, CD271, Cd324, active mutants thereof, and/or active fragments thereof can be active in the absence a dimerizing agent. In some embodiments, the activation element can be an anti-CD3 single chain fragment and include a dimerizing motif selected from the group consisting of CD69, CD71, CD72, CD96, Cd105, Cd161, Cd162, Cd249, CD271, Cd324, active mutants thereof, and/or active fragments thereof. In some embodiments, when present on the surface of replication incompetent recombinant retroviral particles, an activation element including a dimerizing motif can be active in the presence of a dimerizing agent. For example, activation elements including a dimerizing motif from FKBP, GyrB, DHFR, or DmrB can be active in the presence of the respective dimerizing agents or analogs thereof, e.g. rapamycin, coumermycin, methotrexate, and AP20187, respectively. In some embodiments, the activation element can be a single chain antibody fragment against anti-CD3 or anti-CD28, or another molecule that binds CD3 or CD28, and the dimerizing motif and dimerizing agent can be selected from the group consisting of FKBP and rapamycin or analogs thereof, GyrB and coumermycin or analogs thereof, DHFR and methotrexate or analogs thereof, or DmrB and AP20187 or analogs thereof.

In some embodiments, an activation element is fused to a heterologous signal sequence and/or a heterologous membrane attachment sequence or a membrane bound protein, all of which help direct the activation element to the membrane. The heterologous signal sequence targets the activation element to the endoplasmic reticulum, where the heterologous membrane attachment sequence covalently attaches to one or several fatty acids (also known as posttranslational lipid modification) such that the activation elements that are fused to the heterologous membrane attachment sequence are anchored in the lipid rafts of the plasma membrane. In some embodiments, posttranslational lipid modification can occur via myristoylation, palmitoylation, or GPI anchorage. Myristoylation is a post-translational protein modification which corresponds to the covalent linkage of a 14-carbon saturated fatty acid, the myristic acid, to the N-terminal glycine of a eukaryotic or viral protein. Palmitoylation is a post-translational protein modification which corresponds to the covalent linkage of a C16 acyl chain to cysteines, and less frequently to serine and threonine residues, of proteins. GPI anchorage refers to the attachment of glycosylphosphatidylinositol, or GPI, to the C-terminus of a protein during posttranslational modification.

In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology. 2nd edition*. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In illustrative embodiments, the heterologous GPI anchor attachment sequence is derived from Fc receptor FcγRIIIb (CD16b) or decay accelerating factor (DAF), otherwise known as complement decay-accelerating factor or CD55.

In some embodiments, one or both of the activation elements include a heterologous signal sequence to help direct expression of the activation element to the cell membrane. Any signal sequence that is active in the packaging cell line can be used. In some embodiments, the signal sequence is a DAF signal sequence. In illustrative embodiments, an activation element is fused to a DAF signal sequence at its N terminus and a GPI anchor attachment sequence at its C terminus.

In an illustrative embodiment, the activation element includes anti-CD3 scFvFc fused to a GPI anchor attachment sequence derived from CD14 and CD80 fused to a GPI anchor attachment sequence derived from CD16b; and both are expressed on the surface of a replication incompetent recombinant retroviral particle provided herein. In some embodiments, the anti-CD3 scFvFc is fused to a DAF signal sequence at its N terminus and a GPI anchor attachment sequence derived from CD14 at its C terminus and the CD80 is fused to a DAF signal sequence at its N terminus and a GPI anchor attachment sequence derived from CD16b at its C terminus; and both are expressed on the surface of a replication incompetent recombinant retroviral particle provided herein. In some embodiments, the DAF signal sequence includes amino acid residues 1-30 of the DAF protein.

Membrane-Bound Cytokines

Some embodiments of the method and composition aspects provided herein, include a membrane-bound cytokine, or polynucleotides encoding a membrane-bound cytokine. Cytokines are typically, but not always, secreted proteins. Cytokines that are naturally secreted can be engineered as fusion proteins to be membrane-bound. Membrane-bound cytokine fusion polypeptides are included in methods and compositions disclosed herein, and are also an aspect of the invention. In some embodiments, replication incompetent recombinant retroviral particles have a membrane-bound cytokine fusion polypeptide on their surface that is capable of binding a T cell and/or NK cell and promoting proliferation and/or survival thereof. Typically, membrane-bound polypeptides are incorporated into the membranes of replication incompetent recombinant retroviral particles, and when a cell is transduced by the replication incompetent recombinant retroviral particles, the fusion of the retroviral and host cell membranes results in the polypeptide being bound to the membrane of the transduced cell.

In some embodiments, the cytokine fusion polypeptide includes IL-2, IL-7, IL-15, or an active fragment thereof. The membrane-bound cytokine fusion polypeptides are typically a cytokine fused to heterologous signal sequence and/or a heterologous membrane attachment sequence. In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology. 2nd edition*. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In an illustrative embodiment, the heterologous GPI anchor attachment sequence is derived from Fc receptor FcγRIIIb (CD16b). In some embodiments, the GPI anchor is the GPI anchor of DAF.

In illustrative embodiments, the membrane-bound cytokine is a fusion polypeptide of a cytokine fused to DAF. DAF is known to accumulate in lipid rafts that are incorporated into the membranes of replication incompetent recombinant retroviral particles budding from packaging cells. Accordingly, not to be limited by theory, it is believed that DAF fusion proteins are preferentially targeted to portions of membranes of packaging cells that will become part of a recombinant retroviral membrane.

In non-limiting illustrative embodiments, the cytokine fusion polypeptide is an IL-7, or an active fragment thereof, fused to DAF. In a specific non-limiting illustrative embodiment, the fusion cytokine polypeptide includes in order: the DAF signal sequence (residues 1-31 of DAF), IL-7 without its signal sequence, and residues 36-525 of DAF. In some embodiments, the fusion polypeptide can comprise the DAF signal sequence (amino acids 1-34 of SEQ ID NO:462), IL-7 without its signal sequence (amino acids 35-186 of SEQ ID NO:462), and a fragment of DAF that includes its GPI anchor attachment sequence (amino acids 187-532 of SEQ ID NO:462).

Packaging Cell Lines/Methods of Making Recombinant Retroviral Particles

The present disclosure provides mammalian packaging cells and packaging cell lines that produce replication incompetent recombinant retroviral particles. The cell lines that produce replication incompetent recombinant retroviral particles are also referred to herein as packaging cell lines. A non-limiting example of such method is illustrated in WO2019/055946. Further exemplary methods for making retroviral particles are provided herein, for example in the Examples section herein. Such methods include, for example, a 4 plasmid system or a 5 plasmid system when a nucleic acid encoding an additional membrane bound protein, such as a T cell activation element that is not a fusion with the viral envelope, such as a GPI-linked anti-CD3, is included (See WO2019/05546). In an illustrative embodiment, provided herein is a 4 plasmid system in which a T cell activation element, such as a GPI-linked anti-CD3, is encoded on one of the packaging plasmids such as the plasmid encoding the viral envelope or the plasmid encoding REV, and optionally a second viral membrane-associated transgene such as a membrane bound cytokine can be encoded on the other packaging plasmid. In each case the nucleic acid encoding the viral protein is separated from the transgene by an IRES or a ribosomal skip sequence such as P2A or T2A. Such 4 plasmid system and associated polynucleotides as stated in the Examples, provided increased titers as compared to a 5 vector system in transient transfections, and thus provide illustrative embodiments herein. The present disclosure provides packaging cells and mammalian cell lines that are packaging cell lines that produce replication incompetent recombinant retroviral particles that genetically modify target mammalian cells and the target mammalian cells themselves. In illustrative embodiments, the packaging cell comprises nucleic acid sequences encoding a packageable RNA genome of the replication incompetent retroviral particle, a REV protein, a gag polypeptide, a pol polypeptide, and a pseudotyping element.

The cells of the packaging cell line can be adherent or suspension cells. Exemplary cell types are provided hereinbelow. In illustrative embodiments, the packaging cell line can be a suspension cell line, i.e. a cell line that does not adhere to a surface during growth. The cells can be grown in a chemically-defined media and/or a serum-free media. In some embodiments, the packaging cell line can be a suspension cell line derived from an adherent cell line, for example, the HEK293 cell line can be grown in conditions to generate a suspension-adapted HEK293 cell line according to methods known in the art. The packaging cell line is typically grown in a chemically defined media. In some embodiments, the packaging cell line media can include serum. In some embodiments, the packaging cell line media can include a serum replacement, as known in the art. In illustrative embodiments, the packaging cell line media can be serum-free media. Such media can be a chemically defined, serum-free formulation manufactured in compliance with Current Good Manufacturing Practice (CGMP) regulations of the US Food and Drug Administration (FDA). The packaging cell line media can be xeno-free and complete. In some embodiments, the packaging cell line media has been cleared by regulatory agencies for use in ex vivo cell processing, such as an FDA 510(k) cleared device.

Accordingly, in one aspect, provided herein is a method of making a replication incompetent recombinant retroviral particle including: A. culturing a packaging cell in suspension in serum-free media, wherein the packaging cell comprises nucleic acid sequences encoding a packageable RNA genome of the replication incompetent retroviral particle, a REV protein, a gag polypeptide, a pol polypeptide, and a pseudotyping element; and B. harvesting the replication incompetent recombinant retroviral particle from the serum-free media. In another aspect, provided herein is a method of transducing a lymphocyte with a replication incompetent recombinant retroviral particle comprising: A. culturing a packaging cell in suspension in serum-free media, wherein the packaging cell comprises nucleic acid sequences encoding a packageable RNA genome of the replication incompetent retroviral particle, a REV protein, a gag polypeptide, a pol polypeptide, and a pseudotyping element; B. harvesting the replication incompetent recombinant retroviral particle from the serum-free media; and C. contacting the lymphocyte with the replication incompetent recombinant retroviral particle, wherein the contacting is performed for less than 24 hours, 20 hours, 18 hours, 12 hours, 8 hours, 4 hours, 2 hours, 1 hour, 30 minutes, or 15 minutes (or between contacting and no incubation, or 15 minutes, 30 minutes, 1, 2, 3, or 4 hours on the low end of the range and 1, 2, 3, 4, 6, 8, 12, 18, 20, or 24 hours on the high end of the range), thereby transducing the lymphocyte.

The packageable RNA genome, in certain illustrative embodiments, is designed to express one or more target polypeptides, including as a non-limiting example, any of the engineered signaling polypeptides disclosed herein and/or one or more (e.g. two or more) inhibitory RNA molecules in opposite orientation (e.g., encoding on the opposite strand and in the opposite orientation), from retroviral components such as gag and pol. For example, the packageable RNA genome can include from 5' to 3': a 5' long terminal repeat, or active truncated fragment thereof; a nucleic acid sequence encoding a retroviral cis-acting RNA packaging element; a nucleic acid sequence encoding a first and optionally second target polypeptide, such as, but not limited to, an engineered signaling polypeptide(s) in opposite orientation, which can be driven off a promoter in this opposite orientation with respect to the 5' long terminal repeat and the cis-acting RNA packaging element, which in some embodiments is called a "fourth" promoter for convenience only (and sometimes referred to herein as the promoter active in T cells and/or NK cells), which is active in a target cell such as a T cell and/or an NK cell but in illustrative examples is not active in the packaging cell or is only inducibly or minimally active in the packaging cell; and a 3' long terminal repeat, or active truncated fragment thereof. In some embodiments, the packageable RNA genome can include a central polypurine tract (cPPT)/central termination sequence (CTS) element. In some embodiments, the retroviral cis-acting RNA packaging element can be HIV Psi. In some embodiments, the retroviral cis-acting RNA packaging element can be the Rev Response Element. The engineered signaling polypeptide driven by the promoter in the opposite orientation from the 5' long terminal repeat, in illustrative embodiments, is one or more of the engineered signaling polypeptides disclosed herein and can optionally express one or more inhibitory RNA molecules as disclosed in more detail herein and in WO2017/165245A2, WO2018/009923A1, and WO2018/161064A1.

It will be understood that promoter number, such as a first, second, third, fourth, etc. promoter is for convenience only. A promoter that is called a "fourth" promoter should not be taken to imply that there are any additional promoters, such as first, second or third promoters, unless such other promoters are explicitly recited. It should be noted that each of the promoters are capable of driving expression of a transcript in an appropriate cell type and such transcript forms a transcription unit.

In some embodiments, the engineered signaling polypeptide can include a first lymphoproliferative element. Suitable lymphoproliferative elements are disclosed in other sections herein. As a non-limiting example, the lymphoproliferative element can be expressed as a fusion with a recognition domain, such as an eTag, as disclosed herein. In some embodiments, the packageable RNA genome can further include a nucleic acid sequence encoding a second engineered polypeptide including a chimeric antigen receptor, encoding any CAR embodiment provided herein. For example, the second engineered polypeptide can include a first antigen-specific targeting region, a first transmembrane domain, and a first intracellular activating domain Examples of antigen-specific targeting regions, transmembrane domains, and intracellular activating domains are disclosed elsewhere herein. In some embodiments where the target cell is a T cell, the promoter that is active in a target cell is active in a T cell, as disclosed elsewhere herein.

In some embodiments, the engineered signaling polypeptide can include a CAR, and the nucleic acid sequence can encode any CAR embodiment provided herein. For example, the engineered polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments, the packageable RNA genome can further include a nucleic acid sequence encoding a second engineered polypeptide. In some embodiments, the second engineered polypeptide can be a lymphoproliferative element. In some embodiments where the target cell is a T cell or NK cell, the promoter that is active in a target cell is active in a T cell or NK cell, as disclosed elsewhere herein.

In some embodiments, the packageable RNA genome included in any of the aspects provided herein, can further include a riboswitch, as discussed in WO2017/165245A2, WO2018/009923A1, and WO2018/161064A1. In some embodiments, the nucleic acid sequence encoding the engineered signaling polypeptide can be in a reverse orientation with respect to the 5' to 3' orientation established by the 5' LTR and the 3' LTR. In further embodiments, the packageable RNA genome can further include a riboswitch and, optionally, the riboswitch can be in reverse orientation. In any of the embodiments disclosed herein, a polynucleotide including any of the elements can include a primer binding site. In illustrative embodiments, insulators and/or polyadenylation sequences can be placed before, after, between, or near genes to prevent or reduce unregulated transcription. In some embodiments, the insulator can be chicken HS4 insulator, Kaiso insulator, SAR/MAR elements, chimeric chicken insulator-SAR elements, CTCF insulator, the gypsy insulator, or the β-globin insulator or fragments thereof known in the art. In some embodiments, the insulator and/or polyadenylation sequence can be hGH polyA (SEQ ID NO:316), SPA1 (SEQ ID NO:317), SPA2 (SEQ ID NO:318), b-globin polyA spacer B (SEQ ID NO:319), b-globin polyA spacer A (SEQ ID NO:320), 250 cHS4 insulator v1 (SEQ ID NO:321), 250 cHS4 insulator v2 (SEQ ID NO:322), 650 cHS4 insulator (SEQ ID NO:323), 400 cHS4 insulator (SEQ ID NO:324), 650 cHS4 insulator and b-globin polyA spacer B (SEQ ID NO:325), or b-globin polyA spacer B and 650 cHS4 insulator (SEQ ID NO:326).

In any of the embodiments disclosed herein, a nucleic acid sequence encoding Vpx can be on the second or an optional third transcriptional unit, or on an additional transcriptional unit that is operably linked to the first inducible promoter.

Some aspects of the present disclosure include or are cells, in illustrative examples, mammalian cells, that are used as packaging cells to make replication incompetent recombinant retroviral particles, such as lentiviruses, for transduction of T cells and/or NK cells.

Any of a wide variety of cells can be selected for in vitro production of a virus or virus particle, such as a redirected recombinant retroviral particle, according to the invention. Eukaryotic cells are typically used, particularly mammalian cells including human, simian, canine, feline, equine and rodent cells. In illustrative examples, the cells are human cells. In further illustrative embodiments, the cells reproduce indefinitely, and are therefore immortal. Examples of cells that can be advantageously used in the present invention include NIH 3T3 cells, COS cells, Madin-Darby canine kidney cells, human embryonic 293T cells and any cells derived from such cells, such as gpnlslacZ φNX cells, which are derived from 293T cells. Highly transfectable cells, such as human embryonic kidney 293T cells, can be used. By "highly transfectable" it is meant that at least about 50%, more preferably at least about 70% and most preferably at least about 80% of the cells can express the genes of the introduced DNA.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL1O), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, and the like.

Retroviral Genome Size

In the methods and compositions provided herein, the recombinant retroviral genomes, in non-limiting illustrative examples, lentiviral genomes, have a limitation to the number of polynucleotides that can be packaged into the viral particle. In some embodiments provided herein, the polypeptides encoded by the polynucleotide encoding region can be truncations or other deletions that retain a functional activity such that the polynucleotide encoding region is encoded by less nucleotides than the polynucleotide encoding region for the wild-type polypeptide. In some embodiments, the polypeptides encoded by the polynucleotide encoding region can be fusion polypeptides that can be expressed from one promoter. In some embodiments, the fusion polypeptide can have a cleavage signal to generate two or more functional polypeptides from one fusion polypeptide and one promoter. Furthermore, some functions that are not required after initial ex vivo transduction are not included in the retroviral genome, but rather are present on the surface of the replication incompetent recombinant retroviral particles via the packaging cell membrane. These various strategies are used herein to maximize the functional elements that are packaged within the replication incompetent recombinant retroviral particles.

In some embodiments, the recombinant retroviral genome to be packaged can be between 1,000, 2,000, 3,000, 4,000, 5,000, 6,000, 7,000, and 8,000 nucleotides on the low end of the range and 2,000, 3,000, 4,000, 5,000, 6,000, 7,000, 8,000, 9,000, 10,000, and 11,000 nucleotides on the high end of the range. The retroviral genome to be packaged includes one or more polynucleotide regions encoding a first and second engineering signaling polypeptide as disclosed in detail herein. In some embodiments, the recombinant retroviral genome to be packaged can be less than 5,000, 6,000, 7,000, 8,000, 9,000, 10,000, or 11,000 nucleotides. Functions discussed elsewhere herein that can be packaged include required retroviral sequences for retroviral assembly and packaging, such as a retroviral rev, gag, and pol coding regions, as well as a 5' LTR and a 3' LTR, or an active truncated fragment thereof, a nucleic acid sequence encoding a retroviral cis-acting RNA packaging element, and a cPPT/CTS element. Furthermore, in illustrative embodiments a replication incompetent recombinant retroviral particle herein can include any one or more or all of the following, in some embodiments in reverse orientation with respect to a 5' to 3' orientation established by the retroviral 5' LTR and 3' LTR (as illustrated in WO2019/055946 as a non-limiting example): one or more polynucleotide regions encoding a first and second engineering signaling polypeptide, at least one of which includes at least one lymphoproliferative element; a second engineered signaling polypeptide that can include a chimeric antigen receptor; an miRNA, a control element, such as a riboswitch, which typically regulates expression of the first and/or the second engineering signaling polypeptide; a recognition domain, an intron, a promoter that is active in a target cell, such as a T cell, a 2A cleavage signal and/or an IRES.

Recombinant Retroviral Particles

Recombinant retroviral particles are disclosed in methods and compositions provided herein, for example, to transduce T cells and/or NK cells to make genetically modified T cells and/or NK cells. The recombinant retroviral particles are themselves aspects of the present invention. Typically, the recombinant retroviral particles included in aspects provided herein, are replication incompetent, meaning that a recombinant retroviral particle cannot replicate once it leaves the packaging cell. In illustrative embodiments, the recombinant retroviral particles are lentiviral particles.

Provided herein in some aspects are replication incompetent recombinant retroviral particles for use in transducing cells, typically lymphocytes and illustrative embodiments T cells and/or NK cells. The replication incompetent recombinant retroviral particles can include any of the pseudotyping elements discussed elsewhere herein. In some embodiments, the replication incompetent recombinant retroviral particles can include any of the activation elements discussed elsewhere herein. In one aspect, provided herein is a replication incompetent recombinant retroviral particle including a polynucleotide including: A. one or more transcriptional units operatively linked to a promoter active in T cells and/or NK cells, wherein the one or more transcriptional units encode a chimeric antigen receptor (CAR); and B. a pseudotyping element and a T cell activation element on its surface, wherein the T cell activation element is not encoded by a polynucleotide in the replication incompetent recombinant retroviral particle. In some embodiments, the T cell activation element can be any of the activation elements discussed elsewhere herein. In illustrative embodiments, the T cell activation element can be anti-CD3 scFvFc. In another aspect, provided herein is a replication incompetent recombinant retroviral particle, including a polynucleotide including one or more transcriptional units operatively linked to a promoter active in T cells and/or NK cells, wherein the one or more transcriptional units encode a first polypeptide including a chimeric antigen receptor (CAR) and a second polypeptide including a lymphoproliferative element. In some embodiments, the lymphoproliferative element can be a chimeric lymphoproliferative element. In illustrative embodiments, the lymphoproliferative element does not comprise IL-7 tethered to the IL-7 receptor alpha chain or a fragment thereof. In some embodiments the lymphoproliferative element does not comprise IL-15 tethered to the IL-2/IL-15 receptor beta chain.

In some aspects, provided herein is a replication incompetent recombinant retroviral particle, comprising a polynucleotide comprising one or more transcriptional units operatively linked to a promoter active in T cells and/or NK cells, wherein the one or more transcriptional units encode a first polypeptide comprising a chimeric antigen receptor (CAR) and a second polypeptide comprising a chimeric lymphoproliferative element, for example a constitutively active chimeric lymphoproliferative element. In illustrative embodiments, the chimeric lymphoproliferative element does not comprise a cytokine tethered to its cognate receptor or tethered to a fragment of its cognate receptor.

Provided herein in some aspects, is a recombinant retroviral particle that includes (i) a pseudotyping element capable of binding to a T cell and/or NK cell and facilitating membrane fusion of the recombinant retroviral particle thereto; (ii) a polynucleotide having one or more transcriptional units operatively linked to a promoter active in T cells and/or NK cells, wherein the one or more transcriptional units encode a first engineered signaling polypeptide having a chimeric antigen receptor that includes an antigen-specific targeting region, a transmembrane domain, and an intracellular activating domain, and a second engineered signaling polypeptide that includes at least one lymphoproliferative element; wherein expression of the first engineered signaling polypeptide and/or the second engineered signaling polypeptide are regulated by an in vivo control element; and (iii) an activation element on its surface, wherein the activation element is capable of binding to a T cell and/or NK cell and is not encoded by a polynucleotide in the recombinant retroviral particle. In some embodiments, the promoter active in T cells and/or NK cells is not active in the packaging cell line or is only active in the packaging cell line in an inducible manner. In any of the embodiments disclosed herein, either of the first and second engineered signaling polypeptides can have a chimeric antigen receptor and the other engineered signaling polypeptide can have at least one lymphoproliferative element.

Various elements and combinations of elements that are included in replication incompetent, recombinant retroviral particles are provided throughout this disclosure, such as, for example, pseudotyping elements, activation elements, and membrane bound cytokines, as well as nucleic acid sequences that are included in a genome of a replication incompetent, recombinant retroviral particle such as, but not limited to, a nucleic acid encoding a CAR; a nucleic acid encoding a lymphoproliferative element; a nucleic acid encoding a control element, such as a riboswitch; a promoter, especially a promoter that is constitutively active or inducible in a T cell; and a nucleic acid encoding an inhibitory RNA molecule. Furthermore, various aspects provided herein, such as methods of making recombinant retroviral particles, methods for performing adoptive cell therapy, and methods for transducing T cells, produce and/or include replication incompetent, recombinant retroviral particles. Replication incompetent recombinant retroviruses that are produced and/or included in such methods themselves form separate aspects of the present invention as replication incompetent, recombinant retroviral particle compositions, which can be in an isolated form. Such compositions can be in dried down (e.g. lyophilized) form or can be in a suitable solution or medium known in the art for storage and use of retroviral particles.

Accordingly, as a non-limiting example, provided herein in another aspect, is a replication incompetent recombinant retroviral particle having in its genome a polynucleotide having one or more nucleic acid sequences operatively linked to a promoter active in T cells and/or NK cells that in some instances, includes a first nucleic acid sequence that encodes one or more (e.g. two or more) inhibitory RNA molecules directed against one or more RNA targets and a second nucleic acid sequence that encodes a chimeric antigen receptor, or CAR, as described herein. In other embodiments, a third nucleic acid sequence is present that encodes at least one lymphoproliferative element described previously herein that is not an inhibitory RNA molecule. In certain embodiments, the polynucleotide incudes one or more riboswitches as presented herein, operably linked to the first nucleic acid sequence, the second nucleic acid sequence, and/or the third nucleic acid sequence, if present. In such a construct, expression of one or more inhibitory RNAs, the CAR, and/or one or more lymphoproliferative elements that are not inhibitory RNAs is controlled by the riboswitch. In some embodiments, two to 10 inhibitory RNA molecules are encoded by the first nucleic acid sequence. In further embodiments, two to six inhibitory RNA molecules are encoded by the first nucleic acid sequence. In illustrative embodiments, 4 inhibitory RNA molecules are encoded by the first nucleic acid sequence. In some embodiments, the first nucleic acid sequence encodes one or more inhibitory RNA molecules and is located within an intron. In certain embodiments, the intron includes all or a portion of a promoter. The promoter can be a Pol I, Pol II, or Pol III promoter. In some illustrative embodiments, the promoter is a Pol II promoter. In some embodiments, the intron is adjacent to and downstream of the promoter active in a T cell and/or NK cell. In some embodiments, the intron is EF1-α intron A.

Recombinant retroviral particle embodiments herein include those wherein the retroviral particle comprises a genome that includes one or more nucleic acids encoding one or more inhibitory RNA molecules. Various alternative embodiments of such nucleic acids that encode inhibitory RNA molecules that can be included in a genome of a retroviral particle, including combinations of such nucleic acids with other nucleic acids that encode a CAR or a lymphoproliferative element other than an inhibitory RNA molecule, are included for example, in the inhibitory RNA section provided herein, as well as in various other paragraphs that combine these embodiments. Furthermore, various alternatives of such replication incompetent recombinant retroviruses can be identified by exemplary nucleic acids that are disclosed within packaging cell line aspects disclosed herein. A skilled artisan will recognize that disclosure in this section of a recombinant retroviral particle that includes a genome that encodes one or more (e.g. two or more) inhibitory RNA molecules, can be combined with various alternatives for such nucleic acids encoding inhibitory RNA molecules provided in other sections herein. Furthermore, a skilled artisan will recognize that such nucleic acids encoding one or more inhibitory RNA molecules can be combined with various other functional nucleic acid elements provided herein, as for example, disclosed in the section herein that focuses on inhibitory RNA molecules and nucleic acid encoding these molecules. In addition, the various embodiments of specific inhibitory RNA molecules provided herein in other sections can be used in recombinant retroviral particle aspects of the present disclosure.

Necessary elements of recombinant retroviral vectors, such as lentiviral vectors, are known in the art. These elements are included in the packaging cell line section and in details for making replication incompetent, recombinant retroviral particles provided in the Examples section and as illustrated in WO2019/055946. For example, lentiviral particles typically include packaging elements REV, GAG and POL, which can be delivered to packaging cell lines via one or more packaging plasmids, a pseudotyping element, various examples which are provided herein, which can be delivered to a packaging cell line via a pseudotyping plasmid, and a genome, which is produced by a polynucleotide that is delivered to a host cell via a transfer plasmid. This polynucleotide typically includes the viral LTRs and a psi packaging signal. The 5' LTR can be a chimeric 5' LTR fused to a heterologous promoter, which includes 5' LTRs that are not dependent on Tat transactivation. The transfer plasmid can be self-inactivating, for example, by removing a U3 region of the 3' LTR. In some non-limiting embodiments, Vpu, such as a polypeptide comprising Vpu (sometimes called a "Vpu polypeptide" herein) including but not limited to, Src-FLAG-Vpu, is packaged within the retroviral particle for any composition or method aspect and embodiment provided herein that includes a retroviral particle. In some non-limiting embodiments, Vpx, such as Src-FLAG-Vpx, is packaged within the retroviral particle. Not to be limited by theory, upon transduction of a T cells, Vpx enters the cytosol of the cells and promotes the degradation of SAMHD1, resulting in an increased pool of cytoplasmic dNTPs available for reverse transcription. In some non-limiting embodiments, Vpu and Vpx is packaged within the retroviral particle for any composition or method aspect and embodiment that includes a retroviral particle provided herein.

Retroviral particles (e.g. lentiviral particles) included in various aspects of the present invention are in illustrative embodiments, replication incompetent, especially for safety reasons for embodiments that include introducing cells transduced with such retroviral particles into a subject. When replication incompetent retroviral particles are used to transduce a cell, retroviral particles are not produced from the transduced cell. Modifications to the retroviral genome are known in the art to assure that retroviral particles that include the genome are replication incompetent. However, it will be understood that in some embodiments for any of the aspects provided herein, replication competent recombinant retroviral particles can be used.

A skilled artisan will recognize that the functional elements discussed herein can be delivered to packaging cells and/or to T cells using different types of vectors, such as expression vectors. Illustrative aspects of the invention utilize retroviral vectors, and in some particularly illustrative embodiments lentiviral vectors. Other suitable expression vectors can be used to achieve certain embodiments herein. Such expression vectors include, but are not limited to, viral vectors (e.g. viral vectors based on vaccinia virus; poliovirus; adenovirus (see, e.g., Li et al., *Invest Opthalmol Vis Sci* 35:2543 2549, 1994; Borras et al., *Gene Ther* 6:515 524, 1999*; Li and Davidson, PNAS* 92:7700 7704, 1995; Sakamoto et al., *H Gene Ther* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther* 9:81 86, 1998, Flannery et al., *PNAS* 94:6916 6921, 1997; Bennett et al., *Invest Opthalmol Vis Sci* 38:2857 2863, 1997; Jomary et al., *Gene Ther* 4:683 690, 1997, Rolling et al., *Hum Gene Ther* 10:641 648, 1999; Ali et al., *Hum Mol Genet* 5:591 594, 1996; Srivastava in WO 93/09239, Samulski et al., *J. Vir.* (1989) 63:3822-3828; Mendelson et al., *Virol.* (1988) 166:154-165; and Flotte et al., *PNAS* (1993) 90: 10613-10617); SV40; herpes simplex virus; or a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus), for example a gamma retrovirus; or human immunodeficiency virus (see, e.g., Miyoshi et al., *PNAS* 94:10319 23, 1997; Takahashi et al., *J Virol* 73:7812 7816, 1999); and the like.

As disclosed herein, replication incompetent recombinant retroviral particles are a common tool for gene delivery (Miller, Nature (1992) 357:455-460). The ability of replication incompetent recombinant retroviral particles to deliver an unrearranged nucleic acid sequence into a broad range of rodent, primate and human somatic cells makes replication incompetent recombinant retroviral particles well suited for transferring genes to a cell. In some embodiments, the replication incompetent recombinant retroviral particles can be derived from the *Alpharetrovirus* genus, the *Betaretrovirus* genus, the *Gammaretrovirus* genus, the *Deltaretrovirus* genus, the *Epsilonretrovirus* genus, the Lentivirus genus, or the *Spumavirus* genus. There are many retroviruses suitable for use in the methods disclosed herein. For example, murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) can be used. A detailed list of retroviruses may be found in Coffin et al ("Retroviruses" 1997 Cold Spring Harbor Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

In illustrative embodiments, the replication incompetent recombinant retroviral particles can be derived from the *Lentivirus* genus. In some embodiments, the replication incompetent recombinant retroviral particles can be derived from HIV, SIV, or FIV. In further illustrative embodiments, the replication incompetent recombinant retroviral particles can be derived from the human immunodeficiency virus (HIV) in the *Lentivirus* genus. Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages.

In illustrative embodiments, replication incompetent recombinant retroviral particles provided herein contain Vpx polypeptide.

In some embodiments, replication incompetent recombinant retroviral particles provided herein comprise and/or contain Vpu polypeptide.

In illustrative embodiments, a retroviral particle is a lentiviral particle. Such retroviral particle typically includes a retroviral genome within a capsid which is located within a viral envelope.

In some embodiments, DNA-containing viral particles are utilized instead of recombinant retroviral particles. Such viral particles can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different viruses and retroviruses, or retroviral particles. Where viral particles are used that include a DNA genome, a skilled artisan will appreciate that functional units can be included in such genomes to induce integration of all or a portion of the DNA genome of the viral particle into the genome of a T cell transduced with such virus.

In some embodiments, the HIV RREs and the polynucleotide region encoding HIV Rev can be replaced with N-terminal RGG box RNA binding motifs and a polynucleotide region encoding ICP27. In some embodiments, the polynucleotide region encoding HIV Rev can be replaced with one or more polynucleotide regions encoding adenovirus E1B 55-kDa and E4 Orf6.

Provided herein in one aspect is a container, such as a commercial container or package, or a kit comprising the same, comprising isolated replication incompetent recombinant retroviral particles according to any of the replication incompetent recombinant retroviral particle aspects provided herein. Furthermore, provided herein in another aspect is a container, such as a commercial container or package, or a kit comprising the same, comprising isolated packaging cells, in illustrative embodiments isolated packaging cells from a packaging cell line, according to any of the packaging cell and/or packaging cell line aspects provided herein. In some embodiments, the kit includes additional containers that include additional reagents such as buffers or reagents used in methods provided herein. Furthermore provided herein in certain aspects are use of any replication incompetent recombinant retroviral particle provided herein in any aspect, in the manufacture of a kit for genetically modifying a T cell or NK cell according to any aspect provided herein. Furthermore provided herein in certain aspects are use of any packaging cell or packaging cell line provided herein in any aspect, in the manufacture of a kit for producing the replication incompetent recombinant retroviral particles according to any aspect provided herein.

Provided herein in one aspect is a commercial container containing a replication incompetent recombinant retroviral particle and instructions for the use thereof to treat tumor growth in a subject, wherein the replication incompetent recombinant retroviral particle comprises in its genome a polynucleotide comprising one or more nucleic acid sequences operatively linked to a promoter active in T cells and/or NK cells. In some embodiments, a nucleic acid sequence of the one or more nucleic acid sequences can encode a chimeric antigen receptor (CAR) comprising an antigen-specific targeting region (ASTR), a transmembrane domain, and an intracellular activating domain. In some embodiments, a nucleic acid sequence of the one or more nucleic acid sequences can encode two or more inhibitory RNA molecules directed against one or more RNA targets.

The container that contains the recombinant retroviral particles can be a tube, vial, well of a plate, or other vessel for storage of a recombinant retroviral particle. The kit can include two or more containers wherein a second or other container can include, for example, a solution or media for transduction of T cells and/or NK cells, and/or the second or other container can include a pH-modulating pharmacologic agent. Any of these containers can be of industrial strength and grade. The replication incompetent recombinant retroviral particle in such aspects that include a kit and a nucleic acid encoding an inhibitory RNA molecule, can be any of the embodiments for such replication incompetent recombinant retroviral particles provided herein, which include any of the embodiments for inhibitory RNA provided herein.

In another aspect, provided herein is the use of a replication incompetent recombinant retroviral particle in the manufacture of a kit for genetically modifying a T cell or NK cell, wherein the use of the kit includes: contacting the T cell or NK cell ex vivo with the replication incompetent recombinant retroviral particle, wherein the replication incompetent recombinant retroviral particle includes a pseudotyping element on a surface and a T cell activation element on the surface, wherein said contacting facilitates transduction of the T cell or NK cell by the replication incompetent recombinant retroviral particle, thereby producing a genetically modified T cell or NK cell. In some embodiments, the T cell or NK cell can be from a subject. In some embodiments, the T cell activation element can be membrane-bound. In some embodiments, the contacting can be performed for between 1, 2, 3, 4, 5, 6, 7, or 8 hours on the low end of the range and 4, 5, 6, 7, 8, 10, 12, 15, 18, 21, and 24 hours on the high end of the range, for example, between 1 and 12 hours. The replication incompetent recombinant retroviral particle for use in the manufacture of a kit can include any of the aspects, embodiments, or subembodiments discussed elsewhere herein.

In another aspect, provided herein is a pharmaceutical composition for treating or preventing cancer or tumor growth comprising a replication incompetent recombinant retroviral particle as an active ingredient. In another aspect, provided herein is an infusion composition or other delivery solution for treating or preventing cancer or tumor growth comprising a replication incompetent recombinant retroviral particle. The replication incompetent recombinant retroviral particle of the pharmaceutical composition or infusion composition can include any of the aspects, embodiments, or subembodiments discussed above or elsewhere herein.

Genetically Modified T Cells and NK Cells

In embodiments of the methods and compositions herein, genetically modified lymphocytes are produced, which themselves are a separate aspect of the invention. Such genetically modified lymphocytes can be genetically modified and/or transduced lymphocytes. In one aspect, provided herein a genetically modified T cell or NK cell is made using a method according to any aspect for genetically modifying T cells and/or NK cells in blood or a component thereof, provided herein. For example, in some embodiments, the T cell or NK cell has been genetically modified to express a first engineered signaling polypeptide. In illustrative embodiments, the first engineered signaling polypeptide can be a lymphoproliferative element or a CAR that includes an antigen-specific targeting region (ASTR), a transmembrane domain, and an intracellular activating domain. In some embodiments, the T cell or NK cell can further include a second engineered signaling polypeptide that can be a CAR or a lymphoproliferative element. In some embodiments, the lymphoproliferative element can be a chimeric lymphoproliferative element. In some embodiments, the T cell or NK cell can further include a pseudotyping element on a surface. In some embodiments, the T cell or NK cell can further include an activation element on a surface. The CAR, lymphoproliferative element, pseudotyping element, and activation element of the genetically modified T cell or NK cell can include any of the aspects, embodiments, or subembodiments disclosed herein. In illustrative embodiments, the activation element can be anti-CD3 antibody, such as an anti-CD3 scFvFc.

In some embodiments, genetically modified lymphocytes are lymphocytes such as T cells or NK cells that have been genetically modified to express a first engineered signaling polypeptide comprising at least one lymphoproliferative element and/or a second engineered signaling polypeptide comprising a chimeric antigen receptor, which includes an antigen-specific targeting region (ASTR), a transmembrane domain, and an intracellular activating domain. In some embodiments of any of the aspects herein, the NK cells are NKT cells. NKT cells are a subset of T cells that express CD3 and typically coexpress an $\alpha\beta$ T-cell receptor, but also express a variety of molecular markers that are typically associated with NK cells (such as NK1.1 or CD56).

Genetically modified lymphocytes of the present disclosure possess a heterologous nucleic acid sequence that has been introduced into the lymphocyte by a recombinant DNA method. For example, the heterologous sequence in illustrative embodiments is inserted into the lymphocyte during a method for transducing the lymphocyte provided herein. The heterologous nucleic acid is found within the lymphocyte and in some embodiments is or is not integrated into the genome of the genetically modified lymphocyte.

In illustrative embodiments, the heterologous nucleic acid is integrated into the genome of the genetically modified lymphocyte. Such lymphocytes are produced, in illustrative embodiments, using a method for transducing lymphocytes provided herein, that utilizes a recombinant retroviral particle. Such recombinant retroviral particle can include a polynucleotide that encodes a chimeric antigen receptor that typically includes at least an antigen-specific targeting region (ASTR), a transmembrane domain, and an intracellular activating domain. Provided herein in other sections of this disclosure are various embodiments of replication incompetent recombinant retroviral particles and polynucleotides encoded in a genome of the replication incompetent retroviral particle, that can be used to produce genetically modified lymphocytes that themselves form another aspect of the present disclosure.

Genetically modified lymphocytes of the present disclosure can be isolated outside the body. For example, such lymphocytes can be found in media and other solutions that are used for ex vivo transduction as provided herein. The lymphocytes can be present in a genetically unmodified form in blood that is collected from a subject in methods provided herein, and then genetically modified during method of transduction. The genetically modified lymphocytes can be found inside a subject after they are introduced or reintroduced into the subject after they have been genetically modified. The genetically modified lymphocytes can be a resting T cell or a resting NK cell, or the genetically modified T cell or NK cell can be actively dividing, especially after it expresses some of the functional elements provided in nucleic acids that are inserted into the T cell or NK cell after transduction as disclosed herein.

Provided herein in one aspect is a transduced and/or genetically modified T cell or NK cell, comprising a recombinant polynucleotide comprising one or more transcriptional units operatively linked to a promoter active in T cells and/or NK cells, in its genome.

In some embodiments, provided herein are genetically modified lymphocytes, in illustrative embodiments T cells and/or NK cells, that relate to either aspects for transduction of T cells and/or NK cells in blood or a component thereof, that include transcription units that encode one, two, or more (e.g. 1-10, 2-10, 4-10, 1-6, 2-6, 3-6, 4-6, 1-4, 2-4, 3-4) inhibitory RNA molecules. In some embodiments, such inhibitory RNA molecules are lymphoproliferative elements and therefore, can be included in any aspect or embodiment disclosed herein as the lymphoproliferative element as long as they induce proliferation of a T cell and/or an NK cell, or otherwise meet a test for a lymphoproliferative element provided herein.

Inhibitory RNA molecules directed against a variety of target RNAs can be used in embodiments of any of the aspects provided herein. For example, one, most or all of the one (e.g. two) or more inhibitory RNA molecules decrease expression of an endogenous TCR. In some embodiments, the RNA target is mRNA transcribed from a gene selected from the group consisting of: PD-1, CTLA4, TCR alpha, TCR beta, CD3 zeta, SOCS, SMAD2, a miR-155 target, IFN gamma, cCBL, TRAIL2, PP2A, and ABCG1. In some embodiments of this aspect at least one of the one (e.g. two) or more inhibitory RNA molecules is miR-155.

In some embodiments of the aspect immediately above where the T cell or NK cell comprises one or more (e.g. two or more) inhibitory RNA molecules and the CAR, or nucleic acids encoding the same, the ASTR of the CAR is an MRB ASTR and/or the ASTR of the CAR binds to a tumor associated antigen. Furthermore, in some embodiments of the above aspect, the first nucleic acid sequence is operably linked to a riboswitch, which for example is capable of binding a nucleoside analog, and in illustrative embodiments is an antiviral drug such as acyclovir.

In the methods and compositions disclosed herein, expression of engineered signaling polypeptides is regulated by a control element, and in some embodiments, the control element is a polynucleotide comprising a riboswitch. In certain embodiments, the riboswitch is capable of binding a nucleoside analog and when the nucleoside analog is present, one or both of the engineered signaling polypeptides are expressed.

Nucleic Acids

The present disclosure provides nucleic acid encoding polypeptides of the present disclosure. A nucleic acid will in some embodiments be DNA, including, e.g., a recombinant expression vector. A nucleic acid will in some embodiments be RNA, e.g., in vitro synthesized RNA.

In some embodiments, a nucleic acid provides for production of a polypeptide of the present disclosure, e.g., in a mammalian cell. In other cases, a subject nucleic acid provides for amplification of the nucleic acid encoding a polypeptide of the present disclosure.

A nucleotide sequence encoding a polypeptide of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or trans gene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry,* 567-605 and Tropp (2012) Molecular Biology (Jones & Bartlett Publishers, Sudbury, Mass.), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90:7739; and Marodon et al. (2003) *Blood* 101:3416. As another example, a CD8 gene promoter can be used. NK cell-specific expression can be achieved by use of an Neri (p46) promoter; see, e.g., Eckelhart et al. (2011) *Blood* 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GALI promoter, a GAL1O promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacterial.,* 1991: 173(1): 86-93; Alpuche-Aranda et al., *PNAS,* 1992; 89(21): 10079-83), a nirB promoter (Harborne et al. (1992) *Mal. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mal. Microbial.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (Laci repressor protein changes conformation when contacted with lactose, thereby preventing the Laci repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a polypeptide of the disclosure can be present in an expression vector and/or a cloning vector. Nucleotide sequences encoding two separate polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating subject recombinant constructs. The following bacterial vectors are provided by way of example: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). The following eukaryotic vectors are provided by way of example: pWLneo, pSV2cat, pOG44, PXR1, pSG (Stratagene) pSVK3, pBPV, pMSG, and pSVL (Pharmacia).

Expression vectors generally have convenient restriction sites located near the promoter sequence to provide for the insertion of nucleic acid sequences encoding heterologous proteins. A selectable marker operative in the expression host may be present.

As noted above, in some embodiments, a nucleic acid encoding a polypeptide of the present disclosure will in some embodiments be RNA, e.g., in vitro synthesized RNA. Methods for in vitro synthesis of RNA are known in the art; any known method can be used to synthesize RNA including a nucleotide sequence encoding a polypeptide of the present disclosure. Methods for introducing RNA into a host cell are known in the art. See, e.g., Zhao et al. (2010) Cancer Res. 15:9053. Introducing RNA including a nucleotide sequence encoding a polypeptide of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

Various aspects and embodiments that include a polynucleotide, a nucleic acid sequence, and/or a transcriptional unit, and/or a vector including the same, further include one or more of a Kozak-type sequence (also called a Kozak-related sequence herein), a woodchuck hepatitis virus post-transcriptional regulatory element (WPRE), and a double stop codon or a triple stop codon, wherein one or more stop codons of the double stop codon or the triple stop codon define a termination of a reading from of at least one of the one or more transcriptional units. In certain embodiments, a polynucleotide a nucleic acid sequence, and/or a transcriptional unit, and/or a vector including the same, further includes a Kozak-type sequence having a 5' nucleotide within 10 nucleotides upstream of a start codon of at least one of the one or more transcriptional units. Kozak determined the Kozak consensus sequence, (GCC)GCCRCCATG (SEQ ID NO:327), for 699 vertebrate mRNAs, where R is a purine (A or G) (Kozak. Nucleic Acids Res. 1987 Oct. 26; 15(20):8125-48). In one embodiment the Kozak-type sequence is or includes CCACCAT/UG(G) (SEQ ID NO:328), CCGCCAT/UG(G) (SEQ ID NO:329), GCCGCCGCCAT/UG(G) (SEQ ID NO:330), or GCCGCCACCAT/UG(G) (SEQ ID NO:331) (with nucleotides in parenthesis representing optional nucleotides and nucleotides separated by a slash indicated different possible nucleotides at that position, for example depending on whether the nucleic acid is DNA or RNA. In these embodiments that include the AU/TG start codon, the A can be considered position 0. In certain illustrative embodiments, the nucleotides at −3 and +4 are identical, for example the −3 and +4 nucleotides can be G. In another embodiment the Kozak-type sequence includes an A or G in the 3rd position upstream of ATG where ATG is the start codon. In another embodiment the Kozak-type sequence includes an A or G in the 3rd position upstream of AUG where AUG is the start codon. In an illustrative embodiment, the Kozak sequence is (GCC)GCCRCCATG (SEQ ID NO:327), where R is a purine (A or G). In an illustrative embodiment, the Kozak-type sequence is GCCGCCACCAUG (SEQ ID NO:332). In another embodiment, which can be combined with the preceding embodiment that includes a Kozak-type sequence and/or the following embodiment that includes triple stop codon, the polynucleotide includes a WPRE element. WPREs have been characterized in the art (See e.g., (Higashimoto et al., *Gene Ther.* 2007; 14: 1298)) and as illustrated in WO2019/055946. In some embodiments, the WPRE element is located 3' of a stop codon of the one or more transcriptional units and 5' to a 3' LTR of the polynucleotide. In another embodiment, which can be combined with either or both of the preceding embodiments (i.e. an embodiment wherein the polynucleotide includes a Kozak-type sequence and/or an embodiment wherein the polynucleotide includes a WPRE), the one or more transcriptional units terminates with one or more stop codons of a double stop codon or a triple stop codon, wherein the double stop codon includes a first stop codon in a first reading frame and a second stop codon in a second reading frame, or a first stop codon in frame with a second stop codon, and wherein the triple stop codon includes a first stop codon in a first reading frame, a second stop codon in a second reading frame, and a third stop codon in a third reading frame, or a first stop codon in frame with a second stop codon and a third stop codon.

A triple stop codon herein includes three stop codons, one in each reading frame, within 10 nucleotides of each other, and preferably having overlapping sequence, or three stop codons in the same reading frame, preferably at consecutive codons. A double stop codon means two stop codons, each in a different reading frame, within 10 nucleotides of each other, and preferably having overlapping sequences, or two stop codons in the same reading frame, preferably at consecutive codons.

In some of the methods and compositions disclosed herein, the introduction of DNA into PBMCs, B cells, T cells and/or NK cells and optionally the incorporation of the DNA into the host cell genome, is performed using methods that do not utilize replication incompetent recombinant retroviral particles. For example, other viral vectors can be utilized, such as those derived from adenovirus, adeno-associated virus, or herpes simplex virus-1, as non-limiting examples.

In some embodiments, methods provided herein can include transfecting target cells with non-viral vectors. In any of the embodiments disclosed herein that utilize non-viral vectors to transfect target cells, the non-viral vectors, including naked DNA, can be introduced into the target cells, such as for example, PBMCs, B cells, T cells and/or NK cells using methods that include electroporation, nucleofection, liposomal formulations, lipids, dendrimers, cationic polymers such as poly(ethylenimine) (PEI) and poly(l-lysine) (PLL), nanoparticles, cell-penetrating peptides, microinjection, and/or non-integrating lentiviral vectors. In some embodiments, DNA can be introduced into target cells, such as PBMCs, B cells, T cells and/or NK cells in a complex with liposomes and protamine. Other methods for transfecting T cells and/or NK cells ex vivo that can be used in embodiments of methods provided herein, are known in the art (see e.g., Morgan and Boyerinas, Biomedicines. 2016 Apr. 20; 4(2). pii: E9, incorporated by reference herein in its entirety).

In some embodiments of method provided herein, DNA can be integrated into the genome using transposon-based carrier systems by co-transfection, co-nucleofection or co-electroporation of target DNA as plasmid containing the transposon ITR fragments in 5' and 3' ends of the gene of interest and transposase carrier system as DNA or mRNA or protein or site specific serine recombinases such as phiC31 that integrates the gene of interest in pseudo attP sites in the human genome, in this instance the DNA vector contains a 34 to 40 bp attB site that is the recognition sequence for the recombinase enzyme (Bhaskar Thyagarajan et al. Site-Specific Genomic Integration in Mammalian Cells Mediated by Phage φC31 Integrase, Mol Cell Biol. 2001 June; 21(12): 3926-3934) and co transfected with the recombinase. For T cells and/or NK cells, transposon-based systems that can be used in certain methods provided herein utilize the Sleeping Beauty DNA carrier system (see e.g., U.S. Pat. No. 6,489,458 and U.S. patent application Ser. No. 15/434,595, incorporated by reference herein in their entireties), the PiggyBac DNA carrier system (see e.g., Manuri et al., Hum Gene Ther. 2010 April; 21(4):427-37, incorporated by reference herein in its entirety), or the Toll transposon system (see e.g., Tsukahara et al., Gene Ther. 2015 February; 22(2): 209-215, incorporated by reference herein in its entirety) in DNA, mRNA, or protein form. In some embodiments, the transposon and/or transposase of the transposon-based vector systems can be produced as a minicircle DNA vector before introduction into T cells and/or NK cells (see e.g., Hudecek et al., Recent Results Cancer Res. 2016; 209:37-50 and Monjezi et al., Leukemia. 2017 January; 31(1):186-194, incorporated by reference herein in their entireties). The CAR or lymphoproliferative element can also be integrated into the defined and specific sites in the genome using CRISPR or TALEN mediated integration, by adding 50-1000 bp homology arms homologous to the integration 5' and 3' of the target site (Jae Seong Lee et al. Scientific Reports 5, Article number: 8572 (2015), Site-specific integration in CHO cells mediated by CRISPR/Cas9 and homology-directed DNA repair pathway). CRISPR or TALEN provide specificity and genomic-targeted cleavage and the construct will be integrated via homology-mediated end joining (Yao X at al. Cell Res. 2017 June; 27(6):801-814. doi: 10.1038/cr.2017.76. Epub 2017 May 19). The CRISPR or TALEN can be co-transfected with target plasmid as DNA, mRNA, or protein.

Inhibitory RNA Molecules

Embodiments of any of the aspects provided herein can include recombinant retroviral particles whose genomes are constructed to induce expression of one or more, and in illustrative embodiments two or more, inhibitory RNA molecules, such as for example, a miRNA or shRNA, after integration into a host cell, such as a lymphocyte (e.g. a T cell and/or an NK cell). Such inhibitory RNA molecules can be encoded within introns, including for example, an EF1-a intron. This takes advantage of the present teachings of methods to maximize the functional elements that can be included in a packageable retroviral genome to overcome shortcomings of prior teachings and maximize the effectiveness of such recombinant retroviral particles in adoptive T cell therapy.

In some embodiments, the inhibitory RNA molecule includes a 5' strand and a 3' strand (in some examples, sense strand and antisense strand) that are partially or fully complementary to one another such that the two strands are capable of forming a 18-25 nucleotide RNA duplex within a cellular environment. The 5' strand can be 18, 19, 20, 21, 22, 23, 24, or 25 nucleotides in length, and the 3' strand can be 18, 19, 20, 21, 22, 23, 24, or 25 nucleotides in length. The 5' strand and the 3' strand can be the same or different lengths, and the RNA duplex can include one or more mismatches. Alternatively, the RNA duplex has no mismatches.

The inhibitory RNA molecules included in compositions and methods provided herein, in certain illustrative examples, do not exist and/or are not expressed naturally in T cells into whose genome they are inserted. In some embodiments, the inhibitory RNA molecule is a miRNA or an shRNA. In some embodiments, where reference is made herein or in priority filings, to a nucleic acid encoding an siRNA, especially in a context where the nucleic acid is part of a genome, it will be understood that such nucleic acid is capable of forming an siRNA precursor such as miRNA or shRNA in a cell that is processed by DICER to form a double stranded RNA that typically interacts with, or becomes part of a RISK complex. In some embodiments, an inhibitory molecule of an embodiment of the present disclosure is a precursor of a miRNA, such as for example, a Pri-miRNA or a Pre-miRNA, or a precursor of an shRNA. In some embodiments, the miRNA or shRNA are artificially derived (i.e. artificial miRNAs or siRNAs). In other embodiments, the inhibitory RNA molecule is a dsRNA (either transcribed or artificially introduced) that is processed into an siRNA or the siRNA itself. In some embodiments, the miRNA or shRNA has a sequence that is not found in nature, or has at least one functional segment that is not found in nature, or has a combination of functional segments that are not found in nature.

In some embodiments, inhibitory RNA molecules are positioned in the first nucleic acid molecule in a series or multiplex arrangement such that multiple miRNA sequences are simultaneously expressed from a single polycistronic miRNA transcript. In some embodiments, the inhibitory RNA molecules can be adjoined to one another either directly or indirectly by non-functional linker sequence(s). The linker sequence in some embodiments, is between 5 and 120 nucleotides in length, and in some embodiments can be between 10 and 40 nucleotides in length, as non-limiting examples. In illustrative embodiments the first nucleic acid sequence encoding one or more (e.g. two or more) inhibitory RNAs and the second nucleic acid sequence encoding a CAR (e.g. an MRB-CAR) are operably linked to a promoter that is active constitutively or that can be induced in a T cell or NK cell. As such, the inhibitory RNA molecule(s) (e.g. miRNAs) as well as the CAR are expressed in a polycistronic manner Additionally, functional sequences can be expressed from the same transcript. For example, any of the lymphoproliferative elements provided herein that are not inhibitory RNA molecules, can be expressed from the same transcript as the CAR and the one or more (e.g. two or more) inhibitory RNA molecules.

In some embodiments, the inhibitory RNA molecule is a naturally occurring miRNA such as but not limited to miR-155. Alternatively, artificial miRNAs can be produced in which sequences capable of forming a hybridizing/complementary stem structure and directed against a target RNA, are placed in a miRNA framework that includes microRNA flanking sequences for microRNA processing and a loop, which can optionally be derived from the same naturally occurring miRNA as the flanking sequences, between the stem sequences. Thus, in some embodiments, an inhibitory RNA molecule includes from 5' to 3' orientation: a 5' microRNA flanking sequence, a 5' stem, a loop, a 3' stem that is partially or fully complementary to said 5' stem, and a 3' microRNA flanking sequence. In some embodiments, the 5' stem (also called a 5' arm herein) is 18, 19, 20, 21, 22, 23, 24 or 25 nucleotides in length. In some embodiments, the 3' stem (also called a 3' arm herein) is 18, 19, 20, 21, 22, 23, 24, or 25 nucleotides in length. In some embodiments, the loop is 3 to 40, 10 to 40, 20 to 40, or 20 to 30 nucleotides in length, and in illustrative embodiments the loop can be 18, 19, 20, 21, or 22 nucleotides in length. In some embodiments, one stem is two nucleotides longer than the other stem. The longer stem can be the 5' or the 3' stem.

In some embodiments, the 5' microRNA flanking sequence, 3' microRNA flanking sequence, or both, are derived from a naturally occurring miRNA, such as but not limited to miR-155, miR-30, miR-17-92, miR-122, and miR-21. In certain embodiments, the 5' microRNA flanking sequence, 3' microRNA flanking sequence, or both, are derived from a miR-155, such as, e.g., the miR-155 from *Mus musculus* or *Homo sapiens*. Inserting a synthetic miRNA stem-loop into a miR-155 framework (i.e. the 5' microRNA flanking sequence, the 3' microRNA flanking sequence, and the loop between the miRNA 5' and 3' stems) is known to one of ordinary skill in the art (Chung, K. et al. 2006. *Nucleic Acids Research*. 34(7):e53; U.S. Pat. No. 7,387,896). The SIBR (synthetic inhibitory BIC-derived RNA) sequence (Chung et al. 2006 supra), for example, has a 5' microRNA flanking sequence consisting of nucleotides 134-161 (SEQ ID NO:333) of the *Mus musculus* BIC noncoding mRNA (Genbank ID AY096003.1) and a 3' microRNA flanking sequence consisting of nucleotides 223-283 of the *Mus musculus* BIC noncoding mRNA (Genbank ID AY096003.1). In one study, the SIBR sequence was modified (eSIBR) to enhance expression of miRNAs (Fowler, D. K. et al. 2015. Nucleic acids Research 44(5): e48). In some embodiments of the present disclosure, miRNAs can be placed in the SIBR or eSIBR miR-155 framework. In illustrative embodiments herein, miRNAs are placed in a miR-155 framework that includes the 5' microRNA flanking sequence of miR-155 represented by SEQ ID NO:333, the 3' microRNA flanking sequence represented by SEQ ID NO:334 (nucleotides 221-265 of the *Mus musculus* BIC noncoding mRNA); and a modified miR-155 loop (SEQ ID NO:335). Thus, in some embodiments, the 5' microRNA flanking sequence of miR-155 is SEQ ID NO:333 or a functional variant thereof, such as, for example, a sequence that is the same length as SEQ ID NO:333, or 95%, 90%, 85%, 80%, 75%, or 50% as long as SEQ ID NO: 333 or is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:333. In some embodiments, the 3' microRNA flanking sequence of miR-155 is SEQ ID NO:334 or a functional variant thereof, such as, for example, the same length as SEQ ID NO:334, or 95%, 90%, 85%, 80%, 75%, or 50% as long as SEQ ID NO:334 or is a sequence that is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:334. However, any known microRNA framework that is functional to provide proper processing within a cell of miRNAs inserted therein to form mature miRNA capable of inhibiting expression of a target mRNA to which they bind, is contemplated within the present disclosure.

In some embodiments, at least one, at least two, at least three, or at least four of the inhibitory RNA molecules encoded by a nucleic acid sequence in a polynucleotide of a replication incompetent recombinant retroviral particle has the following arrangement in the 5' to 3' orientation: a 5' microRNA flanking sequence, a 5' stem, a loop, a 3' stem that is partially or fully complementary to said 5' stem, and a 3' microRNA flanking sequence. In some embodiments, all of the inhibitory RNA molecules have the following arrangement in the 5' to 3' orientation: a 5' microRNA flanking sequence, a 5' stem, a loop, a 3' stem that is partially or fully complementary to said 5' stem, and a 3' microRNA flanking sequence. As disclosed herein, the inhibitory RNA molecules can be separated by one or more linker sequences, which in some embodiments have no function except to act as spacers between inhibitory RNA molecules.

In some embodiments, where two or more inhibitory RNA molecules (in some examples, 1, 2, 3, 4, 5, 6, 7, 8, 9, or 10 inhibitory RNA molecules) are included, these inhibitory RNA molecules are directed against the same or different RNA targets (such as e.g. mRNAs transcribed from genes of interest). In illustrative embodiments, between 2 and 10, 2 and 8, 2 and 6, 2 and 5, 3 and 5, 3 and 6, or 4 inhibitory RNA molecules are included in the first nucleic acid sequence. In an illustrative embodiment, four inhibitory RNA molecules are included in the first nucleic acid sequence.

In some embodiments, the one or more inhibitor RNA molecules are one or more lymphoproliferative elements, accordingly, in any aspect or embodiment provided herein that includes a lymphoproliferative element, unless incompatible therewith (e.g. a polypeptide lymphoproliferative element), or already state therein. In some embodiments, the RNA targets are mRNAs transcribed from genes that are expressed by T cells such as but not limited to PD-1 (prevent inactivation); CTLA4 (prevent inactivation); TCRα (safety-prevent autoimmunity); TCRb (safety-prevent autoimmunity); CD3Z (safety-prevent autoimmunity); SOCS1 (prevent inactivation); SMAD2 (prevent inactivation); a miR-155 target (promote activation); IFN gamma (reduce CRS); cCBL (prolong signaling); TRAIL2 (prevent death); PP2A (prolong signaling); ABCG1 (increase cholesterol microdomain content by limiting clearance of cholesterol). In illustrative examples, miRNAs inserted into the genome of T cells in methods provided herein, are directed at targets such that proliferation of the T cells is induced and/or enhanced and/or apoptosis is suppressed.

In some embodiments, the RNA targets include mRNAs that encode components of the T cell receptor (TCR) complex. Such components can include components for generation and/or formation of a T cell receptor complex and/or components for proper functioning of a T cell receptor complex. Accordingly, in one embodiment at least one of the two or more of inhibitory RNA molecules causes a decrease in the formation and/or function of a TCR complex, in illustrative embodiments one or more endogenous TCR complexes of a T cell. The T cell receptor complex includes TCRa, TCRb, CD3d, CD3e, CD3 g, and CD3z. It is known that there is a complex interdependency of these components such that a decrease in the expression of any one subunit will result in a decrease in the expression and function of the complex. Accordingly, in one embodiment the RNA target is an mRNA expressing one or more of TCRa, TCRb, CD3d, CD3e, CD3 g, and CD3z endogenous to a transduced T cell. In certain embodiments, the RNA target is mRNA transcribed from the endogenous TCRα or TCRβ gene of the T cell whose genome comprises the first nucleic acid sequence encoding the one or more miRNAs. In illustrative embodiments, the RNA target is mRNA transcribed from the TCRα gene. In certain embodiments, inhibitory RNA molecules directed against mRNAs transcribed from target genes with similar expected utilities can be combined. In other embodiments, inhibitory RNA molecules directed against target mRNAs transcribed from target genes with complementary utilities can be combined. In some embodiments, the two or more inhibitory RNA molecules are directed against the mRNAs transcribed from the target genes CD3Z, PD1, SOCS1, and/or IFN gamma.

In some embodiments, the inhibitory RNA, for example miRNA, targets mRNA encoding Cbl Proto-Oncogene (RNF55) (also known as cCBL and RNF55) (HGNC: 1541, Entrez Gene: 867, OMIM: 165360), T-Cell Receptor T3 Zeta Chain (CD3z) (HGNC: 1677, Entrez Gene: 919, OMIM: 186780), PD1, CTLA4, T Cell Immunoglobulin Mucin 3 (TIM3) (also known as Hepatitis A Virus Cellular Receptor 2) (HGNC: 18437 Entrez Gene: 84868, OMIM: 606652), Lymphocyte Activating 3 (LAG3) (HGNC: 6476, Entrez Gene: 3902, OMIM: 153337), SMAD2, TNF Receptor Superfamily Member 10b (TNFRSF10B) (HGNC: 11905, Entrez Gene: 8795, OMIM: 603612), Protein Phosphatase 2 Catalytic Subunit Alpha (PPP2CA) (HGNC: 9299, Entrez Gene: 5515, OMIM: 176915), Tumor Necrosis Factor Receptor Superfamily Member 6 (TNFRSF6) (also known as Fas Cell Surface Death Receptor (FAS)) (HGNC: 11920, Entrez Gene: 355, OMIM: 134637), B And T Lymphocyte Associated (BTLA) (HGNC: 21087, Entrez Gene: 151888, OMIM: 607925), T Cell Immunoreceptor With Ig And ITIM Domains (TIGIT) (HGNC: 26838, Entrez Gene: 201633, OMIM: 612859), Adenosine Ata Receptor (ADORA2A or A2AR) (HGNC: 263, Entrez Gene: 135, OMIM: 102776), Aryl Hydrocarbon Receptor (AHR) (HGNC: 348, Entrez Gene: 196, OMIM: 600253), Eomesodermin (EOMES) (HGNC: 3372, Entrez Gene: 8320, OMIM: 604615), SMAD Family Member 3 (SMAD3) (HGNC: 6769, Entrez Gene: 4088, OMIM: 603109), SMAD Family Member 4 (SMAD4) (GNC: 6770, Entrez Gene: 4089, OMIM: 600993), TGFBR2, Protein Phosphatase 2 Regulatory Subunit B delta (PPP2R2D) (HGNC: 23732, Entrez Gene: 55844, OMIM: 613992), Tumor Necrosis Factor Ligand Superfamily Member 6 (TNFSF6) (also known as FASL) (HGNC: 11936, Entrez Gene: 356, OMIM: 134638), Caspase 3 (CASP3) HGNC: 1504, Entrez Gene: 836, OMIM: 600636), Suppressor Of Cytokine Signaling 2 (SOCS2) (HGNC: 19382, Entrez Gene: 8835, OMIM: 605117), Kruppel Like Factor 10 (KLF10) (also known as TGFB-Inducible Early Growth Response Protein 1 (TIEG1)) (HGNC: 11810, Entrez Gene: 7071, OMIM: 601878), JunB Proto-Oncogene, AP-1 Transcription Factor Subunit (JunB) (HGNC: 6205, Entrez Gene: 3726, OMIM: 165161), Cbx3, Tet Methylcytosine Dioxygenase 2 (Tet2) (HGNC: 25941, Entrez Gene: 54790, OMIM: 612839), Hexokinase 2 (HK2) (HGNC: 4923, Entrez Gene: 3099, OMIM: 601125), Src homology region 2 domain-containing phosphatase-1 (SHP1) (HGNC: 9658, Entrez Gene: 5777, OMIM: 176883) Src homology region 2 domain-containing phosphatase-2 (SHP2) (HGNC: 9644, Entrez Gene: 5781, OMIM: 176876); or in some embodiments encoding TIM3, LAG3, TNFRSF10B, PPP2CA, TNFRSF6 (FAS), BTLA, TIGIT, A2AR, AHR, EOMES, SMAD3, SMAD4, PPP2R2D, TNFSF6 (FASL), CASP3, SOCS2, TIEG1, JunB, Cbx3, Tet2, HK2, SHP1, or SHP2. In some illustrative embodiments, the inhibitory RNA, for example miRNA, targets mRNA encoding FAS, AHR, CD3z, cCBL, Chromobox 1 (Cbx) (HGNC: 1551, Entrez Gene: 10951, OMIM: 604511), HK2, FASL, SMAD4, or EOMES; or in some illustrative embodiments, the inhibitory RNA, for example miRNA, targets mRNA encoding FAS, AHR, Cbx3, HK2, FASL, SMAD4, or EOMES; or in some illustrative embodiments, the inhibitory RNA, for example miRNA, targets mRNA encoding AHR, Cbx3, HK2, SMAD4, or EOMES.

In some further illustrative embodiments, a vector or genome herein, includes 2 or more, 2-10, 2-8, 2-6, 3-5, 2, 3, 4, 5, 6, 7, or 8 of the inhibitory RNA (e.g. miRNA) identified herein, for example in the paragraph immediately above. In some further illustrative embodiments, a vector or genome herein, includes 2 or more, 2-10, 2-8, 2-6, 3-5, 2, 3, 4, 5, 6, 7, or 8 inhibitory RNA (e.g. miRNA) that target mRNA encoding FAS, cCBL, AHR, CD3z, Cbx, EOMES, or HK2, or a combination of 1 or more inhibitory RNA that target such mRNA. In some further illustrative embodiments, a vector or genome herein, includes 2 or more, 2-10, 2-8, 2-6, 3-5, 2, 3, 4, 5, 6, 7, or 8 inhibitory RNA (e.g. miRNA) that target mRNA encoding AHR, Cbx3, EOMES, or HK2, or a combination of 1 or more inhibitory RNA that target such mRNA.

In some embodiments provided herein, the two or more inhibitory RNA molecules can be delivered in a single intron, such as but not limited to EF1-a intron A. Intron sequences that can be used to harbor miRNAs for the present disclosure include any intron that is processed within a T cell. As indicated herein, one advantage of such an arrangement is that this helps to maximize the ability to include miRNA sequences within the size constraints of a retroviral genome used to deliver such sequences to a T cell in methods provided herein. This is especially true where an intron of the first nucleic acid sequence includes all or a portion of a promoter sequence used to express that intron, a CAR sequence, and other functional sequences provided herein, such as lymphoproliferative element(s) that are not inhibitory RNA molecules, in a polycistronic manner Sequence requirements for introns are known in the art. In some embodiments, such intron processing is operably linked to a riboswitch, such as any riboswitch disclosed herein. Thus, the riboswitch can provide a regulatory element for control of expression of the one or more miRNA sequences on the first nucleic acid sequence. Accordingly, in illustrative embodiments provided herein is a combination of an miRNA directed against an endogenous T cell receptor subunit, wherein the expression of the miRNA is regulated by a riboswitch, which can be any of the riboswitches discussed herein.

In some embodiments, inhibitory RNA molecules can be provided on multiple nucleic acid sequences that can be included on the same or a different transcriptional unit. For example, a first nucleic acid sequence can encode one or more inhibitory RNA molecules and be expressed from a first promoter and a second nucleic acid sequence can encode one or more inhibitory RNA molecules and be expressed from a second promoter. In illustrative embodiments, two or more inhibitory RNA molecules are located on a first nucleic acid sequence that is expressed from a single promoter. The promoter used to express such miRNAs, are typically promoters that are inactive in a packaging cell used to express a retroviral particle that will deliver the miRNAs in its genome to a target T cell, but such promoter is active, either constitutively or in an inducible manner, within a T cell. The promoter can be a Pol I, Pol II, or Pol III promoter. In some illustrative embodiments, the promoter is a Pol II promoter.

Characterization and Commercial Production Methods

The present disclosure provides various methods and compositions that can be used as research reagents in scientific experimentation and for commercial production. Such scientific experimentation can include methods for characterization of lymphocytes, such as NK cells and in illustrative embodiments, T cells using methods for genetically modifying, for example transducing lymphocytes provided herein. Such methods for example, can be used to study activation of lymphocytes and the detailed molecular mechanisms by which activation makes such cells transducible. Furthermore, provided herein are genetically modified lymphocytes that will have utility for example, as research tools to better understand factors that influence T cell proliferation and survival. Such genetically modified lymphocytes, such as NK cells and in illustrative embodiments T cells, can furthermore be used for commercial production, for example for the production of certain factors, such as growth factors and immunomodulatory agents, that can be harvested and tested or used in the production of commercial products.

The scientific experiments and/or the characterization of lymphocytes can include any of the aspects, embodiments, or subembodiments provided herein useful for analyzing or comparing lymphocytes. In some embodiments, T cells and/or NK cells can be transduced with the replication incompetent recombinant retroviral particles provided herein that include polynucleotides. In some embodiments, transduction of the T cells and/or NK cells can include polynucleotides that include polynucleotides encoding polypeptides of the present disclosure, for example, CARs, lymphoproliferative elements, and/or activation elements. In some embodiments, the polynucleotides can include inhibitory RNA molecules as discussed elsewhere herein. In some embodiments, the lymphoproliferative elements can be chimeric lymphoproliferative elements.

EXEMPLARY EMBODIMENTS

Provided in this Exemplary Embodiments section are exemplary aspects and embodiments provided herein and further discussed throughout this specification. For the sake of brevity and convenience, all of the disclosed aspects and embodiments and all of the possible combinations of the disclosed aspects and embodiments are not listed in this section. It will be understood that embodiments are provided that are specific embodiments for many aspects, as discussed in this entire disclosure. It is intended in view of the full disclosure herein, that any individual embodiment recited below or in this full disclosure can be combined with any aspect recited below or in this full disclosure where it is an additional element that can be added to an aspect or because it is a narrower element for an element already present in an aspect. Such combinations are discussed more specifically in other sections of this detailed description.

Unless incompatible with, or already stated in an aspect or embodiment, for any of the methods for genetically modifying and/or transducing lymphocytes (e.g. PBMCs, or T cells and/or NK cells), or uses that include such methods, or genetically modified cells produced using such methods, and any other method or product by process, provided herein, including but not limited to in this Exemplary Embodiments section that includes a contacting step of contacting retroviral particles with lymphocytes (e.g. PBMCs, or T cells and/or NK cells), in certain embodiments, the contacting step can be performed (or can occur) for between 30 seconds and 72 hours, for example, between 1 minute and 12 hours, or between 5 minutes and 12 hours, 10 hours, 8 hours, 6 hours, 4 hours, 2 hours, 1 hour, 30 minutes, or 15 minutes. In some embodiments, the contacting can be performed for less than 24 hours, for example, less than 12 hours, less than 8 hours, less than 4 hours, and in illustrative embodiments less than 2 hours, less than 1 hour, less than 30 minutes or less than 15 minutes, but in each case there is at least an initial contacting step in which retroviral particles and cells are brought into contact in suspension in a transduction reaction mixture. Such suspension can include allowing cells and retroviral particles to settle or causing such settling through application of a force, such as a centrifugal force, to the bottom of a vessel or chamber. However, in certain illustrative embodiments, such force is less than that used for spinoculation, as discussed in more detail herein. After such initial contacting, there can be an additional optional incubating in the reaction mixture containing cells and retroviral particles in suspension in the reaction mixture for the time periods specified without removing retroviral particles that remain free in solution and not associated with cells. In illustrative embodiments, the contacting can be performed (or can occur) for between 30 seconds or 1, 2, 5, 10, 15, 30 or 45 minutes, or 1, 2, 3, 4, 5, 6, 7, or 8 hours on the low end of the range, and between 10 minutes, 15 minutes, 30 minutes, or 1, 2, 4, 6, 8, 10, 12, 18, 24, 36, 48, and 72 hours on the high end of the range. In certain illustrative embodiments, the contacting step can be performed for between 30 seconds, 1 minute, 5 minutes, 10 minutes, 15 minutes, or 30 minutes on the low end of the range and 1 hour, 2 hours, 4 hours, 6 hours, 8 hours, 10 hours, or 12 hours on the high end of the range. In some embodiments, the contacting step is performed for between 30 seconds, 1 minute, and 5 minutes on the low end of the range, and 10 minutes, 15 minutes, 30 minutes, 45 minutes, or 60 minutes on the high end of the range. In another illustrative embodiment, the contacting is performed for between an initial contacting step only (without any further incubating in the reaction mixture including the retroviral particles free in suspension and cells in suspension) without any further incubation in the reaction mixture, or a 5 minute or less, 10 minute or less, 15 minute or less, 30 minute or less, or 1 hour or less incubation in the reaction mixture. In some embodiments, the replication incompetent recombinant retroviral particles can be immediately washed out after adding them to the cell(s) to be genetically modified and/or transduced such that the contacting time is carried out for the length of time it takes to wash out the replication incompetent recombinant retroviral particles. Accordingly, typically the contacting includes at least an in initial contacting step in which a retroviral particle(s) and a cell(s) are brought into contact in suspension in a transduction reaction mixture. Such methods can be performed without prior activation.

In any of the aspects and embodiments provided herein that include, or optionally include, a nucleic acid sequence encoding an inhibitory RNA molecule, including, but not limited to, aspects and embodiments provided in this Exemplary Embodiments section, unless already stated therein, or incompatible therewith, such nucleic acid sequence is included and such inhibitory RNA molecule, in certain embodiments, targets any of the gene (e.g. mRNAs encoding) targets identified for example in the Inhibitory RNA Molecules section herein; or in certain embodiments targets TCRa, TCRb, SOCS1, miR155 target, IFN gamma, cCBL, TRAIL2, PP2A, ABCG1, cCBL, CD3z, CD3z, PD1, CTLA4, TIM3, LAG3, SMAD2, TNFRSF10B, PPP2CA, TNFRSF6 (FAS), BTLA, TIGIT, A2AR, AHR, EOMES, SMAD3, SMAD4, TGFBR2, PPP2R2D, TNFSF6 (FASL), CASP3, SOCS2, TIEG1, JunB, Cbx3, Tet2, HK2, SHP1, or SHP2; or in certain embodiments targets cCBL, CD3z, CD3z, PD1, CTLA4, TIM3, LAG3, SMAD2, TNFRSF10B, PPP2CA, TNFRSF6 (FAS), BTLA, TIGIT, A2AR, AHR, EOMES, SMAD3, SMAD4, TGFBR2, PPP2R2D, TNFSF6 (FASL), CASP3, SOCS2, TIEG1, JunB, Cbx3, Tet2, HK2, SHP1, or SHP2; or in certain embodiments targets mRNA encoding TIM3, LAG3, TNFRSF10B, PPP2CA, TNFRSF6 (FAS), BTLA, TIGIT, A2AR, AHR, EOMES, SMAD3, SMAD4, PPP2R2D, TNFSF6 (FASL), CASP3, SOCS2, TIEG1, JunB, Cbx3, Tet2, HK2, SHP1, or SHP2; or in certain illustrative embodiments, targets mRNA encoding FAS, AHR, CD3z, cCBL, Cbx, HK2, FASL, SMAD4, or EOMES; or in certain illustrative embodiments targets mRNA encoding FAS, AHR, Cbx3, HK2, FASL, SMAD4, or EOMES; or in further illustrative embodiments targets mRNA encoding AHR, Cbx3, HK2, SMAD4, or EOMES. In some embodiments, the inhibitory RNA molecule includes at least one of the sequences of SEQ ID NOs:342-449. In some embodiments, the inhibitory RNA molecule includes at least one of the sequences of SEQ ID NOs:394-401, 406-409, 438-441, or 446-449.

In any of the aspects and embodiments provided herein that include, or optionally include, a nucleic acid sequence encoding an inhibitory RNA molecule, including, but not limited to, aspects and embodiments provided in this Exemplary Embodiments section, unless already stated therein, or incompatible therewith, such nucleic acid sequence is included and such inhibitory RNA molecule, in certain embodiments, include 2 or more, 2-10, 2-8, 2-6, 3-5, 2, 3, 4, 5, 6, 7, or 8 inhibitory RNA, or of the targeted inhibitory RNA (e.g. miRNA) identified herein, for example in the paragraph immediately above; or in certain embodiments such polynucleotide includes 2 or more, 2-10, 2-8, 2-6, 3-5, 2, 3, 4, 5, 6, 7, or 8 inhibitory RNA (e.g. miRNA) that target mRNA encoding FAS, cCBL, AHR, CD3z, Cbx, EOMES, or HK2, or a combination of 1 or more inhibitory RNA that target such mRNA; or in certain further illustrative embodiments, such polynucleotide includes 2 or more, 2-10, 2-8, 2-6, 3-5, 2, 3, 4, 5, 6, 7, or 8 inhibitory RNA (e.g. miRNA) that target mRNA encoding FAS, AHR, Cbx3, EOMES, or HK2, or a combination of 1 or more inhibitory RNA that target such mRNA. Such aspects and embodiments provided herein that include a nucleic acid that encodes an inhibitory RNA molecule, include, but are not limited to, aspects and embodiments provided herein that are directed to polynucleotides or vectors, for example replication incompetent retroviral particles, or aspects comprising a genome, such as isolated cells or replication incompetent retroviral particles.

Provided herein in one aspect is a method for genetically modifying and/or transducing a lymphocyte (e.g. a T cell or an NK cell) or a population thereof, comprising contacting blood cells comprising the lymphocyte (e.g. the T cell or NK cell) or the population thereof, ex vivo with a replication incompetent recombinant retroviral particle comprising in its genome a polynucleotide comprising one or more nucleic acid sequences operatively linked to a promoter active in lymphocytes (e.g. T cells and/or NK cells), wherein a first nucleic acid sequence of the one or more nucleic acid sequences encodes a chimeric antigen receptor (CAR) comprising an antigen-specific targeting region (ASTR), a transmembrane domain, and an intracellular activating domain, and optionally another of the one or more nucleic acid sequences encodes one or more (e.g. two or more) inhibitory RNA molecules directed against one or more RNA targets, and further optionally another of the one or more nucleic acid sequences encodes a polypeptide lymphoproliferative element, wherein said contacting facilitates genetic modification and/or transduction of the lymphocyte (e.g. T cell or NK cell), or at least some of the lymphocytes (e.g. T cells and/or NK cells) by the replication incompetent recombinant retroviral particle, thereby producing a genetically modified and/or transduced lymphocyte (e.g. T cell and/or NK cell). In such method, the contacting is typically performed in a reaction mixture, sometimes referred to herein as a transduction reaction mixture, comprising a population of lymphocytes (e.g. T cells and/or NK cells) and contacted with a population of replication incompetent recombinant retroviral particles. Various contacting times are provided herein, including, but not limited to, in this Exemplary Embodiments section, that can be used in this aspect to facilitate membrane association, and eventual membrane fusion of the lymphocytes (e.g. T cells and/or the NK cells) to the replication incompetent recombinant retroviral particles. In an illustrative embodiment, contacting is performed for less than 15 minutes.

Provided herein in one aspect, is use of replication incompetent recombinant retroviral particles in the manufacture of a kit for genetically modifying lymphocytes (e.g. T cells or NK cells) of a subject, wherein the use of the kit comprises: contacting blood cells comprising the lymphocytes (e.g. T cells and/or the NK cells) ex vivo in a reaction mixture, with the replication incompetent recombinant retroviral particles, wherein the replication incompetent recombinant retroviral particles comprise a pseudotyping element on their surface, wherein the replication incompetent recombinant retroviral particles comprise a polynucleotide comprising one or more nucleic acid sequences, typically transcriptional units operatively linked to a promoter active in lymphocytes (e.g. T cells and/or NK cells), wherein the one or more transcriptional units encode a first polypeptide comprising a chimeric antigen receptor (CAR), a first polypeptide comprising a lymphoproliferative element (LE), or a first polypeptide comprising an LE and a second polypeptide comprising a CAR, thereby producing the genetically modified lymphocytes (e.g. the genetically modified T cells and/or the genetically modified NK cells). Various contacting times are provided herein, including, but not limited to, in this Exemplary Embodiments section, that can be used in this aspect to facilitate membrane association, and eventual membrane fusion of the lymphocytes (e.g. T cells and/or the NK cells) to the replication incompetent recombinant retroviral particles. In an illustrative embodiment, contacting is performed for less than 15 minutes.

In another aspect, provided herein is a genetically modified lymphocyte (e.g. T cell or NK cell) made by genetically modifying lymphocytes (e.g. T cells and/or NK cells) according to a method comprising contacting blood cells comprising the T cells or NK cells ex vivo in a reaction mixture, with replication incompetent recombinant retroviral particles, wherein the replication incompetent recombinant retroviral particles comprise a pseudotyping element on their surface, wherein the replication incompetent recombinant retroviral particles comprise a polynucleotide comprising one or more nucleic acid sequences, typically transcriptional units operatively linked to a promoter active in lymphocytes (e.g. T cells and/or NK cells), wherein the one or more transcriptional units encode a first polypeptide comprising a chimeric antigen receptor (CAR), a first polypeptide comprising a lymphoproliferative element (LE), or a first polypeptide comprising an LE and a second polypeptide comprising a CAR, thereby producing the genetically modified lymphocytes (e.g. T cells and/or the genetically modified NK cells). Various contacting times are provided herein, including, but not limited to, in this Exemplary Embodiments section, that can be used in this aspect to facilitate membrane association, and eventual membrane fusion of the lymphocytes (e.g. T cells and/or the NK cells) to the replication incompetent recombinant retroviral particles. In an illustrative embodiment, contacting is performed for less than 15 minutes.

Provided herein in another aspect is a replication incompetent recombinant retroviral particle for use in a method for genetically modifying lymphocyte, for example a T cell and/or NK cell, wherein the method comprises contacting blood cells comprising the lymphocyte, for example T cell and/or NK cell, of the subject in a reaction mixture, ex vivo, with a replication incompetent recombinant retroviral particle comprising in its genome a polynucleotide comprising one or more nucleic acid sequences operatively linked to a promoter active in T cells and/or NK cells, wherein a first nucleic acid sequence of the one or more nucleic acid sequences encodes a chimeric antigen receptor (CAR) comprising an antigen-specific targeting region (ASTR), a transmembrane domain, and an intracellular activating domain, and optionally another of the one or more nucleic acid sequences encodes one or more (e.g. two or more) inhibitory RNA molecules directed against one or more RNA targets, and further optionally another of the one or more nucleic acid sequences encodes a polypeptide lymphoproliferative element, wherein said contacting facilitates transduction of at least some of the resting T cells and/or NK cells by the replication incompetent recombinant retroviral particles, thereby producing a genetically modified T cell and/or NK cell. Various contacting times are provided herein, including, but not limited to, in this Exemplary Embodiments section, that can be used in this aspect to facilitate membrane association, and eventual membrane fusion of the lymphocytes (e.g. T cells and/or the NK cells) to the replication incompetent recombinant retroviral particles. In an illustrative embodiment, contacting is performed for less than 15 minutes. In some embodiments the method can further include introducing the genetically modified T cell and/or NK cell into a subject. In illustrative embodiments, the blood cells comprising the lymphocyte (e.g. the T cell and/or NK cell) are from the subject, and thus the introducing is a reintroducing. In this aspect, in some embodiments, a population of lymphocytes (e.g. T cells and/or NK cells) are contacted in the contacting step, genetically modified and/or transduced, and introduced into the subject in the introducing step.

Provided herein in another aspect is the use of a replication incompetent recombinant retroviral particle in the manufacture of a kit for genetically modifying a lymphocyte, for example a T cell and/or NK cell of a subject, wherein the use of the kit comprises contacting blood cells comprising the lymphocyte, for example the T cell and/or the NK cell of the subject ex vivo in a reaction mixture, with replication incompetent recombinant retroviral particles comprising in their genome a polynucleotide comprising one or more nucleic acid sequences operatively linked to a promoter active in T cells and/or NK cells, wherein a first nucleic acid sequence of the one or more nucleic acid sequences encodes a chimeric antigen receptor (CAR) comprising an antigen-specific targeting region (ASTR), a transmembrane domain, and an intracellular activating domain, and optionally another of the one or more nucleic acid sequences encodes one or more (e.g. two or more) inhibitory RNA molecules directed against one or more RNA targets, and further optionally another of the one or more nucleic acid sequences encodes a polypeptide lymphoproliferative element, wherein said contacting facilitates genetic modification of at least some of the T cells and/or NK cells by the replication incompetent recombinant retroviral particles, thereby producing a genetically modified T cell and/or NK cell. As indicated herein, various contacting times are provided herein, that can be used in this aspect to facilitate membrane association, and eventual membrane fusion of the lymphocyte (e.g. T cell and/or the NK cell) to the replication incompetent recombinant retroviral particles. In an illustrative embodiment, contacting is performed for less than 15 minutes. In illustrative embodiments, the blood cells comprising the lymphocyte (e.g. the T cell and/or NK cell) are from the subject, and thus the introducing is a reintroducing. In this aspect, in some embodiments, a population of T cells and/or NK cells are contacted in the contacting step, genetically modified and/or transduced, and introduced into the subject in the introducing step.

Provided herein in another aspect is the use of replication incompetent recombinant retroviral particles in the manufacture of a medicament for genetically modifying lymphocytes, for example T cells and/or NK cells of a subject, wherein the use of the medicament comprises:

A) contacting blood cells comprising the T cells and/or NK cells of the subject ex vivo in a reaction mixture, with the replication incompetent recombinant retroviral particles comprising in their genome a polynucleotide comprising one or more nucleic acid sequences operatively linked to a promoter active in T cells and/or NK cells, wherein a first nucleic acid sequence of the one or more nucleic acid sequences encodes a chimeric antigen receptor (CAR) comprising an antigen-specific targeting region (ASTR), a transmembrane domain, and an intracellular activating domain, and optionally another of the one or more nucleic acid sequences encodes one or more (e.g. two or more) inhibitory RNA molecules directed against one or more RNA targets, and further optionally another of the one or more nucleic acid sequences encodes a polypeptide lymphoproliferative element, wherein said contacting facilitates genetic modification of at least some of the lymphocytes (for example, T cells and/or NK cells) by the replication incompetent recombinant retroviral particles, thereby producing genetically modified T cells and/or NK cells; and optionally B) introducing the genetically modified T cell and/or NK cell into the subject, thereby genetically modifying the lymphocytes, for example T cells and/or NK cells of the subject.

In such aspects in the immediately above paragraph, as indicated herein, various contacting times are provided herein, that can be used in this aspect to facilitate membrane association, and eventual membrane fusion of the lymphocytes (e.g. T cells and/or the NK cells) to the replication incompetent recombinant retroviral particles. In an illustrative embodiment, contacting is performed for less than 15 minutes. In some embodiments of such method, the blood cells, lymphocyte(s) (e.g. T cell(s) and/or NK cell(s)) are from a subject, typically in such embodiments from blood collected from the subject. In some embodiments of the method aspect provided in this paragraph, the genetically modified and/or transduced lymphocyte (e.g. T cell and/or NK cell) or population thereof, is introduced or reintroduced into a subject.

In any of the use aspects herein, genetically modified lymphocyte(s) (e.g. T cell(s) or NK(s) cell) aspects herein, or methods aspects for genetically modifying and/or transducing a lymphocyte(s) (e.g. T cell(s) or an NK cell(s)) according to any embodiment herein, including but not limited to, any embodiment in this Exemplary Embodiments section, including those above, unless incompatible with, or already stated, the reaction mixture comprises at least 10%, 20%, 25%, 50%, 75%, 80%, 90%, 95%, or 99% whole blood and optionally an effective amount of an anticoagulant, or the reaction mixture further comprises at least one additional blood or blood preparation component that is not a PBMC, and in further illustrative embodiments such blood or blood preparation component is one or more of the Noteworthy Non-PBMC Blood or Blood Preparation Components provided herein.

In another aspect, provided herein is a reaction mixture, comprising replication incompetent recombinant retroviral particles, a T cell activation element, and blood cells, wherein the recombinant retroviral particles comprise a pseudotyping element on their surface, wherein the blood cells comprise T cells and/or NK cells, wherein the replication incompetent recombinant retroviral particles comprise a polynucleotide comprising one or more nucleic acid sequences, typically transcriptional units operatively linked to a promoter active in T cells and/or NK cells, wherein the one or more transcriptional units encode a first polypeptide comprising a chimeric antigen receptor (CAR), a first polypeptide comprising a lymphoproliferative element (LE), and/or one or more inhibitory RNA molecules, and wherein the reaction mixture comprises at least 10%, 20%, 25%, 50%, 75%, 80%, 90%, 95%, or 99% whole blood. The one or more inhibitory RNA molecule(s) can be directed against any target provided herein, including, but not limited to, in this Exemplary Embodiments section.

In one aspect, provided herein is a reaction mixture, comprising replication incompetent recombinant retroviral particles, and blood cells, wherein the recombinant retroviral particles comprise a pseudotyping element on their surface, wherein the blood cells comprise T cells and/or NK cells, and wherein the reaction mixture comprises at least 10%, 20%, 25%, 50%, 60%, 70%, 75%, 80%, 90%, 95%, or 99% whole blood and optionally an effective amount of an anticoagulant, or wherein the reaction mixture further comprises at least one additional blood or blood preparation component that is not a PBMC, and in illustrative embodiments such blood or blood preparation component is one or more of the Noteworthy Non-PBMC Blood or Blood Preparation Components provided herein.

In another aspect, provided herein is a reaction mixture, comprising replication incompetent recombinant retroviral particles, a T cell activation element, and blood cells, wherein the recombinant retroviral particles comprise a pseudotyping element on their surface, wherein the blood cells comprise T cells and/or NK cells, wherein the replication incompetent recombinant retroviral particles comprise a polynucleotide comprising one or more nucleic acid sequences, typically transcriptional units operatively linked to a promoter active in T cells and/or NK cells, wherein the one or more transcriptional units encode a first polypeptide comprising a chimeric antigen receptor (CAR), a first polypeptide comprising a lymphoproliferative element (LE), and/or one or more inhibitory RNA molecules, and wherein the reaction mixture comprises at least 10%, 20%, 25%, 50%, 75%, 80%, 90%, 95%, or 99% whole blood and optionally an effective amount of an anticoagulant, or wherein the reaction mixture further comprises at least one additional blood or blood preparation component that is not a PB MC, and in illustrative embodiments such blood or blood preparation component is one or more of the Noteworthy Non-PB MC Blood or Blood Preparation Components provided herein. The one or more inhibitory RNA molecule(s) can be directed against any target provided herein, including, but not limited to, in this Exemplary Embodiments section.

In another aspect, provided herein is a method for genetically modifying T cells and/or NK cells in blood or a component thereof, comprising contacting blood cells comprising the T cells and/or NK cells ex vivo, with replication incompetent recombinant retroviral particles in a reaction mixture, wherein the replication incompetent recombinant retroviral particles comprise a pseudotyping element on their surface, wherein said contacting facilitates association of the T cells and/or NK cells with the replication incompetent recombinant retroviral particles, wherein the recombinant retroviral particles genetically modify and/or transduce the T cells and/or NK cells, and wherein the reaction mixture comprises at least 10% 10%, 20%, 25%, 50%, 60%, 70%, 75%, 80%, 90%, 95%, or 99% whole blood and optionally an effective amount of an anticoagulant, or wherein the reaction mixture further comprises at least one additional blood or blood preparation component that is not a PBMC, and in illustrative embodiments such blood or blood preparation component is one or more of the Noteworthy Non-PBMC Blood or Blood Preparation Components provided herein In another aspect, provided herein is use of replication incompetent recombinant retroviral particles in the manufacture of a kit for genetically modifying T cells and/or NK cells of a subject, wherein the use of the kit comprises: contacting blood cells comprising the T cells and/or NKs cell ex vivo in a reaction mixture, with the replication incompetent recombinant retroviral particles, wherein the replication incompetent recombinant retroviral particles comprise a pseudotyping element on their surface, wherein said contacting facilitates association of the T cells or NK cells with the replication incompetent recombinant retroviral particles, wherein the recombinant retroviral particles genetically modify and/or transduce the T cells and/or NK cells, and wherein the blood cells comprise T cells, NK cells, and wherein the reaction mixture comprises at least 10%, 20%, 25%, 50%, 60%, 70%, 75%, 80%, 90%, 95%, or 99% whole blood and optionally an effective amount of an anticoagulant, or wherein the reaction mixture further comprises at least one additional blood or blood preparation component that is not a PBMC, and in illustrative embodiments such blood or blood preparation component is one or more of the Noteworthy Non-PBMC Blood or Blood Preparation Components provided herein.

In another aspect, provided herein is a genetically modified T cell or NK cell made by genetically modifying T cells and/or NK cells according to a method comprising, contacting blood cells comprising the T cells and/or NK cells ex vivo, with replication incompetent recombinant retroviral particles in a reaction mixture, wherein the replication incompetent recombinant retroviral particles comprise a pseudotyping element on their surface, wherein said contacting facilitates association of the T cells and/or NK cells with the replication incompetent recombinant retroviral particles, wherein the recombinant retroviral particles genetically modify and/or transduce the T cells and/or NK cells, and wherein the reaction mixture comprises at least 10%, 20%, 25%, 50%, 60%, 70%, 75%, 80%, 90%, 95%, or 99% whole blood and optionally an effective amount of an anticoagulant, or wherein the reaction mixture further comprises at least one additional blood or blood preparation component that is not a PBMC, and in illustrative embodiments such blood or blood preparation component is one or more of the Noteworthy Non-PBMC Blood or Blood Preparation Components provided herein.

The one or more Noteworthy Non-PBMC Blood or Blood Preparation Components are present in certain illustrative embodiments of any of the reaction mixture, use, genetically modified T cell or NK cell, or method for genetically modifying T cells and/or NK cells provided herein, including but not limited to those provided in this Exemplary Embodiments section, because in these certain illustrative embodiments, the reaction mixture comprises at least 10% whole blood. In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiment, the reaction mixture comprises between 10%, 15%, 20%, 25%, 30%, 40%, 50%, 60%, 70%, and 75% on the low end of the range, and 80%, 90%, 95%, 96%, 97%, 98%, 99%, 99.9%, or 99.99% on the high end of the range of whole blood, or at least 10%, 15%, 20%, 25%, 30%, 40%, 50%, 60%, 70%, 75%, 80%, 90%, 95%, 96%, 97%, 98%, 99%, 99.9%, or 99.99% whole blood.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the blood cells in the reaction mixture comprise at least 10% neutrophils and at least 0.5% eosinophils, as a percent of the white blood cells in the reaction mixture.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture comprises at least 20%, 25%, 30%, or 40% neutrophils as a percent of white blood cells in the reaction mixture, or between 20% and 80%, 25% and 75%, or 40% and 60% neutrophils as a percent of white blood cells in the reaction mixture.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture comprises at least 0.1% eosinophils, or between 0.25% and 8% eosinophils, or between 0.5% and 4% as a percent of white blood cells in the reaction mixture.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the blood cells in the reaction mixture are not subjected to a PBMC enrichment procedure before the contacting.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is formed by adding the recombinant retroviral particles to whole blood.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is formed by adding the recombinant retroviral particles to substantially whole blood comprising an effective amount of an anti-coagulant.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is in a closed cell processing system. In certain embodiments of such a reaction mixture, use, genetically modified T cell or NK cell, or method for genetically modifying T cells and/or NK cells, the blood cells in a reaction mixture are PBMCs and the reaction mixture is in contact with a leukodepletion filter assembly in the closed cell processing system, and in optional further embodiments the leukodepletion filter assembly comprises a HemaTrate filter.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture comprises an anti-coagulant. For example, in certain embodiments, the anti-coagulant is selected from the group consisting of acid citrate dextrose, EDTA, or heparin. In certain embodiments, the anti-coagulant is other than acid citrate dextrose. In certain embodiments, the anti-coagulant comprises an effective amount of heparin.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is in a blood bag during the contacting.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is in contact with a T lymphocyte and/or NK cell-enriching filter in the closed cell processing system before the contacting, and wherein the reaction mixture comprises granulocytes, wherein the granulocytes comprise at least 10% of the white blood cells in the reaction mixture, or wherein the reaction mixture comprises at least 10% as many granulocytes as T cells, wherein the genetically modified lymphocytes (e.g. T cells or NK cells) are subject to a PBMC enrichment process after the contacting.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, blood cells in the reaction mixture are PBMCs and wherein the reaction mixture is in contact with a leukodepletion filter assembly in the closed cell processing system after the contacting comprising an optional incubating in the reaction mixture.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the whole blood is other than cord blood.

In certain embodiments of any of the reaction mixture, use, genetically modified T cell or NK cell, or method for genetically modifying T cells and/or NK cells provided herein, included but not limited to those provided in this Exemplary Embodiments section, unless incompatible with, or already stated in an aspect or embodiments, the reaction mixture is in contact with a leukodepletion filter assembly in a closed cell processing system before the contacting, at the time the recombinant retroviral particles and the blood cells are contacted, during the contacting comprising an optional incubating in the reaction mixture, and/or after the contacting comprising the optional incubating in the reaction mixture, wherein the T cells and/or NK cells, or the genetically modified T cells and/or NK cells are further subjected to a PBMC enrichment procedure.

In one aspect, provided herein is a replication incompetent recombinant retroviral particle comprising in its genome a polynucleotide comprising one or more nucleic acid sequences operatively linked to a promoter active in T cells and/or NK cells, wherein:

a. a first nucleic acid sequence of the one or more nucleic acid sequences encodes one or more (e.g. two or more) inhibitory RNA molecules directed against one or more RNA targets, and b. a second nucleic acid sequence of the one or more nucleic acid sequences encodes a chimeric antigen receptor (CAR) comprising an antigen-specific targeting region (ASTR), a transmembrane domain, and an intracellular activating domain. The one or more inhibitory RNA molecule(s) can be directed against any target provided herein, including, but not limited to, in this Exemplary Embodiments section.

Provided in another aspect herein is a mammalian packaging cell line comprising a packageable RNA genome for a replication incompetent retroviral particle, wherein said packageable RNA genome comprises:

a. a 5' long terminal repeat, or active fragment thereof;

b. a nucleic acid sequence encoding a retroviral cis-acting RNA packaging element;

c. a polynucleotide comprising one or more nucleic acid sequences operatively linked to a promoter active in T cells and/or NK cells, wherein a first nucleic acid sequence of the one or more nucleic acids encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain; and d. a 3' long terminal repeat, or active fragment thereof. The one or more inhibitory RNA molecule(s) can be directed against any target provided herein, including, but not limited to, in this Exemplary Embodiments section. Provided in another aspect herein is a retroviral vector comprising a packageable RNA genome for a replication incompetent retroviral particle, wherein said packageable RNA genome comprises:

a. a 5' long terminal repeat, or active fragment thereof;

b. a nucleic acid sequence encoding a retroviral cis-acting RNA packaging element;

c. a polynucleotide comprising one or more nucleic acid sequences operatively linked to a promoter active in T cells and/or NK cells, wherein a first nucleic acid sequence of the one or more nucleic acids encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain; and a 3' long terminal repeat, or active fragment thereof. The one or more inhibitory RNA molecule(s) can be directed against any target provided herein, including, but not limited to, in this Exemplary Embodiments section.

In some embodiments of the retroviral vector aspect, or the mammalian packaging cell line aspect, the polynucleotide of (c) can be in reverse orientation to the nucleic acid sequence encoding the retroviral cis-acting RNA packaging element (b), the 5' long terminal repeat (a), and/or the 3' long terminal repeat (d).

In some embodiments of the retroviral vector aspect or the mammalian packaging cell line aspect, expression of the packageable RNA genome is driven by an inducible promoter active in the mammalian packaging cell line.

In some embodiments of the retroviral vector aspect or the mammalian packaging cell line aspect, the retroviral cis-acting RNA packaging element can comprise a central polypurine tract (cPPT)/central termination sequence, an HIV Psi, or a combination thereof. The retroviral vector can optionally include an antibiotic resistance gene and/or a detectable marker.

Provided herein in another aspect is a genetically modified T cell and/or NK cell comprising:

a. one or more (e.g. two or more) inhibitory RNA molecules directed against one or more RNA targets; and b. a chimeric antigen receptor (CAR) comprising an antigen-specific targeting region (ASTR), a transmembrane domain, and an intracellular activating domain, wherein said one or more (e.g. two or more) inhibitory RNA molecules and the CAR are encoded by nucleic acid sequences that are genetic modifications of the T cell and/or NK cell. The one or more inhibitory RNA molecule(s) can be directed against any target provided herein, including, but not limited to, in this Exemplary Embodiments section.

In some embodiments of the genetically modified T cell and/or NK cell aspect, the genetically modified T cell and/or NK cell also comprises at least one lymphoproliferative element that is not an inhibitory RNA molecule, typically a polypeptide lymphoproliferative element, wherein said lymphoproliferative element is encoded by a nucleic acid that is a genetic modification of the T cell and/or NK cell. In some embodiments, the inhibitory RNA molecules, the CAR, and/or the at least one polypeptide lymphoproliferative element are expressed in a polycistronic matter. In illustrative embodiments, the inhibitory RNA molecules are expressed from a single polycistronic transcript.

Provided herein in another aspect is a replication incompetent recombinant retroviral particle, wherein the replication incompetent recombinant retroviral particle comprises in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein the method comprises contacting a T cell and/or NK cell of the subject ex vivo, and said contacting facilitates transduction of at least some of the resting T cells and/or NK cells by the replication incompetent recombinant retroviral particles, thereby producing a genetically modified T cell and/or NK cell. The one or more inhibitory RNA molecule(s) can be directed against any target provided herein, including, but not limited to, in this Exemplary Embodiments section.

Provided herein in another aspect is a commercial container containing a replication incompetent recombinant retroviral particle and optionally instructions for the use thereof to treat tumor growth in a subject, wherein the replication incompetent recombinant retroviral particle comprises in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain. The one or more inhibitory RNA molecule(s) can be directed against any target provided herein, including, but not limited to, in this Exemplary Embodiments section.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, the polynucleotide may further include a third nucleic acid sequence that encodes at least one lymphoproliferative element that is not an inhibitory RNA molecule, and in illustrative embodiments is a polypeptide, for example any of the polypeptide lymphoproliferative elements disclosed herein.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, the inhibitory RNA molecule can have any of the structures and/or be any of the embodiments provided herein in the Inhibitory RNA Molecules section. For example, the inhibitory RNA can in some embodiments include a 5' strand and a 3' strand that are partially or fully complementary to one another, wherein said 5' strand and said 3' strand are capable of forming an 18-25 nucleotide RNA duplex. Furthermore, the inhibitory RNA molecule can be a miRNA or an shRNA and in certain embodiments, at least one or all of the inhibitory RNA molecules comprise a 5' arm, 3' arm, or both, derived from a naturally occurring miRNA. For example, such as a naturally occurring miRNA can be selected from the group consisting of: miR-155, miR-30, miR-17-92, miR-122, and miR-21, and in illustrative embodiments miR-155.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, in some embodiments, the first nucleic acid sequence encodes two to four inhibitory RNA molecules. In illustrative embodiments, between 2 and 10, 2 and 8, 2 and 6, 2 and 5, 2 and 4, 3 and 5, or 3 and 6 inhibitory RNA molecules are included in the first nucleic acid sequence. In an illustrative embodiment, four inhibitory RNA molecules are included in the first nucleic acid sequence.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, the one or more (e.g. two or more) inhibitory RNA molecules can be in an intron. In some embodiments, the intron is in a promoter. In illustrative embodiments, the intron is EF-1alpha intron A. In some embodiments, the intron is adjacent to and downstream of a promoter, which in illustrative embodiments, is inactive in a packaging cell used to produce the replication incompetent recombinant retroviral particle.

In any of the reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated at least 10%, 20%, 25%, 30%, 40%, 50%, most, 60%, 70%, 75%, 80%, 90%, 95%, or 99% of the T cells are resting T cells, or of the NK cells are resting NK cells, when they are combined with the replication incompetent retroviral particles to form the reaction mixture.

In any of the use, genetically modified T cell or NK cell, or method for genetically modifying T cells and/or NK cells aspects and embodiments provided herein, including, but not limited to, in this Exemplary Embodiments section, unless incompatible with, or otherwise stated, the cell or cells are not subjected to a spinoculation procedure, for example not subjected to a spinoculation of at least 800 g for at least 30 minutes.

In some embodiments of any of the use, genetically modified T cell or NK cell, or method for genetically modifying T cells and/or NK cells aspects and embodiments provided herein, including, but not limited to, in this Exemplary Embodiments section, unless incompatible with, or otherwise stated, the method further comprises administering the genetically modified T cells and/or NK cells to a subject, optionally wherein the subject is the source of the blood cells. In some subembodiments of these and embodiments of any of the methods and uses herein, including those in this Exemplary Embodiments section, provided that it is not incompatible with, or already stated, the genetically modified and/or transduced lymphocyte (e.g. T cell and/or NK cell) or population thereof, undergoes 4 or fewer cell divisions ex vivo prior to being introduced or reintroduced into the subject. In some embodiments, no more than 8 hours, 6 hours, 4 hours, 2 hours, or 1 hour pass(es) between the time blood is collected from the subject and the time the genetically modified T cells and/or NK cells are reintroduced into the subject. In some embodiments, all steps after the blood is collected and before the blood is reintroduced, are performed in a closed system, optionally in which a person monitors the closed system throughout the processing.

In any of the replication incompetent recombinant retroviral particle, reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the replication incompetent recombinant retroviral particle(s) comprise a membrane-bound T cell activation element on their surface. In some subembodiments of these and embodiments of any of the aspects provided herein, including those in this Exemplary Embodiments section, provided that it is not incompatible with, or already stated, the T cell activation element can be one or more of an anti-CD3 antibody or an anti-CD28 antibody. In some embodiments of these and embodiments of any of the aspects provided herein, including, but not limited to, in this Exemplary Embodiments section, unless incompatible with, or otherwise stated, the T cell activation element is one or more polypeptides, in illustrative embodiments membrane-bound polypeptides capable of binding CD28, OX40, 4-1BB, ICOS, CD9, CD53, CD63, CD81, and/or CD82. In some embodiments, a membrane-bound polypeptide capable of binding to CD3 is fused to a heterologous GPI anchor attachment sequence and/or a membrane-bound polypeptide capable of binding to CD28 is fused to a heterologous GPI anchor attachment sequence. In illustrative embodiments, the membrane-bound polypeptide capable of binding to CD28 is CD80, or an extra-cellular domain thereof, bound to a CD16B GPI anchor attachment sequence. In some embodiments, the T cell activation element further includes one or more polypeptides capable of binding CD3. In some subembodiments of these and embodiments of any of the aspects provided herein, including those in this Exemplary Embodiments section, provided that it is not incompatible with, or already stated, the T cell activation element is a membrane-bound anti-CD3 antibody, wherein the anti-CD3 antibody is bound to the membrane of the recombinant retroviral particles. In some embodiments, the membrane-bound anti-CD3 antibody is anti-CD3 scFv or an anti-CD3 scFvFc. In some embodiments, the membrane-bound anti-CD3 antibody is bound to the membrane by a heterologous GPI anchor. In some embodiments, the anti-CD3 antibody is a recombinant fusion protein with a viral envelope protein. In some embodiments, the anti-CD3 antibody is a recombinant fusion protein with the viral envelope protein from MuLV. In some embodiments, the anti-CD3 is a recombinant fusion protein with the viral envelope protein of MulV which is mutated at a furin cleavage site.

In any of the use, genetically modified T cell or NK cell, or method for genetically modifying T cells and/or NK cells aspects and embodiments provided herein, including, but not limited to, in this Exemplary Embodiments section, unless incompatible with, or otherwise stated, an ABC transporter inhibitor and/or substrate, in further subembodiments an exogenous ABC transporter inhibitor and/or substrate, is not present before, during, or both before and during the genetic modification and/or transduction.

In any of the reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the recombinant retroviral particles are present in the reaction mixture at an MOI of between 0.1 and 50, 0.5 and 50, 0.5 and 20, 0.5 and 10, 1 and 25, 1 and 15, 1 and 10, 1 and 5, 2 and 15, 2 and 10, 2 and 7, 2 and 3, 3 and 10, 3 and 15, or 5 and 15 or at least 0.1, 0.5, 1, 2, 2.5, 3, 5, 10 or 15 or are present in the reaction mixture at an MOI of at least 0.1, 0.5, 1, 2, 2.5, 3, 5, 10 or 15.

In any of the reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, at least 5%, at least 10%, at least 15%, or at least 20% of the T cells and/or NK cells are genetically modified, or between 5%, 10%, 15%, 20%, or 25% on the low end of the range, and 20%, 25%, 50%, 60%, 70%, 80%, or 85% on the high end of the range.

In any of the polynucleotide, replication incompetent recombinant retroviral particle, reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the one or more transcriptional units can encode a polypeptide comprising a lymphoproliferative element (LE). Any of the polypeptide lymphoproliferative elements disclosed herein, for example, but not limited to those disclosed in the "Lymphoproliferative elements" section herein, or functional mutants and/or fragments thereof, can be encoded. In some embodiments, the LE comprises an intracellular domain from CD2, CD3D, CD3E, CD3G, CD4, CD8A, CD8B, CD27, mutated Delta Lck CD28, CD28, CD40, CD79A, CD79B, CRLF2, CSF2RB, CSF2RA, CSF3R, EPOR, FCER1G, FCGR2C, FCGRA2, GHR, ICOS, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL7RA, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL31RA, LEPR, LIFR, LMP1, MPL, MYD88, OSMR, PRLR, TNFRSF4, TNFRSF8, TNFRSF9, TNFRSF14, or TNFRSF18, or functional mutants and/or fragments thereof.

In any of the replication incompetent recombinant retroviral particle, reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the replication incompetent recombinant retroviral particles are lentiviral particles. In further illustrative embodiments, the genetically modified cell is a genetically modified T cell or a genetically modified NKT cell.

In any of the polynucleotide, replication incompetent recombinant retroviral particle, reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the one or more transcriptional units can encode a polypeptide comprising a CAR. In some embodiments, the CAR is a microenvironment restricted biologic (MRB)-CAR. In other embodiments, the ASTR of the CAR binds to a tumor associated antigen. In other embodiments, the ASTR of the CAR is a microenvironment-restricted biologic (MRB)-ASTR.

In certain embodiments, any of the aspects and embodiments provided herein that include a polynucleotide, in some instances in the genome of a replication incompetent recombinant retroviral particle or a genetically modified T cell and/or NK cell, that comprises a nucleic acid sequences operatively linked to a promoter active in T cells and/or NK cells, that encodes at least one polypeptide lymphoproliferative element. In illustrative embodiments, the polypeptide lymphoproliferative element is any of the polypeptide lymphoproliferative elements disclosed herein. In some embodiments, any or all of the nucleic acid sequences provided herein can be operably linked to a riboswitch. In some embodiments, the riboswitch is capable of binding a nucleoside analog. In some embodiments, the nucleoside analog is an antiviral drug.

In any of the aspects and embodiments provided herein that include a replication incompetent recombinant retroviral particle, including, but not limited to aspects and embodiments in this Exemplary Embodiments section, unless incompatible with, or already stated in an aspect or embodiment, in illustrative embodiments, the replication incompetent recombinant retroviral particle comprises a pseudotyping element on its surface that is capable of binding to a T cell and/or NK cell and facilitating membrane fusion of the replication incompetent recombinant retroviral particle thereto. In some embodiments, the pseudotyping element is a viral envelope protein. In some embodiments, the viral envelope protein is one or more of the feline endogenous virus (RD114) envelope protein, the oncoretroviral amphotropic envelope protein, the oncoretroviral ecotropic envelope protein, the vesicular stomatitis virus envelope protein (VSV-G), the baboon retroviral envelope glycoprotein (BaEV), the murine leukemia envelope protein (MuLV), and/or the paramyxovirus Measles envelope proteins H and F, or a fragment of any thereof that retains the ability to bind to resting T cells and/or resting NK cells. In illustrative embodiments, the pseudotyping element is VSV-G. As discussed elsewhere herein, the pseudotyping element can include a fusion with a T cell activation element, which in illustrative embodiments, can be a fusion with any of the envelope protein pseudotyping elements, for example MuLV or VSV-G, with an anti-CD3 antibody. In further illustrative embodiments, the pseudotyping elements include both a VSV-G and a fusion of an antiCD3scFv to MuLV.

In any of the aspects provided herein that include a replication incompetent recombinant retroviral particle, in some embodiments, the replication incompetent recombinant retroviral particle comprises on its surface a nucleic acid encoding a domain recognized by a monoclonal antibody approved biologic.

In certain illustrative embodiments of any of the reaction mixture, use, genetically modified T cell or NK cell, or method for genetically modifying T cells and/or NK cells aspects and embodiments provided herein, including, but not limited to, in this Exemplary Embodiments section, unless incompatible with, or otherwise stated, the blood cells in the reaction mixture are blood cells that were produced by a PBMC enrichment procedure and comprise PBMCs, or the blood cells in illustrative embodiments are PBMCs. In illustrative embodiments, such embodiments including PMBC enrichment are not combined with an embodiment where the reaction mixture includes at least 10% whole blood. Thus, in certain illustrative embodiments herein, the blood cells in a reaction mixture are the PBMC cell fraction from a PBMC enrichment procedure to which retroviral particles are added to form the reaction mixture, and in other illustrative embodiments, the blood cells in a reaction mixture are from whole blood to which retroviral particles are added to form the reaction mixture.

The following non-limiting examples are provided purely by way of illustration of exemplary embodiments, and in no way limit the scope and spirit of the present disclosure.

Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1. Materials and Methods for Transduction Experiments

This Example provides materials and methods used in experiments disclosed in subsequent Examples herein.

Recombinant Lentiviral Particle Production by Transient Transfection.

293T cells (Lenti-X™ 293 T, Clontech) were adapted to suspension culture by serial growth in Freestyle™ 293 Expression Medium (ThermoFisher Scientific), named F1XT cells, and were used as the packaging cells for experiments herein unless noted otherwise.

Where noted, a typical 4 vector packaging system included 3 packaging plasmids that encoded (i) gag/pol, (ii) rev, and (iii) a pseudotyping element such as VSV-G. The $4^{th}$ vector of this packaging system is the genomic plasmid, a third generation lentiviral expression vector (containing a deletion in the 3' LTR leading to self-inactivation) that encoded 1 or more genes of interest. For transfections using 4 plasmids, the total DNA used (1 μg/mL of culture volume) was a mixture of the 4 plasmids at the following molar ratios: 1× gag/pol-containing plasmid, 1× Rev-containing plasmid, 1× viral envelope containing plasmid (VSV-G unless noted otherwise), and 2× genomic plasmid unless noted otherwise. Where noted, a typical 5 vector packaging system was used in which a $5^{th}$ vector encoding, for example, a T cell activation element such as antiCD3-scFvFc-GPI, was added to the otherwise 4 vector packaging system. For transfections using 5 plasmids, the total DNA used (1 μg/mL of culture volume) was a mixture of the 5 plasmids at the following molar ratios: 1× gag/pol-containing plasmid, 1× Rev-containing plasmid, 1×VSV-G containing plasmid, 2× genomic plasmid, and 1× of the $5^{th}$ vector unless noted otherwise.

Plasmid DNA was dissolved in 1.5 ml Gibco™ Opti-MEM™ growth media for every 30 mL of culture containing packaging cells. Polyethylenimine (PEI) (Polysciences) (dissolved in weak acid) was diluted in 1.5 ml Gibco™ Opti-MEM™ to 2 μg/mL. A 3 ml mixture of PEI and DNA was made by combining the two prepared reagents at a ratio of 2 ug of PEI to 1 ug of DNA. After a 5-minute room temperature incubation, the two solutions were mixed together thoroughly, and incubated at room temperature for 20 more minutes. The final volume (3 ml) was added to 30 ml of packaging cells in suspension at $1\times10^6$ cells/mL in a 125 mL Erlenmeyer flask. The cells were then incubated at 37° C. for 72 hours with rotation at 125 rpm and with 8% $CO_2$ for transfection.

After 72 hours, the supernatants were harvested and clarified by centrifugation at 1,200 g for 10 minutes. The clarified supernatants were decanted to a new tube. Virus was purified from the clarified supernatants by centrifugation, polyethylene glycol (PEG) precipitation, or depth filtration. For purification by centrifugation, the lentiviral particles were precipitated by overnight centrifugation at 3,300 g, at 4° C. The supernatant was discarded, and the lentiviral particle pellets were resuspended in 1:100 of the initial volume of packaging cell culture. For purification by PEG precipitation, ¼ volume PEG was added to the clarified supernatant and incubated overnight at 4° C. The mixture was then centrifuged at 1600 g for 1 hour (for 50 ml conical tubes) or 1800 g for 1.5 hours (for 500 ml conical tubes). The supernatant was discarded, and the lentiviral particle pellets were resuspended in 1:100 of the initial volume of packaging cell culture. For purification by depth filtration, the clarified supernatants were concentrated by tangential flow filtration (TFF) and benzonase digested. The virus was then purified and buffer exchanged by diafiltration into the final formulation (PBS with 2% lactose).

Lentiviral particles were titered by serial dilution and analysis of transgene expression, by transduction into 293T and/or Jurkat cells and analysis of transgene expression by FACS or qPCR for lentiviral genome using Lenti-X™ qRT-PCR Titration Kit (#631235) or p24 assay ELISA kit from Takara (Lenti-X™ p24 Rapid Titer Kit #632200).

Genomic Plasmids Used in Examples.

The following lentiviral genomic vectors encode genes and features of interest as indicated:

F1-3-23 encodes a CD19 CAR comprised of an anti-CD19scFv, a CD8 stalk and transmembrane region, and an intracellular domain from CD3z followed by T2A and an eTag (aCD19:CD8:CD3z-T2A-eTag).

Additional lentiviral genomic vectors are described in specific examples.

Example 2. Transduction Efficiency of Unstimulated PBMCs Exposed for 4 Hours to Retroviral Particles Pseudotyped VSV-G or Influenza HA and NA and Optionally Copseudotyped with Envelopes Derived from VSV-G, MV, or MuLV, and Further, Optionally, Displaying an Anti-CD3 scFv on their Surfaces In this example, lentiviral particles pseudotyped or cospeudotyped with various different envelope proteins and optionally displaying a T cell activation element, were exposed to unstimulated human PBMCs for 4 hours and transduction efficiency was assessed.

Recombinant lentiviral particles were produced in F1XT cells. The cells were transiently transfected using PEI with a genomic plasmid and separate packaging plasmids encoding gag/pol, rev, and an envelope plasmid. For certain samples, the transfection reaction mixture also included a plasmid encoding UCHT1scFvFc-GPI, a copseudotyping envelope, or a copseudotyping envelope fused to an antiCD3scFv. The genomic plasmid used for samples in this example was F1-0-03 as disclosed in other examples herein. The pseudotyping and copseudotyping plasmids used for samples in this example encoded envelope proteins from VSV-G (SEQ ID NO:336), U-VSV-G (SEQ ID NO: 455) in which the anti-CD3 scFv from UCHT1 was fused to the amino terminus of the VSV-G envelope, influenza HA from H1N1 PR8 1934 (SEQ ID NO: 311) and NA from H10N7-HKWF446C-07 (SEQ ID NO:312), U-MuLV (SEQ ID NO:341) in which the anti-CD3 scFv from UCHT1 was fused to the amino terminus of the MuLV envelope, U-MuLV variants in which 8 to 31 C-terminal amino acids were deleted from the cytoplasmic tail, U-MuLVSUx (SEQ ID NO: 454) in which the furin-mediated cleavage site Lys-Tyr-Lys-Arg in U-MuLV was replaced with the Ile-Glu-Gly-Arg peptide, or MVHΔ24 (SEQ ID NO: 315) in which the C-terminal 24 amino acids of the measles virus H protein were removed.

In certain samples the U-MuLV envelope protein was endcoded on the rev packaging plasmid in tandem in the format U-MuLV-IRES2-rev (MuLVIR) or in the format U-MuLV-T2A-rev (MuLV2R). By putting the copseudotyping element on a packaging vector such as rev, 4 rather than 5 separate plasmids were used to transfect packaging cells. It was observed herein that transfecting with 4 rather than 5 plasmids resulted in higher viral titers.

On Day 0, PBMCs were prepared from buffy coats from 2 donors as described in Example 1 without any additional steps to remove monocytes. After isolation, $1\times10^6$ unstimulated PBMCs in 1 ml of X-Vivo15 were seeded into each well of a 96 deep-well plates. Viral particles were added at an MOI of 1 or 10 as indicated, and the plates were incubated for 4 hours at 37° C. and 5% CO2. After the 4 hour exposure, the cells were pelleted for 5 minutes at 400 g and washed 3 times by resuspending the cells in 2 mls of DPBS+2% HSA and centrifuging for 5 minutes at 400 g, before the cells in each well were resuspended in 1 ml X-Vivo15 and incubated at 37° C. and 5% CO2. No exogenous cytokines were added to the samples at any time. Each sample was run in duplicate using PBMCs from each of the 2 donors. Samples were collected at Day 6 to determine transduction efficiencies based on eTAG, and CD3 expression as determined by FACs analysis using a lymphocyte gate based on forward and side scatter.

Figure 3A:
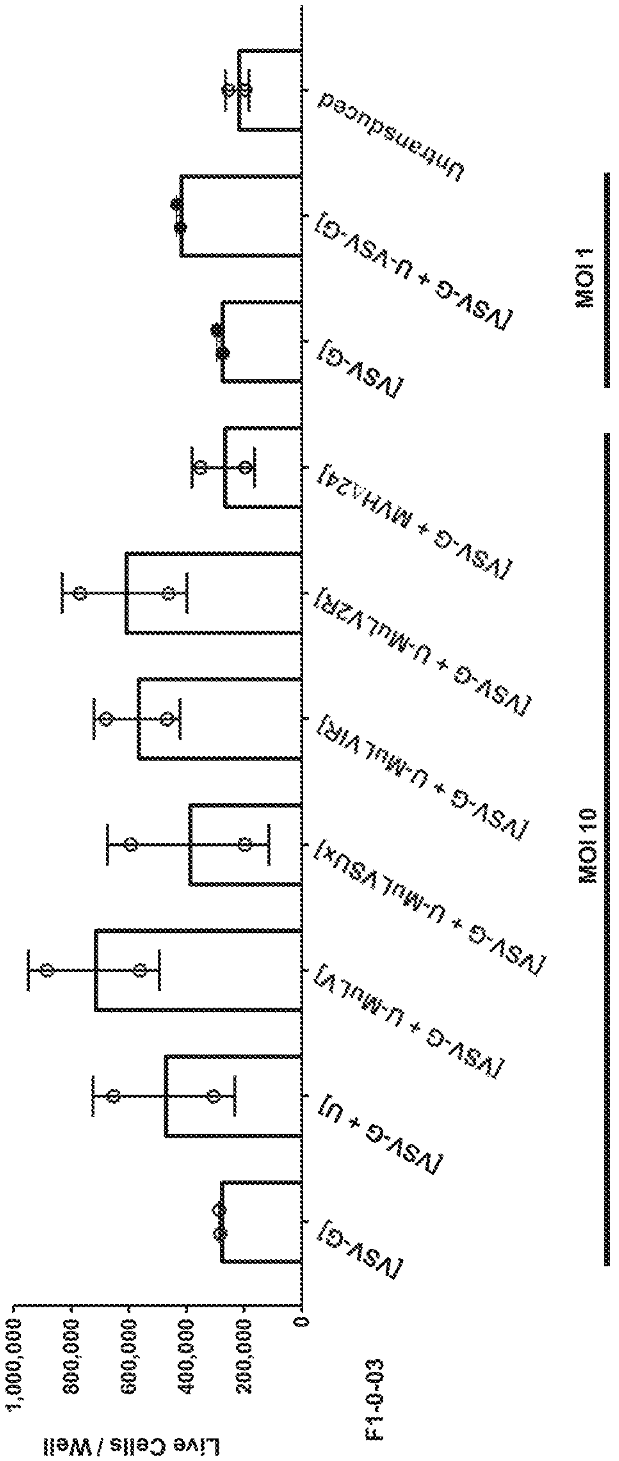
FIGS. 3A and 3B show histograms of experimental results with different pseudotyping elements.

FIG. 3A shows the total number of live cells per well on Day 6 following transduction. Compared to samples exposed to viral particles pseudotyped with VSV-G alone, samples exposed to viral particles pseudotyped with VSV-G and also displaying UCHT1 had a greater number of cells per well. This was observed both when UCHT1scFv was displayed as a GPI-linked scFvFc and when the scFv was fused to either the VSV-G or MuLV viral envelopes. Not to be limited by theory, the stimulation of CD3+T and NK cells by the antiCD3 scFv is believed to lead to proliferation and survival which can account for at least a portion of this increase in cell number.

Figure 3B:
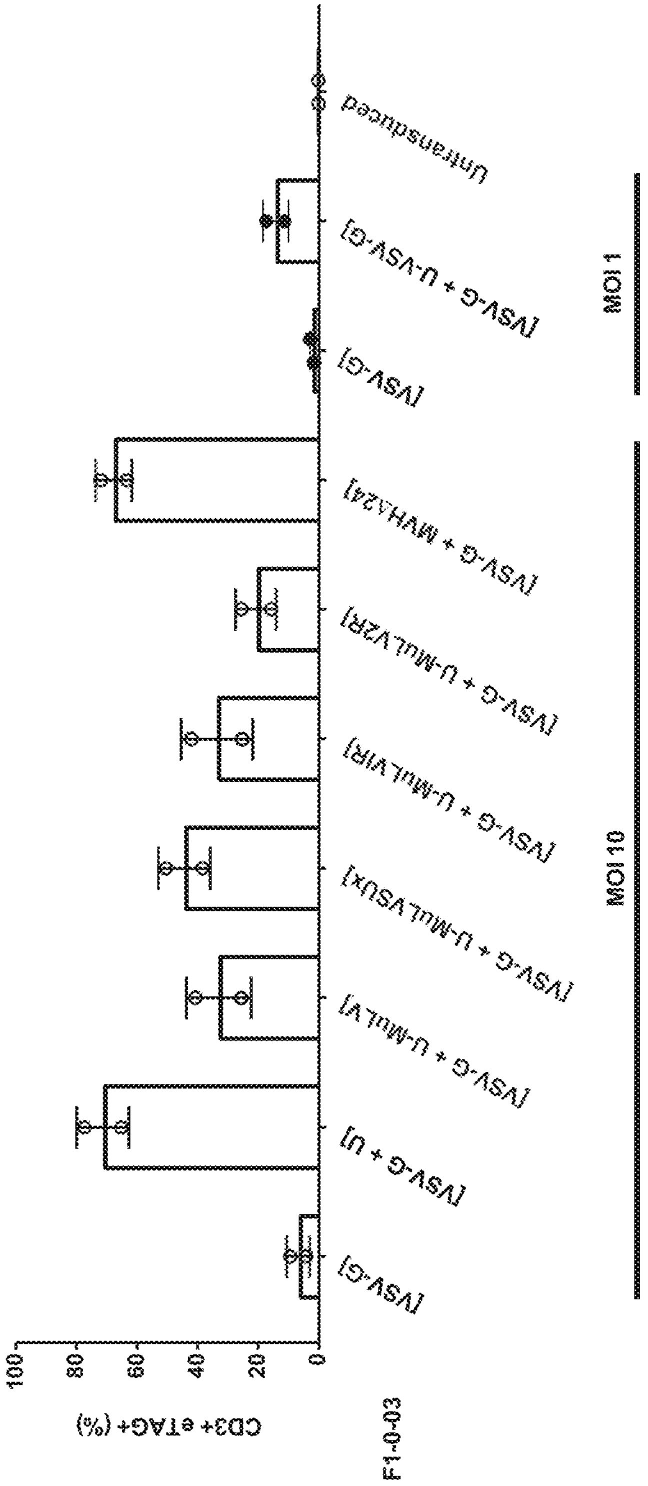

FIG. 3B shows the percent of CD3+ cells transduced as measured by eTAG expression. Samples exposed to viral particles pseudotyped with VSV-G that also either displayed UCHT1ScFvFc-GPI or were copseudotyped with U-MuLV, U-MuLVSUx, U-VSV-G, or MVHΔ24 had higher transduction efficiencies than samples exposed to viral particles pseudotyped with VSV-G alone that didn't display an antiCD3 antibody. Among the 4 samples tested in this experiment at an MOI of 10, the efficiency by which VSV-G+UCHT1scFvFc-GPI viral particles transduced CD3+ unstimulated PBMCs was 64.3%, 66.3%, 78.0%, and 76.7%. Among the 4 samples tested in this experiment at an MOI of 10, the efficiency by which VSV-G+U-MuLV viral particles transduced CD3+ unstimulated PBMCs was 37.6%, 43.8%, 20.5%, and 30.8%. When copseudotyped with VSV-G, individual variants of U-MuLV in which the 4, 8, 12, 16, 20, 24, 28, and 31 C-terminal amino acids were deleted, transduced CD3+ unstimulated PBMCs in 4 hours similar to full length U-MuLV (not shown). Similarly, when copseudotyped with VSV-G, individual variants of U-MuLVSUx in which the Factor X cleavage site (AAAIEGR) between the transmembrane (TM) and surface (SU) units was replaced with (G4S)3 or "AAAIAGA", transduced CD3+ unstimulated PBMCs in 4 hours similar to U-MuLVSUx (not shown). Among the 4 samples tested in this experiment at an MOI of 10, the efficiency by which VSV-G+MVHΔ24 viral particles transduced CD3+ unstimulated PBMCs was 64.5%, 62.4%, 72.3%, and 71.5%. In a separate experiment, viral particles pseudotyped with influenza HA from H1N1 PR8 1934 and NA from H10N7-HKWF446C-07 transduced CD3+ unstimulated PBMCs with comparable efficiency to viral particles copseudotyped with VSV-G+U-MuLV.

Example 3. Efficient Genetic Modification of Resting Lymphocytes by Exposure of Whole Blood to Recombinant Retroviral Particles for 4 Hours Followed by a PBMC Enrichment Procedure In this example, unstimulated human T cells and NKT cells were effectively genetically modified by a 4 hour incubation of a reaction mixture that included whole blood and retroviral particles that were pseudotyped with VSV-G and displayed a T cell activation element on their surface. PBMCs were subsequently isolated from the transduction reaction mixture using a traditional density gradient centrifugation-based PBMC enrichment procedure. Transduction of CD3+ cells was assessed by expression of the eTag transgene using flow cytometry.

Depth filtration was used to purify the following lentiviral particles used in this Example: F1-3-23 pseudotyped with VSV-G (F1-3-23G); and F1-3-23 pseudotyped with VSV-G and displaying the T cell activation element, UCHT1-scFvFc-GPI (F1-3-23GU).

10 ml samples of whole fresh blood in Vacutainer tubes containing anticoagulants were purchased. (StemExpress, San Diego). The anticoagulant in individual samples was either EDTA 1.8 mg/ml or Na-Heparin 16 USP units per mL of blood. Recombinant lentiviral particles were added directly to the Vacutainer tubes of whole blood at an MOI of 5 (assuming $1\times10^6$ PBMCs/ml of blood) to initiate contacting of the lentiviral particles to lymphocytes in the whole blood, and incubated for 4 hours, at 37° C., 5% $CO_2$ with gentle mixing every hour to disrupt any sedimentation. After the 4 hour incubation, PBMCs from each whole blood sample were isolated individually using SepMate50 tubes (STEMCELL Technologies) according to the manufacturer's protocol. PBMCs were collected in 15 ml conical tubes and washed by resuspending the cells in 10 mls DPBS+2% HSA, and centrifuging them for 5 minutes at 400 g. This wash procedure was repeated 3 times before the cells were resuspended in 10 ml X-Vivo15 and cultured upright in T75 flasks at 37° C. and 5% $CO_2$. No exogenous cytokines were added to the samples at any time. Samples were collected at Day 6 to determine transduction efficiencies based on eTag and CD3 expression on live cells as determined by FACs analysis using a lymphocyte gate based on forward and side scatter.

Figure 4A:
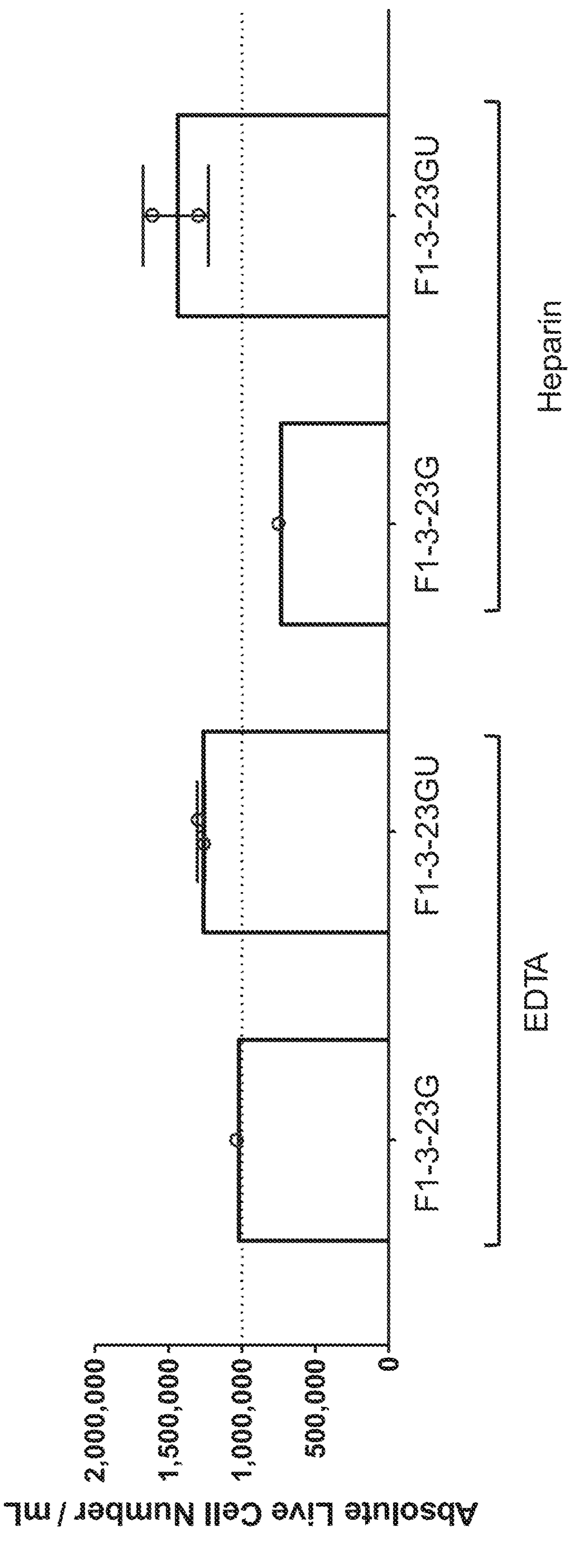
FIGS. 4A and 4B show histograms of experimental results with transduction reaction mixtures that include whole blood, lentiviral particles, and anti-coagulants EDTA or heparin, without PBMC enrichment before the reaction mixture was formed. The process was performed by contacting whole blood for 4 hours with the indicated lentiviral particle F1-3-23G or F1-3-23GU followed by a density gradient centrifugation-based PBMC enrichment procedure.
Figure 4B:
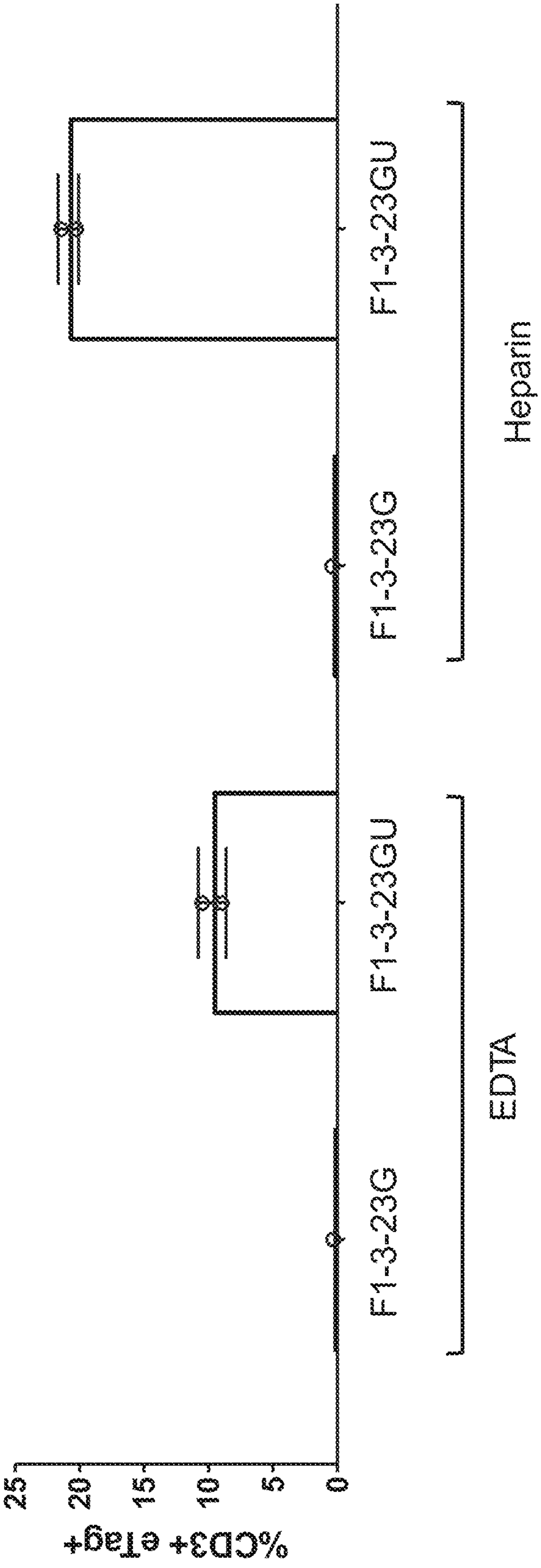

FIGS. 4A and 4B show histograms of the absolute live cell count per ml (FIG. 4A) and the percentage of CD3+ eTag+ cells (i.e. transduced T cells) (FIG. 4B) at Day 6 after transduction of whole blood. Consistent with our previous results and the results of others studying transduction of isolated PBMCs, we see in this Example that recombinant retroviral particles pseudotyped with VSV-G alone are extremely inefficient at transducing PBMCs in whole blood. We have seen previously, however, that recombinant retroviral particles pseudotyped with VSV-G and displaying a T cell activation element, are capable of efficiently transducing isolated PBMCs. Surprisingly, these histograms show that a PBMC enrichment step is not required for retroviral particles to efficiently transduce PBMCs present in whole blood. Rather, retroviral particles pseudotyped with VSV-G and displaying antiCD3-scFvFc when added directly to whole blood containing an anticoagulant can effectively genetically modify and transduce PBMCs therein. Genetic modification can be achieved by a contacting and incubation that is as brief as 4 hours before the cells are washed to remove free recombinant retroviral particles. After the cells are genetically modified, they can be effectively isolated using a PBMC enrichment procedure. As shown in this Example, the anticoagulant can be EDTA or Na-Heparin. Similar results were obtained using ACD as the anticoagulant in other experiments.

Example 4. Time Course of Retroviral Transduction of Unstimulated PBMCs by Exposure Times of 4 Hours to Less than 1 Minute In this experiment, recombinant lentiviral particles were contacted and incubated with unstimulated PBMCs for between 4 hours and less than 1 minute, and were examined for their ability to transduce the PBMCs and promote their survival and/or proliferation in vitro in the absence of any exogenous cytokines.

Methods

Recombinant lentiviral particles were produced in 293T cells (Lenti-X™ 293T, Clontech) that were adapted to suspension culture in Freestyle™ 293 Expression Medium (Thermo Fisher Scientific). The cells were transiently transfected using PEI with a genomic plasmid and separate packaging plasmids encoding gag/pol, rev, and a pseudotyping plasmid encoding VSV-G as described in Example 3 of WO 2019/055946. For certain samples, the transfection reaction mixture also included a plasmid encoding UCHT1scFvFc-GPI as further described in Example 3 of WO 2019/055946. Two genomic plasmids were used in this example. The first plasmid included a Kozak sequence, a CD8a signal peptide, a FLAG tag, and an anti-CD19:CD8:CD3z CAR followed by a triple stop sequence (F1-3-253). The second plasmid included a Kozak sequence, a CD8a signal peptide, a FLAG tag, an anti-CD19:CD8:CD3z CAR, T2A, and the CLE DL3A-4 (E013-T041-5186-5051) followed by a triple stop sequence (F1-3-451).

On Day 0, PBMCs were enriched from buffy coats (San Diego Blood Bank) from 2 donors by density gradient centrifugation with Ficoll-Paque PREMIUM® (GE Healthcare Life Sciences) and SepMate™-50 (Stemcell™ Technologies) according to the manufacturer's instructions. No additional steps were taken to remove monocytes. After isolation, the PBMCs were diluted to $1\times10^6$ PBMCs per 1 ml of X-Vivo15 (LONZA) and 1 ml was seeded into each well of 96 deep-well plates. Cells from each donor were also set aside for phenotype analysis by FACS. No anti-CD3, anti-CD28, IL-2, IL-7, or other exogenous cytokine was added to activate or otherwise stimulate the lymphocytes prior to transduction. Lentiviral particles were added directly to the non-stimulated PBMCs at an MOI of 1. The transductions were incubated at 37° C. and 5% $CO_2$ for either 4 hours, 2 hours, 30 minutes, 15 minutes, 7.5 minutes, 5 minutes, 2.5 minutes or not incubated at all before the cells were spun down using a 5 minute centrifugation at 400 g, and then washed 3 times in 1 ml of DPBS+2% HSA, using 5 minute centrifugations at 400 g. Thus, for a calculation of combined transduction and incubation times, 5 minutes could be added to account for the first centrifugation, in which it is believed that the vast majority of lentiviral particles not associated with cells, were separate away from the cells. The cells in each well were then resuspended in 1 ml X-Vivo15 and incubated at 37° C. and 5% $CO_2$. For samples treated with antiviral drugs, dapivirine or dolutegravir was added to a final concentration of 10 μM during the transduction and the transduction reaction was incubated at 37° C. and 5% $CO_2$ for 4 hours. The drugs were replenished at the same concentrations in the recovery medium after the three washes. No exogenous cytokines were added to the samples at any time. Samples were collected at Day 6 and transduction efficiencies based on FLAG expression was determined by FACS analysis using a lymphocyte gate based on forward and side scatter.

Results

Figure 5:
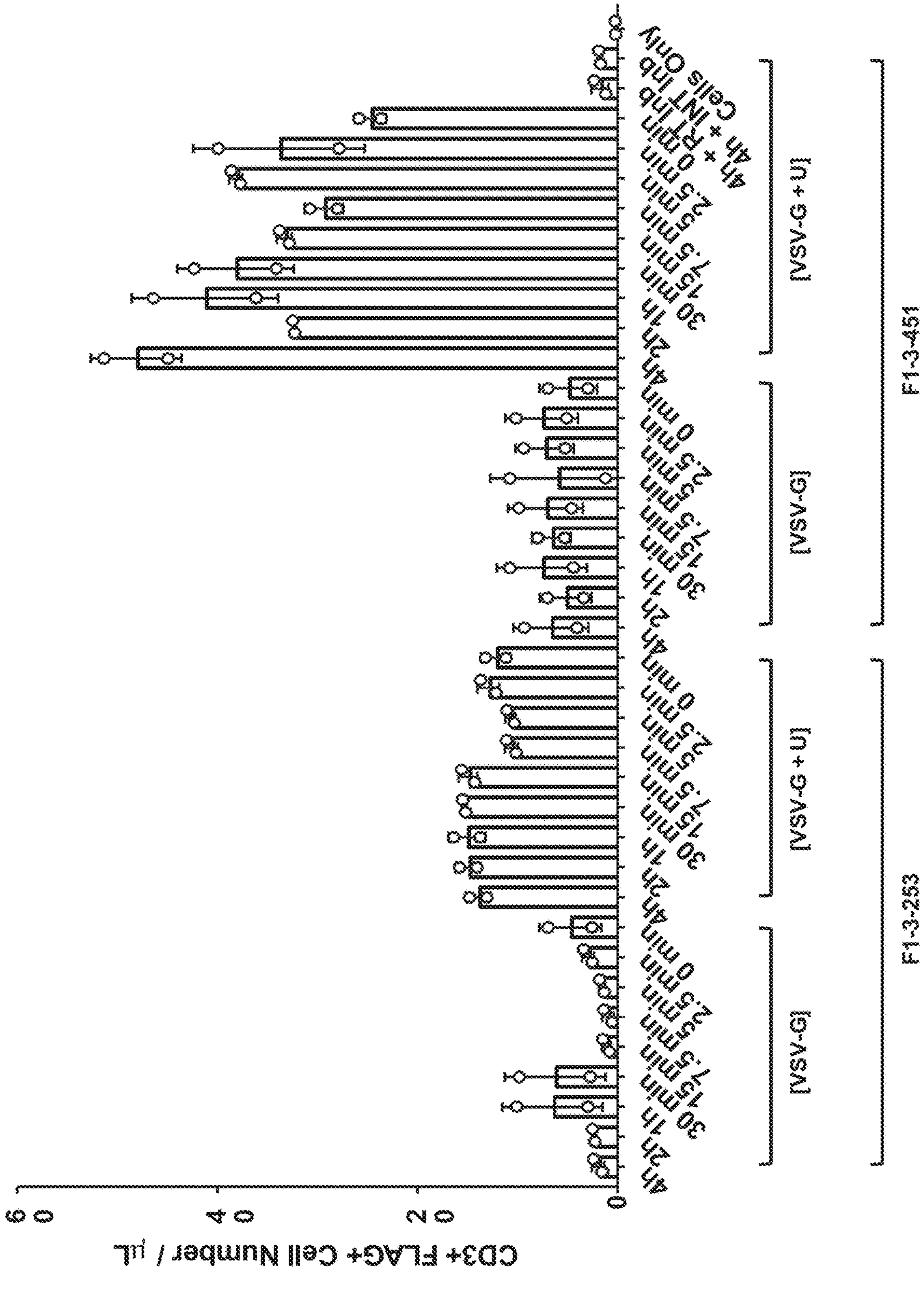
FIG. 5 is a histogram showing the CD3+FLAG+ cell number per μl of culture at Day 6 after transduction of unstimulated PBMCs by the different recombinant lentiviral particles at an MOI of/for the indicated period of time. F1-3-253 encoded an anti-CD19 CAR and F1-3-451 encoded a CLE in addition to the same CAR. The lentiviral particles were pseudotyped with VSV-G [VSV-G] and optionally displayed UCHT1ScFvFc-GPI [VSV-G+U] as indicated. Samples were treated with dapivirine, an inhibitor of reverse transcription (RT inb) or dolutegravir, an inhibitor to integration (INT Inb), as indicated.

In this example, an incubation period of less than 1 minute was found to be as effective at promoting the transduction of unstimulated PBMCs by recombinant lentiviral particles as was an incubation period of 4 hours. FIG. 5 shows the CD3+FLAG+ absolute cell count (per ul) at Day 6 after transduction of unstimulated PBMCs from 1 Donor by the different recombinant lentiviral particles for the indicated period of time. The ability of each of the recombinant lentiviral particles to transduce PBMCs was similar across all incubation periods. This is particularly evident for the lentiviral particles that express anti-CD3scFvFc-GPI and had higher transduction efficiencies than their non anti-CD3scFvFc-GPI expressing counterparts. For all incubation times examined, the total number of transduced PBMCs was greater in those samples transduced by [F1-3-451GU] than by [F1-3-253GU] indicating that the DL3A CLE encoded in F1-3-451 is promoting the survival and/or proliferation of these cells. The inhibition of transduction by dapivirine, a reverse transcriptase, and dolutegravir, an integrase inhibitor, as shown in FIG. 5 demonstrate that genetic modification and transgene expression by these PBMCs is not pseudotransduction, but rather is the result of transduction in which the viral transgene RNA is reverse transcribed, integrated into the genomes of PBMCs, and expressed Similar results were observed using PBMCs from the second Donor.

Example 5. miRNA Expression Increased In Vivo Survival and/or Proliferation of Transduced Cells Expressing a CAR In this example, two miRNA libraries (Library 314 and Library 315) of candidate (putative) blocks of 4 miRNA precursors were assembled in series from pools of individual miRNA precursors. The miRNA blocks were inserted into the EF-1 alpha intron of lentiviral constructs encoding an EF-1 alpha promoter driving expression of a CAR. Human PBMCs were transduced with lentiviral particles encoding these libraries, and injected into tumor-bearing mice. After 20 days, the tumors were harvested and the identity of the miRNA blocks in the PBMCs from the tumors was determined by PCR followed by Sanger Sequencing. Thus, the screen identified miRNA blocks that are able to promote the proliferation and/or survival of transduced PBMCs in a tumor.

Methods

Library Preparation 108 gBlocks® Gene Fragments were used to generate a library of constructs each containing 4 miRNA precursors in series in positions 1 (P1), 2 (P2), 3 (P3), and 4 (P4). Each gBlock® was specific to P1, P2, P3, or P4 and contained a miR-155 framework (SEQ ID NO:457), including a 5' arm and a 3' arm as described in Example 17 of WO 2019/055946, in which a unique miRNA fragment targeting an mRNA transcript corresponding to 1 of 27 different genes was used to replace the miR-155 stem-loop precursor. For clarity, the sequences of miRNA fragments differed for each position P1-P4 even among miRNA fragments that targeted mRNA transcripts corresponding to the same gene. The gBlocks® for each position contained a unique 40 bp overlap sequence and the type IIs assembly method was used to assemble combinations of four gBlocks® in their prescribed order, to generate the library. By these methods, a total diversity of 531,441 unique constructs (27 miRNA at P1×27 miRNA at P2×27 miRNA at P3×27 miRNA at P4) was possible.

The library of miRNA constructs was separately cloned into the EF-1 alpha intron A of F1-1-315 and F1-2-314 to generate Library 315 and Library 314, respectively. In addition to the EF-1 alpha promoter, F1-1-315 included a CD8a signal peptide, an anti-ROR2:CD28:CD3z CAR, T2A, and an eTag. Similarly, in addition to the EF-1 alpha promoter, F1-2-314 included a CD8a signal peptide, an anti-Ax1:CD8:CD3z CAR, T2A, and an eTag. FIGS. 26A and 26B of WO 2019/055946 include a similar lentiviral vector with an EF-1 alpha promoter, including intron A with 4 miRNA precursors, that drove expression of GFP instead of either CAR.

The 27 gene targets in this example and the sequence identification numbers for DNA sequences corresponding to the miRNAs in each position are shown in Table 2 below.

TABLE 2

SEQ ID NOs. of DNA sequences corresponding to miRNA at each position for each target.

| Gene Target | Position 1 | Position 2 | Position 3 | Position 4 |
|---|---|---|---|---|
| cCBL | SEQ ID NO: 342 | SEQ ID NO: 343 | SEQ ID NO: 344 | SEQ ID NO: 345 |
| CD3z | SEQ ID NO: 346 | SEQ ID NO: 347 | SEQ ID NO: 348 | SEQ ID NO: 349 |
| PD1 | SEQ ID NO: 350 | SEQ ID NO: 351 | SEQ ID NO: 352 | SEQ ID NO: 353 |
| CTLA4 | SEQ ID NO: 354 | SEQ ID NO: 355 | SEQ ID NO: 356 | SEQ ID NO: 357 |
| TIM3 | SEQ ID NO: 358 | SEQ ID NO: 359 | SEQ ID NO: 360 | SEQ ID NO: 361 |
| LAGS | SEQ ID NO: 362 | SEQ ID NO: 363 | SEQ ID NO: 364 | SEQ ID NO: 365 |
| SMAD2 | SEQ ID NO: 366 | SEQ ID NO: 367 | SEQ ID NO: 368 | SEQ ID NO: 369 |
| TNFRSF10B | SEQ ID NO: 370 | SEQ ID NO: 371 | SEQ ID NO: 372 | SEQ ID NO: 373 |
| PPP2CA | SEQ ID NO: 374 | SEQ ID NO: 375 | SEQ ID NO: 376 | SEQ ID NO: 377 |
| TNFRSF6 | SEQ ID NO: 378 | SEQ ID NO: 379 | SEQ ID NO: 380 | SEQ ID NO: 381 |
| BTLA | SEQ ID NO: 382 | SEQ ID NO: 383 | SEQ ID NO: 384 | SEQ ID NO: 385 |
| TIGIT | SEQ ID NO: 386 | SEQ ID NO: 387 | SEQ ID NO: 388 | SEQ ID NO: 389 |
| A2AR | SEQ ID NO: 390 | SEQ ID NO: 391 | SEQ ID NO: 392 | SEQ ID NO: 393 |
| AHR | SEQ ID NO: 394 | SEQ ID NO: 395 | SEQ ID NO: 396 | SEQ ID NO: 397 |
| EOMES | SEQ ID NO: 398 | SEQ ID NO: 399 | SEQ ID NO: 400 | SEQ ID NO: 401 |
| SMAD3 | SEQ ID NO: 402 | SEQ ID NO: 403 | SEQ ID NO: 404 | SEQ ID NO: 405 |
| SMAD4 | SEQ ID NO: 406 | SEQ ID NO: 407 | SEQ ID NO: 408 | SEQ ID NO: 409 |
| TGFBR2 | SEQ ID NO: 410 | SEQ ID NO: 411 | SEQ ID NO: 412 | SEQ ID NO: 413 |
| PPP2R2D | SEQ ID NO: 414 | SEQ ID NO: 415 | SEQ ID NO: 416 | SEQ ID NO: 417 |
| TNFSF6 | SEQ ID NO: 418 | SEQ ID NO: 419 | SEQ ID NO: 420 | SEQ ID NO: 421 |
| CASP3 | SEQ ID NO: 422 | SEQ ID NO: 423 | SEQ ID NO: 424 | SEQ ID NO: 425 |
| SOCS2 | SEQ ID NO: 426 | SEQ ID NO: 427 | SEQ ID NO: 428 | SEQ ID NO: 429 |
| TIEG1 | SEQ ID NO: 430 | SEQ ID NO: 431 | SEQ ID NO: 432 | SEQ ID NO: 433 |
| JunB | SEQ ID NO: 434 | SEQ ID NO: 435 | SEQ ID NO: 436 | SEQ ID NO: 437 |
| Cbx3 | SEQ ID NO: 438 | SEQ ID NO: 439 | SEQ ID NO: 440 | SEQ ID NO: 441 |
| Tet2 | SEQ ID NO: 442 | SEQ ID NO: 443 | SEQ ID NO: 444 | SEQ ID NO: 445 |
| HK2 | SEQ ID NO: 446 | SEQ ID NO: 447 | SEQ ID NO: 448 | SEQ ID NO: 449 |

Lentiviral Particle Production

Library 315 and Library 314 were separately used to produce lentiviral particles in 30 ml suspension cultures of 293T cells. The lentiviral particles were harvested and concentrated by PEG precipitation. Other details regarding lentiviral particle production are provided in Example 17 of WO 2019/055946.

Transduction

On Day 0, PBMCs were isolated from ACD peripheral blood and 5.0×10[7] viable PBMCs were seeded into each of two 1L G-Rex devices in 100 ml with Complete OpTmizer™ CTS™ T-Cell Expansion SFM supplemented with 100 IU/ml IL-2 (Novoprotein, GMP-CD66), 10 ng/ml IL-7 (Novoprotein, GMP-CD47), and 50 ng/ml anti-CD3 antibody (Novoprotein, GMP-A018) to activate the PBMCs, which included T cells and NK cells, for viral transduction. Lentiviral particles were added directly to the activated PBMCs in 1 G-Rex for Library 315 and the other G-Rex for Library 314 at an MOI of 5, and incubated overnight. The G-Rex devices were incubated in a standard humidified tissue culture incubator at 37° C. and 5% $CO_2$ with additions of 100 IU/ml recombinant human IL-2 and 10 ng/ml recombinant human IL-7 solution every 48 hours and the cultures were expanded until day 12 at which time the cells are predominantly T cells. Other details regarding PBMC enrichment, transduction, and ex vivo expansion are provided in Example 16 of WO 2019/055946.

Tumor Inoculation and Administration of Transduced Cells

A xenograft model using NOD Scid Gamma (NSG) mice was chosen to probe the ability of human PBMCs transduced with lentiviral particles of Library 315 or Library 314 to survive and/or proliferate in vivo, where the tumors expressed or did not express the antigen recognized by the CAR encoded in the genomes of these lentiviral particles. Mice were handled in accordance with Institutional Animal Care and Use Committee approved protocols. Subcutaneous (sc) tumor xenografts were established in the hind flank of 12 week old female NOD-Prkdc$^{scid}$Il2rg$^{tm1}$/Begen (B-NSG) mice (Beijing Biocytogen Co. Ltd.). Briefly, cultured CHO cells, cultured CHO cells transfected to stably express human ROR2 (CHO-ROR2) or human AXL (CHO-AXL) were separately washed in DPBS (Thermo Fisher), counted, resuspended in cold DPBS and mixed with an appropriate volume of Matrigel ECM (Corning; final concentration 5 mg/mL) at a concentration of $0.47\times10^6$ cells/200 µl on ice Animals were prepared for injection using standard approved anesthesia with hair removal (Nair) prior to injection. 200 µl of either cell suspension in ECM was injected sc into the rear flanks for CHO cells (n=2), CHO-ROR2 cells (n=1), and CHO-AXL cells (n=1), respectively.

5 days after tumor inoculation, 1 mouse bearing a CHO tumor and 1 mouse bearing a CHO-ROR2 tumor were dosed intravenously (IV) by tail vein injection with 200 µl DPBS containing $1\times10^7$ PBMCs transduced with lentiviral particles from Library 315 after 12 days of ex vivo culture. Similarly, 5 days after tumor inoculation, 1 mouse bearing a CHO tumor and 1 mouse bearing a CHO-Ax1 tumor were dosed intravenously (IV) by tail vein injection with 200 µl DPBS containing $1\times10^7$ PBMCs transduced with lentiviral particles from Library 314.

Tumor Harvesting and DNA Sequencing

On day 20 after dosing with transduced PBMCs, the tumors were excised. DNA from half of each tumor was extracted and 4 ug from each tumor was used as a template in a PCR reaction for 25 cycles to amplify the EF-1alpha intron. The amplicons were cloned into a sequencing vector, transformed into bacteria, and streaked onto plates. 18 total colonies (~5 per mouse) were selected and DNA was prepared and analyzed using Sanger sequencing to determine the sequences of a sample of the miRNA constructs present in the tumor.

Results

A mouse xenograft model was used to determine whether miRNA targeting specific gene transcripts were able to increase the proliferation and/or survival of transduced PBMCs expressing CARs in vivo, where the xenografts were tumors with or without expression of the target antigen of the CARs. For this analysis, a library of miRNA constructs was generated consisting of miRNAs directed against 27 distinct targets. The miRNA constructs analyzed contained 4 positions for 4 separate miRNAs, as shown in FIG. 26B and Example 17 and Example 18 of WO 2019/055946. Tumor DNA was analyzed by sequencing the EF-1 alpha intron to identify which miRNA constructs were present 20 days after injection of transduced PBMCs, and therefore which miRNA constructs increased proliferation and/or survival.

531,441 different combinations of 4 miRNAs in series were possible. Of the 18 EF-1 alpha introns sequenced, 13 contained a miRNA construct where all 4 miRNA in the construct were directed against one target, and 2 contained miRNA constructs directed to more than 1 target. Table 3 below shows the miRNA species recovered from each of the 4 tumors examined in this example.

TABLE 3

Identity of miRNA target at each position of the miRNA constructs that were sequenced.

| Library | Tumor | Position 1 | Position 2 | Position 3 | Position 4 |
|---|---|---|---|---|---|
| Library 315 | CHO | FAS | FAS | FAS | FAS |
| | | FAS | FAS | FAS | FAS |
| | | AHR | AHR | AHR | AHR |
| | | FAS | FAS | FAS | FAS |
| | | CD3z | CD3z | CD3z | CD3z |
| Library 315 | CHO-ROR2 | NA | NA | NA | NA |
| | | FAS | FAS | FAS | FAS |
| | | FAS | FAS | FAS | FAS |
| | | cCBL | cCBL | cCBL | cCBL |

TABLE 3-continued

Identity of miRNA target at each position of the miRNA constructs that were sequenced.

| Library | Tumor | Position 1 | Position 2 | Position 3 | Position 4 |
|---|---|---|---|---|---|
| Library 314 | CHO | Cbx | Cbx | Cbx | Cbx |
| | | cCBL | cCBL | cCBL | cCBL |
| | | HK2 | HK2 | HK2 | HK2 |
| | | NA | NA | NA | NA |
| Library 314 | CHO-AXL | NA | NA | NA | NA |
| | | FAS | FAS | FAS | FAS |
| | | FAS | FASL | SMAD4 | HK2 |
| | | SMAD4 | SMAD4 | SMAD4 | SMAD4 |
| | | HOMES | NA | EOMES | AHR |

Notably, 6 EF-1alpha introns contained a miRNA construct with all 4 miRNA directed against TNFRSF6 (FAS). 2 EF-1alpha introns contained a miRNA construct with all 4 miRNA directed against cCBL. For each of AHR, CD3z, Cbx, and HK2, 1 EF-1alpha intron was identified that contained an miRNA construct with all 4 miRNA directed against that gene transcript. "NA" indicated that no miRNA block was identified in that position. Together, these results indicate that knocking down transcripts encoding FAS, cCBL, CD3z, Cbx, HK2, FASL, SMAD4, EOMES, and AHR can promote the survival and/or proliferation of T cells in the tumor microenvironment. The identification of 4 miRNA in series to FAS under each condition in 6 of the 18 samples examined indicates that knocking down FAS transcripts confers a particular advantage for survival and/or proliferation. Furthermore, this data suggests that there is a dosage effect such that 4 species of miRNA directed to FAS, cCBL, AHR, CD3z, Cbx, and HK2, leads to greater knockdown of transcripts encoding these genes than does 1, 2, or 3 species, and that this increased knockdown confers a survival and/or proliferation advantage.

Example 6. Identification of Candidate Chimeric Polypeptide Lymphoproliferative Elements Using an In Vivo Assay In this example, two chimeric polypeptide libraries (Library 6 and Library 8) of candidate (putative) chimeric lymphoproliferative elements (CLEs) were assembled into viral vectors from pools of extracellular-transmembrane block sequences, intracellular block sequences, and a barcode library according to the chimeric polypeptide-encoding construct provided in FIG. 6. The chimeric library candidates (putative CLEs) were screened for the ability of the candidate chimeric polypeptides to promote expansion of T cells in vivo.

Library Constructs

Figure 6:
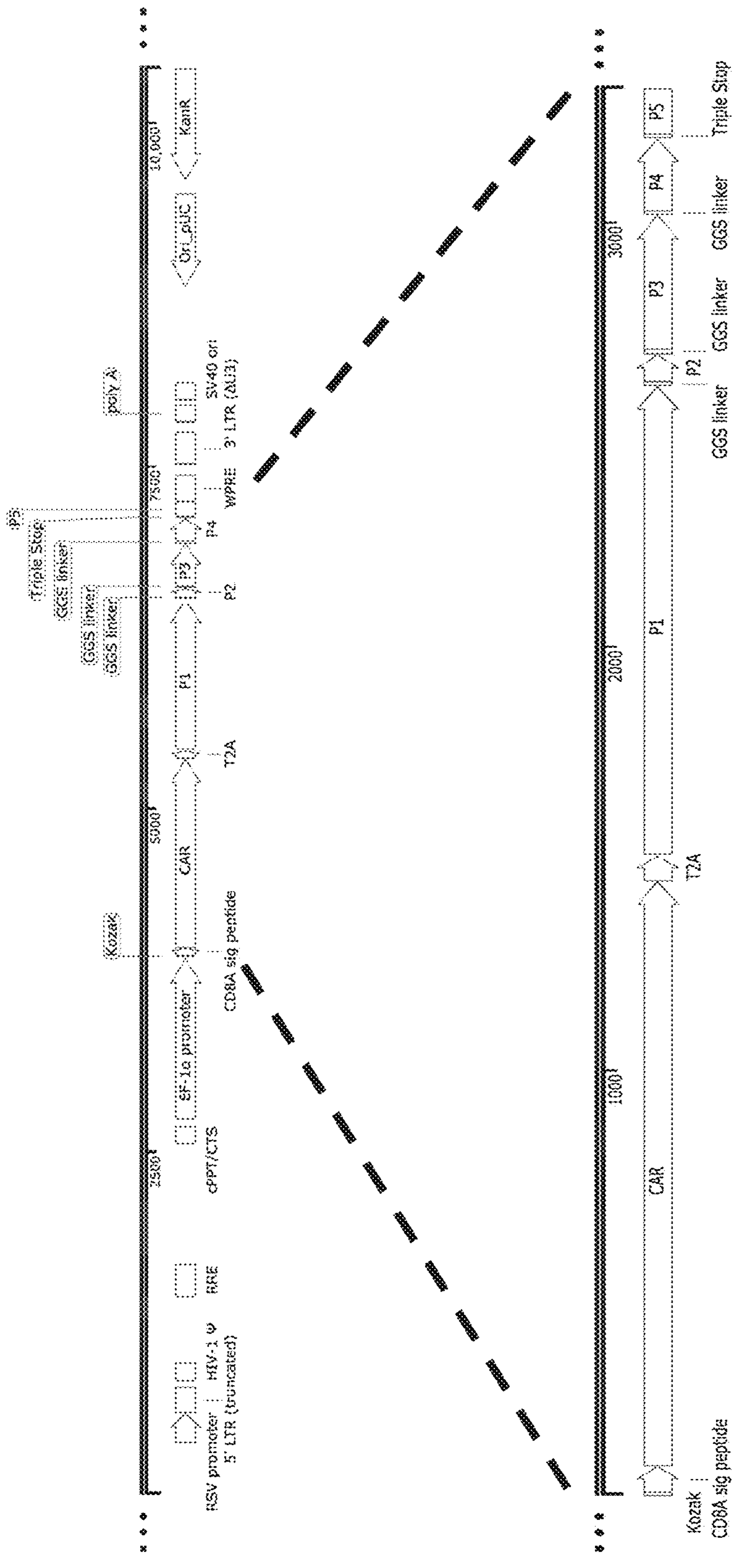
FIG. 6 is a schematic of a non-limiting, exemplary transgene expression cassette containing a polynucleotide sequence encoding a CAR and a candidate CLE of Libraries analyzed in Example 6.

Two libraries were made and analyzed in this study; Library 6 and Library 8. The libraries shared a common structure, which is shown in FIG. 6. FIG. 6 provides a schematic of a non-limiting, exemplary transgene expression cassette containing a polynucleotide sequence encoding a CAR and a candidate CLE from a library having 4 modules driven by an EF-1 alpha promoter and a Kozak-type sequence (GCCGCCACC(SEQ ID NO:450)), in a lentiviral vector backbone. Each candidate lymphoproliferative element included 4 modules; an extracellular module (P1), a transmembrane module (P2), and 2 intracellular modules (P3 and P4). The P1 module encoded an eTAG at the 5' terminus of a c-Jun domain A triple stop sequence (TAATAGTGA (SEQ ID NO:451)) separated P4 from a DNA barcode (P5). A WPRE (GTCCTTTC-CATGGCTGCTCGCCTGTGTTGCCACCTGGAT-TCTGCGCGGGACGTCCTTCTGCTA CGTCCCTTCGGCCCT-CAATCCAGCGGACCTTCCTTCCCGCGGCCTGCT-GCCGGCTCTGCGGCC TCTTCCGCGTCTTCGCCTTCGCCCTCA-GACGAGTCG-GATCTCCCTTTGGGCCGCCTCCCCGCC TG (SEQ ID NO:452)) was present between the last stop codon (starting 4 bp after the last nucleotide of P5) and the 3' LTR (which started 83 nucleotides after the last nucleotide of the WPRE).

The CAR and P1 were separated by a polynucleotide sequence encoding a T2A ribosomal skip sequence. The general design and construction of the library, including the barcode, was as disclosed in Example 11 of WO 2019/055946, except for the P1 and P2 domains, as set out in more detail later in this Example.

The design of Library 6 and Library 8 differed only in the polynucleotide encoding the CAR. The CAR of Library 6 encoded an MRB-ASTR that has an scFv that recognizes human AXL, a CD28 stalk and transmembrane sequence (SEQ ID NO:25), a CD28 intracellular domain deleted for Lck binding (ICA) (SEQ ID NO:55), and an intracellular activating domain from CD3z (SEQ ID NO: 28). The CAR of Library 8 encoded a FLAG-tagged MRB-ASTR that has an scFv that recognizes human ROR2, a CD8 stalk and transmembrane sequence (SEQ ID NO:24), a CD137 intracellular domain (SEQ ID NO:53), and an intracellular activating domain from CD3z (SEQ ID NO: 28).

Synthesis of Viral Vectors and Lentiviral Production

Vectors were synthesized and lentiviral particles were produced for each library as disclosed in Example 11 of WO 2019/055946.

Transduction and Culturing of PBMCs

Whole human blood from 2 healthy donors was collected and processed separately using a Sepax 2 S-100 device to obtain PBMCs as described in Example 12 of WO 2019/055946. 4.75e7 or 5e7 viable PBMCs for Libraries 6 and 8, respectively, were seeded into each of two 1L G-Rex devices in 100 ml and activated, transduced, and the cultures were expanded for 12 days as described in Example 5 above. 3.9e9 total cells were recovered (82-fold expansion) for Library 6, 9.71e7 of which were CD3+eTAG+ transduced T cells. 2.47e9 total cells were recovered (49-fold expansion) for Library 8, 2.44e8 of which were CD3+eTAG+ transduced T cells. 4e6 cells from each expansion were set aside and frozen for later analysis by next generation sequencing.

Tumor Inoculation and Administration of Transduced Cells

A xenograft model using NSG mice was chosen to probe the ability of human PBMCs transduced with lentiviral particles of Library 6 or Library 8 to survive and/or proliferate in vivo, where the tumors expressed or did not express the antigen recognized by the CAR encoded in the genomes of these lentiviral particles. Subcutaneous (sc) CHO, CHO-ROR2, or CHO-AXL tumor xenografts were established in the hind flanks of B-NSG (Beijing Biocytogen Co. Ltd.) mice as described in Example 5.

5 days after tumor inoculation, 6 mice bearing CHO tumors and 5 mice bearing CHO-Ax1 tumors were dosed intravenously (IV) by tail vein injection with 200 μl DPBS containing $7\times10^7$ PBMCs transduced with lentiviral particles from Library 6. Similarly, 5 days after tumor inoculation, 6 mice bearing CHO tumors and 5 mice bearing CHO-ROR2 tumors were dosed IV by tail vein injection with 200 μl DPBS containing $7\times10^7$ PBMCs transduced with lentiviral particles from Library 8. Mice bearing CHO tumors, CHO-AXL tumors, or CHO-ROR2 tumors were also dosed with 200 μl DPBS alone as controls.

Tissue Harvesting, Isolation of Human CD45+ Cells, and DNA Sequencing

Approximately 100 μl of blood was collected from each mouse on days 7, 14, and 21 (for Library 6) or days 7, 14, and 19 (for Library 8) after dosing with transduced PBMCs. Spleen and tumor was also collected when the mice were euthanized on day 21 or day 19. Half of each tissue was processed to isolate human CD45+ cells by mechanically disrupting the tissue, enzymatic digestion with collagenase IV and DNAse I, and magnetic isolation of cells using hCD45 antibody (Biolegend, 304004). Genomic DNA was prepared from these hCD45+ cells and corresponds to "purified spleen" and "purified tumor" samples. Genomic DNA was prepared directly from the other half of each tissue and corresponds to "non purified spleen" and "non purified tumor. Purified genomic DNA was sequenced using an Illumina HiSeq, generating paired-end 150 bp reads. Usually, a subset of 10 million reads was extracted from each indexed fastq file and processed for analysis using barcode reader, a custom R script engineered to extract barcode sequences based on the presence of a constant region. Purified genomic DNA was also sequenced on a PacBio sequencing system to obtain longer read lengths to associate barcodes with constructs.

qPCR

Genomic DNA (gDNA) isolated from tissue samples were evaluated for the presence of transduced lymphocytes by bioanalytical qPCR. Genomic DNA was isolated from the samples using the QIAamp DNA Blood Mini kit (Qiagen 51106) and the DNA was further cleaned using the QIAamp DNA Micro Kit (56304). A TaqMan assay (Thermo Fisher) was performed on the isolated genomic DNA using a primer and probe set specific for the 5' LTR of lentivirus to quantitate lentivirus copy number per ug of tissue.

Data Analysis

DNA barcodes were identified in a 20 million subset of Illumina HiSeq sequenced reads. Count data for all samples was assembled and barcodes present in less than 2 samples were considered artifactual and discarded. Count data from pre-injection PBMCs was used as a representation of the initial barcode population. Full length constructs were identified using an association table created by Long Read Sequencing of a few select samples. After summing up counts for barcodes mapping to the same construct, all data was scaled based on qPCR-quantified lentivirus copy number per ug of tissue. Samples with very low lentivirus copy numbers were removed from the analysis. Ranking of CAR/antigen signal-independent chimeric polypeptide candidates was obtained by calculating the total counts for each construct in each tissue of interest from mice bearing CHO tumors devoid of the cognate target antigen recognized by the CAR Ranking for CAR/antigen signal-dependent drivers was obtained using the following formula: MR*-log 10(P), where the MR was the mean ratio between the count values in the mice bearing tumors with antigen (CHO-AXL or CHO-ROR2) and tumors without antigen (CHO) and P was the p value obtained from a one-sided Mann-Whitney-Wilcoxon test comparing the count values in the mice bearing tumors with or without antigen. One-sided Mann-Whitney-Wilcoxon tests were used to determine whether a particular part was enriched as compared with all other represented parts for a specific position. Individual tissue p values were aggregated using the Stouffer sumz method to obtain final rankings Full construct rankings were obtained by averaging individual tissue ranks.

Results

In this experiment, chimeric polypeptide candidates were designed to have 4 test domains, which included an extracellular domain (P1), a transmembrane domain (P2), a first intracellular domain (P3), and a second intracellular domain (P4) (FIG. 6). As explained in Examples 11 and 12 of WO 2019/055946, the constructs included a DNA barcode to aid in analysis and identification of the construct using next-generation sequencing. Additionally, all of the constructs included nucleic acid sequences encoding a recognition and/or elimination domain in frame with the extracellular domain. The constructs in this Example also encoded a CAR directed to human AXL or human ROR2 upstream of the chimeric polypeptide candidate (FIG. 6). The extracellular domains (P1), transmembrane domains (P2), first intracellular domains (P3), and second intracellular domains (P4) used to generate the chimeric polypeptide candidates in Library 6 and Library 8 were the same as in Example 12 of WO 2019/055946. The libraries did not include all of the possible combinations of P1-P4 domains.

The number of constructs present after transduction of PBMCs and 12 days of growth in culture in the presence of exogenous cytokines was determined for both Library 6 and Library 8 by counting the number of individual barcodes that were present in more than one read in the day 12 cultured sample. Of the 697,410 potential combinations, 219,649 and 127,634 different constructs were detected for Library 6 and Library 8, respectively. Detailed information about the top candidates analyzed can be determined from Table 1 and Tables 4-8. The coding system for constructs is the same as explained for Examples 11 and 12 of WO 2019/055946.

After culturing for 12 days, transduced PBMCs were injected into mice bearing tumors with or without antigen. PBMCs transduced with constructs from Library 6, which encoded the anti-AXL CAR, were injected into mice bearing CHO tumors or CHO-AXL tumors, and PBMCs transduced with constructs from Library 8, which encoded the anti-ROR2 CAR, were injected into mice bearing CHO tumors or CHO-ROR2 tumors. After 21 or 19 days of in vivo expansion (Library 6 and Library 8, respectively), samples from the blood, spleen, and tumor of each mouse were harvested. Half of each spleen and tumor was processed to isolate CD45+ cells and is referred to herein in this example as a "purified" sample. DNA from each sample from each mouse (blood, non-purified spleen, purified spleen, non-purified tumor, and purified tumor) was sequenced. The barcodes on each construct were used to identify and sum the number of sequencing reads for each construct in each sample.

A non-parametric analysis was used to identify constructs that promoted PBMC cell proliferation in vivo in either a CAR/antigen signal-independent or CAR/antigen signal-dependent manner. To identify chimeric polypeptide candidates that were CAR/antigen signal-independent, each sample of each construct was ranked based on the number of sequencing reads in mice bearing CHO tumors. The top constructs were identified as having the best average rank of the 5 tissue samples. The top 100 chimeric polypeptide candidates that were CAR/antigen signal-independent for Library 6 and Library 8 are shown in Tables 4 and 5, respectively.

To identify chimeric polypeptide candidates that were CAR/antigen signal-dependent, the ranking for each sample included the ratio of reads between mice bearing tumors with antigen (CHO-AXL or CHO-ROR2) and mice bearing tumors without antigen (CHO). The top 100 chimeric polypeptide candidates that were CAR/antigen signal-dependent for Library 6 and Library 8 are shown in Tables 6 and 7, respectively.

An additional analysis was run to identify noteworthy chimeric polypeptide candidates that were CAR/antigen signal-independent. For this analysis, 20 parts were first identified that performed the best for any P2, P3, or P4 position, based on a statistical test to determine whether a particular part was enriched as compared with all other represented parts for a specific position. In this combined analysis, from constructs that included at least one of these 20 parts, best-performing constructs from either Library 6 or Library 8 were identified based on the sum of the normalized counts in mice bearing CHO tumors. The 30 best-performing chimeric polypeptide candidates according to this analysis that were CAR/antigen signal-independent are shown in Table 8.

Several of the CLEs identified in the library screen and shown in Table 8 were generated as individual chimeric polypeptides in lentivirus constructs behind the anti-AXL CAR as configured in Library 6 and run in confirmatory in vitro screens. Frozen PBMCs from 3 donors were thawed and rested in Complete OpTmizer™ CTS™ T-Cell Expansion SFM supplemented with 100 IU/ml of IL-2 and 10 ng/ml IL-7 overnight in a standard humidified tissue culture incubator at 37° C. and 5% $CO_2$. The PBMCs were activated on Day 0 with 50 ng/ml anti-CD3 and transduced on Day 1 with viral particles at an MOI of 5. On Day 2 the PBMCs were transferred to the wells of a 24-well G-Rex plate and cultured in Complete OpTmizer™ CTS™ T-Cell Expansion SFM in the absence of any exogenous cytokines until Day 35 days. In replicate experiments performed using PBMCs from 3 donors, CLE's with P2, P3, and P4 configurations T001-5121-5212 and T044-5186-5053 showed particularly noteworthy expansion on Days 14, 21, 28, and 35.

Example 7. Characterization of Individual Lymphoproliferative Elements

In this example, select chimeric lymphoproliferative elements (CLEs) identified in the library screens described in Example 17 and Example 18 of WO2018/161064A1 and Example 11 and Example 12 of WO2019/055946A1 were assessed individually. To further analyze CLEs identified in the screens of Library 2B, activated PBMCs were transduced overnight with lentiviral particles encoding a CLE alone and cultured in the absence of exogenous cytokines. To further analyze CLEs identified in the screens of Library 3A, activated PBMCs were transduced overnight with lentiviral particles encoding a CLE flanked with an anti-CD19 CAR at the 5' end, and cultured in the presence of donor-matched CD19+ B cells added to the culture every 7 days, but in the absence of exogenous cytokines. The cells were cultured for up to 35 days to assess the ability of the CLEs to promote PBMC proliferation. This example further provides methods by which to characterize any individual putative lymphoproliferative element and further confirms the identities of several highly active CLEs.

Figure 7:
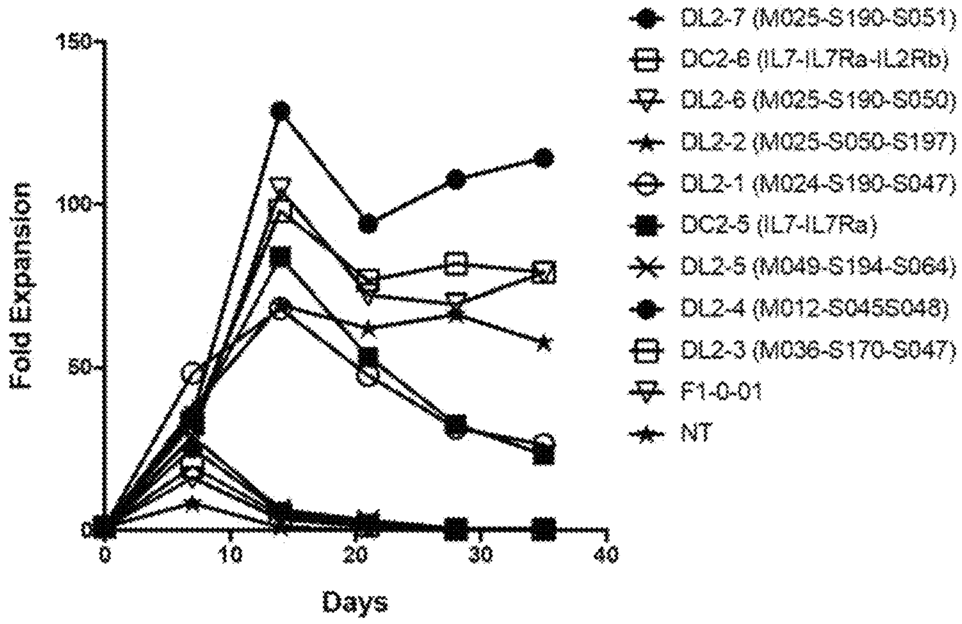
FIG. 7 is a graph showing the fold expansion of PBMCs transduced with lentiviral particles encoding individual CLEs and cultured for 35 days in the absence of exogenous cytokines.
Figure 8:
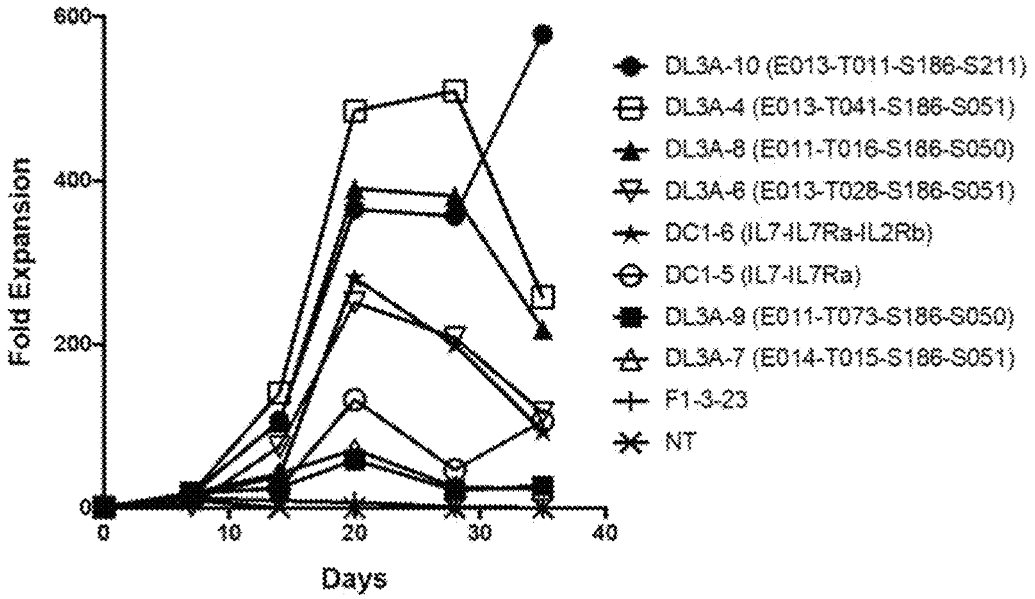
FIG. 8 is a graph showing the fold expansion of PBMCs transduced with lentiviral particles encoding an anti-CD19 CAR construct and individual CLEs and cultured for 35 days in the presence of donor matched PBMCs but in the absence of exogenous cytokines.
Figure 9:
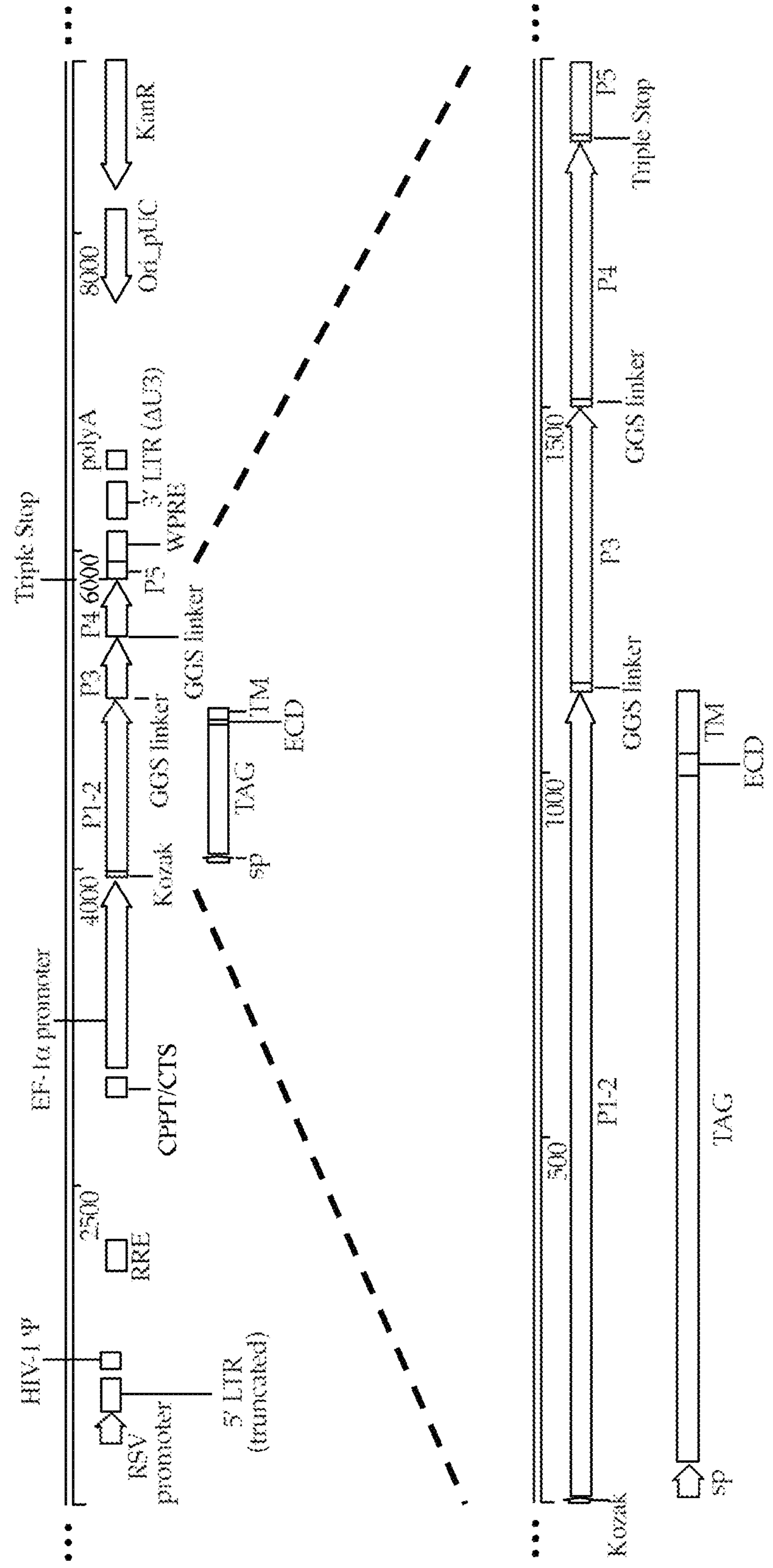
FIG. 9 is a schematic of a non-limiting, exemplary transgene expression cassette containing a polynucleotide sequence encoding a candidate CLE of Libraries 2B and 2.1B.
Figure 10:
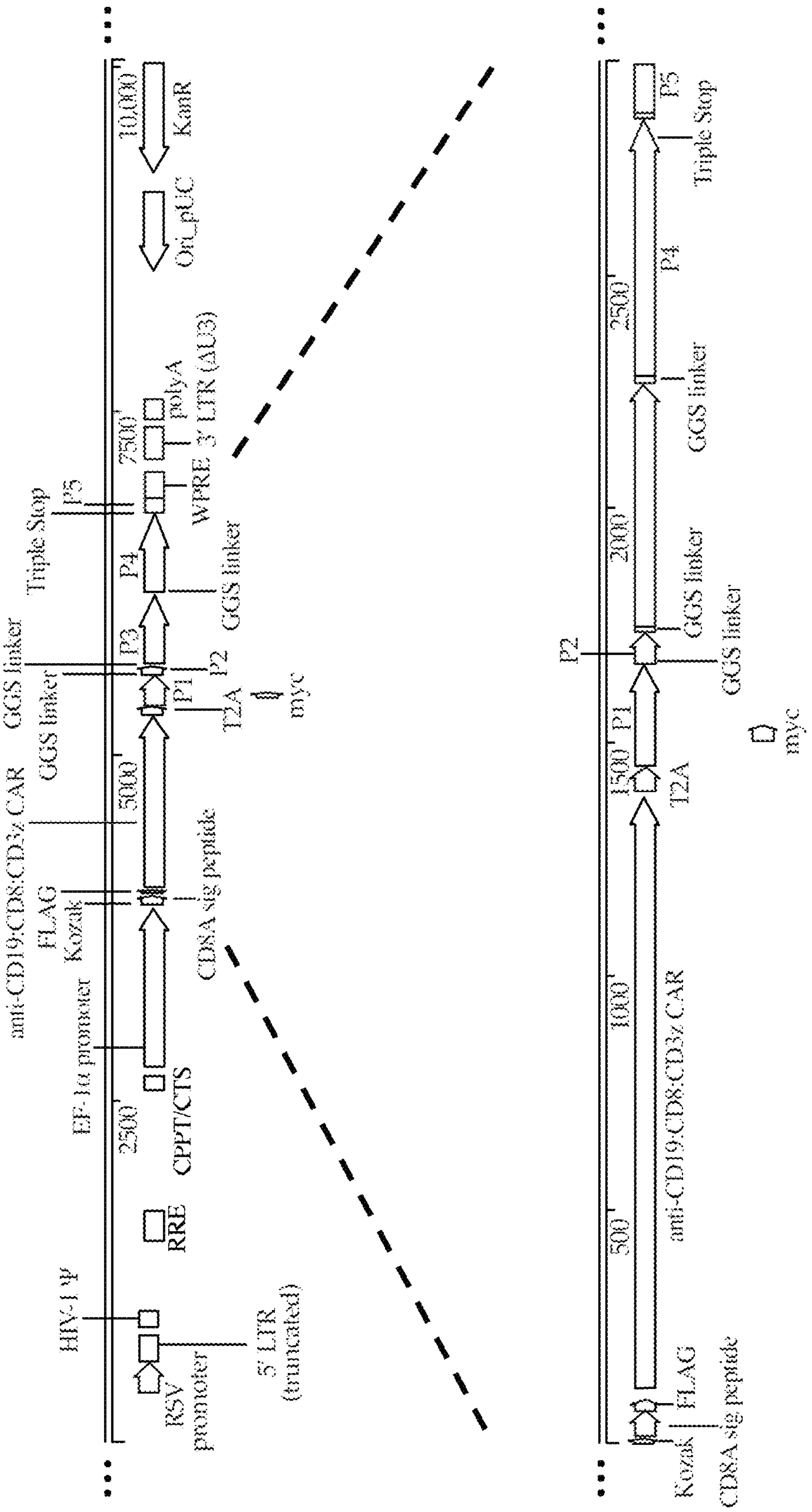
FIG. 10 is a schematic of a non-limiting, exemplary transgene expression cassette containing a polynucleotide sequence encoding a CAR and a candidate CLE of Libraries 3A, 3B, 3.1A, and 3.1B.
Figure 11:
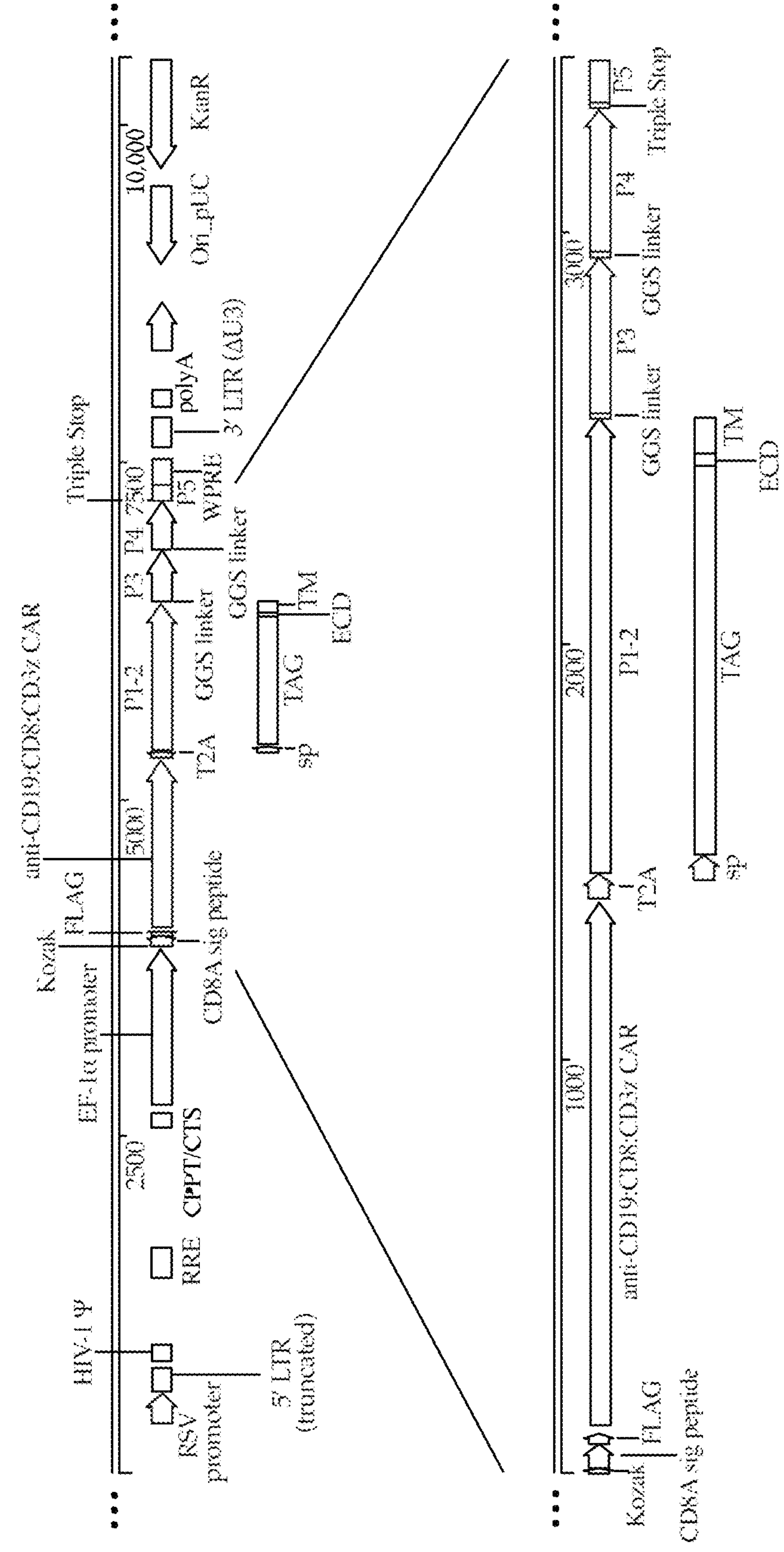
FIG. 11 is a schematic of a non-limiting, exemplary transgene expression cassette containing a polynucleotide sequence encoding a CAR and a candidate chimeric lymphoproliferative element (CLE) of Libraries 1A, 1.1A, and 1.1B.

Recombinant lentiviral particles were produced in 293T cells (Lenti-X™ 293T, Clontech) that were adapted to suspension culture in Freestyle™ 293 Expression Medium (Thermo Fisher Scientific) serum-free chemically defined medium. The cells were transiently transfected using PEI with a genomic plasmid and 3 separate lentiviral packaging plasmids encoding gag/pol, rev, and a pseudotyping plasmid encoding VSV-G as explained in Example 20 of WO2018/161064A1 and Example 4 of WO2019/055946A1. Selected CLEs identified in the library screens described in Example 17 and Example 18 of WO2018/161064A1 and Example 11 and Example 12 of WO2019/055946A1 were regenerated individually from their parts (P1-2, P3, and P4 or P1, P2, P3, and P4) and inserted into the same transgene expression cassettes as that of the library from which they were first identified. The module parts of each of the selected CLEs are shown in FIGS. 7 and 8 and the gene names and amino acids sequences are shown in Table 1. FIGS. 9 and 10 show the cassettes for Libraries 2 and 3, respectively. Cells transduced with lentiviral particles containing constructs identified through library screens are referred to as "DL" followed by the library number. For example, cells transduced with lentiviral particles containing constructs from Library 2 are referred to as DL2. Thus, CLEs with the prefix "DL2" and "DL3" were constructed in the cassette shown in FIGS. 9 and 10, respectively. Similarly, "DC1-5" and "DC1-6" comprise CLEs inserted into the transgene expression cassette used for Library 1 as shown in FIG. 11. The chimeric lymphoproliferative element of DC1-5 encoded from amino to carboxy terminus, human IL-7 (SEQ ID NO:458), a flexible linker (SEQ ID NO:63), and residues 21-458 of the human IL-7Rα (SEQ ID NO:459) which is the full length IL-7Rα without its signal peptide. The CLE of DC1-6 encoded from amino to carboxy terminus, IL-7 (SEQ ID NO:458), a flexible linker (SEQ ID NO:63), the extracellular and transmembrane portions of the IL-7Rα (CD127) (SEQ ID NO:460), and the intracellular domain of the IL-2Rβ (CD122) (SEQ ID NO:461). The chimeric proteins IL-7-IL-7Rα and IL-7-IL-7Rα-IL-2Rβ have been described previously (Hunter et al. *Molecular Immunology* 56(2013):1-11). The IL-7 "DC2-5" and "DC2-6" comprise CLEs inserted into the transgene expression cassette used for Library 2 as shown in FIG. 9. The CLEs in DC2-5 and DC2-6 were the same CLEs as DC1-5 and DC1-6, respectively. Untransduced PBMCs (NT), PMBCs transduced with a vector that encoded an eTag but not a CLE (F1-0-01), and PMBCs transduced with a vector that encoded an anti-CD19 CAR and an eTag but not a CLE (F1-3-23) were included as negative controls.

The constructs from Library 2B used in this Example were: DL2-1 (M024-5190-5047), DL2-2 (M025-5050-5197), DL2-3 (M036-5170-5047), DL2-4 (M012-5045-5048), DL2-5 (M049-5194-5064), DL2-6 (M025-5190-5050), and DL2-7 (M025-5190-5051).

The constructs from Library 3A used in this Example were: DL3A-1 (E013-T047-5158-5080), DL3A-2 (E011-T024-S194-S039), DL3A-3 (E014-T040-S135-S076), DL3A-4 (E013-T041-S186-S051), DL3A-5 (E013-T064-5058-5212), DL3A-6 (E013-T028-S186-S051), DL3A-7 (E014-T015-S186-S051), DL3A-8 (E011-T016-5186-5050), DL3A-9 (E011-T073-5186-5050), and DL3A-10 (E013-T011-S186-S211).

On Day 0, PBMCs were enriched from buffy coats (San Diego Blood Bank) by density gradient centrifugation with Ficoll-Paque PREMIUM® (GE Healthcare Life Sciences) according to the manufacturer's instructions followed by lysis of red blood cells. $1.5\times10^6$ viable PBMCs were seeded in the wells of G-Rex 6 Well Plates (Wilson Wolf, 80240M) in 3 ml Complete OpTmizer™ CTS' T-Cell Expansion SFM supplemented with 100 IU/ml (IL-2), and 50 ng/ml anti-CD3 antibody (317326, Biolegend) to activate the PBMCs for viral transduction. After incubation overnight at 37° C. and 5% $CO_2$, lentiviral particles encoding the constructs described above were added directly to the activated PBMCs at an MOI of 5 and incubated overnight at 37° C. and 5% $CO_2$. The following day, the media volume in each well was brought to 30 ml with Complete OpTmizer™ CTS™ T-Cell Expansion SFM and the plates were returned to the incubator. No IL-2, IL-7, or other exogenous cytokine was added at this or subsequent cell culture steps. The cells from each well were collected on Day 7 to determine cell numbers, percent viability, and percent transduced cells, which was defined as the percent of FLAG-Tag+ or E-Tag+ cells by FACS analysis. The cells were then centrifuged, resuspended in fresh Complete OpTmizer™ CTS™ T-Cell Expansion SFM, and $0.5\times10^6$ cells for each sample were re-seeded into the well of a G-Rex 6 Well Plate in 30 ml of Complete OpTmizer™ CTS™ T-Cell Expansion SFM. Previously cryopreserved Day 0 donor matched PBMCs containing $0.5\times10^6$ CD19+ B cells (as determined by FACS on Day 0) were added to cultures of "DL3A-" to provide CD19+ B-cell activation of the CD19 ASTR. This process was repeated on days 14, 20, and 28 before the cells were harvested on Day 35.

Results

PBMCs transduced with lentiviral particles encoding CLEs were cultured in the absence of exogenous cytokines for 35 days. Proliferation is represented as fold expansion which was calculated by dividing the total number of cells by the number of cells seeded for that time point. PBMCs transduced with each individual selected CLE shown in FIG. 7 proliferated more than the negative controls, which included untransduced PBMCs and PMBCs transduced with a vector that encoded an eTag but not a CLE (FIG. 7). Furthermore, the following CLEs exhibited a fold expansion greater than 23 at days 14, 21, 28, and 35 while the fold expansion of the negative controls was near 0 for these timepoints: DL2-7, DC2-6, DL2-6, DL2-2, DL2-1, and DC2-5. PBMCs transduced with constructs encoding an anti-CD19 CAR and various CLEs (shown in FIG. 8) and cultured in the presence of fresh donor matched PBMCs added every 7 days, but in the absence of exogenous cytokines, proliferated more than the negative controls, which included untransduced PBMCs and PMBCs transduced with a vector that encoded an anti-CD19 CAR and an eTag but not a CLE. All of the CLEs shown in FIG. 8 exhibited a fold expansion greater than 23 at day 35 while the fold expansion of the negative controls was near 0 at day 35. The proliferation of PBMCs transduced with lentiviral particles containing polynucleotides encoding DL3A-1 (E013-T047-S158-S080), DL3A-2 (E011-T024-S194-S039), DL3A-3 (E014-T040-S135-S076), and DL3A-5 (E013-T064-5058-5212) were comparable to the negative controls and are not shown on FIG. 8. Expression of these CLEs in cells transduced with retroviral particles whose genomes encoded these CLEs was not analyzed to confirm that they were indeed expressed.

Example 8. Proof of Concept for Various Illustrative Methods Provided Herein, Including In Vivo Expansion of Genetically Modified Lymphocytes This example provides exemplary methods for transducing PBMCs, including T cells, ex vivo and expanding those transduced PBMCs, including T cells, in vivo. Such methods include an illustrative 4 hour transduction method with illustrative recombinant lentiviral vectors that express certain illustrative chimeric lymphoproliferative elements. Furthermore, such methods provide additional exemplary methods for transducing PBMCs, which in illustrative embodiments are typically T cells, with replication incompetent recombinant retroviral particles in 4 hours wherein the replication incompetent recombinant retroviral particles were produced by transfecting packaging cells with vectors encoding various components of the replication incompetent recombinant retroviral particles in suspension in serum-free, chemically defined media.

Materials and Methods

Figure 12:
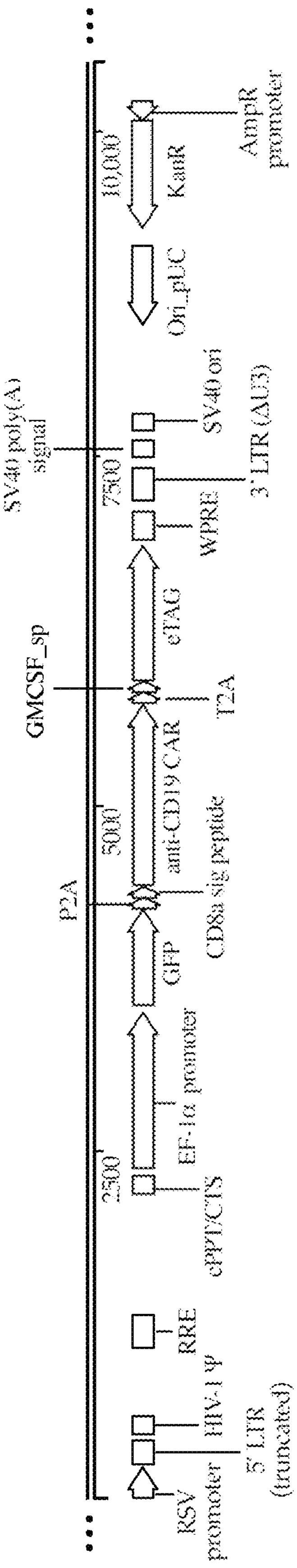
FIG. 12 shows a schematic of the lentiviral expression vector encoding GFP, an anti-CD19 chimeric antigen receptor, and an eTAG referred to herein as F1-0-03.

Recombinant lentiviral particles were produced in 293T cells (Lenti-X™ 293T, Clontech) that were adapted to suspension culture in Freestyle™ 293 Expression Medium (Thermo Fisher Scientific) serum-free chemically defined medium. The cells were transiently transfected using PEI with 1 of 3 genomic plasmids (detailed below) and 3 separate lentiviral packaging plasmids encoding gag/pol, rev, and a pseudotyping plasmid encoding VSV-G as explained in Example 20 of WO2018/161064A1 and Example 4 of WO2019/055946A1. To produce retroviral particles that also display a membrane-bound activation element, a fourth packing plasmid encoding a membrane-bound polypeptide capable of binding to CD3 (UCHT1scFvFc-GPI) was co-transfected as described in Example 20 of WO2018/161064A1 and Example 4 of WO2019/055946A1. The genomic plasmids were third generation lentiviral expression vectors containing a deletion in the 3'LTR leading to self-inactivation wherein the plasmids encoded the following:

(1) Anti-ROR2 MRB-CAR:T2A:eTag (F1-1-27): This genomic plasmid is identical to that shown in FIG. 12 except that the sequence encoding anti-CD19 CAR was replaced with an MRB-ASTR that has an scFv that recognizes human ROR2, a CD8 stalk and transmembrane sequence (SEQ ID NO:24), CD137 (SEQ ID NO:298), and CD3z (SEQ ID NO:28). Recombinant lentiviral particles encoding this construct are called F1-1-27;

(2) Flag-Anti-ROR2 MRB-CAR:T2A:CLE (F1-1-228 and F1-1-228U): This genomic plasmid is identical to that shown in FIG. 12 except that the sequence encoding anti-CD19 was replaced with a Flag-tag covalently linked to the anti-ROR2 MRB-CAR described in (1) above, and the GMCSFR ss:eTag was replaced with a CLE. The CLE was a type I transmembrane protein comprising an extracellular dimerization module (P1), a transmembrane module (P2), and 2 intracellular modules (P3 and P4). The genes in positions P1-P2-P3-P4 were MycTag 2A Jun-IL13RA-MPL-CD40. The codes for these modules are E013-T041-S186-S051 (See Table 1). This CLE was first identified in libraries 3A, 3B, and 4B and was the $6^{th}$ most enriched CLE between days 7 and 35 in library 3A. Recombinant lentiviral particles encoding this construct are called F1-1-228 and recombinant lentiviral particles encoding this construct and displaying UCHT1scFvFc-GPI are called F1-1-228U; or (3) Flag-Anti-CD19 CAR:T2A:CLE (F1-3-219 and F1-3-219U): This genomic plasmid is identical to the anti-human CD19 CAR shown in FIG. 12 except that a Flag-tag was inserted between the CD8ss and the CAR, and the sequence encoding the GMCSFRss:eTag was replaced with a CLE. The CLE was a type I transmembrane protein comprising an interleukin polypeptide covalently linked via a flexible linker to the extracellular and transmembrane domains of its cognate interleukin receptor and covalently linked to the intracellular domain of a dissimilar cytokine receptor. In particular, from amino to carboxy terminus the plasmid encoded IL-7 (SEQ ID NO:458), a flexible linker (SEQ ID NO:63), the extracellular and transmembrane portions of the IL-7Rα (CD127) (SEQ ID NO:460), and the intracellular domain of the IL-2Rβ (CD122) (SEQ ID NO:461). Recombinant lentiviral particles encoding this construct are called F1-3-219 and recombinant lentiviral particles encoding this construct and displaying UCHT1scFvFc-GPI are called F1-3-219U.

PBMC isolation, overnight transduction of PBMCs after ex vivo stimulation, followed by 15 day ex vivo expansion of engineered lymphocytes On Day 0, PBMCs were isolated from ACD peripheral blood from a healthy volunteer with informed consent by density gradient centrifugation with Ficoll-Pacque™ (General Electric) using a CS-900.2 kit (BioSafe; 1008) on a Sepax 2 S-100 device (Biosafe; 14000) according to the manufacturer's instructions. $3.0\times10^7$ viable PBMCs were seeded in a 1 L G-Rex (Wilson-Wolf) and the volume was brought to 60 ml with Complete OpTmizer™ CTS™ T-Cell Expansion SFM supplemented with 100 IU/ml IL-2 (Novoprotein, GMP-CD66), 10 ng/ml IL-7 (Novoprotein, GMP-CD47), and 50 ng/ml anti-CD3 antibody (OKT3, Novoprotein) to activate the PBMCs, which included T cells and NK cells, for viral transduction. After incubation overnight at 37° C. and 5% $CO_2$, lentiviral particles encoding the anti-ROR2 MRB-CAR, F1-1-27, were added directly to the activated PBMCs at an MOI of 5 (440 μl) and incubated overnight at 37° C. and 5% $CO_2$. Following the overnight incubation, the cells were fed by bringing the total volume of media in the G-Rex to 100 ml with Complete OpTmizer™ CTS™ T-Cell Expansion SFM supplemented with NAC (Sigma) to increase the final concentration by 10 mM along with 100 IU/ml recombinant human IL-2 and 10 ng/ml recombinant human IL-7. The G-Rex device was incubated in a standard humidified tissue culture incubator at 37° C. and 5% $CO_2$ with additions of 100 IU/ml recombinant human IL-2 and 10 ng/ml recombinant human IL-7 solution every 48 hours. The cells were expanded through Day 15 before being harvested. These transduced cells were washed in freezing media (70% RPMI 1640, 20% heat-inactivated FBS, 10% DMSO) and cryopreserved in 1 ml aliquots at $5.0\times10^7$ cells/ml for later use. Two days prior to use in Group A of the experiments in this example below, 8 vials ($4.0\times10^8$) of these cryopreserved F1-1-27 transduced PBMCs were thawed and rested for 2 days in a G-Rex100M containing 377 ml Complete OpTmizer™ CTS™ T-Cell Expansion SFM (OpTmizer™ CTS™ T-Cell Expansion Basal Medium 1 L (Thermo Fisher, A10221) supplemented with 26 ml OpTmizer™ CTS™ T-Cell Expansion Supplement (Thermo Fisher, A10484-02), 25 ml CTS™ Immune Cell SR (Thermo Fisher, A2596101), and 10 ml CTS™ GlutaMAX™-I Supplement (Thermo Fisher, A1286001) according to manufacturer's instructions) supplemented with 100 IU/ml of IL-2 (Novoprotein), 10 ng/ml IL-7 (Novoprotein), and sufficient NAC to increase the final concentration by 10 mM.

PBMC Isolation and Advantageously Fast Transduction of Resting Lymphocytes without Prior Ex Vivo Stimulation and without Ex Vivo Cell Expansion Whole human blood from 2 healthy volunteers with informed consent was collected into multiple 100 mm Vacutainer tubes (Becton Dickenson; 364606) containing 1.5 ml of Acid Citrate Dextrose Solution A anticoagulant (ACD peripheral blood). For each volunteer, blood from the Vacutainer tubes was pooled (185.2 ml for Group B, 182.5 ml for Group C) and distributed to 2 standard 500 ml blood collection bags. The following steps of PBMCs enrichment through transduction were performed in a closed system.

The blood in the 2 blood bags from each volunteer was processed sequentially using density gradient centrifugation with Ficoll-Paque™ (General Electric) using a CS-900.2 kit (BioSafe; 1008) on a Sepax 2 S-100 device (Biosafe; 14000) using 2 wash cycles according to the manufacturer's instructions, to obtain 45 ml of isolated PBMCs from each run. The wash solution used in the Sepax 2 process was Normal Saline (Chenixin Pharm)+2% human serum albumin (HSA) (Sichuan Yuanda Shuyang Pharmaceutical). The final cell resuspension solution was 45 ml Complete OpTmizer™ CTS™ T-Cell Expansion SFM (OpTmizer™ CTS™ T-Cell Expansion Basal Medium 1 L (Thermo Fisher, A10221-03) supplemented with 26 ml OpTmizer™ CTS™ T-Cell Expansion Supplement (Thermo Fisher, A10484-02), 25 ml CTS™ Immune Cell SR (Thermo Fisher, A2596101), and 10 ml CTS™ GlutaMAX™-I Supplement (Thermo Fisher, A1286001)). Each processing step on the Sepax 2 machine was approximately 1 hour and 12 minutes. Enriched PBMCs obtained from the 2 processing runs were pooled separately for Group B and Group C, and the cells counted.

$5.5\times10^7$ freshly enriched, viable PBMCs were seeded into each of 4 standard blood collection bags for Group B and the volume was brought to 55 ml with Complete OpTmizer™ CTS™ T-Cell Expansion SFM such that the cells were at a density of $1.0\times10^6$/ml. $1.12\times10^8$ freshly enriched, viable PBMCs were seeded into each of 2 standard blood collection bags for Group C and the volume was brought to 110 ml with Complete OpTmizer™ CTS™ T-Cell Expansion SFM such that the cells were at a density of $1.0\times10^6$/ml. No anti-CD3, anti-CD28, IL-2, IL-7, or other exogenous cytokine was added to activate or otherwise stimulate the lymphocyte ex vivo prior to transduction. Lentiviral particles were added directly to the non-stimulated PBMCs in blood collection bags at an MOI of 1 as follows: 0.779 ml of F1-1-228 was added to one bag and 3.11 ml of F1-1-228U was added to the other bag of Group B PBMCs; 0.362 ml of F1-3-219 was added to one bag and 3.52 ml of F1-3-219U was added to the other bag of Group C PBMCs. The transduction reaction mixtures were gently massaged to mix the contents then incubated for four (4) hours in the blood collection bags in a standard humidified tissue culture incubator at 37° C. and 5% $CO_2$. The PBMCs from each bag were then transferred to a 50 ml Conical tube (thus removing the cells from the closed system in this proof of concept experiment) and washed 3 times in DPBS+2% HSA before being resuspended in 5 mls DPBS+2% HSA and counted. The table below shows the duration of each step in the process and the total time elapsed. No further processing was performed on these PBMCs prior to their use in the experiments in this example.

TABLE 9

Elapsed times for steps after blood draw and pooling.

| | Group B | | Group C | |
|---|---|---|---|---|
| | Time | Total Elapsed | Time | Total Elapsed |
| Blood draw & pooling | 9:00- | | 10:00 | |
| 1st Sepax run | 10:08-11:16 | 2 hr 16 min | 10:30-11:45 | 1 hr 45 min |
| 2nd Sepax run | 11:21-12:30 | 3 hr 30 min | 11:48-13:04 | 3 hr 4 min |
| Cell counting | 12:40-13:00 | 4 hr 0 min | 13:11-13:35 | 3 hr 35 min |
| Dispense into bags | 13:55-14:03 | 5 hr 3 min | 13:37-13:44 | 3 hr 44 min |
| Media addition | 14:06-14:20 | 5 hr 20 min | 13:45-13:58 | 3 hr 58 min |
| Virus addition | 14:55-15:01 | 6 hr 1 min | 14:00-14:30 | 4 hr 30 min |
| Transduction | 15:10-19:10 | 10 hr 10 min | 14:30-18:30 | 8 hr 30 min |
| Transfer & Pellet | 19:10-19:36 | 10 hr 36 min | 18:30-19:04 | 8 hr 4 min |
| 1st wash | 19:55-20:10 | 11 hr 10 min | 19:14-19:30 | 9 hr 30 min |
| 2nd wash | 20:21-20:36 | 11 hr 36 min | 19:35-19:51 | 9 hr 51 min |
| 3rd wash | 20:47-21:02 | 12 hr 2 min | 19:56-20:02 | 9 hr 2 min |
| Cell counting | 21:12-22:10 | 13 hr 10 min | 20:03-20:50 | 10 hr 50 min |
| Transportation | 21:58-23:10 | 14 hr 10 min | 21:50-21:25 | 11 hr 25 min |
| Dosing mice | 23:12-23:30 | 14 hr 30 min | 21:25-21:30 | 11 hr 30 min |

Transduction Efficiency and Cytokine-Independent Survival/Proliferation In Vitro of PBMCs Transduced by the Methods Above $2.0\times10^6$ PBMCs that included T cells and NK cells and that were contacted with retroviruses for 4 hours as disclosed immediately above, were seeded in duplicate or triplicate into the wells of a 6 well tissue culture plate for each sample. The plates were centrifuged and each sample was resuspended in 2 ml of Complete OpTmizer™ CTS' T-Cell Expansion SFM. No cytokines were added. The plates were incubated in a standard humidified tissue culture incubator at 37° C. and 5% $CO_2$ for 6 days. Half (1 ml) of the cell suspension from each well was removed on day 3 and the remaining cells removed on day 6 to determine cell numbers, percent viability, and percent transduced cells, which was defined as the percent of FLAG-Tag+ cells by FACS analysis. Total cell counts on day 6 were doubled to account for removing half of the cells on day 3.

Proliferation/Survival and Target Killing of Tumors In Vivo by Effector PBMCs Transduced by the Methods Above A xenograft model using NSG, or NOD Scid Gamma mice was chosen to probe the ability of human PBMCs transduced with F1-1-27, F1-1-228, F1-1-228U, F1-3-219, and F1-3-219U to survive, proliferate, and kill cognate antigen-expressing tumors in vivo. NSG is a strain of mice that lack mature T cells, NK cells, and B cells and is among the most immunodeficient mouse strain described to date. Removal of these cellular components of the immune system is typically performed to enable human PBMCs to engraft without innate, humoral or adaptive immune reactions from the host. Concentrations of homeostatic cytokines normally present only after radiation or lymphodepleting chemotherapy in humans is achieved due to the absence of the murine extracellular common gamma chain, which enables adoptively transferred human cells to receive such cytokines. At the same time, these animals can also be utilized to engraft tumor xenograft targets to examine the efficacy of CARs to kill target-expressing tumors. While the presence of xenoreactive T cell receptor antigens in the effector cellular product will eventually give rise to graft versus host disease, these models enable short term evaluation of animal pharmacology and acute tolerability.

Raji cells (ATCC, Manassas, Va.) which express endogenous human CD19, and CHO cells (ATCC, Manassas, Va.) transfected to stably express human ROR2 (CHO-ROR2) were utilized to provide antigen to stimulate the CAR effector cells and to generate uniform target tumors to determine the efficacy of CAR effector cells to kill cognate antigen-expressing tumors. The Raji cells and transgenic CHO variants grew rapidly with disseminated malignancy after subcutaneous administration into NSG mice in combination with Matrigel artificial basement membrane.

Mice were handled in accordance with Institutional Animal Care and Use Committee approved protocols. Subcutaneous (sc) tumor xenografts were established in the hind flank of female NOD-Prkdc$^{scid}$Il2rg$^{tm1}$/Begen (B-NSG) mice (Beijing Biocytogen Co. Ltd.). Briefly, cultured Raji cells and cultured CHO-ROR2 cells were separately washed in DPBS (Thermo Fisher), counted, resuspended in cold DPBS and mixed with an appropriate volume of Matrigel ECM (Corning; final concentration 5 mg/mL) at a concentration of $0.5\times10^6$ cells/200 μl on ice. Animals were prepared for injection using standard approved anesthesia with hair removal (Nair) prior to injection. 200 μl of either cell suspension in ECM was injected sc into the rear flanks of 9 or 10 week old mice for Raji and CHO-ROR2 cells, respectively.

5 days after tumor inoculation, mice bearing CHO-ROR2 tumors, which averaged 77 $mm^3$ in volume, were dosed intravenously (IV) by tail vein injection as follows: NSG mice in Group A received $1\times10^7$ PBMCs transduced with F1-1-27 lentiviral particles in 200 μl DPBS (n=4), or 200 μl DPBS alone (n=2); NSG mice in Group B received $0.85\times10^7$ PBMCs transduced with F1-1-228 lentiviral particles in 200 μl DPBS (n=2), $0.85\times10^7$ PBMCs transduced with F1-1-228U lentiviral particles in 200 μl DPBS (n=2), or 200 μl DPBS alone (n=2) Similarly, 5 days after tumor inoculation, mice in Group C bearing Raji tumors, which averaged 76 $mm^3$ in volume, were dosed intravenously (IV) by tail vein injection with 200 μl DPBS alone (n=4) or $1\times10^7$ PBMCs transduced with either F1-3-219 lentiviral particles in 200 μl DPBS (n=3) or F1-3-219U lentiviral particles in 200 μl DPBS (n=3). Note that the protocol for the advantageously fast transduction of resting lymphocytes prior to ex vivo activation and without ex vivo cell expansion was used to transduce the PBMCs with F1-1-228, F1-1-228U, F1-3-219, and F1-3-219U used for dosing these mice. The total time elapsed from whole human blood collection to IV dosing of the mice with transduced PBMCs was 14.5 hours for F1-1-228 and F1-1-228U, and 11.5 hours for F1-3-219 and F1-3-219U.

Tumors were measured using calipers 2 times a week and tumor volume was calculated using the following equation: (longest diameter*shortest diameter$^2$)/2. Approximately 100 μl of blood was collected from each mouse on days 7, 14, and 21 for analysis by FACS and qPCR. Blood, spleen, and tumor was also collected when the mice were euthanized consistent with necropsy guidelines from tumor burden.

Flow Cytometry

For cells harvested from in vitro culture—cells were spun down and resuspended in 0.5 ml FACS Staining Buffer (554656, BD). 2.5 μl human Fc Block (BD, 564220) was added to each sample and incubated at room temperature for 10 minutes. Cells were stained with 0.5 μl anti-FLAG Tag PE ((anti-DYKDDDDK) 637310, Biolegend) and 0.5 μl Live/Dead Fixable Green Dead cell stain (L34970, Thermo Fisher) for 30 mins on ice. Cells were washed twice in FACS buffer, fixed in a 1:1 mixture of the FACS buffer and BD Cytofix (554655, BD), processed with Novocyte (ACEA), and the resulting data was analyzed with NovoExpress software (ACEA) using live gates based on forward and side scatter and the live dead stain. Transduced lymphocytes were measured as FLAG Tag+ cells.

For cells obtained from blood—red blood cells in the freshly collected blood were lysed using Lysing Buffer (555899, BD) and the remaining cells resuspended in 100 μl of FACS Staining Buffer. 2.5 μl human Fc Block (BD, 564220) was added to each sample and incubated at room temperature for 10 minutes. Cells were stained with biotinylated-cetuximab for 30 mins on ice. Stained cells were washed with FACS buffer and further stained with 5 μl anti-human CD45-PE-Cy7 and 0.5 μl anti-mouse CD45-FITC. 0.4 μl SA-PE was added to samples from mice dosed with cells transduced with F1-1-27, F1-1-228, F1-1-228U, and PBS controls for these groups. 1 μl anti-FLAG Tag PE ((anti-DYKDDDDK) 637310, Biolegend) was added to samples from mice dosed with cells transduced with F1-3-219 and F1-3-219U and PBS controls for this group. Cells were incubated for 30 mins on ice, washed twice in FACS buffer, and resuspended in 100 μl FACS Staining Buffer with 1 μl 7-AAD (420404, Biolegend). Freshly stained samples were processed with Novocyte (ACEA), and the resulting data was analyzed with NovoExpress software (ACEA) using live gates based on forward and side scatter, a live gate based on 7-AAD, human CD45+ and examined for the expression of FLAG or eTag.

qPCR

Genomic DNA (gDNA) isolated from blood samples were evaluated for the presence of transduced lymphocytes by bioanalytical qPCR. Genomic DNA was isolated from 50 μl blood samples using the QIAamp DNA Blood Mini kit (Qiagen 51106) and the DNA was further cleaned using the QIAamp DNA Micro Kit (56304). A TaqMan assay (Thermo Fisher) was performed on the isolated genomic DNA using a primer and probe set specific for the 5' LTR of lentivirus to detect transduced cells.

Results

Lentiviral particles pseudotyped with VSV-G and encoding a CAR and a lymphoproliferative element were used in this experiment. Lentiviral particles F1-1-228 and F1-1-228U encoded a MRB-CAR to ROR2 and a CLE that included a MycTag and a 2A Jun dimerization domain, an IL13RA transmembrane domain and MPL and CD40 intracellular domains and lentiviral particles F1-2-219 and F1-3-219U encoded a CAR to CD19 and a CLE that encoded IL7 covalently linked to the extracellular and transmembrane portions of the IL-7Rα (CD127) (SEQ ID NO:460), and the intracellular domain of the IL-2Rβ (CD122). Lentiviral particles F1-1-228U and F1-3-219U also displayed UCHT1scFvFc-GPI on their surface. PBMCs were isolated from human blood by density gradient centrifugation with Ficoll-Paque™. The fresh PBMCs were transduced with the lentiviral particles in standard blood bags without prior activation of the cells ex vivo. After a 4 hour transduction, the cells were washed and used in the experiments below. A skilled artisan will understand that the entire process from blood collection to washed cells could be performed in a closed system. As a control, PBMCs were activated overnight, transduced with lentiviral particles encoding a CAR without a lymphoproliferative element or UCHT1scFvFc-GPI (F1-1-27), and cultured ex vivo for 15 days.

Figure 13:
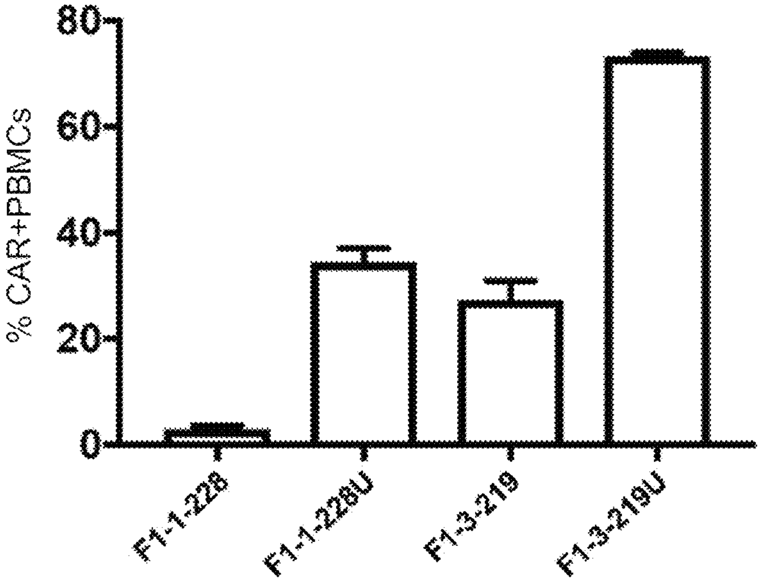
FIG. 13 is a graph showing the efficiency by which the indicated lentiviral particle transduced resting PBMCs in 4 hours. Transduction efficiency was measured as the % CAR+ PBMCs after 6 days in culture in the absence of exogenous cytokines as determined by FACS. Each lentiviral particle encoded a CAR and a CLE. Lentiviral particles F1-1-228U and F1-3-219U displayed UCHT1scFvFc-GPI on their surface.
Figure 14B:
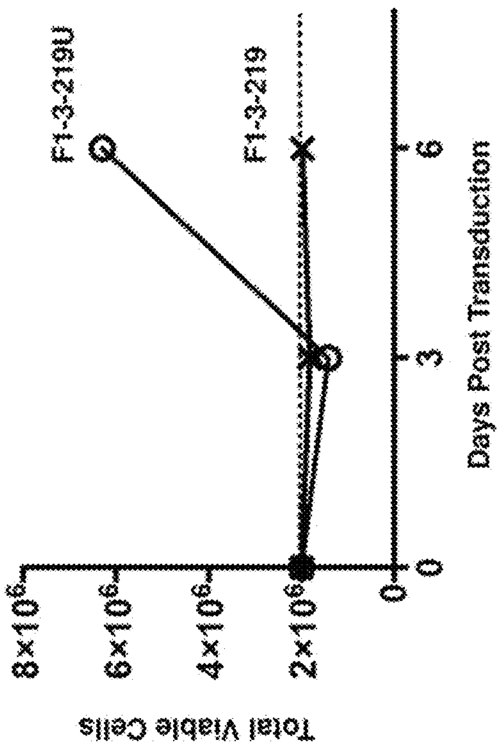
FIGS. 14A and 14B are graphs showing a time course of the total number of viable cells after resting PBMCs were transduced with the indicated lentiviral particle for 4 hours and cultured in vitro in the absence of exogenous cytokines for 6 days. Each lentiviral particle encoded a CAR and a CLE. Lentiviral particles F1-1-228U and F1-3-219U displayed UCHT1scFvFc-GPI on their surface.
Figure 14A:
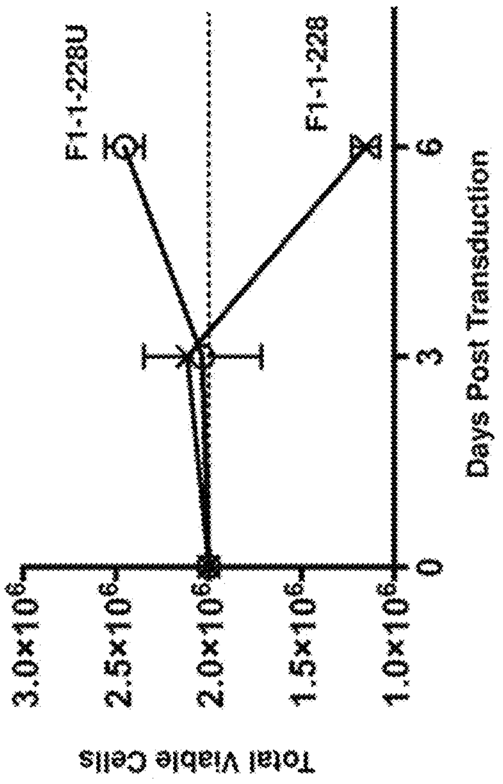

Transduced PBMCs were cultured in vitro in the absence of cytokines. FIG. 13 shows transduction efficiencies at Day 6. UCHT1scFvFc-GPI increased the transduction efficiency of both F1-1-228 and F1-3-219. Resting PBMCs, when exposed for 4 hours to F1-1-228U or F1-3-219U had transduction efficiencies of 34% and 73%, respectively. FIG. 14 shows the total number of viable cells in these cultures between days 3 and 6. Resting PBMCs transduced with either F1-1-228U or F1-3-219U survived and even proliferated between day 3 and day 6 in the absence of exogenous cytokines while PBMCs transduced with either F1-1-228 or F1-3-219 did not. These results demonstrate that retroviral particles displaying an activation element and encoding a lymphoproliferative element can transduce resting PBMCs in 4 hours and that these transduced PMBCs can proliferate and survive in vitro when cultured for 6 days in the absence of exogenous cytokines.

Figure 15A:
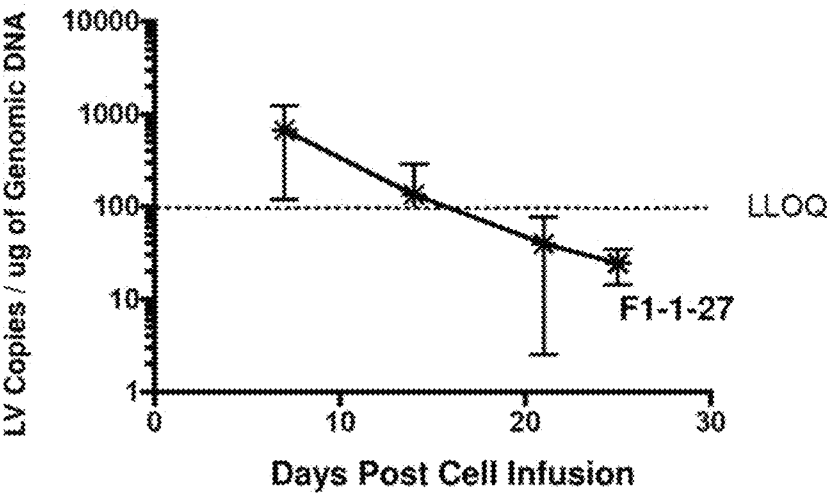
FIGS. 15A, 15B, and 15C are graphs showing a time course of the copies of lentiviral genome per μg of genomic DNA from the blood of tumor-bearing NSG mice dosed with human PBMCs transduced with the indicated lentiviral particle for 4 hours and injected intravenously without the PBMCs having been expanded ex vivo. Each lentiviral particle encoded a CAR. F1-1-228, F1-1-228U, F1-3-219, and F1-3-219U also encoded a CLE. Lentiviral particles F1-1-228U and F1-3-219U also displayed UCHT1scFvFc-GPI on their surface.
Figure 15B:
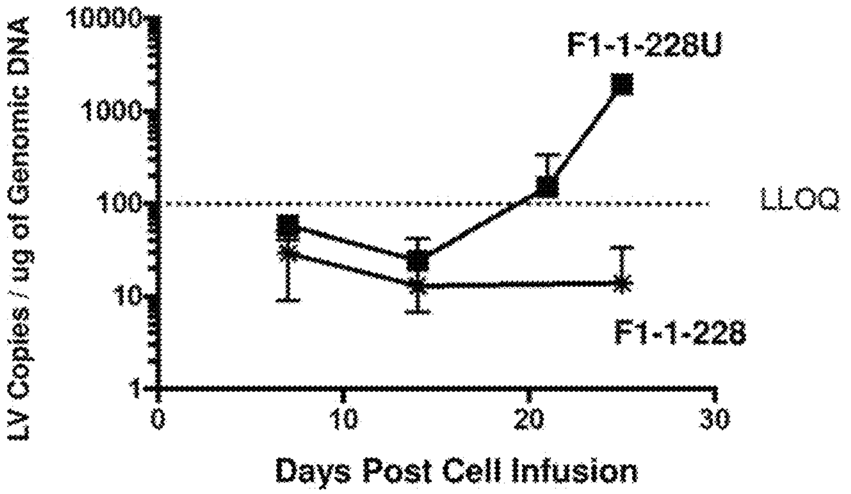
Figure 15C:
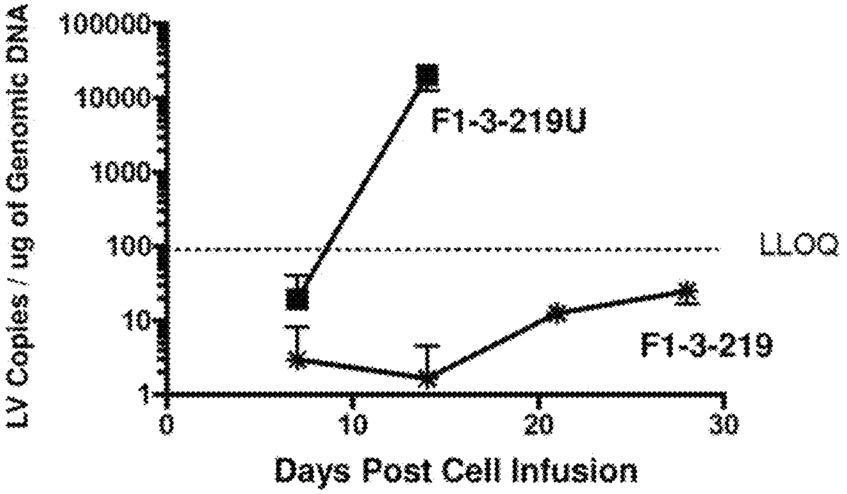
Figure 16:
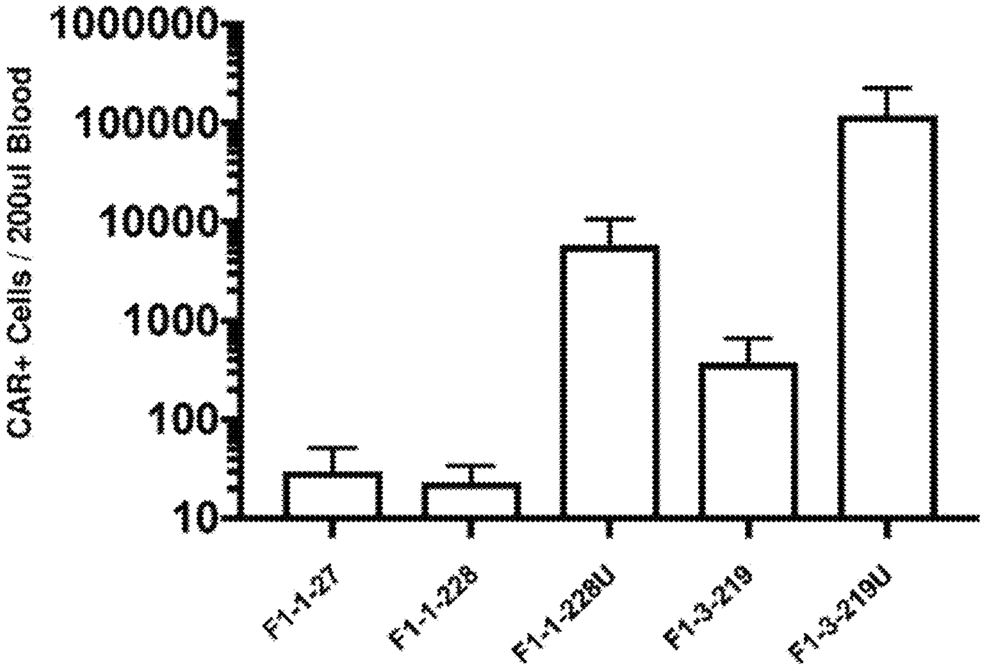
FIG. 16 is a graph showing the number of CAR+ cells per 200 μl of blood of tumor-bearing NSG mice dosed with human PBMCs transduced with the indicated lentiviral particle for 4 hours and injected intravenously without the PBMCs having been expanded ex vivo. Blood was sampled at the time the mice were euthanized. Each lentiviral particle encoded a CAR. F1-1-228, F1-1-228U, F1-3-219, and F1-3-219U also encoded a CLE. Lentiviral particles F1-1-228U and F1-3-219U also displayed UCHT1scFvFc-GPI on their surface.

Immunodeficient mice bearing ROR2 or CD19 tumors were dosed intravenously with $1\times10^7$ PBMCs that express a CAR to ROR2 or CD19, respectively. The ability of the transduced PBMCs to survive and proliferate in vivo was examined over time. FIGS. 15A-C show the lentiviral copies per μg of genomic DNA isolated from blood of the CAR-expressing PBMC dosed mice by qPCR as a readout for transduced cells. FIG. 15A shows that lentiviral copies per μg of genomic DNA for F1-1-27, which does not encode for a lymphoproliferative element, decreased from an average of 884 on day 7 to below the lower limit of quantitation (LLOQ) by day 21. FIG. 15B shows that the lentiviral copies for F1-1-228U was below the LLOQ on days 7 and 14, but increased above the LLOQ by day 21 and increased to an average of 1,939 on day 25. FIG. 15C shows that the lentiviral copies for F1-3-219U increased from below the LLOQ on day 7 to 20,430 on day 14 when the mice were euthanized. Lentiviral copies in the control samples, F1-1-228 and F1-3-219, remained below the LLOQ. FIG. 16 shows the number of transduced cells per 200 μl of blood at the time the mice were euthanized (the last time points are shown in FIG. 15) as determined by FACS analysis for the eTag or FLAG-Tag of the CAR construct. Significant numbers of CAR+ cells were detected per 200 μl of blood from mice dosed with cells transduced with F1-1-228U (5,857) and F1-3-219U (121,324).

Figure 17B:
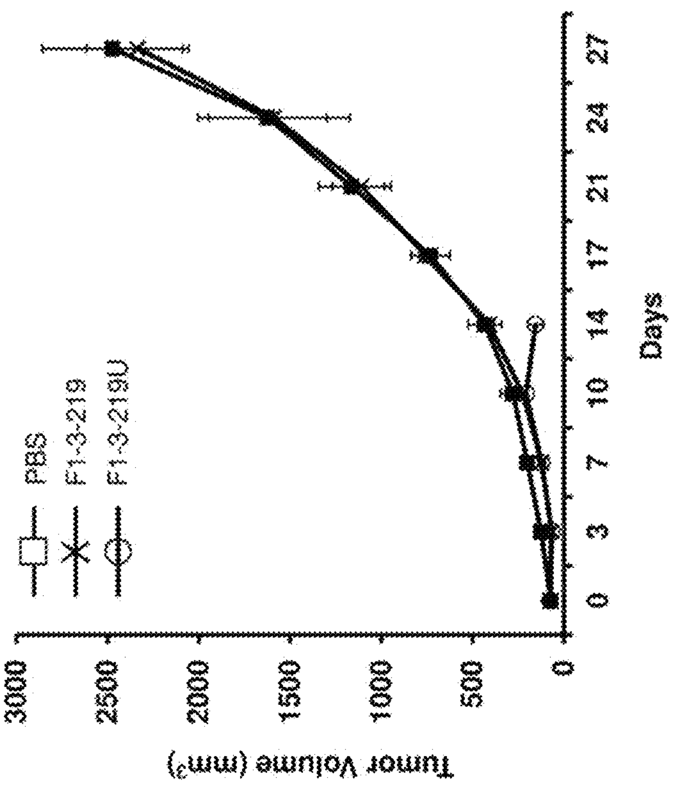
FIG. 17B is a graph showing the mean tumor volume of Raji tumors in NSG mice dosed intravenously with PBS or human PBMCs transduced with the indicated lentiviral particle encoding an anti-CD19 CAR and a CLE for 4 hours without the PBMCs having been expanded ex vivo. Lentiviral particles F1-1-228U and F1-3-219U displayed UCHT1scFvFc-GPI on their surface.
Figure 17A:
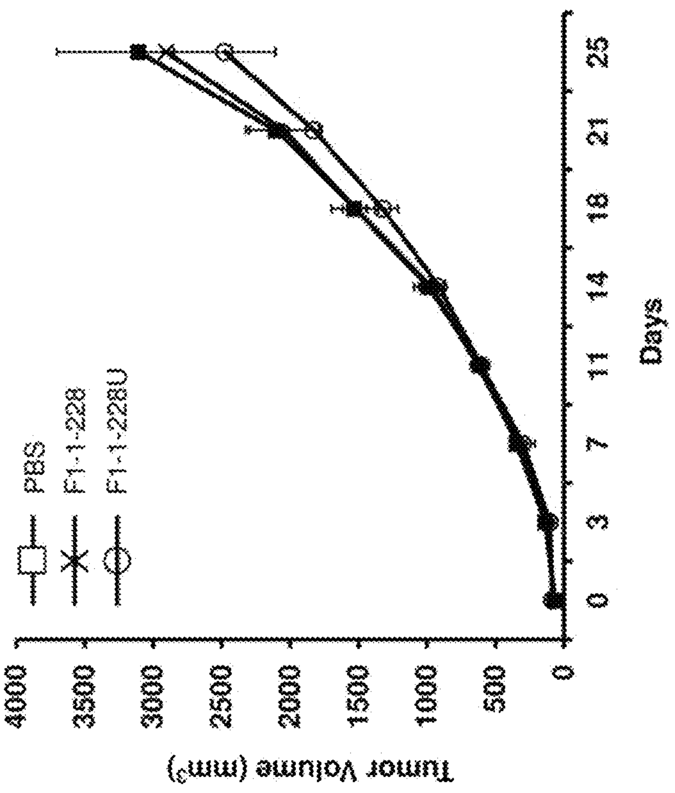
FIG. 17A is a graph showing the mean tumor volume of CHO-ROR2 tumors in NSG mice dosed intravenously with PBS or human PBMCs transduced with the indicated lentiviral particle encoding an anti-ROR2 MRB CAR and a CLE for 4 hours without the PBMCs having been expanded ex vivo.

The anti-tumor activity of PMBCs that were genetically modified to express a lymphoproliferative element and an anti-CD19 CAR or an anti-ROR2 CAR was analyzed. Mice bearing mice bearing CHO-ROR2 tumors or CD-19 expressing tumors were produced as provided above. Lymphocytes transduced with F1-1-228U or F1-3-219U killed tumors expressing their target antigen in vivo (FIGS. 17A and 17B). In both cases the lymphocytes reduced the tumor volume in a delayed manner. Not to be limited by theory, but this delay is consistent with a need for the injected cells to expand, which took time as seen by qPCR. Later time points could not be studied in this experiment because the mice harboring ROR2 tumors reach euthanasia guidelines for tumor burden and the mice harboring Raji tumors developed graft-versus-host disease caused by the significant number of transduced and expanded lymphocytes in the mice.

Together these data show that retroviral particles displaying an activation element and encoding a lymphoproliferative element can transduce resting PBMCs in 4 hours and that these transduced PMBCs can proliferate and survive in vivo. Both lymphoproliferative elements tested in this experiment, MycTag 2A Jun-IL13Ra-MPL-CD40 and IL-7-IL-7Rα-IL-2Rβ, displayed the ability to promote survival and proliferation in vivo. Furthermore, these lymphocytes transduced in this manner expressing a MRB-CAR (F1-1-228U) or a traditional CAR (F1-3-219U) were able to recognize and kill tumor cells in vivo.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

TABLE 1

| Parts, names, and amino acid sequences for domains of lymphoproliferative parts P1-P2, P1, P2, P3, and P4. | | |
|---|---|---|
| Part | Name | Amino Acid Sequence |
| M001 | eTAG IL7RA Ins PPCL (interleukin 7 receptor) | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPEINNSSGEMDPILLPPCLTISILSFFSVALLVILACVL (SEQ ID NO: 84) |
| M002 | eTAG IL7RA Ins PPCL (interleukin 7 receptor) | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQPEINNSSGEMDPILLPPCLTISILSFFSVALLVILACVL (SEQ ID NO: 85) |
| M007 | Myc Tag LMP1 NC_007605_1 | MEQKLISEEDLEHDLERGPPGPRRPPRGPPLSSSLGLALLLLLLALLFWLYIVMSDWTGGALLVLYSFALMLIIIILIIFIFRRDLLCPLGALCILLLMITLLLIALWNLHGQALFLGIVLFIFGCLLVLGIWIYLLEMLWRLGATIWQLLAFFLAFFLDLILLIIALYLQQNWWILLVDLLWLLLFLAILIWM (SEQ ID NO: 86) |
| M008 | Myc LMP1 NC_007605_1 | MEQKLISEEDLSSSLGLALLULLALLFWLYIVMSDWIGGALLVLYSFALMLIIIILIIFIFRRDLLCPLGALCILLLMITLLLIALWNLHGQALFLGIVLFIFGCLLVLGIWIYLLEMLWRLGATIWQLLAFFLAFFLDLILLIIALYLQQNWWTLLVDLLWLLLFLAILIWM (SEQ ID NO: 87) |
| M009 | LMP1 NC_007605_1 | MEHDLERGPPGPRRPPRGPPLSSSLGLALLLLLLALLFWLYIVMSDWTGGALLVLYSFALMLIIIILIIFIFRRDLLCPLGALCILLLMITLLLIALWNLHGQALFLGIVLFIFGCLLVLGIWIYLLEMLWRLGATIWQLLAFFLAFFLDLILLIIALYLQQNWWTLLVDLLWLLLFLAILIWM (SEQ ID NO: 88) |
| M010 | LMP1 NC_007605_1 | MSLGLALLLLLLALLFWLYIVMSDWTGGALLVLYSFALMLIIIILIIFIFRRDLLCPLGALCILLLMITLLLIALWNLHGQALFLGIVLFIFGCLLVLGIWIYLLEMLWRLGATIWQLLAFFLAFFLDLILLIIALYLQQNWWILLVDLLWLLLFLAILIWM (SEQ ID NO: 89) |
| M012 | eTAG CRLF2 transcript variant 1 NM_022148_3 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGAETPTPPKPKLSKCILISSLAILLMVSLLLLSLW (SEQ ID NO: 90) |
| M013 | eTAG CRLF2 transcript variant 1 NM_022148_3 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQAETPTPPKPKLSKCILISSLAILLMVSLLLLSLW (SEQ ID NO: 91) |
| M018 | eTAG CSF2RB NM_000395_2 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGTESVLPMWVLALIEIFLTIAVLLAL (SEQ ID NO: 92) |
| M019 | eTAG CSF2RB NM_000395_2 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQTESVLPMWVLALIEIFLTIAVLLAL (SEQ ID NO: 93) |

TABLE 1-continued

Parts, names, and amino acid sequences for domains of lymphoproliferative parts P1-P2, P1, P2, P3, and P4.

| Part | Name | Amino Acid Sequence |
|---|---|---|
| M024 | eTAG CSF3R transcript variant 1 NM_000760_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGTPEGSELHIILGLFGLLLLLNCLCGTAWLCC (SEQ ID NO: 94) |
| M025 | eTAG CSF3R transcript variant 1 NM_000760_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQTPEGSELHIILGLFGLLLLLNCLCGTAWLCC (SEQ ID NO: 95) |
| M030 | eTAG EPOR transcript variant 1 NM_000121_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGTPSDLDPCCLTLSLILVVILVLLTVLALLS (SEQ ID NO: 96) |
| M031 | eTAG EPOR transcript variant 1 NM_000121_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQTPSDLDPCCLTLSLILVVILVLLTVLALLS (SEQ ID NO: 97) |
| M036 | eTAG GHR transcript variant 1 NM_000163_4 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGTLPQMSCIFTCCEDFYFPWLLCIIFGIFGLTVMLFVFLFS (SEQ ID NO: 98) |
| M037 | eTAG GHR transcript variant 1 NM_000163_4 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQTLPQMSQFTCCEDFYFPWLLCIIFGIFGLTVMLFVFLFS (SEQ ID NO: 99) |
| M042 | eTAG truncated after Fn F523C IL27RA NM_004843_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGHLPDNTLRWKVLPGILCLWGLFLLGCGLSLA (SEQ ID NO: 100) |
| M043 | eTAG truncated after Fn F523C IL27RA NM_004843_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQHLPDNTLRWKVLPGILCLWGLFLLGCGLSLA (SEQ ID NO: 101) |
| M048 | eTAG truncated after Fn S505N MPL NM_005373_2 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGETATETAWISLVTALHLVLGLNAVLGLLLL (SEQ ID NO: 102) |

TABLE 1-continued

Parts, names, and amino acid sequences for domains of lymphoproliferative parts P1-P2, P1, P2, P3, and P4.

| Part | Name | Amino Acid Sequence |
|---|---|---|
| M049 | eTAG truncated after Fn S505N MPL NM_005373_2 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQETATETAWISLVTALHLVLGLNAVLGLLLL (SEQ ID NO: 103) |
| E006 | eTag 0A JUN NM_002228_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGLERIARLEEKVKTLKAQNSELASTANMLREQVAQLKQKV (SEQ ID NO: 104) |
| E007 | eTag 1A JUN NM_002228_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGLERIARLEEKVKTLKAQNSELASTANMLREQVAQLKQKVA (SEQ ID NO: 105) |
| E008 | eTag 2A JUN NM_002228_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KFGTSGQKTKIISNRGENSCKATGQVCHALCSPEGCWGPEPRDCVSCRNVSRGRECVDKCNLLEGEPREFVENSECIQC HPECLPQAMNITCTGRGPDNCIQCAHYIDGPHCVKTCPAGVMGENNTLVWKYADAGHVCHLCHPNCTYGCTGPGLE GCPTNGLERIARLEEKVKTLKAQNSELASTANMLREQVAQLKQKVAA (SEQ ID NO: 106) |
| E009 | eTag 3A JUN NM_002228_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGLERIARLEEKVKTLKAQNSELASTANMLREQVAQLKQKVAAA (SEQ ID NO: 107) |
| E010 | eTag 4A JUN NM_002228_3 | MLLLVTSLLLCELPHPAFLLIPRKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDGDVIISGNKNLCYANTINWK KLFGTSGQKTKIISNRGENSCKATGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADAGHVCHLCHPNCTYGCTGPGL EGCPTNGLERIARLEEKVKTLKAQNSELASTANMLREQVAQLKQKVAAAA (SEQ ID NO: 108) |
| E011 | Myc Tag OA JUN NM_002228_3 | MTILGTTFGMVFSLLQVVSGEQKLISEEDLLERIARLEEKVKTLKAQNSELASTANMLREQVAQLKQKV (SEQ ID NO: 109) |
| E012 | Myc Tag 1A JUN NM_002228_3 | MTILGTTFGMVFSLLQVVSGEQKLISEEDLLERIARLEEKVKTLKAQNSELASTANMLREQVAQLKQKVA (SEQ ID NO: 110) |
| E013 | Myc Tag 2A JUN NM_002228_3 | MTILGTTFGMVFSLLQVVSGEQKLISEEDLLERIARLEEKVKTLKAQNSELASTANMLREQVAQLKQKVAA (SEQ ID NO: 111) |
| E014 | Myc Tag 3A JUN NM_002228_3 | MTILGTTFGMVFSLLQVVSGEQKLISEEDLLERIARLEEKVKTLKAQNSELASTANMLREQVAQLKQKVAAA (SEQ ID NO: 112) |

TABLE 1-continued

Parts, names, and amino acid sequences for domains of lymphoproliferative parts P1-P2, P1, P2, P3, and P4.

| Part | Name | Amino Acid Sequence |
|---|---|---|
| E015 | Myc Tag 4A JUN NM_002228_3 | MTILGTTFGMVFSLLQVVSGEQKLISEEDLLERIARLEEKVKTLKAQNSELASTANMLREQVAQLKQKVAAAA (SEQ ID NO: 113) |
| T001 | CD2 transcript variant 1 NM_001328609_1 | LIIGICGGGSLLMVFVALLVFYI (SEQ ID NO: 114) |
| T002 | CD3D transcript variant 1 NM_000732_4 | GIIVTDVIATLLLALGVFCFA (SEQ ID NO: 115) |
| T003 | CD3E NM_000733_3 | VMSVATIVIVDICITGGLLLLVYYWS (SEQ ID NO: 116) |
| T004 | CD3G NM_000073_2 | GFLFAEIVSIFVLAVGVYFIA (SEQ ID NO: 117) |
| T005 | CD3Z CD247 transcript variant 1 NM_198053_2 | LCYLLDGILFIYGVILTALFL (SEQ ID NO: 118) |
| T006 | CD4 transcript variant land 2 NM_000616_4 | MALIVLGGVAGLLLFIGFIGLGIFF (SEQ ID NO: 119) |
| T007 | CD8A transcript variant 1 NM_001768_6 | IYIWAPLAGTCGVLLLSLVIT (SEQ ID NO: 120) |
| T008 | CD8B transcript variant 2 NM_172213_3 | LGLLVAGVLVLLVSLGVAIHLCC (SEQ ID NO: 121) |
| T009 | CD27 NM_001242_4 | ILVIFSGMFLVFTLAGALFLH (SEQ ID NO: 122) |
| T010 | CD28 transcript variant 1 NM_006139_3 | FWVLVVVGGVLACYSLLVTVAFIIFWV (SEQ ID NO: 123) |
| T011 | CD40 transcript variant 1 and 6 NM_001250_5 | ALVVIPIIFGILFAILLVLVFI (SEQ ID NO: 124) |
| T012 | CD79A transcript variant 1 NM_001783_3 | IITAEGIILLFCAVVPGTLLLF (SEQ ID NO: 125) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T013 | CD796 transcript variant 3 NM_001039933_2 | GIIMIQTLLIILFIIVPIFLLL (SEQ ID NO: 126) |
| T014 | CRLF2 transcript variant 1 NM_022148_3 | FILISSLAILLMVSLLLLSLW (SEQ ID NO: 127) |
| T015 | CRLF2 transcript variant 1 NM_022148_3 | CILISSLAILLMVSLLLLSLW (SEQ ID NO: 128) |
| T016 | CSF2RA transcript variant 7 and 8 NM_001161529_1 | NLGSVYIYVLLIVGTLVCGIVLGFLF (SEQ ID NO: 129) |
| T017 | CSF2RB NM_000395_2 | MWVLALIVIFLTIAVLLAL (SEQ ID NO: 130) |
| T018 | CSF2RB NM_000395_2 | MWVLALIEIFLTIAVLLAL (SEQ ID NO: 131) |
| T019 | CSF3R transcript variant 1 NM_000760_3 | IILGLFGLLLLLTCLCGTAWLCC (SEQ ID NO: 132) |
| T020 | CSF3R transcript variant 1 NM_000760_3 | IILGLFGLLLLLNCLCGTAWLCC (SEQ ID NO: 133) |
| T021 | EPOR transcript variant 1 NM_000121_3 | LILTLSLILVVILVLLTVLALLS (SEQ ID NO: 134) |
| T022 | EPOR transcript variant 1 NM_000121_3 | CCLTLSLILVVILVLLTVLALLS (SEQ ID NO: 135) |
| T023 | FCER1G NM_004106_1 | LCYILDAILFLYGIVLTLLYC (SEQ ID NO: 136) |
| T024 | FCGR2C NM_201563_5 | IIVAVVTGIAVAAIVAAVVALIY (SEQ ID NO: 137) |
| T025 | FCGRA2 transcript variant 1 NM_001136219_1 | IIVAVVIATAVAAIVAAVVALIY (SEQ ID NO: 138) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T026 | GHR transcript variant 1 NM_000163_4 | FPWLLIIIFGIFGLTVMLFVFLFS (SEQ ID NO: 139) |
| T027 | GHR transcript variant 1 NM_000163_4 | FPWLLCIIFGIFGLTVMLFVFLFS (SEQ ID NO: 140) |
| T028 | ICOS NM_012092.3 | FWLPIGCAAFVVVCILGCILI (SEQ ID NO: 141) |
| T029 | IFNAR1 NM_000629_2 | IWLIVGICIALFALPFVIYAA (SEQ ID NO: 142) |
| T030 | IFNAR2 transcript variant 1 NM_207585_2 | IGGIITVFLIALVLTSTIVTL (SEQ ID NO: 143) |
| T031 | IFNGR1 NM_000416_2 | SLWIPVVAALLLFLVLSLVFI (SEQ ID NO: 144) |
| T032 | IFNGR2 transcript variant 1 NM_001329128_1 | VILISVGTFSLLSVLAGACFF (SEQ ID NO: 145) |
| T033 | IFNLR1 NM_170743_3 | FLVLPSLLILLLVIAAGGVIW (SEQ ID NO: 146) |
| T034 | IL1R1 transcript variant 2 NM_001288706_1 | HMIGICVTLTVIIVCSVFIYKIF (SEQ ID NO: 147) |
| T035 | IL1RAP transcript variant 1 NM_002182_3 | VLLVVILIVVYHVYWLEMVLF (SEQ ID NO: 148) |
| T036 | IL1RL1 transcript variant 1 NM_016232.4 | IYCIIAVCSVFLMLINVLVII (SEQ ID NO: 149) |
| T037 | IL1RL2 NM_003854.2 | AYLIGGLIALVAVAVSVVYIY (SEQ ID NO: 150) |
| T038 | IL2RA transcript variant 1 NM_000417_2 | VAVAGCVFLLISVLLLSGL (SEQ ID NO: 151) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T039 | IL2RB transcript variant 1 NM_000878_4 | IPWLGHLLVGLSGAFGFIILVYLLI (SEQ ID NO: 152) |
| T040 | IL2RG NM_000206_2 | VVISVGSMGLIISLLCVYFWL (SEQ ID NO: 153) |
| T041 | IL3RA transcript variant 1 and 2 NM_002183_3 | TSLLIALGTLLALVCVFVIC (SEQ ID NO: 154) |
| T042 | IL4R transcript variant 1 NM_000418_3 | LLLGVSVSCIVILAVCLLCYVSIT (SEQ ID NO: 155) |
| T043 | IL5RA transcript variant 1 NM_000564_4 | FVIVIMATICFILLILSLIC (SEQ ID NO: 156) |
| T044 | IL6R transcript variant 1 NM_000565_3 | TFLVAGGSLAFGTLLCIAIVL (SEQ ID NO: 157) |
| T045 | IL6ST transcript variant 1 and 3 NM_002184_3 | AIVVPVCLAFLLTTLLGVLFCF (SEQ ID NO: 158) |
| T046 | IL7RA NM_002185_3 | ILLTISILSFFSVALLVILACVL (SEQ ID NO: 159) |
| T047 | IL7RA Ins PPCL (interleukin 7 receptor) | ILLPPCLTISILSFFSVALLVILACVL (SEQ ID NO: 160) |
| T048 | IL9R transcript variant 1 NM_002186_2 | GNTLVAVSIFLLLTGPTYLLF (SEQ ID NO: 161) |
| T049 | IL10RA transcript variant 1 NM_001558_3 | VIIFFAFVLLLSGALAYCLAL (SEQ ID NO: 162) |
| T050 | IL10RB NM_000628_4 | WMVAVILMASVFMVCLALLGCF (SEQ ID NO: 163) |
| T051 | IL11RA NM_001142784_2 | SLGILSFLGLVAGALALGLWL (SEQ ID NO: 164) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T052 | IL12RB1 transcript variant land 4 NM_005535_2 | WLIFFASLGSFLSILLVGVLGYLGL (SEQ ID NO: 165) |
| T053 | IL12RB2 transcript variant land 3 NM_001559_2 | WMAFVAPSICIAIIMVGIFST (SEQ ID NO: 166) |
| T054 | IL13RA1 NM_001560_2 | LYITMLLIVPVIVAGAIIVLLLYL (SEQ ID NO: 167) |
| T055 | IL13RA2 NM_000640_2 | FWLPFGFILILVIFVTGLLL (SEQ ID NO: 168) |
| T056 | IL15RA transcript variant 4 NM_001256765_1 | VAISTSTVLLCGLSAVSLLACYL (SEQ ID NO: 169) |
| T057 | IL17RA NM_014339_6 | VYWFITGISILLVGSVILLIV (SEQ ID NO: 170) |
| T058 | IL17RB NM_018725_3 | LLLLSLLVATWVLVAGIYLMW (SEQ ID NO: 171) |
| T059 | IL17RC transcript variant 1 NM_153460_3 | WALVWLACLLFAAALSLILLL (SEQ ID NO: 172) |
| T060 | IL17RD transcript variant 2 NM_017563_4 | AVAITVPLVVISAFATLFTVM (SEQ ID NO: 173) |
| T061 | IL17RE transcript variant 1 NM_153480_1 | LGLLILALLALLTLLGVVLAL (SEQ ID NO: 174) |
| T062 | IL18R1 transcript variant 1 NM_003855_3 | GMHAVLILVAVVCLVTVCVI (SEQ ID NO: 175) |
| T063 | IL18RAP NM_003853_3 | GVVLLYILLGTIGTLVAVLAA (SEQ ID NO: 176) |
| T064 | IL20RA transcript variant 1 NM_014432_3 | IIFWYVLPISITVFLFSVMGY (SEQ ID NO: 177) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T065 | IL20RB NM_144717_3 | VLALFAFVGFMLILVVVPLFV (SEQ ID NO: 178) |
| T066 | IL21R transcript variant 2 NM_181078_2 | GWNPHLLLLLLLVIVFIPAFW (SEQ ID NO: 179) |
| T067 | IL22RA1 NM_021258_3 | YSFSGAFLFSMGFLVAVLCYL (SEQ ID NO: 180) |
| T068 | IL23R NM_144701_2 | LLLGMIVFAVMLSILSLIGIF (SEQ ID NO: 181) |
| T069 | IL27RA NM_004843_3 | VLPGILFLWGLFLLGCGLSLA (SEQ ID NO: 182) |
| T070 | IL27RA NM_004843_3 | VLPGILCLWGLFLLGCGLSLA (SEQ ID NO: 183) |
| T071 | IL31RA transcript variant 1 NM_139017_5 | IILITSLIGGGLLILIILTVAYGL (SEQ ID NO: 184) |
| T072 | LEPR transcript variant 1 NM_002303_5 | AGLYVIVPVIISSSILLLGTLLI (SEQ ID NO: 185) |
| T073 | LIFR NM_001127671_1 | VGLIIAILIPVAVAVIVGVVTSILC (SEQ ID NO: 186) |
| T074 | MPL NM_005373_2 | ISLVTALHLVLGLSAVLGLLLL (SEQ ID NO: 187) |
| T075 | MPL NM_005373_2 | ISLVTALHLVLGLNAVLGLLLL (SEQ ID NO: 188) |
| T076 | OSMR transcript variant 4 NM_001323505_1 | LIHILLPMVFCVLLIMVMCYL (SEQ ID NO: 189) |
| T077 | PRLR transcript variant 1 NM_000949_6 | TTVWISVAVLSAVICLIIVWAVAL (SEQ ID NO: 190) |
| T078 | TNFRSF4 NM_003327_3 | VAAILGLGLVLGLLGPLAILL (SEQ ID NO: 191) |

TABLE 1-continued

Parts, names, and amino acid sequences for domains of lymphoproliferative parts P1-P2, P1, P2, P3, and P4.

| Part | Name | Amino Acid Sequence |
|---|---|---|
| T079 | TNFRSF8 transcript variant 1 NM_001243_4 | PVLDAGPVLFWVILVLVVVVGSSAFLLC (SEQ ID NO: 192) |
| T080 | TNFRSF9 NM_001561_5 | IISFFLALTSTALLFLLFFLTLRFSVV (SEQ ID NO: 193) |
| T081 | TNFRSF14 transcript variant 1 NM_003820_3 | WWFLSGSLVIVIVCSTVGLII (SEQ ID NO: 194) |
| T082 | TNFRSF18 transcript variant 1 NM_004195_2 | LGWLTVVLLAVAACVLLLTSA (SEQ ID NO: 195) |
| S036 | CD2 transcript variant 1 NM_001328609_1 | TKRKKQRSRRNDEELETRAHRVATEERGRKPHQIPASTPQNPATSQHPPPPPGHRSQAPSHRPPPPGHRVQHQPQKR PPAPSGTQVHQQKGPPLPRPRVQPKPPHGAAENSLSPSSN (SEQ ID NO: 196) |
| S037 | CD3D transcript variant 1 NM_000732_4 | GHETGRLSGAADTQALLRNDQVYQPLRDRDDAQYSHLGGNWARNK (SEQ ID NO: 197) |
| S038 | CD3E NM_000733_3 | KNRKAKAKPVTRGAGAGGRQRGQNKERPPPVPNPDYEPIRKGQRDLYSGLNQRRI (SEQ ID NO: 198) |
| S039 | CD3G NM_000073_2 | GQDGVRQSRASDKQTLLPNDQLYQPLKDREDDQYSHLQGNQLRRN (SEQ ID NO: 199) |
| S042 | CD4 transcript variant land 2 NM_000616_4 | CVRCRHRRRQAERMSQIKRLLSEKKTCQCPHRFQKTCSPI (SEQ ID NO: 200) |
| S043 | CD8A transcript variant 1 NM_001768_6 | LYCNHRNRRRVCKCPRPVVKSGDKPSLSARYV (SEQ ID NO: 201) |
| S044 | CD8B transcript variant 2 NM_172213_3 | RRRRARLRFMKQPQGEGISGTFVPQCLHGYYSNTTTSQKLLNPWILKT (SEQ ID NO: 202) |
| S045 | CD8B transcript variant 3 NM_172101_3 | RRRRARLRFMKQLRLHPLEKCSRMDY (SEQ ID NO: 203) |
| S046 | CD8B transcript variant 5 NM_004931_4 | RRRRARLRFMKQFYK (SEQ ID NO: 204) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S047 | CD27 NM_001242_4 | QRRKYRSNKGESPVEPAEPCRYSCPREEEGSTIPIQEDYRKPEPACSP (SEQ ID NO: 205) |
| S048 | mutated Delta Lck CD28 transcript variant 1 NM_006139_3 | RSKRSRLLHSDYMNMTPRRPGPTRKHYQAYAAARDFAAYRS (SEQ ID NO: 206) |
| S049 | CD28 transcript variant 1 NM_006139_3 | RSKRSRLLHSDYMNMTPRRPGPTRKHYQPYAPPRDFAAYRS (SEQ ID NO: 207) |
| S050 | CD40 transcript variant land 6 NM_001250_5 | KKVAKKPTNKAPHPKQEPQEINFPDDLPGSNTAAPVQETLHGCQPVTQEDGKESRISVQERQ (SEQ ID NO: 208) |
| S051 | CD40 transcript variant 5 NM_001322421_1 | SESSEKVAKKPTNKAPHPKQEPQEINFPDDLPGSNTAAPVQETLHGCQPVTQEDGKESRISVQERQ (SEQ ID NO: 209) |
| S052 | CD79A transcript variant 1 NM_001783_3 | RKRWCINEKLGLDAGDEYEDENLYEGLNLDDCSMYEDISRGLQGTYQDVGSLNIGDVQLEKP (SEQ ID NO: 210) |
| S053 | CD796 transcript variant 3 NM_001039933_2 | LDKDDSKAGMEEDHTYEGLDIDQTATYEDIVTLRTGEVKWSVGEHPGQE (SEQ ID NO: 211) |
| S054 | CRLF2 transcript variant 1 NM_022148_3 | KLWRVKKFLIPSVPDPKSIFPGLFEIHQGNFQEWITDTQNVAHLHKMAGAEQESGPEEPLVVQLAKTEAESPRMLDPQ TEEKEASGGSLQLPHQPLQGGDVVTIGGFTFVMNDRSYVAL (SEQ ID NO: 212) |
| S057 | CSF2RB NM_000395_2 | RFCGIYGYRLRRKWEEKIPNPSKSHLFQNGSAELWPPGSMSAFTSGSPPHQGPWGSRFPELEGVFPVGFGDSEVSPLTI EDPKHVCDPPSGPDTTPAASDLPTEQPPSPQPGPPAASHTPEKQASSFDFNGPYLGPPHSRSLPDILGQPEPPQEGGSQ KSPPPGSLEYLCLPAGGQVQLVPLAQAMGPGQAVEVERRPSQGAAGSPSLESGGGPAPPALGPRVGGQDQKDSPVAI PMSSGDTEDPGVASGYVSSADLVFTPNSGASSVSLVPSLGLPSDQTPSLCPGLASGPPGAPGPVKSGFEGYVELPPIEGR SPRSPRNNPVPPEAKSPVLNPGERPADVSPTSPCIPEGLLVLQQVGDYCFLPGLGPGPLSLRSKPSSPGPGPEIKNLDQAF QVKKPPGQAVPQVPVIQLFKALKQQDYLSLPPWEVNKPGEVC (SEQ ID NO: 213) |
| S058 | CSF2RA transcript variant 7 and 8 NM_001161529_1 | KRFLRIQRLFPPVPQIKDKLNDNHEVEDEIIWEEFTPEEGKGYREEVLTVKEIT (SEQ ID NO: 214) |
| S059 | CSF2RA transcript variant 9 NM_001161531_1 | KRFLRIQRLFPPVPQIKDKLNDNHEVEDEMGPQRHHRCGWNLYPTPGPSPGSGSSPRLGSESSL (SEQ ID NO: 215) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S062 | CSF3R transcript variant 1 NM_000760_3 | SPNRKNPLWPSVPDPAHSSLGSWVPTIMEEDAFQLPGLGTPPITKLTVLEEDEKKPVPWESHNSSETCGLPTLVQTYVLQGDPRAVSTQPQSQSGTSDQVLYGQLLGSPTSPGPGHYLRCDSTQPLLAGLTPSPKSYENLWFQASPLGTLVTPAPSQEDDCVFGPLLNFPLLQGIRVHGMEALGSF (SEQ ID NO: 216) |
| S063 | CSF3R transcript variant 3 NM_156039_3 | SPNRKNPLWPSVPDPAHSSLGSWVPTIMEELPGPRQGQWLGQTSEMSRALTPHPCVQDAFQLPGLGTPPITKLTVLEEDEKKPVPWESHNSSETCGLPTLVQTYVLQGDPRAVSTQPQSQSGTSDQVLYGQLLGSPTSPGPGHYLRCDSTQPLLAGLTPSPKSYENLWFQASPLGTLVTPAPSQEDDCVFGPLLNFPLLQGIRVHGMEALGSF (SEQ ID NO: 217) |
| S064 | CSF3R transcript variant 4 NM_172313_2 | SPNRKNPLWPSVPDPAHSSLGSWVPTIMEEDAFQLPGLGTPPITKLTVLEEDEKKPVPWESHNSSETCGLPTLVQTYVLQGDPRAVSTQPQSQSGTSDQAGPPRRSAYFKDQIMLHPAPPNGLLCLFPITSVL (SEQ ID NO: 218) |
| S069 | EPOR transcript variant 1 NM_000121_3 | HRRALKQKIWPGIPSPESEFEGLFTTHKGNFQLWLYQNDGCLWWSPCTPFTEDPPASLEVLSERCWGTMQAVEPGTDDEGPLLEPVGSEHAQDTYLVLDKWLLPRNPPSEDLPGPGGSVDIVAMDEGSEASSCSSALASKPSPEGASAASFEYTILDPSSQLLRPWTLCPELPPTPPHLKYLYLVVSDSGISTDYSSGDSQGAQGGLSDGPYSNPYENSLIPAAEPLPPSYVACS (SEQ ID NO: 219) |
| S072 | EPOR transcript variant 1 NM_000121_3 | HRRALKQKIWPGIPSPESEFEGLFTTHKGNFQLWLYQNDGCLWWSPCTPFTEDPPASLEVLSERCWGTMQAVEPGTDDEGPLLEPVGSEHAQDTYLVLDKWLLPRNPPSEDLPGPGGSVDIVAMDEGSEASSCSSALASKPSPEGASAASFEYTILDPSSQLLRPWTLCPELPPTPPHLKFLFLVVSDSGISTDYSSGDSQGAQGGLSDGPYSNPYENSLIPAAEPLPPSYVACS (SEQ ID NO: 220) |
| S074 | FCER1G NM_004106_1 | RLKIQVRKAAITSYEKSDGVYTGLSTRNQETYETLKHEKPPQ (SEQ ID NO: 221) |
| S075 | FCGR2C NM_201563_5 | CRKKRISANSTDPVKAAQFEPPGRQMIAIRKRQPEETNNDYETADGGYMTLNPRAPTDDDKNIYLTLPPNDHVNSNN (SEQ ID NO: 222) |
| S076 | FCGRA2 transcript variant 1 NM_001136219_1 | CRKKRISANSTDPVKAAQFEPPGRQMIAIRKRQLEETNNDYETADGGYMTLNPRAPTDDDKNIYLTLPPNDHVNSNN (SEQ ID NO: 223) |
| S077 | GHR transcript variant 1 NM_000163_4 | KQQRIKMLILPPVPVPKIKGIDPDLLKEGKLEEVNTILAIHDSYKPEFHSDDSWVEFIELDIDEPDEKTEESDTDRLLSSDHEKSHSNLGVKDGDSGRTSCCEPDILETDFNANDIHEGTSEVAQPQRLKGEADLLCLDQKNQNNSPYHDACPATQQPSVIQAEKNKPCIPLPTEGAESTHQAAHIQLSNPSSLSNIDFYAQVSDITPAGSVVLSPGQKNKAGMSQCDMHPEMVSLCQENFLMDNAYFCEADAKKCIPVAPHIKVESHIQPSLNQEDIYITTESLTTAAGRPGTGEHVPGSEMPVPDYTSIHIVQSPQGLILNATALPLPDKEFLSSCGYVSTDQLNKIMP (SEQ ID NO: 224) |
| S080 | ICOS NM_012092.3 | CWLTKKKYSSSVHDPNGEYMFMRAVNTAKKSRLTDVTL (SEQ ID NO: 225) |
| S081 | IFNAR1 NM_000629_2 | KVFLRCINYVFFPSLKPSSSIDEYFSEQPLKNLLLSTSEEQIEKCFIIENISTIATVEETNQTDEDHKKYSSQTSQDSGNYSNEDESESKTSEELQQDFV (SEQ ID NO: 226) |
| S082 | IFNAR2 transcript variant 1 NM_207585_2 | KWIGYICLRNSLPKVLNFHNFLAWPFPNLPPLEAMDMVEVIYINRKKKVWDYNYDDESDSDTEAAPRTSGGGYTMHGLTVRPLGQASATSTESQLIDPESEEEPDLPEVDVELPTMPKDSPQQLELLSGPCERRKSPLQDPFPEEDYSSTEGSGGRITFNVDLNSVFLRVLDDEDSDDLEAPLMLSSHLEEMVDPEDPDNVQSNHLLASGEGTQPTFPSPSSEGLWSEDAPSDQSDTSESDVDLGDGYIMR (SEQ ID NO: 227) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S083 | IFNAR2 transcript variant 2 NM_000874_4 | KWIGYICLRNSLPKVLRQGLAKGWNAVAIHRCSHNALQSETPELKQSSCLSFPSSWDYKRASLCPSD (SEQ ID NO: 228) |
| S084 | IFNGR1 NM_000416_2 | CFYIKKINPLKEKSIILPKSLISVVRSATLETKPESKYVSLITSYQPFSLEKEVVCEEPLSPATVPGMHTEDNPGKVEHTEELSSI TEVVTTEENIPDVVPGSHLTPIERESSSPLSSNQSEPGSIALNSYHSRNCSESDHSRNGFDTDSSCLESHSSLSDSEFPPNN KGEIKTEGQELITVIKAPTSFGYDKPHVLVDLLVDDSGKESLIGYRPTEDSKEFS (SEQ ID NO: 229) |
| S085 | IFNGR2 transcript variant 1 NM_001329128_1 | LVLKYRGLIKYWFHTPPSIPLQIEEYLKDPTQPILEALDKDSSPKDDVWDSVSIISFPEKEQEDVLQTL (SEQ ID NO: 230) |
| S086 | IFNLR1 NM_170743_3 | KTLMGNPWFQRAKMPRALDFSGHTHPVATFQPSRPESVNDLFLCPQKELTRGVRPTPRVRAPATQQTRWKKDLAED EEEEDEEDTEDGVSFQPYIEPPSFLGQEHQAPGHSEAGGVDSGRPRAPLVPSEGSSAWDSSDRSWASTVDSSWDRAG SSGYLAEKGPGQGPGGDGHQESLPPPEFSKDSGFLEELPEDNLSSWATWGTLPPEPNLVPGGPPVSLQTLTFCWESSP EEEEEARESEIEDSDAGSWGAESTQRTEDRGRTLGHYMAR (SEQ ID NO: 231) |
| S087 | IFNLR1 transcript variant 2 NM_173064_2 | KTLMGNPWFQRAKMPRALELTRGVRPTPRVRAPATQQTRWKKDLAEDEEEEDEEDTEDGVSFQPYIEPPSFLGQEHQ APGHSEAGGVDSGRPRAPLVPSEGSSAWDSSDRSWASTVDSSWDRAGSSGYLAEKGPGQGPGGDGHQESLPPPEFS KDSGFLEELPEDNLSSWATWGTLPPEPNLVPGGPPVSLQTLTFCWESSPEEEEEARESEIEDSDAGSWGAESTQRTEDR GRTLGHYMAR (SEQ ID NO: 232) |
| S098 | IL1R1 transcript variant 2 NM_001288706_1 | KIDIVLWYRDSCYDFLPIKVLPEVLEKQCGYKLFIYGRDDYVGEDIVEVINENVKKSRRLIIILVRETSGFSWLGGSSEEQIA MYNALVQDGIKVVLLELEKIQDYEKMPESIKFIKQKHGAIRWSGDFTQGPQSAKTRFWKNVRYHMPVQRRSPSSKHQ LLSPATKEKLQREAHVPLG (SEQ ID NO: 233) |
| S099 | IL1R1 transcript variant 3 NM_001320978_1 | KIDIVLWYRDSCYDFLPIKASDGKTYDAYILYPKTVGEGSTSDCDIFVFKVLPEVLEKQCGYKLFIYGRDDYVGEDIVEVINE NVKKSRRLIIILVRETSGFSWLGGSSEEQIAMYNALVQDGIKVVLLELEKIQDYEKMPESIKFIKQKHGAIRWSGDFTQGP QSAKTRFWKNVRYHMPVQRRSPSSKHQLLSPATKEKLQREAHVPLG (SEQ ID NO: 234) |
| S100 | IL1RAP transcript variant 1 NM_002182_3 | YRAHFGTDETILDGKEYDIYVSYARNAEEEEFVLLTLRGVLENEFGYKLCIFDRDSLPGGIVTDETLSFIQKSRRLLVVLSPNY VLQGTQALLELKAGLENMASRGNINVILVQYKAVKETKVKELKRAKTVLTVIKWKGEKSKYPQGRFWKQLQVAMPVKK SPRRSSSDEQGLSYSSLKNV (SEQ ID NO: 235) |
| S101 | IL1RAP transcript variant 6 NM_001167931_1 | YRAHFGTDETILDGKEYDIYVSYARNAEEEEFVLLTLRGVLENEFGYKLCIFDRDSLPGGNTVEAVFDFIQRSRRMIVVLSP DYVTEKSISMLEFKLGVMCQNSIATKLIVVEYRPLEHPHPGILQLKESVSFVSWKGEKSKHSGSKFWKALRLALPLRSLSA SSGWNESCSSQSDISLDHVQRRRSRLKEPPELQSSERAAGSPPAPGTMSKHRGKSSATCRCCVTYCEGENHLRNKSRAE IHNQPQWETHLCKPVPQESETQWIQNGTRLEPPAPQISALALHHFTDLSNNNDFYIL (SEQ ID NO: 236) |
| S102 | IL1RL1 transcript variant 1 NM_016232.4 | LKMFWIEATLLWRDIAKPYKTRNDGKLYDAYVVYPRNYKSSTDGASRVEHFVHQILPDVLENKCGYTLCIYGRDMLPGE DVVTAVETNIRKSRRHIFILTPQITHNKEFAYEQEVALHCALIQNDAKVILIEMEALSELDMLQAEALQDSLQHLMKVQG TIKWREDHIANKRSLNSKFWKHVRYQMPVPSKIPRKASSLTPLAAQKQ (SEQ ID NO: 237) |
| S103 | 2IL1RL NM_003854.2 | NIFKIDIVLWYRSAFHSTETIVDGKLYDAYVLYPKPHKESQRHAVDALVLNILPEVLERQCGYKLFIFGRDEFPGQAVANVI DENVKLCRRLIVIVVPESLGFGLLKNLSEEQIAVYSALIQDGMKVILIELEKIEDYTVMPESIQYIKQKHGAIRWHGDFTEQS QCMKTKFWKTVRYHMPPRRCRPFPPVQLLQHTPCYRTAGPELGSRRKKCTLTTG (SEQ ID NO: 238) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S104 | IL2RA transcript variant 1 NM_000417_2 | TWQRRQRKSRRTI (SEQ ID NO: 239) |
| S105 | IL2RB transcript variant 1 NM_000878_4 | NCRNTGPWLKKVLKCNTPDPSKFFSQLSSEHGGDVQKWLSSPFPSSSFSPGGLAPEISPLEVLERDKVTQLLLQQDKVPE PASLSSNHSLTSCFTNQGYFFFHLPDALEIEACQVYFTYDPYSEEDPDEGVAGAPTGSSPQPLQPLSGEDDAYCTFPSRD DLLLFSPSLLGGPSPPSTAPGGSGAGEERMPPSLQERVPRDWDPQPLGPPTPGVPDLVDFQPPPELVLREAGEEVPDA GPREGVSFPWSRPPGQGEFRALNARLPLNTDAYLSLQELQGQDPTHLV (SEQ ID NO: 240) |
| S106 | IL2RG NM_000206_2 | ERTMPRIPTLKNLEDLVTEYHGNFSAWSGVSKGLAESLQPDYSERLCLVSEIPPKGGALGEGPGASPCNQHSPYWAPPC YTLKPET (SEQ ID NO: 241) |
| S109 | IL3RA transcript variant 1 and 2 NM_002183_3 | RRYLVMQRLFPRIPHMKDPIGDSFQNDKLVVWEAGKAGLEECLVTEVQVVQKT (SEQ ID NO: 242) |
| S110 | IL4R transcript variant 1 NM_000418_3 | KIKKEWWDQIPNPARSRLVAIIIQDAQGSQWEKRSRGQEPAKCPHWKNCLTKLLPCFLEHNMKRDEDPHKAAKEMPF QGSGKSAWCPVEISKTVLWPESISVVRCVELFEAPVECEEEEEVEEEKGSFCASPESSRDDFQEGREGIVARLTESLFLDLL GEENGGFCQQDMGESCLLPPSGSTSAHMPWDEFPSAGPKEAPPWGKEQPLHLEPSPPASPTQSPDNLTCTETPLVIA GNPAYRSFSNSLSQSPCPRELGPDPLLARHLEEVEPEMPCVPQLSEPTTVPQPEPETWEQILRRNVLQHGAAAAPVSAP TSGYQEFVHAVEQGGTQASAVVGLGPPGEAGYKAFSSLLASSAVSPEKCGFGASSGEEGYKPFQDLIPGCPGDPAPVPV PLFTFGLDREPPRSPQSSHLPSSSPEHLGLEPGEKVEDMPKPPLPQEQATDPLVDSLGSGIVYSALTCHLCGHLKQCHGQ EDGGQTPVMASPCCGCCCGDRSSPPTTPLRAPDPSPGGVPLEASLCPASLAPSGISEKSKSSSSFHPAPGNAQSSSQTPK IVNFVSVGPTYMRVS (SEQ ID NO: 243) |
| S113 | IL4R transcript variant 1 NM_000418_3 | KIKKEWWDQIPNPARSRLVAIIIQDAQGSQWEKRSRGQEPAKCPHWKNCLTKLLPCFLEHNMKRDEDPHKAAKEMPF QGSGKSAWCPVEISKTVLWPESISVVRCVELFEAPVECEEEEEVEEEKGSFCASPESSRDDFQEGREGIVARLTESLFLDLL GEENGGFCQQDMGESCLLPPSGSTSAHMPWDEFPSAGPKEAPPWGKEQPLHLEPSPPASPTQSPDNLTCTETPLVIA GNPAYRSFSNSLSQSPCPRELGPDPLLARHLEEVEPEMPCVPQLSEPTTVPQPEPETWEQILRRNVLQHGAAAAPVSAP TSGYQEFVHAVEQGGTQASAVVGLGPPGEAGYKAFSSLLASSAVSPEKCGFGASSGEEGYKPFQDLIPGCPGDPAPVPV PLFTFGLDREPPRSPQSSHLPSSSPEHLGLEPGEKVEDMPKPPLPQEQATDPLVDSLGSGIVFSALTCHLCGHLKQCHGQ EDGGQTPVMASPCCGCCCGDRSSPPTTPLRAPDPSPGGVPLEASLCPASLAPSGISEKSKSSSSFHPAPGNAQS5SQTPK IVNFVSVGPTYMRVS (SEQ ID NO: 244) |
| S115 | IL5RA transcript variant 1 NM_000564_4 | KICHLWIKLFPPIPAPKSNIKDLFVTTNYEKAGSSETEIEVICYIEKPGVETLEDSVF (SEQ ID NO: 245) |
| S116 | IL6R transcript variant 1 NM_000565_3 | RFKKTWKLRALKEGKTSMHPPYSLGQLVPERPRPTPVLVPLISPPVSPSSLGSDNTSSHNRPDARDPRSPYDISNTDYFFP R (SEQ ID NO: 246) |
| S117 | IL6ST transcript variant 1 and 3 NM_002184_3 | NKRDLIKKHIWPNVPDPSKSHIAQWSPHTPPRHNFNSKDQMYSDGNFTDVSVVEIEANDKKPFPEDLKSLDLFKKEKIN TEGHSSGIGGSSCMSSSRPSISSSDENESSQNTSSTVQYSTVVHSGYRHQVPSVQVFSRSESTQPLLDSEERPEDLQLVD HVDGGDGILPRQQYFKQNCSQHESSPDISHFERSKQVSSVNEEDFVRLKQQ1SDHISQ5CGSGQMKMFQEVSAADAF GPGTEGQVERFETVGMEAATDEGMPKSYLPQTVRQGGYMPQ (SEQ ID NO: 247) |

TABLE 1-continued

Parts, names, and amino acid sequences for domains of lymphoproliferative parts P1-P2, P1, P2, P3, and P4.

| Part | Name | Amino Acid Sequence |
| --- | --- | --- |
| S120 | IL7RA Isoform 1<br>NM_002185.4 | WKKRIKPIVWPSLPDHKKTLEHLCKKPRKNLNVSFNPESFLDCQIHRVDDIQARDEVEGFLQDTFPQQLEESEKQRLGG<br>DVQSPNCPSEDVVITPESFGRDSSLTCLAGNVSACDAPILSSSRSLDCRESGKNGPHVYQDLLLSLGTTNSTLPPPFSLQS<br>GILTLNPVAQGQPILTSLGSNQEEAYVTMSSFYQNQ (SEQ ID NO: 248) |
| S121 | IL7RA Isoform 3<br>(C-term deletion)<br>(interleukin 7<br>receptor) | WKKRIKPIVWPSLPDHKKTLEHLCKKPRKVSVFGA (SEQ ID NO: 249) |
| S126 | IL9R transcript<br>variant 1<br>NM_002186_2 | KLSPRVKRIFYQNVPSPAMFFQPLYSVHNGNFQTWMGAHGAGVLLSQDCAGTPQGALEPCVQEATALLTCGPARPW<br>KSVALEEEQEGPGTRLPGNLSSEDVLPAGCTEWRVQTLAYLPQEDWAPTSLTRPAPPDSEGSRSSSSSSSSNNNNYCAL<br>GCYGGWHLSALPGNTQSSGPIPALACGLSCDHQGLETQQGVAWVLAGHCQRPGLHEDLQGMLLPSVLSKARSWTF<br>(SEQ ID NO: 250) |
| S129 | IL10RA transcript<br>variant 1<br>NM_001558_3 | QLYVRRRKKLPSVLLFKKPSPFIFISQRPSPETQDTIHPLDEEAFLKVSPELKNLDLHGSTDSGFGSTKPSLQTEEPQFLLPD<br>PHPQADRTLGNREPPVLGDSCSSGSSNSTDSGICLQEPSLSPSTGPTWEQQVGSNSRGQDDSGIDLVQNSEGRAGDT<br>QGGSALGHHSPPEPEVPGEEDPAAVAFQGYLRQTRCAEEKATKTGCLEEESPLTDGLGPKFGRCLVDEAGLHPPALAK<br>GYLKQDPLEMTLASSGAPTGQWNQPTEEWSLLALSSCSDLGISDWSFAHDLAPLGCVAAPGGLLGSFNSDLVTLPLISS<br>LQSSE (SEQ ID NO: 251) |
| S130 | IL10RB<br>NM_000628_4 | ALLWCVYKKTKYAFSPRNSLPQHLKEFLGHPHHNTLLFFSFPLSDENDVFDKLSVIAEDSESGKQNPGDSCSLGTPPGQG<br>PQS (SEQ ID NO: 252) |
| S135 | IL11RA<br>NM_001142784_2 | RLRRGGKDGSPKPGFLASVIPVDRRPGAPNL (SEQ ID NO: 253) |
| S136 | IL12RB1 transcript<br>variant 1 and 4<br>NM_005535_2 | NRAARHLCPPLPTPCASSAIEFPGGKETWQWINPVDFQEEASLQEALVVEMSWDKGERTEPLEKTELPEGAPELALDTE<br>LSLEDGDRCKAKM (SEQ ID NO: 254) |
| S137 | IL12RB1 transcript<br>variant 3<br>NM_001290023_1 | NRAARHLCPPLPTPCASSAIEFPGGKETWQWINPVDFQEEASLQEALVVEMSWDKGERTEPLEKTELPEGAPELALDTE<br>LSLEDGDRCDR (SEQ ID NO: 255) |
| S138 | IL12RB2 transcript<br>variant 1 and 3<br>NM_001559_2 | HYFQQKVFVLLAALRPQWCSREIPDPANSTCAKKYPIAEEKTQLPLDRLLIDWPTPEDPEPLVISEVLHQVTPVFRHPPCS<br>NWPQREKGIQGHQASEKDMMHSASSPPPPRALQAESRQLVDLYKVLESRGSDPKPENPACPWTVLPAGDLPTHDGY<br>LPSNIDDLPSHEAPLADSLEELEPQHISLSVFP5SSLHPLTFSCGDKLTLDQLKMRCDSLML (SEQ ID NO: 256) |
| S141 | IL13RA1<br>NM_001560_2 | KRLKIIIFPPIPDPGKIFKEMFGDQNDDTLHWKKYDIYEKQTKEETDSVVLIENLKKASQ (SEQ ID NO: 257) |
| S142 | IL13RA2<br>NM_000640_2 | RKPNTYPKMIPEFFCDT (SEQ ID NO: 258) |
| S143 | IL15RA transcript<br>variant 4<br>NM_001256765_1 | KSRQTPPLASVEMEAMEALPVTWGTSSRDEDLENCSHHL (SEQ ID NO: 259) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S144 | IL17RA NM_014339_6 | CMTWRLAGPGSEKYSDDTKYTDGLPAADLIPPPLKPRKVWIIYSADHPLYVDVVLKFAQFLLTACGTEVALDLLEEQAISE AGVMTWVGRQKQEMVESNSKIIVLCSRGTRAKWQALLGRGAPVRLRCDHGKPVGDLFTAAMNMILPDFKRPACFG TYVVCYFSEVSCDGDVPDLFGAAPRYPLMDRFEEVYFRIQDLEMFQPGRMHRVGELSGDNYLRSPGGRQLRAALDRF RDWQVRCPDWFECENLYSADDQDAPSLDEEVFEEPLLPPGTGIVKRAPLVREPGSQACLAIDPLVGEEGGAAVAKLEP HLQPRGQPAPQPLHTLVLAAEEGALVAAVEPGPLADGAAVRLALAGEGEACPLLGSPGAGRNSVLFLPVDPEDSPLGSS TPMASPDLLPEDVREHLEGLMLSLFEQSLSCQAQGGCSRPAMVLTDPHTPYEEEQRQSVCISDQGYISRSSPQPPEGLT EMEEEEEEEQDPGKPALPLSPEDLESLRSLQRQLLFRQLQKNSGWDTMGSESEGPSA (SEQ ID NO: 260) |
| S145 | IL17RB NM_018725_3 | RHERIKKTSFSTTTLLPPIKVLVVYPSEICFHHTICYFTEFLQNHCRSEVILEKWQKKKIAEMGPVQWLATQKKAADKVVFL LSNDVNSVCDGTCGKSEGSPSENSQDLFPLAFNLFCSDLRSQIHLHKYVVVYFREIDTKDDYNALSVCPKYHLMKDATAF CAELLHVKQQVSAGKRSQACHDGCCSL (SEQ ID NO: 261) |
| S146 | IL17RC transcript variant 1 NM_153460_3 | KKDHAKGWLRLLKQDVRSGAAARGRAALLLYSADDSGFERLVGALASALCQLPLRVAVDLWSRRELSAQGPVAWFHA QRRQTLQEGGVVVLLFSPGAVALCSEWLQDGVSGPGAHGPHDAFRASLSCVLPDFLQGRAPGSYVGACFDRLLHPDA VPALFRTVPVFTLPSQLPDFLGALQQPRAPRSGRLQERAEQVSRALQPALDSYFHPPGTPAPGRGVGPGAGPGAGDGT (SEQ ID NO: 262) |
| S147 | IL17RC transcript variant 4 NM_001203263_1 | KKDHAKAAARGRAALLLYSADDSGFERLVGALASALCQLPLRVAVDLWSRRELSAQGPVAWFHAQRRQTLQEGGVVV LLFSPGAVALCSEWLQDGVSGPGAHGPHDAFRASLSCVLPDFLQGRAPGSYVGACFDRLLHPDAVPALFRTVPVFTLPS QLPDFLGALQQPRAPRSGRLQERAEQVSRALQPALDSYFHPPGTPAPGRGVGPGAGPGAGDGT (SEQ ID NO: 263) |
| S148 | IL17RD transcript variant 2 NM_017563_4 | CRKKQQENIYSHLDEESSESSTYTAALPRERLRPRPKVFLCYSSKDGQNHMNVVQCFAYFLQDFCGCEVALDLWEDFSL CREGQREWVIQKIHESQFIIVVCSKGMKYFVDKKNYKHKGGGRGSGKGELFLVAVSAIAEKLRQAKQSSSAALSKFIAVY FDYSCEGDVPGILDLSTKYRLMDNLPQLCSHLHSRDHGLQEPGQHTRQGSRRNYFRSKSGRSLYVAICNMHQFIDEEPD WFEKQFVPFHPPPLRYREPVLEKFDSGLVLNDVMCKPGPESDFCLKVEAAVLGATGPADSQHESQHGGLDQDGEARP ALDGSAALQPLLHTVKAGSPSDMPRDSGIYDSSVPSSELSLPLMEGLSTDQTETSSLTESVSSSSGLGEEEPPALPSKLLSS GSCKADLGCRSYTDELHAVAPL (SEQ ID NO: 264) |
| S149 | IL17RE transcript variant 1 NM_153480_1 | TCRRPQSGPGPARPVLLLHAADSEAQRRLVGALAELLRAALGGGRDVIVDLWEGRHVARVGPLPWLWAARTRVARE QGTVLLLWSGADLRPVSGPDPRAAPLLALLHAAPRPLLLLAYFSRLCAKGDIPPPLRALPRYRLLRDLPRLLRALDARPFAE ATSWGRLGARQRRQSRLELCSRLEREAARLADLG (SEQ ID NO: 265) |
| S154 | IL18R1 transcript variant 1 NM_003855_3 | YRVDLVLFYRHLTRRDETLTDGKTYDAFVSYLKECRPENGEEHTFAVEILPRVLEKHFGYKLCIFERDVVPGGAVVDEIHSL IEKSRRLIIVLSKSYMSNEVRYELESGLHEALVERKIKIILIEFTPVTDFTFLPQSLKLLKSHRVLKWKADKSLSYNSRFWKNLL YLMPAKTVKPGRDEPEVLPVLSES (SEQ ID NO: 266) |
| S155 | IL18RAP NM_003853_3 | SALLYRHWIEIVLLYRTYQSKDQTLGDKKDFDAFVSYAKWSSFPSEATSSLSEEHLALSLFPDVLENKYGYSLCLLERDVAP GGVYAEDIVSIIKRSRRGIFILSPNYVNGPSIFELQAAVNLALDDQTLKLILIKFCYFQEPESLPHLVKKALRVLPTVTWRGLK SVPPNSRFWAKMRYHMPVKNSQGFTWNQLRITSRIFQWKGLSRTETTGRSSQPKEW (SEQ ID NO: 267) |
| S156 | IL20RA transcript variant 1 NM_014432_3 | SIYRYIHVGKEKHPANLILIYGNEFDKRFFVPAEKIVINFITLNISDDSKISHQDMSLLGKSSDVSSLNDPQPSGNLRPPQEE EEVKHLGYASHLMEIFCDSEENTEGTSLTQQESLSRTIPPDKTVIEYEYDVRTTDICAGPEEQELSLQEEVSTQGTLLESQA ALAVLGPQTLQYSYTPQLQDLDPLAQEHTDSEEGPEEEPSTTLVDWDPQTGRLCIPSLSSFDQDSEGCEPSEGDGLGEE GLLSRLYEEPAPDRPPGENETYLMQFMEEWGLYVQMEN (SEQ ID NO: 268) |
| S157 | IL20RB NM_144717_3 | WKMGRLLQYSCCPVVVLPDTLKITNSPQKLISCRREEVDACATAVMSPEELLRAWIS (SEQ ID NO: 269) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S158 | IL21R transcript variant 2 NM_181078_2 | SLKTHPLWRLWKKIWAVPSPERFFMPLYKGCSGDFKKWVGAPFTGSSLELGPWSPEVPSTLEVYSCHPPRSPAKRLQLTELQEPAELVESDGVPKPSFWPTAQNSGGSAYSEERDRPYGLVSIDTVTVLDAEGPCTWPCSCEDDGYPALDLDAGLEPSPGLEDPLLDAGTTVLSCGCVSAGSPGLGGPLGSLLDRLKPPLADGEDWAGGLPWGGRSPGGVSESEAGSPLAGLDMDTFDSGFVGSDCSSPVECDFTSPGDEGPPRSYLRQWVVIPPPLSSPGPQAS (SEQ ID NO: 270) |
| S161 | IL22RA1 NM_021258_3 | SYRYVTKPPAPPNSLNVQRVLTFQPLRFIQEHVLIPVFDLSGPSSLAQPVQYSQIRVSGPREPAGAPQRHSLSEITYLGQPDISILQPSNVPPPQILSPLSYAPNAAPEVGPPSYAPQVTPEAQFPFYAPQAISKVQPSSYAPQATPDSWPPSYGVCMEGSGKDSPTGTLSSPKHLRPKGQLQKEPPAGSCMLGGLSLQEVTSLAMEESQEAKSLHQPLGICTDRTSDPNVLHSGEEGTPQYLKGQLPLLSSVQIEGHPMSLPLQPPSRPCSPSDQGPSPWGLLESLVCPKDEAKSPAPETSDLEQPTELDSLFRGLALTVQWES (SEQ ID NO: 271) |
| S165 | IL23R NM_144701_2 | NRSFRTGIKRRILLLIPKWLYEDIPNMKNSNVVKMLQENSELMNNNSSEQVLYVDPMITEIKEIFIPEHKPTDYKKENTGPLETRDYPQNSLFDNTTVVYIPDLNTGYKPQISNFLPEGSHLSNNNEITSLTLKPPVDSLDSGNNPRLQKHPNFAFSVSSVNSLSNTIFLGELSLILNQGECSSPDIQNSVEEETTMLLENDSPSETIPEQTLLPDEFVSCLGIVNEELPSINTYFPQNILESHFNRISLLEK (SEQ ID NO: 272) |
| S168 | IL27RA NM_004843_3 | TSGRCYHLRHKVLPRWVWEKVPDPANSSSGQPHMEQVPEAQPLGDLPILEVEEMEPPPVMESSQPAQATAPLDSGYEKHFLPTPEELGLLGPPRPQVLA (SEQ ID NO: 273) |
| S169 | IL27RA NM_004843_3 | TSWVWEKVPDPANSSSGQPHMEQVPEAQPLGDLPILEVEEMEPPPVMESSQPAQATAPLDSGYEKHFLPTPEELGLLGPPRPQVLA (SEQ ID NO: 274) |
| S170 | IL31RA transcript variant 1 NM_139017_5 | KKPNKLTHLCWPTVPNPAESSIATWHGDDFKDKLNLKESDDSVNTEDRILKPCSTPSDKLVIDKLVVNFGNVLQEIFTDEARTGQENNLGGEKNGYVTCPFRPDCPLGKSFEELPVSPEIPPRKSQYLRSRMPEGTRPEAKEQLLFSGQ5LVPDHLCEEGAPNPYLKNSVTAREFLVSEKLPEHTKGEV (SEQ ID NO: 275) |
| S171 | IL31RA transcript variant 4 NM_001242638_1 | KKPNKLTHLCWPTVPNPAESSIATWHGDDFKDKLNLKESDDSVNTEDRILKPCSTPSDKLVIDKLVVNFGNVLQEIFTDEARTGQENNLGGEKNGTRILSSCPTSI (SEQ ID NO: 276) |
| S174 | LEPR transcript variant 1 NM_002303_5 | SHQRMKKLFWEDVPNPKNCSWAQGLNFQKPETFEHLFIKHTASVTCGPLLLEPETISEDISVDTSWKNKDEMMPTTVVSLLSTTDLEKGSVCISDQFNSVNFSEAEGTEVTYEDESQRQPFVKYATLISNSKPSETGEEQGLINSSVTKCFSSKNSPLKDSFSNSSWEIEAQAFFILSDQHPNIISPHLTFSEGLDELLKLEGNFPEENNDKKSIYYLGVTSIKKRESGVLLTDKSRVSCPFPAPCLFTDIRVLQDSCSHFVENNINLGTSSKKTFASYMPQFQTCSTQTHKIMENKMCDLTV (SEQ ID NO: 277) |
| S175 | LEPR transcript variant 2 NM_001003680_3 | SHQRMKKLFWEDVPNPKNCSWAQGLNFQKMLEGSMFVKSHHHSLISSTQGHKHCGRPQGPLHRKTRDLCSLVYLLTLPPLLSYDPAKSPSVRNTQE (SEQ ID NO: 278) |
| S176 | LEPR transcript variant 3 NM_001003679_3 | SHQRMKKLFWEDVPNPKNCSWAQGLNFQKRTDIL (SEQ ID NO: 279) |
| S177 | LEPR transcript variant 5 NM_001198688_1 | SHQRMKKLFWEDVPNPKNCSWAQGLNFQKKMPGTKELLGGGWLT (SEQ ID NO: 280) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S180 | LIFR NM_001127671_1 | YRKREWIKETFYPDIPNPENCKALQFQKSVCEGSSALKTLEMNPCTPNNVEVLETRSAFPKIEDTEIISPVAERPEDRSDAE PENHVVVSYCPPIIEEEIPNPAADEAGGTAQVIYIDVQ5MYQPQAKPEEEQENDPVGGAGYKPQMHLPINSTVEDIAAE EDLDKTAGYRPQANVNTWNLVSPDSPRSIDSNSEIVSFGSPCSINSRQFLIPPKDEDSPKSNGGGW5FTNFFQNKPND (SEQ ID NO: 281) |
| S183 | LMP1 NC_007605_1 | YYHGQRHSDEHHHDDSLPHPQQATDDSGHESDSNSNEGRHHLLVSGAGDGPPLCSQNLGAPGGGPDNGPQDPDN TDDNGPQDPDNTDDNGPHDPLPQDPDNTDDNGPQDPDNTDDNGPHDPLPHSPSDSAGNDGGPPQLTEEVENKG GDQGPPLMTDGGGGHSHDSGHGGGDPHLPTLLLGSSGSGGDDDDPHGPVQLSYYD (SEQ ID NO: 282) |
| S186 | MPL NM_005373_2 | RWQFPAHYRRLRHALWPSLPDLHRVLGQYLRDTAALSPPKATVSDTCEEVEPSLLEILPKSSERTPLPLCSSQAQMDYRR LQPSCLGTMPLSVCPPMAESGSCCTTHIANHSYLPLSYWQQP (SEQ ID NO: 283) |
| S189 | MYD88 transcript variant 1 NM_001172567_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGH MPERFDAFICYCPSDIQFVQEMIRQLEQTNYRLKLCVSDRDVLPGTCVWSIASELIEKRLARRPRGGCRRMVVVVSDDY LQSKECDFQTKFALSLSPGAHQKRLIPIKYKAMKKEFPSILRFITVCDYTNPCTKSWFWTRLAKALSLP (SEQ ID NO: 284) |
| S190 | MYD88 transcript variant 2 NM_002468_4 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGH MPERFDAFICYCPSDIQFVQEMIRQLEQTNYRLKLCVSDRDVLPGTCVWSIASELIEKRCRRMVVVVSDDYLQSKECDF QTKFALSLSPGAHQKRLIPIKYKAMKKEFPSILRFITVCDYTNPCTKSWFWTRLAKALSLP (SEQ ID NO: 285) |
| S191 | MYD88 transcript variant 3 NM_001172568_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIGHMPERFDAFICYCPSDIQFVQEMIRQLEQTNYRLKLCVSDRDVLPG TCVWSIASELIEKRCRRMVVVVSDDYLQSKECDFQTKFALSLSPGAHQKRLIPIKYKAMKKEFPSILRFITVCDYTNPCTKS WFWTRLAKALSLP (SEQ ID NO: 286) |
| S192 | MYD88 transcript variant 4 NM_001172569_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGAA GWWWLSLMITCRARNVTSRPNLHSASLQVPIRSD (SEQ ID NO: 287) |
| S193 | MYD88 transcript variant 5 NM_001172566_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIGAAGWWWLSLMITCRARNVTSRPNLHSASLQVPIRSD (SEQ ID NO: 288) |
| S194 | MYD88 transcript variant 1 NM_001172567_1 | MAAGGPGAGSAAPVSSTSSLPLAALNMRVRRRLSLFLNVRTQVAADWTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGH MPERFDAFICYCPSDI (SEQ ID NO: 289) |
| S195 | MYD88 transcript variant 3 NM_001172568_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIGHMPERFDAFICYCPSDI (SEQ ID NO: 290) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S196 | MYD88 transcript variant 1 NM_001172567_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGH MPERFDAFICYCPSDIQFVQEMIRQLEQTNYRLKLCVSDRDVLPGTCVWSIASELIEKRLARRPRGGCRRMVVVVSDDY LQSKECDFQTKFALSLSPGAHQKRPIPIKYKAMKKEFPSILRFITVCDYTNPCTKSWFWTRLAKALSLP (SEQ ID NO: 291) |
| S197 | MYD88 transcript variant 2 NM_002468_4 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIEEDCQKYILKQQQEEAEKPLQVAAVDSSVPRTAELAGITTLDDPLGH MPERFDAFICYCPSDIQFVQEMIRQLEQTNYRLKLCVSDRDVLPGTCVWSIASELIEKRCRRMVVVVSDDYLQSKECDF QTKFALSLSPGAHQKRPIPIKYKAMKKEFPSILRFITVCDYTNPCTKSWFWTRLAKALSLP (SEQ ID NO: 292) |
| S198 | MYD88 transcript variant 3 NM_001172568_1 | MAAGGPGAGSAAPVSSTSSLPLAALNMRVRRRLSLFLNVRTQVAADVVTALAEEMDFEYLEIRQLETQADPTGRLLDA WQGRPGASVGRLLELLTKLGRDDVLLELGPSIGHMPERFDAFICYCPSDIQFVQEMIRQLEQTNYRLKLCVSDRDVLPG TCVWSIASELIEKRCRRMVVVVSDDYLQSKECDFQTKFALSLSPGAHQKRPIPIKYKAMKKEFPSILRFITVCDYTNPCTKS WFWTRLAKALSLP (SEQ ID NO: 293) |
| S199 | OSMR transcript variant 4 NM_001323505_1 | KSQWIKETCYPDIPDPYKSSILSLIKFKENPHLIIMNVSDCIPDAIEVVSKPEGTKIQFLGTRKSLTETELTKPNYLYLLPTEKN HSGPGPCICFENLTYNQAASDSGSCGHVPVSPKAPSMLGLMTSPENVLKALEKNYMNSLGEIPAGETSLNYVSQLASP MFGDKDSLPTNPVEAPHCSEYKMQMAVSLRLALPPPTENSSLSSITLLDPGEHYC (SEQ ID NO: 294) |
| S202 | PRLR transcript variant 1 NM_000949_6 | KGYSMVTCIFPPVPGPKIKGFDAHLLEKGKSEELLSALGCQDFPPTSDYEDLLVEYLEVDDSEDQHLMSVHSKEHPSQG MKPTYLDPDTDSGRGSCDSPSLLSEKCEEPQANPSTFYDPEVIEKPENPETTHTWDPQCISMEGKIPYFHAGGSKCSTW PLPQPSQHNPRSSYHNITDVCELAVGPAGAPATLLNEAGKDALKSSQTIKSREEGKATQQREVESFHSETDQDTPWLLP QEKTPFGSAKPLDYVEIHKVNKDGALSLLPKCIRENSGKPKKPGTPENNKEYAKVSGVMDNNILVLVPDPHAKNVACFE ESAKEAPPSLEQNQAEKALANFTATSSKCRLQLGGLDYLDPACFTHSFH (SEQ ID NO: 295) |
| S211 | TNFRSF4 NM_003327_3 | ALYLLRRDQRLPPDAHKPPGGGSFRTPIQEEQADAHSTLAKI (SEQ ID NO: 296) |
| S212 | TNFRSF8 transcript variant 1 NM_001243_4 | HRRACRKRIRQKLHLCYPVQTSQPKLELVDSRPRRSSTQLRSGASVTEPVAEERGLMSQPLMETCHSVGAAYLESLPLQ DASPAGGPSSPRDLPEPRVSTEHTNNKIEKIYIMKADTVIVGTVKAELPEGRGLAGPAEPELEEELEADHTPHYPEQETEP PLGSCSDVMLSVEEEGKEDPLPTAASGK (SEQ ID NO: 297) |
| S213 | TNFRSF9 NM_001561_5 | KRGRKKLLYIFKQPFMRPVQTTQEEDGCSCRFPEEEEGGCEL (SEQ ID NO: 298) |
| S214 | TNFRSF14 transcript variant 1 NM_003820_3 | CVKRRKPRGDVVKVIVSVCIRKRQEAEGEATVIEALQAPPDVTTVAVEETIPSFTGRSPNH (SEQ ID NO: 299) |
| S215 | TNFRSF18 transcript variant 1 NM_004195_2 | QLGLHIWQLRSQCMWPRETQLLLEVPPSTEDARSCQFPEEERGERSAEEKGRLGDLWV (SEQ ID NO: 300) |

TABLE 1-continued

Parts, names, and amino acid sequences for domains of lymphoproliferative parts P1-P2, P1, P2, P3, and P4.

| Part | Name | Amino Acid Sequence |
|---|---|---|
| S216 | TNFRSF18 transcript variant 3_NM_148902_1 | QLGLHIWQLRKTQLLLEVPPSTEDARSCQFPEEERGERSAEEKGRLGDLW (SEQ ID NO: 301) |
| X001 | Linker | GSGGSEGGGSEGGAATAGSGSGS (SEQ ID NO: 302) |

TABLE 4

Constructs present in Library 6 Top 100 in vivo, antigen independent.

| Ranking | Block Sequence |
|---|---|
| 1 | E006-T030-S129-S047 |
| 2 | E006-T023-S171-S211 |
| 3 | E008-T001-S121-S212 |
| 4 | E006-T064-S190-S080 |
| 5 | E006-T047-S141-S050 |
| 6 | E008-T001-S064-S047 |
| 7 | E006-T048-X001-S211 |
| 8 | E009-T073-S062-S053 |
| 9 | E010-T035-S190-S047 |
| 10 | E010-T055-S192-S051 |
| 11 | E006-T071-S165-S076 |
| 12 | E009-T075-S165-S050 |
| 13 | E010-T027-S117-S053 |
| 14 | E007-T054-S197-S212 |
| 15 | E007-T056-S170-S050 |
| 16 | E007-T050-S190-S051 |
| 17 | E008-T060-S190-S074 |
| 18 | E007-T080-S059-S080 |
| 19 | E007-T057-S059-S075 |
| 20 | E006-T045-S177-S216 |
| 21 | E010-T077-S058-S053 |
| 22 | E006-T073-S120-S048 |
| 23 | E009-T063-S192-S053 |
| 24 | E008-T067-S190-S074 |
| 25 | E009-T057-S117-S074 |
| 26 | E007-T045-S190-S211 |
| 27 | E009-T068-S083-S212 |
| 28 | E007-T039-S197-S080 |
| 29 | E010-T036-S058-S048 |
| 30 | E008-T056-S190-S050 |
| 31 | E010-T026-S120-S038 |
| 32 | E006-T017-S062-S039 |
| 33 | E009-T073-S142-X002 |
| 34 | E009-T077-S192-S212 |
| 35 | E007-T052-S199-S049 |
| 36 | E007-T061-S186-S211 |
| 37 | E009-T009-S197-S038 |
| 38 | E008-T029-S161-S216 |
| 39 | E010-T006-S190-X002 |
| 40 | E010-T081-S190-X002 |
| 41 | E008-T045-S062-S211 |
| 42 | E008-T049-S116-S076 |
| 43 | E009-T029-S190-S211 |
| 44 | E008-T068-S158-S076 |
| 45 | E007-T058-S194-S037 |
| 46 | E010-T024-S115-S039 |
| 47 | E010-T070-S190-S216 |
| 48 | E010-T049-S115-S074 |
| 49 | E006-T059-S190-S051 |
| 50 | E006-T035-S197-S039 |
| 51 | E009-T076-S190-S051 |
| 52 | E007-T032-S117-S051 |
| 53 | E010-T078-S197-S051 |
| 54 | E006-T026-S165-S037 |
| 55 | E007-T081-S194-S047 |
| 56 | E010-T003-S194-S215 |
| 57 | E009-T069-S194-S050 |
| 58 | E010-T057-S190-S211 |
| 59 | E008-T006-S129-S216 |
| 60 | E008-T078-S190-S211 |
| 61 | E006-T065-S194-S080 |
| 62 | E009-T012-S171-S074 |
| 63 | E009-T041-S165-S038 |
| 64 | E006-T057-S194-S038 |
| 65 | E006-T012-S176-S076 |
| 66 | E008-T052-S197-S050 |
| 67 | E007-T016-S135-S212 |
| 68 | E009-T007-S192-S051 |
| 69 | E006-T065-S165-S047 |
| 70 | E008-T011-S135-S075 |
| 71 | E007-T002-S190-S051 |
| 72 | E006-T037-S165-S053 |
| 73 | E007-T021-S130-S212 |
| 74 | E010-T071-S194-S211 |
| 75 | E007-T023-S158-S080 |

TABLE 4-continued

Constructs present in Library 6 Top 100 in vivo, antigen independent.

| Ranking | Block Sequence |
|---|---|
| 76 | E008-T078-S177-S215 |
| 77 | E010-T008-S196-S049 |
| 78 | E006-T026-S199-S053 |
| 79 | E006-T027-S084-S037 |
| 80 | E007-T034-S189-S212 |
| 81 | E010-T074-S130-S212 |
| 82 | E008-T072-S192-S075 |
| 83 | E008-T021-S109-S039 |
| 84 | E006-T065-S135-S214 |
| 85 | E006-T073-X001-S074 |
| 86 | E008-T032-S175-X002 |
| 87 | E010-T072-S192-S050 |
| 88 | E008-T067-S189-S050 |
| 89 | E008-T073-S192-S074 |
| 90 | E006-T023-S183-S076 |
| 91 | E010-T041-S147-S076 |
| 92 | E010-T067-S130-S074 |
| 93 | E008-T023-S194-S212 |
| 94 | E006-T063-S190-S211 |
| 95 | E006-T053-S194-X002 |
| 96 | E008-T019-S194-S211 |
| 97 | E007-T020-S109-S050 |
| 98 | E006-T024-S194-S074 |
| 99 | E009-T049-S194-S050 |
| 100 | E008-T027-S126-S053 |

TABLE 5

Constructs present in Library 8 Top 100 in vivo, antigen independent.

| Ranking | Block Sequence |
|---|---|
| 1 | E006-T032-S197-S075 |
| 2 | E006-T013-S196-S048 |
| 3 | E008-T030-S057-S037 |
| 4 | E006-T069-S177-S080 |
| 5 | E009-T056-S104-S080 |
| 6 | E006-T006-S171-S215 |
| 7 | E006-T023-S117-S080 |
| 8 | E006-T057-S180-S051 |
| 9 | E007-T032-S064-S052 |
| 10 | E006-T044-S186-S053 |
| 11 | E009-T020-S121-S037 |
| 12 | E009-T012-S154-X002 |
| 13 | E010-T042-S194-S050 |
| 14 | E009-T062-S190-S074 |
| 15 | E006-T018-S141-S213 |
| 16 | E009-T026-S100-S047 |
| 17 | E006-T053-S186-S074 |
| 18 | E010-T021-S197-S049 |
| 19 | E007-T005-S143-S211 |
| 20 | E009-T005-S157-S216 |
| 21 | E006-T038-S192-S039 |
| 22 | E007-T005-S170-S076 |
| 23 | E009-T069-S143-S049 |
| 24 | E006-T057-S189-S038 |
| 25 | E008-T065-S069-S053 |
| 26 | E009-T042-S058-S074 |
| 27 | E006-T045-S072-S051 |
| 28 | E010-T011-S121-S038 |
| 29 | E009-T072-S154-X002 |
| 30 | E010-T072-S194-S047 |
| 31 | E008-T038-S165-S052 |
| 32 | E010-T057-S141-S050 |
| 33 | E006-T056-S196-S212 |
| 34 | E010-T066-S197-S051 |
| 35 | E008-T031-S083-S212 |
| 36 | E009-T006-S062-S053 |
| 37 | E010-T043-S186-S075 |
| 38 | E008-T003-S138-S039 |
| 39 | E008-T057-S141-S049 |

TABLE 5-continued

| Constructs present in Library 8 Top 100 in vivo, antigen independent. | |
|---|---|
| Ranking | Block Sequence |
| 40 | E008-T056-S192-S039 |
| 41 | E009-T049-S199-S037 |
| 42 | E006-T045-S197-S053 |
| 43 | E007-T012-S130-S052 |
| 44 | E007-T015-S069-S038 |
| 45 | E009-T065-S062-X002 |
| 46 | E008-T014-X001-S051 |
| 47 | E008-T026-S058-S050 |
| 48 | E008-T048-S161-S050 |
| 49 | E006-T067-S145-S052 |
| 50 | E009-T049-S135-S052 |
| 51 | E006-T080-S121-S074 |
| 52 | E009-T044-S130-S037 |
| 53 | E007-T016-S165-S037 |
| 54 | E008-T047-S194-X002 |
| 55 | E006-T050-S186-S039 |
| 56 | E008-T055-X001-S216 |
| 57 | E008-T013-S197-S216 |
| 58 | E010-T072-S192-S212 |
| 59 | E007-T001-S064-S215 |
| 60 | E007-T065-S197-S075 |
| 61 | E010-T040-S189-S047 |
| 62 | E009-T039-S117-S074 |
| 63 | E007-T042-S177-S048 |
| 64 | E010-T061-S175-S213 |
| 65 | E008-T063-S069-S075 |
| 66 | E008-T070-S165-S212 |
| 67 | E009-T012-S064-S211 |
| 68 | E006-T006-S194-S211 |
| 69 | E010-T035-S121-S214 |
| 70 | E006-T011-S170-S211 |
| 71 | E006-T048-S058-S053 |
| 72 | E009-T040-S058-S214 |
| 73 | E009-T019-S146-S050 |
| 74 | E010-T045-S135-S075 |
| 75 | E006-T071-S058-S049 |
| 76 | E008-T031-S170-S211 |
| 77 | E007-T030-S176-S048 |
| 78 | E008-T007-S192-S213 |
| 79 | E006-T035-S121-S075 |
| 80 | E008-T060-S064-S214 |
| 81 | E010-T077-S117-S037 |
| 82 | E007-T066-S054-X002 |
| 83 | E008-T023-S194-S214 |
| 84 | E009-T044-S083-S038 |
| 85 | E007-T077-S062-S074 |
| 86 | E006-T063-S130-S052 |
| 87 | E009-T010-S170-S074 |
| 88 | E010-T072-S192-S038 |
| 89 | E010-T016-S168-S037 |
| 90 | E010-T036-S197-S074 |
| 91 | E010-T004-S194-S216 |
| 92 | E009-T049-S085-S075 |
| 93 | E009-T059-S193-S039 |
| 94 | E007-T042-S099-S053 |
| 95 | E008-T031-S104-S076 |
| 96 | E006-T039-S115-S080 |
| 97 | E006-T073-S117-S053 |
| 98 | E010-T032-X001-S049 |
| 99 | E007-T029-S104-S049 |
| 100 | E006-T072-S158-S047 |

TABLE 6

| Constructs present in Library 6 Top 100 in vivo, antigen dependent | |
|---|---|
| Ranking | Block Sequence |
| 1 | E006-T066-S109-X002 |
| 2 | E010-T012-S192-S214 |
| 3 | E009-T028-S130-S212 |
| 4 | E010-T032-S186-S050 |

TABLE 6-continued

| Constructs present in Library 6 Top 100 in vivo, antigen dependent | |
|---|---|
| Ranking | Block Sequence |
| 5 | E007-T052-S197-S075 |
| 6 | E007-T052-S102-S049 |
| 7 | E009-T023-S190-S050 |
| 8 | E008-T008-S194-S215 |
| 9 | E010-T058-S121-S080 |
| 10 | E009-T019-S194-S049 |
| 11 | E008-T004-S142-S212 |
| 12 | E007-T012-S054-S076 |
| 13 | E010-T077-S192-S074 |
| 14 | E006-T073-X001-S074 |
| 15 | E006-T070-S197-S037 |
| 16 | E006-T069-S197-S053 |
| 17 | E006-T061-S190-S080 |
| 18 | E008-T032-S190-S213 |
| 19 | E008-T022-S109-S052 |
| 20 | E009-T078-S190-S047 |
| 21 | E009-T015-S083-S053 |
| 22 | E010-T072-S146-S047 |
| 23 | E010-T078-S197-S051 |
| 24 | E007-T063-S196-S050 |
| 25 | E010-T055-S192-S051 |
| 26 | E006-T059-S190-S051 |
| 27 | E006-T026-S199-S053 |
| 28 | E010-T002-S194-S050 |
| 29 | E009-T075-S165-S050 |
| 30 | E010-T082-X001-S052 |
| 31 | E008-T032-S083-S074 |
| 32 | E007-T040-S192-S049 |
| 33 | E007-T045-S192-S051 |
| 34 | E010-T025-S194-S047 |
| 35 | E006-T078-S082-S048 |
| 36 | E010-T082-S186-S047 |
| 37 | E010-T072-S192-S050 |
| 38 | E007-T039-S197-S080 |
| 39 | E010-T072-S186-S037 |
| 40 | E008-T035-S176-S038 |
| 41 | E008-T056-S190-S050 |
| 42 | E007-T021-S130-S212 |
| 43 | E009-T049-S194-S050 |
| 44 | E007-T032-S117-S051 |
| 45 | E009-T052-S102-S049 |
| 46 | E010-T005-S192-S214 |
| 47 | E007-T061-S186-S211 |
| 48 | E009-T057-S117-S074 |
| 49 | E007-T016-S135-S212 |
| 50 | E009-T073-S062-S053 |
| 51 | E008-T049-S116-S076 |
| 52 | E006-T023-S171-S211 |
| 53 | E006-T048-X001-S211 |
| 54 | E010-T035-S190-S047 |
| 55 | E007-T054-S197-S212 |
| 56 | E006-T045-S177-S216 |
| 57 | E006-T071-S165-S076 |
| 58 | E009-T049-S194-S051 |
| 59 | E009-T049-S197-S051 |
| 60 | E010-T072-S176-S074 |
| 61 | E009-T049-S190-S051 |
| 62 | E008-T067-S197-S074 |
| 63 | E009-T049-S196-S051 |
| 64 | E006-T026-S165-S037 |
| 65 | E009-T049-S189-S051 |
| 66 | E006-T035-S197-S039 |
| 67 | E006-T012-S176-S076 |
| 68 | E006-T065-S194-S080 |
| 69 | E009-T073-S142-X002 |
| 70 | E009-T069-S194-S050 |
| 71 | E007-T045-S190-S211 |
| 72 | E009-T076-S190-S051 |
| 73 | E010-T070-S190-S216 |
| 74 | E010-T049-S115-S074 |
| 75 | E010-T024-S115-S039 |
| 76 | E007-T081-S194-S047 |
| 77 | E007-T058-S194-S037 |
| 78 | E009-T029-S190-S211 |
| 79 | E006-T073-S120-S048 |
| 80 | E008-T045-S062-S211 |

TABLE 6-continued

| Constructs present in Library 6 Top 100 in vivo, antigen dependent | |
|---|---|
| Ranking | Block Sequence |
| 81 | E009-T063-S192-S053 |
| 82 | E008-T067-S190-S074 |
| 83 | E010-T026-S120-S038 |
| 84 | E009-T068-S083-S212 |
| 85 | E010-T081-S190-X002 |
| 86 | E008-T060-S190-S074 |
| 87 | E007-T080-S059-S080 |
| 88 | E010-T077-S058-S053 |
| 89 | E006-T047-S141-S050 |
| 90 | E009-T009-S197-S038 |
| 91 | E008-T001-S121-S212 |
| 92 | E007-T056-S170-S050 |
| 93 | E008-T068-S158-S076 |
| 94 | E006-T064-S190-S080 |
| 95 | E007-T050-S190-S051 |
| 96 | E006-T030-S129-S047 |
| 97 | E008-T001-S064-S047 |
| 98 | E007-T052-S199-S049 |
| 99 | E010-T027-S117-S053 |
| 100 | E010-T036-S058-S048 |

TABLE 7

| Constructs present in Library 8 Top 100 in vivo, antigen dependent | |
|---|---|
| Ranking | Block Sequence |
| 1 | E006-T077-S129-X002 |
| 2 | E006-T031-S109-S216 |
| 3 | E007-T057-S195-S213 |
| 4 | E006-T006-S062-S052 |
| 5 | E008-T033-S197-S216 |
| 6 | E009-T010-S177-S037 |
| 7 | E006-T049-S109-S074 |
| 8 | E007-T029-S069-S076 |
| 9 | E006-T044-S062-S053 |
| 10 | E007-T048-S186-S053 |
| 11 | E009-T032-X001-S211 |
| 12 | E010-T018-S165-S051 |
| 13 | E006-T038-S154-X002 |
| 14 | E007-T021-S194-S211 |
| 15 | E009-T005-S142-S076 |
| 16 | E008-T012-S157-S216 |
| 17 | E009-T005-S197-S051 |
| 18 | E007-T021-S190-S047 |
| 19 | E010-T066-S129-S039 |
| 20 | E010-T033-S149-S215 |
| 21 | E006-T070-S085-S076 |
| 22 | E009-T041-S190-S214 |
| 23 | E007-T031-S130-S047 |
| 24 | E008-T073-S165-X002 |
| 25 | E010-T068-S194-S050 |
| 26 | E008-T006-S197-S213 |
| 27 | E010-T072-S104-S215 |
| 28 | E008-T045-S165-S080 |
| 29 | E008-T041-S104-S048 |
| 30 | E008-T001-S165-S048 |
| 31 | E009-T046-S155-S038 |
| 32 | E006-T026-S146-S212 |
| 33 | E010-T002-S192-S039 |
| 34 | E007-T052-S135-S074 |
| 35 | E006-T001-S158-S215 |
| 36 | E008-T031-S117-S215 |
| 37 | E007-T082-S142-S211 |
| 38 | E008-T044-X001-S211 |
| 39 | E007-T029-S197-S038 |
| 40 | E010-T032-X001-S049 |
| 41 | E009-T070-S161-X002 |
| 42 | E008-T011-S135-S213 |
| 43 | E007-T009-S059-S076 |
| 44 | E007-T037-S141-S216 |
| 45 | E010-T072-S192-S038 |
| 46 | E006-T015-S085-X002 |

TABLE 7-continued

| Constructs present in Library 8 Top 100 in vivo, antigen dependent | |
|---|---|
| Ranking | Block Sequence |
| 47 | E008-T012-S146-S052 |
| 48 | E008-T068-S165-S050 |
| 49 | E006-T044-S192-S038 |
| 50 | E006-T026-S135-S074 |
| 51 | E007-T042-S169-X002 |
| 52 | E006-T007-S192-S049 |
| 53 | E008-T025-S121-S076 |
| 54 | E008-T065-S192-S213 |
| 55 | E008-T073-S069-S080 |
| 56 | E008-T073-S192-S214 |
| 57 | E010-T026-S064-S074 |
| 58 | E007-T001-S197-S216 |
| 59 | E009-T001-S109-S212 |
| 60 | E007-T063-S192-S047 |
| 61 | E009-T031-S063-S215 |
| 62 | E006-T044-S186-S053 |
| 63 | E008-T040-S069-S050 |
| 64 | E006-T005-S064-S213 |
| 65 | E007-T063-S069-S074 |
| 66 | E009-T078-S192-S214 |
| 67 | E007-T004-S194-S047 |
| 68 | E006-T057-S180-S051 |
| 69 | E009-T012-S154-X002 |
| 70 | E008-T073-S069-S076 |
| 71 | E010-T073-S189-S038 |
| 72 | E009-T073-S062-S211 |
| 73 | E009-T049-S142-S038 |
| 74 | E009-T078-S165-S074 |
| 75 | E009-T078-S197-S080 |
| 76 | E010-T044-S104-S048 |
| 77 | E009-T013-S175-S211 |
| 78 | E007-T029-S197-S211 |
| 79 | E006-T038-S192-S039 |
| 80 | E006-T048-S115-S216 |
| 81 | E010-T043-S117-S048 |
| 82 | E007-T012-S142-S211 |
| 83 | E010-T065-S130-S075 |
| 84 | E007-T016-S106-S037 |
| 85 | E006-T032-S138-S053 |
| 86 | E007-T022-S121-S076 |
| 87 | E007-T070-S054-S074 |
| 88 | E010-T051-S115-S051 |
| 89 | E010-T079-S072-S039 |
| 90 | E007-T003-S142-S080 |
| 91 | E009-T008-S062-S037 |
| 92 | E007-T063-S142-S075 |
| 93 | E007-T024-S135-S074 |
| 94 | E010-T057-S197-S211 |
| 95 | E009-T065-S145-S051 |
| 96 | E008-T012-S141-S213 |
| 97 | E007-T025-S202-S214 |
| 98 | E009-T036-S138-S047 |
| 99 | E009-T032-S141-S213 |
| 100 | E009-T058-S195-S048 |

TABLE 8

| Constructs present in combined Library 6 and Library 8 sum of means analysis, Top 30 in vivo, antigen independent | | |
|---|---|---|
| Rank | Block | Sum |
| 1 | E006-T006-S171-S215 | 370,424 |
| 2 | E008-T001-S121-S212 | 320,942 |
| 3 | E009-T056-S104-S080 | 169,035 |
| 4 | E008-T030-S057-S037 | 167,467 |
| 5 | E006-T023-S117-S080 | 139,222 |
| 6 | E006-T032-S197-S075 | 120,909 |
| 7 | E009-T062-S190-S074 | 97,498 |
| 8 | E007-T032-S064-S052 | 93,519 |
| 9 | E010-T072-S192-S212 | 84,725 |
| 10 | E006-T044-S186-S053 | 71,737 |
| 11 | E006-T064-S190-S080 | 69,102 |

TABLE 8-continued

Constructs present in combined Library 6 and Library 8 sum of means analysis, Top 30 in vivo, antigen independent

| Rank | Block | Sum |
|---|---|---|
| 12 | E009-T006-S062-S053 | 53,397 |
| 13 | E008-T003-S138-S039 | 52,634 |
| 14 | E006-T038-S192-S039 | 49,701 |
| 15 | E009-T073-S062-S053 | 40,515 |
| 16 | E009-T032-S170-S074 | 35,245 |
| 17 | E010-T021-S197-S049 | 33,588 |
| 18 | E007-T005-S170-S076 | 22,931 |
| 19 | E007-T054-S197-S212 | 22,916 |
| 20 | E007-T039-S197-S080 | 19,845 |
| 21 | E008-T038-S165-S052 | 17,583 |
| 22 | E008-T078-S190-S211 | 16,857 |
| 23 | E008-T031-S083-S212 | 16,809 |
| 24 | E010-T066-S197-S051 | 16,457 |
| 25 | E006-T056-S196-S212 | 15,881 |
| 26 | E008-T065-S069-S053 | 15,512 |
| 27 | E008-T001-S064-S047 | 15,240 |
| 28 | E009-T010-S170-S074 | 14,526 |
| 29 | E006-T006-S194-S211 | 13,077 |
| 30 | E006-T045-S072-S051 | 12,177 |

What is claimed is:

1. A replication incompetent recombinant retroviral particle comprising:

A. one or more pseudotyping elements on the surface of the replication incompetent recombinant retroviral particle; and B. a polynucleotide comprising one or more transcriptional units, wherein each of the one or more transcriptional units is operatively linked to a promoter active in T cells, and wherein the one or more transcriptional units encode:

i. a first engineered signaling polypeptide, wherein said first engineered signaling polypeptide is a chimeric polypeptide comprising an extracellular domain, a transmembrane domain, and a first intracellular signaling domain comprising a cytokine receptor polypeptide that is capable of activating a cellular signaling pathway, wherein said transmembrane domain is covalently attached to said extracellular domain and said first intracellular signaling domain, wherein said transmembrane domain is between 15 and 100 amino acids, wherein said first intracellular signaling domain comprises an intracellular signaling domain of thrombopoietin receptor having at least 90% sequence identity to the sequence of SEQ ID NO:283, and comprises a JAK-2 binding domain comprising a Box1 motif according to SEQ ID NO:306, and wherein said extracellular domain comprises a leucine zipper dimerizing motif, and ii. a second engineered signaling polypeptide comprising a chimeric antigen receptor (CAR).

2. The replication incompetent recombinant retroviral particle of claim 1, wherein the leucine zipper dimerizing motif is from a jun polypeptide.

3. The replication incompetent recombinant retroviral particle of claim 1, wherein a linker of between 1 and 4 alanine residues is present between the extracellular domain and the transmembrane domain.

4. The replication incompetent recombinant retroviral particle of claim 1, wherein the first engineered signaling polypeptide is encoded in a reverse orientation with respect to a cis-acting RNA packaging element of the replication incompetent recombinant retroviral particle, in the genome of the replication incompetent recombinant retroviral particle.

5. The replication incompetent recombinant retroviral particle of claim 1, wherein the first intracellular signaling domain comprises the Box1 motif having amino acids 17-20 of SEQ ID NO:283.

6. The replication incompetent recombinant retroviral particle of claim 1, wherein the intracellular signaling domain does not comprise a ubiquitin targeting motif having a lysine residue corresponding to K40 of SEQ ID NO:283 or a lysine residue corresponding to K60 of SEQ ID NO:283.

7. The replication incompetent recombinant retroviral particle of claim 1, wherein the intracellular signaling domain comprises a tyrosine residue corresponding to Y8 of SEQ ID NO:283, Y29 of SEQ ID NO:283, Y78 of SEQ ID NO:283, Y113 of SEQ ID NO:283, and Y118 of SEQ ID NO:283, and wherein the intracellular signaling domain contains the Shc phosphotyrosine-binding motif NXXY (SEQ ID NO:307), where each X can be any amino acid.

8. The replication incompetent recombinant retroviral particle of claim 1, wherein the intracellular signaling domain comprises a STAT3 consensus binding sequence YXXQ (SEQ ID NO:308) where each X can be any amino acid, corresponding to amino acids 118-121 of SEQ ID NO:283.

9. The replication incompetent recombinant retroviral particle of claim 5, wherein the intracellular signaling domain comprises the sequence YLXL (SEQ ID NO:309) corresponding to amino acid 113-116 of SEQ ID NO:283, where X can be any amino acid.

10. The replication incompetent recombinant retroviral particle of claim 1, wherein the intracellular signaling domain of said first intracellular signaling domain is at least 95% identical to SEQ ID NO:283.

11. The replication incompetent recombinant retroviral particle of claim 1, wherein the transmembrane domain does not comprise the transmembrane domain of the thrombopoietin receptor.

12. The replication incompetent recombinant retroviral particle of claim 1, wherein the replication incompetent recombinant retroviral particle is a lentivirus, and wherein the first engineered signaling polypeptide comprises a second intracellular signaling domain, wherein the second intracellular signaling domain is a signaling domain from a gene other than the thrombopoietin receptor, that promotes proliferation, survival, and/or provides a co-stimulatory signal that enhances a differentiation state, proliferative potential, or resistance to cell death.

13. The replication incompetent recombinant retroviral particle of claim 12, wherein the second intracellular signaling domain is from a gene selected from CD27, CD40, CRLF2, CSF2RA, CSF3R, EPOR, FCER1G, FCGR2A, FCGR2C, GHR, IFNAR1, IFNAR2, IFNGR2, IL1R1, IL1RL1, IL2RA, IL2RG, IL3RA, IL5RA, IL6R, IL7R, IL9R, IL10RB, IL11RA, IL12RB1, IL12RB2, IL13RA1, IL13RA2, IL15RA, IL17RB, IL18R1, IL18RAP, IL20RB, IL22RA1, IL27RA, IL31RA, LEPR, OSMR, PRLR, TNFRSF4, TNFRSF8, TNFRSF9, TNFRSF14, or TNFRSF18.

14. The replication incompetent recombinant retroviral particle of claim 13, wherein the second intracellular signaling domain is a CD40 intracellular signaling domain.

15. The replication incompetent recombinant retroviral particle of claim 14, wherein the second intracellular signaling domain is between 50 and 66 amino acids in length, comprises the TRAF binding sites from the CD40 intracellular signaling domain, and is at least 90% identical to the CD40 intracellular signaling domain.

16. The replication incompetent recombinant retroviral particle of claim 1, wherein the replication incompetent recombinant retroviral particle further comprises a membrane-bound T cell activation element, and wherein the membrane-bound T cell activation element is an anti-CD3 antibody.

17. The replication incompetent recombinant retroviral particle of claim 16, wherein the anti-CD3 antibody is an anti-CD3 scFvFc antibody, wherein the membrane-bound T cell activation element is fused to a heterologous membrane attachment sequence, and wherein the heterologous membrane attachment sequence is a GPI anchor attachment sequence.

18. The replication incompetent recombinant retroviral particle of claim 1, wherein one of the one or more pseudotyping elements is selected from a MuLV envelope protein, a BaEV envelope protein, a VSV-G envelope protein, an influenza HA, an influenza NA, a paramyxovirus Measles envelope protein H, and a paramyxovirus Measles envelope protein F.

19. The replication incompetent recombinant retroviral particle of claim 1, wherein one of the one or more pseudotyping elements is MuLV fused to an anti-CD3 antibody.

20. The replication incompetent recombinant retroviral particle of claim 1, wherein the first engineered signaling polypeptide is a fusion polypeptide comprising a recognition domain that is recognized by a monoclonal antibody approved biologic.

21. The replication incompetent recombinant retroviral particle of claim 1, wherein the first engineered signaling polypeptide possesses the property of:

a) improving expansion of pre-activated PBMCs transduced with a retroviral particle comprising a nucleic acid construct encoding the first engineered signaling polypeptide when transduced along with a nucleic acid encoding an anti-CD19 CAR comprising a CD3 zeta intracellular activating domain but no co-stimulatory domain, between day 7 and day 21 of in vitro culturing in the absence of exogenously added cytokines, compared to a control construct identical to the nucleic acid construct comprising the first engineered signaling polypeptide but without the first engineered signaling polypeptide, under identical conditions; and/or b) expanding pre-activated PBMCs transduced with a nucleic acid construct encoding the first engineered signaling polypeptide at least 2-fold between day 7 and day 21 of in vitro culturing in the absence of exogenously added cytokines, when transduced along with a nucleic acid encoding an anti-CD19 CAR comprising a CD3 zeta intracellular activating domain but no costimulatory domain.

22. The replication incompetent recombinant retroviral particle of claim 1, wherein the replication incompetent recombinant retroviral particle further comprises a membrane-bound cytokine on the surface of the replication incompetent recombinant retroviral particle, wherein the membrane-bound cytokine comprises a fusion polypeptide of IL-7 and DAF, and wherein the fusion polypeptide comprises the amino acid sequence of SEQ ID NO:462.

23. A method for genetically modifying a T cell of a subject, wherein the method comprises:

contacting a population of T cells comprising the T cell ex vivo, with a population of replication incompetent recombinant retroviral particles according to claim 16, wherein said contacting is performed for less than 12 hours to facilitate membrane fusion of the T cell to the replication incompetent recombinant retroviral particle, thereby genetically modifying the T cell.

24. The method of claim 23, wherein the method further comprises:

collecting blood comprising the population of T cells from a subject before contacting the population of T cells ex vivo with the population of replication incompetent recombinant retroviral particles; and reintroducing the genetically modified T cell into the subject.

25. The method of claim 24, wherein the genetically modified T cell is not expanded ex vivo after said contacting and before being reintroduced into the subject.

26. The method of claim 23, wherein the population of T cells comprises between 90% and 100% resting T cells.

27. The method of claim 24, wherein the population of T cells undergoes 4 or fewer cell divisions ex vivo prior to being reintroduced into the subject.

* * * * *